US012448400B2

(12) United States Patent
Dai et al.

(10) Patent No.: US 12,448,400 B2
(45) Date of Patent: Oct. 21, 2025

(54) KRAS G12D MODULATING COMPOUNDS

(71) Applicant: Gilead Sciences, Inc., Foster City, CA (US)

(72) Inventors: Chaodi Dai, San Mateo, CA (US); Juan A. Guerrero, Clayton, CA (US); Darryl Kato, San Francisco, CA (US); Scott E. Lazerwith, San Francisco, CA (US); Jonathan William Medley, San Bruno, CA (US); Thomas C. J. Mies, Burlingame, CA (US); Hyung-Jung Pyun, Fremont, CA (US); Hayato Shiotsu, San Francisco, CA (US); Maoqun Tian, Foster City, CA (US); William J. Watkins, Saratoga, CA (US); Jennifer R. Zhang, Union City, CA (US)

(73) Assignee: Gilead Sciences, Inc., Foster City, CA (US)

( * ) Notice: Subject to any disclaimer, the term of this patent is extended or adjusted under 35 U.S.C. 154(b) by 0 days.

(21) Appl. No.: 19/000,200

(22) Filed: Dec. 23, 2024

(65) Prior Publication Data

US 2025/0136621 A1 May 1, 2025

Related U.S. Application Data

(63) Continuation of application No. 18/827,510, filed on Sep. 6, 2024.

(60) Provisional application No. 63/640,100, filed on Apr. 29, 2024, provisional application No. 63/562,155, filed on Mar. 6, 2024, provisional application No. 63/581,551, filed on Sep. 8, 2023.

(51) Int. Cl.
*C07D 519/00* (2006.01)
*A61K 31/55* (2006.01)

(52) U.S. Cl.
CPC ............ *C07D 519/00* (2013.01); *A61K 31/55* (2013.01)

(58) Field of Classification Search
CPC .................................................... C07D 519/00
See application file for complete search history.

(56) References Cited

U.S. PATENT DOCUMENTS

| | | | |
|---|---|---|---|
| 2022/0389033 A1 | 12/2022 | Sokolsky et al. | |
| 2023/0339981 A1 | 10/2023 | Dai et al. | |
| 2023/0374036 A1 | 11/2023 | Dai et al. | |
| 2024/0270736 A1 | 8/2024 | Wu | |
| 2024/0383922 A1 | 11/2024 | Cortopassi Coelho et al. | |

FOREIGN PATENT DOCUMENTS

| | | | |
|---|---|---|---|
| CN | 112300195 | A | 2/2021 |
| CN | 112390818 | A | 2/2021 |
| CN | 112745335 | A | 5/2021 |
| CN | 114437107 | A | 5/2022 |
| CN | 114539293 | A | 5/2022 |
| CN | 113853373 | B | 8/2022 |
| CN | 114874234 | A | 8/2022 |
| CN | 114989195 | A | 9/2022 |
| CN | 115141215 | A | 10/2022 |
| CN | 115181106 | A | 10/2022 |
| CN | 115197245 | A | 10/2022 |
| CN | 115304623 | A | 11/2022 |
| CN | 115368381 | A | 11/2022 |
| CN | 115368382 | A | 11/2022 |
| CN | 115385937 | A | 11/2022 |
| CN | 115385938 | A | 11/2022 |
| CN | 115466272 | A | 12/2022 |
| CN | 115490709 | A | 12/2022 |
| CN | 115785124 | A | 3/2023 |
| CN | 115785199 | A | 3/2023 |
| CN | 115850267 | A | 3/2023 |
| CN | 115960105 | A | 4/2023 |
| CN | 116102559 | A | 5/2023 |
| CN | 116143805 | A | 5/2023 |
| CN | 116143806 | A | 5/2023 |
| CN | 116162099 | A | 5/2023 |
| CN | 116199703 | A | 6/2023 |
| CN | 116262759 | A | 6/2023 |
| CN | 116332938 | A | 6/2023 |
| CN | 116332948 | A | 6/2023 |
| CN | 116375742 | A | 7/2023 |
| CN | 116514846 | A | 8/2023 |
| CN | 116554208 | A | 8/2023 |
| CN | 116731044 | A | 9/2023 |
| CN | 116731045 | A | 9/2023 |
| CN | 116969977 | A | 10/2023 |
| CN | 117164605 | A | 12/2023 |
| CN | 117186095 | A | 12/2023 |
| CN | 117263959 | A | 12/2023 |
| CN | 117285590 | A | 12/2023 |
| CN | 117327102 | A | 1/2024 |

(Continued)

OTHER PUBLICATIONS

Lee Jong Bong et al., "Lipophilic activated ester prodrug approach for drug delivery to the intestinal lymphatic system" Journal of Controlled Release 286:10-19, 2018.

(Continued)

*Primary Examiner* — Yong S. Chong

(74) *Attorney, Agent, or Firm* — Mintz, Levin, Cohn, Ferris, Glovsky and Popeo, P.C.

(57) ABSTRACT

Provided herein are compounds, and pharmaceutically acceptable salts thereof, useful as KRAS G12D and/or KRAS G12C inhibitors, methods of making and using the same (singly or in combination with additional agents), and pharmaceutical compositions thereof.

15 Claims, No Drawings

(56) References Cited

FOREIGN PATENT DOCUMENTS

| | | | |
|---|---|---|---|
| CN | 117462688 | A | 1/2024 |
| CN | 117486901 | A | 2/2024 |
| CN | 117586280 | A | 2/2024 |
| CN | 117624190 | A | 3/2024 |
| CN | 117624194 | A | 3/2024 |
| CN | 117683051 | A | 3/2024 |
| CN | 117736226 | A | 3/2024 |
| CN | 117800976 | A | 4/2024 |
| CN | 117800989 | A | 4/2024 |
| CN | 117800990 | A | 4/2024 |
| CN | 2024118126064 | A | 6/2024 |
| CN | 2024118580238 | A | 9/2024 |
| CN | 2024118666870 | A | 9/2024 |
| CN | 2024118724924 | A | 10/2024 |
| CN | 2024118772176 | A | 10/2024 |
| CN | 2024118791505 | A | 10/2024 |
| CN | 2024118955610 | A | 11/2024 |
| CN | 2024119019382 | A | 11/2024 |
| CN | 2024119060049 | A | 12/2024 |
| CN | 2024119060066 | A | 12/2024 |
| KR | 20240159370 | A | 11/2024 |
| WO | 2020221239 | A1 | 11/2020 |
| WO | 2021000885 | A1 | 1/2021 |
| WO | 2021023154 | A1 | 2/2021 |
| WO | 2021041671 | A1 | 3/2021 |
| WO | 2021081212 | A1 | 4/2021 |
| WO | 2021108683 | A1 | 6/2021 |
| WO | 2021142252 | A1 | 7/2021 |
| WO | 2021211864 | A1 | 10/2021 |
| WO | 2021215544 | A1 | 10/2021 |
| WO | 2022015375 | A1 | 1/2022 |
| WO | 2022105857 | A1 | 5/2022 |
| WO | 2022119748 | A1 | 6/2022 |
| WO | 2022132200 | A1 | 6/2022 |
| WO | 2022133038 | A1 | 6/2022 |
| WO | 2022133345 | A1 | 6/2022 |
| WO | 2022148421 | A1 | 7/2022 |
| WO | 2022148422 | A1 | 7/2022 |
| WO | 2022157629 | A1 | 7/2022 |
| WO | 2022161443 | A1 | 8/2022 |
| WO | 2022161489 | A1 | 8/2022 |
| WO | 2022165142 | A1 | 8/2022 |
| WO | 2022166974 | A1 | 8/2022 |
| WO | 2022170999 | A1 | 8/2022 |
| WO | 2022171013 | A1 | 8/2022 |
| WO | 2022171143 | A1 | 8/2022 |
| WO | 2022171147 | A1 | 8/2022 |
| WO | 2022173032 | A1 | 8/2022 |
| WO | 2022173033 | A1 | 8/2022 |
| WO | 2022173678 | A1 | 8/2022 |
| WO | 2022177917 | A2 | 8/2022 |
| WO | 2022184178 | A1 | 9/2022 |
| WO | 2022187411 | A1 | 9/2022 |
| WO | 2022187527 | A1 | 9/2022 |
| WO | 2022187528 | A1 | 9/2022 |
| WO | 2022188729 | A1 | 9/2022 |
| WO | 2022192790 | A1 | 9/2022 |
| WO | 2022192794 | A1 | 9/2022 |
| WO | 2022193871 | A1 | 9/2022 |
| WO | 2022194066 | A1 | 9/2022 |
| WO | 2022194191 | A1 | 9/2022 |
| WO | 2022194192 | A1 | 9/2022 |
| WO | 2022194245 | A1 | 9/2022 |
| WO | 2022198904 | A1 | 9/2022 |
| WO | 2022198905 | A1 | 9/2022 |
| WO | 2022199170 | A1 | 9/2022 |
| WO | 2022199586 | A1 | 9/2022 |
| WO | 2022199587 | A1 | 9/2022 |
| WO | 2022206723 | A1 | 10/2022 |
| WO | 2022206724 | A1 | 10/2022 |
| WO | 2022212611 | A1 | 10/2022 |
| WO | 2022214102 | A1 | 10/2022 |
| WO | 2022217042 | A1 | 10/2022 |
| WO | 2022221386 | A1 | 10/2022 |
| WO | 2022221739 | A1 | 10/2022 |
| WO | 2022222871 | A1 | 10/2022 |
| WO | 2022223020 | A1 | 10/2022 |
| WO | 2022227987 | A1 | 11/2022 |
| WO | 2022228543 | A1 | 11/2022 |
| WO | 2022228568 | A1 | 11/2022 |
| WO | 2022228576 | A1 | 11/2022 |
| WO | 2022232331 | A1 | 11/2022 |
| WO | 2022232332 | A1 | 11/2022 |
| WO | 2022236578 | A1 | 11/2022 |
| WO | 2022237649 | A1 | 11/2022 |
| WO | 2022246092 | A1 | 11/2022 |
| WO | 2022247757 | A1 | 12/2022 |
| WO | 2022247760 | A1 | 12/2022 |
| WO | 2022247770 | A1 | 12/2022 |
| WO | 2022248885 | A2 | 12/2022 |
| WO | 2022250170 | A1 | 12/2022 |
| WO | 2022256459 | A1 | 12/2022 |
| WO | 2022261154 | A1 | 12/2022 |
| WO | 2022261210 | A1 | 12/2022 |
| WO | 2022262686 | A1 | 12/2022 |
| WO | 2022262838 | A1 | 12/2022 |
| WO | 2022266015 | A1 | 12/2022 |
| WO | 2022266069 | A1 | 12/2022 |
| WO | 2022268051 | A1 | 12/2022 |
| WO | 2023001123 | A1 | 1/2023 |
| WO | 2023001141 | A1 | 1/2023 |
| WO | 2023274324 | A1 | 1/2023 |
| WO | 2023274383 | A1 | 1/2023 |
| WO | 2023278600 | A1 | 1/2023 |
| WO | 2023280026 | A1 | 1/2023 |
| WO | 2023280280 | A1 | 1/2023 |
| WO | 2023283933 | A1 | 1/2023 |
| WO | 2023284537 | A1 | 1/2023 |
| WO | 2023284730 | A1 | 1/2023 |
| WO | 2023284881 | A1 | 1/2023 |
| WO | 2023287896 | A1 | 1/2023 |
| WO | 2023014570 | A1 | 2/2023 |
| WO | 2023018699 | A1 | 2/2023 |
| WO | 2023018809 | A1 | 2/2023 |
| WO | 2023018810 | A1 | 2/2023 |
| WO | 2023018812 | A1 | 2/2023 |
| WO | 2023020347 | A1 | 2/2023 |
| WO | 2023020518 | A1 | 2/2023 |
| WO | 2023020519 | A1 | 2/2023 |
| WO | 2023020521 | A1 | 2/2023 |
| WO | 2023020523 | A1 | 2/2023 |
| WO | 2023025116 | A1 | 3/2023 |
| WO | 2023030385 | A1 | 3/2023 |
| WO | 2023030495 | A1 | 3/2023 |
| WO | 2023030517 | A1 | 3/2023 |
| WO | 2023034290 | A1 | 3/2023 |
| WO | 2023040989 | A1 | 3/2023 |
| WO | 2023046135 | A1 | 3/2023 |
| WO | 2023051586 | A1 | 4/2023 |
| WO | 2023056421 | A1 | 4/2023 |
| WO | 2023056951 | A1 | 4/2023 |
| WO | 2023059594 | A1 | 4/2023 |
| WO | 2023059596 | A1 | 4/2023 |
| WO | 2023059597 | A1 | 4/2023 |
| WO | 2023059598 | A1 | 4/2023 |
| WO | 2023059600 | A1 | 4/2023 |
| WO | 2023061294 | A1 | 4/2023 |
| WO | 2023061463 | A1 | 4/2023 |
| WO | 2023064857 | A1 | 4/2023 |
| WO | 2023066371 | A1 | 4/2023 |
| WO | 2023072188 | A1 | 5/2023 |
| WO | 2023072297 | A1 | 5/2023 |
| WO | 2023077441 | A1 | 5/2023 |
| WO | 2023081476 | A1 | 5/2023 |
| WO | 2023097227 | A1 | 6/2023 |
| WO | 2023098425 | A1 | 6/2023 |
| WO | 2023098426 | A1 | 6/2023 |
| WO | 2023098832 | A1 | 6/2023 |
| WO | 2023101928 | A1 | 6/2023 |
| WO | 2023103523 | A1 | 6/2023 |
| WO | 2023103906 | A1 | 6/2023 |
| WO | 2023104018 | A1 | 6/2023 |
| WO | 2023105491 | A1 | 6/2023 |

(56) References Cited

FOREIGN PATENT DOCUMENTS

| | | | |
|---|---|---|---|
| WO | 2023114733 | A1 | 6/2023 |
| WO | 2023116934 | A1 | 6/2023 |
| WO | 2023119677 | A1 | 6/2023 |
| WO | 2023122154 | A1 | 6/2023 |
| WO | 2023122662 | A1 | 6/2023 |
| WO | 2023125627 | A1 | 7/2023 |
| WO | 2023125989 | A1 | 7/2023 |
| WO | 2023133183 | A1 | 7/2023 |
| WO | 2023134465 | A1 | 7/2023 |
| WO | 2023137223 | A1 | 7/2023 |
| WO | 2023138524 | A1 | 7/2023 |
| WO | 2023138583 | A1 | 7/2023 |
| WO | 2023138589 | A1 | 7/2023 |
| WO | 2023138601 | A1 | 7/2023 |
| WO | 2023141300 | A1 | 7/2023 |
| WO | 2023143312 | A1 | 8/2023 |
| WO | 2023143352 | A1 | 8/2023 |
| WO | 2023143623 | A1 | 8/2023 |
| WO | 2023150284 | A2 | 8/2023 |
| WO | 2023151621 | A1 | 8/2023 |
| WO | 2023152255 | A1 | 8/2023 |
| WO | 2023154766 | A1 | 8/2023 |
| WO | 2023159086 | A1 | 8/2023 |
| WO | 2023159087 | A1 | 8/2023 |
| WO | 2023171781 | A1 | 9/2023 |
| WO | 2023173014 | A1 | 9/2023 |
| WO | 2023173016 | A1 | 9/2023 |
| WO | 2023173017 | A1 | 9/2023 |
| WO | 2023179629 | A1 | 9/2023 |
| WO | 2023179703 | A1 | 9/2023 |
| WO | 2023183585 | A1 | 9/2023 |
| WO | 2023185864 | A1 | 10/2023 |
| WO | 2023193085 | A1 | 10/2023 |
| WO | 2023197984 | A1 | 10/2023 |
| WO | 2023198078 | A1 | 10/2023 |
| WO | 2023205719 | A1 | 10/2023 |
| WO | 2023213269 | A1 | 11/2023 |
| WO | 2023215801 | A1 | 11/2023 |
| WO | 2023215802 | A1 | 11/2023 |
| WO | 2023215906 | A1 | 11/2023 |
| WO | 2023220421 | A1 | 11/2023 |
| WO | 2023244600 | A1 | 12/2023 |
| WO | 2023244615 | A1 | 12/2023 |
| WO | 2023244713 | A1 | 12/2023 |
| WO | 2023246777 | A1 | 12/2023 |
| WO | 2023246903 | A1 | 12/2023 |
| WO | 2023246914 | A1 | 12/2023 |
| WO | 2024001839 | A1 | 1/2024 |
| WO | 2024002373 | A1 | 1/2024 |
| WO | 2024008068 | A1 | 1/2024 |
| WO | 2024008178 | A1 | 1/2024 |
| WO | 2024008179 | A1 | 1/2024 |
| WO | 2024009191 | A1 | 1/2024 |
| WO | 2024012519 | A1 | 1/2024 |
| WO | 2024015262 | A1 | 1/2024 |
| WO | 2024017392 | A1 | 1/2024 |
| WO | 2024019103 | A1 | 1/2024 |
| WO | 2024022444 | A1 | 2/2024 |
| WO | 2024022507 | A1 | 2/2024 |
| WO | 2024027814 | A1 | 2/2024 |
| WO | 2024030633 | A1 | 2/2024 |
| WO | 2024030647 | A1 | 2/2024 |
| WO | 2024031088 | A1 | 2/2024 |
| WO | 2024032703 | A1 | 2/2024 |
| WO | 2024032704 | A1 | 2/2024 |
| WO | 2024033537 | A1 | 2/2024 |
| WO | 2024033538 | A1 | 2/2024 |
| WO | 2024034123 | A1 | 2/2024 |
| WO | 2024034591 | A1 | 2/2024 |
| WO | 2024034593 | A1 | 2/2024 |
| WO | 2024034657 | A1 | 2/2024 |
| WO | 2024040080 | A1 | 2/2024 |
| WO | 2024040109 | A2 | 2/2024 |
| WO | 2024041573 | A1 | 2/2024 |
| WO | 2024041589 | A1 | 2/2024 |
| WO | 2024041606 | A1 | 2/2024 |
| WO | 2024041621 | A1 | 2/2024 |
| WO | 2024044334 | A2 | 2/2024 |
| WO | 2024044649 | A2 | 2/2024 |
| WO | 2024044667 | A2 | 2/2024 |
| WO | 2024045066 | A1 | 3/2024 |
| WO | 2024046370 | A1 | 3/2024 |
| WO | 2024046406 | A1 | 3/2024 |
| WO | 2024050640 | A1 | 3/2024 |
| WO | 2024050742 | A1 | 3/2024 |
| WO | 2024051721 | A1 | 3/2024 |
| WO | 2024051763 | A1 | 3/2024 |
| WO | 2024051852 | A1 | 3/2024 |
| WO | 2024054625 | A2 | 3/2024 |
| WO | 2024054647 | A1 | 3/2024 |
| WO | 2024054926 | A1 | 3/2024 |
| WO | 2024055112 | A1 | 3/2024 |
| WO | 2024061333 | A1 | 3/2024 |
| WO | 2024061365 | A1 | 3/2024 |
| WO | 2024061370 | A1 | 3/2024 |
| WO | 2024063576 | A1 | 3/2024 |
| WO | 2024063578 | A1 | 3/2024 |
| WO | 2024064335 | A1 | 3/2024 |
| WO | 2024123102 | | 3/2024 |
| WO | 2024123913 | | 3/2024 |
| WO | 2024067575 | A1 | 4/2024 |
| WO | 2024067714 | A1 | 4/2024 |
| WO | 2024078555 | A1 | 4/2024 |
| WO | 2024083246 | A1 | 4/2024 |
| WO | 2024083256 | A1 | 4/2024 |
| WO | 2024083258 | A1 | 4/2024 |
| WO | 2024088069 | A1 | 5/2024 |
| WO | 2024091409 | A1 | 5/2024 |
| WO | 2024104425 | A1 | 5/2024 |
| WO | 2024109233 | | 5/2024 |
| WO | 2024230734 | | 5/2024 |
| WO | 2024118926 | | 6/2024 |
| WO | 2024119277 | | 6/2024 |
| WO | 2024120419 | | 6/2024 |
| WO | 2024120433 | A1 | 6/2024 |
| WO | 2024125600 | | 6/2024 |
| WO | 2024125642 | | 6/2024 |
| WO | 2024149275 | | 7/2024 |
| WO | 2024149389 | | 7/2024 |
| WO | 2024153116 | | 7/2024 |
| WO | 2024153119 | | 7/2024 |
| WO | 2024153180 | | 7/2024 |
| WO | 2024153208 | | 7/2024 |
| WO | 2024158242 | | 8/2024 |
| WO | 2024159470 | | 8/2024 |
| WO | 2024159471 | | 8/2024 |
| WO | 2024160225 | | 8/2024 |
| WO | 2024169914 | | 8/2024 |
| WO | 2024173842 | | 8/2024 |
| WO | 2024175659 | | 8/2024 |
| WO | 2024175662 | | 8/2024 |
| WO | 2024178304 | | 8/2024 |
| WO | 2024178313 | | 8/2024 |
| WO | 2024179546 | | 9/2024 |
| WO | 2024192424 | | 9/2024 |
| WO | 2024193698 | | 9/2024 |
| WO | 2024197503 | | 10/2024 |
| WO | 2024206747 | | 10/2024 |
| WO | 2024206766 | | 10/2024 |
| WO | 2024207892 | | 10/2024 |
| WO | 2024208305 | | 10/2024 |
| WO | 2024208934 | | 10/2024 |
| WO | 2024209339 | | 10/2024 |
| WO | 2024211663 | | 10/2024 |
| WO | 2024211712 | | 10/2024 |
| WO | 2024213122 | | 10/2024 |
| WO | 2024215862 | | 10/2024 |
| WO | 2024218686 | | 10/2024 |
| WO | 2024220532 | | 10/2024 |
| WO | 2024220645 | | 10/2024 |
| WO | 2024222864 | | 10/2024 |
| WO | 2024227091 | | 10/2024 |
| WO | 2024230707 | | 11/2024 |
| WO | 2024233776 | | 11/2024 |

(56) References Cited

FOREIGN PATENT DOCUMENTS

| | | |
|---|---|---|
| WO | 2024234360 | 11/2024 |
| WO | 2024235225 | 11/2024 |
| WO | 2024235286 | 11/2024 |
| WO | 2024236452 | 11/2024 |
| WO | 2024238343 | 11/2024 |
| WO | 2024243025 | 11/2024 |
| WO | 2024246099 | 12/2024 |
| WO | 2024249299 | 12/2024 |
| WO | 2024254334 | 12/2024 |
| WO | 2024254404 | 12/2024 |
| WO | 2025002302 | 1/2025 |
| WO | 2025002430 | 1/2025 |
| WO | 2025006962 | 1/2025 |
| WO | 2025007000 | 1/2025 |

OTHER PUBLICATIONS

PCT/US2024/045695 Search Report and Written Opinion dated Dec. 3, 2024.

International Search Report & Written Opinion Issued in PCT Application No. PCT/US2023/065991, mailed on Jun. 26, 2023, 11 pages.

International Search Report & Written Opinion Issued in PCT Application No. PCT/US2024/023867, mailed on Jul. 29, 2024, 12 pages.

Kwan et al. (2022) “The Path to the Clinic: A Comprehensive Review on Direct KRASG12C Inhibitors”, Journal of Experimental & Clinical Cancer Research, 41(1):27 (23 pages).

KRAS G12D MODULATING COMPOUNDS

CROSS-REFERENCE TO RELATED APPLICATIONS

This application is a continuation of U.S. application Ser. No. 18/827,510, filed Sep. 6, 2024, which claims the benefit under 35 U.S.C. § 119(e) of U.S. Provisional Application No. 63/581,551, filed on Sep. 8, 2023, U.S. Provisional Application No. 63/562,155, filed on Mar. 6, 2024, and U.S. Provisional Application No. 63/640,100, filed on Apr. 29, 2024, each of which is incorporated herein by reference in its entirety for all purposes.

BACKGROUND

The KRAS protein, Kirsten Rat Sarcoma 2 Viral Oncogene Homolog ("KRAS"), is a GTPase. KRAS gene mutations have been observed in a number of conditions including, for instance, pancreatic cancer, endometrial cancer, lung adenocarcinoma, colorectal cancer, rectal carcinoma, gall bladder cancer, thyroid cancer, bile duct cancer, small cell lung cancer, and non-small cell lung cancer (NSCLC). Accordingly, there is a need for compounds, pharmaceutical compositions, and methods for inhibiting KRAS (e.g., KRAS G12C and/or KRAS G12D) and treating associated cancers.

SUMMARY

In one embodiment, the present disclosure provides a compound of Formula J:

Formula J

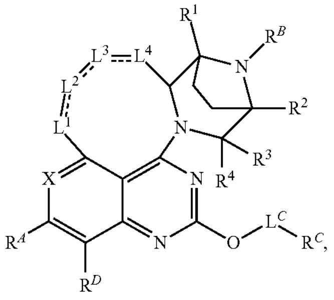

or a pharmaceutically acceptable salt thereof, wherein

X is N, CH, or $CR^x$;

$R^x$ is $C_{1-3}$ alkyl, $C_{2-4}$ alkenyl, $C_{1-3}$ alkoxy, $C_{1-3}$ thioalkyl, —CN, $(CH_2)_m$CN, halo, $C_{1-3}$ haloalkyl, or $C_{3-6}$ cycloalkyl;

m is 0, 1, 2 or 3;

$R^1$, $R^2$, $R^3$, and $R^4$ are each independently H or $C_1$-$C_3$ alkyl;

$L^1$ is O, S, $CR^{1a}R^{1b}$, $C({=}CR^{1c}R^{1d})$, C(═O), or —$C(R^{1e})$═;

$R^{1a}$ and $R^{1b}$ are each independently H, $C_1$-$C_3$ alkyl, $C_1$-$C_3$ alkoxy, halo, $C_1$-$C_6$ haloalkyl, $C_1$-$C_6$ haloalkoxy, —OH, —CN, $C_1$-$C_3$ cyanoalkyl, or $C_3$-$C_6$ cycloalkyl;

alternatively, $R^{1a}$ and $R^{1b}$ can combine with the atom to which they are attached to form a $C_3$-$C_6$ cycloalkyl or a 3 to 6 membered heterocyclyl having 1 heteroatom that is O, wherein each cycloalkyl and heterocyclyl is substituted with 0, 1, 2, or 3 $R^{1x}$;

$R^{1c}$ and $R^{1d}$ are each independently H, $C_1$-$C_3$ alkyl, halo, $C_1$-$C_6$ haloalkyl, —CN, $C_1$-$C_3$ cyanoalkyl, or $C_3$-$C_6$ cycloalkyl;

alternatively, $R^{1c}$ and $R^{1d}$ can combine with the atom to which they are attached to form a $C_3$-$C_6$ cycloalkyl or a 3 to 6 membered heterocyclyl having 1 heteroatom that is O, wherein each cycloalkyl and heterocyclyl is substituted with 0, 1, 2, or 3 $R^{1x}$;

$R^{1c}$ is H, $C_1$-$C_3$ alkyl, halo, $C_1$-$C_6$ haloalkyl, —CN, $C_1$-$C_3$ cyanoalkyl, or $C_3$-$C_6$ cycloalkyl; each $R^{1x}$ is independently $C_1$-$C_3$ alkyl, $C_1$-$C_3$ alkoxy, halo, $C_1$-$C_6$ haloalkyl, $C_1$-$C_6$ haloalkoxy, or —OH;

$L^2$ is absent, O, S, $CR^{2a}R^{2b}$, $C({=}CR^{2c}R^{2d})$, C(═O), or ═$C(R^{2e})$—, such that when $L^2$ is O or S, then $L^1$ is $CR^{1a}R^{1b}$;

$R^{2a}$ and $R^{2b}$ are each independently H, $C_1$-$C_3$ alkyl, $C_1$-$C_3$ alkoxy, halo, $C_1$-$C_6$ haloalkyl, $C_1$-$C_6$ haloalkoxy, —OH, —CN, $C_1$-$C_3$ cyanoalkyl, or $C_3$-$C_6$ cycloalkyl;

alternatively, $R^{2a}$ and $R^{2b}$ can combine with the atom to which they are attached to form a $C_3$-$C_6$ cycloalkyl;

alternatively, $R^{1b}$ and $R^{2b}$ can combine with the atoms to which they are attached to form a $C_3$-$C_6$ cycloalkyl, 4- to 10-membered heterocyclyl, $C_6$-$C_{10}$ aryl, or 5- to 14-membered heteroaryl, wherein each cycloalkyl, heterocyclyl, aryl and heteroaryl is substituted with 0, 1, 2, or 3 $R^{2x}$;

$R^{2c}$ and $R^{2d}$ are each independently H, $C_1$-$C_3$ alkyl, halo, $C_1$-$C_6$ haloalkyl, —CN, $C_1$-$C_3$ cyanoalkyl, or $C_3$-$C_6$ cycloalkyl;

alternatively, $R^{2c}$ and $R^{2d}$ can combine with the atom to which they are attached to form a $C_3$-$C_6$ cycloalkyl or a 3 to 6 membered heterocyclyl having 1 heteroatom that is O, wherein each cycloalkyl and heterocyclyl is substituted with 0, 1, 2, or 3 $R^{2x}$;

$R^{2e}$ is H, $C_1$-$C_3$ alkyl, halo, $C_1$-$C_6$ haloalkyl, —CN, $C_1$-$C_3$ cyanoalkyl, or $C_3$-$C_6$ cycloalkyl;

alternatively, $R^{1e}$ and $R^{2e}$ can combine with the atoms to which they are attached to form a $C_5$-$C_6$ cycloalkyl, 5- to 10-membered heterocyclyl, $C_6$-$C_{10}$ aryl, or 5- to 14-membered heteroaryl, wherein each cycloalkyl, heterocyclyl, aryl and heteroaryl is substituted with 0, 1, 2, or 3 $R^{2x}$;

each $R^{2x}$ is independently $C_1$-$C_3$ alkyl, $C_1$-$C_3$ alkoxy, halo, $C_1$-$C_6$ haloalkyl, $C_1$-$C_6$ haloalkoxy, or —OH;

alternatively $L^1$ and $L^2$ can combine to form

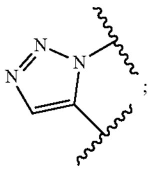 [SMILES: *c1cnnn1*]

;

$L^3$ is absent, $CR^{3a}R^{3b}$, $C({=}CR^{3c}R^{3d})$, C(═O), or ═$C(R^{3e})$—;

$R^{3a}$ and $R^{3b}$ are each independently H, $C_1$-$C_3$ alkyl, $C_1$-$C_3$ alkoxy, halo, $C_1$-$C_6$ haloalkyl, $C_1$-$C_6$ haloalkoxy, —OH, —CN, $C_1$-$C_3$ cyanoalkyl, or $C_3$-$C_6$ cycloalkyl;

alternatively, $R^{3a}$ and $R^{3b}$ can combine with the atom to which they are attached to form a $C_3$-$C_6$ cycloalkyl;

alternatively, $R^{2b}$ and $R^{3b}$ can combine with the atoms to which they are attached to form a $C_3$-$C_6$ cycloalkyl;

$R^{3c}$ and $R^{3d}$ are each independently H, $C_1$-$C_3$ alkyl, halo, $C_1$-$C_6$ haloalkyl, —CN, $C_1$-$C_3$ cyanoalkyl, or $C_3$-$C_6$ cycloalkyl;

alternatively, $R^{3c}$ and $R^{3d}$ can combine with the atom to which they are attached to form a $C_3$-$C_6$ cycloalkyl or a 3 to 6 membered heterocyclyl having 1 heteroatom that is O, wherein each cycloalkyl and heterocyclyl is substituted with 0, 1, 2, or 3 $R^{3x}$;

each $R^{3x}$ is independently $C_1$-$C_3$ alkyl, $C_1$-$C_3$ alkoxy, halo, $C_1$-$C_6$ haloalkyl, $C_1$-$C_6$ haloalkoxy, or —OH;

$R^{3e}$ is H, $C_1$-$C_3$ alkyl, halo, $C_1$-$C_6$ haloalkyl, —CN, $C_1$-$C_3$ cyanoalkyl, or $C_3$-$C_6$ cycloalkyl;

alternatively, $R^{2e}$ and $R^{3e}$ can combine with the atoms to which they are attached to form a $C_5$-$C_6$ cycloalkyl, 5- to 10-membered heterocyclyl, $C_6$-$C_{10}$ aryl, or 5- to 14-membered heteroaryl; $L^4$ is absent, $CR^{4a}R^{4b}$, $C(=CR^{4c}R^{4d})$, C(=O), or $=C(R^{4e})$—;

$R^{4a}$ and $R^{4b}$ are each independently H, $C_1$-$C_3$ alkyl, $C_1$-$C_3$ alkoxy, halo, $C_1$-$C_6$ haloalkyl, $C_1$-$C_6$ haloalkoxy, —OH, —CN, $C_1$-$C_3$ cyanoalkyl, or $C_3$-$C_6$ cycloalkyl;

alternatively, $R^{4a}$ and $R^{4b}$ can combine with the atom to which they are attached to form a $C_3$-$C_6$ cycloalkyl;

alternatively, $R^{3b}$ and $R^{4b}$ can combine with the atoms to which they are attached to form a $C_3$-$C_6$ cycloalkyl;

$R^{4c}$ and $R^{4d}$ are each independently H, $C_1$-$C_3$ alkyl, halo, $C_1$-$C_6$ haloalkyl, —CN, $C_1$-$C_3$ cyanoalkyl, or $C_3$-$C_6$ cycloalkyl;

alternatively, $R^{4c}$ and $R^{4d}$ can combine with the atom to which they are attached to form a $C_3$-$C_6$ cycloalkyl or a 3 to 6 membered heterocyclyl having 1 heteroatom that is O, wherein each cycloalkyl and heterocyclyl is substituted with 0, 1, 2, or 3 $R^{4x}$;

each $R^{4x}$ is independently $C_1$-$C_3$ alkyl, $C_1$-$C_3$ alkoxy, halo, $C_1$-$C_6$ haloalkyl, $C_1$-$C_6$ haloalkoxy, or —OH;

$R^{4e}$ is H, $C_1$-$C_3$ alkyl, halo, $C_1$-$C_6$ haloalkyl, —CN, $C_1$-$C_3$ cyanoalkyl, or $C_3$-$C_6$ cycloalkyl;

alternatively, $R^{3c}$ and $R^{4d}$ can combine with the atoms to which they are attached to form a $C_5$-$C_6$ cycloalkyl;

such that when $L^2$ is $=C(R^{2e})$— then $L^1$ is $—C(R^{1e})=$ or $L^3$ is $=C(R^{3e})$—, and when $L^3$ is $=C(R^{3e})$— then $L^2$ is $=C(R^{2e})$— or $L^4$ is $=C(R^{4e})$—;

$R^A$ is phenyl, naphthyl, or 5- to 14-membered heteroaryl, wherein $R^A$ is substituted with 0, 1, 2, 3, 4, or 5 $R^{A2}$;

each $R^{A2}$ is independently —OH, $C_1$-$C_{10}$ alkyl, $C_2$-$C_6$ alkenyl, $C_2$-$C_6$ alkynyl, $C_1$-$C_{10}$ alkoxy, $C_1$-$C_{10}$ hydroxyalkyl, $C_2$-$C_{10}$ alkoxyalkyl, $C_1$-$C_6$ alkyl-N$(R^{A2a})(R^{A2b})$, $C_1$-$C_{10}$ thioalkyl, halo, $C_1$-$C_6$ haloalkyl, —CN, $—C(O)R^{A2a}$, $—C(O)OR^{A2a}$, $—OC(O)R^{A2a}$, $—OC(O)OR^{A2a}$, $—C(O)N(R^{A2a})(R^{A2b})$, $—N(R^{A2a})C(O)(R^{A2b})$, $—OC(O)N(R^{A2a})(R^{A2b})$, $—N(R^{A2a})C(O)(OR^{A2b})$, oxo, $—OR^{A2a}$, $—SR^{A2a}$, $—S(O)_2R^{A2a}$, $—S(O)_2OR^{A2a}$, $—N(R^{A2a})(R^{A2b})$, —($C_0$-$C_3$ alkyl)-$SF_5$, $—OP(O)(OR^{A2a})(OR^{A2b})$, $C_3$-$C_8$ cycloalkyl, —($C_1$-$C_6$ alkyl)-($C_3$-$C_8$ cycloalkyl), 3- to 14-membered heterocyclyl, —($C_1$-$C_6$ alkyl)-(3- to 14-membered heterocyclyl), $C_6$-$C_{14}$ aryl, —($C_1$-$C_6$ alkyl)-($C_6$-$C_{14}$ aryl), 5- to 14-membered heteroaryl, or —($C_1$-$C_6$ alkyl)-(5- to 14-membered heteroaryl), wherein each alkyl, alkenyl, alkynyl, alkoxy, hydroxyalkyl, and haloalkyl is substituted with 0, 1, 2, or 3 $R^{A3}$, and wherein each cycloalkyl, alkyl-cycloalkyl, heterocyclyl, alkyl-heterocyclyl, aryl, alkyl-aryl, heteroaryl, and alkyl-heteroaryl is substituted with 0, 1, 2, or 3 $R^{A4}$;

each $R^{A2a}$ and $R^{A2b}$ is independently H, $C_1$-$C_{10}$ alkyl, $C_1$-$C_6$ haloalkyl, or $C_3$-$C_5$ cycloalkyl; each $R^{A3}$ is independently halo, —CN, $—OR^{A3a}$, $SR^{A3a}$, $—N(R^{A3a})(R^{A3b})$, $C_3$-$C_8$ cycloalkyl, or 5- to 14-membered heteroaryl;

each $R^{A3a}$ and $R^{A3b}$ is independently H, $C_1$-$C_{10}$ alkyl, $C_1$-$C_6$ haloalkyl, or $C_3$-$C_5$ cycloalkyl;

each $R^{A4}$ is independently $C_1$-$C_6$ alkoxy, $C_1$-$C_6$ hydroxyalkyl, $C_2$-$C_6$ alkoxyalkyl, $C_1$-$C_6$ haloalkyl, $C_1$-$C_6$ haloalkoxy, $C_1$-$C_6$ haloalkylthio, $C_3$-$C_5$ cycloalkyl, —($C_1$-$C_6$ alkyl)-($C_6$-$C_{10}$ aryl), halo, —CN, —OH, or $—N(R^{A4a})(R^{A4b})$;

each $R^{A4a}$ and $R^{A4b}$ is independently H or $C_1$-$C_6$ alkyl;

alternatively, two $R^{A2}$ can combine to form a $C_3$-$C_{10}$ cycloalkyl, $C_6$-$C_{10}$ aryl, a 3- to 10-membered heterocyclyl, or 5- to 14-membered heteroaryl on two adjacent atoms on $R^A$, wherein each cycloalkyl, aryl, heterocyclyl, and heteroaryl is substituted with 0, 1, 2, or 3 $R^{A5}$;

each $R^{A5}$ is independently $C_1$-$C_{10}$ alkyl, $C_2$-$C_{10}$ alkenyl, $C_2$-$C_{10}$ alkynyl, halo, $C_1$-$C_6$ haloalkyl, —CN, or $C_3$-$C_5$ cycloalkyl;

$R^B$ is H or $R^{B1}$;

wherein when $R^B$ is H, then at least one $R^{A2}$ is $—OR^{A2x}$;

$R^{B1}$ and $R^{A2x}$ are each independently:

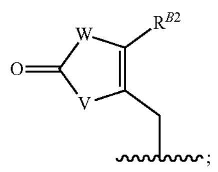

W and V are each independently $NR^{B2}$, O, or S;

each $R^{B2}$ is independently $C_1$-$C_{12}$ alkyl, $C_1$-$C_6$ alkoxy, $C_2$-$C_6$ alkoxyalkyl, $C_1$-$C_6$ alkyl-N$(R^{B2a})(R^{B2b})$, $C_1$-$C_{10}$ thioalkyl, $C_1$-$C_6$haloalkyl, $C_1$-$C_6$haloalkoxy, $C_3$-$C_8$ cycloalkyl, $C_6$-$C_{14}$ aryl, or 5- to 14-membered heteroaryl, wherein the $C_3$-$C_8$ cycloalkyl, $C_6$-$C_{14}$ aryl or 5- to 14-membered heteroaryl are substituted with 0, 1, 2, or 3 $R^{B2c}$;

each $R^{B2a}$ and $R^{B2b}$ is independently H, $C_1$-$C_6$ alkyl, $C_1$-$C_6$ haloalkyl, or $C_3$-$C_8$ cycloalkyl;

each $R^{B2c}$ is independently $C_1$-$C_6$ alkyl, $C_1$-$C_6$ alkoxy, $C_2$-$C_6$ alkoxyalkyl, halo, $C_1$-$C_6$ haloalkyl, $C_1$-$C_6$ haloalkoxy, oxo, —OH, —CN, or $C_3$-$C_{10}$ cycloalkyl;

$L^C$ is a bond or

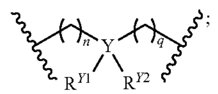

Y is C or Si;

n is 0, 1, 2, or 3;

q is 0, 1, 2, or 3;

$R^{Y1}$ is H or $C_1$-$C_3$ alkyl;

$R^{Y2}$ is H or $C_1$-$C_3$ alkyl;

alternatively, $R^{Y1}$ and $R^{Y2}$ combine to form a $C_3$-$C_{10}$ cycloalkyl or a 3- to 10-membered heterocyclyl;

$R^C$ is H, $C_1$-$C_6$ alkyl, $C_1$-$C_6$ alkoxy, $C_1$-$C_6$ hydroxyalkyl, $C_2$-$C_6$ alkoxyalkyl, $C_1$-$C_6$ haloalkyl, $C_1$-$C_6$ haloalkoxy, $—NH_2$, $—NHR^{C1}$, $—N(R^{C1})_2$, $C_3$-$C_5$ cycloalkyl, 3- to 14-membered heterocyclyl, $C_6$-$C_{14}$ aryl, or 5- to 14-membered heteroaryl, wherein each $C_3$-$C_5$ cycloalkyl, 3- to 14-membered heterocyclyl, $C_6$-$C_{14}$ aryl, and 3- to 14-membered heteroaryl, is substituted with 0, 1, 2, 3, or 4 $R^{C3}$;

each $R^{C1}$ is independently selected from $C_1$-$C_6$ alkyl;

each $R^{C3}$ is independently $C_1$-$C_6$ alkyl, $C_2$-$C_6$ alkenyl, $C_2$-$C_8$ alkynyl, $C_1$-$C_6$ alkoxyalkyl, $C_1$-$C_6$ hydroxyalkyl, halo, $C_1$-$C_6$ haloalkyl, $C_1$-$C_6$ heteroalkyl, —($C_1$-$C_6$ alkyl)-N($R^{c3a}$)($R^{c3b}$), —CN, —C(O)$R^{c3a}$, —C(O)$OR^{c3a}$, —C(O)N($R^{c3a}$)($R^{c3b}$), —N($R^{c3a}$)C(O)($R^{c3b}$), —OC(O)N($R^{c3a}$)($R^{c3b}$), —N($R^{c3a}$)C(O)($OR^{c3b}$), =$CH_2$, =CHF, =$CF_2$, oxo, —$OR^{c3a}$, —$SR^{C3a}$, —N($R^{c3a}$)($R^{c3b}$), —$N_3$, $SF_5$, $C_3$-$C_8$ cycloalkyl, —($C_1$-$C_6$ alkyl)-($C_3$-$C_8$ cycloalkyl), 3- to 10-membered heterocyclyl, —($C_1$-$C_6$ alkyl)-(3- to 10-membered heterocyclyl), $C_6$-$C_{10}$ aryl, —($C_1$-$C_6$ alkyl)-($C_6$-$C_{10}$ aryl), 5- to 10-membered heteroaryl, or —($C_1$-$C_6$ alkyl)-(5- to 10-membered heteroaryl), wherein each alkyl is substituted with 0, 1, 2, or 3 —CN, —C(O)$OR^{c3a1}$, —C(O)N($R^{c3a1}$)($R^{c3a2}$), —N($R^{c3a1}$)C(O)($R^{c3a2}$), —OC(O)N($R^{c3a1}$)($R^{c3a2}$), —$OR^{c3a1}$, —$SR^{c3a1}$, $N_3$, $SF_5$, or 3- to 10-membered heterocyclyl substituted with 0, 1, 2, or 3 $R^{c3a2}$, each cycloalkyl, alkyl-cycloalkyl, heterocyclyl, alkyl-heterocyclyl, aryl, alkyl-aryl, heteroaryl, and alkyl-heteroaryl is substituted with 0, 1, 2, or 3 halo, —CN, or $R^{c3a2}$, each alkenyl is substituted with 0, 1, 2, or 3 halo, and each alkoxyalkyl and alkynyl is substituted with 0, 1, 2, or 3 $C_1$-$C_6$ alkyl, $C_1$-$C_6$ haloalkyl, $C_3$-$C_5$ cycloalkyl substituted with 0 or 1 $C_1$-$C_6$ haloalkyl, $C_6$-$C_{10}$ aryl, or 5- to 10-membered heteroaryl;

each $R^{c3a}$ and $R^{c3b}$ is independently H, $C_1$-$C_{10}$ alkyl, $C_1$-$C_6$ haloalkyl, $C_6$-$C_{10}$ aryl, $C_3$-$C_6$ cycloalkyl, 3- to 6-membered heterocyclyl, or 5- to 10-membered heteroaryl, wherein each aryl and heteroaryl is substituted with 0, 1, 2, or 3 halo, —CN, or $R^{C3a2}$.

alternatively, $R^{C3a}$ and $R^{C3b}$ together with the N to which they are attached form a 3- to 8-membered heterocycle;

each $R^{C3a1}$ and $R^{C3a2}$ is independently $C_1$-$C_3$ alkyl, halo, $C_1$-$C_6$ haloalkyl, $C_3$-$C_5$ cycloalkyl, —($C_1$-$C_3$ alkyl)-($C_3$-$C_8$ cycloalkyl), 3- to 10-membered heterocyclyl, —($C_1$-$C_3$ alkyl)-(3- to 10-membered heterocyclyl), $C_6$-$C_{10}$ aryl, —($C_1$-$C_3$ alkyl)-($C_6$-$C_{10}$ aryl), —($C_2$-$C_4$ alkynyl)-($C_6$-$C_{10}$ aryl), 5- to 10-membered heteroaryl, —($C_1$-$C_3$ alkyl)-(5- to 10-membered heteroaryl), or $SF_5$, wherein each cycloalkyl, alkyl-cycloalkyl, heterocyclyl, alkyl-heterocyclyl, aryl, alkyl-aryl, alkynyl-aryl, heteroaryl, and alkyl-heteroaryl is substituted with 0, 1, 2, or 3 halo, $C_1$-$C_3$ haloalkyl, $C_1$-$C_3$ haloalkoxy, or $SF_5$;

alternatively, $R^{C3a1}$ and $R^{C3a2}$ together with the N to which they are attached form a 3- to 8-membered heterocycle;

$R^D$ is halo;

each heterocyclyl has 1, 2, 3, or 4 heteroatoms selected from N, O, S, and Si; and each heteroaryl has 1, 2, 3, or 4 heteroatoms selected from N, O, and S.

In another embodiment, the present disclosure provides a pharmaceutical composition comprising a compound of the present disclosure, and a pharmaceutically acceptable excipient.

In another embodiment, the present disclosure provides a method of inhibiting KRAS G12D protein in a subject in need thereof, the method comprising administering to the subject a therapeutically effective amount of a compound of the present disclosure, or a pharmaceutically acceptable salt thereof, or a pharmaceutical composition of the present disclosure.

In another embodiment, the present disclosure provides a method of treating cancer in a subject in need thereof, the method comprising administering to the subject a therapeutically effective amount of a compound of the present disclosure, or a pharmaceutically acceptable salt thereof, or a pharmaceutical composition of the present disclosure.

In another embodiment, the present disclosure provides a method for manufacturing a medicament for treating cancer in a subject in need thereof, characterized in that a compound of the present disclosure, or a pharmaceutically acceptable salt thereof, is used.

In another embodiment, the present disclosure provides a method for manufacturing a medicament for inhibiting cancer metastasis in a subject in need thereof, characterized in that a compound of the present invention, or a pharmaceutically acceptable salt thereof, is used.

In another embodiment, the present disclosure provides use of the compound of the present disclosure, or a pharmaceutically acceptable salt thereof, for the manufacture of a medicament for the treatment of cancer in a subject.

In another embodiment, the present disclosure provides use of the compound of the present disclosure, or a pharmaceutically acceptable salt thereof, for the manufacture of a medicament for inhibiting cancer metastasis in a subject.

In another embodiment, the present disclosure provides the compound of the present disclosure, or a pharmaceutically acceptable salt thereof, for use in the treatment of cancer in a subject in need thereof.

In another embodiment, the present disclosure provides the compound of the present disclosure, or a pharmaceutically acceptable salt thereof, for use in inhibiting cancer metastasis in a subject in need thereof.

In another embodiment, the present disclosure provides the compound of the present disclosure, or a pharmaceutically acceptable salt thereof, for use in therapy.

Also disclosed herein are compounds and pharmaceutically acceptable salts thereof of sub-formulas of Formula J, such as Formula (I-1), (I-2), (I-3), (Ib), (Ib-1), (Ib-2), (Ib-3), (Ib-4), (IIb), (IIb-1), or (IIb-2).

DETAILED DESCRIPTION

I. General

The disclosure relates generally to methods and compounds, and pharmaceutically acceptable salts thereof, for inhibiting $KRAS^{G12D}$ and/or $KRAS^{G12C}$. The following description sets forth exemplary methods, parameters and the like. It should be recognized, however, that such description is not intended as a limitation on the scope of the present disclosure but is instead provided as a description of exemplary embodiments.

II. Definitions

As used in the present specification, the following words, phrases and symbols are generally intended to have the meanings as set forth below, except to the extent that the context in which they are used indicates otherwise.

A dash ("-") that is not between two letters or symbols is used to indicate a point of attachment for a substituent. For example, —$CONH_2$ is attached through the carbon atom. A dash at the front or end of a chemical group is a matter of convenience; chemical groups can be depicted with or without one or more dashes without losing their ordinary meaning. A wavy line drawn through a line in a structure indicates a point of attachment of a group. Unless chemically or structurally required, no directionality is indicated or implied by the order in which a chemical group is written or named.

A squiggly line on a chemical group as shown below, for example,

indicates a point of attachment, i.e., it shows the broken bond by which the group is connected to another described group.

As used herein, "a compound of the disclosure" can mean a compound of any of the Formula J, (I-1), (I-2), (I-3), (Ib), (Ib-1), (Ib-2), (Ib-3), (Ib-4), (IIb), (IIb-1), and (IIb-2), or a pharmaceutically acceptable salt thereof. Similarly, the phrase "a compound of Formula (number)" means a compound of that formula and pharmaceutically acceptable salts thereof.

The prefix "$C_u$-$C_v$" indicates that the following group has from u to v carbon atoms. For example, "$C_1$-$C_8$ alkyl" indicates that the alkyl group has from 1 to 8 carbon atoms.

"Alkyl" refers to an unbranched or branched saturated hydrocarbon chain. For example, an alkyl group can have 1 to 20 carbon atoms (i.e., $C_1$-$C_{20}$ alkyl), 1 to 8 carbon atoms (i.e., $C_1$-$C_8$ alkyl), 1 to 6 carbon atoms (i.e., $C_1$-$C_6$ alkyl), or 1 to 3 carbon atoms (i.e., $C_1$-$C_3$ alkyl). Examples of suitable alkyl groups include, but are not limited to, methyl (Me, —$CH_3$), ethyl (Et, —$CH_2CH_3$), 1-propyl (n-Pr, n-propyl, —$CH_2CH_2CH_3$), 2-propyl (i-Pr, i-propyl, —$CH(CH_3)_2$), 1-butyl (n-Bu, n-butyl, —$CH_2CH_2CH_2CH_3$), 2-methyl-1-propyl (i-Bu, i-butyl, —$CH_2CH(CH_3)_2$), 2-butyl (s-Bu, s-butyl, —$CH(CH_3)CH_2CH_3$), 2-methyl-2-propyl (t-Bu, t-butyl, —$C(CH_3)_3$), 1-pentyl (n-pentyl, —$CH_2CH_2CH_2CH_2CH_3$), 2-pentyl (—$CH(CH_3)CH_2CH_2CH_3$), 3-pentyl (—$CH(CH_2CH_3)_2$), 2-methyl-2-butyl (—$C(CH_3)_2CH_2CH_3$), 3-methyl-2-butyl (—$CH(CH_3)CH(CH_3)_2$), 3-methyl-1-butyl (—$CH_2CH_2CH(CH_3)_2$), 2-methyl-1-butyl (—$CH_2CH(CH_3)CH_2CH_3$), 1-hexyl (—$CH_2CH_2CH_2CH_2CH_2CH_3$), 2-hexyl (—$CH(CH_3)CH_2CH_2CH_2CH_3$), 3-hexyl (—$CH(CH_2CH_3)(CH_2CH_2CH_3)$), 2-methyl-2-pentyl (—$C(CH_3)_2CH_2CH_2CH_3$), 3-methyl-2-pentyl (—$CH(CH_3)CH(CH_3)CH_2CH_3$), 4-methyl-2-pentyl (—$CH(CH_3)CH_2CH(CH_3)_2$), 3-methyl-3-pentyl (—$C(CH_3)(CH_2CH_3)_2$), 2-methyl-3-pentyl (—$CH(CH_2CH_3)CH(CH_3)_2$), 2,3-dimethyl-2-butyl (—$C(CH_3)_2CH(CH_3)_2$), and 3,3-dimethyl-2-butyl (—$CH(CH_3)C(CH_3)_3$. Other alkyl groups include, but are not limited to, heptyl, octyl, nonyl, decyl, undecyl, dodecyl, pentadcyl, hexadecyl, heptadecyl and octadecyl.

"Alkenyl" refers to an unbranched or branched hydrocarbon chain containing at least two carbon atoms and at least one carbon-carbon double bond. As used herein, alkenyl can have from 2 to 20 carbon atoms (i.e., $C_{2-20}$ alkenyl), 2 to 8 carbon atoms (i.e., $C_{2-s}$ alkenyl), 2 to 6 carbon atoms (i.e., $C_{2-6}$ alkenyl), or 2 to 4 carbon atoms (i.e., $C_{2-4}$ alkenyl). Alkenyl can include any number of carbons, such as $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, or any range therein. Alkenyl groups can have any suitable number of double bonds, including, but not limited to, 1, 2, 3, 4, 5 or more. Examples of alkenyl groups include, but are not limited to, vinyl (ethenyl), propenyl, isopropenyl, 1-butenyl, 2-butenyl, isobutenyl, butadienyl, 1-pentenyl, 2-pentenyl, isopentenyl, 1,3-pentadienyl, 1,4-pentadienyl, 1-hexenyl, 2-hexenyl, 3-hexenyl, 1,3-hexadienyl, 1,4-hexadienyl, 1,5-hexadienyl, 2,4-hexadienyl, or 1,3,5-hexatrienyl.

"Alkynyl" refers to an unbranched or branched hydrocarbon chain containing at least one carbon-carbon triple bond. For example, an alkynyl group can have from 2 to 20 carbon atoms (i.e., $C_{2-20}$ alkynyl), 2 to 8 carbon atoms (i.e., $C_{2-8}$ alkynyl), 2 to 6 carbon atoms (i.e., $C_{2-6}$ alkynyl), or 2 to 4 carbon atoms (i.e., $C_{2-4}$ alkynyl). The term "alkynyl" also includes those groups having one triple bond and one double bond. Examples of $C_{2-6}$alkynyl include, but are not limited to, ethynyl, prop-1-ynyl, but-1-ynyl, pent-1-ynyl, pent-4-ynyl and penta-1,4-diynyl.

"Alkoxy" means a group having the formula —O-alkyl, in which an alkyl group, as defined above, is attached to the parent molecule via an oxygen atom. The alkyl portion of an alkoxy group can have 1 to 20 carbon atoms (i.e., $C_1$-$C_{20}$ alkoxy), 1 to 12 carbon atoms (i.e., $C_1$-$C_{12}$ alkoxy), 1 to 8 carbon atoms (i.e., $C_1$-$C_8$ alkoxy), 1 to 6 carbon atoms (i.e., $C_1$-$C_6$ alkoxy) or 1 to 3 carbon atoms (i.e., $C_1$-$C_3$ alkoxy). Examples of suitable alkoxy groups include, but are not limited to, methoxy (—O—$CH_3$ or —OMe), ethoxy (—$OCH_2CH_3$ or —OEt), isopropoxy (—O—$CH(CH_3)_2$), t-butoxy (—O—$C(CH_3)_3$ or —OtBu) and the like. Other examples of suitable alkoxy groups include, but are not limited to, sec-butoxy, tert-butoxy, pentoxy, hexoxy, and the like.

"Alkoxyalkyl" refers an alkoxy group linked to an alkyl group which is linked to the remainder of the compound. Alkoxyalkyl can have any suitable number of carbon, such as from 2 to 6 ($C_{2-6}$ alkoxyalkyl), 2 to 5 ($C_{2-5}$ alkoxyalkyl), 2 to 4 ($C_{2-4}$ alkoxyalkyl), or 2 to 3 ($C_{2-3}$ alkoxyalkyl). Alkoxy and alkyl are as defined above. Examples of "alkoxyalkyl" include, but are not limited to, methoxymethyl ($CH_3OCH_2$—), and methoxyethyl ($CH_3OCH_2CH_2$).

"Bridged" means a ring system in which non-adjacent atoms on a ring are connected by a divalent substituent, such as an alkylenyl or heteroalkylenyl group or a single heteroatom.

"Hydroxyalkyl" refers to a hydroxy group, —OH, linked to an alkyl group which is linked to the remainder of the compound such that the alkyl group is divalent. Hydroxyalkyl can have any suitable number of carbons, such as from 1 to 8 ($C_{1-8}$ hydroxyalkyl), 1 to 6 ($C_{1-6}$ hydroxyalkyl), 2 to 6 ($C_{2-6}$ hydroxyalkyl), 2 to 4 ($C_{2-4}$ hydroxyalkyl), or 2 to 3 ($C_{2-3}$ hydroxyalkyl). Alkyl is as defined above where the alkyl is divalent.

"Halo" or "halogen" as used herein refers to fluoro (—F), chloro (—Cl), bromo (—Br) and iodo (—I).

"Haloalkyl" is an alkyl group, as defined above, in which one or more hydrogen atoms of the alkyl group is replaced with a halogen atom. The alkyl portion of a haloalkyl group can have 1 to 20 carbon atoms (i.e., $C_1$-$C_{20}$ haloalkyl), 1 to 12 carbon atoms (i.e., $C_1$-$C_{12}$ haloalkyl), 1 to 8 carbon atoms (i.e., $C_1$-$C_8$ haloalkyl), 1 to 6 carbon atoms (i.e., $C_1$-$C_6$ alkyl) or 1 to 3 carbon atoms (i.e., $C_1$-$C_3$ alkyl). The alkyl groups can be substituted with 1, 2, 3, 4, 5, 6, 7, 8, 9 or more halogens. Examples of suitable haloalkyl groups include, but are not limited to, —$CF_3$, —$CHF_2$, —$CFH_2$, —$CH_2CF_3$, fluorochloromethyl, difluorochloromethyl, 1,1,1-trifluoroethyl and pentafluoroethyl.

"Haloalkoxy" refers to an alkoxy group where some or all of the hydrogen atoms are substituted with halogen atoms. As for an alkyl group, haloalkoxy groups can have any suitable number of carbon atoms, such as $C_{1-6}$. The alkoxy groups can be substituted with 1, 2, 3, 4, 5, 6, 7, 8, 9 or more halogens. When all the hydrogens are replaced with a halogen, for example by fluorine, the compounds are per-substituted, for example, perfluorinated. Haloalkoxy includes, but is not limited to, trifluoromethoxy, 2,2,2,-trifluoroethoxy, perfluoroethoxy, etc.

"Thioalkyl" refers to a thio group, —SH, linked to an alkyl group which is linked to the remainder of the compound such that the alkyl group is divalent. Thioalkyl can have any suitable number of carbons, such as from 1 to 8 ($C_{1-8}$ thioalkyl), 1 to 6 ($C_{1-6}$ thioalkyl), 2 to 6 ($C_{2-6}$ thioalkyl), 2 to 4 ($C_{2-4}$ thioalkyl), or 2 to 3 ($C_{2-3}$ thioalkyl). Alkyl is as defined above where the alkyl is divalent.

"Haloalkylthio" is an alkylthio group, as defined above, in which one or more hydrogen atoms of the alkyl group is replaced with a halogen atom. The alkyl portion of a haloalkylthio group can have 1 to 20 carbon atoms (i.e., $C_1$-$C_{20}$ haloalkylthio), 1 to 12 carbon atoms (i.e., $C_1$-$C_{12}$ haloalkylthio), 1 to 8 carbon atoms (i.e., $C_1$-$C_8$ haloalkylthio), 1 to 6 carbon atoms (i.e., $C_1$-$C_6$ alkylthio) or 1 to 3 carbon atoms (i.e., $C_1$-$C_3$ alkylthio). The alkylthio groups can be substituted with 1, 2, 3, 4, 5, 6, 7, 8, 9 or more halogens.

"Heteroalkyl" refers to an unbranched or branched saturated hydrocarbon chain containing from 1 to 4 heteroatoms.

"Cyanoalkyl" refers to a cyano group, —CN, linked to an alkyl group which is linked to the remainder of the compound such that the alkyl group is divalent. Cyanoalkyl can have any suitable number of carbons, such as from 1 to 8 ($C_{1-8}$ cyanoalkyl), 1 to 6 ($C_{1-6}$ cyanoalkyl), 2 to 6 ($C_{2-6}$ cyanoalkyl), 2 to 4 ($C_{2-4}$ cyanoalkyl), or 2 to 3 ($C_{2-3}$ cyanoalkyl). Alkyl is as defined above where the alkyl is divalent.

"Cycloalkyl" refers to a saturated or partially saturated cyclic alkyl group having a single ring or multiple rings, such as 2, 3, 4 or more, wherein the multiple rings can be fused, bridged, spiro, or any combination thereof. As used herein, cycloalkyl has from 3 to 20 ring carbon atoms (i.e., $C_{3-20}$ cycloalkyl), 3 to 12 ring carbon atoms (i.e., $C_{3-12}$ cycloalkyl), 3 to 10 ring carbon atoms (i.e., $C_{3-10}$ cycloalkyl), 3 to 8 ring carbon atoms (i.e., $C_{3-8}$ cycloalkyl), or 3 to 6 ring carbon atoms (i.e., $C_{3-6}$ cycloalkyl). Examples of cycloalkyl groups include, but are not limited to, cyclopropyl, cyclobutyl, cyclopentyl, cyclohexyl, cycloheptyl, and cyclooctyl. Cycloalkyl groups also include partially unsaturated ring systems containing one or more double bonds, including fused ring systems with one aromatic ring and one non-aromatic ring, but not fully aromatic ring systems.

The term "fused" refers to a ring system in which two or more rings in the system share a pair of adjacent ring atoms.

"Spiro" refers to at least two rings are linked together by one common atom. "Spiro" also refers to a ring substituent which is joined by two bonds at the same carbon atom. Examples of spiro groups include, but are not limited to, 1,1-diethylcyclopentane, dimethyl-dioxolane, and 4-benzyl-4-methylpiperidine, wherein the cyclopentane and piperidine, respectively, are the spiro substituents.

"Alkyl-cycloalkyl" refers to a radical having an alkyl component and a cycloalkyl component, where the alkyl component links the cycloalkyl component to the point of attachment. The alkyl component is as defined above, except that the alkyl component is at least divalent, an alkylene, to link to the cycloalkyl component and to the point of attachment. In some instances, the alkyl component can be absent. The alkyl component can include any number of carbons, such as $C_{1-6}$, $C_{1-2}$, $C_{1-3}$, $C_{1-4}$, $C_{1-5}$, $C_{2-3}$, $C_{2-4}$, $C_{2-5}$, $C_{2-6}$, $C_{3-4}$, $C_{3-5}$, $C_{3-6}$, $C_{4-5}$, $C_{4-6}$ and $C_{5-6}$. The cycloalkyl component is as defined within. Exemplary alkyl-cycloalkyl groups include, but are not limited to, methyl-cyclopropyl, methyl-cyclobutyl, methyl-cyclopentyl and methyl-cyclohexyl.

"Heterocycle" or "heterocyclyl" or "heterocycloalkyl" refer to a saturated or unsaturated cyclic alkyl group, with one or more ring heteroatoms independently selected from nitrogen, oxygen, sulfur and silicon. A heterocyclyl can be a single ring or multiple rings, such as 2, 3, 4 or more, wherein the multiple rings can be fused, bridged, spiro, or any combination thereof. As used herein, heterocyclyl has 3 to 20 ring atoms (i.e., 3 to 20 membered heterocyclyl), 3 to 12 ring atoms (i.e., 3 to 12 membered heterocyclyl), 3 to 10 ring atoms (i.e., 3 to 10 membered heterocyclyl), 3 to 8 ring atoms (i.e., 3 to 8 membered heterocyclyl), 4 to 12 ring carbon atoms (i.e., 4 to 12 membered heterocyclyl), 4 to 8 ring atoms (i.e., 4 to 8 membered heterocyclyl), or 4 to 6 ring atoms (i.e., 4 to 6 membered heterocyclyl). Examples of heterocyclyl groups include pyrrolidinyl, piperidinyl, piperazinyl, oxetanyl, dioxolanyl, azetidinyl, and morpholinyl.

"Alkyl-heterocycloalkyl" refers to a radical having an alkyl component and a heterocycloalkyl component, where the alkyl component links the heterocycloalkyl component to the point of attachment. The alkyl component is as defined above, except that the alkyl component is at least divalent, an alkylene, to link to the heterocycloalkyl component and to the point of attachment. The alkyl component can include any number of carbons, such as $C_{0-6}$, $C_{1-2}$, $C_{1-3}$, $C_{1-4}$, $C_{1-5}$, $C_{1-6}$, $C_{2-3}$, $C_{2-4}$, $C_{2-5}$, $C_{2-6}$, $C_{3-4}$, $C_{3-5}$, $C_{3-6}$, $C_{4-5}$, $C_{4-6}$ and $C_{5-6}$. In some instances, the alkyl component can be absent. The heterocycloalkyl component is as defined above.

"Aryl" means an aromatic hydrocarbon radical derived by the removal of one hydrogen atom from a single carbon atom of a parent aromatic ring system. For example, an aryl group can have 6 to 20 carbon atoms, 6 to 14 carbon atoms, or 6 to 10 carbon atoms. Exemplary aryl groups include, but are not limited to, radicals derived from benzene (e.g., phenyl), naphthalene, anthracene, biphenyl, and the like.

"Alkyl-aryl" refers to a radical having an alkyl component and an aryl component, where the alkyl component links the aryl component to the point of attachment. The alkyl component is as defined above, except that the alkyl component is at least divalent, an alkylene, to link to the aryl component and to the point of attachment. The alkyl component can include any number of carbons, such as $C_{0-6}$, $C_{1-2}$, $C_{1-3}$, $C_{1-4}$, $C_{1-5}$, $C_{1-6}$, $C_{2-3}$, $C_{2-4}$, $C_{2-5}$, $C_{2-6}$, $C_{3-4}$, $C_{3-5}$, $C_{3-6}$, $C_{4-5}$, $C_{4-6}$ and $C_{5-6}$. In some instances, the alkyl component can be absent. The aryl component is as defined above. Examples of alkyl-aryl groups include, but are not limited to, benzyl and ethyl-benzene.

"Heteroaryl" refers to an aromatic group, including groups having an aromatic tautomer or resonance structure, having a single ring, multiple rings, or multiple fused rings, with at least one heteroatom in the ring, i.e., one or more ring heteroatoms independently selected from nitrogen, oxygen, and sulfur, wherein the nitrogen or sulfur can be oxidized. Thus, the term includes rings having one or more annular O, N, S, S(O), $S(O)_2$, and N-oxide groups. The term includes rings having one or more annular C(O) groups. As used herein, heteroaryl include 5 to 20 ring atoms (i.e., 5- to 20-membered heteroaryl), 5 to 12 ring atoms (i.e., 5- to 12-membered heteroaryl), or 5 to 10 ring atoms (i.e., 5- to 10-membered heteroaryl), and 1 to 5 heteroatoms independently selected from nitrogen, oxygen, and sulfur, and oxidized forms of the heteroatoms. Examples of heteroaryl groups include, but are not limited to, pyridin-2(1H)-one, pyridazin-3(2H)-one, pyrimidin-4(3H)-one, quinolin-2(1H)-one, pyrimidinyl, purinyl, pyridyl, pyridazinyl, benzothiazolyl, and pyrazolyl. Heteroaryl does not encompass or overlap with aryl as defined above.

"Alkyl-heteroaryl" refers to a radical having an alkyl component and a heteroaryl component, where the alkyl component links the heteroaryl component to the point of attachment. The alkyl component is as defined above, except that the alkyl component is at least divalent, an alkylene, to link to the heteroaryl component and to the point of attachment. The alkyl component can include any number of carbons, such as $C_{0-6}$, $C_{1-2}$, $C_{1-3}$, $C_{1-4}$, $C_{1-5}$, $C_{1-6}$, $C_{2-3}$, $C_{2-4}$, $C_{2-5}$, $C_{2-6}$, $C_{3-4}$, $C_{3-5}$, $C_{3-6}$, $C_{4-5}$, $C_{4-6}$ and $C_{5-6}$. In some instances, the alkyl component can be absent. The heteroaryl component is as defined within.

"KRAS G12D" refers to the G12D mutation of the KRAS protein, where aspartic acid replaces glycine at amino acid position 12.

"KRAS G12D inhibitor" refers to compounds of the present disclosure, including compounds of Formulas J, (I-1), (I-2), (I-3), (Ib), (Ib-1), (Ib-2), (Ib-3), (Ib-4), (1Ib), (IIb-1), and (IIb-2)). The compounds modulate or inhibit some or all of the activity of KRAS G12D.

"KRAS G12D-associated disease or disorder" refers to diseases or disorders associated with or mediated by or having a KRAS G12D mutation. Representative diseases or disorders include, but are not limited to, KRAS G12D-associated cancer.

"Oxo" refers to the group (=O) or (O).

Provided are also pharmaceutically acceptable salts, hydrates, solvates, tautomeric forms, polymorphs, and prodrugs of the compounds described herein. "Pharmaceutically acceptable" or "physiologically acceptable" refer to compounds, salts, formulations, dosage forms and other materials which are useful in preparing a pharmaceutical composition that is suitable for veterinary or human pharmaceutical use.

The compounds described herein can be prepared and/or formulated as pharmaceutically acceptable salts or when appropriate as a free base. Pharmaceutically acceptable salts are non-toxic salts of a free base form of a compound that possess the desired pharmacological activity of the free base. These salts can be derived from inorganic or organic acids or bases. For example, a compound that contains a basic nitrogen can be prepared as a pharmaceutically acceptable salt by contacting the compound with an inorganic or organic acid. Non-limiting examples of pharmaceutically acceptable salts include sulfates, pyrosulfates, bisulfates, sulfites, bisulfites, phosphates, monohydrogen-phosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, sulfonates, methylsulfonates, propylsulfonates, besylates, xylenesulfonates, naphthalene-1-sulfonates, naphthalene-2-sulfonates, phenylacetates, phenylpropionates, phenylbutyrates, citrates, lactates, γ-hydroxybutyrates, glycolates, tartrates, and mandelates. Lists of other suitable pharmaceutically acceptable salts are found in REMINGTON: THE SCIENCE AND PRACTICE OF PHARMACY, $21^{st}$ Edition, Lippincott Williams and Wilkins, Philadelphia, Pa., 2006.

Examples of "pharmaceutically acceptable salts" of the compounds disclosed herein also include salts derived from an appropriate base, such as an alkali metal (for example, sodium, potassium), an alkaline earth metal (for example, magnesium), ammonium and $NX_4^+$ (wherein X is $C_1$-$C_4$ alkyl). Also included are base addition salts, such as sodium or potassium salts.

Provided are also compounds described herein or pharmaceutically acceptable salts, isomers, or a mixture thereof, in which from 1 to n hydrogen atoms attached to a carbon atom can be replaced by a deuterium atom or D, in which n is the number of hydrogen atoms in the molecule. As known in the art, the deuterium atom is a non-radioactive isotope of the hydrogen atom. Such compounds can increase resistance to metabolism, and thus can be useful for increasing the half-life of the compounds described herein or pharmaceutically acceptable salts, isomer, or a mixture thereof when administered to a mammal. See, e.g., Foster, "Deuterium Isotope Effects in Studies of Drug Metabolism," TRENDS PHARMACOL. SCI., 5(12):524-527 (1984). Such compounds are synthesized by means well known in the art, for example by employing starting materials in which one or more hydrogen atoms have been replaced by deuterium.

Examples of isotopes that can be incorporated into the disclosed compounds also include isotopes of hydrogen, carbon, nitrogen, oxygen, phosphorous, fluorine, chlorine, and iodine, such as $^{2}H$, $^{3}H$, $^{11}C$, $^{13}C$, $^{14}C$, $^{13}N$, $^{15}N$, $^{15}O$, $^{17}O$, $^{18}O$, $^{31}P$, $^{32}P$, $^{35}S$, $^{18}F$, $^{36}Cl$, $^{123}I$, and $^{125}I$, respectively. Substitution with positron emitting isotopes, such as $^{11}C$, $^{18}F$, $^{15}O$ and $^{13}N$, can be useful in Positron Emission Topography (PET) studies for examining substrate receptor occupancy. Isotopically-labeled compounds of Formulas J, (I-1), (I-2), (I-3), (Ib), (Ib-1), (Ib-2), (Ib-3), (Ib-4), (IIb), (IIb-1), and (IIb-2), can generally be prepared by conventional techniques known to those skilled in the art or by processes analogous to those described in the Examples as set out below using an appropriate isotopically-labeled reagent in place of the non-labeled reagent previously employed.

The compounds of the embodiments disclosed herein, or their pharmaceutically acceptable salts can contain one or more asymmetric centers and can thus give rise to enantiomers, diastereomers, and other stereoisomeric forms that can be defined, in terms of absolute stereochemistry, as (R)- or (S)- or, as (D)- or (L)- for amino acids. The present disclosure is meant to include all such possible isomers, as well as their racemic and optically pure forms. Optically active (+) and (−), (R)- and (S)-, or (D)- and (L)-isomers can be prepared using chiral synthons or chiral reagents, or resolved using conventional techniques, for example, chromatography and fractional crystallization. Conventional techniques for the preparation/isolation of individual enantiomers include chiral synthesis from a suitable optically pure precursor or resolution of the racemate (or the racemate of a salt or derivative) using, for example, chiral high-pressure liquid chromatography (HPLC). When the compounds described herein contain olefinic double bonds or other centers of geometric asymmetry, and unless specified otherwise, it is intended that the compounds include both E and Z geometric isomers. Likewise, all tautomeric forms are also intended to be included. Where compounds are represented in their chiral form, it is understood that the embodiment encompasses, but is not limited to, the specific diastereomerically or enantiomerically enriched form. Where chirality is not specified but is present, it is understood that the embodiment is directed to either the specific diastereomerically or enantiomerically enriched form; or a racemic or scalemic mixture of such compound(s). As used herein, "scalemic mixture" is a mixture of stereoisomers at a ratio other than 1:1.

"Racemates" refers to a mixture of enantiomers. The mixture can comprise equal or unequal amounts of each enantiomer.

"Stereoisomer" and "stereoisomers" refer to compounds that differ in the chirality of one or more stereocenters. Stereoisomers include enantiomers and diastereomers. The compounds can exist in stereoisomeric form if they possess one or more asymmetric centers or a double bond with asymmetric substitution and, therefore, can be produced as individual stereoisomers or as mixtures. Unless otherwise indicated, the description is intended to include individual stereoisomers as well as mixtures. The methods for the determination of stereochemistry and the separation of stereoisomers are well-known in the art (see, e.g., Chapter 4 of Advanced Organic Chemistry, 4th ed., J. March, John Wiley & Sons, New York, 1992).

A "subject" or "patient" is meant to describe a human or vertebrate animal including a dog, cat, pocket pet, marmoset, horse, cow, pig, sheep, goat, elephant, giraffe, chicken, lion, monkey, owl, rat, squirrel, slender loris, and mouse. A "pocket pet" refers to a group of vertebrate animals capable of fitting into a commodious coat pocket such as, for example, hamsters, chinchillas, ferrets, rats, guinea pigs, gerbils, rabbits and sugar gliders.

Unless defined otherwise, all technical and scientific terms used herein have the same meaning as commonly understood by one of ordinary skill in the art. A dash at the front or end of a chemical group is a matter of convenience; chemical groups can be depicted with or without one or more dashes without losing their ordinary meaning. A wavy line drawn through a line in a structure indicates a point of attachment of a group. A dashed line indicates an optional bond. Unless chemically or structurally required, no directionality is indicated or implied by the order in which a chemical group is written or the point at which it is attached to the remainder of the molecule. For instance, the group "$-SO_2CH_2-$" is equivalent to "$-CH_2SO_2-$" and both can be connected in either direction. Similarly, an "arylalkyl" group, for example, can be attached to the remainder of the molecule at either an aryl or an alkyl portion of the group. A prefix such as "$C_u$-$C_v$" or "($C_u$-$C_v$)" indicates that the following group has from u to v carbon atoms. For example, "$C_{1-6}$ alkyl" and "$C_1$-$C_6$ alkyl" both indicate that the alkyl group has from 1 to 6 carbon atoms.

Unless otherwise specified, the carbon atoms of the compounds of Formula J, (I-1), (I-2), (I-3), (Ib), (Ib-1), (Ib-2), (Ib-3), (Ib-4), (IIb), (IIb-1), and (IIb-2), are intended to have a valence of four. If in some chemical structure representations, carbon atoms do not have a sufficient number of variables attached to produce a valence of four, the remaining carbon substituents needed to provide a valence of four should be assumed to be hydrogen.

"Treatment" or "treating" is an approach for obtaining beneficial or desired results including clinical results. Beneficial or desired clinical results may include one or more of the following: (a) inhibiting the disease or condition (e.g., decreasing one or more symptoms resulting from the disease or condition, and/or diminishing the extent of the disease or condition); (b) slowing or arresting the development of one or more clinical symptoms associated with the disease or condition (e.g., stabilizing the disease or condition, preventing or delaying the worsening or progression of the disease or condition, and/or preventing or delaying the spread (e.g., metastasis) of the disease or condition); and/or (c) relieving the disease, that is, causing the regression of clinical symptoms (e.g., ameliorating the disease state, providing partial or total remission of the disease or condition, enhancing effect of another medication, delaying the progression of the disease, increasing the quality of life, and/or prolonging survival.

The term "therapeutically effective amount," as used herein, is the amount of compound disclosed herein present in a formulation described herein that is needed to provide a desired level of drug in the secretions and tissues of the airways and lungs, or alternatively, in the bloodstream of a subject to be treated to give an anticipated physiological response or desired biological effect when such a formulation is administered by the chosen route of administration. The precise amount will depend upon numerous factors, for example the particular compound disclosed herein, the specific activity of the formulation, the delivery device employed, the physical characteristics of the formulation, its intended use, as well as subject considerations such as severity of the disease state, subject cooperation, etc., and can readily be determined by one skilled in the art based upon the information provided herein. The term "therapeutically effective amount" or "effective amount" also means amounts that eliminate or reduce the subject's viral burden and/or viral reservoir.

"Administering" refers to oral administration, administration as a suppository, topical contact, parenteral, intravenous, intraperitoneal, intramuscular, intralesional, intranasal or subcutaneous administration, intrathecal administration, or the implantation of a slow-release device e.g., a mini-osmotic pump, to the subject. The administration can be carried out according to a schedule specifying frequency of administration, dose for administration, and other factors.

"Co-administration" as used herein refers to administration of unit dosages of the compounds disclosed herein before or after administration of unit dosages of one or more additional therapeutic agents, for example, administration of the compound disclosed herein within seconds, minutes, or hours of the administration of one or more additional therapeutic agents. For example, in some embodiments, a unit dose of a compound of the present disclosure is administered first, followed within seconds or minutes by administration of a unit dose of one or more additional therapeutic agents. Alternatively, in other embodiments, a unit dose of one or more additional therapeutic agents is administered first, followed by administration of a unit dose of a compound of the present disclosure within seconds or minutes. In some embodiments, a unit dose of a compound of the present disclosure is administered first, followed, after a period of hours (e.g., 1-12 hours), by administration of a unit dose of one or more additional therapeutic agents. In other embodiments, a unit dose of one or more additional therapeutic agents is administered first, followed, after a period of hours (e.g., 1-12 hours), by administration of a unit dose of a compound of the present disclosure. Co-administration of a compound disclosed herein with one or more additional therapeutic agents generally refers to simultaneous or sequential administration of a compound disclosed herein and one or more additional therapeutic agents, such that therapeutically effective amounts of each agent are present in the body of the patient.

"Subject" refers to animals such as mammals, including, but not limited to, primates (e.g., humans), cows, sheep, goats, horses, dogs, cats, rabbits, rats, mice and the like. In some embodiments, the subject is a human.

"Disease" or "condition" refer to a state of being or health status of a patient or subject capable of being treated with a compound, pharmaceutical composition, or method provided herein. The disease may be an autoimmune, inflammatory, cancer, infectious (e.g., a viral infection), metabolic, developmental, cardiovascular, liver, intestinal, endocrine, neurological, or other disease. In some embodiments, the disease is cancer (e.g. lung cancer, ovarian cancer, osteosarcoma, bladder cancer, cervical cancer, liver cancer, kidney cancer, skin cancer (e.g., Merkel cell carcinoma), testicular cancer, leukemia, lymphoma, head and neck cancer, colorectal cancer, prostate cancer, pancreatic cancer, melanoma, breast cancer, neuroblastoma).

"Cancer" refers to all types of cancer, neoplasm or malignant tumors found in mammals, including leukemias, lymphomas, melanomas, neuroendocrine tumors, carcinomas and sarcomas. Exemplary cancers that may be treated with a compound, pharmaceutical composition, or method provided herein include lymphoma, sarcoma, bladder cancer, bone cancer, brain tumor, cervical cancer, colon cancer, esophageal cancer, gastric cancer, head and neck cancer, kidney cancer, myeloma, thyroid cancer, leukemia, prostate cancer, breast cancer (e.g. triple negative, ER positive, ER negative, chemotherapy resistant, herceptin resistant, HER2 positive, doxorubicin resistant, tamoxifen resistant, ductal carcinoma, lobular carcinoma, primary, metastatic), ovarian cancer, pancreatic cancer, liver cancer (e.g. hepatocellular carcinoma), lung cancer (e.g. non-small cell lung carcinoma, squamous cell lung carcinoma, adenocarcinoma, large cell lung carcinoma, small cell lung carcinoma, carcinoid, sarcoma), glioblastoma multiforme, glioma, melanoma, prostate cancer, castration-resistant prostate cancer, breast cancer, triple negative breast cancer, glioblastoma, ovarian cancer, lung cancer, squamous cell carcinoma (e.g., head, neck, or esophagus), colorectal cancer, leukemia, acute myeloid leukemia, lymphoma, B cell lymphoma, or multiple myeloma.

Additional examples include, cancer of the thyroid, endocrine system, brain, breast, cervix, colon, head & neck, esophagus, liver, kidney, lung, non-small cell lung, melanoma, mesothelioma, ovary, sarcoma, stomach, uterus or Medulloblastoma, Hodgkin's Disease, Non-Hodgkin's Lymphoma, multiple myeloma, neuroblastoma, glioma, glioblastoma multiforme, ovarian cancer, rhabdomyosarcoma, primary thrombocytosis, primary macroglobulinemia, primary brain tumors, cancer, malignant pancreatic insulanoma, malignant carcinoid, urinary bladder cancer, premalignant skin lesions, testicular cancer, lymphomas, thyroid cancer, neuroblastoma, esophageal cancer, genitourinary tract cancer, malignant hypercalcemia, endometrial cancer, adrenal cortical cancer, neoplasms of the endocrine or exocrine pancreas, medullary thyroid cancer, medullary thyroid carcinoma, melanoma, colorectal cancer, papillary thyroid cancer, hepatocellular carcinoma, Paget's Disease of the Nipple, Phyllodes Tumors, Lobular Carcinoma, Ductal Carcinoma, cancer of the pancreatic stellate cells, cancer of the hepatic stellate cells, or prostate cancer.

"Leukemia" refers broadly to progressive, malignant diseases of the blood-forming organs and is generally characterized by a distorted proliferation and development of leukocytes and their precursors in the blood and bone marrow. Leukemia is generally clinically classified on the basis of (1) the duration and character of the disease-acute or chronic; (2) the type of cell involved; myeloid (myelogenous), lymphoid (lymphogenous), or monocytic; and (3) the increase or non-increase in the number abnormal cells in the blood-leukemic or aleukemic (subleukemic). Exemplary leukemias that may be treated with a compound, pharmaceutical composition, or method provided herein include, for example, acute nonlymphocytic leukemia, chronic lymphocytic leukemia, acute granulocytic leukemia, chronic granulocytic leukemia, acute promyelocytic leukemia, adult T-cell leukemia, aleukemic leukemia, a leukocythemic leukemia, basophylic leukemia, blast cell leukemia, bovine leukemia, chronic myelocytic leukemia, leukemia cutis, embryonal leukemia, eosinophilic leukemia, Gross' leukemia, hairy-cell leukemia, hemoblastic leukemia, hemocytoblastic leukemia, histiocytic leukemia, stem cell leukemia, acute monocytic leukemia, leukopenic leukemia, lymphatic leukemia, lymphoblastic leukemia, lymphocytic leukemia, lymphogenous leukemia, lymphoid leukemia, lymphosarcoma cell leukemia, mast cell leukemia, megakaryocyte leukemia, micromyeloblastic leukemia, monocytic leukemia, myeloblastic leukemia, myelocytic leukemia, myeloid granulocytic leukemia, myelomonocytic leukemia, Naegeli leukemia, plasma cell leukemia, multiple myeloma, plasmacytic leukemia, promyelocytic leukemia, Rieder cell leukemia, Schilling's leukemia, stem cell leukemia, subleukemic leukemia, or undifferentiated cell leukemia.

"Sarcoma" generally refers to a tumor which is made up of a substance like the embryonic connective tissue and is generally composed of closely packed cells embedded in a fibrillar or homogeneous substance. Sarcomas that may be treated with a compound, pharmaceutical composition, or method provided herein include a chondrosarcoma, fibrosarcoma, lymphosarcoma, melanosarcoma, myxosarcoma, osteosarcoma, Abemethy's sarcoma, adipose sarcoma, liposarcoma, alveolar soft part sarcoma, ameloblastic sarcoma, botryoid sarcoma, chloroma sarcoma, chorio carcinoma, embryonal sarcoma, Wilms' tumor sarcoma, endometrial sarcoma, stromal sarcoma, Ewing's sarcoma, fascial sarcoma, fibroblastic sarcoma, giant cell sarcoma, granulocytic sarcoma, Hodgkin's sarcoma, idiopathic multiple pigmented hemorrhagic sarcoma, immunoblastic sarcoma of B cells, lymphoma, immunoblastic sarcoma of T-cells, Jensen's sarcoma, Kaposi's sarcoma, Kupffer cell sarcoma, angiosarcoma, leukosarcoma, malignant mesenchymoma sarcoma, parosteal sarcoma, reticulocytic sarcoma, Rous sarcoma, serocystic sarcoma, synovial sarcoma, or telangiectaltic sarcoma.

"Melanoma" is taken to mean a tumor arising from the melanocytic system of the skin and other organs. Melanomas that may be treated with a compound, pharmaceutical composition, or method provided herein include, for example, acral-lentiginous melanoma, amelanotic melanoma, benign juvenile melanoma, Cloudman's melanoma, S91 melanoma, Harding-Passey melanoma, juvenile melanoma, lentigo maligna melanoma, malignant melanoma, nodular melanoma, subungal melanoma, or superficial spreading melanoma.

"Carcinoma" refers to a malignant new growth made up of epithelial cells tending to infiltrate the surrounding tissues and give rise to metastases. Exemplary carcinomas that may be treated with a compound, pharmaceutical composition, or method provided herein include, for example, medullary thyroid carcinoma, familial medullary thyroid carcinoma, acinar carcinoma, acinous carcinoma, adenocystic carcinoma, adenoid cystic carcinoma, carcinoma adenomatosum, carcinoma of adrenal cortex, alveolar carcinoma, alveolar cell carcinoma, basal cell carcinoma, carcinoma basocellulare, basal oid carcinoma, basosquamous cell carcinoma, bronchioalveolar carcinoma, bronchiolar carcinoma, bronchogenic carcinoma, cerebriform carcinoma, cholangiocellular carcinoma, chorionic carcinoma, colloid carcinoma, comedo carcinoma, corpus carcinoma, cribriform carcinoma, carcinoma en cuirasse, carcinoma cutaneum, cylindrical carcinoma, cylindrical cell carcinoma, duct carcinoma, ductal carcinoma, carcinoma durum, embryonal carcinoma, encephaloid carcinoma, epiermoid carcinoma, carcinoma epitheliale adenoides, exophytic carcinoma, carcinoma ex ulcere, carcinoma fibrosum, gelatiniforni carcinoma, gelatinous carcinoma, giant cell carcinoma, carcinoma gigantocellulare, glandular carcinoma, granulosa cell carcinoma, hair-matrix carcinoma, hematoid carcinoma, hepatocellular carcinoma, Hurthle cell carcinoma, hyaline carcinoma, hypernephroid carcinoma, infantile embryonal carcinoma, carcinoma in situ, intraepidermal carcinoma, intraepithelial carcinoma, Krompecher's carcinoma, Kulchitzky-cell carcinoma, large-cell carcinoma, lenticular carcinoma, carcinoma lenticulare, lipomatous carcinoma, lobular carcinoma, lymphoepithelial carcinoma, carcinoma medullare, medullary carcinoma, melanotic carcinoma, carcinoma molle, mucinous carcinoma, carcinoma muciparum, carcinoma mucocellulare, mucoepidermoid carcinoma, carcinoma *mucosum*, mucous carcinoma, carcinoma myxomatodes, nasopharyngeal carcinoma, oat cell carcinoma, carcinoma ossificans, osteoid carcinoma, papillary carcinoma, periportal carcinoma, preinvasive carcinoma, prickle cell carcinoma, pultaceous carcinoma, renal cell carcinoma of kidney, reserve cell carcinoma, carcinoma sarcomatodes, schneiderian carcinoma, scirrhous carcinoma, carcinoma scroti, signet-ring cell carcinoma, carcinoma simplex, small-cell carcinoma, solanoid carcinoma, spheroidal cell carcinoma, spindle cell carcinoma, carcinoma spongiosum, squamous carcinoma, squamous cell carcinoma, string carcinoma, carcinoma telangiectaticum, carcinoma telangiectodes, transitional cell carcinoma, carcinoma *tuberosum*, tubular carcinoma, tuberous carcinoma, verrucous carcinoma, or carcinoma *villosum*.

"Metastasis," "metastatic," and "metastatic cancer" can be used interchangeably and refer to the spread of a proliferative disease or disorder, e.g., cancer, from one organ or another non-adjacent organ or body part. Cancer occurs at an originating site, e.g., breast, which site is referred to as a primary tumor, e.g., primary breast cancer. Some cancer cells in the primary tumor or originating site acquire the ability to penetrate and infiltrate surrounding normal tissue in the local area and/or the ability to penetrate the walls of the lymphatic system or vascular system circulating through the system to other sites and tissues in the body. A second clinically detectable tumor formed from cancer cells of a primary tumor is referred to as a metastatic or secondary tumor. When cancer cells metastasize, the metastatic tumor and its cells are presumed to be similar to those of the original tumor. Thus, if lung cancer metastasizes to the breast, the secondary tumor at the site of the breast consists of abnormal lung cells and not abnormal breast cells. The secondary tumor in the breast is referred to a metastatic lung cancer. Thus, the phrase metastatic cancer refers to a disease in which a subject has or had a primary tumor and has one or more secondary tumors. The phrases non-metastatic cancer or subjects with cancer that is not metastatic refers to diseases in which subjects have a primary tumor but not one or more secondary tumors. For example, metastatic lung cancer refers to a disease in a subject with or with a history of a primary lung tumor and with one or more secondary tumors at a second location or multiple locations, e.g., in the breast.

"Associated" or "associated with" in the context of a substance or substance activity or function associated with a disease (e.g., diabetes, cancer (e.g. prostate cancer, renal cancer, metastatic cancer, melanoma, castration-resistant prostate cancer, breast cancer, triple negative breast cancer, glioblastoma, ovarian cancer, lung cancer, squamous cell carcinoma (e.g., head, neck, or esophagus), colorectal cancer, leukemia, acute myeloid leukemia, lymphoma, B cell lymphoma, or multiple myeloma)) means that the disease (e.g. lung cancer, ovarian cancer, osteosarcoma, bladder cancer, cervical cancer, liver cancer, kidney cancer, skin cancer (e.g., Merkel cell carcinoma), testicular cancer, leukemia, lymphoma, head and neck cancer, colorectal cancer, prostate cancer, pancreatic cancer, melanoma, breast cancer, neuroblastoma) is caused by (in whole or in part), or a symptom of the disease is caused by (in whole or in part) the substance or substance activity or function.

The term "adjacent carbons" as used herein refers to consecutive carbons atoms that are directly attached to each other. For example, in

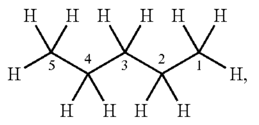

$C_1$ and $C_2$ are adjacent carbons, $C_2$ and $C_3$ are adjacent carbons, $C_3$ and $C_4$ are adjacent carbons, and $C_4$ and $C_5$ are adjacent carbons. Similarly, in

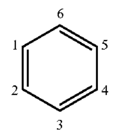

$C_1$ and $C_2$ are adjacent carbons, $C_2$ and $C_3$ are adjacent carbons, $C_3$ and $C_4$ are adjacent carbons, and $C_4$ and $C_5$ are adjacent carbons, $C_5$ and $C_6$ are adjacent carbons and $C_6$ and $C_1$ are adjacent carbons.

"Solvate" as used herein refers to the result of the interaction of a solvent and a compound. Solvates of salts of the compounds described herein are also provided. Hydrates of the compounds described herein are also provided.

"Prodrug" as used herein refers to a derivative of a drug that upon administration to the human body is converted to the parent drug according to some chemical or enzymatic pathway.

As used herein, "pharmaceutically acceptable carrier" or "pharmaceutically acceptable excipient" includes, but is not limited to, any and all solvents, dispersion media, coatings, antibacterial and antifungal agents, isotonic and absorption delaying agents, and combinations thereof. The use of pharmaceutically acceptable carriers and pharmaceutically acceptable excipients for pharmaceutically active substances is well known in the art. Except insofar as any conventional media or agent is incompatible with the active ingredient, its use in the therapeutic formulations is contemplated. Supplementary active ingredients can also be incorporated into the formulations. The carrier(s) must be "acceptable" in the sense of being compatible with the other ingredients of the formulation and physiologically innocuous to the recipient thereof.

III. Compounds

Disclosed herein are, among other things, compounds of Formulas J, (I-1), (I-2), (I-3), (Ib), (Ib-1), (Ib-2), (Ib-3), (Ib-4), (Ib), (IIb-1), and (IIb-2). In some embodiments, the compounds of Formulas J, (I-1), (I-2), (I-3), (Tb), (Ib-1), (Ib-2), (Ib-3), (Ib-4), (IIb), (IIb-1), and (IIb-2) are prodrugs.

In some embodiments, the present disclosure provides a compound of Formula J:

Formula J

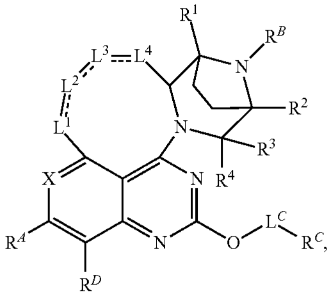

or a pharmaceutically acceptable salt thereof, wherein

X is N, CH, or $CR^X$;

$R^x$ is $C_{1-3}$ alkyl, $C_{2-4}$ alkenyl, $C_{1-3}$ alkoxy, $C_{1-3}$ thioalkyl, —CN, $(CH_2)_mCN$, halo, $C_{1-3}$ haloalkyl, or $C_{3-6}$ cycloalkyl;

m is 0, 1, 2 or 3;

$R^1$, $R^2$, $R^3$, and $R^4$ are each independently H or $C_1$-$C_3$ alkyl;

$L^1$ is O, S, $CR^{1a}R^{1b}$, $C(=CR^{1c}R^{1d})$, C(=O), or $-C(R^{1e})=$;

$R^{1a}$ and $R^{1b}$ are each independently H, $C_1$-$C_3$ alkyl, $C_1$-$C_3$ alkoxy, halo, $C_1$-$C_6$ haloalkyl, $C_1$-$C_6$ haloalkoxy, —OH, —CN, $C_1$-$C_3$ cyanoalkyl, or $C_3$-$C_6$ cycloalkyl;

alternatively, $R^{1a}$ and $R^{1b}$ can combine with the atom to which they are attached to form a $C_3$-$C_6$ cycloalkyl or a 3 to 6 membered heterocyclyl having 1 heteroatom that is O, wherein each cycloalkyl and heterocyclyl is substituted with 0, 1, 2, or 3 $R^{1x}$;

$R^{1c}$ and $R^{1d}$ are each independently H, $C_1$-$C_3$ alkyl, halo, $C_1$-$C_6$ haloalkyl, —CN, $C_1$-$C_3$ cyanoalkyl, or $C_3$-$C_6$ cycloalkyl;

alternatively, $R^{1c}$ and $R^{1d}$ can combine with the atom to which they are attached to form a $C_3$-$C_6$ cycloalkyl or a 3 to 6 membered heterocyclyl having 1 heteroatom that is O, wherein each cycloalkyl and heterocyclyl is substituted with 0, 1, 2, or 3 Rix;

$R^{1e}$ is H, $C_1$-$C_3$ alkyl, halo, $C_1$-$C_6$ haloalkyl, —CN, $C_1$-$C_3$ cyanoalkyl, or $C_3$-$C_6$ cycloalkyl;

each $R^{1x}$ is independently $C_1$-$C_3$ alkyl, $C_1$-$C_3$ alkoxy, halo, $C_1$-$C_6$ haloalkyl, $C_1$-$C_6$ haloalkoxy, or —OH;

$L^2$ is absent, O, S, $CR^{2a}R^{2b}$, $C(=CR^{2c}R^{2d})$, C(=O), or $=C(R^{2e})-$, such that when $L^2$ is O or S, then $L^1$ is $CR^{1a}R^{1b}$;

$R^{2a}$ and $R^{2b}$ are each independently H, $C_1$-$C_3$ alkyl, $C_1$-$C_3$ alkoxy, halo, $C_1$-$C_6$ haloalkyl, $C_1$-$C_6$ haloalkoxy, —OH, —CN, $C_1$-$C_3$ cyanoalkyl, or $C_3$-$C_6$ cycloalkyl;

alternatively, $R^{2a}$ and $R^{2b}$ can combine with the atom to which they are attached to form a $C_3$-$C_6$ cycloalkyl;

alternatively, $R^{1b}$ and $R^{2b}$ can combine with the atoms to which they are attached to form a $C_3$-$C_6$ cycloalkyl, 4- to 10-membered heterocyclyl, $C_6$-$C_{10}$ aryl, or 5- to 14-membered heteroaryl, wherein each cycloalkyl, heterocyclyl, aryl and heteroaryl is substituted with 0, 1, 2, or 3 $R^{2x}$;

$R^{2c}$ and $R^{2d}$ are each independently H, $C_1$-$C_3$ alkyl, halo, $C_1$-$C_6$ haloalkyl, —CN, $C_1$-$C_3$ cyanoalkyl, or $C_3$-$C_6$ cycloalkyl;

alternatively, $R^{2c}$ and $R^{2d}$ can combine with the atom to which they are attached to form a $C_3$-$C_6$ cycloalkyl or a 3 to 6 membered heterocyclyl having 1 heteroatom that is O, wherein each cycloalkyl and heterocyclyl is substituted with 0, 1, 2, or 3 $R^{2x}$;

$R^{2e}$ is H, $C_1$-$C_3$ alkyl, halo, $C_1$-$C_6$ haloalkyl, —CN, $C_1$-$C_3$ cyanoalkyl, or $C_3$-$C_6$ cycloalkyl;

alternatively, $R^{1c}$ and $R^{2e}$ can combine with the atoms to which they are attached to form a $C_5$-$C_6$ cycloalkyl, 5- to 10-membered heterocyclyl, $C_6$-$C_{10}$ aryl, or 5- to 14-membered heteroaryl, wherein each cycloalkyl, heterocyclyl, aryl and heteroaryl is substituted with 0, 1, 2, or 3 $R^{2x}$;

each $R^{2x}$ is independently $C_1$-$C_3$ alkyl, $C_1$-$C_3$ alkoxy, halo, $C_1$-$C_6$ haloalkyl, $C_1$-$C_6$ haloalkoxy, or —OH;

alternatively $L^1$ and $L^2$ can combine to form

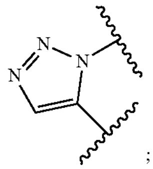

;

$L^3$ is absent, $CR^{3a}R^{3b}$, $C(=CR^{3c}R^{3d})$, C(=O), or $=C(R^{3e})-$;

$R^{3a}$ and $R^{3b}$ are each independently H, $C_1$-$C_3$ alkyl, $C_1$-$C_3$ alkoxy, halo, $C_1$-$C_6$ haloalkyl, $C_1$-$C_6$ haloalkoxy, —OH, —CN, $C_1$-$C_3$ cyanoalkyl, or $C_3$-$C_6$ cycloalkyl;

alternatively, $R^{3a}$ and $R^{3b}$ can combine with the atom to which they are attached to form a $C_3$-$C_6$ cycloalkyl;

alternatively, $R^{2b}$ and $R^{3b}$ can combine with the atoms to which they are attached to form a $C_3$-$C_6$ cycloalkyl;

$R^{3c}$ and $R^{3d}$ are each independently H, $C_1$-$C_3$ alkyl, halo, $C_1$-$C_6$ haloalkyl, —CN, $C_1$-$C_3$ cyanoalkyl, or $C_3$-$C_6$ cycloalkyl;

alternatively, $R^{3c}$ and $R^{3d}$ can combine with the atom to which they are attached to form a $C_3$-$C_6$ cycloalkyl or a 3 to 6 membered heterocyclyl having 1 heteroatom that is O, wherein each cycloalkyl and heterocyclyl is substituted with 0, 1, 2, or 3 $R^{3x}$;

each $R^{3x}$ is independently $C_1$-$C_3$ alkyl, $C_1$-$C_3$ alkoxy, halo, $C_1$-$C_6$ haloalkyl, $C_1$-$C_6$ haloalkoxy, or —OH;

$R^{3e}$ is H, $C_1$-$C_3$ alkyl, halo, $C_1$-$C_6$ haloalkyl, —CN, $C_1$-$C_3$ cyanoalkyl, or $C_3$-$C_6$ cycloalkyl;

alternatively, $R^{2e}$ and $R^{3e}$ can combine with the atoms to which they are attached to form a $C_5$-$C_6$ cycloalkyl, 5- to 10-membered heterocyclyl, $C_6$-$C_{10}$ aryl, or 5- to 14-membered heteroaryl; $L^4$ is absent, $CR^{4a}R^{4b}$, $C(=CR^{4c}R^{4d})$, C(=O), or $=C(R^{4e})-$; $R^{4a}$ and $R^{4b}$ are each independently H, $C_1$-$C_3$ alkyl, $C_1$-$C_3$ alkoxy, halo, $C_1$-$C_6$ haloalkyl, $C_1$-$C_6$ haloalkoxy, —OH, —CN, $C_1$-$C_3$ cyanoalkyl, or $C_3$-$C_6$ cycloalkyl;

alternatively, $R^{4a}$ and $R^{4b}$ can combine with the atom to which they are attached to form a $C_3$-$C_6$ cycloalkyl;

alternatively, $R^{3b}$ and $R^{4b}$ can combine with the atoms to which they are attached to form a $C_3$-$C_6$ cycloalkyl;

$R^{4c}$ and $R^{4d}$ are each independently H, $C_1$-$C_3$ alkyl, halo, $C_1$-$C_6$ haloalkyl, —CN, $C_1$-$C_3$ cyanoalkyl, or $C_3$-$C_6$ cycloalkyl;

alternatively, $R^{4c}$ and $R^{4d}$ can combine with the atom to which they are attached to form a $C_3$-$C_6$ cycloalkyl or a 3 to 6 membered heterocyclyl having 1 heteroatom that is O, wherein each cycloalkyl and heterocyclyl is substituted with 0, 1, 2, or 3 $R^{4x}$;

each $R^{4x}$ is independently $C_1$-$C_3$ alkyl, $C_1$-$C_3$ alkoxy, halo, $C_1$-$C_6$ haloalkyl, $C_1$-$C_6$ haloalkoxy, or —OH;

$R^{4c}$ is H, $C_1$-$C_3$ alkyl, halo, $C_1$-$C_6$ haloalkyl, —CN, $C_1$-$C_3$ cyanoalkyl, or $C_3$-$C_6$ cycloalkyl;

alternatively, $R^{3e}$ and $R^{4e}$ can combine with the atoms to which they are attached to form a $C_5$-$C_6$ cycloalkyl;

such that when $L^2$ is $=C(R^{2e})$— then $L^1$ is —$C(R^{1e})=$ or $L^3$ is $=C(R^{3e})$—, and when $L^3$ is $=C(R^{3e})$— then $L^2$ is $=C(R^{2e})$— or $L^4$ is $=C(R^{4e})$—; $R^A$ is phenyl, naphthyl, or 5- to 14-membered heteroaryl, wherein $R^A$ is substituted with 0, 1, 2, 3, 4, or 5 $R^{A2}$;

each $R^{A2}$ is independently —OH, $C_1$-$C_{10}$ alkyl, $C_2$-$C_6$ alkenyl, $C_2$-$C_6$ alkynyl, $C_1$-$C_{10}$ alkoxy, $C_1$-$C_{10}$ hydroxyalkyl, $C_2$-$C_{10}$ alkoxyalkyl, $C_1$-$C_6$ alkyl-N$(R^{A2a})(R^{A2b})$, $C_1$-$C_{10}$ thioalkyl, halo, $C_1$-$C_6$ haloalkyl, —CN, —C(O)$R^{A2a}$, —C(O)O$R^{A2a}$, —OC(O)$R^{A2a}$, —OC(O)O$R^{A2a}$, —C(O)N$(R^{A2a})(R^{A2b})$, —N$(R^{A2a})$C(O)$(R^{A2b})$, —OC(O)N$(R^{A2a})(R^{A2b})$, —N$(R^{A2a})$C(O)(O$R^{A26}$), oxo, —O$R^{A2a}$, —S$R^{A2a}$, —S(O)$_2R^{A2a}$, —S(O)$_2$O$R^{A2a}$, —N$(R^{A2a})(R^{A2b})$, —($C_0$-$C_3$ alkyl)-$SF_5$, —OP(O)(O$R^{A2a}$)(O$R^{A2b}$), $C_3$-$C_8$ cycloalkyl, —($C_1$-$C_6$ alkyl)-($C_3$-$C_8$ cycloalkyl), 3- to 14-membered heterocyclyl, —($C_1$-$C_6$ alkyl)-(3- to 14-membered heterocyclyl), $C_6$-$C_{14}$ aryl, —($C_1$-$C_6$ alkyl)-($C_6$-$C_{14}$ aryl), 5- to 14-membered heteroaryl, or —($C_1$-$C_6$ alkyl)-(5- to 14-membered heteroaryl), wherein each alkyl, alkenyl, alkynyl, alkoxy, hydroxyalkyl, and haloalkyl is substituted with 0, 1, 2, or 3 $R^{A3}$, and wherein each cycloalkyl, alkyl-cycloalkyl, heterocyclyl, alkyl-heterocyclyl, aryl, alkyl-aryl, heteroaryl, and alkyl-heteroaryl is substituted with 0, 1, 2, or 3 $R^{A4}$;

each $R^{A2a}$ and $R^{A2b}$ is independently H, $C_1$-$C_{10}$ alkyl, $C_1$-$C_6$ haloalkyl, or $C_3$-$C_5$ cycloalkyl;

each $R^{A3}$ is independently halo, —CN, —O$R^{A3a}$, S$R^{A3a}$, —N$(R^{A3a})(R^{A3b})$, $C_3$-$C_8$ cycloalkyl, or 5- to 14-membered heteroaryl;

each $R^{A3a}$ and $R^{A3b}$ is independently H, $C_1$-$C_{10}$ alkyl, $C_1$-$C_6$ haloalkyl, or $C_3$-$C_8$ cycloalkyl;

each $R^{A4}$ is independently $C_1$-$C_6$ alkoxy, $C_1$-$C_6$ hydroxyalkyl, $C_2$-$C_6$ alkoxyalkyl, $C_1$-$C_6$ haloalkyl, $C_1$-$C_6$ haloalkoxy, $C_1$-$C_6$ haloalkylthio, $C_3$-$C_8$ cycloalkyl, —($C_1$-$C_6$ alkyl)-($C_6$-$C_{10}$ aryl), halo, —CN, —OH, or —N$(R^{A4a})(R^{A4b})$;

each $R^{A4a}$ and $R^{A4b}$ is independently H or $C_1$-$C_6$ alkyl;

alternatively, two $R^{A2}$ can combine to form a $C_3$-$C_{10}$ cycloalkyl, $C_6$-$C_{10}$ aryl, a 3- to 10-membered heterocyclyl, or 5- to 14-membered heteroaryl on two adjacent atoms on $R^A$, wherein each cycloalkyl, aryl, heterocyclyl, and heteroaryl is substituted with 0, 1, 2, or 3 $R^{A5}$;

each $R^{A5}$ is independently $C_1$-$C_{10}$ alkyl, $C_2$-$C_{10}$ alkenyl, $C_2$-$C_{10}$ alkynyl, halo, $C_1$-$C_6$ haloalkyl, —CN, or $C_3$-$C_8$ cycloalkyl;

$R^B$ is H or $R^{B1}$;

wherein when $R^B$ is H, then at least one $R^{A2}$ is —O$R^{A2x}$;

$R^{B1}$ and $R^{A2x}$ are each independently:

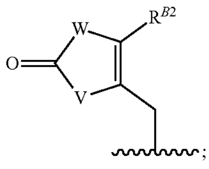

;

W and V are each independently N$R^{B2}$, O, or S;

each $R^{B2}$ is independently $C_1$-$C_{12}$ alkyl, $C_1$-$C_6$ alkoxy, $C_2$-$C_6$ alkoxyalkyl, $C_1$-$C_6$ alkyl-N$(R^{B2a})(R^{B2b})$, $C_1$-$C_0$ thioalkyl, $C_1$-$C_6$ haloalkyl, $C_1$-$C_6$ haloalkoxy, $C_3$-$C_8$ cycloalkyl, $C_6$-$C_{14}$ aryl, or 5- to 14-membered heteroaryl, wherein the $C_3$-$C_5$ cycloalkyl, $C_6$-$C_{14}$ aryl or 5- to 14-membered heteroaryl are substituted with 0, 1, 2, or 3 $R^{B2c}$;

each $R^{B2a}$ and $R^{B2b}$ is independently H, $C_1$-$C_6$ alkyl, $C_1$-$C_6$ haloalkyl, or $C_3$-$C_8$ cycloalkyl;

each $R^{B2c}$ is independently $C_1$-$C_6$ alkyl, $C_1$-$C_6$ alkoxy, $C_2$-$C_6$ alkoxyalkyl, halo, $C_1$-$C_6$ haloalkyl, $C_1$-$C_6$ haloalkoxy, oxo, —OH, —CN, or $C_3$-$C_{10}$ cycloalkyl;

$L^C$ is a bond or

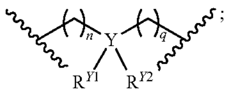

;

Y is C or Si;

n is 0, 1, 2, or 3;

q is 0, 1, 2, or 3;

$R^{Y1}$ is H or $C_1$-$C_3$ alkyl;

$R^{Y2}$ is H or $C_1$-$C_3$ alkyl;

alternatively, $R^{Y1}$ and $R^{Y2}$ combine to form a $C_3$-$C_{10}$ cycloalkyl or a 3- to 10-membered heterocyclyl;

$R^C$ is H, $C_1$-$C_6$ alkyl, $C_1$-$C_6$ alkoxy, $C_1$-$C_6$ hydroxyalkyl, $C_2$-$C_6$ alkoxyalkyl, $C_1$-$C_6$ haloalkyl, $C_1$-$C_6$ haloalkoxy, —$NH_2$, —NH$R^{C1}$, —N$(R^{C1})_2$, $C_3$-$C_8$ cycloalkyl, 3- to 14-membered heterocyclyl, $C_6$-$C_{14}$ aryl, or 5- to 14-membered heteroaryl, wherein each $C_3$-$C_8$ cycloalkyl, 3- to 14-membered heterocyclyl, $C_6$-$C_{14}$ aryl, and 3- to 14-membered heteroaryl, is substituted with 0, 1, 2, 3, or 4 $R^{C3}$.

each $R^{C1}$ is independently selected from $C_1$-$C_6$ alkyl;

each $R^{C3}$ is independently $C_1$-$C_6$ alkyl, $C_2$-$C_6$ alkenyl, $C_2$-$C_8$ alkynyl, $C_1$-$C_6$ alkoxyalkyl, $C_1$-$C_6$ hydroxyalkyl, halo, $C_1$-$C_6$ haloalkyl, $C_1$-$C_6$ heteroalkyl, —($C_1$-$C_6$ alkyl)-N$(R^{c3a})(R^{c3b})$, —CN, —C(O)$R^{c3a}$, —C(O)O$R^{c3a}$, —C(O)N$(R^{c3a})(R^{c3b})$, —N$(R^{c3a})$C(O)$(R^{c3b})$, —OC(O)N$(R^{c3a})(R^{c3b})$, —N$(R^{c3a})$C(O)(O$R^{c3b}$), $=CH_2$, $=CHF$, $=CF_2$, oxo, —O$R^{c3a}$, —S$R^{C3a}$, —N$(R^{c3a})(R^{c3b})$, —$N_3$, $SF_5$, $C_3$-$C_8$ cycloalkyl, —($C_1$-$C_6$ alkyl)-($C_3$-$C_8$ cycloalkyl), 3- to 10-membered heterocyclyl, —($C_1$-$C_6$ alkyl)-(3- to 10-membered heterocyclyl), $C_6$-$C_{10}$ aryl, —($C_1$-$C_6$ alkyl)-($C_6$-$C_{10}$ aryl), 5- to 10-membered heteroaryl, or —($C_1$-$C_6$ alkyl)-(5- to 10-membered heteroaryl), wherein each alkyl is substituted with 0, 1, 2, or 3 —CN, —C(O)O$R^{c3a1}$, —C(O)N$(R^{c3a1})(R^{c3a2})$, —N$(R^{c3a1})$C(O)$(R^{c3a2})$, —OC(O)N$(R^{c3a1})(R^{c3a2})$, —O$R^{c3a1}$, —S$R^{c3a1}$, $N_3$, $SF_5$, or 3- to 10-membered heterocyclyl substituted with 0, 1, 2, or 3 $R^{c3a2}$, each cycloalkyl, alkyl-cycloalkyl, heterocyclyl, alkyl-heterocyclyl, aryl, alkyl-aryl, heteroaryl, and alkyl-heteroaryl is substituted with 0, 1, 2, or 3 halo, —CN, or $R^{c3a2}$, each alkenyl is substituted with 0, 1, 2, or 3 halo, and each alkoxyalkyl and alkynyl is substituted with 0, 1, 2, or 3 $C_1$-$C_6$ alkyl, $C_1$-$C_6$ haloalkyl, $C_3$-$C_8$ cycloalkyl substituted with 0 or 1 $C_1$-$C_6$ haloalkyl, $C_6$-$C_{10}$ aryl, or 5- to 10-membered heteroaryl;

each $R^{c3a}$ and $R^{c3b}$ is independently H, $C_1$-$C_{10}$ alkyl, $C_1$-$C_6$ haloalkyl, $C_6$-$C_{10}$ aryl, $C_3$-$C_6$ cycloalkyl, 3- to 6-membered heterocyclyl, or 5- to 10-membered heteroaryl, wherein each aryl and heteroaryl is substituted with 0, 1, 2, or 3 halo, —CN, or $R^{c3a2}$;

alternatively, $R^{c3a}$ and $R^{c3b}$ together with the N to which they are attached form a 3- to 8-membered heterocycle;

each $R^{c3a1}$ and $R^{c3a2}$ is independently $C_1$-$C_3$ alkyl, halo, $C_1$-$C_6$ haloalkyl, $C_3$-$C_8$ cycloalkyl, —($C_1$-$C_3$ alkyl)-($C_3$-$C_8$ cycloalkyl), 3- to 10-membered heterocyclyl, —($C_1$-$C_3$ alkyl)-(3- to 10-membered heterocyclyl), $C_6$-$C_{10}$ aryl, —($C_1$-$C_3$ alkyl)-($C_6$-$C_{10}$ aryl), —($C_2$-$C_4$ alkynyl)-($C_6$-$C_{10}$ aryl), 5- to 10-membered heteroaryl, —($C_1$-$C_3$ alkyl)-(5- to 10-membered heteroaryl), or $SF_5$, wherein each cycloalkyl, alkyl-cycloalkyl, heterocyclyl, alkyl-heterocyclyl, aryl, alkyl-aryl, alkynyl-aryl, heteroaryl, and alkyl-heteroaryl is substituted with 0, 1, 2, or 3 halo, $C_1$-$C_3$ haloalkyl, $C_1$-$C_3$ haloalkoxy, or $SF_5$;

alternatively, $R^{c3a1}$ and $R^{c3a2}$ together with the N to which they are attached form a 3- to 8-membered heterocycle;

$R^D$ is halo;

each heterocyclyl has 1, 2, 3, or 4 heteroatoms selected from N, O, S, and Si; and each heteroaryl has 1, 2, 3, or 4 heteroatoms selected from N, O, and S.

In one embodiment, the present disclosure provides a compound of Formula J:

Formula J

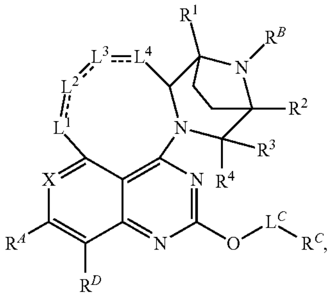

or a pharmaceutically acceptable salt thereof, wherein

X is N, CH, or $CR^x$;

$R^X$ is $C_{1-3}$ alkyl, $C_{2-4}$ alkenyl, $C_{1-3}$ alkoxy, $C_{1-3}$ thioalkyl, —CN, $(CH_2)_mCN$, halo, $C_{1-3}$ haloalkyl, or $C_{3-6}$ cycloalkyl;

m is 0, 1, 2 or 3;

$R^1$, $R^2$, $R^3$, and $R^4$ are each independently H or $C_1$-$C_3$ alkyl;

$L^1$ is O, S, $CR^{1a}R^{1b}$, C(=$CR^{1c}R^{1d}$), C(=O), or —C($R^{1e}$)=;

$R^{1a}$ and $R^{1b}$ are each independently H, $C_1$-$C_3$ alkyl, $C_1$-$C_3$ alkoxy, halo, $C_1$-$C_6$ haloalkyl, $C_1$-$C_6$ haloalkoxy, —OH, —CN, $C_1$-$C_3$ cyanoalkyl, or $C_3$-$C_6$ cycloalkyl;

alternatively, $R^{1a}$ and $R^{1b}$ can combine with the atom to which they are attached to form a $C_3$-$C_6$ cycloalkyl or a 3 to 6 membered heterocyclyl having 1 heteroatom that is O, wherein each cycloalkyl and heterocyclyl is substituted with 0, 1, 2, or 3 $R^{1x}$;

$R^{1c}$ and $R^{1d}$ are each independently H, $C_1$-$C_3$ alkyl, halo, $C_1$-$C_6$ haloalkyl, —CN, $C_1$-$C_3$ cyanoalkyl, or $C_3$-$C_6$ cycloalkyl;

alternatively, $R^{1c}$ and $R^{1d}$ can combine with the atom to which they are attached to form a $C_3$-$C_6$ cycloalkyl or a 3 to 6 membered heterocyclyl having 1 heteroatom that is O, wherein each cycloalkyl and heterocyclyl is substituted with 0, 1, 2, or 3 $R^{1x}$;

$R^{1e}$ is H, $C_1$-$C_3$ alkyl, halo, $C_1$-$C_6$ haloalkyl, —CN, $C_1$-$C_3$ cyanoalkyl, or $C_3$-$C_6$ cycloalkyl;

each $R^{1x}$ is independently $C_1$-$C_3$ alkyl, $C_1$-$C_3$ alkoxy, halo, $C_1$-$C_6$ haloalkyl, $C_1$-$C_6$ haloalkoxy, or —OH;

$L^2$ is absent, O, S, $CR^{2a}R^{2b}$, C(=$CR^{2c}R^{2d}$), C(=O), or =C($R^{2e}$)—, such that when $L^2$ is O or S, then $L^1$ is $CR^{1a}R^{1b}$;

$R^{2a}$ and $R^{2b}$ are each independently H, $C_1$-$C_3$ alkyl, $C_1$-$C_3$ alkoxy, halo, $C_1$-$C_6$ haloalkyl, $C_1$-$C_6$ haloalkoxy, —OH, —CN, $C_1$-$C_3$ cyanoalkyl, or $C_3$-$C_6$ cycloalkyl;

alternatively, $R^{2a}$ and $R^{2b}$ can combine with the atom to which they are attached to form a $C_3$-$C_6$ cycloalkyl;

alternatively, $R^{1b}$ and $R^{2b}$ can combine with the atoms to which they are attached to form a $C_3$-$C_6$ cycloalkyl, 4- to 10-membered heterocyclyl, $C_6$-$C_{10}$ aryl, or 5- to 14-membered heteroaryl, wherein each cycloalkyl, heterocyclyl, aryl and heteroaryl is substituted with 0, 1, 2, or 3 $R^{2x}$;

$R^{2c}$ and $R^{2d}$ are each independently H, $C_1$-$C_3$ alkyl, halo, $C_1$-$C_6$ haloalkyl, —CN, $C_1$-$C_3$ cyanoalkyl, or $C_3$-$C_6$ cycloalkyl;

alternatively, $R^{2c}$ and $R^{2d}$ can combine with the atom to which they are attached to form a $C_3$-$C_6$ cycloalkyl or a 3 to 6 membered heterocyclyl having 1 heteroatom that is O, wherein each cycloalkyl and heterocyclyl is substituted with 0, 1, 2, or 3 $R^{2x}$;

$R^{2e}$ is H, $C_1$-$C_3$ alkyl, halo, $C_1$-$C_6$ haloalkyl, —CN, $C_1$-$C_3$ cyanoalkyl, or $C_3$-$C_6$ cycloalkyl;

alternatively, $R^{1e}$ and $R^{2e}$ can combine with the atoms to which they are attached to form a $C_5$-$C_6$ cycloalkyl, 5- to 10-membered heterocyclyl, $C_6$-$C_{10}$ aryl, or 5- to 14-membered heteroaryl, wherein each cycloalkyl, heterocyclyl, aryl and heteroaryl is substituted with 0, 1, 2, or 3 $R^{2x}$;

each $R^{2x}$ is independently $C_1$-$C_3$ alkyl, $C_1$-$C_3$ alkoxy, halo, $C_1$-$C_6$ haloalkyl, $C_1$-$C_6$ haloalkoxy, or —OH;

alternatively $L^1$ and $L^2$ can combine to form

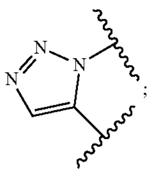 [SMILES: *c1cnnn1*]

;

$L^3$ is absent, $CR^{3a}R^{3b}$, C(=$CR^{3c}R^{3d}$), C(=O), or =C($R^{3e}$)—; $R^{3a}$ and $R^{3b}$ are each independently H, $C_1$-$C_3$ alkyl, $C_1$-$C_3$ alkoxy, halo, $C_1$-$C_6$ haloalkyl, $C_1$-$C_6$ haloalkoxy, —OH, —CN, $C_1$-$C_3$ cyanoalkyl, or $C_3$-$C_6$ cycloalkyl;

alternatively, $R^{3a}$ and $R^{3b}$ can combine with the atom to which they are attached to form a $C_3$-$C_6$ cycloalkyl;

alternatively, $R^{2b}$ and $R^{3b}$ can combine with the atoms to which they are attached to form a $C_3$-$C_6$ cycloalkyl;

$R^{3c}$ and $R^{3d}$ are each independently H, $C_1$-$C_3$ alkyl, halo, $C_1$-$C_6$ haloalkyl, —CN, $C_1$-$C_3$ cyanoalkyl, or $C_3$-$C_6$ cycloalkyl;

alternatively, $R^{3c}$ and $R^{3d}$ can combine with the atom to which they are attached to form a $C_3$-$C_6$ cycloalkyl or a 3 to 6 membered heterocyclyl having 1 heteroatom that is O, wherein each cycloalkyl and heterocyclyl is substituted with 0, 1, 2, or 3 $R^{3x}$;

each $R^{3x}$ is independently $C_1$-$C_3$ alkyl, $C_1$-$C_3$ alkoxy, halo, $C_1$-$C_6$ haloalkyl, $C_1$-$C_6$ haloalkoxy, or —OH;

$R^{3e}$ is H, $C_1$-$C_3$ alkyl, halo, $C_1$-$C_6$ haloalkyl, —CN, $C_1$-$C_3$ cyanoalkyl, or $C_3$-$C_6$ cycloalkyl;

alternatively, $R^{2e}$ and $R^{3e}$ can combine with the atoms to which they are attached to form a $C_5$-$C_6$ cycloalkyl, 5- to 10-membered heterocyclyl, $C_6$-$C_{10}$ aryl, or 5- to 14-membered heteroaryl;

$L^4$ is absent, $CR^{4a}R^{4b}$, $C(=CR^{4c}R^{4d})$, C(=O), or $=C(R^{4e})$—;

$R^{4a}$ and $R^{4b}$ are each independently H, $C_1$-$C_3$ alkyl, $C_1$-$C_3$ alkoxy, halo, $C_1$-$C_6$ haloalkyl, $C_1$-$C_6$ haloalkoxy, —OH, —CN, $C_1$-$C_3$ cyanoalkyl, or $C_3$-$C_6$ cycloalkyl;

alternatively, $R^{4a}$ and $R^{4b}$ can combine with the atom to which they are attached to form a $C_3$-$C_6$ cycloalkyl;

alternatively, $R^{3b}$ and $R^{4b}$ can combine with the atoms to which they are attached to form a $C_3$-$C_6$ cycloalkyl;

$R^{4c}$ and $R^{4d}$ are each independently H, $C_1$-$C_3$ alkyl, halo, $C_1$-$C_6$ haloalkyl, —CN, $C_1$-$C_3$ cyanoalkyl, or $C_3$-$C_6$ cycloalkyl;

alternatively, $R^{4c}$ and $R^{4d}$ can combine with the atom to which they are attached to form a $C_3$-$C_6$ cycloalkyl or a 3 to 6 membered heterocyclyl having 1 heteroatom that is O, wherein each cycloalkyl and heterocyclyl is substituted with 0, 1, 2, or 3 $R^{4x}$;

each $R^{4x}$ is independently $C_1$-$C_3$ alkyl, $C_1$-$C_3$ alkoxy, halo, $C_1$-$C_6$ haloalkyl, $C_1$-$C_6$ haloalkoxy, or —OH;

$R^{4e}$ is H, $C_1$-$C_3$ alkyl, halo, $C_1$-$C_6$ haloalkyl, —CN, $C_1$-$C_3$ cyanoalkyl, or $C_3$-$C_6$ cycloalkyl;

alternatively, $R^{3e}$ and $R^{4e}$ can combine with the atoms to which they are attached to form a $C_5$-$C_6$ cycloalkyl;

such that when $L^2$ is $=C(R^{2e})$— then $L^1$ is $—C(R^{1e})=$ or $L^3$ is $=C(R^{3e})$—, and when $L^3$ is $=C(R^{3e})$— then $L^2$ is $=C(R^{2e})$— or $L^4$ is $=C(R^{4e})$—;

$R^4$ is phenyl, naphthyl, or 5- to 14-membered heteroaryl, wherein $R^4$ is substituted with 0, 1, 2, 3, 4, or 5 $R^{A2}$;

each $R^{A2}$ is independently —OH, $C_1$-$C_{10}$ alkyl, $C_2$-$C_6$ alkenyl, $C_2$-$C_6$ alkynyl, $C_1$-$C_{10}$ alkoxy, $C_1$-$C_{10}$ hydroxyalkyl, $C_2$-$C_{10}$ alkoxyalkyl, $C_1$-$C_6$ alkyl-N$(R^{A2a})(R^{A2b})$, $C_1$-$C_{10}$ thioalkyl, halo, $C_1$-$C_6$ haloalkyl, —CN, $—C(O)R^{A2a}$, $—C(O)OR^{A2a}$, $—OC(O)R^{A2a}$, $—OC(O)OR^{A2a}$, $—C(O)N(R^{A2a})(R^{A2b})$, $—N(R^{A2a})C(O)(R^{A2b})$, $—OC(O)N(R^{A2a})(R^{A2b})$, $—N(R^{A2a})C(O)(OR^{A2b})$, oxo, $—OR^{A2a}$, $—SR^{A2a}$, $—S(O)_2R^{A2a}$, $—S(O)_2OR^{A2a}$, $—N(R^{A2a})(R^{A2b})$, —($C_0$-$C_3$ alkyl)-$SF_5$, $—OP(O)(OR^{A2a})(OR^{A2b})$, $C_3$-$C_8$ cycloalkyl, —($C_1$-$C_6$ alkyl)-($C_3$-$C_8$ cycloalkyl), 3- to 14-membered heterocyclyl, —($C_1$-$C_6$ alkyl)-(3- to 14-membered heterocyclyl), $C_6$-$C_{14}$ aryl, —($C_1$-$C_6$ alkyl)-($C_6$-$C_{14}$ aryl), 5- to 14-membered heteroaryl, or —($C_1$-$C_6$ alkyl)-(5- to 14-membered heteroaryl), wherein each alkyl, alkenyl, alkynyl, alkoxy, hydroxyalkyl, and haloalkyl is substituted with 0, 1, 2, or 3 $R^{A3}$, and wherein each cycloalkyl, alkyl-cycloalkyl, heterocyclyl, alkyl-heterocyclyl, aryl, alkyl-aryl, heteroaryl, and alkyl-heteroaryl is substituted with 0, 1, 2, or 3 $R^{A4}$;

each $R^{A2a}$ and $R^{A2b}$ is independently H, $C_1$-$C_{10}$ alkyl, $C_1$-$C_6$ haloalkyl, or $C_3$-$C_8$ cycloalkyl;

each $R^{A3}$ is independently halo, —CN, $—OR^{A3a}$, $SR^{A3a}$, $—N(R^{A3a})(R^{A3b})$, $C_3$-$C_8$ cycloalkyl, or 5- to 14-membered heteroaryl;

each $R^{A3a}$ and $R^{A3b}$ is independently H, $C_1$-$C_{10}$ alkyl, $C_1$-$C_6$ haloalkyl, or $C_3$-$C_8$ cycloalkyl;

each $R^{A4}$ is independently $C_1$-$C_6$ alkoxy, $C_1$-$C_6$ hydroxyalkyl, $C_2$-$C_6$ alkoxyalkyl, $C_1$-$C_6$ haloalkyl, $C_1$-$C_6$ haloalkoxy, $C_1$-$C_6$ haloalkylthio, $C_3$-$C_8$ cycloalkyl, —($C_1$-$C_6$ alkyl)-($C_6$-$C_{10}$ aryl), halo, —CN, —OH, or $—N(R^{A4a})(R^{A4b})$;

each $R^{A4a}$ and $R^{A4b}$ is independently H or $C_1$-$C_6$ alkyl;

alternatively, two $R^{A2}$ can combine to form a $C_3$-$C_{10}$ cycloalkyl, $C_6$-$C_{10}$ aryl, a 3- to 10-membered heterocyclyl, or 5- to 14-membered heteroaryl on two adjacent atoms on $R^4$, wherein each cycloalkyl, aryl, heterocyclyl, and heteroaryl is substituted with 0, 1, 2, or 3 $R^{A5}$;

each $R^{A5}$ is independently $C_1$-$C_{10}$ alkyl, $C_2$-$C_{10}$ alkenyl, $C_2$-$C_{10}$ alkynyl, halo, $C_1$-$C_6$ haloalkyl, —CN, or $C_3$-$C_8$ cycloalkyl;

$R^B$ is H or $R^{B1}$;

wherein when $R^B$ is H, then at least one $R^{A2}$ is $—OR^{A2x}$;

$R^{B1}$ and $R^{A2x}$ are each independently:

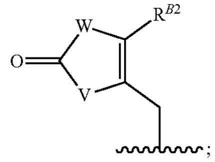

W and V are each independently $NR^{B2}$, O, or S;

each $R^{B2}$ is independently $C_1$-$C_{12}$ alkyl, $C_1$-$C_6$ alkoxy, $C_2$-$C_6$ alkoxyalkyl, $C_1$-$C_6$ alkyl-N$(R^{B2a})(R^{B2b})$, $C_1$-$C_{10}$ thioalkyl, $C_1$-$C_6$haloalkyl, $C_1$-$C_6$haloalkoxy, $C_3$-$C_8$ cycloalkyl, $C_6$-$C_{14}$ aryl, or 5- to 14-membered heteroaryl, wherein the $C_3$-$C_8$ cycloalkyl, $C_6$-$C_{14}$ aryl or 5- to 14-membered heteroaryl are substituted with 0, 1, 2, or 3 $R^{B2c}$;

each $R^{B2a}$ and $R^{B2b}$ is independently H, $C_1$-$C_6$ alkyl, $C_1$-$C_6$ haloalkyl, or $C_3$-$C_8$ cycloalkyl;

each $R^{B2c}$ is independently $C_1$-$C_6$ alkyl, $C_1$-$C_6$ alkoxy, $C_2$-$C_6$ alkoxyalkyl, halo, $C_1$-$C_6$ haloalkyl, $C_1$-$C_6$ haloalkoxy, oxo, —OH, —CN, or $C_3$-$C_{10}$ cycloalkyl;

$L^C$ is a bond or

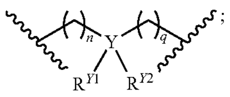

Y is C or Si;

n is 0, 1, 2, or 3;

q is 0, 1, 2, or 3;

$R^{Y1}$ is H or $C_1$-$C_3$ alkyl;

$R^{Y2}$ is H or $C_1$-$C_3$ alkyl;

alternatively, $R^{Y1}$ and $R^{Y2}$ combine to form a $C_3$-$C_{10}$ cycloalkyl or a 3- to 10-membered heterocyclyl;

$R^C$ is H, $C_1$-$C_6$ alkyl, $C_1$-$C_6$ alkoxy, $C_1$-$C_6$ hydroxyalkyl, $C_2$-$C_6$ alkoxyalkyl, $C_1$-$C_6$ haloalkyl, $C_1$-$C_6$ haloalkoxy, $—NH_2$, $—NHR^{C1}$, $—N(R^{C1})_2$, $C_3$-$C_8$ cycloalkyl, 3- to 14-membered heterocyclyl, $C_6$-$C_{14}$ aryl, or 5- to 14-membered heteroaryl, wherein each $C_3$-$C_8$ cycloalkyl, 3- to 14-membered heterocyclyl, $C_6$-$C_{14}$ aryl, and 3- to 14-membered heteroaryl, is substituted with 0, 1, 2, 3, or 4 $R^{C3}$.

each $R^{C1}$ is independently selected from $C_1$-$C_6$ alkyl;

each $R^{C3}$ is independently $C_1$-$C_6$ alkyl, $C_2$-$C_6$ alkenyl, $C_2$-$C_8$ alkynyl, $C_1$-$C_6$ alkoxyalkyl, $C_1$-$C_6$ hydroxyalkyl, halo, $C_1$-$C_6$ haloalkyl, $C_1$-$C_6$ heteroalkyl, —($C_1$-$C_6$ alkyl)-N$(R^{c3a})(R^{c3b})$, —CN, $—C(O)R^{c3a}$, —C(O)

$OR^{c3a}$, —$C(O)N(R^{c3a})(R^{c3b})$, —$N(R^{c3a})C(O)(R^{c3b})$, —$OC(O)N(R^{c3a})(R^{c3b})$, —$N(R^{c3a})C(O)(OR^{c3b})$, =$CH_2$, =$CF_2$, oxo, —$OR^{c3a}$, —$SR^{C3a}$, —$N(R^{c3a})(R^{c3b})$, —$N_3$, $SF_5$, $C_3$-$C_8$ cycloalkyl, —($C_1$-$C_6$ alkyl)-($C_3$-$C_8$ cycloalkyl), 3- to 10-membered heterocyclyl, —($C_1$-$C_6$ alkyl)-(3- to 10-membered heterocyclyl), $C_6$-$C_{10}$ aryl, —($C_1$-$C_6$ alkyl)-($C_6$-$C_{10}$ aryl), 5- to 10-membered heteroaryl, or —($C_1$-$C_6$ alkyl)-(5- to 10-membered heteroaryl), wherein each alkyl is substituted with 0, 1, 2, or 3 —CN, —$C(O)OR^{c3a1}$, —$C(O)N(R^{c3a1})(R^{c3a2})$, —$N(R^{c3a1})C(O)(R^{c3a2})$, —$OC(O)N(R^{c3a1})(R^{c3a2})$, —$OR^{c3a1}$, —$SR^{c3a1}$, $N_3$, $SF_5$, or 3- to 10-membered heterocyclyl substituted with 0, 1, 2, or 3 $R^{c3a2}$, each cycloalkyl, alkyl-cycloalkyl, heterocyclyl, alkyl-heterocyclyl, aryl, alkyl-aryl, heteroaryl, and alkyl-heteroaryl is substituted with 0, 1, 2, or 3 halo, —CN, or $R^{C3a2}$ each alkenyl is substituted with 0, 1, 2, or 3 halo, and each alkoxyalkyl and alkynyl is substituted with 0, 1, 2, or 3 $C_1$-$C_6$ alkyl, $C_1$-$C_6$ haloalkyl, $C_3$-$C_8$ cycloalkyl substituted with 0 or 1 $C_1$-$C_6$ haloalkyl, $C_6$-$C_{10}$ aryl, or 5- to 10-membered heteroaryl;

each $R^{c3a}$ and $R^{c3b}$ is independently H, $C_1$-$C_{10}$ alkyl, $C_1$-$C_6$ haloalkyl, $C_6$-$C_1O$ aryl, $C_3$-$C_6$ cycloalkyl, 3- to 6-membered heterocyclyl, or 5- to 10-membered heteroaryl, wherein each aryl and heteroaryl is substituted with 0, 1, 2, or 3 halo, —CN, or $R^{C3a2}$;

alternatively, $R^{c3a}$ and $R^{c3b}$ together with the N to which they are attached form a 3- to 8-membered heterocycle;

each $R^{c3a1}$ and $R^{c3a2}$ is independently $C_1$-$C_3$ alkyl, halo, $C_1$-$C_6$ haloalkyl, $C_3$-$C_5$ cycloalkyl, —($C_1$-$C_3$ alkyl)-($C_3$-$C_8$ cycloalkyl), 3- to 10-membered heterocyclyl, —($C_1$-$C_3$ alkyl)-(3- to 10-membered heterocyclyl), $C_6$-$C_{10}$ aryl, —($C_1$-$C_3$ alkyl)-($C_6$-$C_{10}$ aryl), —($C_2$-$C_4$ alkynyl)-($C_6$-$C_{10}$ aryl), 5- to 10-membered heteroaryl, —($C_1$-$C_3$ alkyl)-(5- to 10-membered heteroaryl), or $SF_5$, wherein each cycloalkyl, alkyl-cycloalkyl, heterocyclyl, alkyl-heterocyclyl, aryl, alkyl-aryl, alkynyl-aryl, heteroaryl, and alkyl-heteroaryl is substituted with 0, 1, 2, or 3 halo, $C_1$-$C_3$ haloalkyl, $C_1$-$C_3$ haloalkoxy, or $SF_5$;

alternatively, $R^{c3a1}$ and $R^{c3a2}$ together with the N to which they are attached form a 3- to 8-membered heterocycle;

$R^D$ is halo;

each heterocyclyl has 1, 2, 3, or 4 heteroatoms selected from N, O, S, and Si; and each heteroaryl has 1, 2, 3, or 4 heteroatoms selected from N, O, and S.

In some embodiments, the present disclosure provides the compound of Formula J, wherein $R^1$, $R^2$, $R^3$, and $R^4$ are each independently H or methyl. In some embodiments, the present disclosure provides the compound of Formula J, wherein one of two of $R^1$, $R^2$, $R^3$, and $R^4$ are methyl. In some embodiments, the present disclosure provides the compound of Formula J, wherein $R^1$ and $R^2$ are methyl. In some embodiments, the present disclosure provides the compound of Formula J, wherein $R^1$, $R^2$, $R^3$, and $R^4$ are each H.

In some embodiments, the present disclosure provides the compound of Formula J, or a pharmaceutically acceptable salt thereof, having the structure of Formula (I-1):

(I-1)

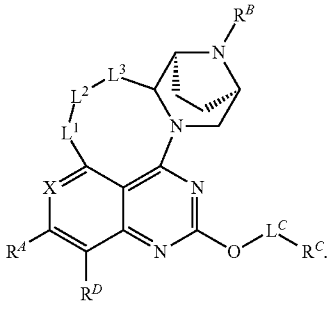

In some embodiments, the present disclosure provides the compound of Formula J or I-1, or a pharmaceutically acceptable salt thereof, having the structure of Formula (I-2):

(I-2)

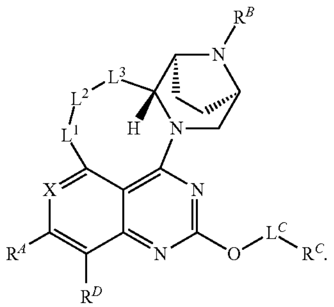

In some embodiments, the present disclosure provides the compound of Formula J or I-1, or a pharmaceutically acceptable salt thereof, having the structure of Formula (I-3):

(I-3)

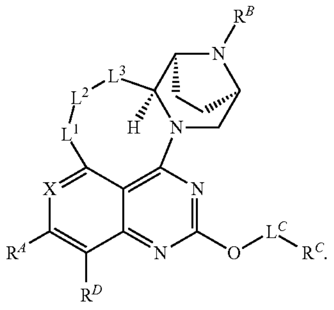

In some embodiments, the present disclosure provides the compound of Formula J, (I-1), (I-2), (I-3), (Ib), (Ib-1), (Ib-2), (Ib-3), (Ib-4), (IIb), (IIb-1), or (IIb-2), or a pharmaceutically acceptable salt thereof, wherein X is N. In some embodiments, the present disclosure provides the compound of Formula J, (I-1), (I-2), (I-3), (Ib), (b-1), (Ib-2), (Ib-3), (Ib-4), (IIb), (IIb-1), or (IIb-2), or a pharmaceutically acceptable salt thereof, wherein X is CH. In some embodiments, the present disclosure provides the compound of Formula J, (I-1), (I-2), (I-3), (Ib), (b-1), (Ib-2), (Ib-3), (Ib-4), (IIb), (IIb-1), or (IIb-2), or a pharmaceutically acceptable salt thereof, wherein X is $CR^x$, wherein $R^x$ is $(CH_2)_mCN$, and m is 0, 1, 2 or 3. In some embodiments, the present disclosure provides the compound of Formula J, (I-1), (I-2), (I-3), (Ib), (Ib-1), (Ib-2), (Ib-3), (Ib-4), (IIb), (IIb-1), or (IIb-2), or a pharmaceutically acceptable salt thereof, wherein X is $CR^x$, wherein $R^x$ is $CH_2CN$. In some embodiments, the present disclosure provides the compound of Formula J, (I-1), (I-2), (I-3), (Ib), (b-1), (Ib-2), (Ib-3), (Ib-4), (IIb), (IIb-1), or (IIb-2), or a pharmaceutically acceptable salt thereof, wherein X is $CR^x$, wherein $R^x$ is halo. In some embodiments, the present disclosure provides the compound of Formula J, (I-1), (I-2), (I-3), (Ib), (Ib-1), (b-2), (b-3), (Ib-4), (IIb), (IIb-1), or (IIb-2), or a pharmaceutically acceptable salt thereof, wherein X is C—F. In some embodiments, the present disclosure provides the compound of Formula J, (I-1), (I-2), (I-3), (Ib), (Ib-1), (Ib-2), (Ib-3), (Ib-4), (Ib), (IIb-1), or (IIb-2), or a pharmaceutically acceptable salt thereof, wherein X is C—Cl.

In some embodiments, the present disclosure provides the compound of Formula J, I-1, I-2, or I-3, or a pharmaceutically acceptable salt thereof, wherein $L^1$ is $CHR^{1b}$. In some embodiments, the present disclosure provides the compound of Formula J, I-1, I-2, or I-3, or a pharmaceutically acceptable salt thereof, wherein $L^1$ is $CH_2$. In some embodiments, the present disclosure provides the compound of Formula J, I-1, I-2, or I-3, or a pharmaceutically acceptable salt thereof, wherein $L^1$ is $CH(CH_3)$. In some embodiments, the present disclosure provides the compound of Formula J, I-1, I-2, or I-3, or a pharmaceutically acceptable salt thereof, wherein $R^{1a}$ and $R^{1b}$ are each independently H, $C_1$-$C_3$ alkyl, or halo. In some embodiments, the present disclosure provides the compound of Formula J, I-1, I-2, or I-3, or a pharmaceutically acceptable salt thereof, wherein $R^{1b}$ is $C_1$-$C_3$ alkyl or halo. In some embodiments, the present disclosure provides the compound of Formula J, I-1, I-2, or I-3, or a pharmaceutically acceptable salt thereof, wherein $R^{1b}$ is H or methyl. In some embodiments, the present disclosure provides the compound of Formula J, I-1, I-2, or I-3, or a pharmaceutically acceptable salt thereof, wherein $R^{1b}$ is H. In some embodiments, the present disclosure provides the compound of Formula J, I-1, I-2, or I-3, or a pharmaceutically acceptable salt thereof, wherein $R^{1b}$ is methyl.

In some embodiments, the present disclosure provides the compound of Formula J, I-1, I-2, or I-3, or a pharmaceutically acceptable salt thereof, having the structure of Formula (Ib):

(Ib)

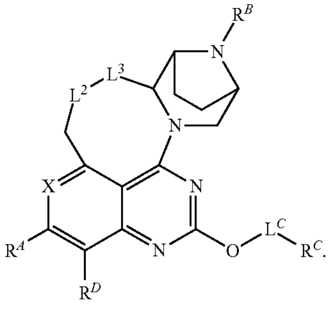

In some embodiments, the present disclosure provides the compound of Formula J, I-1, I-2, I-3, or (Ib), or a pharmaceutically acceptable salt thereof, wherein $R^{2a}$ and $R^{2b}$ are each independently H, $C_1$-$C_3$ alkyl, halo, or $C_1$-$C_6$ haloalkyl. In some embodiments, the present disclosure provides the compound of Formula J, I-1, I-2, I-3, or (Ib), or a pharmaceutically acceptable salt thereof, wherein $L^2$ is $CHR^{2b}$. In some embodiments, the present disclosure provides the compound of Formula J, I-1, I-2, I-3, or (Ib), or a pharmaceutically acceptable salt thereof, wherein $R^{2b}$ is H or $C_1$-$C_3$ alkyl. In some embodiments, the present disclosure provides the compound of Formula J, I-1, I-2, I-3, or (Ib), or a pharmaceutically acceptable salt thereof, wherein $R^{2b}$ is H. In some embodiments, the present disclosure provides the compound of Formula J, I-1, I-2, I-3, or (Ib), or a pharmaceutically acceptable salt thereof, wherein $R^{2b}$ is $C_1$-$C_3$ alkyl. In some embodiments, the present disclosure provides the compound of Formula J, I-1, I-2, I-3, or (Ib), or a pharmaceutically acceptable salt thereof, wherein $R^{2b}$ is methyl.

In some embodiments, the present disclosure provides the compound of Formula J, I-1, I-2, I-3, or (Ib), or a pharmaceutically acceptable salt thereof, wherein $L^3$ is a bond.

In some embodiments, the present disclosure provides the compound of Formula J, I-1, I-2, I-3, or (Ib), or a pharmaceutically acceptable salt thereof, having the structure of Formula (IIb):

(IIb)

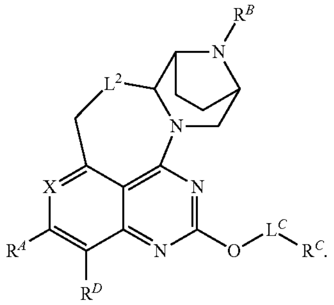

In some embodiments, the present disclosure provides the compound of Formula J, I-1, I-2, I-3, (Ib), or (IIb), or a pharmaceutically acceptable salt thereof, having the structure of Formula (IIb-1):

(IIb-1)

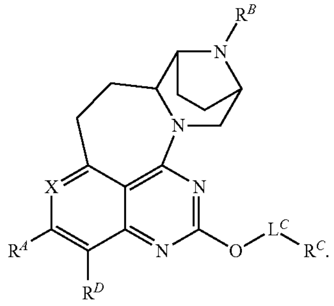

In some embodiments, the present disclosure provides the compound of Formula J, I-1, I-2, I-3, (Ib), or (IIb), or a pharmaceutically acceptable salt thereof, having the structure of Formula (IIb-2):

(IIb-2)

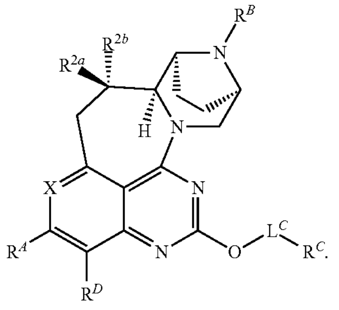

In some embodiments, the present disclosure provides the compound of Formula J, I-1, I-2, I-3, or (Ib), or a pharmaceutically acceptable salt thereof, wherein $L^3$ is $CR^{3a}R^{3b}$. In some embodiments, the present disclosure provides the compound of Formula J, I-1, I-2, I-3, or (b), or a pharmaceutically acceptable salt thereof, wherein $R^{3a}$ and $R^{3b}$ are H.

In some embodiments, the present disclosure provides the compound of Formula J, I-1, I-2, I-3, or (Ib), or a pharmaceutically acceptable salt thereof, having the structure of Formula (Ib-1):

(Ib-1)

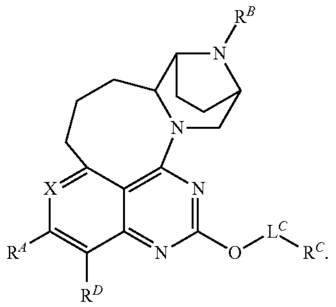

In some embodiments, the present disclosure provides the compound of Formula J, I-1, I-2, I-3, Ib, or Ib-1, or a pharmaceutically acceptable salt thereof, having the structure of Formula (Ib-2):

(Ib-2)

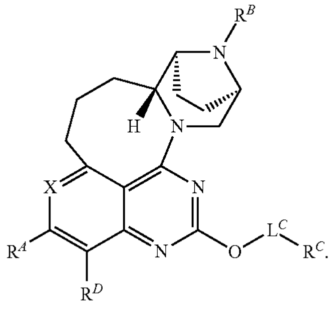

In some embodiments, the present disclosure provides the compound of Formula J, I-1, I-2, I-3, Tb, or Ib-1, or a pharmaceutically acceptable salt thereof, having the structure of Formula (Ib-3):

(Ib-3)

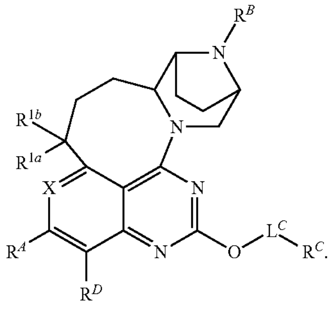

In some embodiments, the present disclosure provides the compound of Formula J, I-1, I-2, I-3, Ib, or Ib-1, or a pharmaceutically acceptable salt thereof, having the structure of Formula (Ib-4):

(Ib-4)

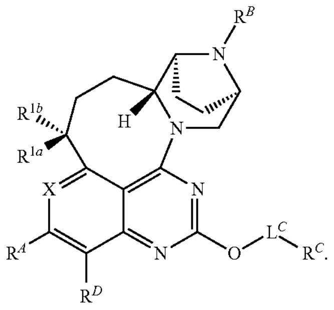

In some embodiments, the present disclosure provides the compound of Formula J, (I-1), (I-2), (I-3), (Ib), (Ib-1), (Ib-2), (Ib-3), (Ib-4), (IIb), (IIb-1), or (IIb-2), or a pharmaceutically acceptable salt thereof, wherein $R^A$ is phenyl substituted with 0, 1, 2, 3, 4, or 5 $R^{A2}$. In some embodiments, the present disclosure provides the compound of Formula J, (I-1), (I-2), (I-3), (Ib), (Ib-1), (Ib-2), (Ib-3), (Ib-4), (IIb), (IIb-1), or (IIb-2), or a pharmaceutically acceptable salt thereof, wherein $R^A$ is phenyl substituted with 0, 1, or 2 $R^{A2}$. In some embodiments, the present disclosure provides the compound of Formula J, (I-1), (I-2), (I-3), (Ib), (Ib-1), (Ib-2), (Ib-3), (Ib-4), (IIb), (IIb-1), or (IIb-2), or a pharmaceutically acceptable salt thereof, wherein $R^A$ is naphthyl substituted with 0, 1, 2, 3, 4, or 5 $R^{A2}$. In some embodiments, the present disclosure provides the compound of Formula J, (I-1), (I-2), (I-3), (Ib), (Ib-1), (Ib-2), (Ib-3), (Ib-4), (IIb), (IIb-1), or (IIb-2), or a pharmaceutically acceptable salt thereof, wherein $R^A$ is naphthyl substituted with 2 or 3 $R^{A2}$. In some embodiments, the present disclosure provides the compound of Formula J, (I-1), (I-2), (I-3), (Ib), (Ib-1), (Ib-2), (Ib-3), (Ib-4), (IIb), (IIb-1), or (IIb-2), or a pharmaceutically acceptable salt thereof, wherein $R^A$ is pyridyl, benzothienyl, benzothiazolyl, or isoquinolinyl, each substituted with 0, 1, 2, 3, 4, or 5 $R^{A2}$.

In some embodiments, the present disclosure provides the compound of Formula J, (I-1), (I-2), (I-3), (Ib), (Ib-1), (Ib-2), (Ib-3), (Ib-4), (IIb), (IIb-1), or (IIb-2), or a pharmaceutically acceptable salt thereof, wherein each $R^{A2}$ is independently $C_1$-$C_6$ alkyl, —OH, $C_2$-$C_6$ alkenyl, $C_2$-$C_6$alkynyl, halo, $C_1$-$C_6$ haloalkyl, —$OR^{A2a}$, —$SR^{A2a}$, or —($C_1$-$C_6$ alkyl)-($C_3$-$C_8$ cycloalkyl), wherein each alkenyl is substituted with 0, 1, 2, or 3 $R^{A3}$; each $R^{A2a}$ is independently $C_1$-$C_6$ haloalkyl, or $C_3$-$C_8$ cycloalkyl; and each $R^{A3}$ is independently halo. In some embodiments, the present disclosure provides the compound of Formula J, (I-1), (I-2), (I-3), (Ib), (Ib-1), (Ib-2), (Ib-3), (Ib-4), (IIb), (IIb-1), or (IIb-2), or a pharmaceutically acceptable salt thereof, wherein each $R^{A2}$ is independently Me, —OH, —C(Cl)═$CH_2$, —CH═$CHF_2$, —C≡CH, F, Cl, —$CH_2CF_3$, —$OCF_3$, —O— cyclopropyl, —$SCF_3$, or —$CH_2$-cyclopropyl. In some embodiments, the present disclosure provides the compound of Formula J, (I-1), (I-2), (I-3), (Ib), (Ib-1), (Ib-2), (Ib-3), (Ib-4), (IIb), (IIb-1), or (IIb-2), or a pharmaceutically acceptable salt thereof, wherein each $R^{A2}$ is independently —OH, $NH_2$, —C≡CH, F, or —$CH_2CH_3$.

In some embodiments, the present disclosure provides the compound of Formula J, (I-1), (I-2), (I-3), (Ib), (Ib-1), (Ib-2), (Ib-3), (Ib-4), (Ib), (IIb-1), or (IIb-2), or a pharmaceutically acceptable salt thereof, wherein $R^A$ is

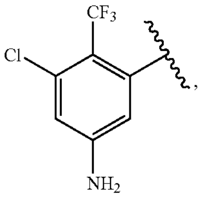,
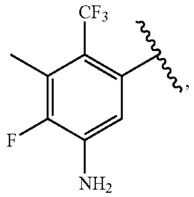,
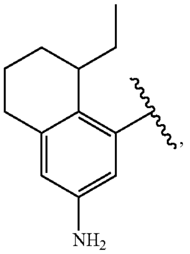,
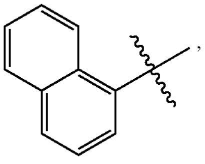,
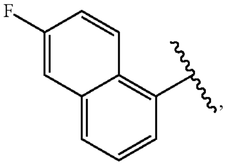,
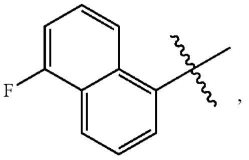,
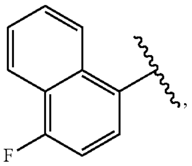,
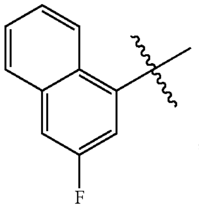,
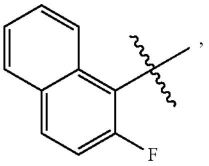,
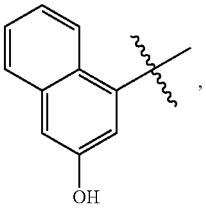, -continued

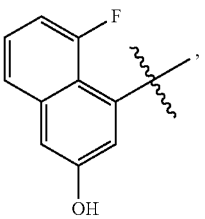,
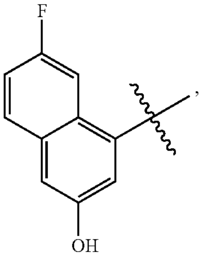,
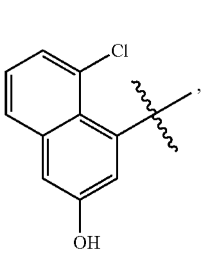,
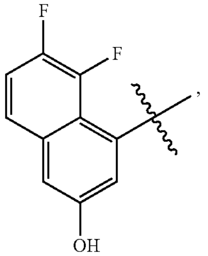,
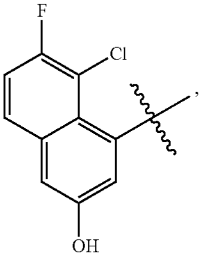,
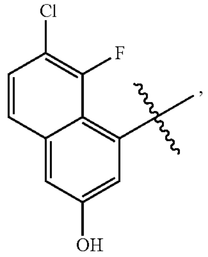,
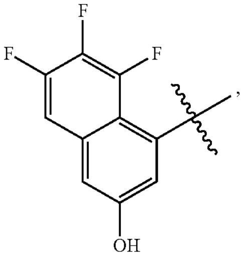,
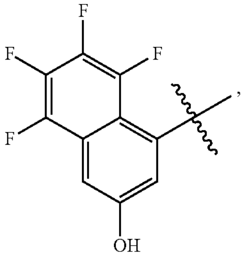,
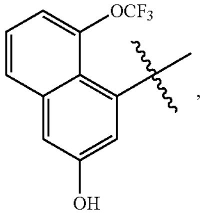,
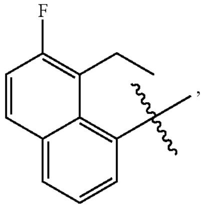,
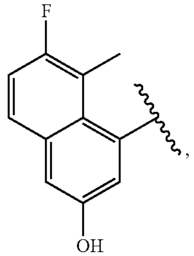,
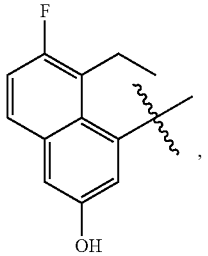, -continued
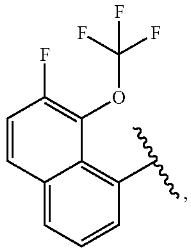,
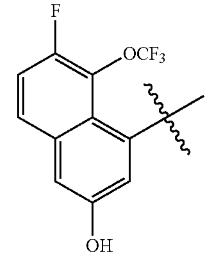,
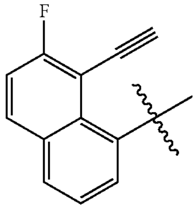,
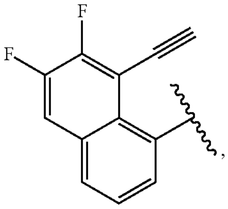,
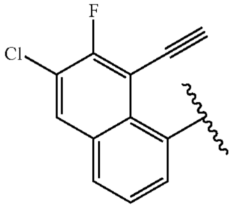,
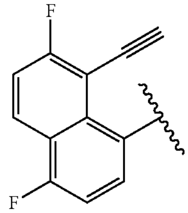,
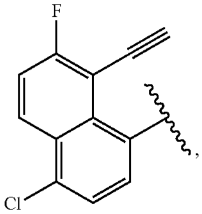,
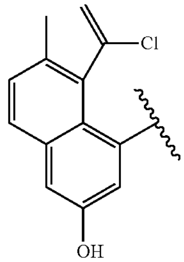,
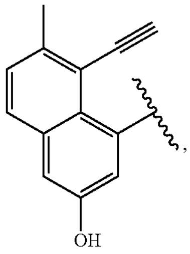,
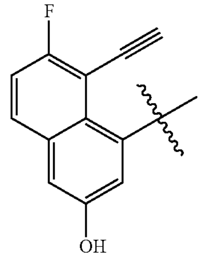,
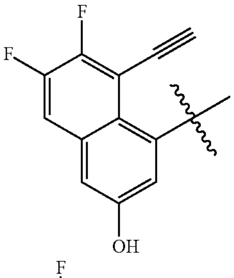,
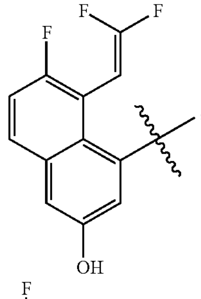,
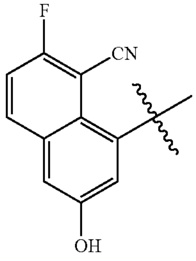,
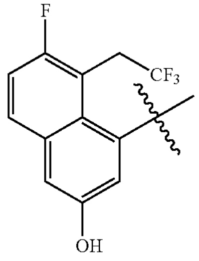,
-continued
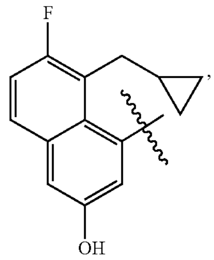,
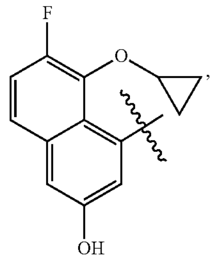,
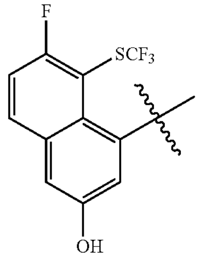,
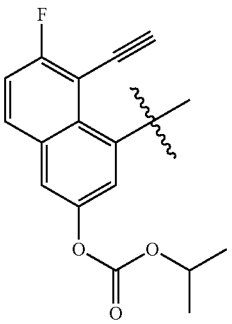,
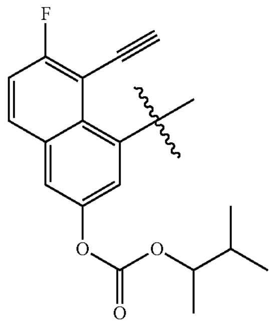,
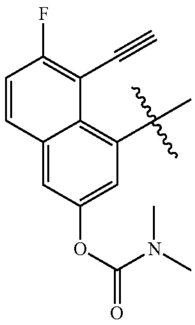,
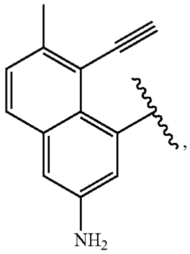,
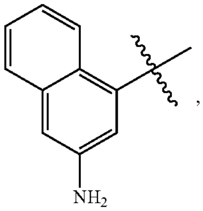,
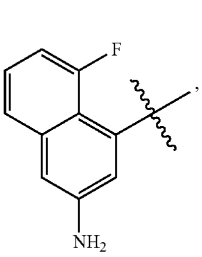,
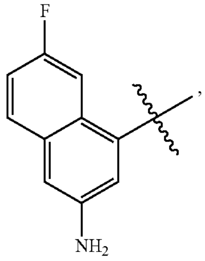,
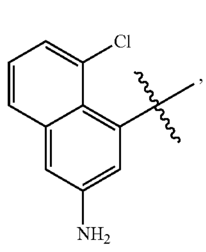,
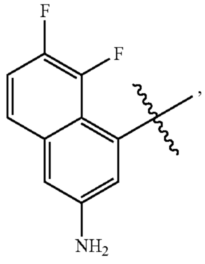, -continued
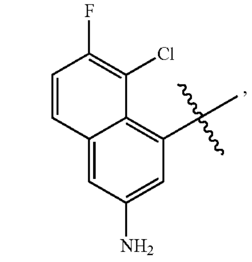,
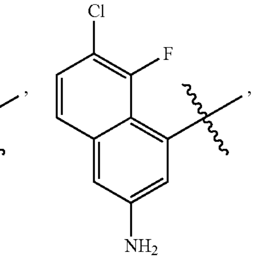,
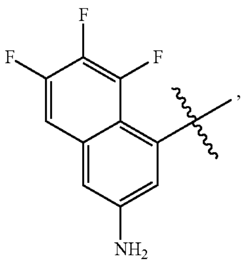,
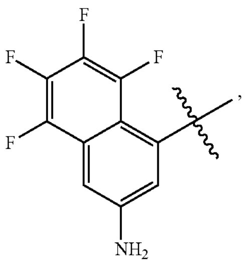,
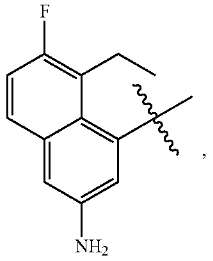,
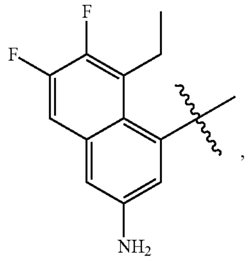,
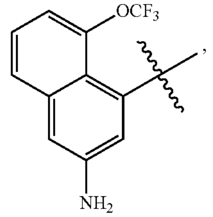,
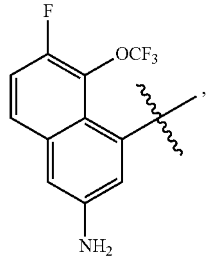,
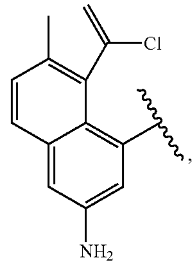,
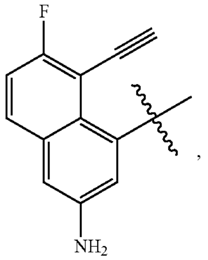,
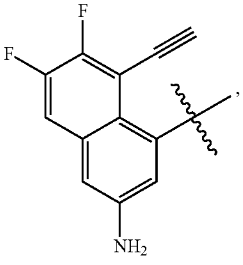,
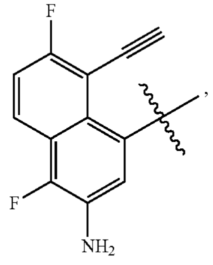,
-continued
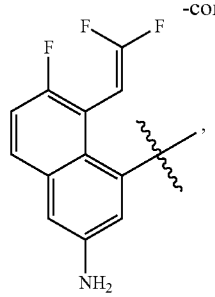,
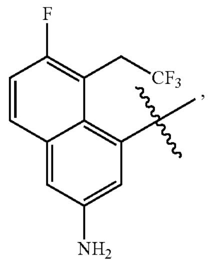,
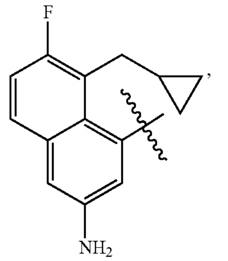,
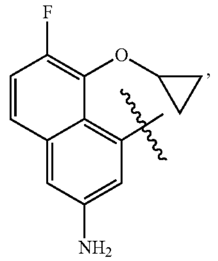,
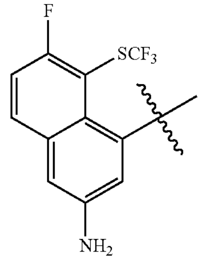,
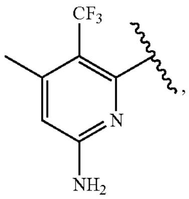,
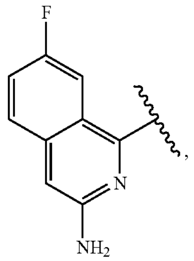,
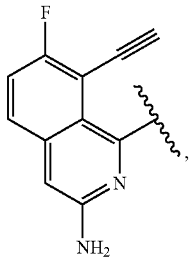,
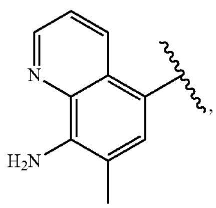,
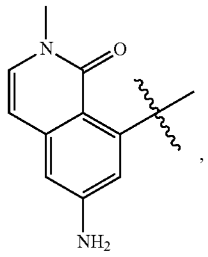,
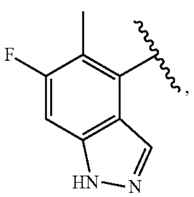,
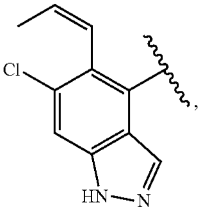,
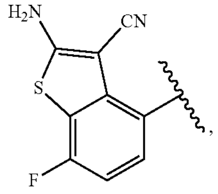,
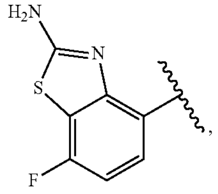, -continued
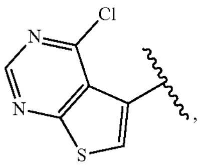,
or
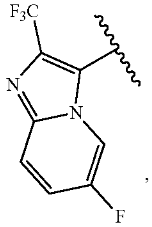,
In some embodiments, the present disclosure provides the compound of Formula J, (I-1), (I-2), (I-3), (Ib), (Ib-1), (Ib-2), (Ib-3), (Ib-4), (Ib), (IIb-1), or (IIb-2), or a pharmaceutically acceptable salt thereof, wherein $R^A$ is
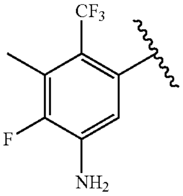,
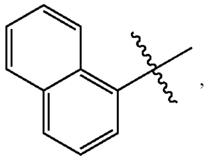,
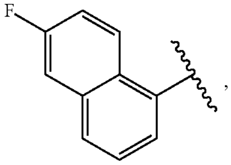,
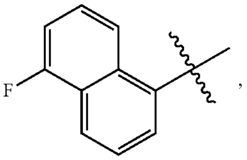,
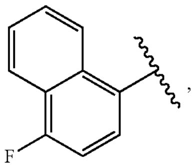,
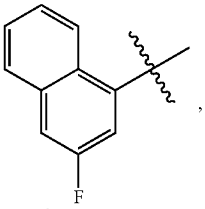,
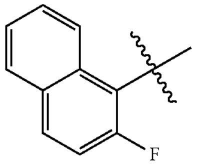,
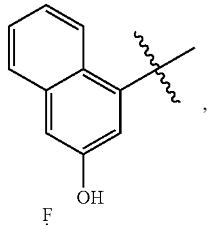,
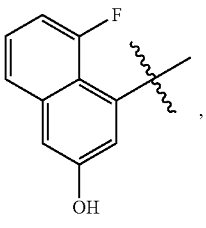,
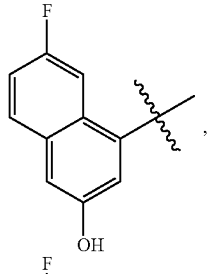,
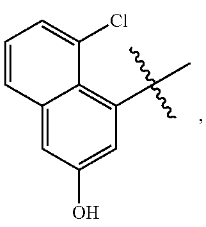,
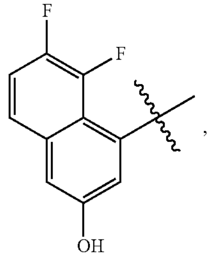,
-continued
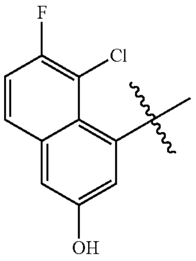,
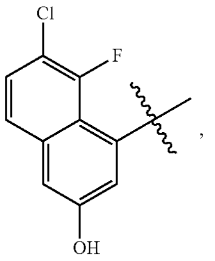,
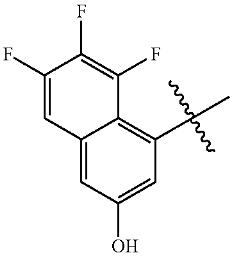,
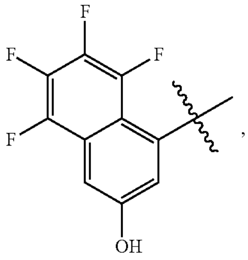,
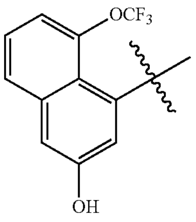,
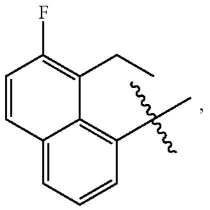,
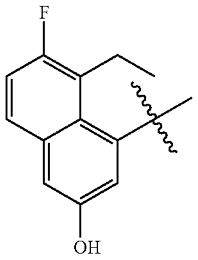,
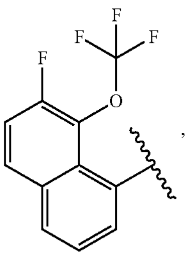,
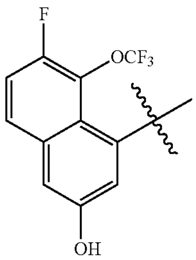,
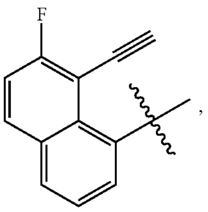,
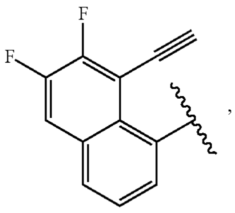,
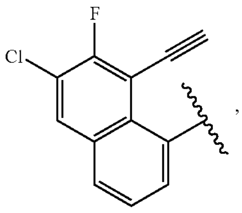,
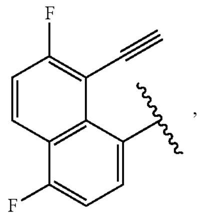,
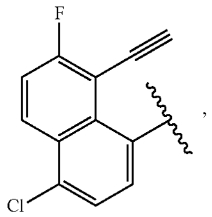, -continued
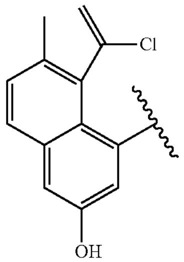,
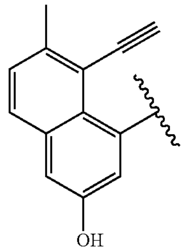,
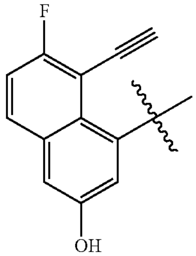,
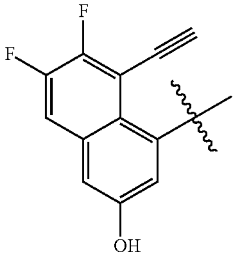,
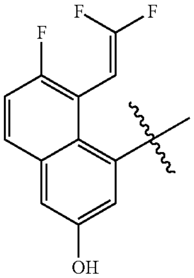,
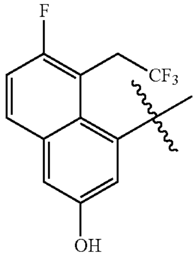,
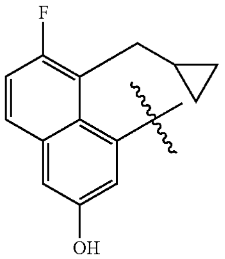,
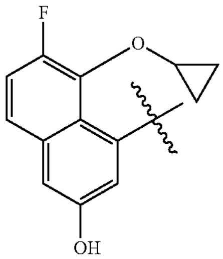,
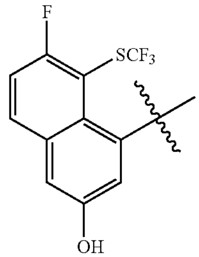,
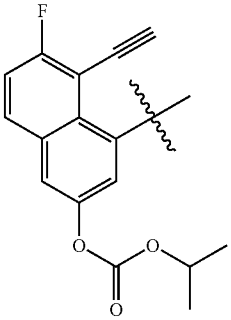,
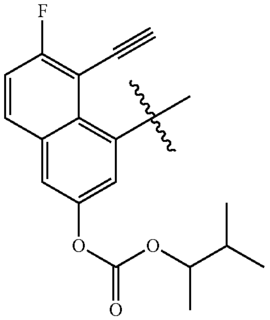,
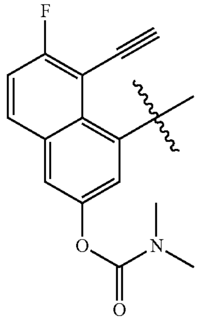,
-continued
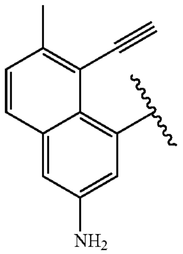,
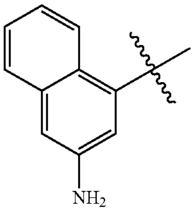,
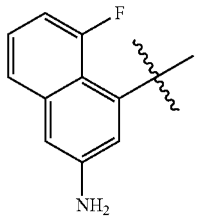,
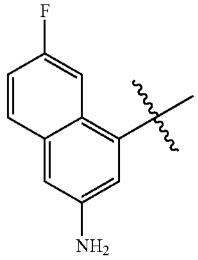,
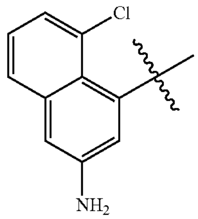,
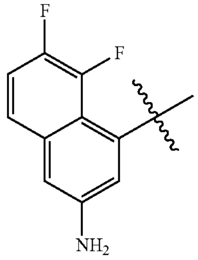,
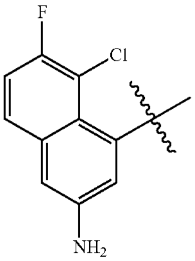,
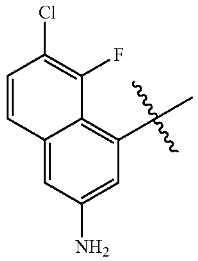,
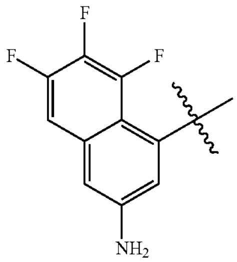,
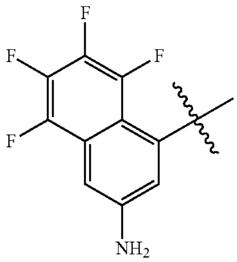,
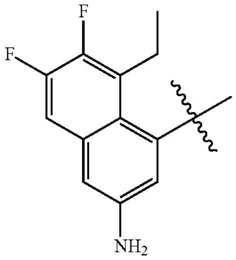,
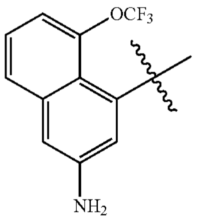, -continued
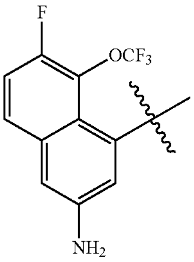, 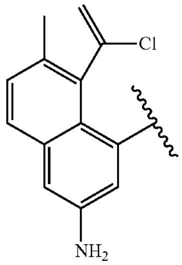,
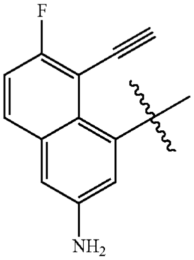, 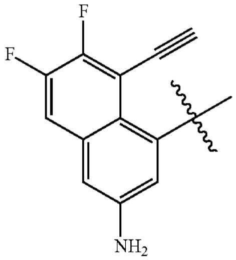,
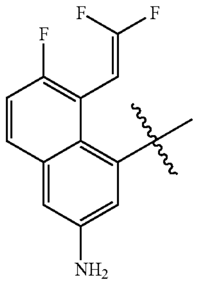, 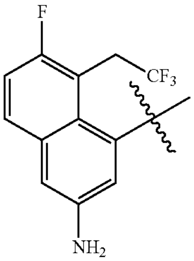,
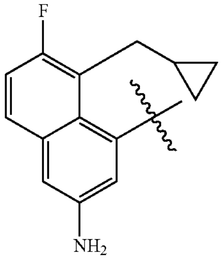, 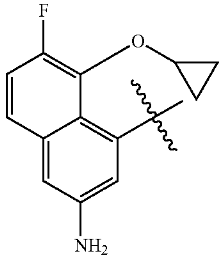,
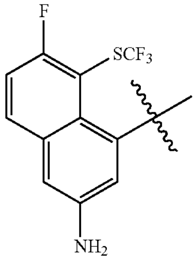, 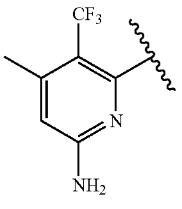,
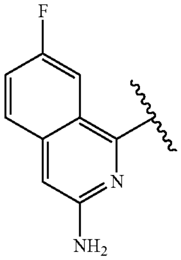, 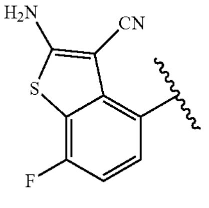, or
-continued
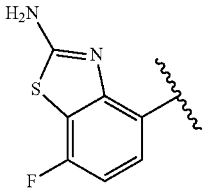.
In some embodiments, the present disclosure provides the compound of Formula J, (I-1), (I-2), (I-3), (Ib), (Ib-1), (Ib-2), (Ib-3), (Ib-4), (Ib), (IIb-1), or (IIb-2), or a pharmaceutically acceptable salt thereof, wherein $R^A$ is
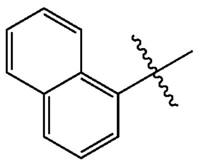, 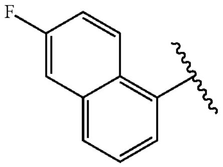,
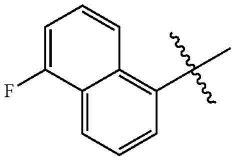, 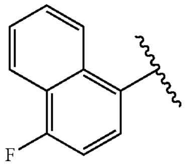,
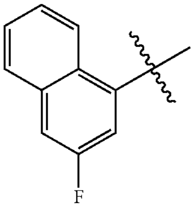, 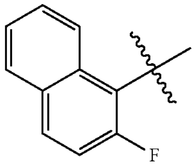,
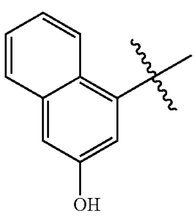, 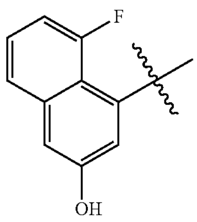,
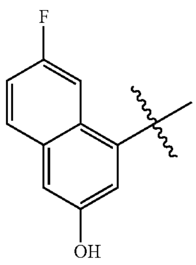, 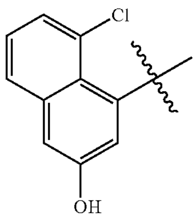,
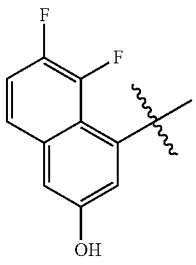, 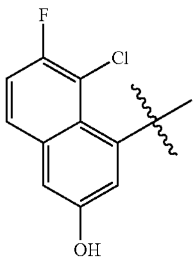, -continued
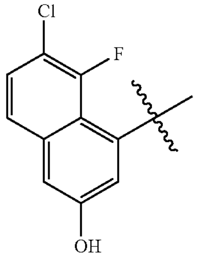, 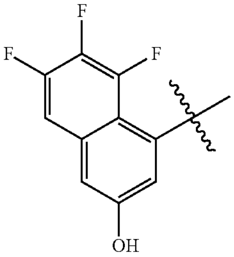,
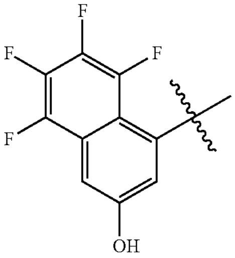, 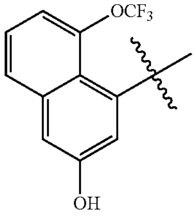,
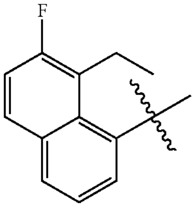, 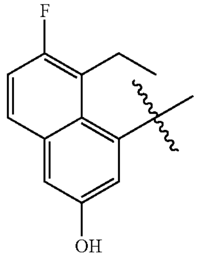,
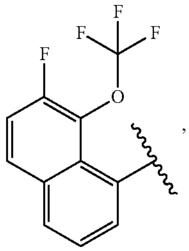, 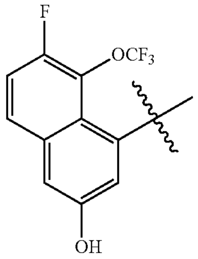,
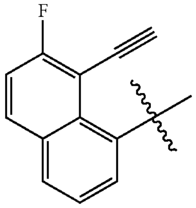, 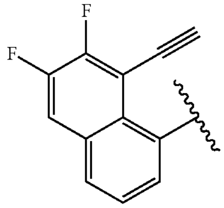,
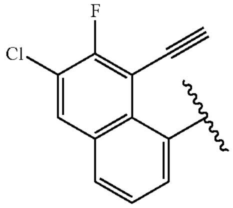, 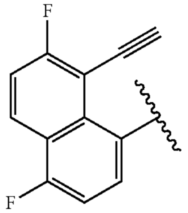,
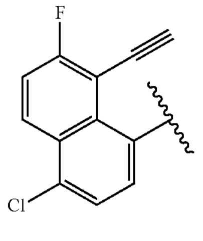, 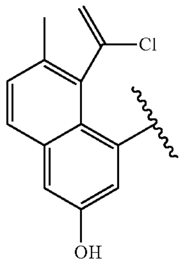,
-continued
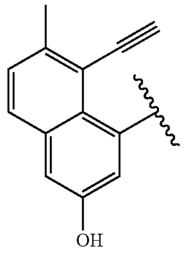, 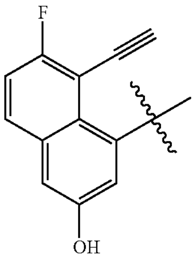,
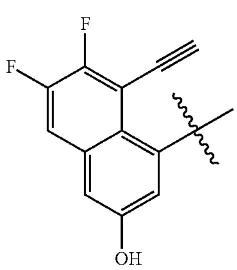, 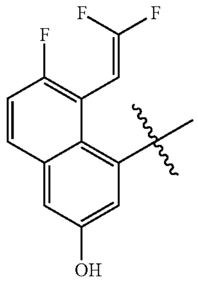,
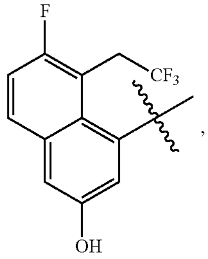, 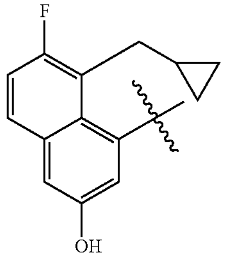,
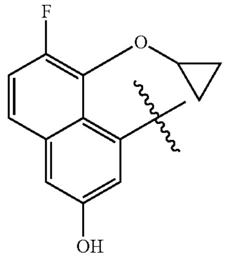, 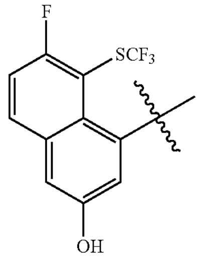,
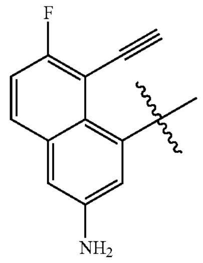, 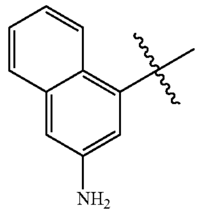,
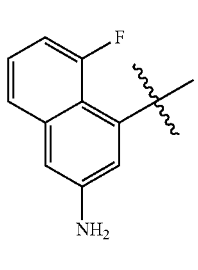, 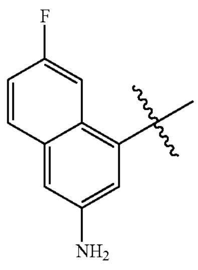, -continued
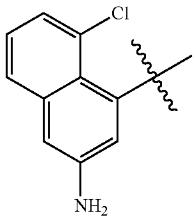
,
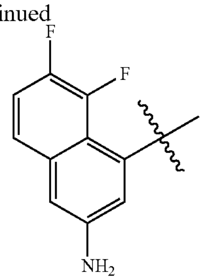
,
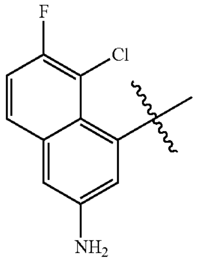
,
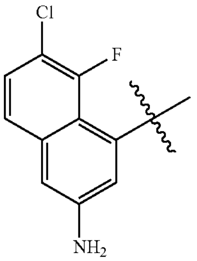
,
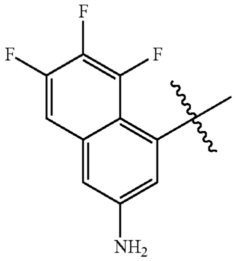
,
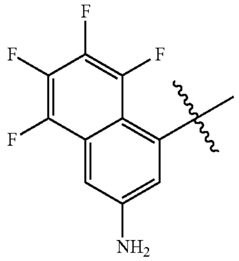
,
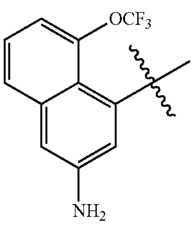
,
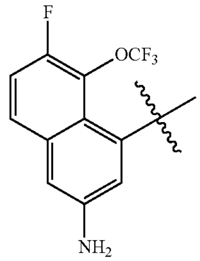
,
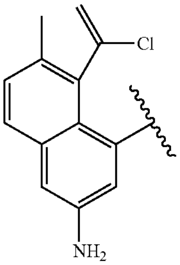
,
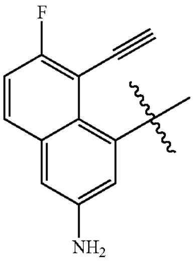 [SMILES: *c1cc(N)cc2ccc(F)c(C#C)c12]
,
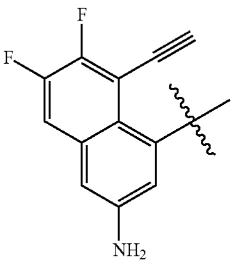
,
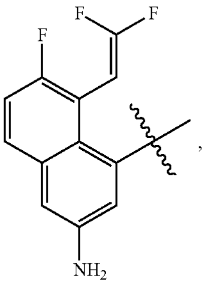
,
-continued
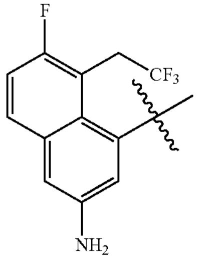
,
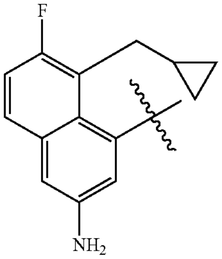
,
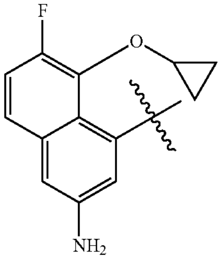
,
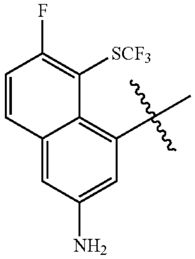
, or
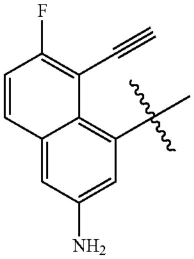
.
In some embodiments, the present disclosure provides the compound of Formula J, (I-1), (I-2), (I-3), (Ib), (Ib-1), (Ib-2), (Ib-3), (Ib-4), (Ib), (IIb-1), or (IIb-2) or a pharmaceutically acceptable salt thereof, wherein $R^A$ is
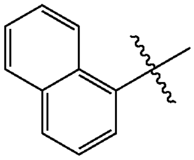
,
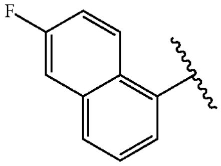
,
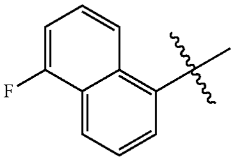
,
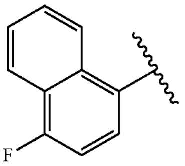
,
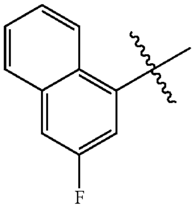
,
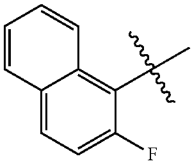
,
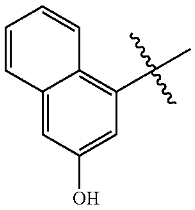
,
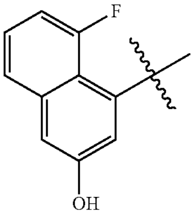
, -continued
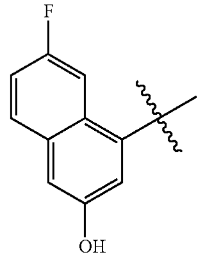,
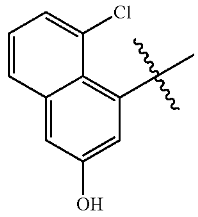,
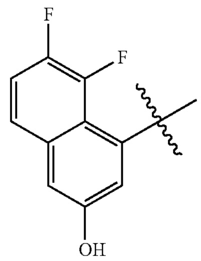,
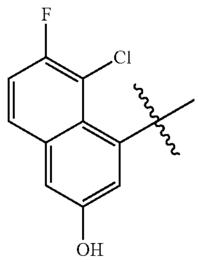,
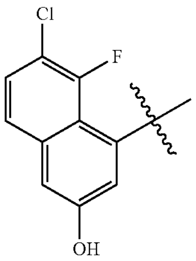,
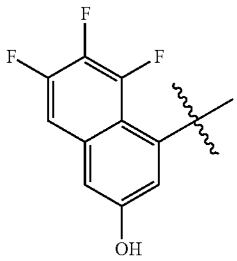,
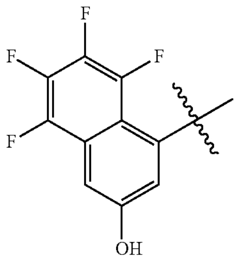,
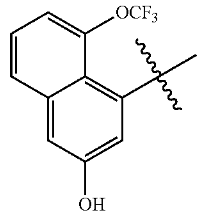,
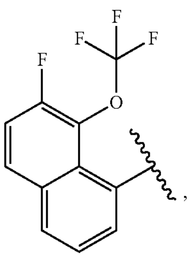,
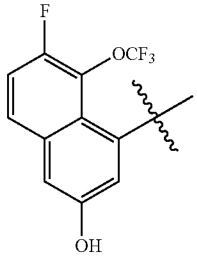,
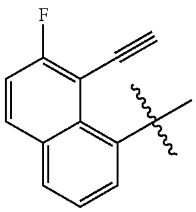,
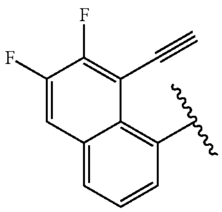,
-continued
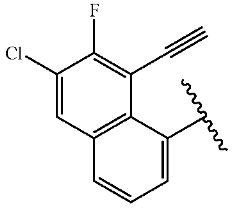,
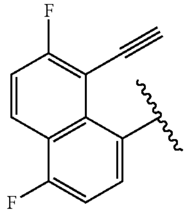,
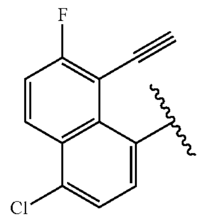,
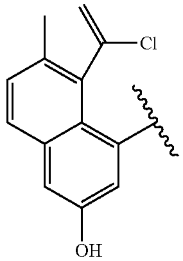,
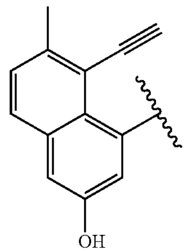,
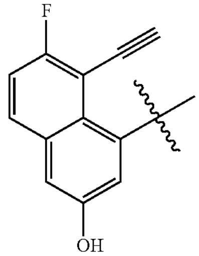,
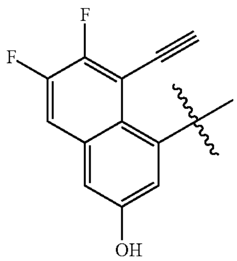,
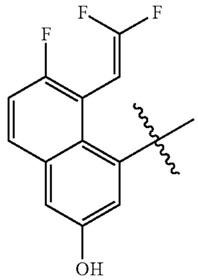,
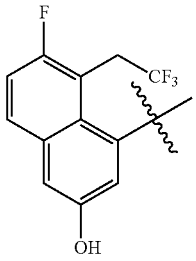,
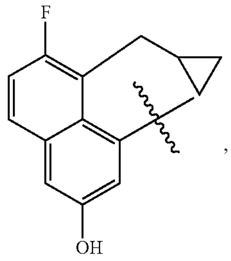,
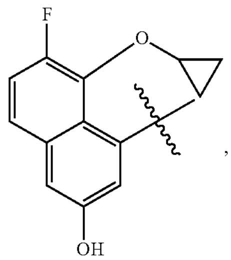, or
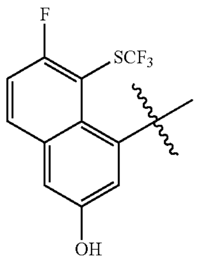.
In some embodiments, the present disclosure provides the compound of Formula J, (I-1), (I-2), (I-3), (Ib), (Ib-1), (Ib-2), (Ib-3), (Ib-4), (Ib), (IIb-1), or (IIb-2), or a pharmaceutically acceptable salt thereof, wherein $R^A$ is

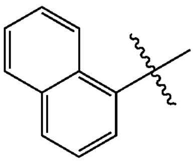,
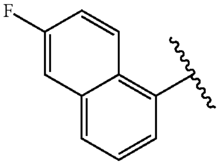,
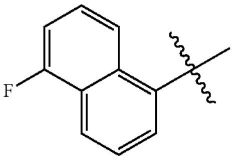,
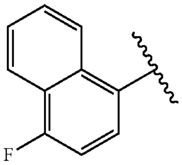,
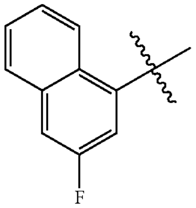,
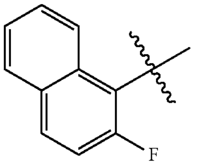,
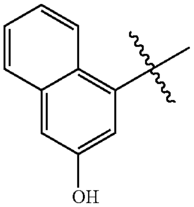,
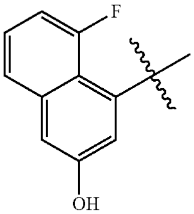,
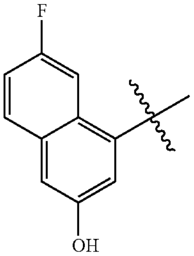,
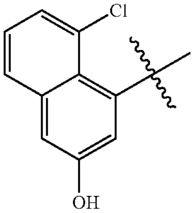,
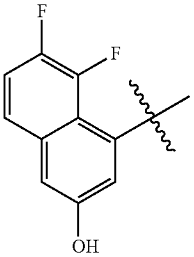,
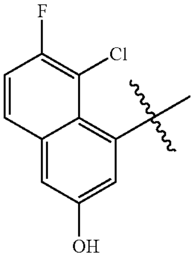,
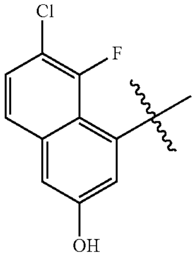,
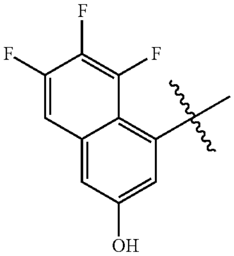,
-continued
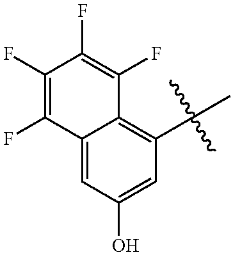,
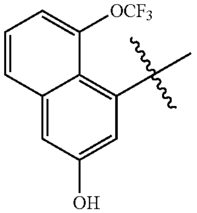,
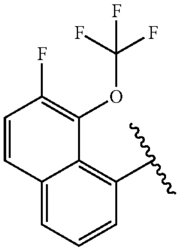,
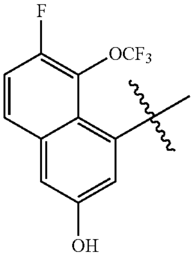,
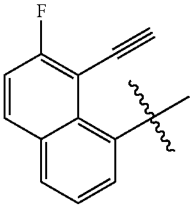,
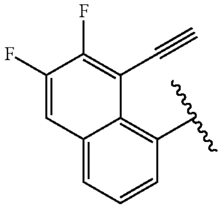,
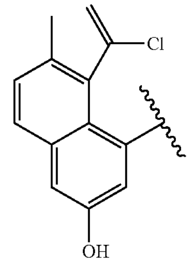,
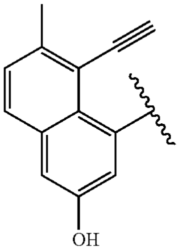,
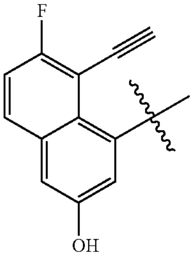,
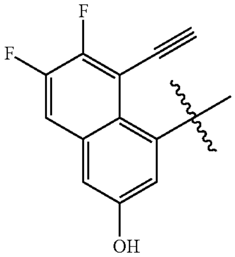,
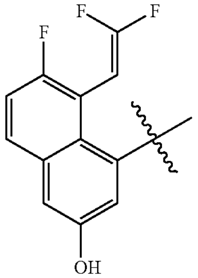,
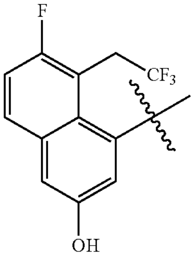, -continued

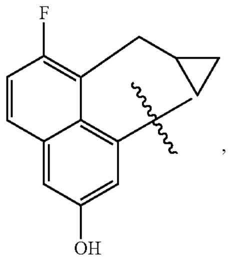
,
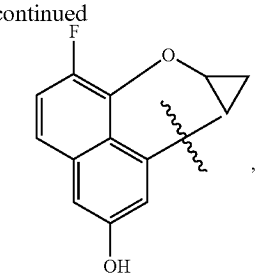
, or
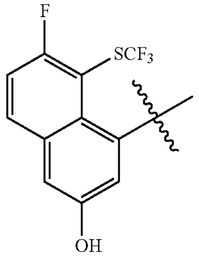
.

In some embodiments, the present disclosure provides the compound of Formula J, (I-1), (I-2), (I-3), (Ib), (Ib-1), (Ib-2), (Ib-3), (Ib-4), (Ib), (IIb-1), or (IIb-2), or a pharmaceutically acceptable salt thereof, wherein $R^A$ is

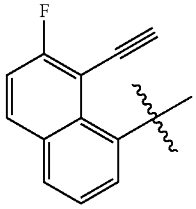
,
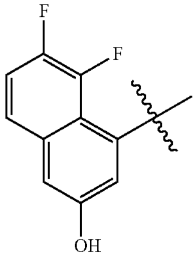
,
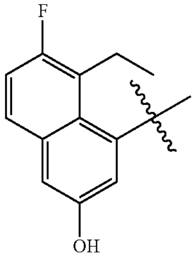
,
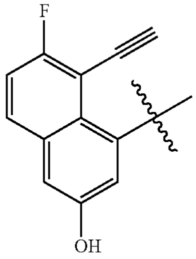
, or
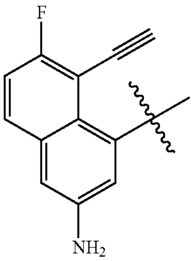
.

In some embodiments, the present disclosure provides the compound of Formula J, (I-1), (I-2), (I-3), (Ib), (Ib-1), (Ib-2), (Ib-3), (Ib-4), (IIb), (IIb-1), or (IIb-2), or a pharmaceutically acceptable salt thereof, wherein $R^A$ is

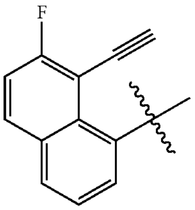
.

In some embodiments, the present disclosure provides the compound of Formula J, (I-1), (I-2), (I-3), (Ib), (b-1), (Ib-2), (Ib-3), (Ib-4), (IIb), (IIb-1), or (Ib-2), or a pharmaceutically acceptable salt thereof, wherein $R^A$ is

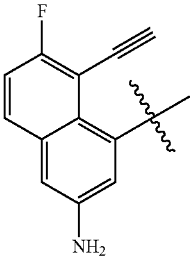

In some embodiments, the present disclosure provides the compound of Formula J, (I-1), (I-2), (I-3), (Ib), (b-1), (Ib-2), (Ib-3), (Ib-4), (IIb), (IIb-1), or (Ib-2), or a pharmaceutically acceptable salt thereof, wherein $R^A$ is

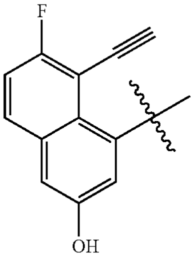
.

In some embodiments, the present disclosure provides the compound of Formula J, (I-1), (I-2), (I-3), (Ib), (Ib-1), (Ib-2), (Ib-3), (Ib-4), (IIb), (IIb-1), or (IIb-2), or a pharmaceutically acceptable salt thereof, wherein $R^B$ is $R^{B1}$.

In some embodiments, the present disclosure provides the compound of Formula J, (I-1), (I-2), (I-3), (Ib), (Ib-1), (Ib-2), (Ib-3), (Ib-4), (IIb), (IIb-1), or (IIb-2), or a pharmaceutically acceptable salt thereof, wherein $R^B$ is H, and at least one $R^{A2}$ is —$OR^{A2x}$.

In some embodiments, the present disclosure provides the compound of Formula J, (I-1), (I-2), (I-3), (Ib), (Ib-1), (Ib-2), (Ib-3), (Ib-4), (IIb), (IIb-1), or (IIb-2), or a pharmaceutically acceptable salt thereof, wherein $R^B$ is $R^{B1}$, and at least one $R^{A2}$ is —$OR^{A2x}$.

In some embodiments, the present disclosure provides the compound of Formula J, (I-1), (I-2), (I-3), (Ib), (Ib-1), (Ib-2), (Ib-3), (Ib-4), (IIb), (IIb-1), or (IIb-2), or a pharmaceutically acceptable salt thereof, wherein $R^{B1}$ and $R^{A2x}$ are each independently:

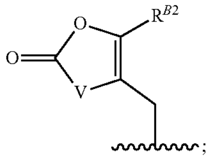;

and

V is each independently $NR^{B2}$ or O.

In some embodiments, the present disclosure provides the compound of Formula J, (I-1), (I-2), (I-3), (Ib), (b-1), (Ib-2), (Ib-3), (Ib-4), (IIb), (IIb-1), or (IIb-2), or a pharmaceutically acceptable salt thereof, wherein $R^{B1}$ and $R^{A2x}$ are each independently:

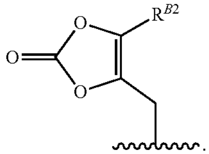.

In some embodiments, the present disclosure provides the compound of Formula J, (I-1), (I-2), (I-3), (Ib), (Ib-1), (Ib-2), (Ib-3), (Ib-4), (IIb), (IIb-1), or (IIb-2), or a pharmaceutically acceptable salt thereof, wherein each $R^{B2}$ is independently $C_1$-$C_6$ alkyl, $C_3$-$C_8$ cycloalkyl, $C_6$-$C_{14}$ aryl, or 5- to 14-membered heteroaryl, wherein the $C_3$-$C_8$ cycloalkyl, $C_6$-$C_{14}$ aryl or 5- to 14-membered heteroaryl are substituted with 0, 1, or 2 $R^{B2}$c; and each $R^{B2}$c is independently $C_1$-$C_6$ alkyl, halo, $C_1$-$C_6$ haloalkyl, —CN, or $C_3$-$C_{10}$ cycloalkyl. In some embodiments, the present disclosure provides the compound of Formula J, (I-1), (I-2), (I-3), (Ib), (Ib-1), (Ib-2), (Ib-3), (Ib-4), (IIb), (IIb-1), or (IIb-2), or a pharmaceutically acceptable salt thereof, wherein each $R^{B2}$ is independently $C_1$-$C_4$ alkyl or $C_6$-$C_{10}$ aryl. In some embodiments, the present disclosure provides the compound of Formula J, (I-1), (I-2), (I-3), (Ib), (Ib-1), (Ib-2), (Ib-3), (Ib-4), (IIb), (IIb-1), or (IIb-2), or a pharmaceutically acceptable salt thereof, wherein each $R^{B2}$ is independently methyl, ethyl, n-propyl, n-butyl, tert-butyl, n-pentyl, n-hexyl, n-octyl, cyclohexyl, or Ph. In some embodiments, the present disclosure provides the compound of Formula J, (I-1), (I-2), (I-3), (Ib), (Ib-1), (Ib-2), (Ib-3), (Ib-4), (IIb), (IIb-1), or (IIb-2), or a pharmaceutically acceptable salt thereof, wherein each $R^{B2}$ is independently methyl, ethyl, n-propyl, iso-propyl, tert-butyl, or Ph. In some embodiments, the present disclosure provides the compound of Formula J, (I-1), (I-2), (I-3), (Ib), (Ib-1), (Ib-2), (Ib-3), (Ib-4), (IIb), (IIb-1), or (IIb-2), or a pharmaceutically acceptable salt thereof, wherein each $R^{B2}$ is independently methyl, or ethyl.

In some embodiments, the present disclosure provides the compound of Formula J, (I-1), (I-2), (I-3), (Ib), (Ib-1), (Ib-2), (Ib-3), (Ib-4), (IIb), (IIb-1), or (Ib-2), or a pharmaceutically acceptable salt thereof, wherein $R^{B1}$ is

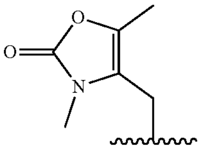,

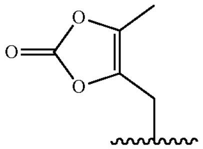,

-continued

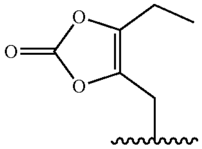,

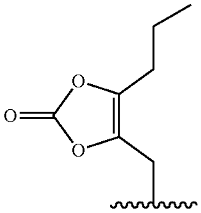,

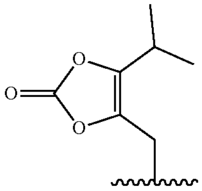,

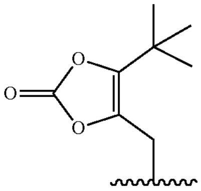,

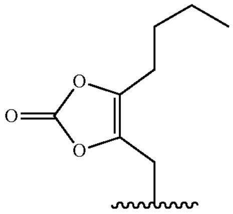,

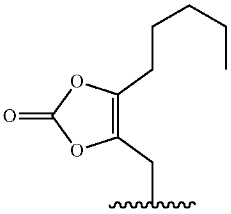,

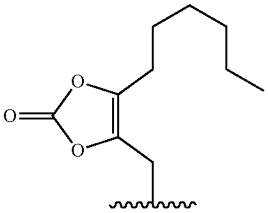,

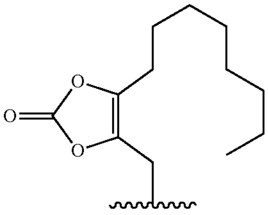,

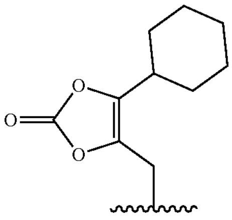, or

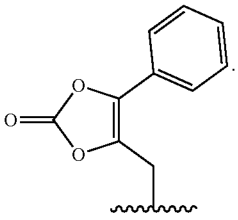.

In some embodiments, the present disclosure provides the compound of Formula J, (I-1), (I-2), (I-3), (b), (Ib-1), (b-2), (Ib-3), (b-4), (Ib), (IIb-1), or (Ib-2), or a pharmaceutically acceptable salt thereof, wherein $R^{B1}$ is

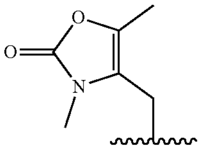,

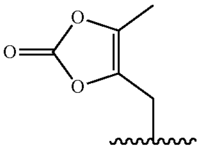,

-continued

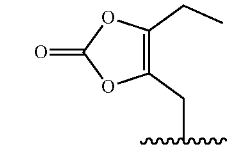,
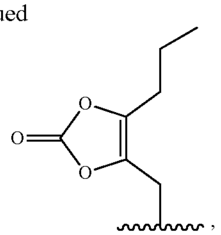,

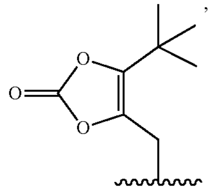,
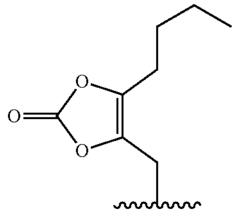,

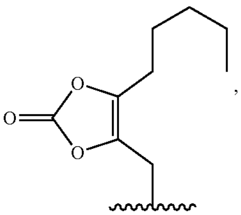,
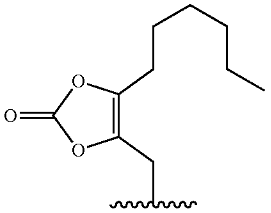,

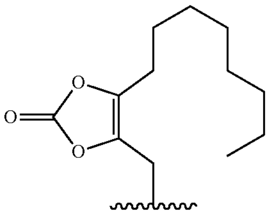,

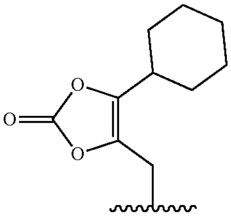, or
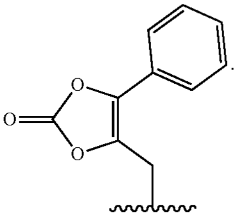.

In some embodiments, the present disclosure provides the compound of Formula J, (I-1), (I-2), (I-3), (Ib), (Ib-1), (Ib-2), (Ib-3), (Ib-4), (Ib), (IIb-1), or (IIb-2), or a pharmaceutically acceptable salt thereof, wherein $R^{B1}$ is

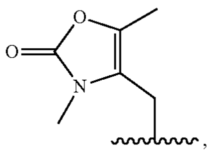,
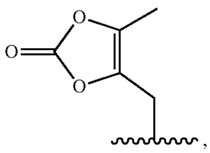,

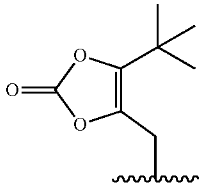, or
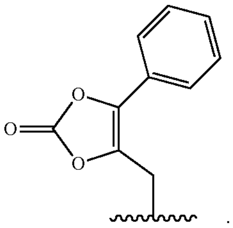.

In some embodiments, the present disclosure provides the compound of Formula J, (I-1), (I-2), (I-3), (b), (Ib-1), (b-2), (Ib-3), (b-4), (Ib), (IIb-1), or (Ib-2), or a pharmaceutically acceptable salt thereof, wherein $R^{B1}$ and $R^{A2x}$ are each

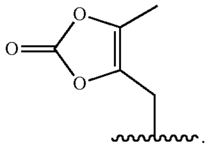 [SMILES: *Cc1oc(=O)oc1C].

In some embodiments, the present disclosure provides the compound of Formula J, (I-1), (I-2), (I-3), (Ib), (Ib-1), (Ib-2), (Ib-3), (Ib-4), (Ib), (IIb-1), or (IIb-2), or a pharmaceutically acceptable salt thereof, wherein $R^{B1}$ and $R^{A2x}$ are each

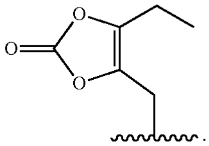 [SMILES: *Cc1oc(=O)oc1CC].

In some embodiments, the present disclosure provides the compound of Formula J, (I-1), (I-2), (I-3), (Ib), (Ib-1), (Ib-2), (Ib-3), (Ib-4), (IIb), (IIb-1), or (IIb-2), or a pharmaceutically acceptable salt thereof, wherein $R^{B1}$ is

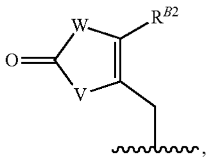, $R^{B2}$ is $C_1$-$C_3$ alkyl; and each $R^{A2}$ is independently —OH, F, $C_1$-$C_3$ alkyl, $NH_2$, $C_2$-$C_3$ alkynyl, or $C_1$-$C_3$ haloalkyl. In some embodiments, each $R^{A2}$ is independently —OH, F, $NH_2$, or ethynyl.

In some embodiments, the present disclosure provides the compound of Formula J, (I-1), (I-2), (I-3), (Ib), (b-1), (b-2), (Ib-3), (b-4), (IIb), (IIb-1), or (Ib-2), or a pharmaceutically acceptable salt thereof, wherein $L^C$ is

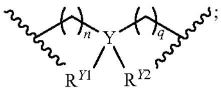;

Y is C or Si; n is 0 or 1; q is 0 or 1; $R^{Y1}$ is H or $C_1$-$C_3$ alkyl; and $R^{Y2}$ is H or $C_1$-$C_3$ alkyl; alternatively, $R^{Y1}$ and $R^{Y2}$ combine to form a $C_3$-$C_6$ cycloalkyl.

In some embodiments, the present disclosure provides the compound of Formula J, (I-1), (I-2), (I-3), (Ib), (Ib-1), (Ib-2), (Ib-3), (Ib-4), (IIb), (IIb-1), or (IIb-2), or a pharmaceutically acceptable salt thereof, wherein $L^C$ is

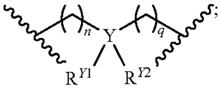;

Y is C or Si; n is 0 or 1; q is 0 or 1; $R^{Y1}$ is H or Me; and $R^{Y2}$ is H or Me; alternatively, $R^{Y1}$ and $R^{Y2}$ combine to form a cyclopropyl.

In some embodiments, the present disclosure provides the compound of Formula J, (I-1), (I-2), (I-3), (Ib), (Ib-1), (Ib-2), (Ib-3), (Ib-4), (IIb), (IIb-1), or (IIb-2), or a pharmaceutically acceptable salt thereof, wherein $R^C$ is 3- to 14-membered heterocyclyl, substituted with 0, 1, 2, or 3 $R^{C3}$;

each $R^{C3}$ is independently $C_1$-$C_6$ alkyl, halo, $C_1$-$C_6$ haloalkyl, $=CH_2$, $—OR^{C3a}$, or $—(C_1$-$C_6$ alkyl)-(5- to 10-membered heteroaryl), wherein each alkyl is substituted with 1-OC(O)N($R^{C3a1}$)($R^{C3a2}$), $—OR^{C3a1}$, or $N_3$;

each $R^{c3a}$ is independently $C_1$-$C_6$ haloalkyl; and each $R^{c3a1}$ and $R^{c3a2}$ is independently $C_1$-$C_3$ alkyl, $C_1$-$C_6$ haloalkyl, $C_6$-$C_{10}$ aryl, or 5- to 10-membered heteroaryl wherein each aryl or heteroaryl, is substituted with 0, 1, 2, 3, or 4 halo, $C_1$-$C_3$haloalkyl, $C_1$-$C_3$ haloalkoxy, or $SF_5$;

alternatively, $R^{c3a1}$ and $R^{c3a2}$ together with the N to which they are attached form a 3- to 8-membered heterocycle.

In some embodiments, the present disclosure provides the compound of Formula J, (I-1), (I-2), (I-3), (Ib), (Ib-1), (Ib-2), (Ib-3), (Ib-4), (IIb), (IIb-1), or (IIb-2), or a pharmaceutically acceptable salt thereof, wherein $R^C$ is 3- to 14-membered heterocyclyl, substituted with 0, 1, 2, or 3 $R^{C3}$;

each $R^{C3}$ is independently $C_1$-$C_6$ alkyl, halo, $C_1$-$C_6$ haloalkyl, $=CH_2$, $—OR^{c3a}$, or $—(C_1$-$C_6$ alkyl)-(5- to 10-membered heteroaryl), wherein each alkyl is substituted with 1-OC(O)N($R^{C3a1}$)($R^{C3a2}$), $—OR^{C3a1}$, or $N_3$;

each $R^{C3a}$ is independently $C_1$-$C_6$ haloalkyl; and each $R^{C3a1}$ and $R^{C3a2}$ is independently $C_1$-$C_3$ alkyl, $C_1$-$C_6$ haloalkyl, or $C_6$-$C_{10}$ aryl, wherein each aryl, is substituted with 1 $SF_5$;

alternatively, $R^{C3a1}$ and $R^{C3a2}$ together with the N to which they are attached form a 3- to 8-membered heterocycle.

In some embodiments, the present disclosure provides the compound of Formula J, (I-1), (I-2), (I-3), (Ib), (b-1), (b-2), (Ib-3), (b-4), (IIb), (IIb-1), or (Ib-2), or a pharmaceutically acceptable salt thereof, wherein $L^C$ is

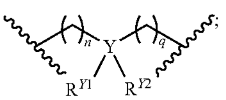

Y is C; n is 0; q is 0; $R^{Y1}$ is H; and $R^{Y2}$ H. In some embodiments, the present disclosure provides the compound of Formula J, (I-1), (I-2), (I-3), (Ib), (Ib-1), (Ib-2), (Ib-3), (Ib-4), (IIb), (IIb-1), or (IIb-2), or a pharmaceutically acceptable salt thereof, wherein $L^C$ is $—CH_2—$.

In some embodiments, the present disclosure provides the compound of Formula J, (I-1), (I-2), (I-3), (Ib), (Ib-1), (Ib-2), (Ib-3), (Ib-4), (IIb), (IIb-1), or (IIb-2), or a pharmaceutically acceptable salt thereof, wherein $R^C$ is 8- to 14-membered heterocyclyl, is substituted with 0, 1, 2, or 3 $R^{C3}$;

each $R^{C3}$ is independently $C_1$-$C_6$ alkyl, halo, $=CH_2$, $—OR^{c3a}$, or $—(C_1$-$C_6$ alkyl)-(5- to 10-membered heteroaryl), wherein each alkyl is substituted with 1 —OC(O)N($R^{C3a1}$)($R^{C3a2}$), $—OR^{c3a1}$ or $N_3$;

each $R^{C3a}$ is independently $C_1$-$C_6$ haloalkyl; and each $R^{C3a1}$ and $R^{C3a2}$ is independently $C_1$-$C_3$ alkyl, $C_1$-$C_6$ haloalkyl, or $C_6$-$C_{10}$ aryl, wherein each aryl is substituted with 1 $SF_5$;

alternatively, $R^{C3a1}$ and $R^{C3a2}$ together with the N to which they are attached form a 3- to 8-membered heterocycle.

In some embodiments, the present disclosure provides the compound of Formula J, (I-1), (I-2), (I-3), (Ib), (b-1), (b-2), (Ib-3), (b-4), (IIb), (IIb-1), or (Ib-2), or a pharmaceutically acceptable salt thereof, wherein $L^C$ is

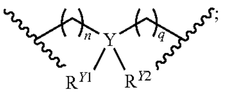

Y is C or Si; n is 1; q is 1; $R^{Y1}$ is Me; and $R^{Y2}$ is Me; alternatively, $R^{Y1}$ and $R^{Y2}$ combine to form a cyclopropyl. In some embodiments, the present disclosure provides the compound of Formula J, (I-1), (I-2), (I-3), (Ib), (Ib-1), (Ib-2), (Ib-3), (Ib-4), (Ib), (IIb-1), or (IIb-2), or a pharmaceutically acceptable salt thereof, wherein $R^C$ is 3- to 7-membered heterocyclyl, substituted with 0, 1, or 2 $R^{C3}$; and each $R^{C3}$ is independently halo or $C_1$-$C_6$ haloalkyl.

In some embodiments, the present disclosure provides the compound of Formula J, (I-1), (I-2), (I-3), (Ib), (Ib-1), (Ib-2), (Ib-3), (Ib-4), (Ib), (IIb-1), or (IIb-2), or a pharmaceutically acceptable salt thereof, wherein $R^{1b}$ is H or methyl; $R^{C3}$ is $—CH_2OR^{C3a1}$ or F; and $R^{c3a1}$ is 5- to 6-membered heteroaryl substituted with one halo or $C_1$-$C_2$ haloalkyl. In some embodiments, the present disclosure provides the compound of Formula J, (I-1), (I-2), (I-3), (Ib), (Ib-1), (Ib-2), (Ib-3), (Ib-4), (Ib), (IIb-1), or (IIb-2), or a pharmaceutically acceptable salt thereof, wherein $R^{1b}$ is H or methyl; and $R^{C3}$ is F. In some embodiments, the present disclosure provides the compound of Formula J, (I-1), (I-2), (I-3), (Ib), (Ib-1), (Ib-2), (Ib-3), (Ib-4), (IIb), (IIb-1), or (IIb-2), or a pharmaceutically acceptable salt thereof, wherein $R^{1b}$ is H or methyl; $R^{C3}$ is $—CH_2OR^{C3a1}$; and $R^{c3a1}$ is 6-membered heteroaryl substituted with one $C_1$ haloalkyl. In some embodiments, the present disclosure provides the compound of Formula J, (I-1), (I-2), (I-3), (Ib), (b-1), (Ib-2), (Ib-3), (Ib-4), (IIb), (IIb-1), or (IIb-2), or a pharmaceutically acceptable salt thereof, wherein $R^{1b}$ is H or methyl; $R^{C3}$ is $—CH_2OR^{C3a1}$; and $R^{c3a1}$ is pyridazine, pyrimidine, or pyrazine, wherein the pyridazine, pyrimidine, or pyrazine is substituted with one $CF_3$.

In some embodiments, the present disclosure provides the compound of Formula J, (I-1), (I-2), (I-3), (Ib), (b-1), (Ib-2), (Ib-3), (Ib-4), (IIb), (IIb-1), or (Ib-2), or a pharmaceutically acceptable salt thereof, wherein $L^C$ is $—CH_2—$; $R^C$ is 3- to 14-membered heterocyclyl substituted with 1 $R^{C3}$; $R^{C3}$ is $C_1$-$C_6$ alkyl substituted with one $—OR^{c3a1}$ or $—SR^{C3a1}$; and $R^{c3a1}$ is 5- to 10-membered heteroaryl substituted with 0, 1, or 2 $C_1$-$C_3$ haloalkyl or $C_1$-$C_3$ haloalkoxy. In some embodiments, the present disclosure provides the compound of Formula J, (I-1), (I-2), (I-3), (Ib), (b-1), (b-2), (b-3), (b-4), (IIb), (IIb-1), or (IIb-2), or a pharmaceutically acceptable salt thereof, wherein $L^C$ is $—CH_2—$; $R^C$ is 4- to 8-membered heterocyclyl substituted with 1 $R^{C3}$; $R^{C3}$ is $—CH_2OR^{C3a1}$; and $R^{C3a1}$ is a pyrimidine, wherein the pyrimidine is substituted with 1 trifluoromethyl group.

In some embodiments, the present disclosure provides the compound of Formula J, (I-1), (I-2), (I-3), (Ib), (b-1), (b-2), (Ib-3), (b-4), (IIb), (IIb-1), or (Ib-2), or a pharmaceutically acceptable salt thereof, wherein the —O-$L^C$-$R^C$ moiety is
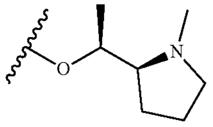
,
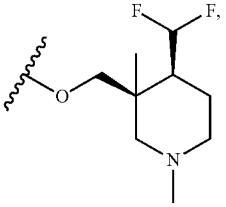
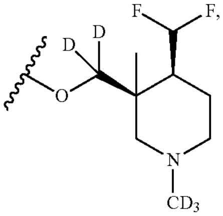
,
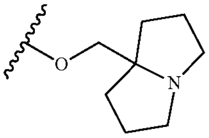
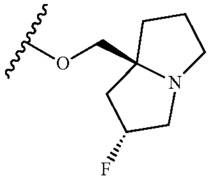
,
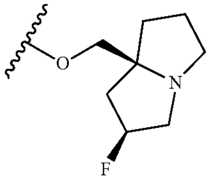
,
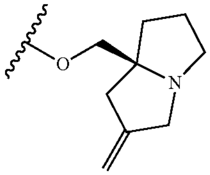
,
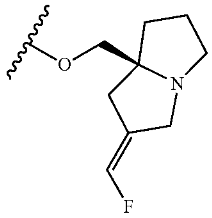
,
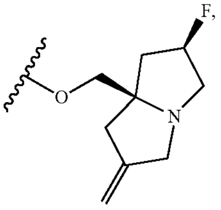
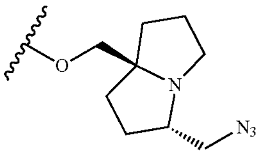
,
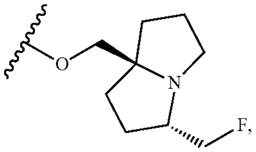
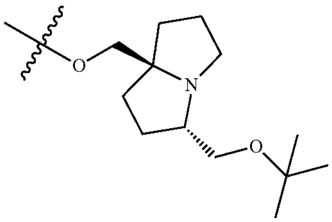
,
-continued
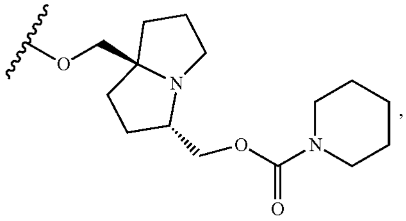
,
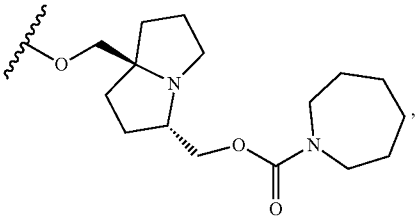
,
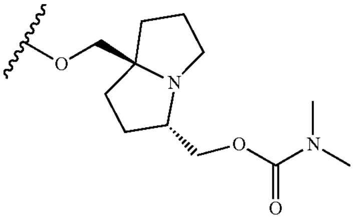
,
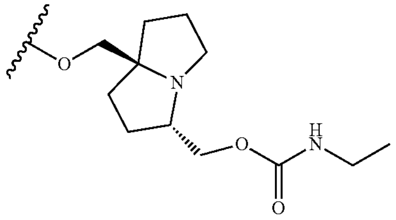
,
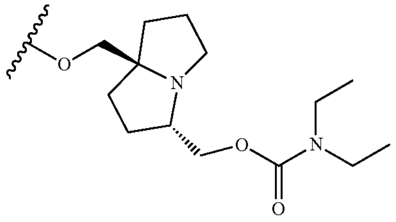
,
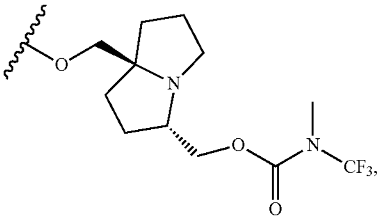
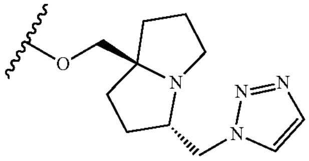
,
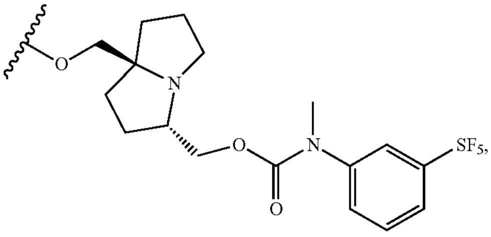

-continued
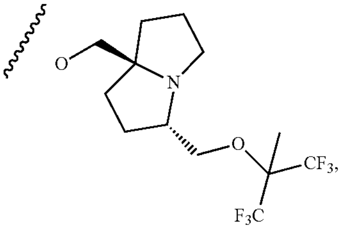
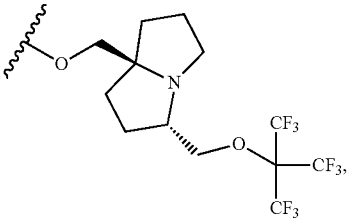
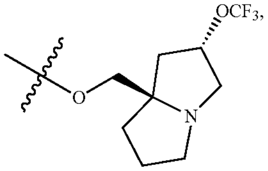
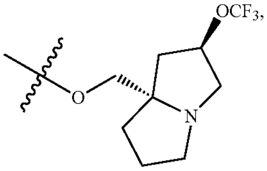
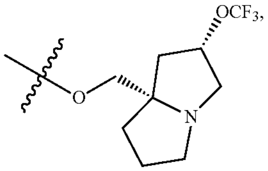
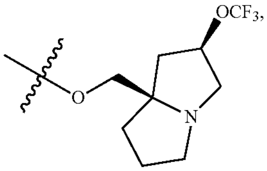
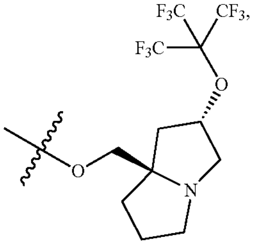
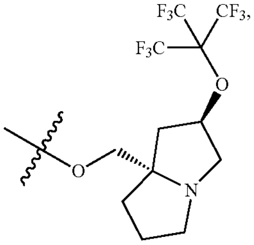
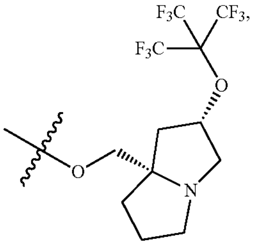
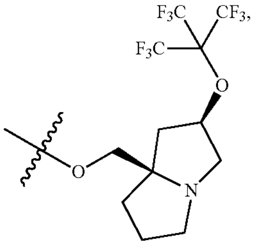
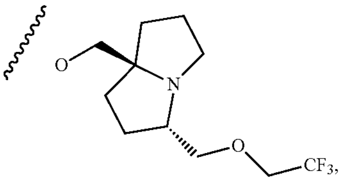
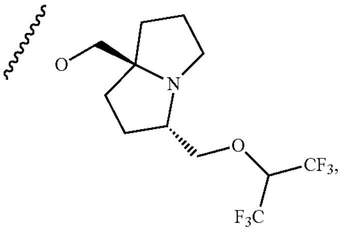
-continued
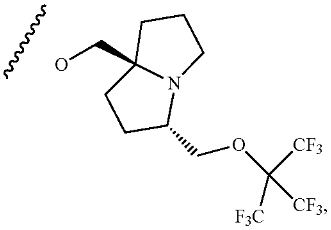
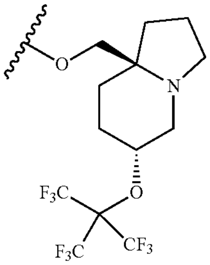
,
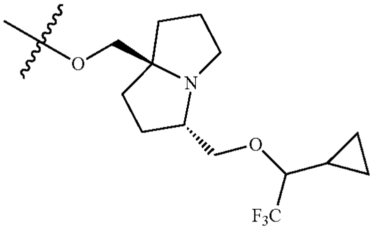
,
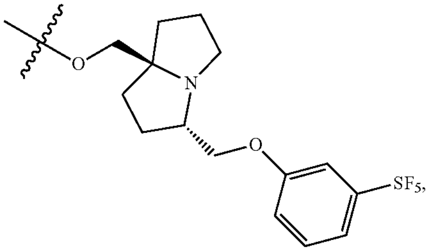
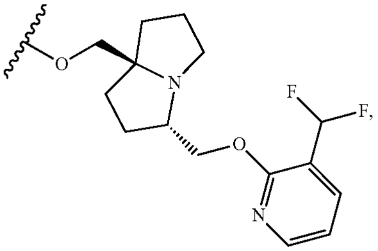
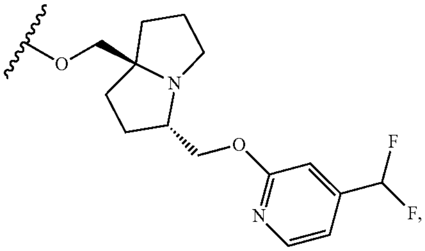
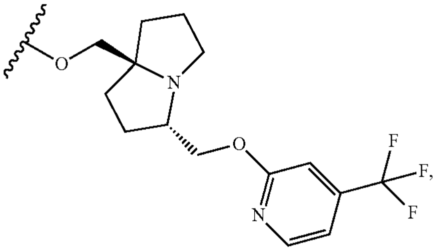

-continued
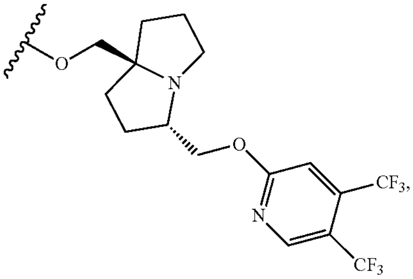
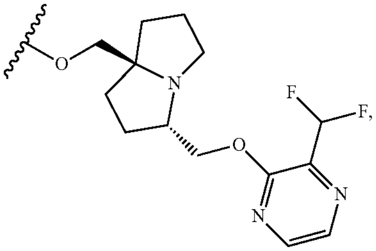
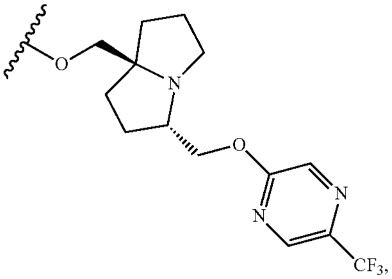
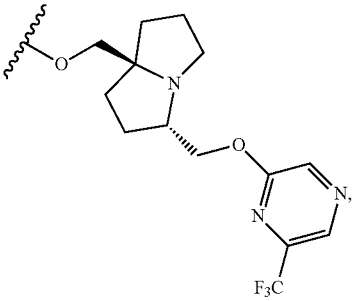
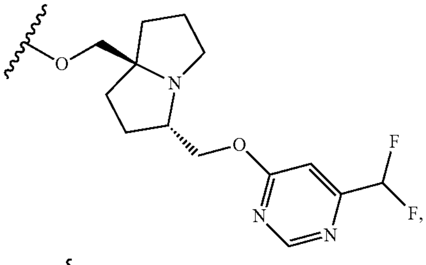
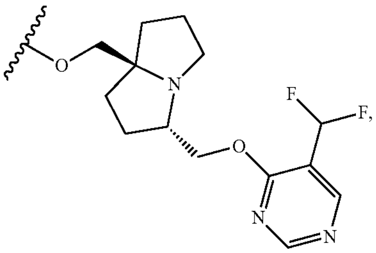
-continued
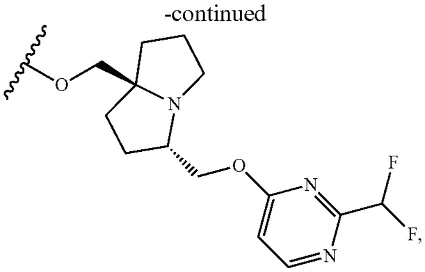
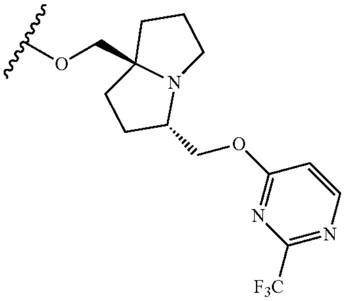
,
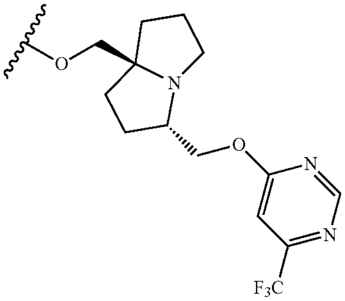
,
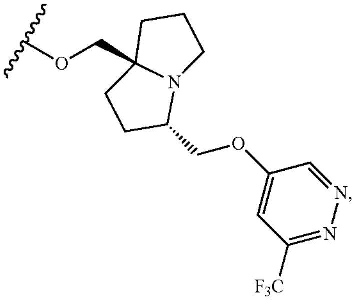
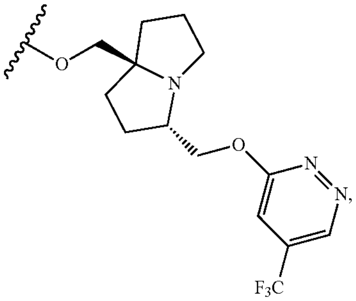
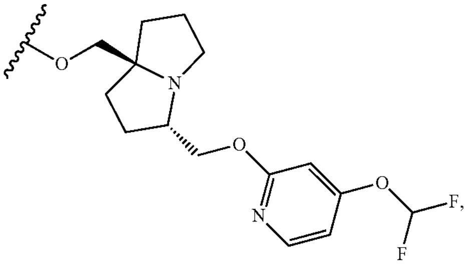

-continued
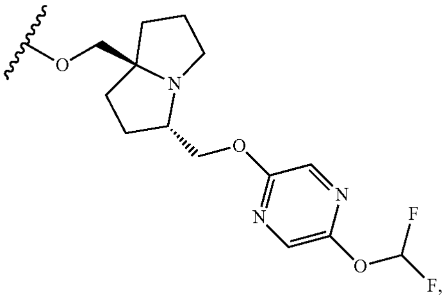
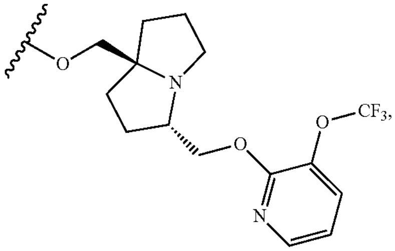
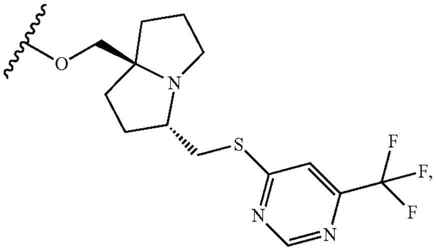
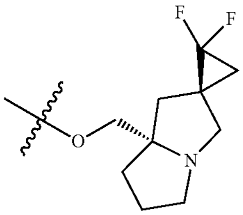
,
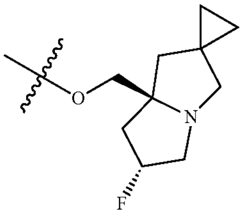
,
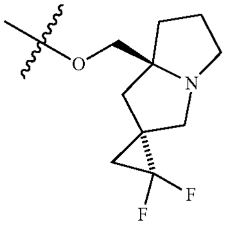
,
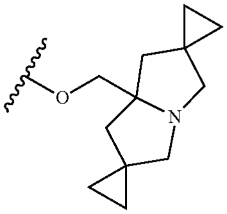
,
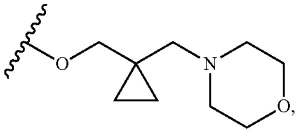
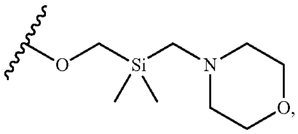
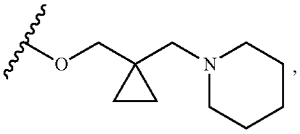
-continued
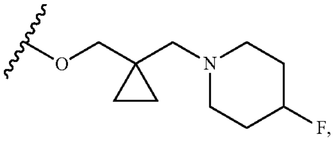
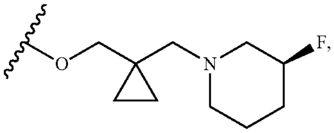
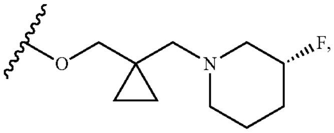
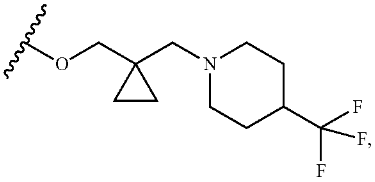
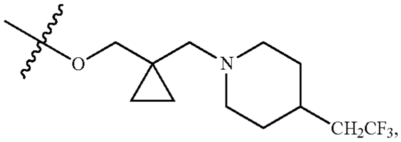
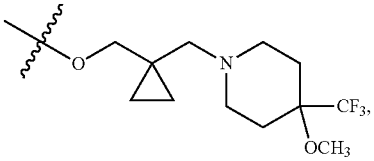
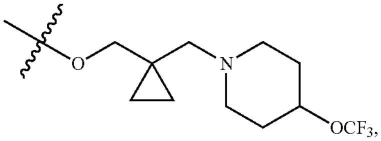
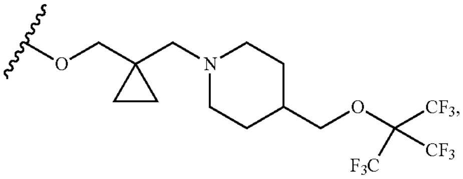
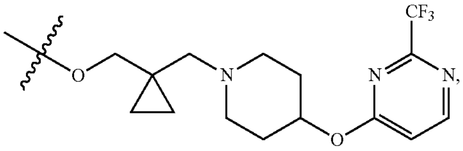
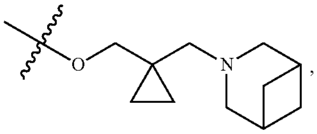
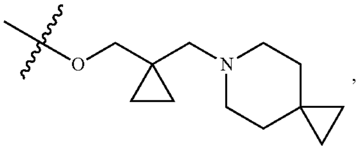

-continued
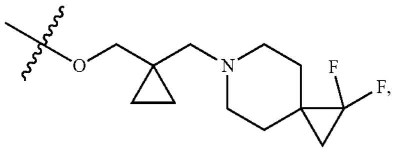
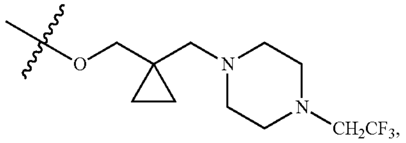
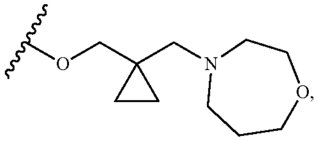
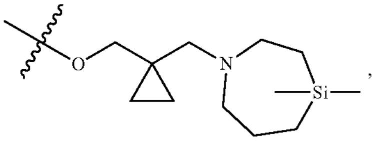
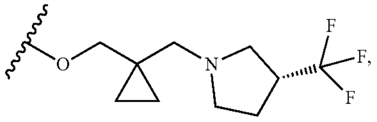
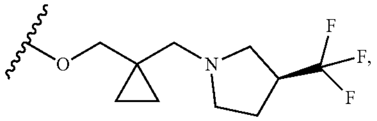
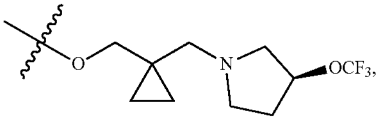
or
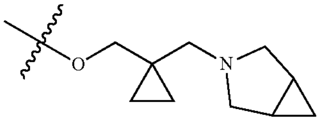
In some embodiments, the present disclosure provides the compound of Formula J, (I-1), (I-2), (I-3), (Ib), (Ib-1), (Ib-2), (Ib-3), (Ib-4), (Ib), (IIb-1), or (IIb-2), or a pharmaceutically acceptable salt thereof, wherein the —O-$L^C$-$R^C$ moiety is
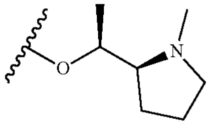
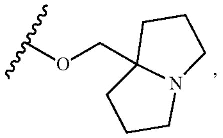
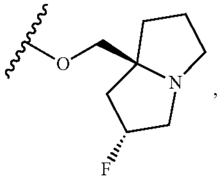
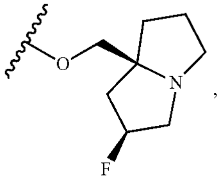
-continued
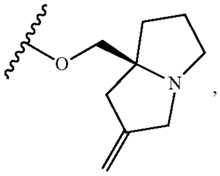
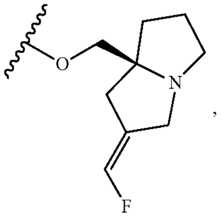
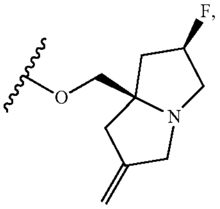
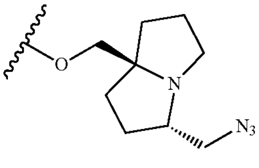
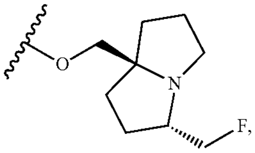
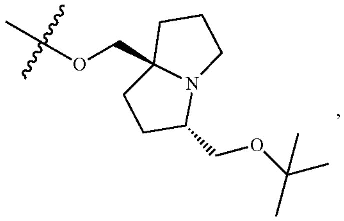
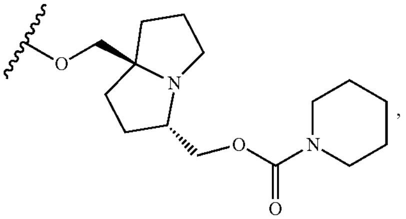
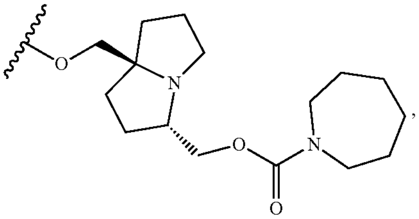
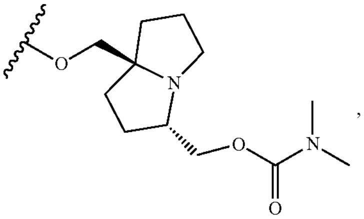
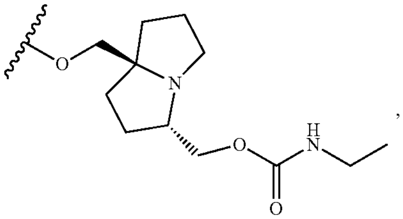

-continued
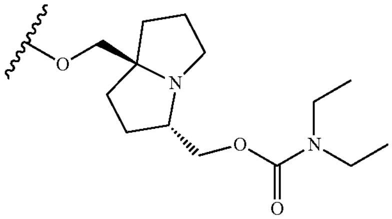
,
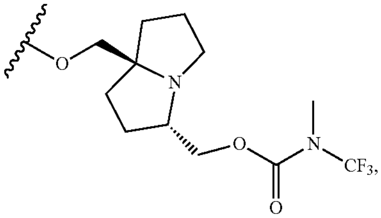
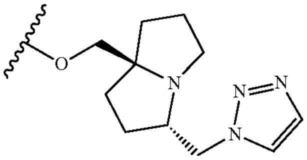
,
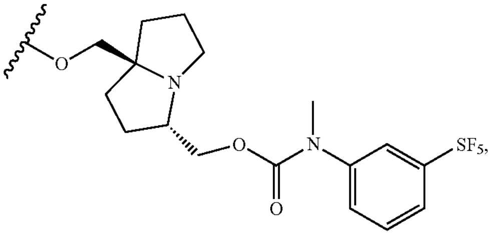
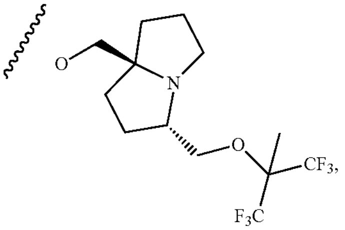
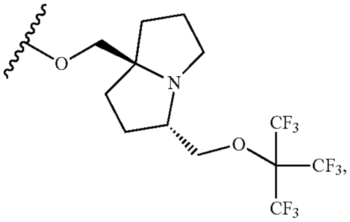
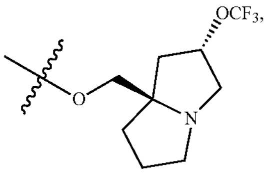
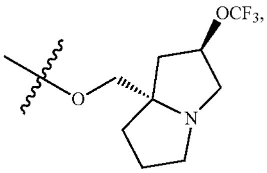
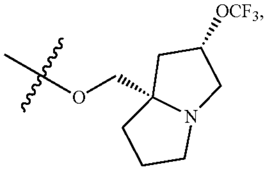
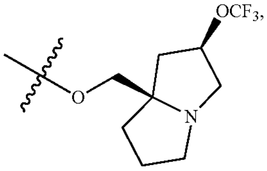
-continued
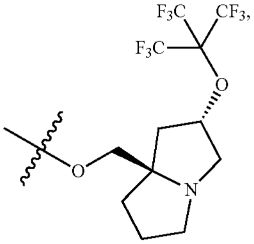
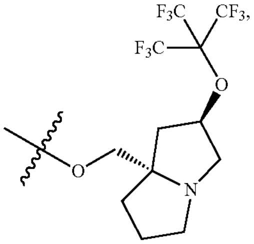
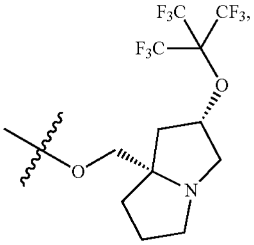
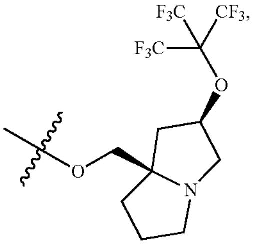
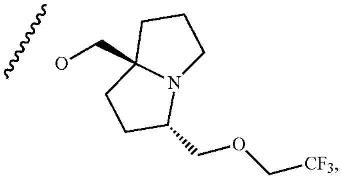
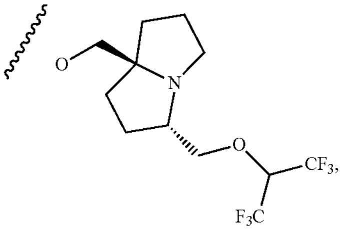
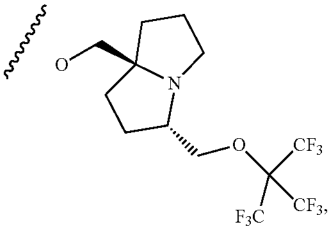
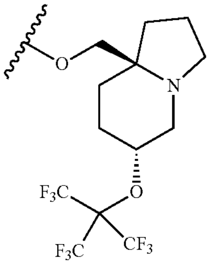
,
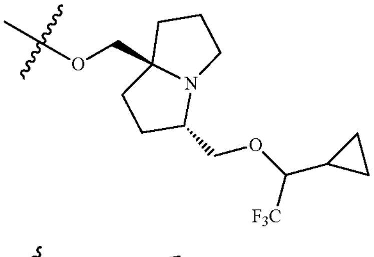
,
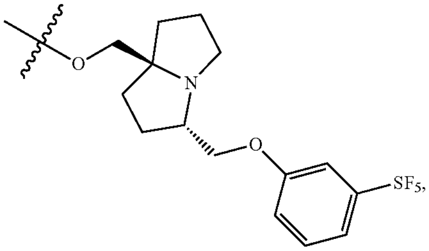

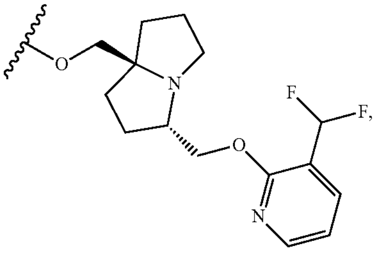
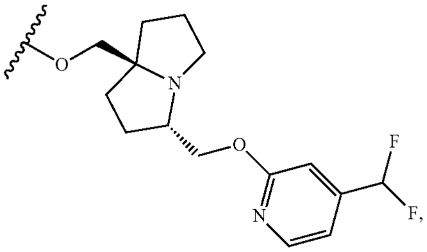
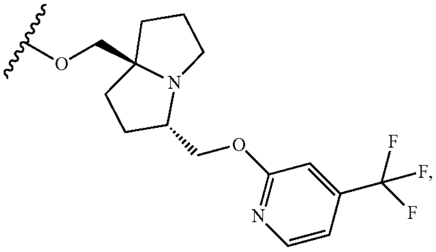
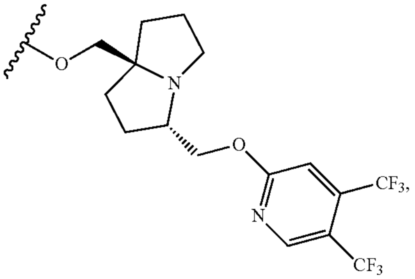
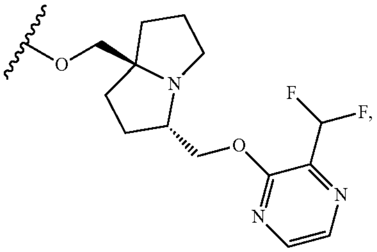
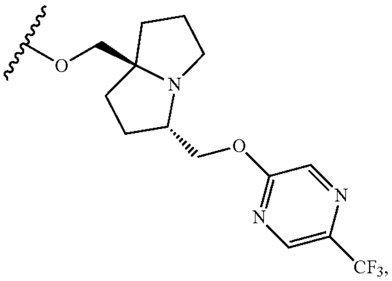
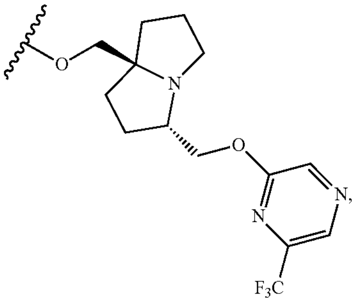
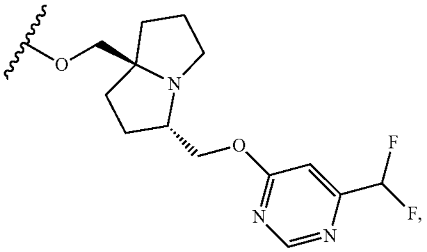
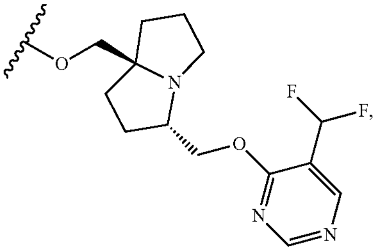
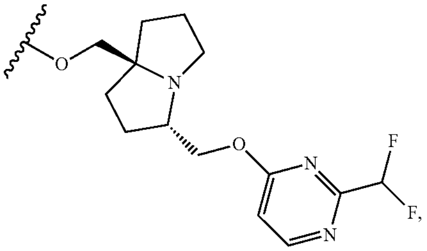
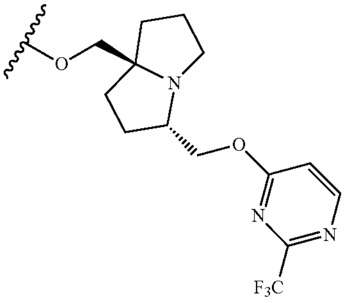
,
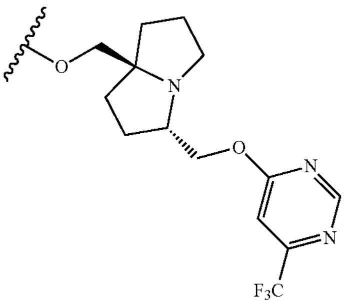
, -continued
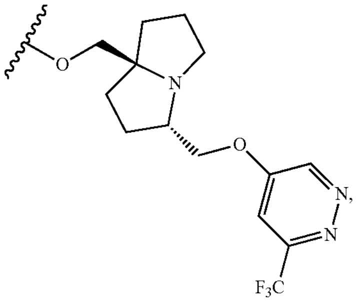
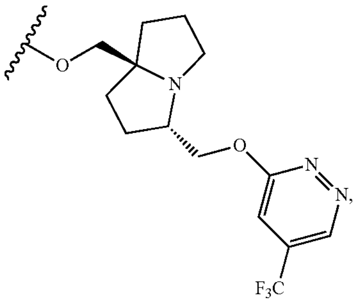
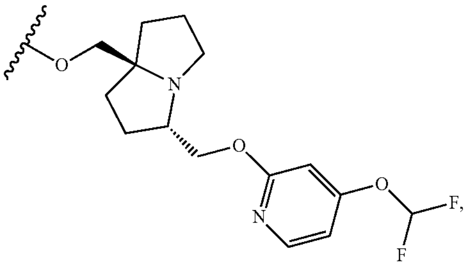
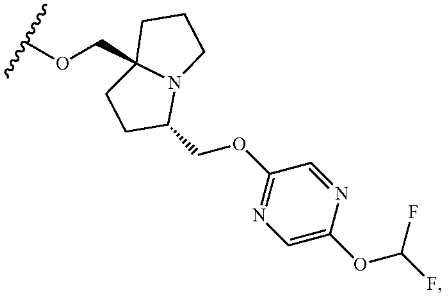
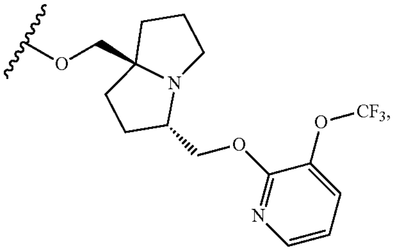
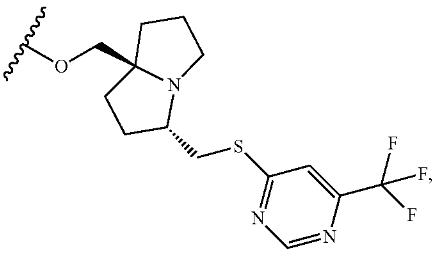
-continued
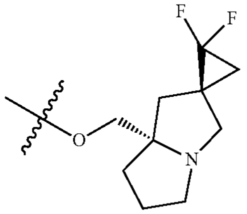
,
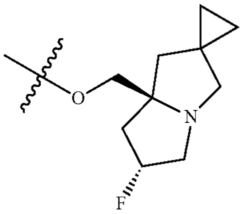
,
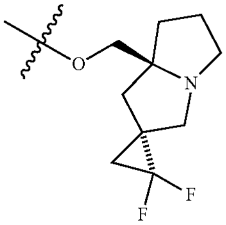
,
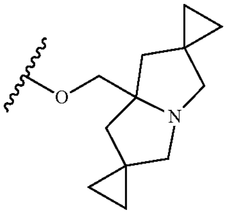
,
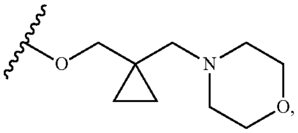
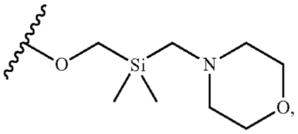
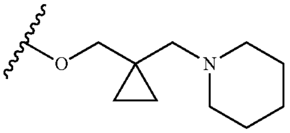
,
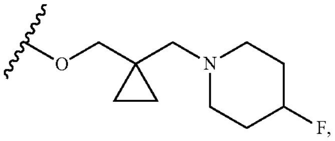
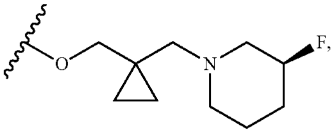
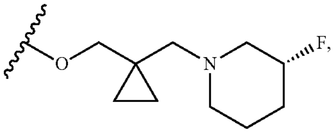
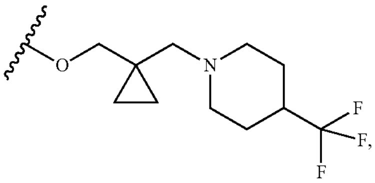
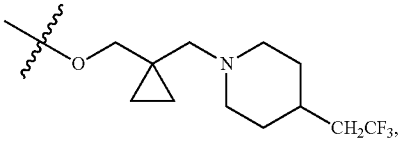
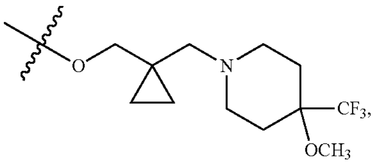

-continued
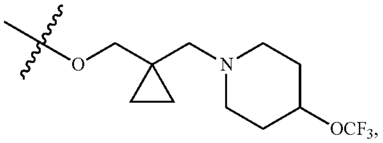
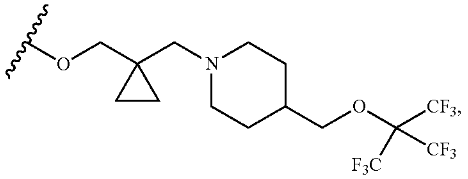
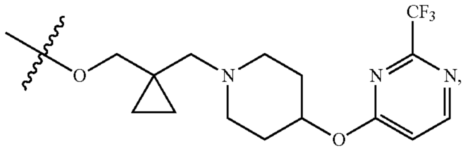
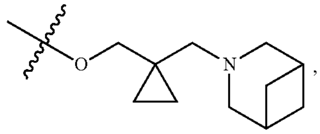
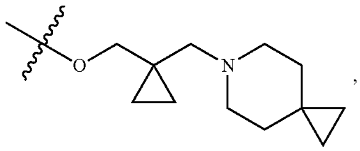
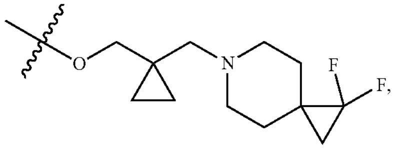
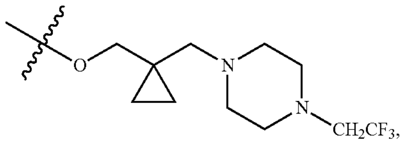
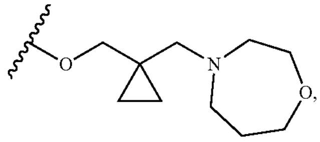
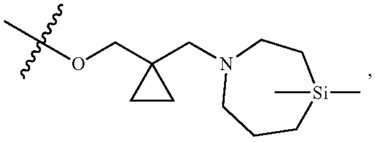
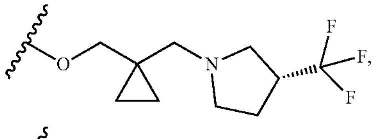
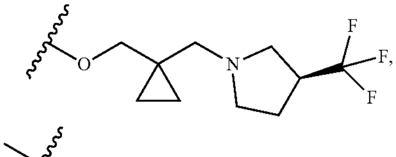
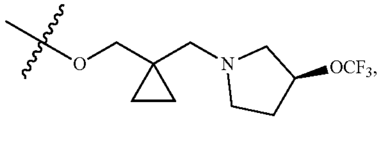
or
-continued
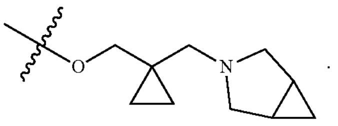
In some embodiments, the present disclosure provides the compound of Formula J, (I-1), (I-2), (I-3), (Ib), (Ib-1), (Ib-2), (Ib-3), (Ib-4), (IIb), (IIb-1), or (IIb-2), or a pharmaceutically acceptable salt thereof, wherein the —O-$L^C$-$R^C$ moiety is
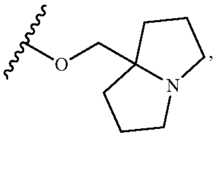
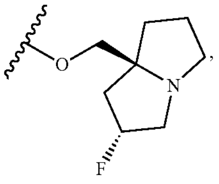
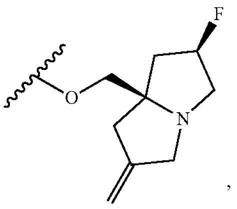
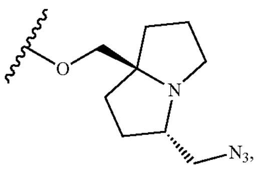
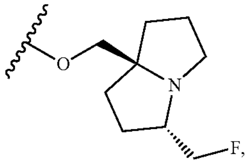
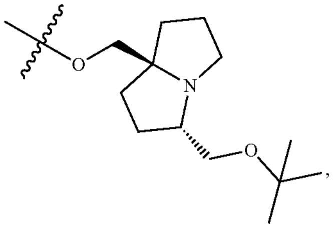
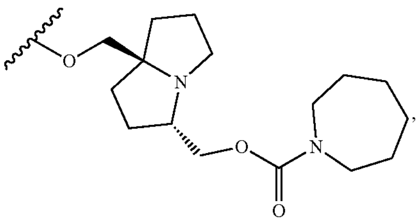
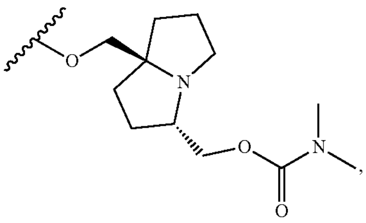

-continued
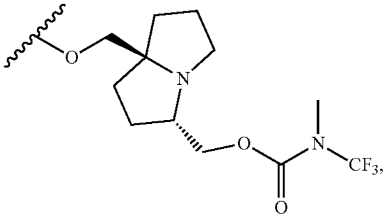
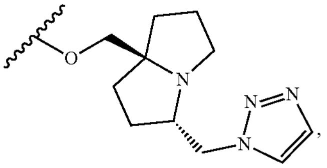
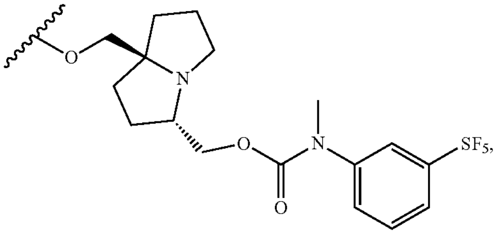
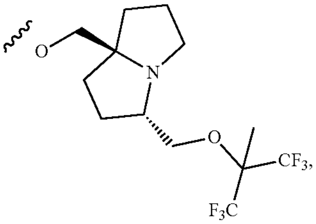
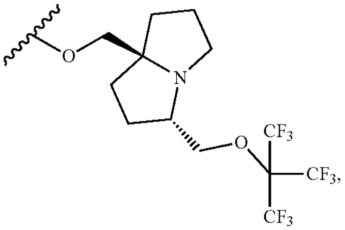
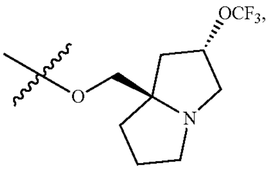
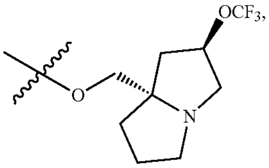
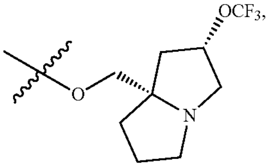
-continued
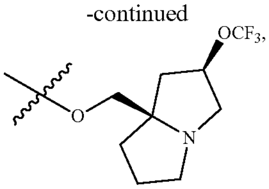
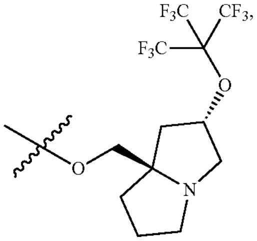
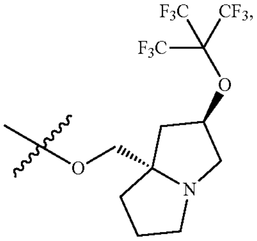
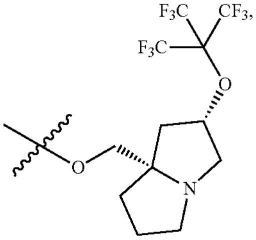
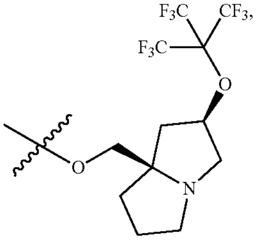
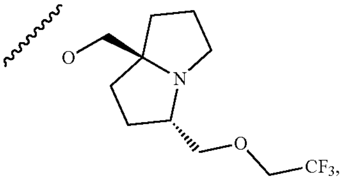
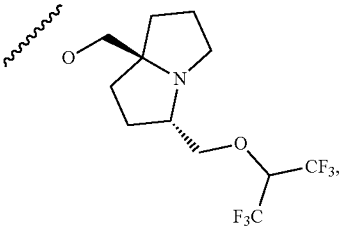
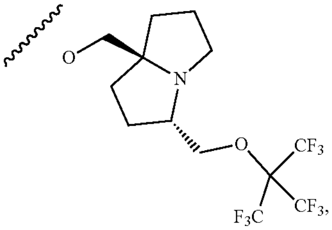
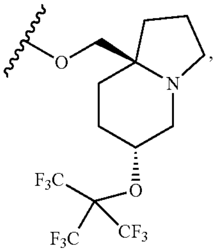

-continued
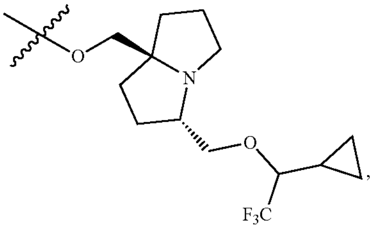
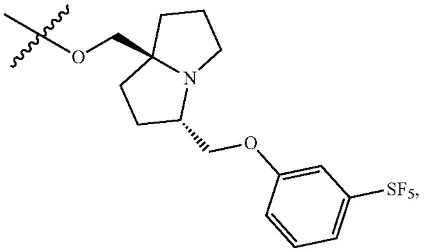
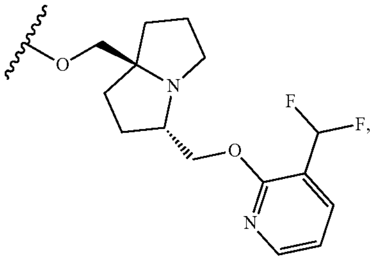
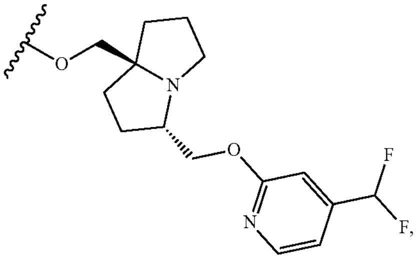
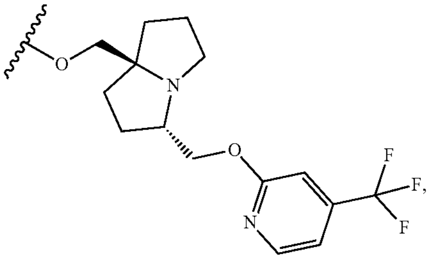
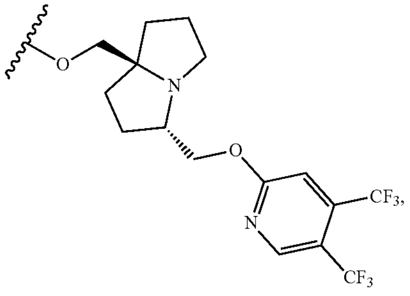
-continued
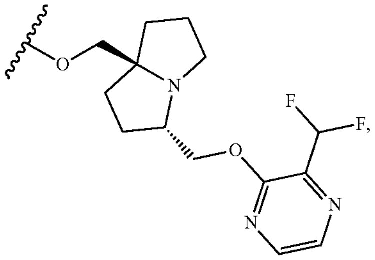
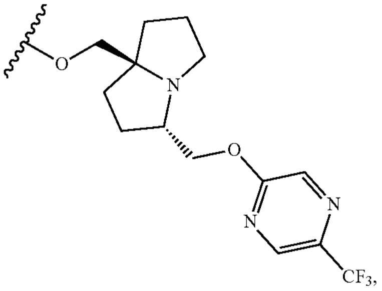
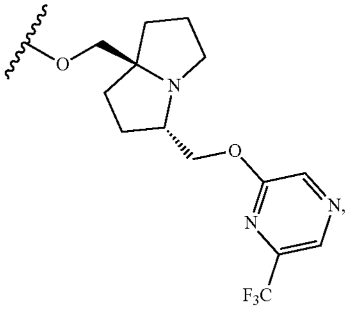
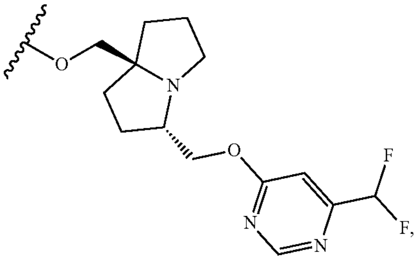
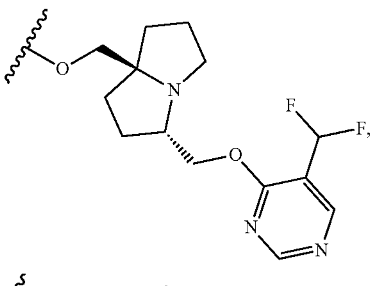
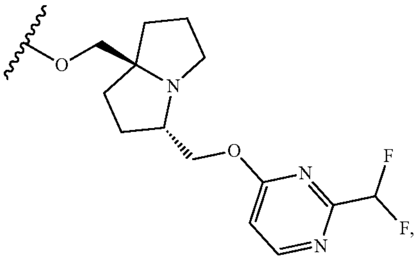

-continued
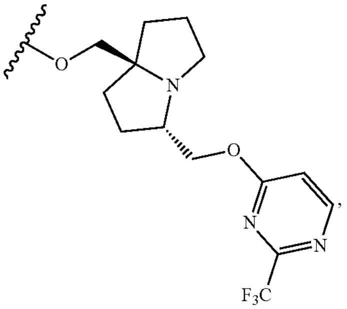
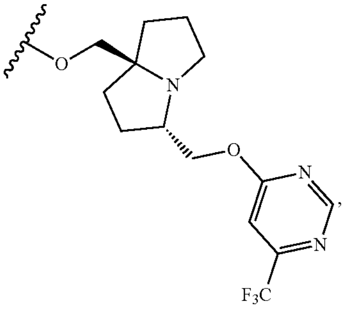
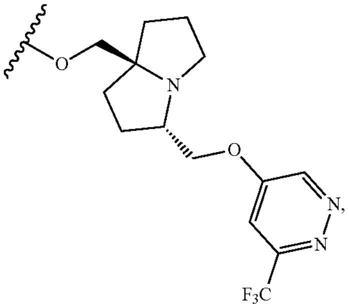
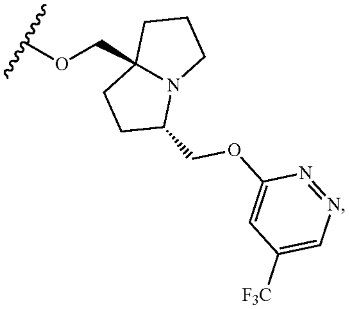
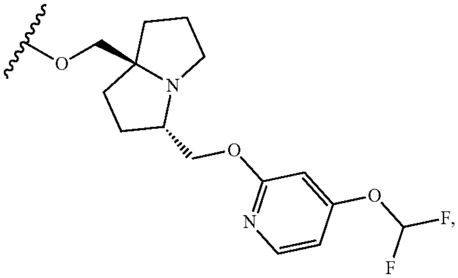
-continued
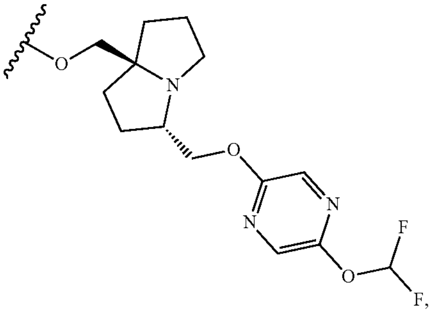
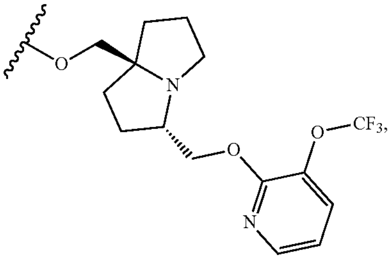
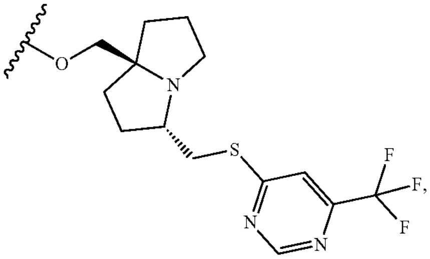
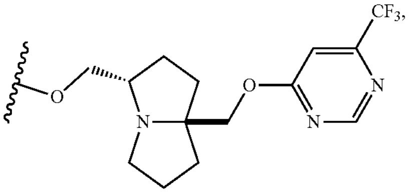
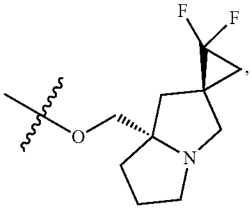
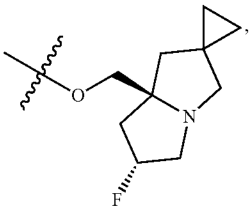
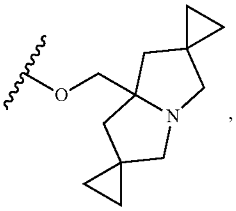
,
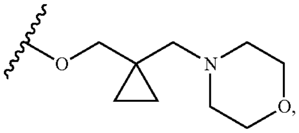
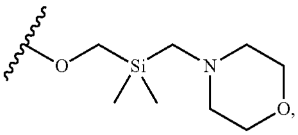

-continued
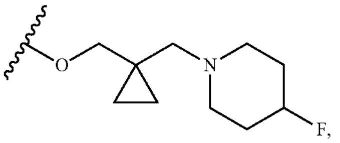
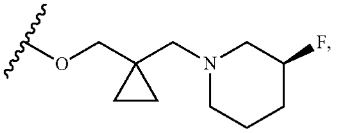
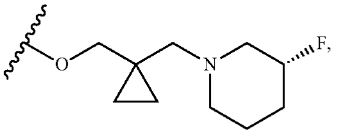
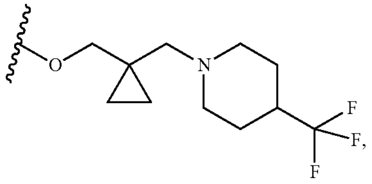
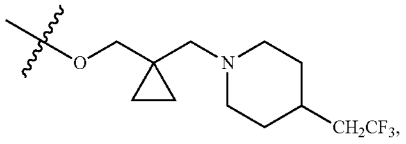
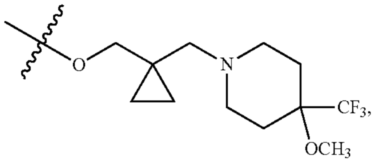
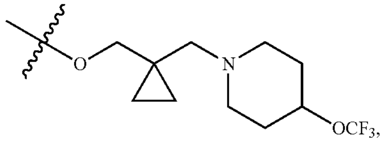
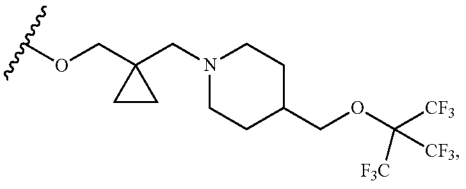
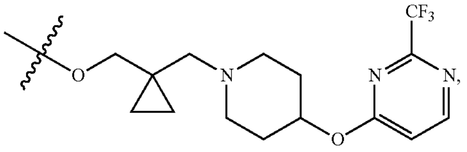
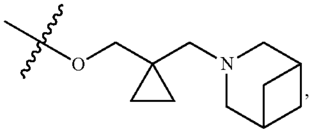
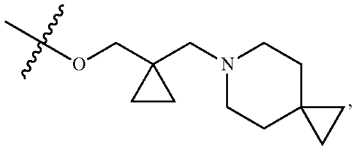
-continued
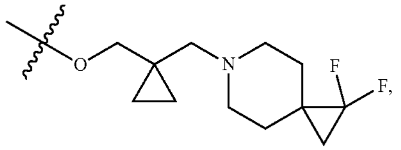
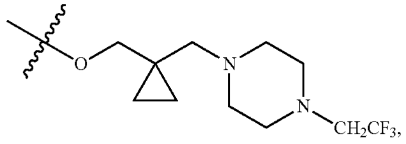
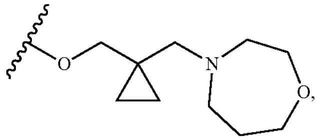
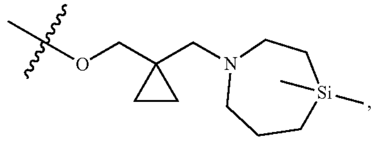
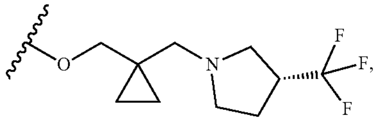
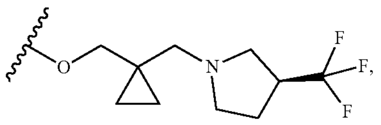
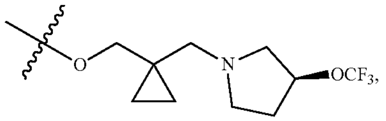
or
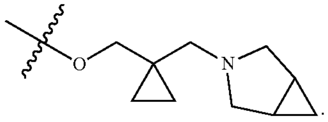
In some embodiments, the present disclosure provides the compound of Formula J, (I-1), (I-2), (I-3), (Ib), (Ib-1), (Ib-2), (Ib-3), (Ib-4), (Ib), (IIb-1), or (IIb-2), or a pharmaceutically acceptable salt thereof, wherein the —O-$L^C$-$R^C$ moiety is
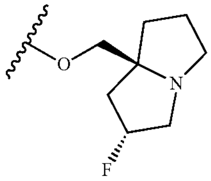
,
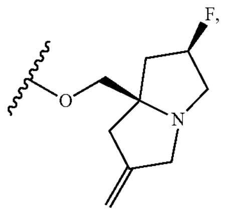
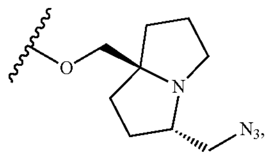

-continued
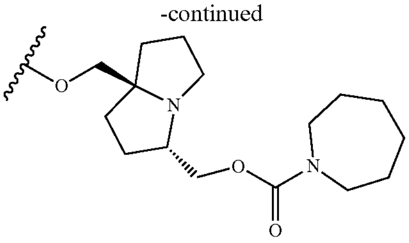
,
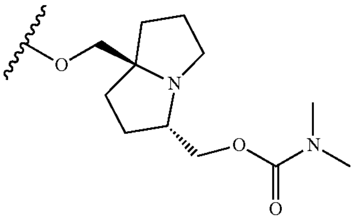
,
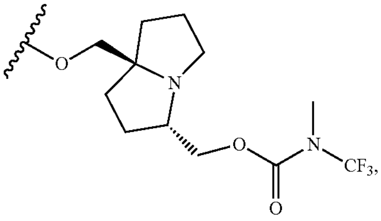
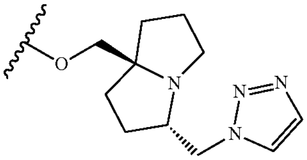
,
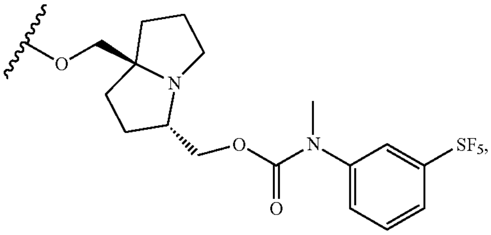
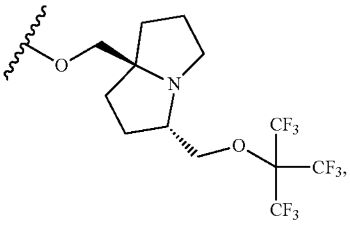
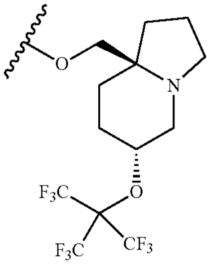
,
-continued
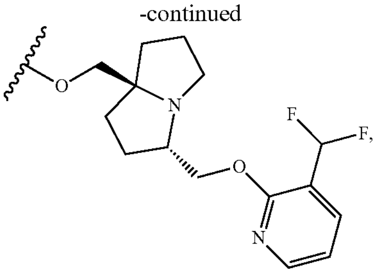
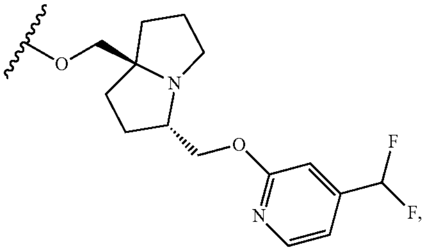
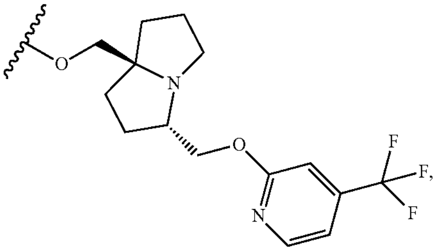
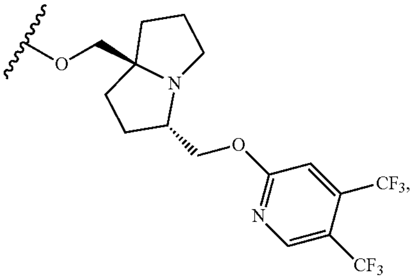
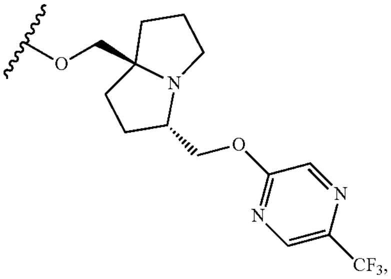
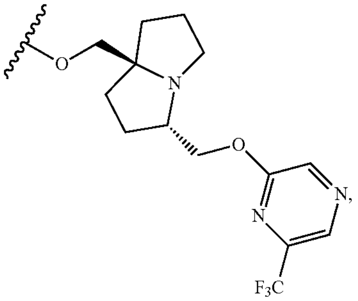

-continued
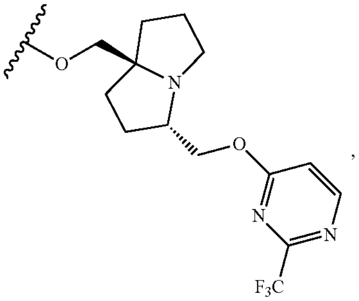
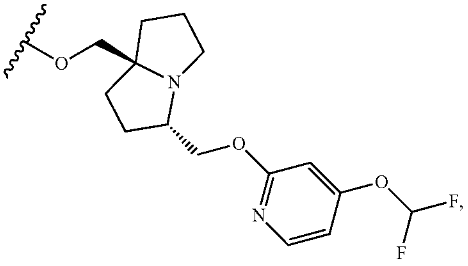
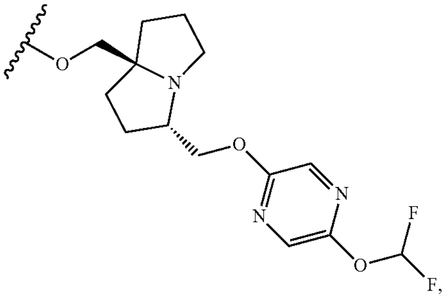
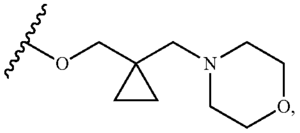
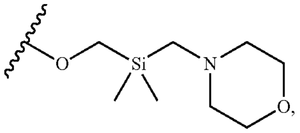
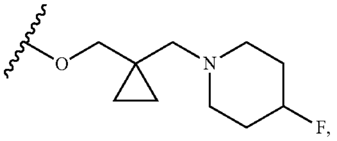
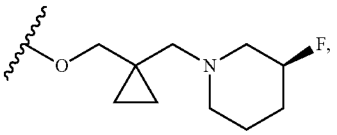
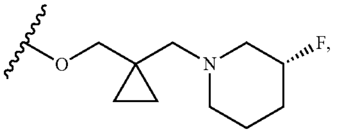
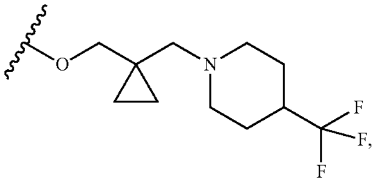
-continued
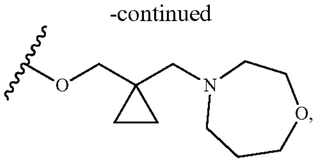
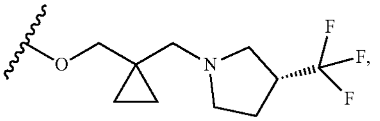
or
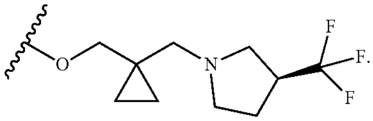
In some embodiments, the present disclosure provides the compound of Formula J, (I-1), (I-2), (I-3), (Ib), (Ib-1), (Ib-2), (Ib-3), (Ib-4), (Ib), (IIb-1), or (IIb-2), or a pharmaceutically acceptable salt thereof, wherein the —O-$L^C$-$R^C$ moiety is
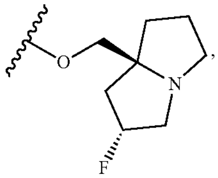 [SMILES: *OC[C@@]12CCCN1C[C@H](F)C2]
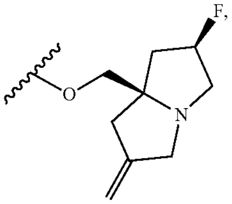
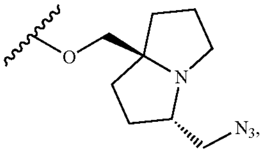
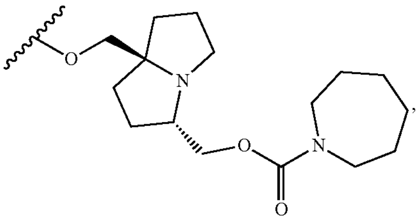
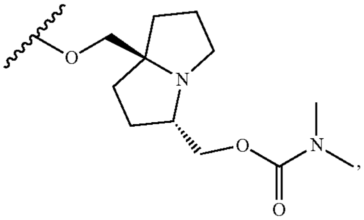
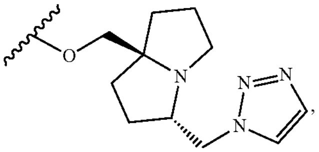

-continued
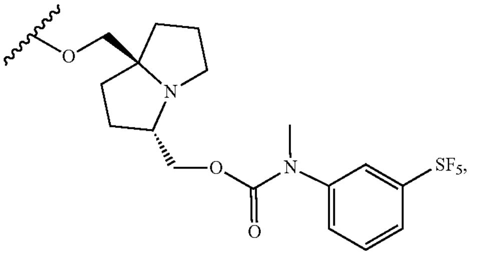
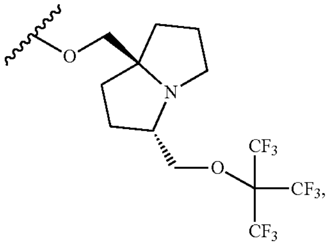
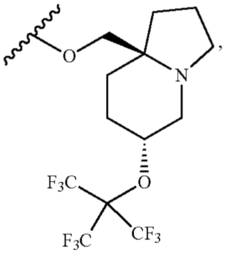
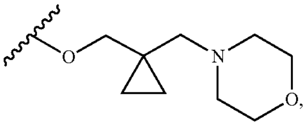
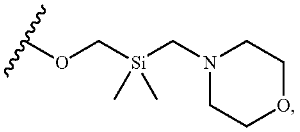
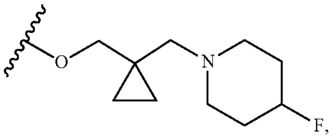
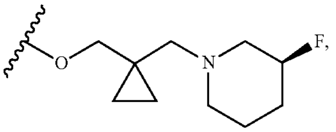
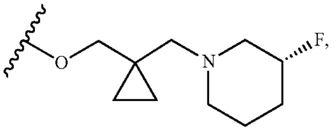
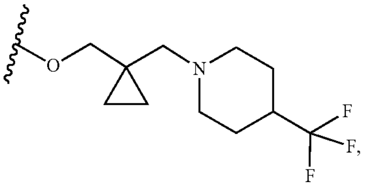
-continued
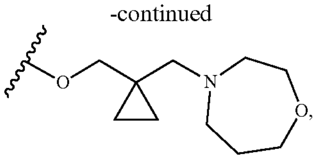
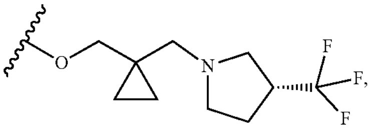
or
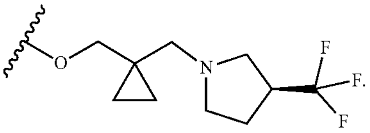
In some embodiments, the present disclosure provides the compound of Formula J, (I-1), (I-2), (I-3), (Ib), (Ib-1), (Ib-2), (Ib-3), (Ib-4), (Ib), (IIb-1), or (IIb-2), or a pharmaceutically acceptable salt thereof, wherein the —O-$L^C$-$R^C$ moiety is
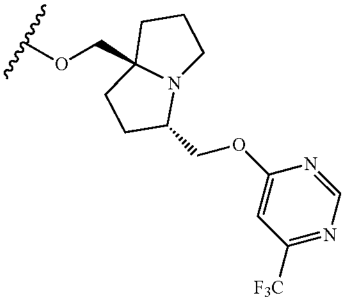
,
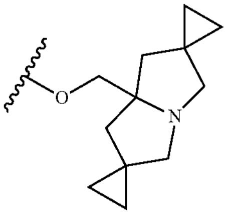
,
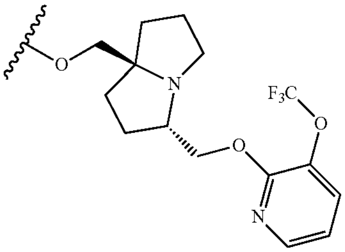
,
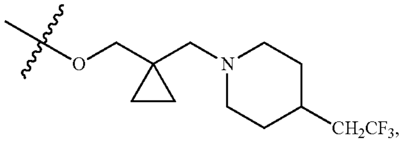
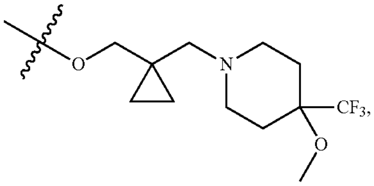

-continued
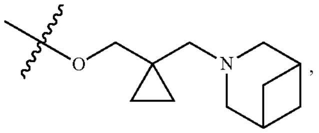
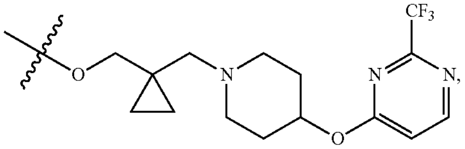
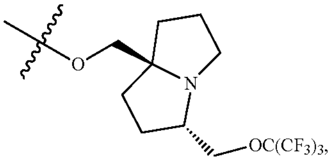
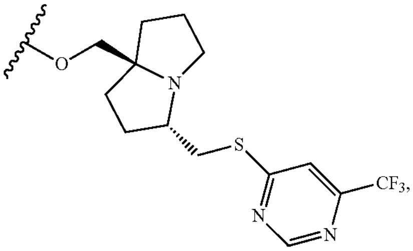
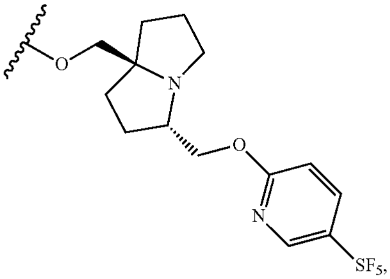
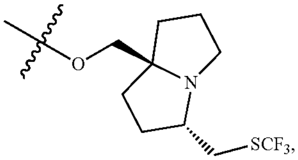
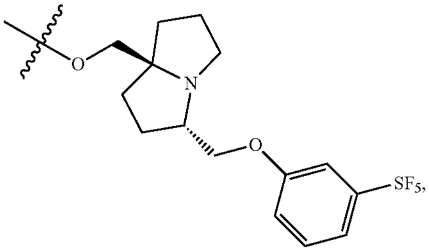
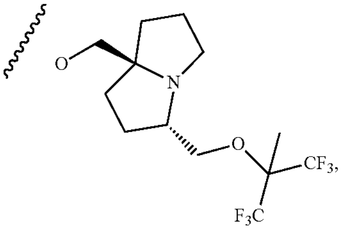
-continued
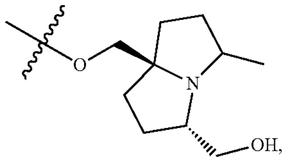
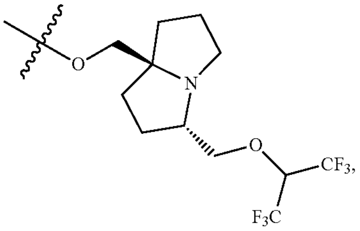
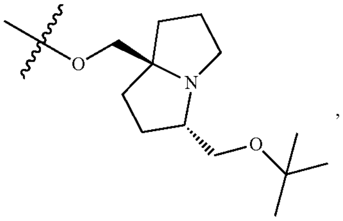
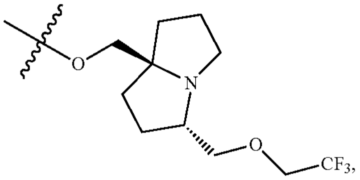
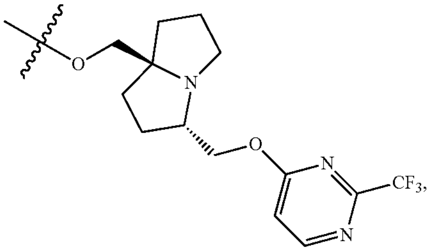
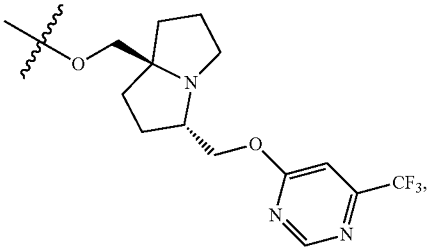
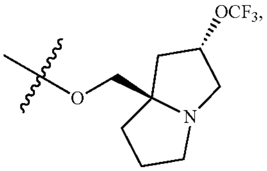
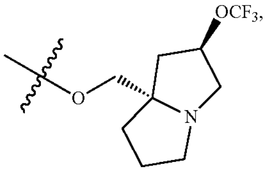
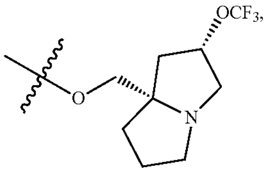
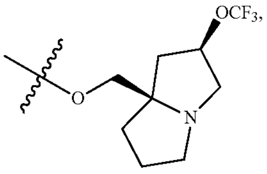

-continued
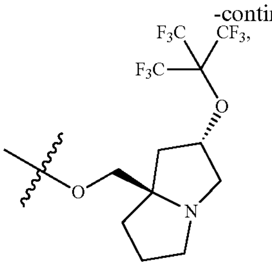
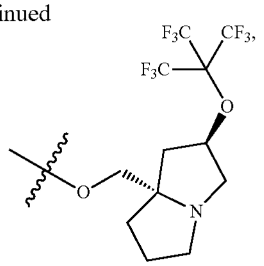
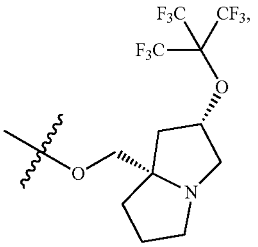
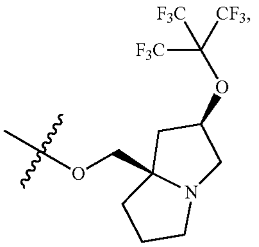
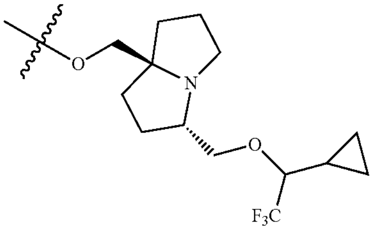
,
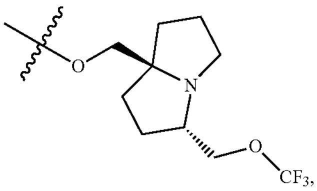
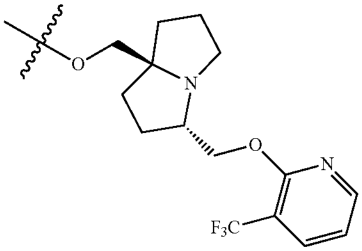
,
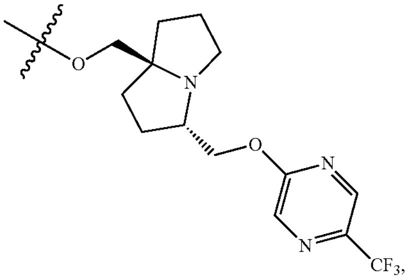
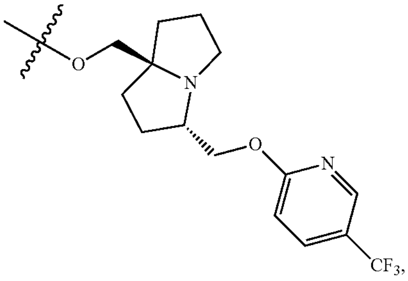
-continued
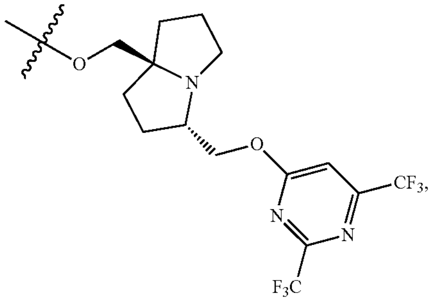
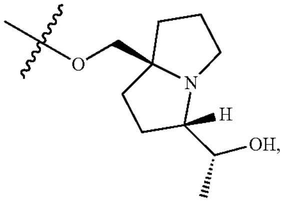
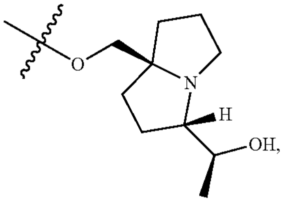
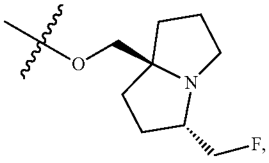
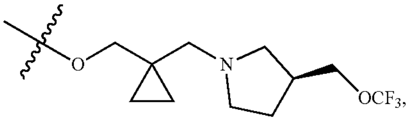
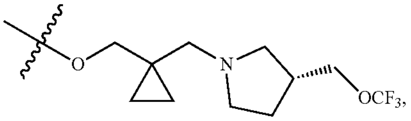
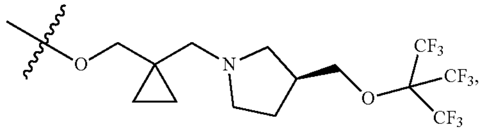
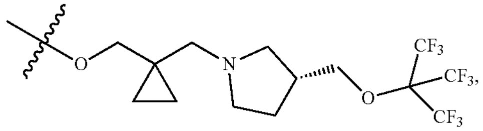
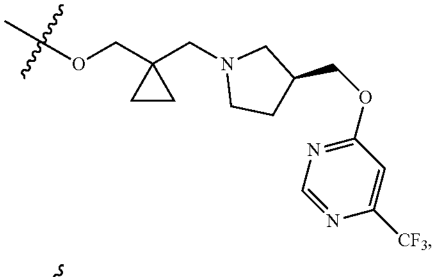
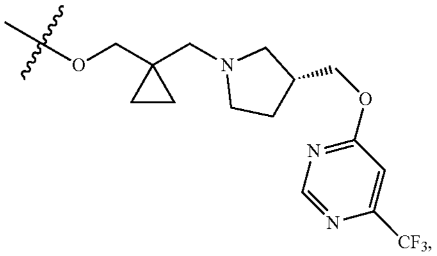

-continued
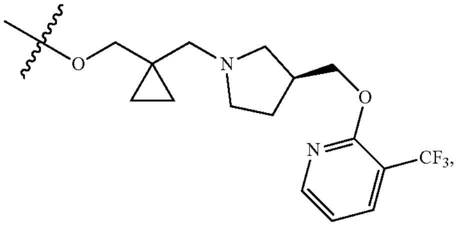
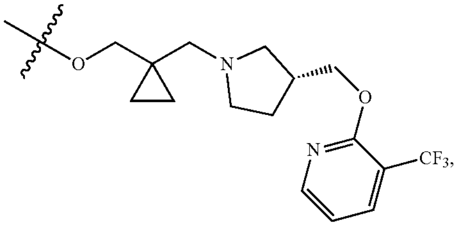
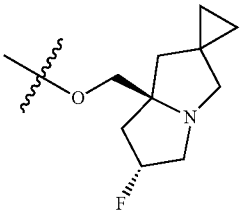
,
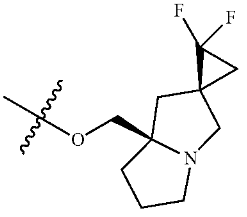
,
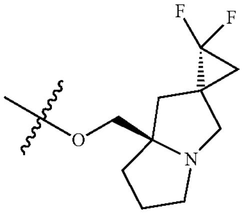
,
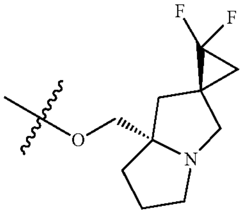
,
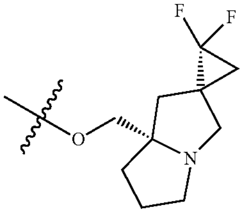
,
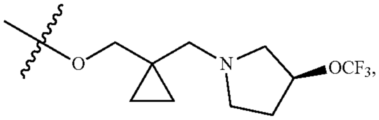
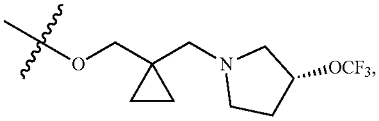
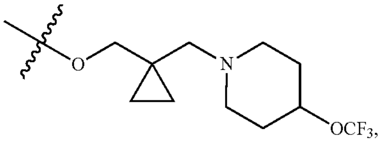
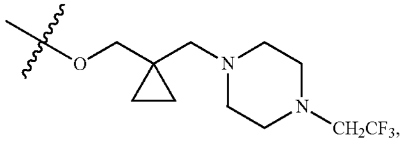
-continued
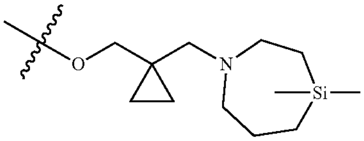
,
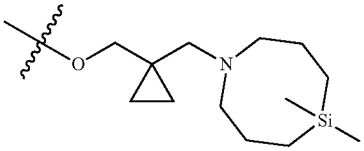
,
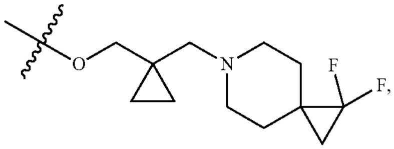
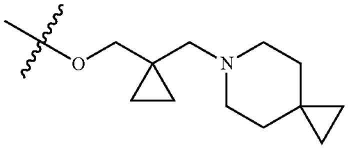
,
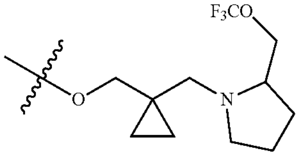
,
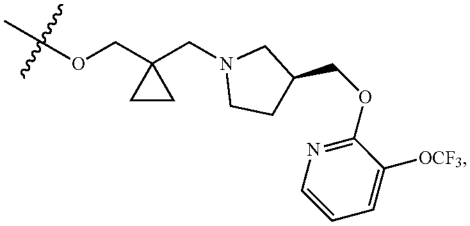
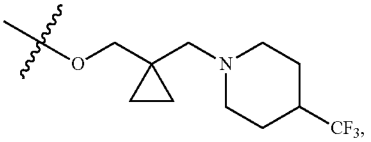
or
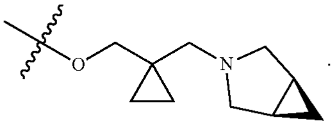
.
In some embodiments, the present disclosure provides the compound of Formula J, (I-1), (I-2), (I-3), (Ib), (Ib-1), (Ib-2), (Ib-3), (Ib-4), (Ib), (IIb-1), or (IIb-2), or a pharmaceutically acceptable salt thereof, wherein the —O-$L^C$-$R^C$ moiety is
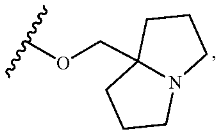
, -continued

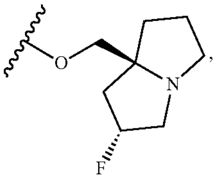
,

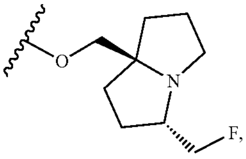
,

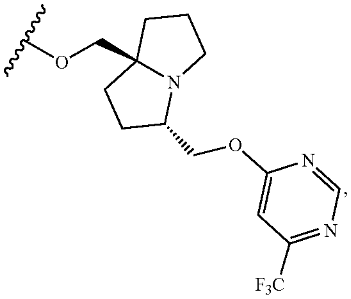
, or

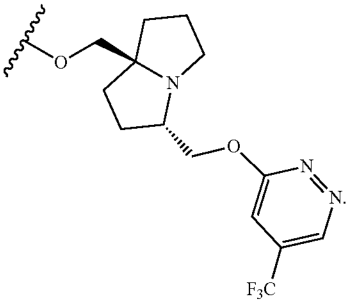
.

In some embodiments, the present disclosure provides the compound of Formula J, (I-1), (I-2), (I-3), (b), (Ib-1), (b-2), (Ib-3), (b-4), (Ib), (IIb-1), or (Ib-2), or a pharmaceutically acceptable salt thereof, wherein the —O-$L^C$-$R^C$ moiety is

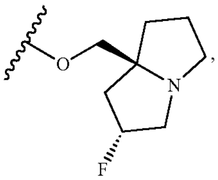
,

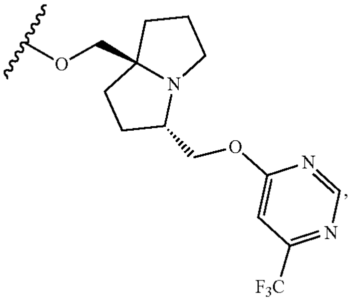
, or

-continued

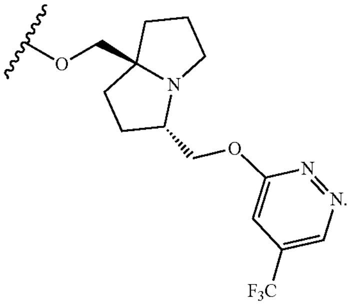
.

In some embodiments, the present disclosure provides the compound of Formula J, (I-1), (I-2), (I-3), (Ib), (Ib-1), (Ib-2), (Ib-3), (Ib-4), (Ib), (IIb-1), or (IIb-2), or a pharmaceutically acceptable salt thereof, wherein the —O-$L^C$-$R^C$ moiety is

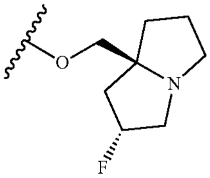
.

In some embodiments, the present disclosure provides the compound of Formula J, (I-1), (I-2), (I-3), (b), (Ib-1), (Ib-2), (Ib-3), (Ib-4), (Ib), (IIb-1), or (IIb-2), or a pharmaceutically acceptable salt thereof, wherein $R^D$ is F or $C_1$. In some embodiments, the present disclosure provides the compound of Formula J, (I-1), (I-2), (I-3), (b), (Ib-1), (b-2), (b-3), (b-4), (Ib), (IIb-1), or (Ib-2), or a pharmaceutically acceptable salt thereof, wherein $R^D$ is F.

In some embodiments, the present disclosure provides the compound of Formula J, (I-1), (I-2), (I-3), (b), (Ib-1), (b-2), (Ib-3), (b-4), (Ib), (IIb-1), or (Ib-2), or a pharmaceutically acceptable salt thereof, wherein the compound has the structure:

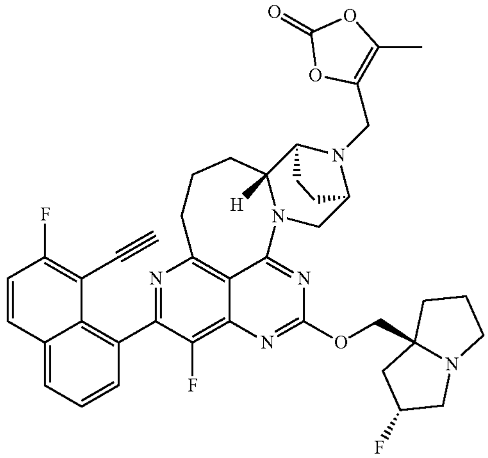

-continued
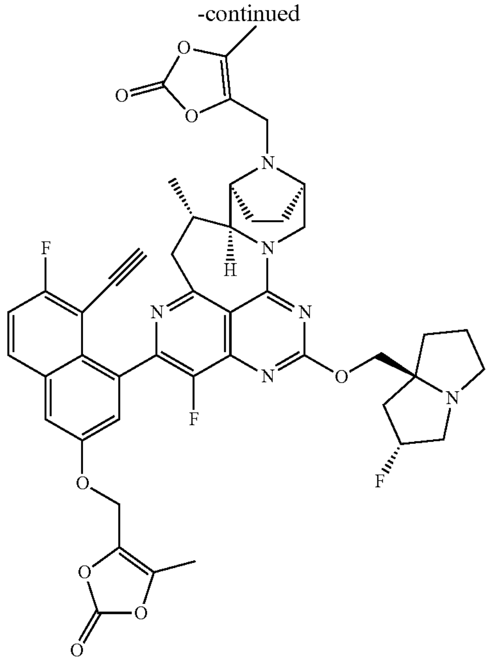
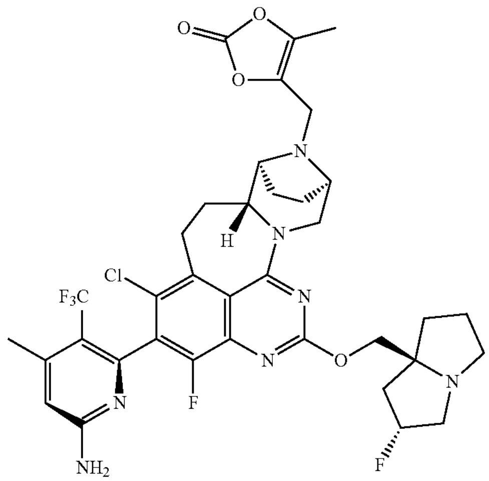
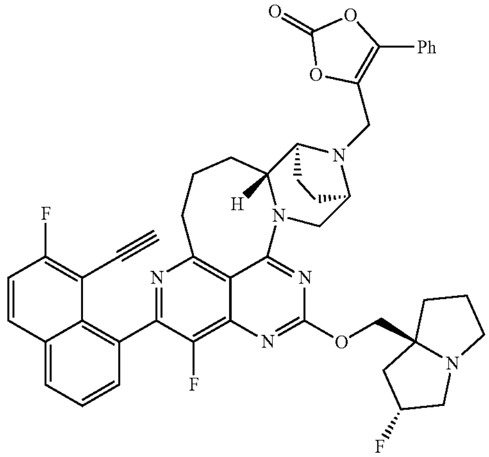
-continued
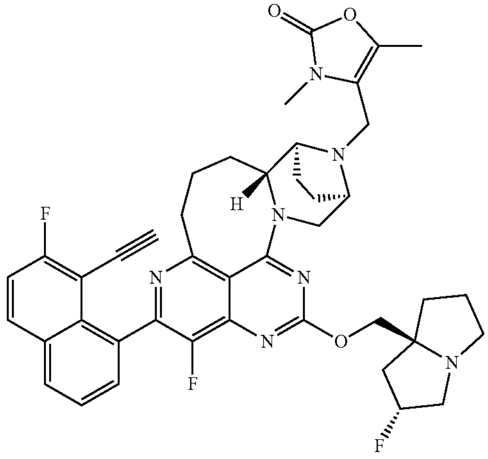
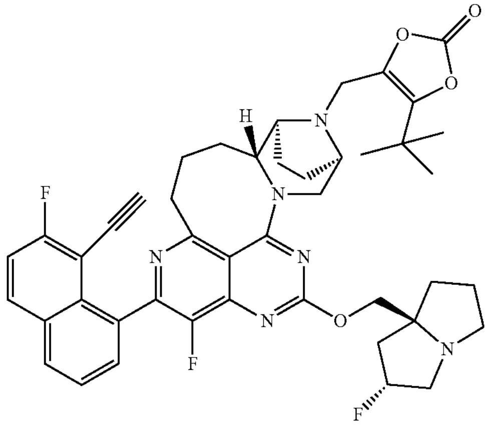
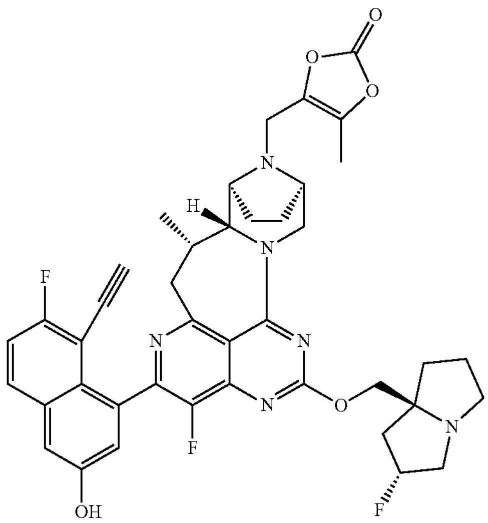

-continued
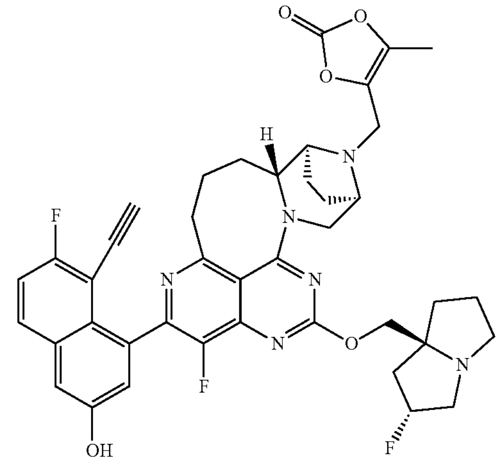
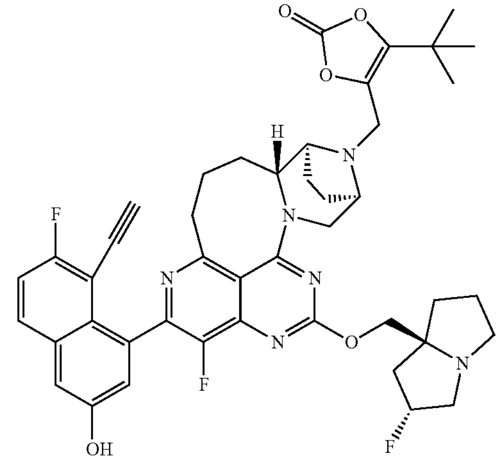
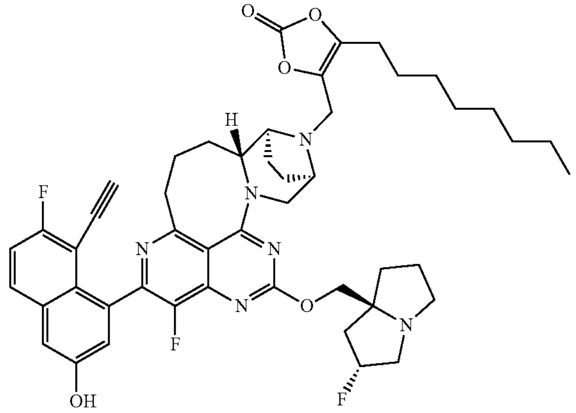
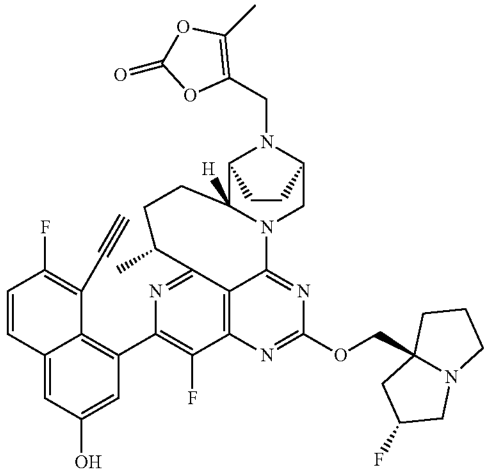
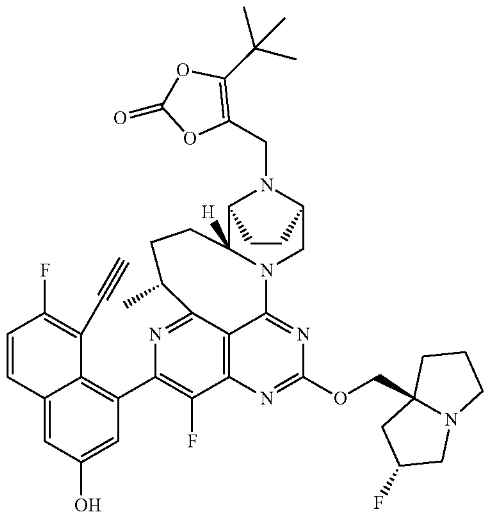
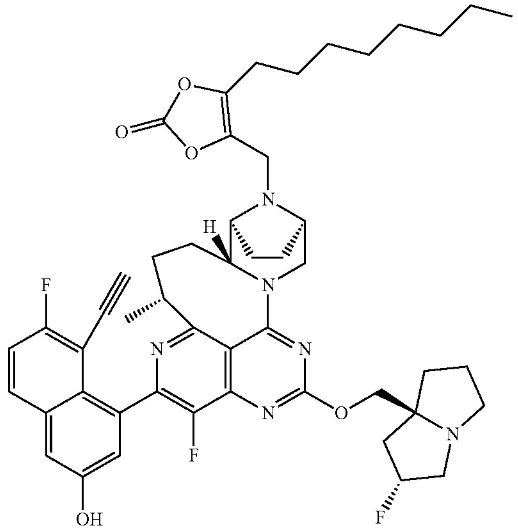
-continued -continued
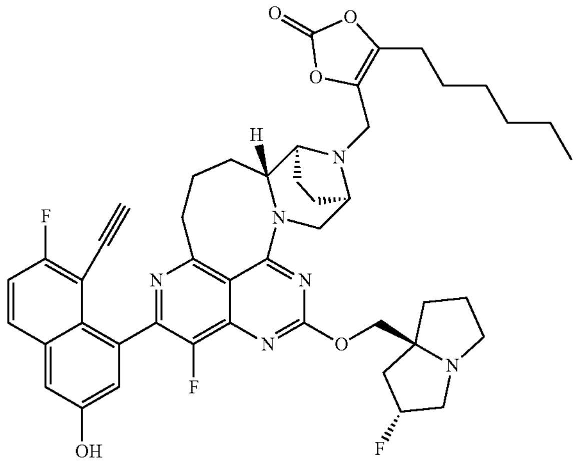
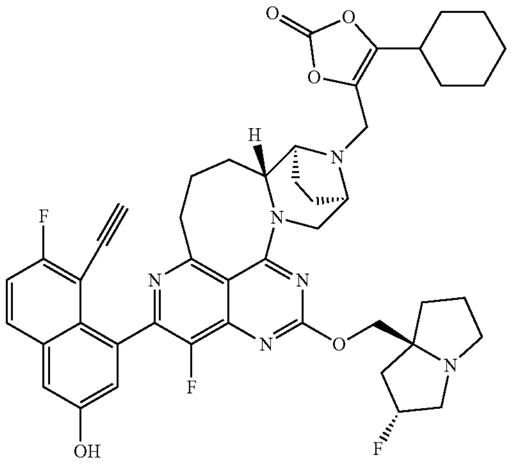
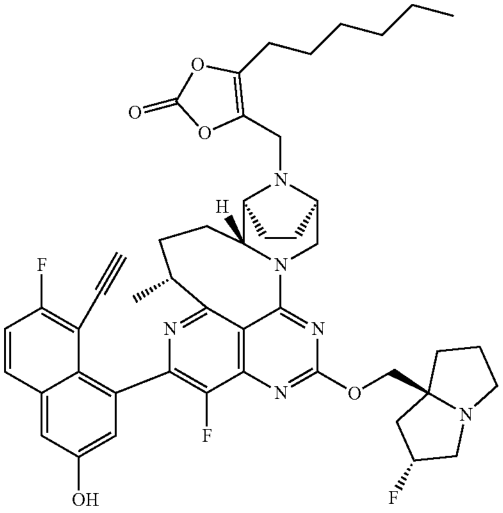
-continued
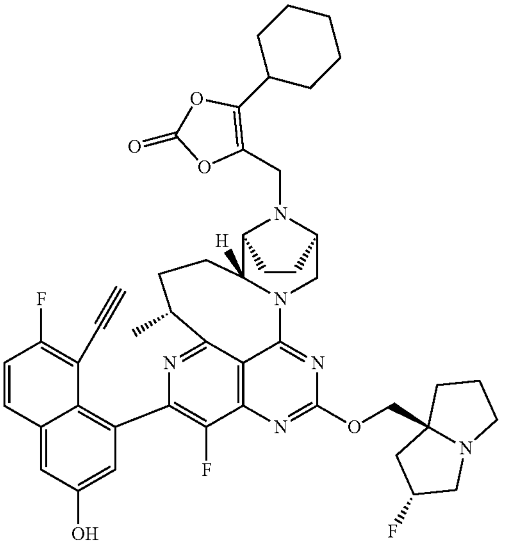
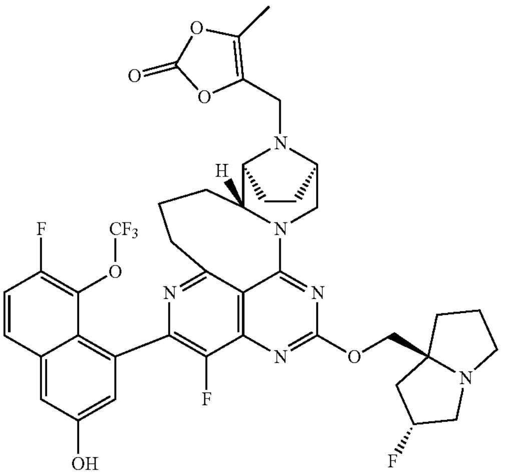
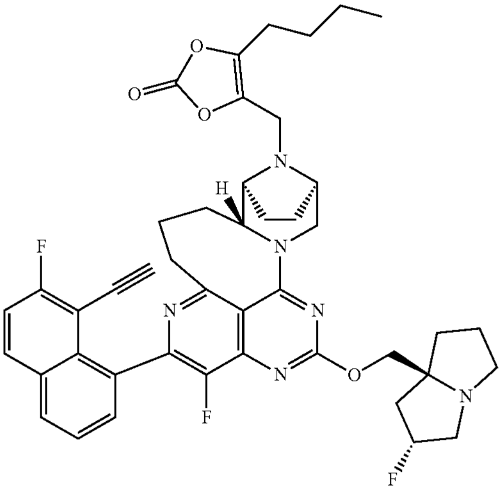

-continued
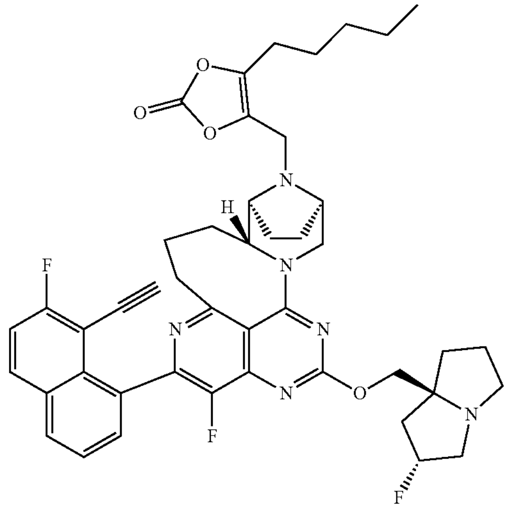
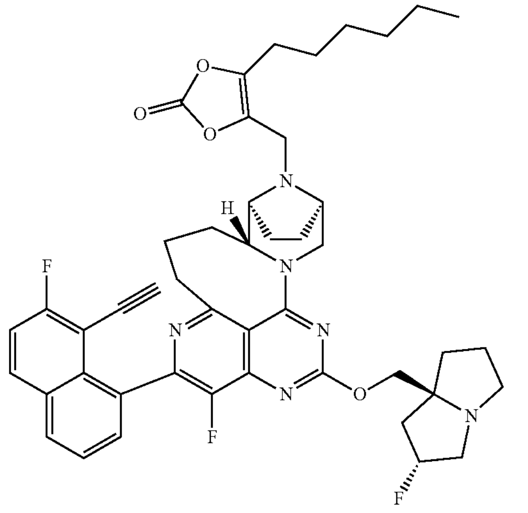
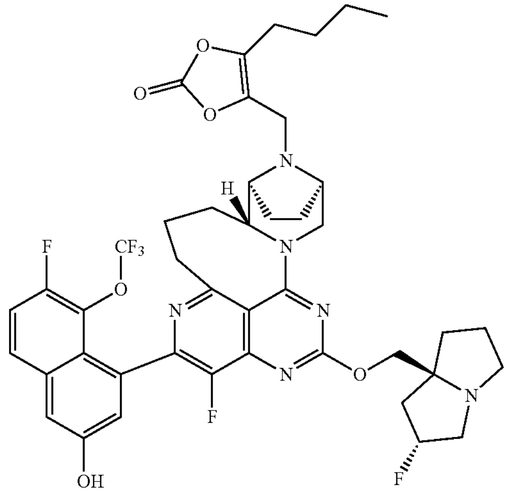
-continued
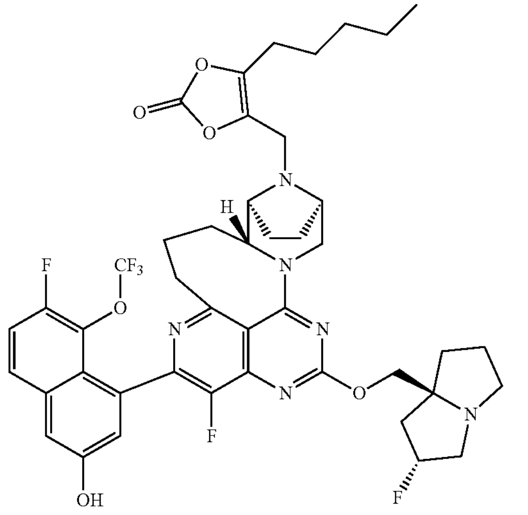
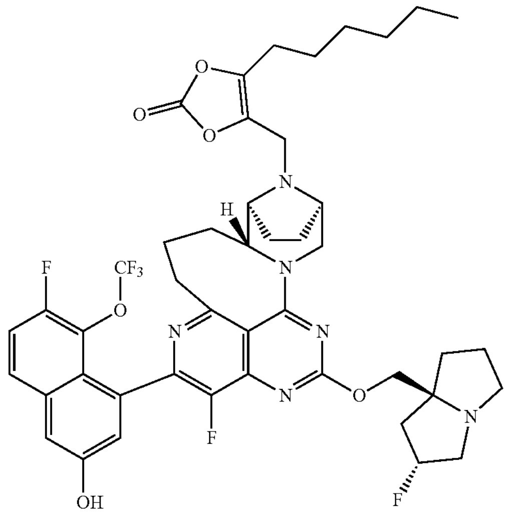
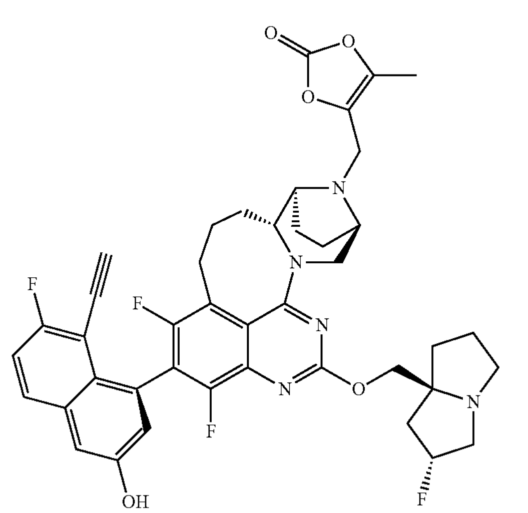

-continued
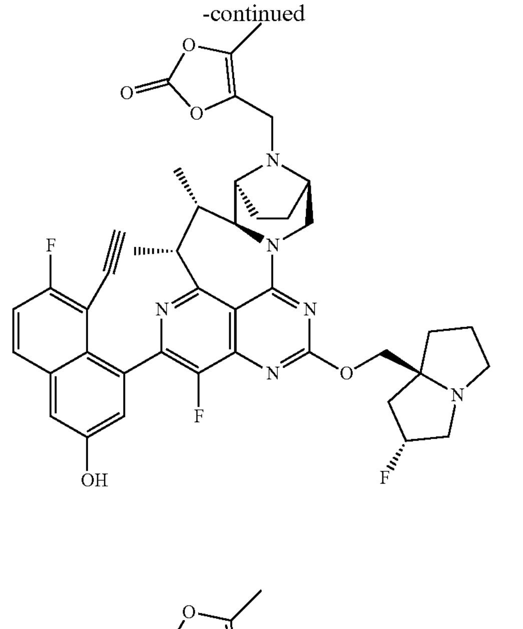
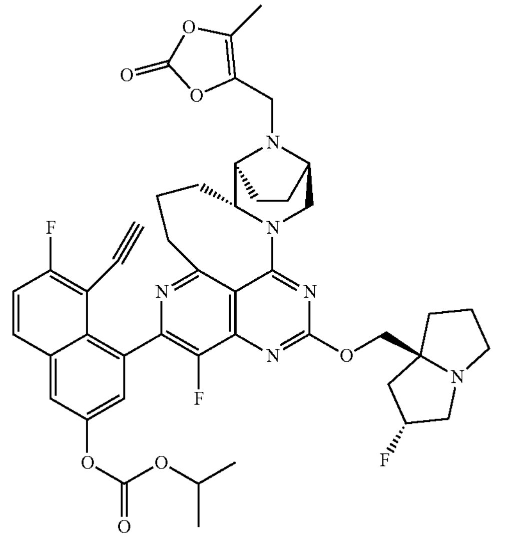
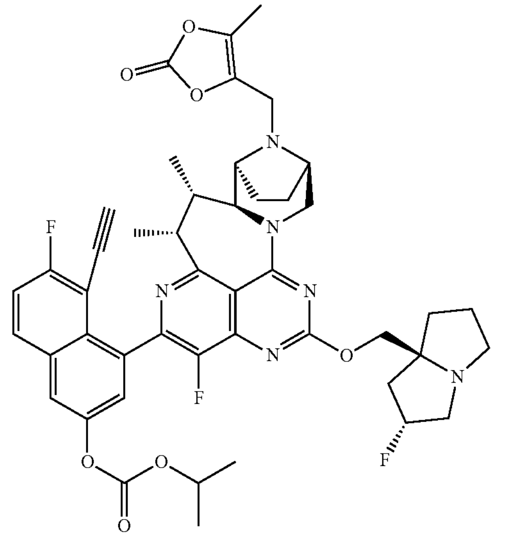
-continued
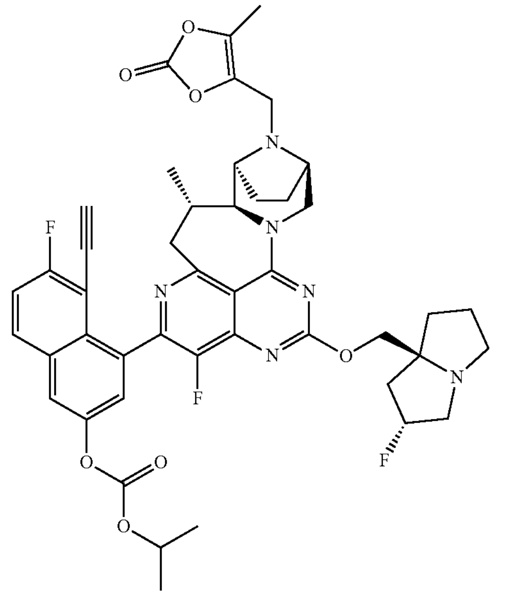
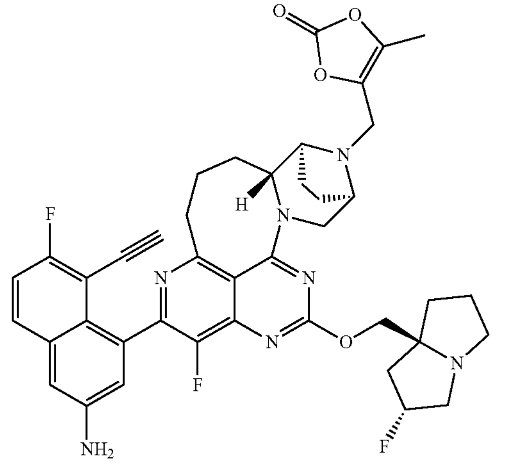
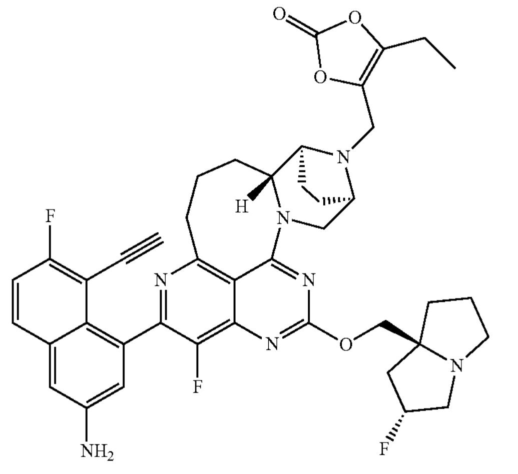

-continued
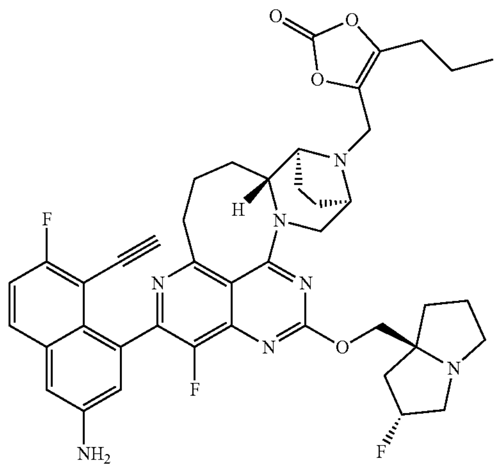
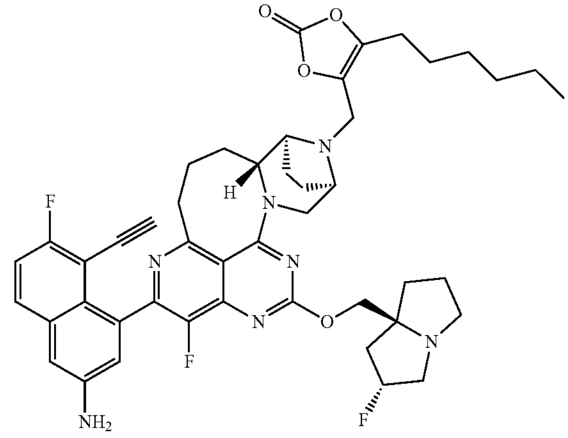
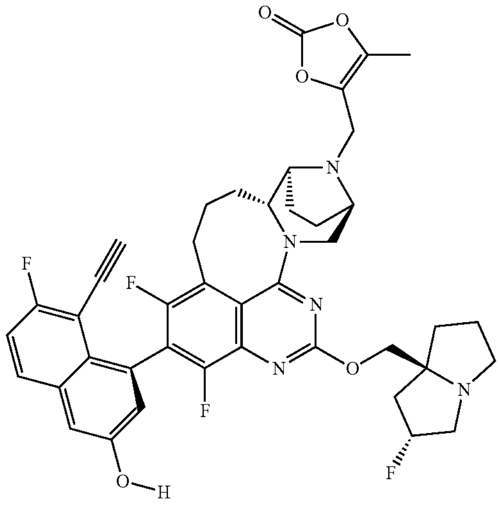
-continued
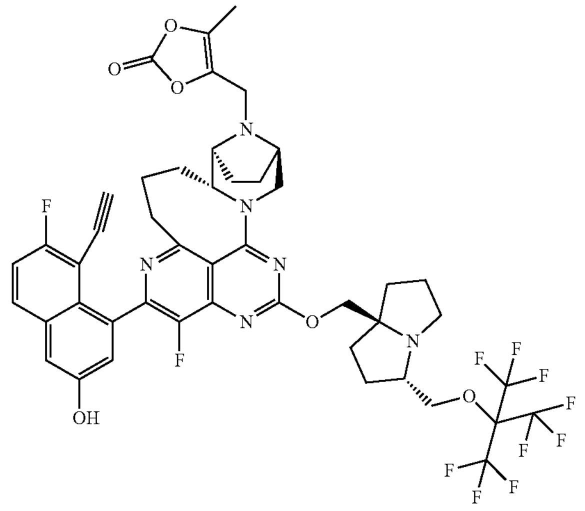
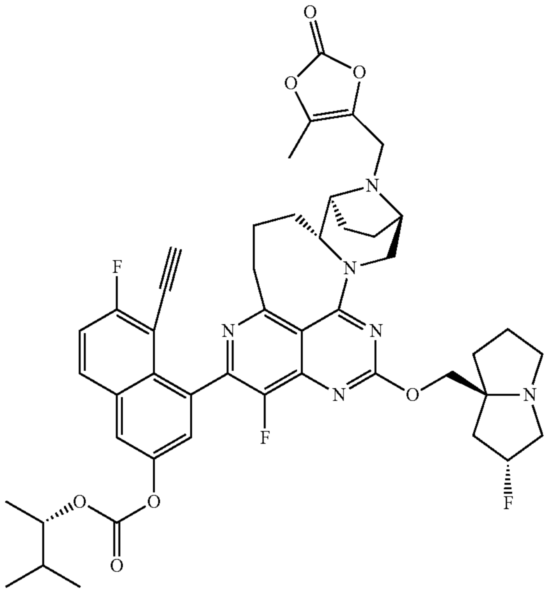
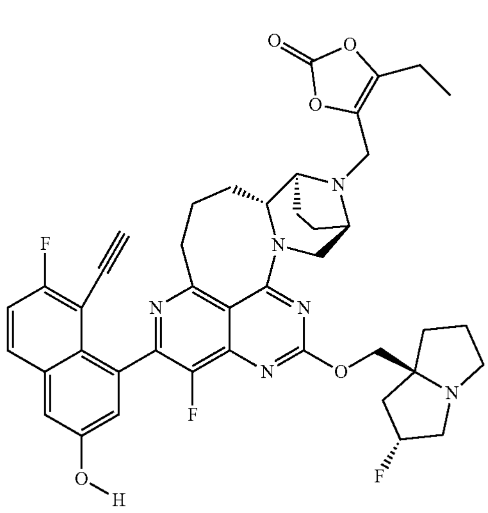

-continued
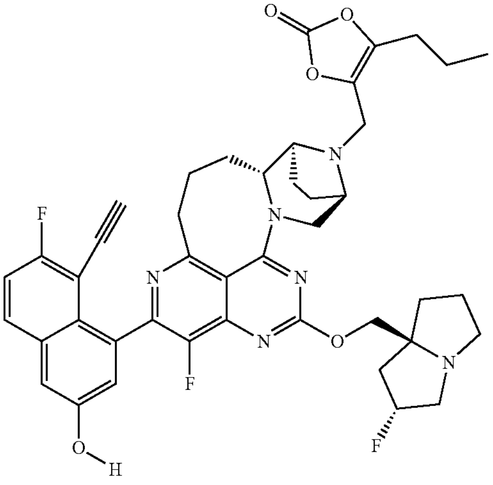
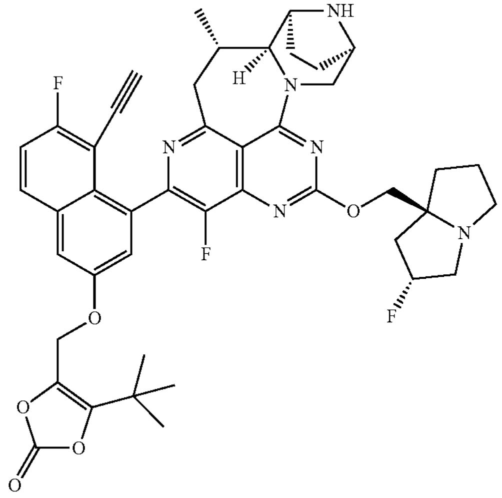
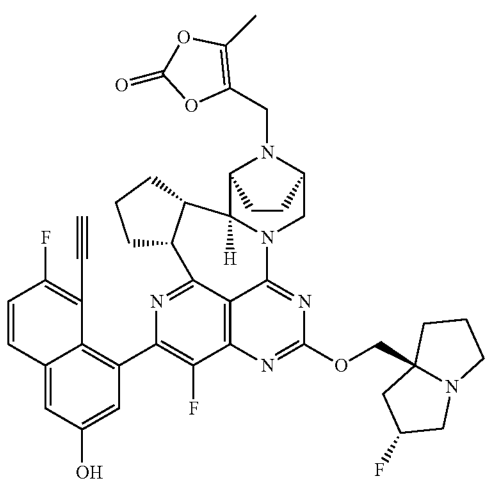
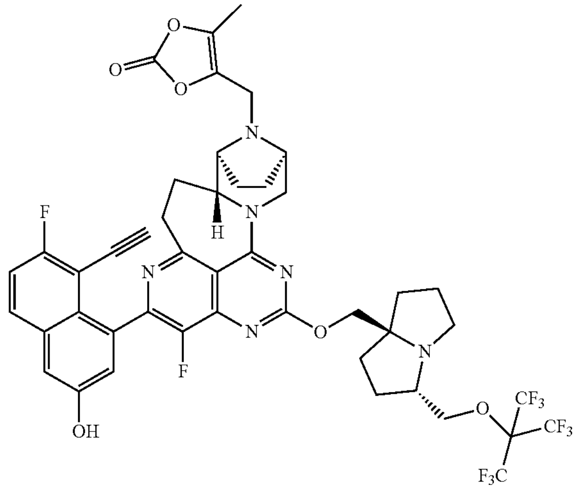
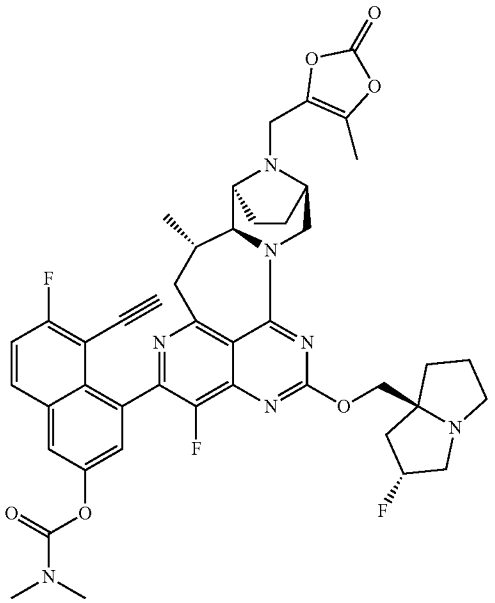
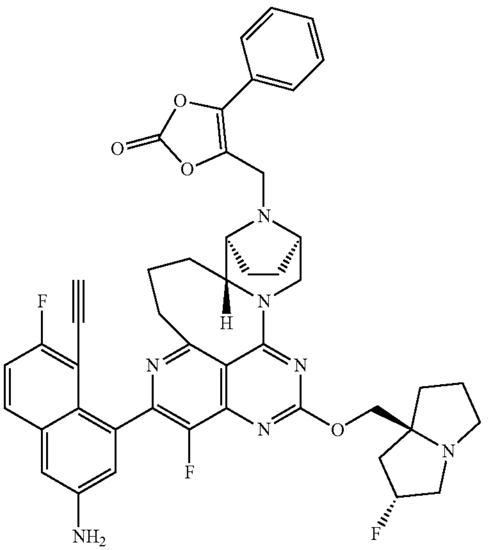
-continued -continued
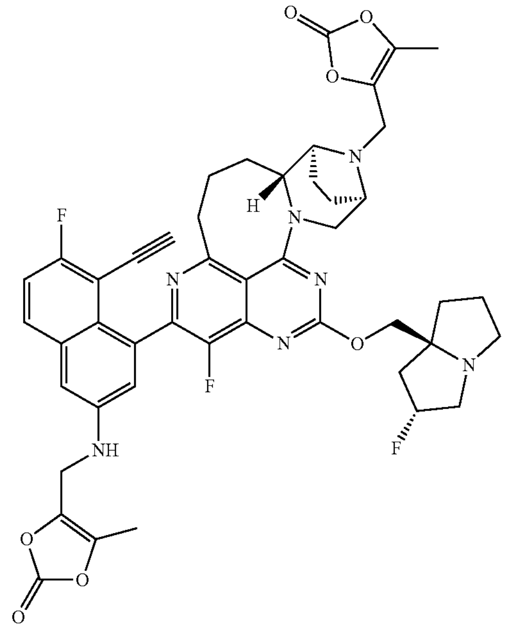
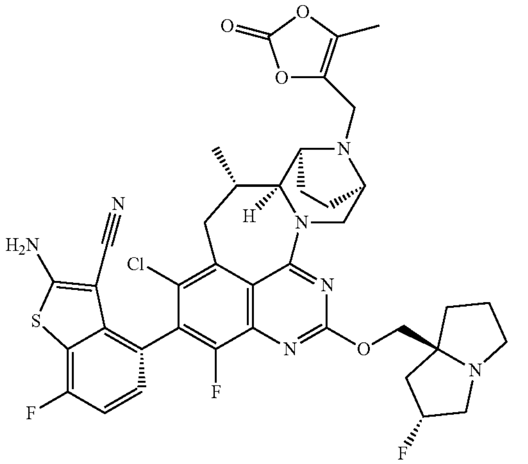
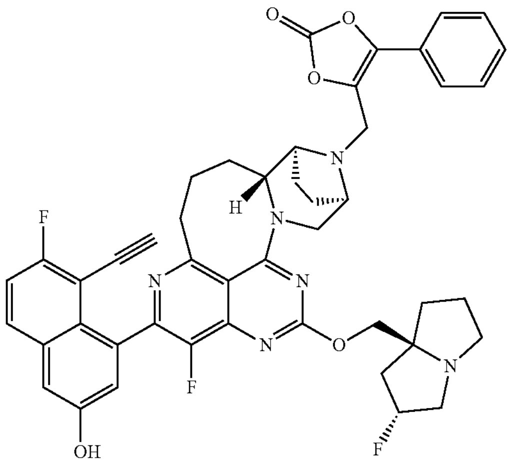
-continued
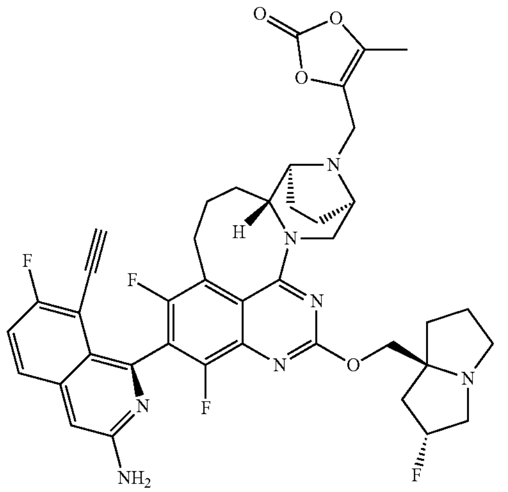
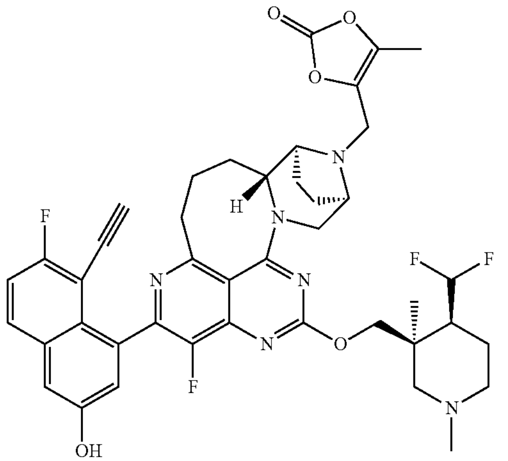
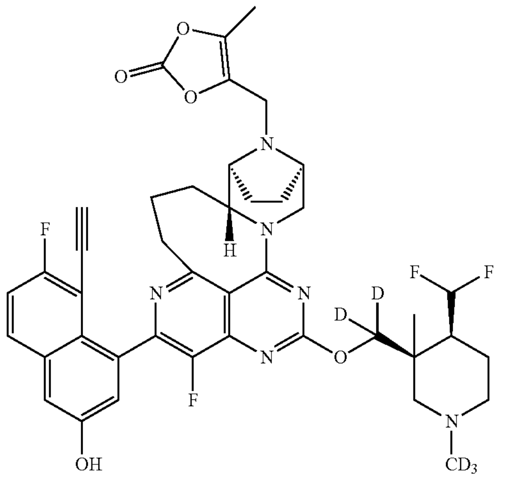

-continued
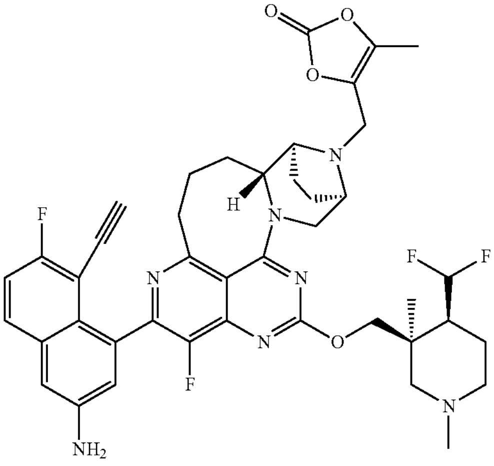
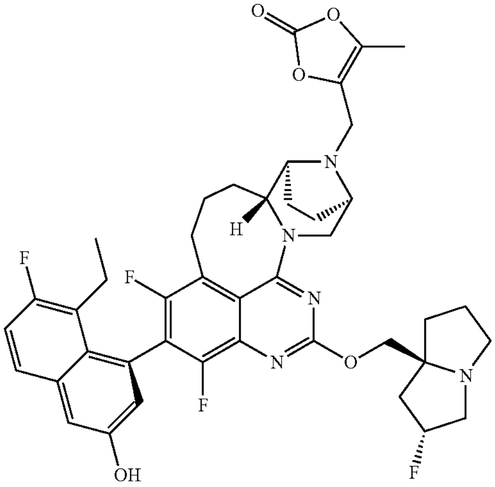
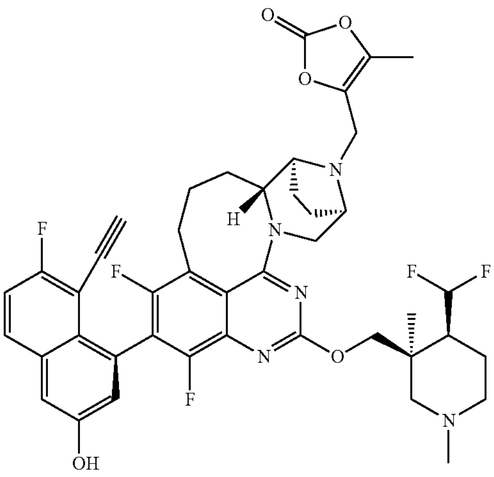
-continued
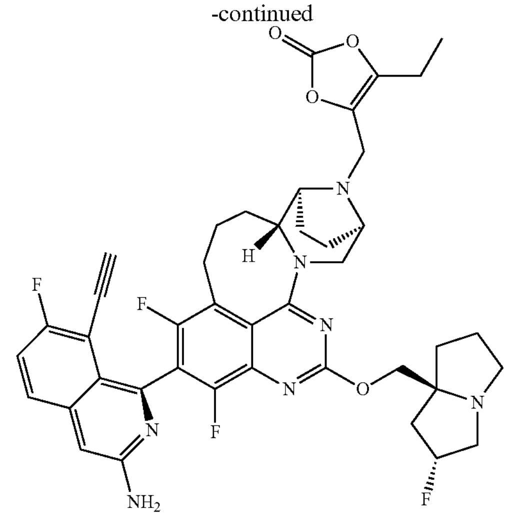
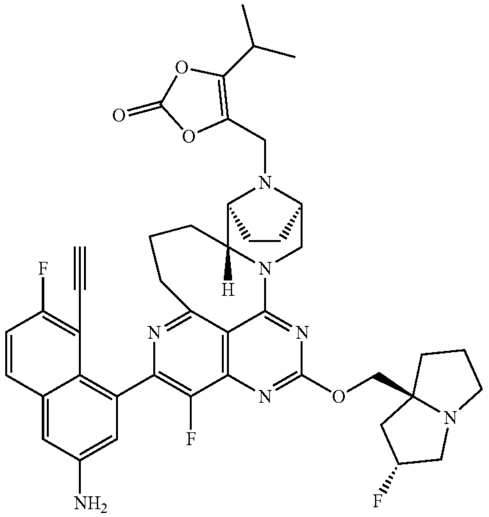
or
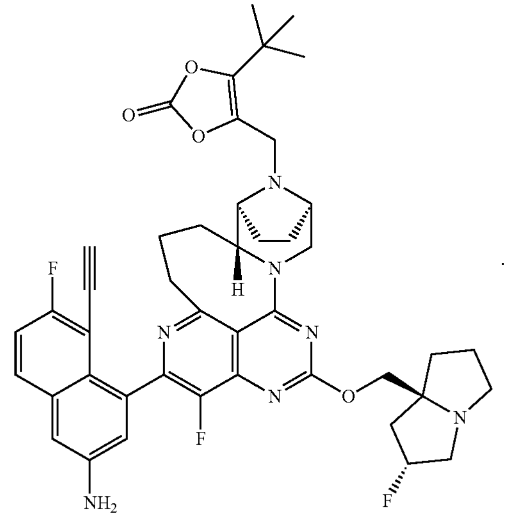
In some embodiments, the present disclosure provides a compound or a pharmaceutically acceptable salt thereof, wherein the compound has the structure:

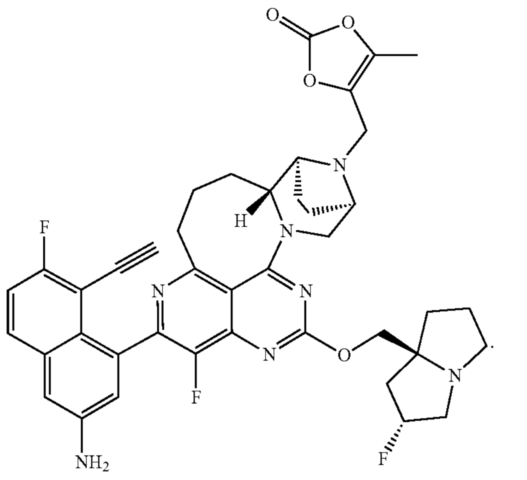

In some embodiments, the present disclosure provides a compound or a pharmaceutically acceptable salt thereof, wherein the compound has the structure:

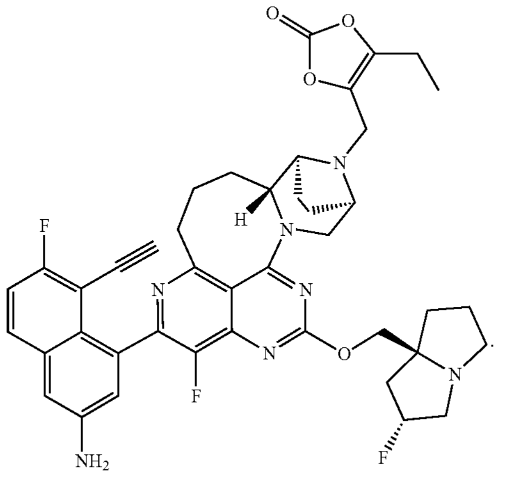

In some embodiments, the present disclosure provides a compound or a pharmaceutically acceptable salt thereof, wherein the compound has the structure:

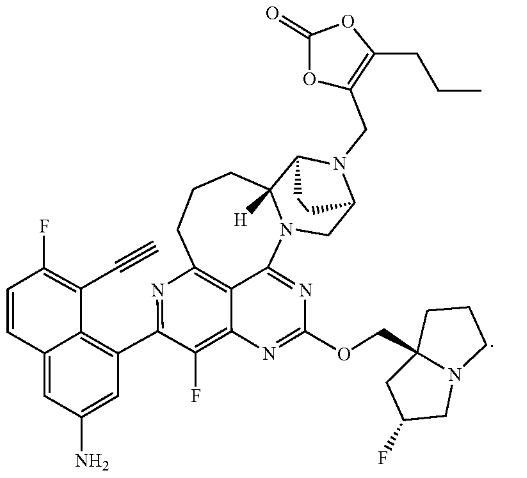

In some embodiments, the present disclosure provides a compound or a pharmaceutically acceptable salt thereof, wherein the compound has the structure:

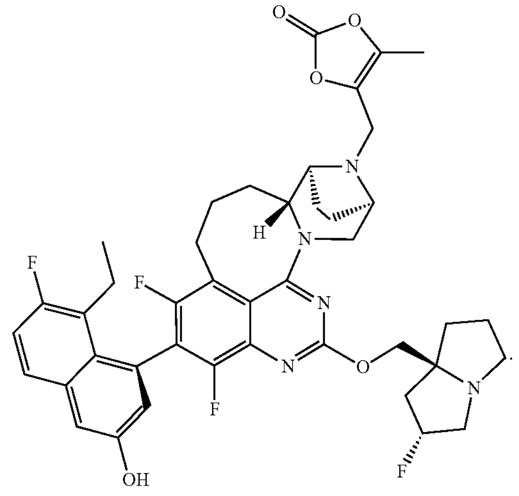

In some embodiments, the present disclosure provides a compound or a pharmaceutically acceptable salt thereof, wherein the compound has the structure:

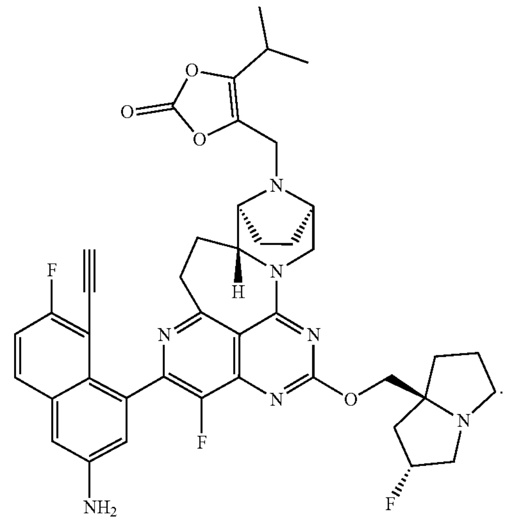

In some embodiments, the present disclosure provides a compound or a pharmaceutically acceptable salt thereof, wherein the compound has the structure:

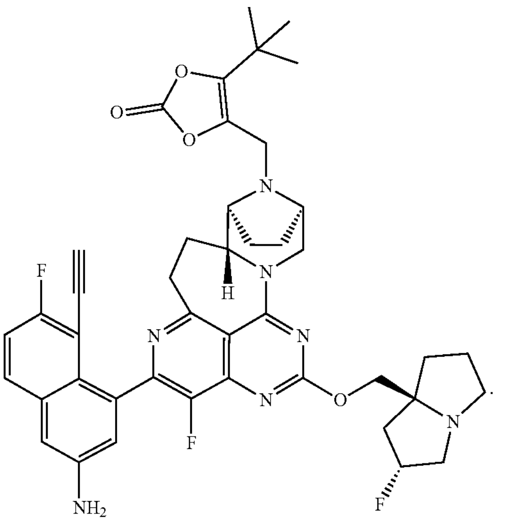
In some embodiments, the present disclosure provides a compound or a pharmaceutically acceptable salt thereof, wherein the compound has the structure:
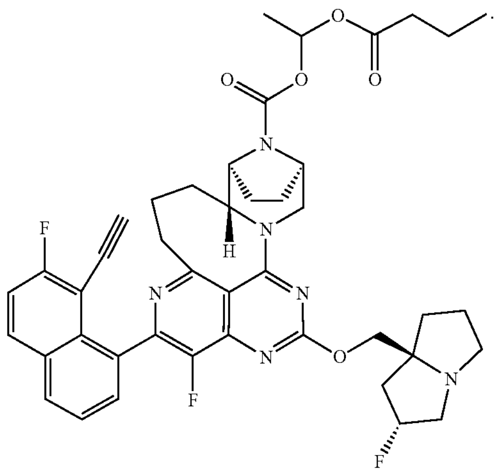
In some embodiments, the present disclosure provides a compound or a pharmaceutically acceptable salt thereof, wherein the compound has the structure:
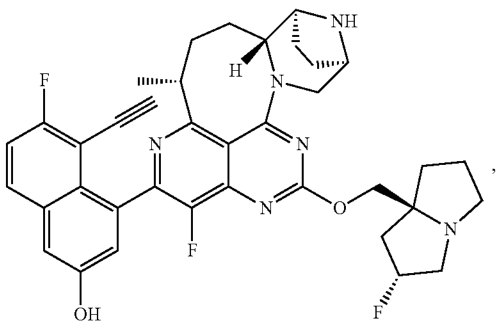
-continued
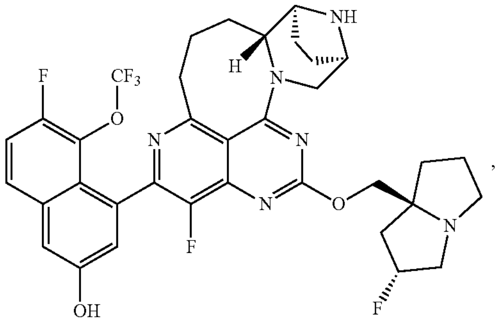
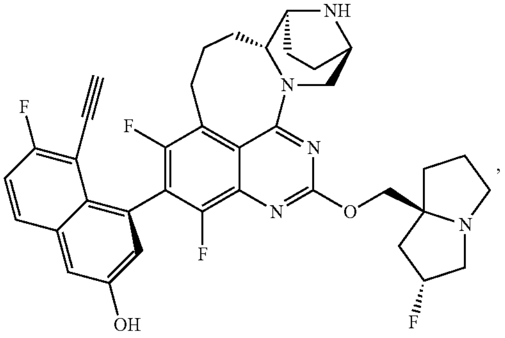
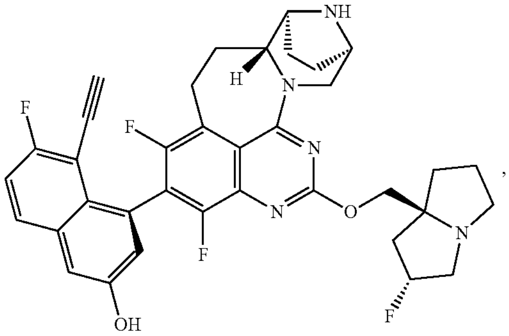
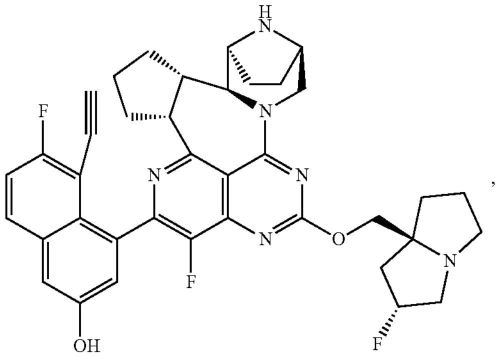
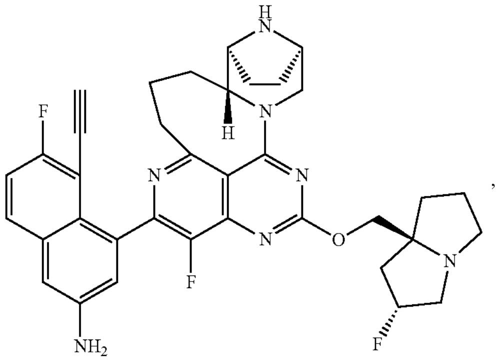

-continued

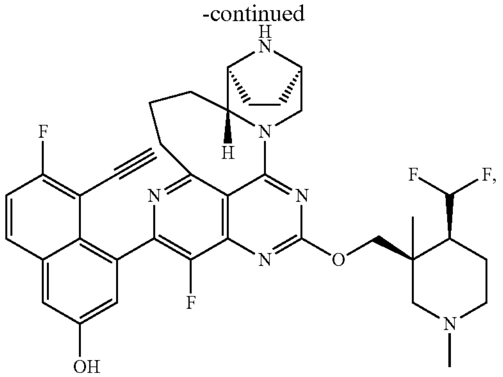

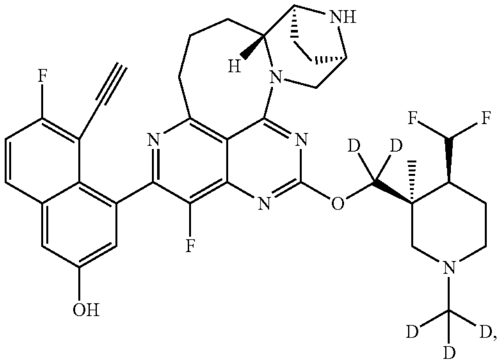

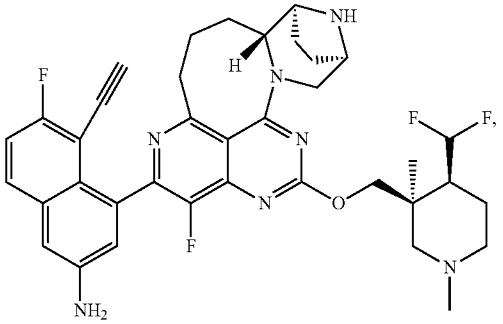

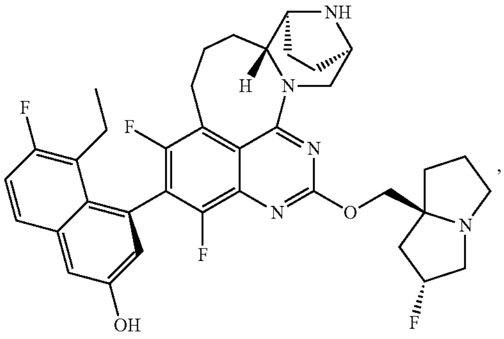

, or

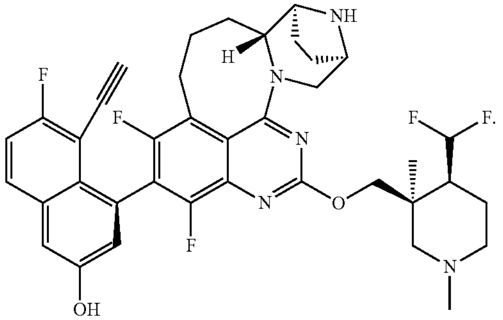

Also falling within the scope herein are the in vivo metabolic products of the compounds described herein. Such products may result for example from the oxidation, reduction, hydrolysis, amidation, esterification and the like of the administered compound, primarily due to enzymatic processes. Accordingly, included are novel and unobvious compounds produced by a process comprising contacting a compound with a mammal for a period of time sufficient to yield a metabolic product thereof. Such products typically are identified by preparing a radiolabelled (e.g., $^{14}C$ or $^{3}H$) compound, administering it parenterally in a detectable dose (e.g., greater than about 0.5 mg/kg) to an animal such as rat, mouse, guinea pig, monkey, or to man, allowing sufficient time for metabolism to occur (typically about 30 seconds to 30 hours) and isolating its conversion products from the urine, blood or other biological samples. These products are easily isolated since they are labeled (others are isolated by the use of antibodies capable of binding epitopes surviving in the metabolite). The metabolite structures are determined in conventional fashion, e.g., by MS or NMR analysis. In general, analysis of metabolites is done in the same way as conventional drug metabolism studies. The conversion products, so long as they are not otherwise found in vivo, are useful in diagnostic assays for therapeutic dosing of the compounds even if they possess no HSV antiviral activity of their own.

Recipes and methods for determining stability of compounds in surrogate gastrointestinal secretions are known. Compounds are defined herein as stable in the gastrointestinal tract where less than about 50 mole percent of the protected groups are deprotected in surrogate intestinal or gastric juice upon incubation for 1 hour at 37° C. Simply because the compounds are stable to the gastrointestinal tract does not mean that they cannot be hydrolyzed in vivo. The prodrugs typically will be stable in the digestive system but may be substantially hydrolyzed to the parental drug in the digestive lumen, liver, lung or other metabolic organ, or within cells in general. As used herein, a prodrug is understood to be a compound that is chemically designed to efficiently liberate the parent drug after overcoming biological barriers to oral delivery.

In some embodiments, the compound of Formula J, (I-1), (I-2), (I-3), (Ib), (Ib-1), (Ib-2), (Ib-3), (Ib-4), (IIb), (IIb-1), or (IIb-2), or pharmaceutically acceptable salt thereof, is a prodrug. In some embodiments, the prodrug as described herein exhibits an improved biological property after in vivo administration in a subject, including enhanced pharmacokinetics, such as higher exposure, higher oral bioavailability, and/or higher maximum blood concentration, and enhanced tissue distribution, compared to in vivo administration of an equivalent amount of the parent drug in the subject.

IV. Pharmaceutical Compositions

Also disclosed herein are pharmaceutical compositions comprising a pharmaceutically effective amount of a compound of the present disclosure (e.g., a compound of Formula J, (I-1), (I-2), (I-3), (Ib), (Ib-1), (Ib-2), (Ib-3), (Ib-4), (IIb), (IIb-1), or (IIb-2),) or a pharmaceutically acceptable salt thereof, and a pharmaceutically acceptable carrier or excipient. Also provided herein is a pharmaceutical composition comprising a pharmaceutically effective amount of a compound of the present disclosure, or a pharmaceutically acceptable salt thereof, and a pharmaceutically acceptable carrier or excipient. For example, provided herein is a pharmaceutical composition comprising a pharmaceutically effective amount of a compound of the present disclosure, or a pharmaceutically acceptable salt thereof, and a pharmaceutically acceptable excipient.

The compounds disclosed herein can be formulated with conventional carriers and excipients. Tablets can contain, for instance, excipients, glidants, fillers, binders, or a combination thereof. Aqueous formulations are prepared in sterile form, and when intended for delivery by other than oral administration generally will be isotonic. Exemplary excipients include, but are not limited to, those set forth in the "Handbook of Pharmaceutical Excipients" (1986). Excipients can include, for example, ascorbic acid and other antioxidants, chelating agents such as EDTA, carbohydrates such as dextran, hydroxyalkylcellulose, hydroxyalkylmethylcellulose, stearic acid, and combinations thereof. In some embodiments, the formulation is basic. In some embodiments, the formulation is acidic. In some embodiments, the formulation has a neutral pH. In some embodiments, the pH of the formulations is from 2 to 11 (e.g., 2, 3, 4, 5, 6, 7, 8, 9, 10, 11, 2-3, 2-4, 2-5, 2-6, 2-7, 2-8, 2-9, 2-10, 3-4, 3-5, 3-6, 3-7, 3-8, 3-9, 3-10, 4-5, 4-6, 4-7, 4-8, 4-9, 4-10, 4-11, 5-6, 5-7, 5-8, 5-9, 5-10, 5-11, 6-7, 6-8, 6-9, 6-10, 6-11, 7-8, 7-9, 7-10, 7-11, 8-9, 8-10, 8-11, 9-10, or 9-11).

In some embodiments, the compounds disclosed herein have pharmacokinetic properties (e.g., oral bioavailability) suitable for oral administration of the compounds. Formulations suitable for oral administration can, for instance, be presented as discrete units such as capsules, cachets or tablets, each containing a predetermined amount of the active ingredient; as a powder or granules; as a solution or a suspension in an aqueous or non-aqueous liquid; or as an oil-in-water liquid emulsion or a water-in-oil liquid emulsion. The active ingredient can also be administered, for instance, as a bolus, electuary, or paste.

A tablet can be made by compression or molding, optionally with at least accessory ingredients. Compressed tablets can be prepared by compressing in a suitable machine the active ingredient in a free-flowing form such as, for instance, a powder or granules, optionally mixed with a binder, lubricant, inert diluent, preservative, surface active, dispersing agent, or a combination thereof. Molded tablets can be made by molding in a suitable machine a mixture of the powdered active ingredient moistened with an inert liquid diluent. The tablets can optionally be coated or scored and optionally are formulated so as to provide slow or controlled release of the active ingredient therefrom.

For infections of the eye or other external tissues (e.g., mouth and skin), the formulations can be applied as a topical ointment or cream containing the active ingredient(s) in an amount of, for example, 0.075 to 20% w/w (including active ingredient(s) in a range from 0.1% to 20% in increments of 0.1% w/w such as 0.6% w/w, 0.7% w/w, etc.), from 0.2% to 15% w/w, or from 0.5% to 10% w/w. When formulated in an ointment, the active ingredients can be employed in some embodiments, with either a paraffinic or a water-miscible ointment base. Alternatively, the active ingredients can be formulated in a cream with an oil-in-water cream base.

In some embodiments, the aqueous phase of the cream base can include, for example, from 30% to 90% (e.g., 35%, 40%, 45%, 50%, 55%, 60%, 65%, 70%, 75%, 80%, 85%) w/w of a polyhydric alcohol, i.e., an alcohol having two or more hydroxyl groups such as propylene glycol, butane 1,3-diol, mannitol, sorbitol, glycerol and polyethylene glycol (including PEG 400) and mixtures thereof. In some embodiments, the cream base can include, for instance, a compound that enhances absorption or penetration of the active ingredient through the skin or other affected areas. Examples of such dermal penetration enhancers include, but are not limited to, dimethyl sulfoxide and related analogs. In some embodiments, the cream or emulsion does not include water.

The oily phase of the emulsions can be constituted from known ingredients in a known manner. In some embodiments, the phase comprises merely an emulsifier (otherwise known as an emulgent). In some embodiments, the phase comprises a mixture of at least one emulsifier with a fat, an oil, or a combination thereof. In some embodiments, a hydrophilic emulsifier is included together with a lipophilic emulsifier that acts as a stabilizer. Together, the emulsifier(s) with or without stabilizer(s) can make up the so-called emulsifying wax, and the wax together with the oil and fat make up the so-called emulsifying ointment base that can form the oily dispersed phase of the cream formulations.

Emulgents and emulsion stabilizers suitable for use in the formulation can include, but are not limited to, TWEEN® 60, TWEEN® 80, SPAN® 80, cetostearyl alcohol, benzyl alcohol, myristyl alcohol, glyceryl mono-stearate, sodium lauryl sulfate, and combinations thereof.

The choice of suitable oils or fats for the formulation can be based on achieving the desired cosmetic properties. In some embodiments, the cream can be a non-greasy, non-staining, and washable product with suitable consistency to avoid leakage from tubes or other containers. In some embodiments, esters can be included, such as, for example, straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate, a blend of branched chain esters known as CRODAMOL® CAP, or a combination thereof. In some embodiments, high melting point lipids such as white soft paraffin and/or liquid paraffin or other mineral oils can be included.

In some embodiments, the compounds disclosed herein are administered alone. In some embodiments, the compounds disclosed herein are administered in pharmaceutical compositions. In some embodiments, the pharmaceutical compositions are for veterinary use. In some embodiments, the pharmaceutical compositions are for human use. In some embodiments, the pharmaceutical compositions disclosed herein include at least one additional therapeutic agent. In some embodiments, the pharmaceutical compositions disclosed herein include one or more additional therapeutic agent. In some embodiments, the one or more additional therapeutic agents is independently a chemotherapeutic agent, an immunotherapeutic agent, a hormonal agent, an anti-hormonal agent, a targeted therapy agent, or an anti-angiogenesis agent.

Pharmaceutical compositions disclosed herein can be in any form suitable for the intended method of administration. The pharmaceutical compositions disclosed herein can be presented in unit dosage form and can be prepared by any of the methods well known in the art of pharmacy. Exemplary techniques and formulations can be found, for instance, in Remington's Pharmaceutical Sciences (Mack Publishing Co., Easton, PA). Such methods can include the step of bringing into association a compound disclosed herein with the carrier that constitutes at least accessory ingredients. In general, the formulations can be prepared by uniformly and intimately bringing into association the active ingredient with liquid carriers or finely divided solid carriers or both, and then, if necessary, shaping the product.

When used for oral use for example, tablets, troches, lozenges, aqueous or oil suspensions, dispersible powders or granules, emulsions, hard or soft capsules, solutions, syrups or elixirs can be prepared. Formulations intended for oral use can be prepared according to any method known to the art for the manufacture of pharmaceutical compositions and such formulations can contain at least agents including sweetening agents, flavoring agents, coloring agents and preserving agents, in order to provide a palatable preparation. Tablets containing the active ingredient in admixture with non-toxic pharmaceutically acceptable excipient which are suitable for manufacture of tablets are acceptable. These excipients can be, for example, inert diluents, such as calcium or sodium carbonate, lactose, calcium or sodium phosphate; granulating and disintegrating agents, such as maize starch, or alginic acid; binding agents, such as starch, gelatin or acacia; and lubricating agents, such as magnesium stearate, stearic acid or talc. Tablets can be uncoated or can be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax can be employed.

Formulations for oral use can be also presented as hard gelatin capsules where the active ingredient is mixed with an inert solid diluent, for example calcium phosphate or kaolin, or as soft gelatin capsules wherein the active ingredient is mixed with water or an oil medium, such as peanut oil, liquid paraffin, or olive oil.

Aqueous suspensions can contain the active materials in admixture with excipients suitable for the manufacture of aqueous suspensions. Such excipients can include, for instance, a suspending agent, such as sodium carboxymethylcellulose, methylcellulose, hydroxypropyl methylcellulose, sodium alginate, polyvinylpyrrolidone, gum tragacanth and gum acacia, and dispersing or wetting agents such as a naturally-occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycetanol), a condensation product of ethylene oxide with a partial ester derived from a fatty acid and a hexitol anhydride (e.g., polyoxyethylene sorbitan monooleate). The aqueous suspension can also contain, for example, at least preservatives such as ethyl or n-propyl p-hydroxy-benzoate, one or more coloring agents, one or more flavoring agents, one or more sweetening agents (such as sucrose or saccharin), or combinations thereof. Further non-limiting examples of suspending agents include cyclodextrin. In some embodiments, the suspending agent is sulfobutyl ether beta-cyclodextrin (SEB-beta-CD), for example CAPTISOL®.

Oil suspensions can be formulated by suspending the active ingredient in a vegetable oil (e.g., *arachis* oil, olive oil, sesame oil, coconut oil, or a combination thereof), a mineral oil such as liquid paraffin, or a combination thereof. The oral suspensions can contain, for instance, a thickening agent, such as beeswax, hard paraffin, cetyl alcohol, or a combination thereof. In some embodiments, sweetening agents, such as those set forth above, and/or flavoring agents, are added to provide a palatable oral preparation. In some embodiments, the formulations disclosed herein are preserved by the addition of an antioxidant such as ascorbic acid.

Dispersible powders and granules suitable for preparation of an aqueous suspension by the addition of water can provide the active ingredient in admixture with a dispersing or wetting agent, a suspending agent, a preservative, and combinations thereof. Suitable dispersing or wetting agents and suspending agents are exemplified by those disclosed above. Additional excipients, for example sweetening, flavoring and coloring agents, can also be present.

The pharmaceutical compositions can also be in the form of oil-in-water emulsions. The oily phase can be a vegetable oil, such as olive oil or *arachis* oil, a mineral oil, such as liquid paraffin, or a mixture of these. Suitable emulsifying agents include naturally-occurring gums, such as gum acacia and gum tragacanth, naturally-occurring phosphatides, such as soybean lecithin, esters or partial esters derived from fatty acids and hexitol anhydrides, such as sorbitan monooleate, and condensation products of these partial esters with ethylene oxide, such as polyoxyethylene sorbitan monooleate. The emulsion can also contain sweetening and flavoring agents. Syrups and elixirs can be formulated with sweetening agents, such as for instance, glycerol, sorbitol or sucrose. Such formulations can also contain, for instance, a demulcent, a preservative, a flavoring, a coloring agent, or a combination thereof.

The pharmaceutical compositions can be in the form of a sterile injectable or intravenous preparation, such as a sterile injectable aqueous or oleaginous suspension. This suspension can be formulated according to the known art using those suitable dispersing or wetting agents and suspending agents which have been mentioned above. The sterile injectable or intravenous preparation can also be a sterile injectable solution or suspension in a non-toxic parenterally acceptable diluent or solvent, such as a solution in 1,3-butane-diol or prepared as a lyophilized powder. Among the acceptable vehicles and solvents that can be employed are water, Ringer's solution and isotonic sodium chloride solution. In addition, sterile fixed oils can be employed as a solvent or suspending medium. For this purpose, any bland fixed oil can be employed including synthetic mono- or diglycerides. In addition, fatty acids such as oleic acid can likewise be used in the preparation of injectables. Among the acceptable vehicles and solvents that can be employed include, but are not limited to, water, Ringer's solution isotonic sodium chloride solution, and hypertonic sodium chloride solution.

The amount of active ingredient that can be combined with the carrier material to produce a single dosage form will vary depending upon the host treated and the particular mode of administration. For example, a time-release formulation intended for oral administration to humans can contain approximately 1 mg to 2000 mg of active material compounded with an appropriate and convenient amount of carrier material, which can vary from 5% to 95% of the total formulations (weight:weight). For example, a time-release formulation intended for oral administration to humans can contain approximately 1 mg to 1000 mg of active material compounded with an appropriate and convenient amount of carrier material, which can vary from 5% to 95% of the total formulations (weight:weight). The pharmaceutical composition can be prepared to provide easily measurable amounts for administration. For example, an aqueous solution intended for intravenous infusion can contain from 3 μg to 500 μg of the active ingredient per milliliter of solution in order that infusion of a suitable volume at a rate of 30 mL/hr can occur.

Formulations suitable for topical administration to the eye also include eye drops wherein the active ingredient is dissolved or suspended in a suitable carrier, especially an aqueous solvent for the active ingredient. In some embodiments, the compounds disclosed herein are included in the pharmaceutical compositions disclosed herein in a concentration of 0.5% to 20% (e.g., 0.5% to 10%, 1.5% w/w).

Formulations suitable for topical administration in the mouth include lozenges can comprise an active ingredient (i.e., a compound disclosed herein and/or additional therapeutic agents) in a flavored basis, usually sucrose and acacia or tragacanth; pastilles comprising the active ingredient in an inert basis such as gelatin and glycerin, or sucrose and acacia; and mouthwashes comprising the active ingredient in a suitable liquid carrier.

Formulations for rectal administration can be presented as a suppository with a suitable base comprising for example cocoa butter or a salicylate.

Formulations suitable for vaginal administration can be presented as pessaries, tampons, creams, gels, pastes, foams or spray formulations containing in addition to the active ingredient such carriers as are known in the art to be appropriate.

Formulations suitable for parenteral administration include aqueous and non-aqueous sterile injection solutions that can contain anti-oxidants, buffers, bacteriostats and solutes that render the formulation isotonic with the blood of the intended recipient; and aqueous and non-aqueous sterile suspensions that can include suspending agents and thickening agents.

The formulations can be presented in unit-dose or multi-dose containers, for example, sealed ampoules and vials, and can be stored in a freeze-dried (lyophilized) condition requiring only the addition of the sterile liquid carrier, for example water for injection, immediately before use. Extemporaneous injection solutions and suspensions are prepared from sterile powders, granules and tablets of the kind previously described. Preferred unit-dosage formulations are those containing a daily dose or unit daily sub-dose, as herein above recited, or an appropriate fraction thereof, of the active ingredient.

It should be understood that in addition to the ingredients particularly mentioned above the formulations can include other agents conventional in the art having regard to the type of formulation in question, for example those suitable for oral administration can include flavoring agents.

Further provided are veterinary formulations comprising a compound disclosed herein together with a veterinary carrier therefor.

Veterinary carriers are materials useful for the purpose of administering the formulation and can be solid, liquid or gaseous materials which are otherwise inert or acceptable in the veterinary art and are compatible with the active ingredient. These veterinary formulations can be administered orally, parenterally, or by any other desired route.

Compounds herein are used to provide controlled release pharmaceutical compositions containing as active ingredient one or more of the compounds ("controlled release formulations") in which the release of the active ingredient can be controlled and regulated to allow less frequency dosing or to improve the pharmacokinetic or toxicity profile of a given active ingredient.

Effective dose of active ingredient depends at least on the nature of the condition being treated, toxicity, whether the compound is being used prophylactically (lower doses) or against an active viral infection, the method of delivery, and the pharmaceutical composition, and will be determined by the clinician using conventional dose escalation studies. In some embodiments, the effective dose is from 0.0001 to 100 mg/kg body weight per day; for instance, from 10 to 30 mg/kg body weight per day; from 15 to 25 mg/kg body weight per day; from 10 to 15 mg/kg body weight per day; or from 20 to 30 mg/kg body weight per day. For example, the daily candidate dose for an adult human of approximately 70 kg body weight can range from 1 mg to 2000 mg (e.g., from 5 mg to 500 mg, from 500 mg to 1000 mg, from 1000 mg to 1500 mg, from 1500 mg to 2000 mg), and can take the form of single or multiple doses. For example, the daily candidate dose for an adult human of approximately 70 kg body weight can range from 1 mg to 1000 mg (e.g., from 5 mg to 500 mg), and can take the form of single or multiple doses.

V. Kits

Also provided herein are kits that includes a compound disclosed herein or a pharmaceutically acceptable salt thereof. In some embodiments the kits described herein can comprise a label and/or instructions for use of the compound in the treatment of a disease or condition in a subject (e.g., human) in need thereof. In some embodiments, the disease or condition is viral infection.

In some embodiments, the kit can also comprise one or more additional therapeutic agents and/or instructions for use of additional therapeutic agents in combination with the compound disclosed herein in the treatment of the disease or condition in a subject (e.g., human) in need thereof.

In some embodiments, the kits provided herein comprise individual dose units of a compound as described herein, or a pharmaceutically acceptable salt, racemate, enantiomer, diastereomer, tautomer, polymorph, pseudopolymorph, amorphous form, hydrate or solvate thereof. Examples of individual dosage units can include pills, tablets, capsules, prefilled syringes or syringe cartridges, IV bags, inhalers, nebulizers etc., each comprising a therapeutically effective amount of the compound in question, or a pharmaceutically acceptable salt, racemate, enantiomer, diastereomer, tautomer, polymorph, pseudopolymorph, amorphous form, hydrate or solvate thereof. In some embodiments, the kit can contain a single dosage unit and in others multiple dosage units are present, such as the number of dosage units required for a specified regimen or period.

Also provided are articles of manufacture that include a compound disclosed herein, or a pharmaceutically acceptable salt, stereoisomer, mixture of stereoisomers or tautomer thereof; and a container. In some embodiments, the container of the article of manufacture is a vial, jar, ampoule, preloaded syringe, blister package, tin, can, bottle, box, an intravenous bag, an inhaler, or a nebulizer.

VI. Administration

One or more of the compounds of Formula J, (I-1), (I-2), (I-3), (Ib), (Ib-1), (Ib-2), (Ib-3), (Ib-4), (IIb), (IIb-1), or (IIb-2), (herein referred to as the active ingredients) are administered by any route appropriate to the condition to be treated. Suitable routes include oral, rectal, nasal, pulmonary, topical (including buccal and sublingual), vaginal and parenteral (including subcutaneous, intramuscular, intravenous, intradermal, intrathecal and epidural), and the like. It will be appreciated that the route may vary with for example the condition of the recipient. An advantage of the compounds herein is that they are orally bioavailable and can be dosed orally.

The compounds of the present disclosure (also referred to herein as the active ingredients), can be administered by any route appropriate to the condition to be treated.

Suitable routes include oral, rectal, nasal, topical (including buccal and sublingual), transdermal, vaginal and parenteral (including subcutaneous, intramuscular, intravenous, intradermal, intrathecal and epidural), and the like. It will be appreciated that the route may vary with for example the condition of the recipient. An advantage of certain compounds disclosed herein is that they are orally bioavailable and can be dosed orally.

A compound of the present disclosure may be administered to an individual in accordance with an effective dosing regimen for a desired period of time or duration, such as at least about one month, at least about 2 months, at least about 3 months, at least about 6 months, or at least about 12 months or longer. In some embodiments, the compound is administered on a daily or intermittent schedule for the duration of the individual's life.

The dosage or dosing frequency of a compound of the present disclosure may be adjusted over the course of the treatment, based on the judgment of the administering physician.

The compound may be administered to an individual (e.g., a human) in an effective amount. In some embodiments, the compound is administered once daily.

The compound can be administered by any useful route and means, such as by oral or parenteral (e.g., intravenous) administration. Therapeutically effective amounts of the compound may include from about 0.00001 mg/kg body weight per day to about 10 mg/kg body weight per day, such as from about 0.0001 mg/kg body weight per day to about 10 mg/kg body weight per day, or such as from about 0.001 mg/kg body weight per day to about 1 mg/kg body weight per day, or such as from about 0.01 mg/kg body weight per day to about 1 mg/kg body weight per day, or such as from about 0.05 mg/kg body weight per day to about 0.5 mg/kg body weight per day, or such as from about 0.3 mg to about 30 mg per day, or such as from about 30 mg to about 300 mg per day.

A compound of the present disclosure may be combined with one or more additional therapeutic agents in any dosage amount of the compound of the present disclosure (e.g., from about 1 mg to about 1000 mg of compound). Therapeutically effective amounts may include from about 1 mg per dose to about 1000 mg per dose, such as from about 50 mg per dose to about 500 mg per dose, or such as from about 100 mg per dose to about 400 mg per dose, or such as from about 150 mg per dose to about 350 mg per dose, or such as from about 200 mg per dose to about 300 mg per dose. Other therapeutically effective amounts of the compound of the present disclosure are about 100, about 125, about 150, about 175, about 200, about 225, about 250, about 275, about 300, about 325, about 350, about 375, about 400, about 425, about 450, about 475, or about 500 mg per dose. Other therapeutically effective amounts of the compound of the present disclosure are about 100 mg per dose, or about 125, about 150, about 175, about 200, about 225, about 250, about 275, about 300, about 325, about 350, about 375, about 400, about 425, about 450, or about 500 mg per dose. A single dose can be administered hourly, daily, or weekly. For example, a single dose can be administered once about every 1 hour, about 2, about 3, about 4, about 6, about 8, about 12, about 16 or once about every 24 hours. A single dose can also be administered once about every 1 day, about 2, about 3, about 4, about 5, about 6, or once about every 7 days. A single dose can also be administered once about every 1 week, about 2, about 3, or once about every 4 weeks. In some embodiments, a single dose can be administered once about every week. A single dose can also be administered once about every month.

Other therapeutically effective amounts of the compound of the present disclosure are about 20, about 25, about 30, about 35, about 40, about 45, about 50, about 55, about 60, about 65, about 70, about 75, about 80, about 85, about 90, about 95, or about 100 mg per dose.

The frequency of dosage of the compound of the present disclosure can be determined by the needs of the individual patient and can be, for example, once per day or twice, or more times, per day. Administration of the compound continues for as long as necessary to treat the disease or condition. For example, a compound can be administered to a human having cancer for a period of from about 20 days to about 180 days or, for example, for a period of from about 20 days to about 90 days or, for example, for a period of from about 30 days to about 60 days.

Administration can be intermittent, with a period of several or more days during which a patient receives a daily dose of the compound of the present disclosure followed by a period of several or more days during which a patient does not receive a daily dose of the compound. For example, a patient can receive a dose of the compound every other day, or three times per week. Again by way of example, a patient can receive a dose of the compound each day for a period of from about 1 to about 14 days, followed by a period of about 7 to about 21 days during which the patient does not receive a dose of the compound, followed by a subsequent period (e.g., from about 1 to about 14 days) during which the patient again receives a daily dose of the compound. Alternating periods of administration of the compound, followed by non-administration of the compound, can be repeated as clinically required to treat the patient.

In some embodiments, pharmaceutical compositions comprising a compound of the present disclosure, or a pharmaceutically acceptable salt thereof, in combination with one or more (e.g., one, two, three, four, one or two, one to three, or one to four) additional therapeutic agents, and a pharmaceutically acceptable excipient are provided.

In some embodiments, kits comprising a compound of the present disclosure, or a pharmaceutically acceptable salt thereof, in combination with one or more (e.g., one, two, three, four, one or two, one to three, or one to four) additional therapeutic agents are provided.

In some embodiments, a compound of the present disclosure, or a pharmaceutically acceptable salt thereof, is combined with one, two, three, four or more additional therapeutic agents. In some embodiments, a compound of the present disclosure, or a pharmaceutically acceptable salt thereof, is combined with two additional therapeutic agents. In some embodiments, a compound of the present disclosure, or a pharmaceutically acceptable salt thereof, is combined with three additional therapeutic agents. In some embodiments, a compound of the present disclosure, or a pharmaceutically acceptable salt thereof, is combined with four additional therapeutic agents. The one, two, three, four or more additional therapeutic agents can be different therapeutic agents selected from the same class of therapeutic agents, and/or they can be selected from different classes of therapeutic agents.

In some embodiments, when a compound of the present disclosure is combined with one or more additional therapeutic agents as described herein, the components of the composition are administered as a simultaneous or sequential regimen. When administered sequentially, the combination may be administered in two or more administrations.

In some embodiments, a compound of the present disclosure is combined with one or more additional therapeutic agents in a unitary dosage form for simultaneous administration to a patient, for example as a solid dosage form for oral administration.

In some embodiments, a compound of the present disclosure is co-administered with one or more additional therapeutic agents.

In order to prolong the effect of a compound of the present disclosure, it is often desirable to slow the absorption of a compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending a compound in an oil vehicle. Injectable depot forms are made by forming microencapsule matrices of a compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping a compound in liposomes or microemulsions that are compatible with body tissues.

VII. Methods of Use

The disclosure further relates to the use of compounds disclosed herein for the treatment and/or prophylaxis of diseases and/or conditions through inhibition of KRAS G12D and/or G12C. Further, the present disclosure relates to the use of said compounds for the preparation of a medicament for the treatment and/or prophylaxis of cancer.

Medicaments as referred to herein can be prepared by conventional processes, including the combination of a compound according to the present disclosure and a pharmaceutically acceptable carrier.

In some embodiments, provided herein is a method of inhibiting KRAS G12D protein in a subject in need thereof, the method comprising administering to the subject a therapeutically effective amount of a compound of Formula J, (I-1), (I-2), (I-3), (Ib), (Ib-1), (Ib-2), (Ib-3), (Ib-4), (IIb), (IIb-1), or (IIb-2), or a pharmaceutically acceptable salt thereof, or a pharmaceutical composition comprising a compound of Formula J, (I-1), (I-2), (I-3), (Ib), (Ib-1), (Ib-2), (Ib-3), (Ib-4), (IIb), (IIb-1), or (IIb-2).

In some embodiments, provided herein is treating cancer in a subject in need thereof, the method comprising administering to the subject a therapeutically effective amount of a compound of Formula J, (I-1), (I-2), (I-3), (Ib), (Ib-1), (Ib-2), (Ib-3), (Ib-4), (IIb), (IIb-1), or (IIb-2), or a pharmaceutically acceptable salt thereof, or a pharmaceutical composition comprising a compound of Formula J, (I-1), (I-2), (I-3), (Ib), (Ib-1), (Ib-2), (Ib-3), (Ib-4), (IIb), (IIb-1), or (IIb-2).

In some embodiments, provided herein is a method of treating and/or preventing a cancer.

In some embodiments, provided herein is a method of treating and/or preventing a KRAS G12D-associated cancer.

In some embodiments, provided herein is a method of reducing the proliferation of a cell comprising contacting the cell with a compound of Formula J, (I-1), (I-2), (I-3), (Ib), (Ib-1), (Ib-2), (Ib-3), (Ib-4), (IIb), (IIb-1), or (IIb-2).

In some embodiments, the KRAS G12D associated disease or condition includes cancer. In some embodiments, the cancer is a hematological cancer. In some embodiments, the cancer includes a solid tumor. In some embodiments, the cancer includes a malignant tumor. In some embodiments the cancer includes a metastatic cancer. In some embodiments, the cancer is resistant or refractory to one or more anticancer therapies. In some embodiments, greater than about 50% of the cancer cells detectably express one or more cell surface immune checkpoint receptors (e.g., so-called "hot" cancer or tumor). In some embodiments, greater than about 1% and less than about 50% of the cancer cells detectably express one or more cell surface immune checkpoint receptors (e.g., so called "warm" cancer or tumor). In some embodiments, less than about 1% of the cancer cells detectably express one or more cell surface immune checkpoint receptors (e.g., so called "cold" cancer or tumor).

In some embodiments, the KRAS G12D associated disease or condition is a hematological cancer, e.g., a leukemia (e.g., Acute Myelogenous Leukemia (AML), Acute Lymphoblastic Leukemia (ALL), B-cell ALL, Myelodysplastic Syndrome (MDS), myeloproliferative disease (MPD), Chronic Myelogenous Leukemia (CML), Chronic Lymphocytic Leukemia (CLL), undifferentiated leukemia), a lymphoma (e.g., small lymphocytic lymphoma (SLL), mantle cell lymphoma (MCL), follicular lymphoma (FL), T-cell lymphoma, B-cell lymphoma, diffuse large B-cell lymphoma (DLBCL), marginal zone lymphoma (MZL), Waldestrom's macroglobulinemia (WM)) and/or a myeloma (e.g., multiple myeloma (MM)).

In some embodiments, the KRAS G12D associated disease or condition is an epithelial tumor (e.g., a carcinoma, a squamous cell carcinoma, a basal cell carcinoma, a squamous intraepithelial neoplasia), a glandular tumor (e.g., an adenocarcinoma, an adenoma, an adenomyoma), a mesenchymal or soft tissue tumor (e.g., a sarcoma, a rhabdomyosarcoma, a leiomyosarcoma, a liposarcoma, a fibrosarcoma, a dermatofibrosarcoma, a neurofibrosarcoma, a fibrous histiocytoma, an angiosarcoma, an angiomyxoma, a leiomyoma, a chondroma, a chondrosarcoma, an alveolar soft-part sarcoma, an epithelioid hemangioendothelioma, a Spitz tumor, a synovial sarcoma), or a lymphoma.

In some embodiments, the KRAS G12D associated disease or condition includes a solid tumor in or arising from a tissue or organ, such as:

- bone (e.g., adamantinoma, aneurysmal bone cysts, angiosarcoma, chondroblastoma, chondroma, chondromyxoid fibroma, chondrosarcoma, chordoma, dedifferentiated chondrosarcoma, enchondroma, epithelioid hemangioendothelioma, fibrous dysplasia of the bone, giant cell tumor of bone, haemangiomas and related lesions, osteoblastoma, osteochondroma, osteosarcoma, osteoid osteoma, osteoma, periosteal chondroma, Desmoid tumor, Ewing sarcoma);
- lips and oral cavity (e.g., odontogenic ameloblastoma, oral leukoplakia, oral squamous cell carcinoma, primary oral mucosal melanoma); salivary glands (e.g., pleomorphic salivary gland adenoma, salivary gland adenoid cystic carcinoma, salivary gland mucoepidermoid carcinoma, salivary gland Warthin's tumors);
- esophagus (e.g., Barrett's esophagus, dysplasia and adenocarcinoma);
- gastrointestinal tract, including stomach (e.g., gastric adenocarcinoma, primary gastric lymphoma, gastrointestinal stromal tumors (GISTs), metastatic deposits, gastric carcinoids, gastric sarcomas, neuroendocrine carcinoma, gastric primary squamous cell carcinoma, gastric adenoacanthomas), intestines and smooth muscle (e.g., intravenous leiomyomatosis), colon (e.g., colorectal adenocarcinoma), rectum, anus;
- pancreas (e.g., serous neoplasms, including microcystic or macrocystic serous cystadenoma, solid serous cystadenoma, Von Hippel-Landau (VHL)-associated serous cystic neoplasm, serous cystadenocarcinoma; mucinous cystic neoplasms (MCN), intraductal papillary mucinous neoplasms (IPMN), intraductal oncocytic papillary neoplasms (IOPN), intraductal tubular neoplasms, cystic acinar neoplasms, including acinar cell cystadenoma, acinar cell cystadenocarcinoma, pancreatic adenocarcinoma, invasive pancreatic ductal adenocarcinomas, including tubular adenocarcinoma, adenosquamous carcinoma, colloid carcinoma, medullary carcinoma, hepatoid carcinoma, signet ring cell carcinoma, undifferentiated carcinoma, undifferentiated carcinoma with osteoclast-like giant cells, acinar cell carcinoma, neuroendocrine neoplasms, neuroendocrine microadenoma, neuroendocrine tumors (NET), neuroendocrine carcinoma (NEC), including small cell or large cell NEC, insulinoma, gastrinoma, glucagonoma, serotonin-producing NET, somatostatinoma, VIPoma, solid-pseudopapillary neoplasms (SPN), pancreatoblastoma);

gall bladder (e.g. carcinoma of the gallbladder and extrahepatic bile ducts, intrahepatic cholangiocarcinoma);

neuro-endocrine (e.g., adrenal cortical carcinoma, carcinoid tumors, phaeochromocytoma, pituitary adenomas);

thyroid (e.g., anaplastic (undifferentiated) carcinoma, medullary carcinoma, oncocytic tumors, papillary carcinoma, adenocarcinoma);

liver (e.g., adenoma, combined hepatocellular and cholangiocarcinoma, fibrolamellar carcinoma, hepatoblastoma, hepatocellular carcinoma, mesenchymal, nested stromal epithelial tumor, undifferentiated carcinoma; hepatocellular carcinoma, intrahepatic cholangiocarcinoma, bile duct cystadenocarcinoma, epithelioid hemangioendothelioma, angiosarcoma, embryonal sarcoma, rhabdomyosarcoma, solitary fibrous tumor, teratoma, York sac tumor, carcinosarcoma, rhabdoid tumor);

kidney (e.g., ALK-rearranged renal cell carcinoma, chromophobe renal cell carcinoma, clear cell renal cell carcinoma, clear cell sarcoma, metanephric adenoma, metanephric adenofibroma, mucinous tubular and spindle cell carcinoma, nephroma, nephroblastoma (Wilms tumor), papillary adenoma, papillary renal cell carcinoma, renal oncocytoma, renal cell carcinoma, succinate dehydrogenase-deficient renal cell carcinoma, collecting duct carcinoma);

breast (e.g., invasive ductal carcinoma, including without limitation, acinic cell carcinoma, adenoid cystic carcinoma, apocrine carcinoma, cribriform carcinoma, glycogen-rich/clear cell, inflammatory carcinoma, lipid-rich carcinoma, medullary carcinoma, metaplastic carcinoma, micropapillary carcinoma, mucinous carcinoma, neuroendocrine carcinoma, oncocytic carcinoma, papillary carcinoma, sebaceous carcinoma, secretory breast carcinoma, tubular carcinoma; lobular carcinoma, including without limitation, pleomorphic carcinoma, signet ring cell carcinoma;

peritoneum (e.g., mesothelioma; primary peritoneal cancer);

female sex organ tissues, including ovary (e.g., choriocarcinoma, epithelial tumors, germ cell tumors, sex cord-stromal tumors), Fallopian tubes (e.g., serous adenocarcinoma, mucinous adenocarcinoma, endometrioid adenocarcinoma, clear cell adenocarcinoma, transitional cell carcinoma, squamous cell carcinoma, undifferentiated carcinoma, Müllerian tumors, adenosarcoma, leiomyosarcoma, teratoma, germ cell tumors, choriocarcinoma, trophoblastic tumors), uterus (e.g., carcinoma of the cervix, endometrial polyps, endometrial hyperplasia, intraepithelial carcinoma (EIC), endometrial carcinoma (e.g., endometrioid carcinoma, serous carcinoma, clear cell carcinoma, mucinous carcinoma, squamous cell carcinoma, transitional carcinoma, small cell carcinoma, undifferentiated carcinoma, mesenchymal neoplasia), leiomyoma (e.g., endometrial stromal nodule, leiomyosarcoma, endometrial stromal sarcoma (ESS), mesenchymal tumors), mixed epithelial and mesenchymal tumors (e.g., adenofibroma, carcinofibroma, adenosarcoma, carcinosarcoma (malignant mixed mesodermal sarcoma—MMMT)), endometrial stromal tumors, endometrial malignant mullerian mixed tumors, gestational trophoblastic tumors (partial hydatiform mole, complete hydatiform mole, invasive hydatiform mole, placental site tumor)), vulva, vagina;

male sex organ tissues, including prostate, testis (e.g., germ cell tumors, spermatocytic seminoma), penis;

bladder (e.g., squamous cell carcinoma, urothelial carcinoma, bladder urothelial carcinoma);

brain, (e.g., gliomas (e.g., astrocytomas, including non-infiltrating, low-grade, anaplastic, glioblastomas; oligodendrogliomas, ependymomas), meningiomas, gangliogliomas, schwannomas (neurilemmomas), craniopharyngiomas, chordomas, Non-Hodgkin lymphomas (NHLs), indolent non-Hodgkin's lymphoma (iNHL), refractory iNHL, pituitary tumors;

eye (e.g., retinoma, retinoblastoma, ocular melanoma, posterior uveal melanoma, iris hamartoma);

head and neck (e.g., nasopharyngeal carcinoma, Endolymphatic Sac Tumor (ELST), epidermoid carcinoma, laryngeal cancers including squamous cell carcinoma (SCC) (e.g., glottic carcinoma, supraglottic carcinoma, subglottic carcinoma, transglottic carcinoma), carcinoma in situ, verrucous, spindle cell and basaloid SCC, undifferentiated carcinoma, laryngeal adenocarcinoma, adenoid cystic carcinoma, neuroendocrine carcinomas, laryngeal sarcoma), head and neck paragangliomas (e.g., carotid body, jugulotympanic, vagal);

thymus (e.g., thymoma);

heart (e.g., cardiac myxoma);

lung (e.g., small cell carcinoma (SCLC), non-small cell lung carcinoma (NSCLC), including squamous cell carcinoma (SCC), adenocarcinoma and large cell carcinoma, carcinoids (typical or atypical), carcinosarcomas, pulmonary blastomas, giant cell carcinomas, spindle cell carcinomas, pleuropulmonary blastoma);

lymph (e.g., lymphomas, including Hodgkin's lymphoma, non-Hodgkin's lymphoma (NHL), indolent non-Hodgkin's lymphoma (iNHL), refractory iNHL, Epstein-Barr virus (EBV)-associated lymphoproliferative diseases, including B cell lymphomas and T cell lymphomas (e.g., Burkitt lymphoma; large B cell lymphoma, diffuse large B-cell lymphoma (DLBCL), mantle cell lymphoma, indolent B-cell lymphoma, low grade B cell lymphoma, fibrin-associated diffuse large cell lymphoma; primary effusion lymphoma; plasmablastic lymphoma; extranodal NK/T cell lymphoma, nasal type; peripheral T cell lymphoma, cutaneous T cell lymphoma, angioimmunoblastic T cell lymphoma; follicular T cell lymphoma; systemic T cell lymphoma), lymphangioleiomyomatosis);

central nervous system (CNS) (e.g., gliomas including astrocytic tumors (e.g., pilocytic astrocytoma, pilomyxoid astrocytoma, subependymal giant cell astrocytoma, pleomorphic xanthoastrocytoma, diffuse astrocytoma, fibrillary astrocytoma, gemistocytic astrocytoma, protoplasmic astrocytoma, anaplastic astrocytoma, glioblastoma (e.g., giant cell glioblastoma, gliosarcoma, glioblastoma multiforme) and gliomatosis cerebri), oligodendroglial tumors (e.g., oligodendroglioma, anaplastic oligodendroglioma), oligoastrocytic tumors (e.g., oligoastrocytoma, anaplastic oligoastrocytoma), ependymal tumors (e.g., subependymom, myxopapillary ependymoma, ependymomas (e.g., cellular, papillary, clear cell, tanycytic), anaplastic ependymoma), optic nerve glioma, and non-gliomas (e.g., choroid plexus tumors, neuronal and mixed neuronal-glial tumors, pineal region tumors, embryonal tumors, medulloblastoma, meningeal tumors, primary CNS lymphomas, germ cell tumors, Pituitary adenomas, cranial and paraspinal nerve tumors, stellar region tumors); neurofibroma, meningioma, peripheral nerve sheath tumors, peripheral neuroblastic tumors (including without limitation neuroblastoma, ganglioneuroblastoma, ganglioneuroma), trisomy 19 ependymoma);

neuroendocrine tissues (e.g., paraganglionic system including adrenal medulla (pheochromocytomas) and extra-adrenal paraganglia ((extra-adrenal) paragangliomas);

skin (e.g., clear cell hidradenoma, cutaneous benign fibrous histiocytomas, cylindroma, hidradenoma, melanoma (including cutaneous melanoma, mucosal melanoma), pilomatricoma, Spitz tumors); and soft tissues (e.g., aggressive angiomyxoma, alveolar rhabdomyosarcoma, alveolar soft part sarcoma, angiofibroma, angiomatoid fibrous histiocytoma, synovial sarcoma, biphasic synovial sarcoma, clear cell sarcoma, dermatofibrosarcoma protuberans, desmoid-type fibromatosis, small round cell tumor, desmoplastic small round cell tumor, elastofibroma, embryonal rhabdomyosarcoma, Ewing's tumors/primitive neurectodermal tumors (PNET), extraskeletal myxoid chondrosarcoma, extraskeletal osteosarcoma, paraspinal sarcoma, inflammatory myofibroblastic tumor, lipoblastoma, lipoma, chondroid lipoma, liposarcoma/malignant lipomatous tumors, liposarcoma, myxoid liposarcoma, fibromyxoid sarcoma, lymphangioleiomyoma, malignant myoepithelioma, malignant melanoma of soft parts, myoepithelial carcinoma, myoepithelioma, myxoinflammatory fibroblastic sarcoma, undifferentiated sarcoma, pericytoma, rhabdomyosarcoma, non-rhabdomyosarcoma soft tissue sarcoma (NRSTS), soft tissue leiomyosarcoma, undifferentiated sarcoma, well-differentiated liposarcoma.

In some embodiments, the KRAS G12D associated disease or condition is a cancer selected from a lung cancer, a colorectal cancer, a breast cancer, a prostate cancer, a cervical cancer, a pancreatic cancer and a head and neck cancer. In some embodiments, the cancer is metastatic.

In some embodiments, the KRAS G12D associated disease or condition is a cancer selected from non-small lung cancer (NSCLC), melanoma, triple-negative breast cancer (TNBC), nasopharyngeal cancer (NPC), microsatellite stable colorectal cancer (mssCRC), thymoma, and gastrointestinal stromal tumor (GIST). In some embodiments, the cancer is metastatic.

In some embodiments, the KRAS G12D associated disease or condition is a cancer of pancreatic cancer, bladder cancer, colorectal cancer, breast cancer, prostate cancer, renal cancer, hepatocellular cancer, lung cancer, ovarian cancer, cervical cancer, uterine cancer, gastric cancer, bile duct cancer, testicular cancer, esophageal cancer, head and neck cancer, melanoma, neuroendocrine cancer, CNS cancer, brain cancer, bone cancer, soft tissue sarcoma, non-small cell lung cancer, small-cell lung cancer, myelodysplastic syndrome, thyroid cancer, or colon cancer.

In some embodiments, the KRAS G12D associated disease or condition is a cancer of pancreatic cancer, colorectal cancer, non-small cell lung cancer, endometrial cancer, uterine endometrical carcinoma, cholangio carcinoma, testicular germ cell cancer, cervical squamous carcinoma, or myelodysplastic syndrome.

In some embodiments, the cancer is or myelodysplastic syndrome. In some embodiments, the cancer is high risk myelodysplastic syndrome or low risk myelodysplastic syndrome. In some embodiments, the cancer is high risk myelodysplastic syndrome. In some embodiments, the cancer is high risk myelodysplastic syndrome.

In some embodiments, the cancer is colorectal cancer. In some embodiments, the cancer is non-small cell lung cancer. In some embodiments, the cancer is pancreatic cancer. In some embodiments, the cancer is endometrial cancer. In some embodiments, the cancer is uterine endometrical carcinoma. In some embodiments, the cancer is testicular germ cell cancer. In some embodiments, the cancer is cervical squamous carcinoma. In some embodiments, the cancer is cholangio carcinoma.

The effective dosage of active ingredient employed may vary depending on the particular compound employed, the mode of administration, the condition being treated and the severity of the condition being treated. Such dosage may be ascertained readily by a person skilled in the art.

When treating or preventing a KRAS G12D associated disease or condition for which compounds of the present disclosure are indicated, generally satisfactory results are obtained when the compounds of the present disclosure are administered at a daily dosage of from about 0.1 milligram to about 300 milligram per kilogram of animal body weight. In some embodiments, the compounds of the present disclosure are given as a single daily dose or in divided doses two to six times a day, or in sustained release form. For most large mammals, the total daily dosage is from about 1 milligram to about 1000 milligrams, or from about 1 milligram to about 50 milligrams. In the case of a 70 kg adult human, the total daily dose will generally be from about 0.1 milligrams to about 200 milligrams. This dosage regimen may be adjusted to provide the optimal therapeutic response. In some embodiments, the total daily dosage is from about 1 milligram to about 900 milligrams, about 1 milligram to about 800 milligrams, about 1 milligram to about 700 milligrams, about 1 milligram to about 600 milligrams, about 1 milligram to about 400 milligrams, about 1 milligram to about 300 milligrams, about 1 milligram to about 200 milligrams, about 1 milligram to about 100 milligrams, about 1 milligram to about 50 milligrams, about 1 milligram to about 20 milligram, or about 1 milligram to about 10 milligrams.

The compounds of the present application or the compositions thereof may be administered once, twice, three, or four times daily, using any suitable mode described above. Also, administration or treatment with the compounds may be continued for a number of days; for example, commonly treatment would continue for at least 7 days, 14 days, or 28 days, for one cycle of treatment. Treatment cycles are frequently alternated with resting periods of about 1 to 28 days, commonly about 7 days or about 14 days, between cycles. The treatment cycles, in other embodiments, may also be continuous.

In some embodiments, the methods provided herein comprise administering to the subject an initial daily dose of about 1 to 800 mg of a compound described herein and increasing the dose by increments until clinical efficacy is achieved. Increments of about 5, 10, 25, 50, or 100 mg can be used to increase the dose. The dosage can be increased daily, every other day, twice per week, or once per week.

In some embodiments, the compound or pharmaceutically acceptable salt thereof of the present disclosure is administered in combination with one or more additional therapeutic agent or therapeutic modality.

In some embodiments, the present disclosure provides the pharmaceutical composition or the method wherein the one or more more additional therapeutic agent or additional therapeutic modality comprises one, two, three, or four additional therapeutic agents and/or therapeutic modalities.

In some embodiments, the present disclosure provides the pharmaceutical composition or the method wherein the additional therapeutic agent or therapeutic modalities are selected from an immune checkpoint modulator, an antibody-drug conjugate (ADC), an antiapoptotic agent, a targeted anticancer therapeutic, a chemotherapeutic agent, surgery, or radiation therapy.

In some embodiments, the present disclosure provides the pharmaceutical composition or the method wherein the immune checkpoint modulator is selected from an anti-PD-(L)1 antibody, an anti-TIGIT antibody, an anti-CTLA4 antibody, an anti-CCR8 antibody, an anti-TREM1 antibody, an anti-TREM2 antibody, a CD47 inhibitor, a DGKα inhibitor, an HPK1 inhibitor, a FLT3 agonist, an adenosine receptor antagonist, a CD39 inhibitor, a CD73 inhibitor, an IL-2 variant (IL-2v), and a CAR-T cell therapy.

In some embodiments, the present disclosure provides the pharmaceutical composition or the method wherein the anti-PD-(L)1 antibody is selected from pembrolizumab, nivolumab, cemiplimab, pidilizumab, spartalizumab, atezolizumab, avelumab, durvalumab, cosibelimab, sasanlimab, tislelizumab, retifanlimab, balstilimab, toripalimab, cetrelimab, genolimzumab, prolgolimab, lodapolimab, camrelizumab, budigalimab, avelumab, dostarlimab, envafolimab, sintilimab, and zimberelimab.

In some embodiments, the present disclosure provides the pharmaceutical composition or the method wherein the anti-TIGIT antibody is selected from tiragolumab, vibostolimab, domvanalimab, AB308, AK127, BMS-986207, and etigilimab.

In some embodiments, the present disclosure provides the pharmaceutical composition or the method wherein the anti-CTLA4 antibody is selected from ipilimumab, tremelimumab, and zalifrelimab.

In some embodiments, the present disclosure provides the pharmaceutical composition or the method wherein the CD47 inhibitor is selected from magrolimab, letaplimab, lemzoparlimab, AL-008, RRx-001, CTX-5861, FSI-189 (GS-0189), ES-004, BI-765063, ADU1805, CC-95251, and Q-1801.

In some embodiments, the present disclosure provides the pharmaceutical composition or the method wherein the adenosine receptor antagonist is etrumadenant (AB928), taminadenant, TT-10, TT-4, or M1069.

In some embodiments, the present disclosure provides the pharmaceutical composition or the method wherein the CD39 inhibitor is TTX-030.

In some embodiments, the present disclosure provides the pharmaceutical composition or the method wherein the CD73 inhibitor is quemliclustat (AB680), uliledlimab, mupadolimab, ORIC-533, ATG-037, PT-199, AK131, NZV930, BMS-986179, or oleclumab.

In some embodiments, the present disclosure provides the pharmaceutical composition or the method wherein the IL-2v is aldesleukin (Proleukin), bempegaldesleukin (NKTR-214), nemvaleukin alfa (ALKS-4230), THOR-202 (SAR-444245), BNT-151, ANV-419, XTX-202, RG-6279 (RO-7284755), NL-201, STK-012, SHR-1916, or GS-4528.

In some embodiments, the present disclosure provides the pharmaceutical composition or the method wherein the ADC is selected from sacituzumab govitecan, datopotamab deruxtecan, enfortumab vedotin, and trastuzumab deruxtecan.

In some embodiments, the present disclosure provides the pharmaceutical composition or the method wherein the additional therapeutic agent is selected from idealisib, sacituzumab govitecan, magrolimab, GS-0189, GS-3583, zimberelimab, GS-4224, GS-9716, GS-6451, GS-1811 (JTX-1811), quemliclustat (AB680), etrumadenant (AB928), domvanalimab, AB308, PY159, PY314, AGEN-1223, AGEN-2373, axicabtagene ciloleucel and brexucabtagene autoleucel.

In some embodiments, the method includes administering one or more additional therapeutic agents. The one or more additional therapeutic agents can be one or more therapeutic agents as described below. In some embodiments, the one or more additional therapeutic agents is independently a chemotherapeutic agent, an immunotherapeutic agent, a hormonal agent, an anti-hormonal agent, a targeted therapy agent, or an anti-angiogenesis agent.

In some embodiments, the one or more additional therapeutic agents includes therapeutic agents used to treat high risk myelodysplastic syndrome (HR MDS), low risk myelodyplastic syndrome (LR MDS), colorectal cancer, non-small cell lung cancer (NSCLC), pancreatic cancer, or endometrial cancer. In some embodiments, the one or more additional therapeutic agents includes therapeutic agents used to treat high risk myelodysplastic syndrome (HR MDS). In some embodiments, the one or more additional therapeutic agents includes azacitidine (Vidaza®), decitabine (Dacogen®), lenalidomide (Reylimid®), cytarabine, idarubicin, daunorubicin, cytarabine+daunorubicin, cytarabine+idarubicin, pevonedistat, venetoclax, sabatolimab, guadecitabine, rigosertib, ivosidenib, enasidenib, selinexor, BGB324, DSP-7888, or SNS-301.

In some embodiments, the one or more additional therapeutic agents includes therapeutic agents used to treat low risk myelodyplastic syndrome (LR MDS). In some embodiments, the one or more additional therapeutic agents includes lenalidomide, azacytidine, roxadustat, luspatercept, imetelstat, LB-100, or rigosertib.

In some embodiments, the one or more additional therapeutic agents includes therapeutic agents used to treat colorectal cancer. In some embodiments, the one or more additional therapeutic agents includes bevacizumab, capecitabine, cetuximab, fluorouracil, irinotecan, leucovorin, oxaliplatin, panitumumab, ziv-aflibercept, bevacizumab (Avastin®), leucovorin, 5-FU, oxaliplatin (FOLFOX), pembrolizumab (Keytruda®), FOLFIRI, regorafenib (Stivarga®), aflibercept (Zaltrap®), cetuximab (Erbitux®), Lonsurf (Orcantas®), XELOX, FOLFOXIRI, bevacizumab+leucovorin+5-FU+oxaliplatin (FOLFOX), bevacizumab+FOLFIRI, bevacizumab+FOLFOX, aflibercept+FOLFIRI, cetuximab+FOLFIRI, bevacizumab+XELOX, bevacizumab+FOLFOXIRI, binimetinib+encorafenib+cetuximab, trametinib+dabrafenib+panitumumab, trastuzumab+pertuzumab, napabucasin+FOLFIRI+bevacizumab, or nivolumab+ipilimumab.

In some embodiments, the one or more additional therapeutic agents includes therapeutic agents used to treat non-small cell lung cancer (NSCLC). In some embodiments, the one or more additional therapeutic agents includes afatinib, albumin-bound paclitaxel, alectinib, atezolizumab, bevacizumab, bevacizumab, cabozantinib, carboplatin, cisplatin, crizotinib, dabrafenib, docetaxel, erlotinib, etoposide, gemcitabine, nivolumab, paclitaxel, pembrolizumab, pemetrexed, ramucirumab, trametinib, trastuzumab, vandetanib, vemurafenib, vinblastine, vinorelbine, alectinib (Alecensa®), dabrafenib (Tafinlar®), trametinib (Mekinist®), osimertinib (Tagrisso®), entrectinib (Tarceva®), crizotinib (Xalkori®), pembrolizumab (Keytruda®), carboplatin, pemetrexed (Alimta®), nab-paclitaxel (Abraxane®), ramucirumab (Cyramza®), docetaxel, bevacizumab (Avastin®), brigatinib, gemcitabine, cisplatin, afatinib (Gilotrif®), nivolumab (Opdivo®), gefitinib (Iressa®), dabrafenib+trametinib, pembrolizumab+carboplatin+pemetrexed, pembrolizumab+carboplatin+nab-paclitaxel, ramucirumab+docetaxel, bevacizumab+carboplatin+pemetrexed, pembrolizumab+pemetrexed+carboplatin, cisplatin+pemetrexed, bevacizumab+carboplatin+nab-paclitaxel, cisplatin+gemcitabine, nivolumab+docetaxel, carboplatin+pemetrexed, carboplatin+nab-paclitaxel, or pemetrexed+cisplatin+carboplatin, datopotamab deruxtecan (DS-1062), trastuzumab deruxtecan (Enhertu®), enfortumab vedotin (Padcev®), durvalumab, canakinumab, cemiplimab, nogapendekin alfa, avelumab, tiragolumab, domvanalimab, vibostolimab, ociperlimab, datopotamab deruxtecan+pembrolizumab, datopotamab deruxtecan+durvalumab, durvalumab+tremelimumab, pembrolizumab+lenvatinib+pemetrexed, pembrolizumab+olaparib, nogapendekin alfa (N-803)+pembrolizumab, tiragolumab+atezolizumab, vibostolimab+pembrolizumab, or ociperlimab+tislelizumab.

In some embodiments, the one or more additional therapeutic agents includes therapeutic agents used to treat pancreatic cancer. In some embodiments, the one or more additional therapeutic agents includes 5-FU, leucovorin, oxaliplatin, irinotecan, gemcitabine, nab-paclitaxel (Abraxane®), FOLFIRINOX, 5-FU+leucovorin+oxaliplatin+irinotecan, 5-FU+nanoliposomal irinotecan, leucovorin+nanoliposomal irinotecan, or gemcitabine+nab-paclitaxel.

In some embodiments, the one or more additional therapeutic agents includes therapeutic agents used to treat endometrial cancer. In some embodiments, the one or more additional therapeutic agents includes carboplatin, paclitaxel, cisplatin, doxorubicin, ifosfamide, progesterone, anastrozole (Arimidex®), letrozole (Femara®), exemestane (Aromasin®), pembrolizumab (Keytruda®), lenvatinib (Lenvima®), or dostarlimab (Jemperli®).

In some embodiments, the one or more additional therapeutic agents is independently SNS-301, 5-FU+leucovorin+oxaliplatin+irinotecan, 5-FU+nanoliposomal irinotecan, 5-FU, afatinib (Gilotrif®), aflibercept (Zaltrap®), aflibercept+FOLFIRI, albumin-bound paclitaxel, alectinib (Alecensa®), anastrozole (Arimidex®), atezolizumab, avelumab, azacitidine (Vidaza®), bevacizumab (Avastin®), bevacizumab+carboplatin+nab-paclitaxel, bevacizumab+carboplatin+pemetrexed, bevacizumab+FOLFIRI, bevacizumab+FOLFOX, bevacizumab+FOLFOXIRI, bevacizumab+leucovorin+5-FU+oxaliplatin (FOLFOX), bevacizumab+XELOX, bevacizumab, BGB324, binimetinib+encorafenib+cetuximab, brigatinib, cabozantinib, canakinumab, capecitabine, carboplatin+nab-paclitaxel, carboplatin+pemetrexed, carboplatin, cemiplimab, cetuximab (Erbitux®), cetuximab+FOLFIRI, cisplatin+gemcitabine, cisplatin+pemetrexed, cisplatin, crizotinib (Xalkori®), cytarabine+daunorubicin, cytarabine+idarubicin, cytarabine, dabrafenib (Tafinlar®), dabrafenib+trametinib, datopotamab deruxtecan (DS-1062), datopotamab deruxtecan+durvalumab, datopotamab deruxtecan+pembrolizumab, daunorubicin, decitabine (Dacogen®), docetaxel, domvanalimab, dostarlimab (Jemperli®), doxorubicin, DSP-7888, durvalumab+tremelimumab, durvalumab, enasidenib, enfortumab vedotin (Padcev®), entrectinib (Tarceva®), erlotinib, etoposide, exemestane (Aromasin®), fluorouracil, FOLFIRI, FOLFIRINOX, FOLFOXIRI, gefitinib (Iressa®), gemcitabine+nab-paclitaxel, gemcitabine, guadecitabine, idarubicin, ifosfamide, imetelstat, irinotecan, ivosidenib, LB-100, lenalidomide (Reylimid®), lenalidomide, lenvatinib (Lenvima®), letrozole (Femara®), leucovorin+nanoliposomal irinotecan, leucovorin, Lonsurf (Orcantas®), luspatercept, nab-paclitaxel (Abraxane®), napabucasin+FOLFIRI+bevacizumab, nivolumab (Opdivo®), nivolumab+docetaxel, nivolumab+ipilimumab, nogapendekin alfa (N-803)+pembrolizumab, nogapendekin alfa, ociperlimab+tislelizumab, ociperlimab, osimertinib (Tagrisso®), oxaliplatin (FOLFOX), paclitaxel, panitumumab, pembrolizumab (Keytruda®), pembrolizumab+carboplatin+nab-paclitaxel, pembrolizumab+carboplatin+pemetrexed, pembrolizumab+lenvatinib+pemetrexed, pembrolizumab+olaparib, pembrolizumab+pemetrexed+carboplatin, pemetrexed (Alimta®), pemetrexed+cisplatin+carboplatin, pevonedistat, progesterone, ramucirumab (Cyramza®), ramucirumab+docetaxel, regorafenib (Stivarga®), rigosertib, roxadustat, sabatolimab, selinexor, tiragolumab+atezolizumab, tiragolumab, trametinib (Mekinist®), trametinib+dabrafenib+panitumumab, trastuzumab+pertuzumab, trastuzumab deruxtecan (Enhertu®), trastuzumab, vandetanib, vemurafenib, venetoclax, vibostolimab+pembrolizumab, vibostolimab, vinblastine, vinorelbine, XELOX, or ziv-aflibercept.

In another embodiment, the present disclosure provides a method for manufacturing a medicament for treating cancer in a subject in need thereof, characterized in that a compound of the present disclosure, or a pharmaceutically acceptable salt thereof, is used.

In another embodiment, the present disclosure provides a method for manufacturing a medicament for inhibiting cancer metastasis in a subject in need thereof, characterized in that a compound of the present invention, or a pharmaceutically acceptable salt thereof, is used.

In another embodiment, the present disclosure provides use of the compound of the present disclosure, or a pharmaceutically acceptable salt thereof, for the manufacture of a medicament for the treatment of cancer in a subject.

In another embodiment, the present disclosure provides use of the compound of the present disclosure, or a pharmaceutically acceptable salt thereof, for the manufacture of a medicament for inhibiting cancer metastasis in a subject.

In another embodiment, the present disclosure provides the compound of the present disclosure, or a pharmaceutically acceptable salt thereof, for use in the treatment of cancer in a subject in need thereof.

In another embodiment, the present disclosure provides the compound of the present disclosure, or a pharmaceutically acceptable salt thereof, for use in inhibiting cancer metastasis in a subject in need thereof.

In another embodiment, the present disclosure provides the compound of the present disclosure, or a pharmaceutically acceptable salt thereof, for use in therapy.

VIII. Combination Therapy

In some embodiments, a compound of Formula J, (I-1), (I-2), (I-3), (Ib), (Ib-1), (Ib-2), (Ib-3), (Ib-4), (Ib), (IIb-1), or (IIb-2), provided herein, or pharmaceutically acceptable salt thereof, is administered in combination with one or more additional therapeutic agents to treat or prevent a disease or condition disclosed herein. In some embodiments, the one or more additional therapeutic agents are one, two, three, or four additional therapeutic agents. In some embodiments, the one or more additional therapeutic agents are one additional therapeutic agent. In some embodiments, the one or more additional therapeutic agents are two additional therapeutic agents. In some embodiments, the one or more additional therapeutic agents are three additional therapeutic agents. In some embodiments, the one or more additional therapeutic agents are four additional therapeutic agents.

In some embodiments, the pharmaceutical compositions provided herein have a compound of Formula J, (I-1), (I-2), (I-3), (Ib), (Ib-1), (Ib-2), (Ib-3), (Ib-4), (IIb), (IIb-1), or (IIb-2), provided herein, or pharmaceutically acceptable salt thereof, and one or more additional therapeutic agents. In some embodiments, the one or more additional therapeutic agents are one, two, three, or four additional therapeutic agents. In some embodiments, the one or more additional therapeutic agents are one additional therapeutic agent. In some embodiments, the one or more additional therapeutic agents are two additional therapeutic agents. In some embodiments, the one or more additional therapeutic agents are three additional therapeutic agents. In some embodiments, the one or more additional therapeutic agents are four additional therapeutic agents.

In some embodiments, the additional therapeutic agent includes, e.g., an inhibitory immune checkpoint blocker or inhibitor, a stimulatory immune checkpoint stimulator, agonist or activator, a chemotherapeutic agent, an anti-cancer agent, a radiotherapeutic agent, an anti-neoplastic agent, an anti-proliferation agent, an anti-angiogenic agent, an anti-inflammatory agent, an immunotherapeutic agent, a therapeutic antigen-binding molecule (e.g., a mono- and multi-specific antibody, or fragment thereof, in any format, such as DART®, Duobody®, BiTE®, BiKE, TriKE, XmAb®, TandAb®, scFv, Fab, Fab derivative), a bi-specific antibody, a non-immunoglobulin antibody mimetic (e.g., including adnectin, affibody, affilin, affimer, affitin, alphabody, anticalin, peptide aptamer, armadillo repeat protein (ARM), atrimer, avimer, designed ankyrin repeat protein (DARPin®), fynomer, knottin, Kunitz domain peptide, monobody, and nanoCLAMPs), an antibody-drug conjugate (ADC), antibody-peptide conjugate), an oncolytic virus, a gene modifier or editor, a cell comprising a chimeric antigen receptor (CAR), e.g., including a T-cell immunotherapeutic agent, an NK-cell immunotherapeutic agent, or a macrophage immunotherapeutic agent, a cell comprising an engineered T-cell receptor (TCR-T), or any combination thereof.

Illustrative Targets

In some embodiments, the one or more additional therapeutic agents include, e.g., an inhibitor, agonist, antagonist, ligand, modulator, stimulator, blocker, activator or suppressor of a target (e.g., polypeptide or polynucleotide), such as: 2'-5'-oligoadenylate synthetase (OAS1; NCBI Gene ID: 4938); 5'-3' exoribonuclease 1 (XRN1; NCBI Gene ID: 54464); 5'-nucleotidase ecto (NT5E, CD73; NCBI Gene ID: 4907); ABL proto-oncogene 1, non-receptor tyrosine kinase (ABL1, BCR-ABL, c-ABL, v-ABL; NCBI Gene ID: 25); absent in melanoma 2 (AIM2; NCBI Gene ID: 9447); acetyl-CoA acyltransferase 2 (ACAA2; NCBI Gene ID: 10499); acid phosphatase 3 (ACP3; NCBI Gene ID: 55); adenosine deaminase (ADA, ADA1; NCBI Gene ID: 100); adenosine receptors (e.g., ADORA1 (A1), ADORA2A (A2a, A2AR), ADORA2B (A2b, A2BR), ADORA3 (A3); NCBI Gene IDs: 134, 135, 136, 137); AKT serine/threonine kinase 1 (AKT1, AKT, PKB; NCBI Gene ID: 207); alanyl aminopeptidase, membrane (ANPEP, CD13; NCBI Gene ID: 290); ALK receptor tyrosine kinase (ALK, CD242; NCBI Gene ID: 238); alpha fetoprotein (AFP; NCBI Gene ID: 174); amine oxidase copper containing (e.g., AOC1 (DA01), AOC2, AOC3 (VAP1); NCBI Gene IDs: 26, 314, 8639); androgen receptor (AR; NCBI Gene ID: 367); angiopoietins (ANGPT1, ANGPT2; NCBI Gene IDs: 284, 285); angiotensin II receptor type 1 (AGTR1; NCBI Gene ID: 185); angiotensinogen (AGT; NCBI Gene ID: 183); apolipoprotein A1 (APOA1; NCBI Gene ID: 335); apoptosis inducing factor mitochondria associated 1 (AIFM1, AIF; NCBI Gene ID: 9131); arachidonate 5-lipoxygenase (ALOX5; NCBI Gene ID: 240); asparaginase (ASPG; NCBI Gene ID: 374569); asteroid homolog 1 (ASTE1; NCBI Gene ID: 28990); ATM serine/threonine kinase (ATM; NCBI Gene ID: 472); ATP binding cassette subfamily B member 1 (ABCB1, CD243, GP170; NCBI Gene ID: 5243); ATP-dependent Clp-protease (CLPP; NCBI Gene ID: 8192); ATR serine/threonine kinase (ATR; NCBI Gene ID: 545); AXL receptor tyrosine kinase (AXL; NCBI Gene ID: 558); B and T lymphocyte associated (BTLA, CD272; NCBI Gene ID: 151888); baculoviral IAP repeat containing proteins (BIRC2 (cIAP1), BIRC3 (cIAP2), XIAP (BIRC4, IAP3), BIRC5 (survivin); NCBI Gene IDs: 329, 330, 331, 332); basigin (Ok blood group) (BSG, CD147; NCBI Gene ID: 682); B-cell lymphoma 2 (BCL2; NCBI Gene ID: 596); BCL2 binding component 3 (BBC3, PUMA; NCBI Gene ID: 27113); BCL2 like (e.g., BCL2L1 (Bcl-x), BCL2L2 (BIM); Bcl-x; NCBI Gene IDs: 598, 10018); beta 3-adrenergic receptor ($ADR^{B3}$; NCBI Gene ID: 155); bone gamma-carboxyglutamate protein (BGLAP; NCBI Gene ID: 632); bone morphogenetic protein-10 ligand (BMP10; NCBI Gene ID: 27302); bradykinin receptors (e.g., BDKRB1, BDKRB2; NCBI Gene IDs: 623, 624); B-RAF (BRAF; NCBI Gene ID: 273); breakpoint cluster region (BCR; NCBI Gene ID: 613); bromodomain and external domain (BET) bromodomain containing proteins (e.g., BRD2, BRD3, BRD4, BRDT; NCBI Gene IDs: 6046, 8019, 23476, 676); Bruton's tyrosine kinase (BTK; NCBI Gene ID: 695); cadherins (e.g., CDH3 (p-cadherin), CDH6 (k-cadherin); NCBI Gene IDs: 1001, 1004); cancer/testis antigens (e.g., CTAG1A, CTAG1B, CTAG2; NCBI Gene IDs: 1485, 30848, 246100); cannabinoid receptors (e.g., CNR1 (CB1), CNR2 (CB2); NCBI Gene IDs: 1268, 1269); carbohydrate sulfotransferase 15 (CHST15; NCBI Gene ID: 51363); carbonic anhydrases (e.g., CA1, CA2, CA3, CA4, CA5A, CA5B, CA6, CA7, CA8, CA9, CA10, CA11, CA12, CA13, CA14; NCBI Gene IDs: 759, 760, 761, 762, 763, 765, 766, 767, 768, 770, 771, 11238, 23632, 56934, 377677); carcinoembryonic antigen related cell adhesion molecules (e.g., CEACAM3 (CD66d), CEACAM5 (CD66e), CEACAM6 (CD66c); NCBI Gene IDs: 1048, 1084, 4680); casein kinases (e.g., CSNK1A1 (CK1), CSNK2A1 (CK2); NCBI Gene IDs: 1452, 1457); caspases (e.g., CASP3, CASP7, CASP8; NCBI Gene IDs: 836, 840, 841, 864); catenin beta 1 (CTNNB1; NCBI Gene ID: 1499); cathepsin G (CTSG; NCBI Gene ID: 1511); Cbl proto-oncogene B (CBLB, Cbl-b; NCBI Gene ID: 868); C-C motif chemokine ligand 21 (CCL21; NCBI Gene ID: 6366); C-C motif chemokine receptor 2 (CCR2; NCBI Gene ID: 729230); C-C motif chemokine receptors (e.g., CCR3 (CD193), CCR4 (CD194), CCR5 (CD195), CCR8 (CDw198); NCBI Gene IDs: 1232, 1233, 1234, 1237); CCAAT enhancer binding protein alpha (CEBPA, CEBP; NCBI Gene ID: 1050); cell adhesion molecule 1 (CADM1; NCBI Gene ID: 23705); cell division cycle 7 (CDC7; NCBI Gene ID: 8317); cellular communication network factor 2 (CCN2; NCBI Gene ID: 1490); cereblon (CRBN; NCBI Gene ID: 51185); checkpoint kinases (e.g., CHEK1 (CHK1), CHEK2 (CHK2); NCBI Gene IDs: 1111, 11200); cholecystokinin B receptor (CCKBR; NCBI Gene ID: 887); chorionic somatomammotropin hormone 1 (CSH1; NCBI Gene ID: 1442); claudins (e.g., CLDN6, CLDN18; NCBI Gene IDs: 9074, 51208); cluster of differentiation markers (e.g., CD1A, CD1C, CD1D, CD1E, CD2, CD3 alpha (TRA), CD beta (TRB), CD gamma (TRG), CD delta (TRD), CD4, CD8A, CD8B, CD19, CD20 (MS4A1), CD22, CD24, CD25 (IL2RA, TCGFR), CD28, CD33 (SIGLEC3), CD37, CD38, CD39 (ENTPD1), CD40 (TNFRSF5), CD44 (MIC4, PGP1), CD47 (IAP), CD48 (BLAST1), CD52, CD55 (DAF), CD58 (LFA3), CD74, CD79a, CD79b, CD80 (B7-1), CD84, CD86 (B7-2), CD96 (TACTILE), CD99 (MIC2), CD115 (CSF1R), CD116 (GMCSFR, CSF2RA), CD122 (IL2RB), CD123 (IL3RA), CD128 (IL8R1), CD132 (IL2RG), CD135 (FLT3), CD137 (TNFRSF9, 4-1BB), CD142 (TF, TFA), CD152 (CTLA4), CD160, CD182 (IL8R2), CD193 (CCR3), CD194 (CCR4), CD195 (CCR5), CD207, CD221 (IGF1R), CD222 (IGF2R), CD223 (LAG3), CD226 (DNAM1), CD244, CD247, CD248, CD276 (B7-H3), CD331 (FGFR1), CD332 (FGFR2), CD333 (FGFR3), CD334 (FGFR4); NCBI Gene IDs: 909, 911, 912, 913, 914, 919, 920, 923, 925, 926, 930, 931, 933, 940, 941, 942, 945, 951, 952, 953, 958,960, 961, 962, 965, 972, 973, 974, 1043, 1232, 1233, 1234, 1237, 1436, 1438, 1493, 1604, 2152, 2260, 2261, 2263, 2322, 3480, 3482, 3559, 3560, 3561, 3563, 3577, 3579, 3604, 3902, 4267, 6955, 6957, 6964, 6965, 8832, 10666, 11126, 50489, 51744, 80381, 100133941); elusterin (CLU; NCBI Gene ID: 1191); coagulation factors (e.g., F7, FXA; NCBI Gene IDs: 2155, 2159); collagen type IV alpha chains (e.g., COL4A1, COL4A2, COL4A3, COL4A4, COL4A5; NCBI Gene IDs: 1282, 1284, 1285, 1286, 1287); collectin subfamily member 10 (COLEC10; NCBI Gene ID: 10584); colony stimulating factors (e.g., CSF1 (MCSF), CSF2 (GMCSF), CSF3 (GCSF); NCBI Gene IDs: 1435, 1437, 1440); complement factors (e.g., C3, C5; NCBI Gene IDs: 718, 727); COP9 signalosome subunit 5 (COPS5; NCBI Gene ID: 10987); C-type lectin domain family member (e.g., CLEC4C (CD303), CLEC9A (CD370), CLEC12A (CD371); CD371; NCBI Gene ID: 160364, 170482, 283420); C-X-C motif chemokine ligand 12 (CXCL12; NCBI Gene ID: 6387); C-X-C motif chemokine receptors (CXCR1 (IL8R1, CD128), CXCR2 (IL8R2, CD182), CXCR3 (CD182, CD183, IP-10R), CXCR4 (CD184); NCBI Gene ID: 2833, 3577, 3579, 7852); cyclin D1 (CCND1, BCL1; NCBI Gene ID: 595); cyclin dependent kinases (e.g., CDK1, CDK2, CDK3, CDK4, CDK5, CDK6, CDK7, CDK8, CDK9, CDK10, CDK12; NCBI Gene ID: 983, 1017, 1018, 1019, 1020, 1021, 1022, 1024, 1025, 8558, 51755); cyclin G1 (CCNG1; NCBI Gene ID: 900); cytochrome P450 family members (e.g., CYP2D6, CYP3A4, CYP11A1, CYP11B2, CYP17A1, CYP19A1, CYP51A1; NCBI Gene IDs: 1565, 1576, 1583, 1585, 1586, 1588, 1595); cytochrome P450 oxidoreductase (POR; NCBI Gene ID: 5447); cytokine inducible SH2 containing protein (CISH; NCBI Gene ID: 1154); cytotoxic T-lymphocyte associated protein 4 (CTLA4, CD152; NCBI Gene ID: 1493); DEAD-box helicases (e.g., DDX5, DDX6, DDX58; NCBI Gene IDs: 1655, 1656, 23586); delta like canonical Notch ligands (e.g., DLL3, DLL4; NCBI Gene IDs: 10683, 54567); diablo IAP-binding mitochondrial protein (DIABLO, SMAC; NCBI Gene ID: 56616); diacylglycerol kinases (e.g., DGKA, DGKZ; NCBI Gene IDs: 1606, 8525); dickkopf WNT signaling pathway inhibitors (e.g., DKK1, DKK3; NCBI Gene ID: 22943, 27122); dihydrofolate reductase (DHFR; NCBI Gene ID: 1719); dihydropyrimidine dehydrogenase (DPYD; NCBI Gene ID: 1806); dipeptidyl peptidase 4 (DPP4; NCBI Gene ID: 1803); discoidin domain receptor tyrosine kinases (e.g., DDR1 (CD167), DDR2; CD167; NCBI Gene ID: 780, 4921); DNA dependent protein kinase (PRKDC; NCBI Gene ID: 5591); DNA topoisomerases (e.g., TOP1, TOP2A, TOP2B, TOP3A, TOP3B; NCBI Gene ID: 7150, 7153, 7155, 7156, 8940); dopachrome tautomerase (DCT; NCBI Gene ID: 1638); dopamine receptor D2 (DRD2; NCBI Gene ID: 1318); DOT1 like histone lysine methyltransferase (DOT1L; NCBI Gene ID: 84444); ectonucleotide pyrophosphatase/phosphodiesterase 3 (ENPP3, CD203c; NCBI Gene ID: 5169); EMAP like 4 (EML4; NCBI Gene ID: 27436); endoglin (ENG; NCBI Gene ID: 2022); endoplasmic reticulum aminopeptidases (e.g., ERAP1, ERAP2; NCBI Gene ID: 51752, 64167); enhancer of zeste 2 polycomb repressive complex 2 subunit (EZH2; NCBI Gene ID: 2146); ephrin receptors (e.g., EPHA1, EPHA2EPHA3, EPHA4, EPHA5, EPHA7, EPHB4; NCBIGene ID:1969, 2041, 2042, 2043, 2044, 2045, 2050); ephrins (e.g., EFNA1, EFNA4, EFNB2; NCBI Gene ID: 1942, 1945, 1948); epidermal growth factor receptors (e.g., ERBB1 (HER1, EGFR), ERBB1 variant III (EGFRvIII), ERBB2 (HER2, NEU, CD340), ERBB3 (HER3), ERBB4 (HER4); NCBI Gene ID: 1956, 2064, 2065, 2066); epithelial cell adhesion molecule (EPCAM; NCBI Gene ID: 4072); epithelial mitogen (EPGN; NCBI Gene ID: 255324); eukaryotic translation elongation factors (e.g., EEF1A2, EEF2; NCBI Gene ID: 1917, 1938); eukaryotic translation initiation factors (e.g., EIF4A1, EIFSA; NCBI Gene ID: 1973, 1984); exportin-1 (XPO1; NCBI Gene ID: 7514); farnesoid X receptor (NR1H4, FXR; NCBI Gene ID: 9971); Fas ligand (FASLG, FASL, CD95L, CD178, TNFSF6; NCBI Gene ID: 356); fatty acid amide hydrolase (FAAH; NCBI Gene ID: 2166); fatty acid synthase (FASN; FAS; NCBI Gene ID: 2194); Fc fragment of Ig receptors (e.g., FCER1A, FCGRT, FCGR3A (CD16); NCBI Gene IDs: 2205, 2214, 2217); Fc receptor like 5 (FCRL5, CD307; NCBI Gene ID: 83416); fibroblast activation protein alpha (FAP; NCBI Gene ID: 2191); fibroblast growth factor receptors (e.g., FGFR1 (CD331), FGFR2 (CD332), FGFR3 (CD333), FGFR4 (CD334); NCBI Gene IDs: 2260, 2261, 2263, 2264); fibroblast growth factors (e.g., FGF1 (FGF alpha), FGF2 (FGF beta), FGF4, FGF5; NCBI Gene IDs: 2246, 2247, 2249, 2250); fibronectin 1 (FN1, MSF; NCBI Gene ID: 2335); fms related receptor tyrosine kinases (e.g., FLT1 (VEGFR1), FLT3 (STK1, CD135), FLT4 (VEGFR2); NCBI Gene IDs: 2321, 2322, 2324); fms related receptor tyrosine kinase 3 ligand (FLT3LG; NCBI Gene ID: 2323); focal adhesion kinase 2 (PTK2, FAK1; NCBI Gene ID: 5747); folate hydrolase 1 (FOLH1, PSMA; NCBI Gene ID: 2346); folate receptor 1 (FOLR1; NCBI Gene ID: 2348); forkhead box protein M1 (FOXM1; NCBI Gene ID: 2305); FURIN (FURIN, PACE; NCBI Gene ID: 5045); FYN tyrosine kinase (FYN, SYN; NCBI Gene ID: 2534); galectins (e.g., LGALS3, LGALS8 (PCTA1), LGALS9; NCBI Gene ID: 3958, 3964, 3965); glucocorticoid receptor (NR3C1, GR; NCBI Gene ID: 2908); glucuronidase beta (GUSB; NCBI Gene ID: 2990); glutamate metabotropic receptor 1 (GRM1; NCBI Gene ID: 2911); glutaminase (GLS; NCBI Gene ID: 2744); glutathione S-transferase Pi (GSTP1; NCBI Gene ID: 2950); glycogen synthase kinase 3 beta (GSK3B; NCBI Gene ID: 2932); glypican 3 (GPC3; NCBI Gene ID: 2719); gonadotropin releasing hormone 1 (GNRH1; NCBI Gene ID: 2796); gonadotropin releasing hormone receptor (GNRHR; NCBI Gene ID: 2798); GPNMB glycoprotein nmb (GPNMB, osteoactivin; NCBI Gene ID: 10457); growth differentiation factor 2 (GDF2, BMP9; NCBI Gene ID: 2658); growth factor receptor-bound protein 2 (GRB2, ASH; NCBI Gene ID: 2885); guanylate cyclase 2C (GUCY2C, STAR, MECIL, MUCIL, NCBI Gene ID: 2984); H19 imprinted maternally expressed transcript (H19; NCBI Gene ID: 283120); HCK proto-oncogene, Src family tyrosine kinase (HCK; NCBI Gene ID: 3055); heat shock proteins (e.g., HSPA5 (HSP70, BIP, GRP78), HSPB1 (HSP27), HSP90B1 (GP96); NCBI Gene IDs: 3309, 3315, 7184); heme oxygenases (e.g., HMOX1 (HO1), HMOX2 (HO1); NCBI Gene ID: 3162, 3163); heparanase (HPSE; NCBI Gene ID: 10855); hepatitis A virus cellular receptor 2 (HAVCR2, TIM3, CD366; NCBI Gene ID: 84868); hepatocyte growth factor (HGF; NCBI Gene ID: 3082); HERV-H LTR-associating 2 (HHLA2, B7-H7; NCBI Gene ID: 11148); histamine receptor H2 (HRH2; NCBI Gene ID: 3274); histone deacetylases (e.g., HDAC1, HDAC7, HDAC9; NCBI Gene ID: 3065, 9734, 51564); HRas proto-oncogene, GTPase (HRAS; NCBI Gene ID: 3265); hypoxia-inducible factors (e.g., HIF1A, HIF2A (EPAS1); NCBI Gene IDs: 2034, 3091); I-Kappa-B kinase (IKK beta; NCBI Gene IDs: 3551, 3553); IKAROS family zinc fingers (IKZF1 (LYF1), IKZF3; NCBI Gene ID: 10320, 22806); immunoglobulin superfamily member 11 (IGSF11; NCBI Gene ID: 152404); indoleamine 2,3-dioxygenases (e.g., IDO1, ID02; NCBI Gene IDs: 3620, 169355); inducible T cell costimulator (ICOS, CD278; NCBI Gene ID: 29851); inducible T cell costimulator ligand (ICOSLG, B7-H2; NCBI Gene ID: 23308); insulin like growth factor receptors (e.g., IGF1R, IGF2R; NCBI Gene ID: 3480, 3482); insulin like growth factors (e.g., IGF1, IGF2; NCBI Gene IDs: 3479, 3481); insulin receptor (INSR, CD220; NCBI Gene ID: 3643); integrin subunits (e.g., ITGA5 (CD49e), ITGAV (CD51), ITGB1 (CD29), ITGB2 (CD18, LFA1, MAC1), ITGB7; NCBI Gene IDs: 3678, 3685, 3688, 3695, 3698); intercellular adhesion molecule 1 (ICAM1, CD54; NCBI Gene ID: 3383); interleukin 1 receptor associated kinase 4 (IRAK4; NCBI Gene ID: 51135); interleukin receptors (e.g., IL2RA (TCGFR, CD25), IL2RB (CD122), IL2RG (CD132), IL3RA, IL6R, IL13RA2 (CD213A2), IL22RA1; NCBI Gene IDs: 3598, 3559, 3560, 3561, 3563, 3570, 58985); interleukins (e.g., IL1A, IL1B, IL2, IL3, IL6 (HGF), IL7, IL8 (CXCL8), IL10 (TGIF), IL12A, IL12B, IL15, IL17A (CTLA8), IL18, IL23A, IL24, IL-29 (IFNL1); NCBI Gene IDs: 3552, 3553, 3558, 3562, 3565, 3569, 3574, 3586, 3592, 3593, 3600, 3605, 3606, 11009, 51561, 282618); isocitrate dehydrogenases (NADP(+)1) (e.g., IDH1, IDH2; NCBI Gene IDs: 3417, 3418); Janus kinases (e.g., JAK1, JAK2, JAK3; NCBI Gene IDs: 3716, 3717, 3718); kallikrein related peptidase 3 (KLK3; NCBI Gene ID: 354); killer cell immunoglobulin like receptor, Ig domains and long cytoplasmic tails (e.g., KIR2DL1 (CD158A), KIR2DL2 (CD158B1), KIR2DL3 (CD158B), KIR2DL4 (CD158D), KIR2DL5A (CD158F), KIR2DL5B, KIR3DL1 (CD158E1), KIR3DL2 (CD158K), KIR3DP1 (CD158c), KIR2DS2 (CD158J); NCBI Gene IDs: 3802, 3803, 3804, 3805, 3811, 3812, 57292, 553128, 548594, 100132285); killer cell lectin like receptors (e.g., KLRC1 (CD159A), KLRC2 (CD159c), KLRC3, KLRRC4, KLRD1 (CD94), KLRG1, KLRK1 (NKG2D, CD314); NCBI Gene IDs: 3821, 3822, 3823, 3824, 8302, 10219, 22914); kinase insert domain receptor (KDR, CD309, VEGFR2; NCBI Gene ID: 3791); kinesin family member 11 (KIF11; NCBI Gene ID: 3832); KiSS-1 metastasis suppressor (KISS1; NCBI Gene ID: 3814); KIT proto-oncogene, receptor tyrosine kinase (KIT, C-KIT, CD117; NCBI Gene ID: 3815); KRAS proto-oncogene, GTPase (KRAS; NCBI Gene ID: 3845); lactotransferrin (LTF; NCBI Gene ID: 4057); LCK proto-oncogene, Src family tyrosine kinase (LCK; NCBI Gene ID: 3932); LDL receptor related protein 1 (LRP1, CD91, IGFBP3R; NCBI Gene ID: 4035); leucine rich repeat containing 15 (LRRC15; NCBI Gene ID: 131578); leukocyte immunoglobulin like receptors (e.g., LILRB1 (ILT2, CD85J), LILRB2 (ILT4, CD85D); NCBI Gene ID: 10288, 10859); leukotriene A4 hydrolase (LTA4H; NCBI Gene ID: 4048); linker for activation of T-cells (LAT; NCBI Gene ID: 27040); luteinizing hormone/choriogonadotropin receptor (LHCGR; NCBI Gene ID: 3973); LY6/PLAUR domain containing 3 (LYPD3; NCBI Gene ID: 27076); lymphocyte activating 3 (LAG3; CD223; NCBI Gene ID: 3902); lymphocyte antigens (e.g., LY9 (CD229), LY75 (CD205); NCBI Gene IDs: 4063, 17076); LYN proto-oncogene, Src family tyrosine kinase (LYN; NCBI Gene ID: 4067); lypmphocyte cytosolic protein 2 (LCP2; NCBI Gene ID: 3937); lysine demethylase 1A (KDM1A; NCBI Gene ID: 23028); lysophosphatidic acid receptor 1 (LPAR1, EDG2, LPA1, GPR26; NCBI Gene ID: 1902); lysyl oxidase (LOX; NCBI Gene ID: 4015); lysyl oxidase like 2 (LOXL2; NCBI Gene ID: 4017); macrophage migration inhibitory factor (MIF, GIF; NCBI Gene ID: 4282); macrophage stimulating 1 receptor (MST1R, CD136; NCBI Gene ID: 4486); MAGE family members (e.g., MAGEA1, MAGEA2, MAGEA2B, MAGEA3, MAGEA4, MAGEA5, MAGEA6, MAGEA10, MAGEA11, MAGEC1, MAGEC2, MAGED1, MAGED2; NCBI Gene IDs: 4100, 4101, 4102, 4103, 4104, 4105, 4109, 4110, 9500, 9947, 10916, 51438, 266740); major histocompatibility complexes (e.g., HLA-A, HLA-E, HLA-F, HLA-G; NCBI Gene IDs: 3105, 3133, 3134, 3135); major vault protein (MVP, VAULT1; NCBI Gene ID: 9961); MALT1 paracaspase (MALT1; NCBI Gene ID: 10892); MAPK activated protein kinase 2 (MAPKAPK2; NCBI Gene ID: 9261); MAPK interacting serine/threonine kinases (e.g., MKNK1, MKNK2; NCBI Gene IDs: 2872, 8569); matrix metallopeptidases (e.g., MMP1, MMP2, MMP3, MMP7, MMP8, MMP9, MMP10, MMP11, MMP12, MMP13, MMP14, MMP15, MMP16, MMP17, MMP19, MMP20, MMP21, MMP24, MMP25, MMP26, MMP27, MMP28; NCBI Gene IDs: 4312, 4313, 4314, 4316, 4317, 4318, 4319, 4320, 4321, 4322, 4323, 4324, 4325, 4326, 4327, 9313, 10893, 56547, 64066, 64386, 79148, 118856); MCL1 apoptosis regulator, BCL2 family member (MCL1; NCBI Gene ID: 4170); MDM2 proto-oncogene (MDM2; NCBI Gene ID: 4193); MDM4 regulator of p53 (MDM4; BMFS6; NCBI Gene ID: 4194); mechanistic target of rapamycin kinase (MTOR, FRAP1; NCBI Gene ID: 2475); melan-A (MLANA; NCBI Gene ID: 2315); melanocortin receptors (MC1R, MC2R; NCBI Gene IDs: 4157, 4148); MER proto-oncogene, tyrosine kinase (MERTK; NCBI Gene ID: 10461); mesothelin (MSLN; NCBI Gene ID: 10232); MET proto-oncogene, receptor tyrosine kinase (MET, c-Met, HGFR; NCBI Gene ID: 4233); methionyl aminopeptidase 2 (METAP2, MAP2; NCBI Gene ID: 10988); MHC class I polypeptide-related sequences (e.g., MICA, MICB; NCBI Gene IDs: 4277, 100507436); mitogen activated protein kinases (e.g., MAPK1 (ERK2), MAPK3 (ERK1), MAPK8 (JNK1), MAPK9 (JNK2), MAPK10 (JNK3), MAPK11 (p38 beta), MAPK12; NCBI Gene IDs: 5594, 5595, 5599, 5600, 5601, 5602, 819251); mitogen-activated protein kinase kinase kinases (e.g., MAP3K5 (ASK1), MAP3K8 (TPL2, AURA2); NCBI Gene IDs: 4217, 1326); mitogen-activated protein kinase kinase kinase kinase 1 (MAP4K1, HPK1; NCBI Gene ID: 11184); mitogen-activated protein kinase kinases (e.g., MAP2K1 (MEK1), MAP2K2 (MEK2), MAP2K7 (MEK7); NCBI Gene IDs: 5604, 5605, 5609); MPL proto-oncogene, thrombopoietin receptor (MPL; NCBI Gene ID: 4352); mucins (e.g., MUC1 (including splice variants thereof (e.g., including MUC1/A, C, D, X, Y, Z and REP)), MUC5AC, MUC16 (CA125); NCBI Gene IDs: 4582, 4586, 94025); MYC proto-oncogene, bHLH transcription factor (MYC; NCBI Gene ID: 4609); myostatin (MSTN, GDF8; NCBI Gene ID: 2660); myristoylated alanine rich protein kinase C substrate (MARCKS; NCBI Gene ID: 4082); natriuretic peptide receptor 3 (NPR3; NCBI Gene ID: 4883); natural killer cell cytotoxicity receptor 3 ligand 1 (NCR3LG1, B7-H6; NCBI Gene ID: 374383); necdin, MAGE family member (NDN; NCBI Gene ID: 4692); nectin cell adhesion molecules (e.g., NECTIN2 (CD112, PVRL2), NECTIN4 (PVRL4); NCBI Gene IDs: 5819, 81607); neural cell adhesion molecule 1 (NCAM1, CD56; NCBI Gene ID: 4684); neuropilins (e.g., NRP1 (CD304, VEGF165R), NRP2 (VEGF165R2); NCBI Gene IDs: 8828, 8829); neurotrophic receptor tyrosine kinases (e.g., NTRK1 (TRKA), NTRK2 (TRKB), NTRK3 (TRKC); NCBI Gene IDs: 4914, 4915, 4916); NFKB activating protein (NKAP; NCBI Gene ID: 79576); NIMA related kinase 9 (NEK9; NCBI Gene ID: 91754); NLR family pyrin domain containing 3 (NLRP3, NALP3; NCBI Gene ID: 114548); notch receptors (e.g., NOTCH1, NOTCH2, NOTCH3, NOTCH4; NCBI Gene IDs: 4851, 4853, 4854, 4855); NRAS proto-oncogene, GTPase (NRAS; NCBI Gene ID: 4893); nuclear factor kappa B (NFKB1, NFKB2; NCBI Gene IDs: 4790, 4791); nuclear factor, erythroid 2 like 2 (NFE2L2; NRF2; NCBI Gene ID: 4780); nuclear receptor subfamily 4 group A member 1 (NR4A1; NCBI Gene ID: 3164); nucleolin (NCL; NCBI Gene ID: 4691); nucleophosmin 1 (NPM1; NCBI Gene ID: 4869); nucleotide binding oligomerization domain containing 2 (NOD2; NCBI Gene ID: 64127); nudix hydrolase 1 (NUDT1; NCBI Gene ID: 4521); 0-6-methylguanine-DNA methyltransferase (MGMT; NCBI Gene ID: 4255); opioid receptor delta 1 (OPRD1; NCBI Gene ID: 4985); ornithine decarboxylase 1 (ODC1; NCBI Gene ID: 4953); oxoglutarate dehydrogenase (OGDH; NCBI Gene ID: 4967); parathyroid hormone (PTH; NCBI Gene ID: 5741); PD-L1 (CD274; NCBI Gene ID: 29126); periostin (POSTN; NCBI Gene ID: 10631); peroxisome proliferator activated receptors (e.g., PPARA (PPAR alpha), PPARD (PPAR delta), PPARG (PPAR gamma); NCBI Gene IDs: 5465, 5467, 5468); phosphatase and tensin homolog (PTEN; NCBI Gene ID: 5728); phosphatidylinositol-4,5-bisphosphate 3-kinases (PIK3CA (PI3K alpha), PIK3CB (PI3K beta), PIK3CD (PI3K delta), PIK3CG (PI3K gamma); NCBI Gene IDs: 5290, 5291, 5293, 5294); phospholipases (e.g., PLA2G1B, PLA2G2A, PLA2G2D, PLA2G3, PLA2G4A, PLA2G5, PLA2G7, PLA2G10, PLA2G12A, PLA2G12B, PLA2G15; NCBI Gene IDs: 5319, 5320, 5321, 5322, 7941, 8399, 50487, 23659, 26279, 81579, 84647); Pim proto-oncogene, serine/threonine kinases (e.g., PIM1, PIM2, PIM3; NCBI Gene IDs: 5292, 11040, 415116); placenta growth factor (PGF; NCBI Gene ID: 5228); plasminogen activator, urokinase (PLAU, u-PA, ATF; NCBI Gene ID: 5328); platelet derived growth factor receptors (e.g., PDGFRA (CD140A, PDGFR2), FDGFRB (CD140B, PDGFR1); NCBI Gene IDs: 5156, 5159); plexin B1 (PLXNB1; NCBI Gene ID: 5364); poliovirus receptor (PVR) cell adhesion molecule (PVR, CD155; NCBI Gene ID: 5817); polo like kinase 1 (PLK1; NCBI Gene ID: 5347); poly(ADP-ribose) polymerases (e.g., PARP1, PARP2, PARP3; NCBI Gene IDs: 142, 10038, 10039); polycomb protein EED (EED; NCBI Gene ID: 8726); porcupine O-acyltransferase (PORCN; NCBI Gene ID: 64840); PRAME nuclear receptor transcriptional regulator (PRAME; NCBI Gene ID: 23532); premelanosome protein (PMEL; NCBI Gene ID: 6490); progesterone receptor (PGR; NCBI Gene ID: 5241); programmed cell death 1 (PDCD1, PD-1, CD279; NCBI Gene ID: 5133); programmed cell death 1 ligand 2 (PDCD1LG2, CD273, PD-L2; NCBI Gene ID: 80380); prominin 1 (PROM1, CD133; NCBI Gene ID: 8842); promyelocytic leukemia (PML; NCBI Gene ID: 5371); prosaposin (PSAP; NCBI Gene ID: 5660); prostaglandin E receptor 4 (PTGER4; NCBI Gene ID: 5734); prostaglandin E synthase (PTGES; NCBI Gene ID: 9536); prostaglandin-endoperoxide synthases (PTGS1 (COX1), PTGS2 (COX2); NCBI Gene ID: 5742, 5743); proteasome 20S subunit beta 9 (PSMB9; NCBI Gene ID: 5698); protein arginine methyltransferases (e.g., PRMT1, PRMT5; NCBI Gene ID: 3276, 10419); protein kinase N3 (PKN3; NCBI Gene ID: 29941); protein phosphatase 2A (PPP2CA; NCBI Gene ID: 5515); protein tyrosine kinase 7 (inactive) (PTK7; NCBI Gene ID: 5754); protein tyrosine phosphatase receptors (PTPRB (PTPB), PTPRC (CD45R); NCBI Gene ID: 5787, 5788); prothymosin alpha (PTMA; NCBI Gene ID: 5757); purine nucleoside phosphorylase (PNP; NCBI Gene ID: 4860); purinergic receptor P2X 7 (P2RX7; NCBI Gene ID: 5027); PVR related immunoglobulin domain containing (PVRIG, CD112R; NCBI Gene ID: 79037); Raf-1 proto-oncogene, serine/threonine kinase (RAFI, c-Raf; NCBI Gene ID: 5894); RAR-related orphan receptor gamma (RORC; NCBI Gene ID: 6097); ras homolog family member C (RHOC); NCBI Gene ID: 389); Ras homolog, mTORC1 binding (RHEB; NCBI Gene ID: 6009); RB transcriptional corepressor 1 ($R^{B1}$; NCBI Gene ID: 5925); receptor-interacting serine/threonine protein kinase 1 (RIPK1; NCBI Gene ID: 8737); ret proto-oncogene (RET; NCBI Gene ID: 5979); retinoic acid early transcripts (e.g., RAET1E, RAET1G, RAET1L; NCBI Gene IDs: 135250, 154064, 353091); retinoic acid receptors alpha (e.g., RARA, RARG; NCBI Gene IDs: 5914, 5916); retinoid X receptors (e.g., RXRA, RXRB, RXRG; NCBI Gene IDs: 6256, 6257, 6258); Rho associated coiled-coil containing protein kinases (e.g., ROCK1, ROCK2; NCBI Gene IDs: 6093, 9475); ribosomal protein S6 kinase B1 (RPS6KB1, S6K-beta 1; NCBI Gene ID: 6198); ring finger protein 128 (RNF128, GRAIL; NCBI Gene ID: 79589); ROS proto-oncogene 1, receptor tyrosine kinase (ROS1; NCBI Gene ID: 6098); roundabout guidance receptor 4 (ROBO4; NCBI Gene ID: 54538); RUNX family transcription factor 3 (RUNX3; NCBI Gene ID: 864); S100 calcium binding protein A9 (S100A9; NCBI Gene ID: 6280); secreted frizzled related protein 2 (SFRP2; NCBI Gene ID: 6423); secreted phosphoprotein 1 (SPP1; NCBI Gene ID: 6696); secretoglobin family 1A member 1 (SCGB1A1; NCBI Gene ID: 7356); selectins (e.g., SELE, SELL (CD62L), SELP (CD62); NCBI Gene IDs: 6401, 6402, 6403); semaphorin 4D (SEMA4D; CD100; NCBI Gene ID: 10507); sialic acid binding Ig like lectins (SIGLEC7 (CD328), SIGLEC9 (CD329), SIGLEC10; NCBI Gene ID: 27036, 27180, 89790); signal regulatory protein alpha (SIRPA, CD172A; NCBI Gene ID: 140885); signal transducer and activator of transcription (e.g., STAT1, STAT3, STAT5A, STAT5B; NCBI Gene IDs: 6772, 6774, 6776, 6777); sirtuin-3 (SIRT3; NCBI Gene ID: 23410); signaling lymphocytic activation molecule (SLAM) family members (e.g., SLAMF1 (CD150), SLAMF6 (CD352), SLAMF7 (CD319), SLAMF8 (CD353), SLAMF9; NCBI Gene IDs: 56833, 57823, 89886, 114836); SLIT and NTRK like family member 6 (SLITRK6; NCBI Gene ID: 84189); smoothened, frizzled class receptor (SMO; NCBI Gene ID: 6608); soluble epoxide hydrolase 2 (EPHX2; NCBI Gene ID: 2053); solute carrier family members (e.g., SLC3A2 (CD98), SLC5A5, SLC6A2, SLC10A3, SLC34A2, SLC39A6, SLC43A2 (LAT4), SLC44A4; NCBI Gene IDs: 6520, 6528, 6530, 8273, 10568, 25800, 80736, 124935); somatostatin receptors (e.g., SSTR1, SSTR2, SSTR3, SSTR4, SSTR5; NCBI Gene IDs: 6751, 6752, 6753, 6754, 6755); sonic hedgehog signaling molecule (SHH; NCBI Gene ID: 6469); Spl transcription factor (SP1; NCBI Gene ID: 6667); sphingosine kinases (e.g., SPHK1, SPHK2; NCBI Gene IDs: 8877, 56848); sphingosine-1-phosphate receptor 1 (S1PR1, CD363; NCBI Gene ID: 1901); spleen associated tyrosine kinase (SYK; NCBI Gene ID: 6850); splicing factor 3B factor 1 (SF3B1; NCBI Gene ID: 23451); SRC proto-oncogene, non-receptor tyrosine kinase (SRC; NCBI Gene ID: 6714); stabilin 1 (STAB1, CLEVER-1; NCBI Gene ID: 23166); STEAP family member 1 (STEAP1; NCBI Gene ID: 26872); steroid sulfatase (STS; NCBI Gene ID: 412); stimulator of interferon response cGAMP interactor 1 (STINGI; NCBI Gene ID: 340061); superoxide dismutase 1 (SOD1, ALS1; NCBI Gene ID: 6647); suppressors of cytokine signaling (SOCS1 (CISH1), SOCS3 (CISH3); NCBI Gene ID: 8651, 9021); synapsin 3 (SYN3; NCBI Gene ID: 8224); syndecan 1 (SDC1, CD138, syndecan; NCBI Gene ID: 6382); synuclein alpha (SNCA, PARK1; NCBI Gene ID: 6622); T cell immunoglobulin and mucin domain containing 4 (TIMD4, SMUCKLER; NCBI Gene ID: 91937); T cell immunoreceptor with Ig and ITIM domains (TIGIT; NCBI Gene ID: 201633); tachykinin receptors (e.g., TACR1, TACR3; NCBI Gene ID: 6869, 6870); TANK binding kinase 1 (TBK1; NCBI Gene ID: 29110); tankyrase (TNKS; NCBI Gene ID: 8658); TATA-box binding protein associated factor, RNA polymerase I subunit B (TAF1B; NCBI Gene ID: 9014); T-box transcription factor T (TBXT; NCBI Gene ID: 6862); TCDD inducible poly(ADP-ribose) polymerase (TIPARP, PAPR7; NCBI Gene ID: 25976); tec protein tyrosine kinase (TEC; NCBI Gene ID: 7006); TEK receptor tyrosine kinase (TEK, CD202B, TIE2; NCBI Gene ID: 7010); telomerase reverse transcriptase (TERT; NCBI Gene ID: 7015); tenascin C (TNC; NCBI Gene ID: 3371); three prime repair exonucleases (e.g., TREX1, TREX2; NCBI Gene ID: 11277, 11219); thrombomodulin (THBD, CD141; NCBI Gene ID: 7056); thymidine kinases (e.g., TK1, TK2; NCBI Gene IDs: 7083, 7084); thymidine phosphorylase (TYMP; NCBI Gene ID: 1890); thymidylate synthase (TYMS; NCBI Gene ID: 7298); thyroid hormone receptor (THRA, THRB; NCBI Gene IDs: 7606, 7608); thyroid stimulating hormone receptor (TSHR; NCBI Gene ID: 7253); TNF superfamily members (e.g., TNFSF4 (OX40L, CD252), TNFSF5 (CD40L), TNFSF7 (CD70), TNFSF8 (CD153, CD30L), TNFSF9 (4-1BB-L, CD137L), TNFSF10 (TRAIL, CD253, APO2L), TNFSF11 (CD254, RANKL2, TRANCE), TNFSF13 (APRIL, CD256, TRAIL2), TNFSF13b (BAFF, BLYS, CD257), TNFSF14 (CD258, LIGHT), TNFSF18 (GITRL); NCBI Gene IDs: 944, 959, 970, 7292, 8600, 8740, 8741, 8743, 8744, 8995); toll like receptors (e.g., TLR1 (CD281), TLR2 (CD282), TLR3 (CD283), TLR4 (CD284), TLR5, TLR6 (CD286), TLR7, TLR8 (CD288), TLR9 (CD289), TLR10 (CD290); NCBI Gene IDs: 7096, 7097, 7098, 7099, 10333, 51284, 51311, 54106, 81793); transferrin (TF; NCBI Gene ID: 7018); transferrin receptor (TFRC, CD71; NCBI Gene ID: 7037); transforming growth factors (e.g., TGFA, TGFB1; NCBI Gene ID: 7039, 7040); transforming growth factor receptors (e.g., TGFBR1, TGFBR2, TGFBR3; NCBI Gene ID: 7046, 7048, 7049); transforming protein E7 (E7; NCBI Gene ID: 1489079); transglutaminase 5 (TGM5; NCBI Gene ID: 9333); transient receptor potential cation channel subfamily V member 1 (TRPV1, VR1; NCBI Gene ID: 7442); transmembrane and immunoglobulin domain containing 2 (TMIGD2, CD28H, IGPR1; NCBI Gene ID: 126259); triggering receptors expressed on myeloid cells (e.g., TREM1 (CD354), TREM2; NCBI Gene ID: 54209, 54210); trophinin (TRO, MAGED3; NCBI Gene ID: 7216); trophoblast glycoprotein (TPBG; NCBI Gene ID: 7162); tryptophan 2,3-dioxygenase (TDO2; NCBI Gene ID: 6999); tryptophan hydroxylases (e.g., TPH1, TPH2; NCBI Gene ID: 7166, 121278); tumor associated calcium signal transducer 2 (TACSTD2, TROP2, EGP1; NCBI Gene ID: 4070); tumor necrosis factor (TNF; NCBI Gene ID: 7124); tumor necrosis factor (TNF) receptor superfamily members (e.g., TNFRSF1A (CD120a), TNFRSF1B (CD120b), TNFRSF4 (OX40), TNFRSF5 (CD40), TNFRSF6 (CD95, FAS receptor), TNFRSF7 (CD27), TNFRSF8 (CD30), TNFRSF9 (CD137, 4-1BB), TNFRSF10A (CD261), TNFRSF10B (TRAIL, DR5, CD262), TNFRSF10C, TNFRSF10D, TNFRSF11A, TNFRSF11B (OPG), TNFRSF12A, TNFRSF13B, TNFR13C (, CD268, BAFFR), TNFRSF14 (CD270, LIGHTR), TNFRSF16, TNFRSF17 (CD269, BCMA), TNFRSF18 (GITR, CD357), TNFRSF19, TNFRSF21, TNFRSF25; NCBI Gene IDs: 355, 608, 939, 943, 958, 3604, 4804, 4982, 7132, 7133, 7293, 8718, 8764, 8784, 8792, 8793, 8794, 8795, 8797, 23495, 27242, 51330, 55504); tumor protein p53 (TP53; NCBI Gene ID: 7157); tumor suppressor 2, mitochondrial calcium regulator (TUSC2; NCBI Gene ID: 11334); TYRO3 protein tyrosine kinase (TYRO3; BYK; NCBI Gene ID: 7301); tyrosinase (TYR; NCBI Gene ID: 7299); tyrosine hydroxylase (TH; NCBI Gene ID: 7054); tyrosine kinase with immunoglobulin like and EGF like domains 1 (e.g., TIE1, TIE1; NCBI Gene ID: 7075); tyrosine-protein phosphatase non-receptor type 11 (PTPN11, SHP2; NCBI Gene ID: 5781); ubiquitin conjugating enzyme E2 I (UBE2I, UBC9; NCBI Gene ID: 7329); ubiquitin C-terminal hydrolase L5 (UCHL5; NCBI Gene ID: 51377); ubiquitin specific peptidase 7 (USP7; NCBI Gene ID: 7874); ubiquitin-like modifier activating enzyme 1 (UBA1; NCBI Gene ID: 7317); UL16 binding proteins (e.g., ULBP1, ULBP2, ULBP3; NCBI Gene ID: 79465, 80328, 80328); valosin-containing protein (VCP, CDC48; NCBI Gene ID: 7415); vascular cell adhesion molecule 1 (VCAM1, CD106; NCBI Gene ID: 7412); vascular endothelial growth factors (e.g., VEGFA, VEGFB; NCBI Gene ID: 7422, 7423); vimentin (VIM; NCBI Gene ID: 7431); vitamin D receptor (VDR; NCBI Gene ID: 7421); V-set domain containing T cell activation inhibitor 1 (VTCN1, B7-H4; NCBI Gene ID: 79679); V-set immunoregulatory receptor (VSIR, VISTA, B7-H5; NCBI Gene ID: 64115); WEE1 G2 checkpoint kinase (WEE1; NCBI Gene ID: 7465); WRN RecQ like helicase (WRN; RECQ3; NCBI Gene ID: 7486); WT1 transcription factor (WT1; NCBI Gene ID: 7490); WW domain containing transcription regulator 1 (WWTR1; TAZ; NCBI Gene ID: 25937); X-C motif chemokine ligand 1 (XCL1, ATAC; NCBI Gene ID: 6375); X-C motif chemokine receptor 1 (XCR1, GPR5, CCXCR1; NCBI Gene ID: 2829); Yesl associated transcriptional regulator (YAP1; NCBI Gene ID: 10413); zeta chain associated protein kinase 70 (ZAP70; NCBI Gene ID: 7535).

In some embodiments, the one or more additional therapeutic agents include, e.g., an agent targeting 5'-nucleotidase ecto (NT5E or CD73; NCBI Gene ID: 4907); adenosine A2A receptor (ADORA2A; NCBI Gene ID: 135); adenosine $A2_B$ receptor (ADORA2B; NCBI Gene ID: 136); C-C motif chemokine receptor 8 (CCR8, CDwl98; NCBI Gene ID: 1237); cytokine inducible SH2 containing protein (CISH; NCBI Gene ID: 1154); diacylglycerol kinase alpha (DGKA, DAGK, DAGK1 or DGK-alpha; NCBI Gene ID: 1606); fms like tyrosine kinase 3 (FLT3, CD135; NCBI Gene ID: 2322); integrin associated protein (IAP, CD47; NCBI Gene ID: 961); interleukine-2 (IL2; NCBI Gene ID:3558); interleukine 2 receptor (IL2RA, IL2RB, IL2RG; NCBI Gene IDs: 3559, 3560, 3561); Kirsten rat sarcoma virus (KRAS; NCBI Gene ID: 3845; including mutations, such as KRAS G12C or G12D); mitogen-activated protein kinase kinase kinase kinase 1 (MAP4K1) (also called Hematopoietic Progenitor Kinase 1 (HPK1), NCBI Gene ID: 11184); myeloid cell leukemia sequence 1 apoptosis regulator (MCL1; NCBI Gene ID: 4170); phosphatidylinositol-4,5-bisphosphate 3-kinase, catalytic subunit delta (PIK3CD; NCBI Gene ID: 5293); programmed death-ligand 1 (PD-L1, CD274; NCBI Gene ID 29126); programmed cell death protein 1 (PD-1, CD279; NCBI Gene ID: 5133); proto-oncogen c-KIT (KIT, CD117; NCBI Gene ID: 3815); signal-regulatory protein alpha (SIRPA, CD172A; NCBI Gene ID: 140885); TCDD inducible poly(ADP-ribose) polymerase (TIPARP, PARP7; NCBI Gene ID: 25976); T cell immunoreceptor with Ig and ITIM domains (TIGIT; NCBI Gene ID: 201633); triggering receptor expressed on myeloid cells 1 (TREM1; NCBI Gene ID: 54210); triggering receptor expressed on myeloid cells 2 (TREM2; NCBI Gene ID: 54209); tumor-associated calcium signal transducer 2 (TACSTD2, TROP2, EGP1; NCBI Gene ID: 4070); tumor necrosis factor receptor superfamily, member 4 (TNFRSF4, CD134, OX40; NCBI Gene ID:7293); tumor necrosis factor receptor superfamily, member 9 (TNFRSF9, 4-1BB, CD137; NCBI Gene ID: 3604); tumor necrosis factor receptor superfamily, member 18 (TNFRSF18, CD357, GITR; NCBI Gene ID: 8784); WRN RecQ like helicase (WRN; NCBI Gene ID: 7486); zinc finger protein Helios (IKZF2; NCBI Gene ID: 22807).

Illustrative Mechanisms of Action

Immune Checkpoint Modulators

In some embodiments, a compound provided herein is administered with one or more blockers or inhibitors of inhibitory immune checkpoint proteins or receptors and/or with one or more stimulators, activators or agonists of one or more stimulatory immune checkpoint proteins or receptors. Blockade or inhibition of inhibitory immune checkpoints can positively regulate T-cell or NK cell activation and prevent immune escape of cancer cells within the tumor microenvironment. Activation or stimulation of stimulatory immune check points can augment the effect of immune checkpoint inhibitors in cancer therapeutics. In some embodiments, the immune checkpoint proteins or receptors regulate T cell responses (e.g., reviewed in Xu, et al., *J Exp Clin Cancer Res*. (2018) 37:110). In some embodiments, the immune checkpoint proteins or receptors regulate NK cell responses (e.g., reviewed in Davis, et al., *Semin Immunol*. (2017) 31:64-75 and Chiossone, et al., *Nat Rev Immunol*. (2018) 18(11):671-688). Inhibition of regulatory T-cells (Treg) or Treg depletion can alleviate their suppression of antitumor immune responses and have anticancer effects (e.g., reviewed in Plitas and Rudensky, *Annu. Rev. Cancer Biol*. (2020) 4:459-77; Tanaka and Sakaguchi, *Eur. J. Immunol*. (2019) 49:1140-1146).

Examples of immune checkpoint proteins or receptors include CD27 (NCBI Gene ID: 939), CD70 (NCBI Gene ID: 970); CD40 (NCBI Gene ID: 958), CD40LG (NCBI Gene ID: 959); CD47 (NCBI Gene ID: 961), SIRPA (NCBI Gene ID: 140885); CD48 (SLAMF2; NCBI Gene ID: 962), transmembrane and immunoglobulin domain containing 2 (TMIGD2, CD28H; NCBI Gene ID: 126259), CD84 (LY9B, SLAMF5; NCBI Gene ID: 8832), CD96 (NCBI Gene ID: 10225), CD160 (NCBI Gene ID: 11126), MS4A1 (CD20; NCBI Gene ID: 931), CD244 (SLAMF4; NCBI Gene ID: 51744); CD276 (B7H3; NCBI Gene ID: 80381); V-set domain containing T cell activation inhibitor 1 (VTCN1, B7H4); V-set immunoregulatory receptor (VSIR, B7H5, VISTA; NCBI Gene ID: 64115); immunoglobulin superfamily member 11 (IGSF11, VSIG3; NCBI Gene ID: 152404); natural killer cell cytotoxicity receptor 3 ligand 1 (NCR3LG1, B7H6; NCBI Gene ID: 374383); HERV-H LTR-associating 2 (HHLA2, B7H7; NCBI Gene ID: 11148); inducible T cell co-stimulator (ICOS, CD278; NCBI Gene ID: 29851); inducible T cell co-stimulator ligand (ICOSLG, B7H2; NCBI Gene ID: 23308); TNF receptor superfamily member 4 (TNFRSF4, OX40; NCBI Gene ID: 7293); TNF superfamily member 4 (TNFSF4, OX40L; NCBI Gene ID: 7292); TNFRSF8 (CD30; NCBI Gene ID: 943), TNFSF8 (CD30L; NCBI Gene ID: 944); TNFRSF10A (CD261, DR4, TRAILR1; NCBI Gene ID: 8797), TNFRSF9 (CD137; NCBI Gene ID: 3604), TNFSF9 (CD137L; NCBI Gene ID: 8744); TNFRSF10B (CD262, DR5, TRAILR2; NCBI Gene ID: 8795), TNFRSF10 (TRAIL; NCBI Gene ID: 8743); TNFRSF14 (HVEM, CD270; NCBI Gene ID: 8764), TNFSF14 (HVEML; NCBI Gene ID: 8740); CD272 (B and T lymphocyte associated (BTLA); NCBI Gene ID: 151888); TNFRSF17 (BCMA, CD269; NCBI Gene ID: 608), TNFSF13B (BAFF; NCBI Gene ID: 10673); TNFRSF18 (GITR; NCBI Gene ID: 8784), TNFSF18 (GITRL; NCBI Gene ID: 8995); MHC class I polypeptide-related sequence A (MICA; NCBI Gene ID: 100507436); MHC class I polypeptide-related sequence B (MICB; NCBI Gene ID: 4277); CD274 (CD274, PDL1, PD-L1; NCBI Gene ID: 29126); programmed cell death 1 (PDCD1, PD1, PD-1; NCBI Gene ID: 5133); cytotoxic T-lymphocyte associated protein 4 (CTLA4, CD152; NCBI Gene ID: 1493); CD80 (B7-1; NCBI Gene ID: 941), CD28 (NCBI Gene ID: 940); nectin cell adhesion molecule 2 (NECTIN2, CD 112; NCBI Gene ID: 5819); CD226 (DNAM-1; NCBI Gene ID: 10666); Poliovirus receptor (PVR) cell adhesion molecule (PVR, CD155; NCBI Gene ID: 5817); PVR related immunoglobulin domain containing (PVRIG, CD112R; NCBI Gene ID: 79037); T cell immunoreceptor with Ig and ITIM domains (TIGIT; NCBI Gene ID: 201633); T cell immunoglobulin and mucin domain containing 4 (TIMD4; TIM4; NCBI Gene ID: 91937); hepatitis A virus cellular receptor 2 (HAVCR2, TIMD3, TIM3; NCBI Gene ID: 84868); galectin 9 (LGALS9; NCBI Gene ID: 3965); lymphocyte activating 3 (LAG3, CD223; NCBI Gene ID: 3902); signaling lymphocytic activation molecule family member 1 (SLAMF1, SLAM, CD150; NCBI Gene ID: 6504); lymphocyte antigen 9 (LY9, CD229, SLAMF3; NCBI Gene ID: 4063); SLAM family member 6 (SLAMF6, CD352; NCBI Gene ID: 114836); SLAM family member 7 (SLAMF7, CD319; NCBI Gene ID: 57823); UL16 binding protein 1 (ULBP1; NCBI Gene ID: 80329); UL16 binding protein 2 (ULBP2; NCBI Gene ID: 80328); UL16 binding protein 3 (ULBP3; NCBI Gene ID: 79465); retinoic acid early transcript 1E (RAETIE; ULBP4; NCBI Gene ID: 135250); retinoic acid early transcript 1G (RAETIG; ULBP5; NCBI Gene ID: 353091); retinoic acid early transcript 1L (RAETIL; ULBP6; NCBI Gene ID: 154064); killer cell immunoglobulin like receptor, three Ig domains and long cytoplasmic tail 1 (KIR, CD158E1; NCBI Gene ID: 3811, e.g., lirilumab (IPH-2102, IPH-4102)); killer cell lectin like receptor C1 (KLRC1, NKG2A, CD159A; NCBI Gene ID: 3821); killer cell lectin like receptor K1 (KLRK1, NKG2D, CD314; NCBI Gene ID: 22914); killer cell lectin like receptor C2 (KLRC2, CD159c, NKG2C; NCBI Gene ID: 3822); killer cell lectin like receptor C3 (KLRC3, NKG2E; NCBI Gene ID: 3823); killer cell lectin like receptor C4 (KLRC4, NKG2F; NCBI Gene ID: 8302); killer cell immunoglobulin like receptor, two Ig domains and long cytoplasmic tail 1 (KIR2DL1; NCBI Gene ID: 3802); killer cell immunoglobulin like receptor, two Ig domains and long cytoplasmic tail 2 (KIR2DL2; NCBI Gene ID: 3803); killer cell immunoglobulin like receptor, two Ig domains and long cytoplasmic tail 3 (KIR2DL3; NCBI Gene ID: 3804); killer cell immunoglobulin like receptor, three Ig domains and long cytoplasmic tail 1 (KIR3DL1); killer cell lectin like receptor D1 (KLRD1; NCBI Gene ID: 3824); killer cell lectin like receptor G1 (KLRG1; CLEC15A, MAFA, 2F1; NCBI Gene ID: 10219); sialic acid binding Ig like lectin 7 (SIGLEC7; NCBI Gene ID: 27036); and sialic acid binding Ig like lectin 9 (SIGLEC9; NCBI Gene ID: 27180).

In some embodiments, a compound provided herein is administered with one or more blockers or inhibitors of one or more T-cell inhibitory immune checkpoint proteins or receptors. Illustrative T-cell inhibitory immune checkpoint proteins or receptors include CD274 (CD274, PDL1, PD-L1); programmed cell death 1 ligand 2 (PDCDILG2, PD-L2, CD273); programmed cell death 1 (PDCD1, PD1, PD-1); cytotoxic T-lymphocyte associated protein 4 (CTLA4, CD152); CD276 (B7H3); V-set domain containing T cell activation inhibitor 1 (VTCN1, B7H4); V-set immunoregulatory receptor (VSIR, B7H5, VISTA); immunoglobulin superfamily member 11 (IGSF11, VSIG3); TNFRSF14 (HVEM, CD270), TNFSF14 (HVEML); CD272 (B and T lymphocyte associated (BTLA)); PVR related immunoglobulin domain containing (PVRIG, CDI12R); T cell immunoreceptor with Ig and ITIM domains (TIGIT); lymphocyte activating 3 (LAG3, CD223); hepatitis A virus cellular receptor 2 (HAVCR2, TIMD3, TIM3); galectin 9 (LGALS9); killer cell immunoglobulin like receptor, three Ig domains and long cytoplasmic tail 1 (KIR, CD158E1); killer cell immunoglobulin like receptor, two Ig domains and long cytoplasmic tail 1 (KIR2DL1); killer cell immunoglobulin like receptor, two Ig domains and long cytoplasmic tail 2 (KIR2DL2); killer cell immunoglobulin like receptor, two Ig domains and long cytoplasmic tail 3 (KIR2DL3); and killer cell immunoglobulin like receptor, three Ig domains and long cytoplasmic tail 1 (KIR3DL1). In some embodiments, the compound provided herein is administered with one or more agonist or activators of one or more T-cell stimulatory immune checkpoint proteins or receptors. Illustrative T-cell stimulatory immune checkpoint proteins or receptors include without limitation CD27, CD70; CD40, CD40LG; inducible T cell costimulator (ICOS, CD278); inducible T cell costimulator ligand (ICOSLG, B7H2); TNF receptor superfamily member 4 (TNFRSF4, OX40); TNF superfamily member 4 (TNFSF4, OX40L); TNFRSF9 (CD137), TNFSF9 (CD137L); TNFRSF18 (GITR), TNFSF18 (GITRL); CD80 (B7-1), CD28; nectin cell adhesion molecule 2 (NECTIN2, CD112); CD226 (DNAM-1); CD244 (2B4, SLAMF4), Poliovirus receptor (PVR) cell adhesion molecule (PVR, CD155). See, e.g., Xu, et al., J Exp Clin Cancer Res. (2018) 37:110.

In some embodiments, the compound provided herein is administered with one or more blockers or inhibitors of one or more NK-cell inhibitory immune checkpoint proteins or receptors. Illustrative NK-cell inhibitory immune checkpoint proteins or receptors include killer cell immunoglobulin like receptor, three Ig domains and long cytoplasmic tail 1 (KIR, CD158E1); killer cell immunoglobulin like receptor, two Ig domains and long cytoplasmic tail 1 (KIR2DL1); killer cell immunoglobulin like receptor, two Ig domains and long cytoplasmic tail 2 (KIR2DL2); killer cell immunoglobulin like receptor, two Ig domains and long cytoplasmic tail 3 (KIR2DL3); killer cell immunoglobulin like receptor, three Ig domains and long cytoplasmic tail 1 (KIR3DL1); killer cell lectin like receptor C1 (KLRC1, NKG2A, CD159A); killer cell lectin like receptor D1 (KLRD1, CD94), killer cell lectin like receptor G1 (KLRG1; CLEC15A, MAFA, 2F1); sialic acid binding Ig like lectin 7 (SIGLEC7); and sialic acid binding Ig like lectin 9 (SIGLEC9). In some embodiments, the compound provided herein is administered with one or more agonist or activators of one or more NK-cell stimulatory immune checkpoint proteins or receptors. Illustrative NK-cell stimulatory immune checkpoint proteins or receptors include CD16, CD226 (DNAM-1); CD244 (2B4, SLAMF4); killer cell lectin like receptor K1 (KLRK1, NKG2D, CD314); SLAM family member 7 (SLAMF7). See, e.g., Davis, et al., *Semin Immunol.* (2017) 31:64-75; Fang, et al., *Semin Immunol.* (2017) 31:37-54; and Chiossone, et al., *Nat Rev Immunol.* (2018) 18(11):671-688.

In some embodiments, the one or more immune checkpoint inhibitors comprises a proteinaceous (e.g., antibody or fragment thereof, or antibody mimetic) inhibitor of PD-L1 (CD274), PD-1 (PDCD1), CTLA4, or TIGIT. In some embodiments, the one or more immune checkpoint inhibitors comprises a small organic molecule inhibitor of PD-L1 (CD274), PD-1 (PDCD1), CTLA4, or TIGIT. In some embodiments, the one or more immune checkpoint inhibitors comprises a proteinaceous (e.g., antibody or fragment thereof, or antibody mimetic) inhibitor of LAG3.

Examples of inhibitors of CTLA4 that can be co-administered include ipilimumab, tremelimumab, BMS-986218, AGEN1181, zalifrelimab (AGEN1884), BMS-986249, MK-1308, REGN-4659, ADU-1604, CS-1002 (ipilimumab biosimilar), BCD-145, APL-509, JS-007, BA-3071, ONC-392, AGEN-2041, HBM-4003, JHL-1155, KN-044, CG-0161, ATOR-1144, PBI-5D3H5, BPI-002, as well as multi-specific inhibitors FPT-155 (CTLA4/PD-L1/CD28), PF-06936308 (PD-1/CTLA4), MGD-019 (PD-1/CTLA4), KN-046 (PD-1/CTLA4), MEDI-5752 (CTLA4/PD-1), XmAb-20717 (PD-1/CTLA4), and AK-104 (CTLA4/PD-1).

Examples of inhibitors of PD-L1 (CD274) or PD-1 (PDCD1) that can be co-administered include pembrolizumab, nivolumab, cemiplimab, pidilizumab, AMP-224, MEDIO680 (AMP-514), spartalizumab, atezolizumab, avelumab, durvalumab, BMS-936559, cosibelimab (CK-301), sasanlimab (PF-06801591), tislelizumab (BGB-A317), GLS-010 (WBP-3055), AK-103 (HX-008), AK-105, CS-1003, HLX-10, retifanlimab (MGA-012), BI-754091, balstilimab (AGEN-2034), AMG-404, toripalimab (JS-001), cetrelimab (JNJ-63723283), genolimzumab (CBT-501), LZM-009, prolgolimab (BCD-100), lodapolimab (LY-3300054), SHR-1201, camrelizumab (SHR-1210), Sym-021, budigalimab (ABBV-181), PD1-PIK, BAT-1306, avelumab (MSB0010718C), CX-072, CBT-502, dostarlimab (TSR-042), MSB-2311, JTX-4014, BGB-A333, SHR-1316, CS-1001 (WBP-3155, envafolimab (KN-035), sintilimab (IBI-308), HLX-20, KL-A167, STI-A1014, STI-A1015 (IMC-001), BCD-135, FAZ-053, TQB-2450, MDX1105-01, GS-4224, GS-4416, INCB086550, MAX10181, zimberelimab (AB122), spartalizumab (PDR-001), and compounds disclosed in WO2018195321, WO2020014643, WO2019160882, or WO2018195321, as well as multi-specific inhibitors FPT-155 (CTLA4/PD-L1/CD28), PF-06936308 (PD-1/CTLA4), MGD-013 (PD-1/LAG-3), FS-118 (LAG-3/PD-L1), RO-7247669 (PD-1/LAG-3), MGD-019 (PD-1/CTLA4), KN-046 (PD-1/CTLA4), MEDI-5752 (CTLA4/PD-1), RO-7121661 (PD-1/TIM-3), RG7769 (PD-1/TIM-3), TAK-252 (PD-1/OX40L), XmAb-20717 (PD-1/CTLA4), AK-104 (CTLA4/PD-1), FS-118 (LAG-3/PD-L1), FPT-155 (CTLA4/PD-L1/CD28), GEN-1046 (PD-L1/4-1BB), bintrafusp alpha (M7824; PD-L1/TGFβ-EC domain), CA-170 (PD-L1/VISTA), CDX-527 (CD27/PD-L1), LY-3415244 (TIM3/PDL1), and INBRX-105 (4-1BB/PDL1). In some embodiments, the PD-L1 inhibitor is a small molecule inhibitor, such as CA-170, GS-4224, GS-4416 and lazertinib (GNS-1480; PD-L1/EGFR).

Examples of inhibitors of TIGIT that can be co-administered include tiragolumab (RG-6058), vibostolimab, domvanalimab, domvanalimab (AB154), AB308, BMS-986207, AGEN-1307, COM-902, or etigilimab.

Examples of inhibitors of LAG3 that can be co-administered include leramilimab (LAG525).

Inhibition of regulatory T-cell (Treg) activity or Treg depletion can alleviate their suppression of antitumor immune responses and have anticancer effects. See, e.g., Plitas and Rudensky, *Annu. Rev. Cancer Biol.* (2020) 4:459-77; Tanaka and Sakaguchi, *Eur. J. Immunol.* (2019) 49:1140-1146. In some embodiments, a compound provided herein is administered with one or more inhibitors of Treg activity or a Treg depleting agent. Treg inhibition or depletion can augment the effect of immune checkpoint inhibitors in cancer therapeutics.

In some embodiments, a compound provided herein is administered with one or more Treg inhibitors. In some embodiments, the Treg inhibitor can suppress the migration of Tregs into the tumor microenvironment. In some embodiments, Treg inhibitor can reduce the immunosuppressive function of Tregs. In some embodiments, the Treg inhibitor can modulate the cellular phenotype and induce production of proinflammatory cytokines. Exemplary Treg inhibitors include without limitation, CCR4 (NCBI Gene ID: 1233) antagonists and degraders of Ikaros zinc-finger proteins (e.g., Ikaros (IKZF1; NCBI Gene ID: 10320), Helios (IKZF2; NCBI Gene ID: 22807), Aiolos (IKZF3; NCBI Gene ID: 22806), and Eos (IKZF4; NCBI Gene ID: 64375).

Examples of Helios degraders that can be co-administered include without limitation I-57 (Novartis) and compounds disclosed in WO2019038717, WO2020012334, WO20200117759, and WO2021101919.

In some embodiments, a compound provided herein is administered with one or more Treg depleting agents. In some embodiments, the Treg depleting agent is an antibody. In some embodiments, the Treg depleting antibody has antibody-dependent cytotoxic (ADCC) activity. In some embodiments, the Treg depleting antibody is Fc-engineered to possess an enhanced ADCC activity. In some embodiments, the Treg depleting antibody is an antibody-drug conjugate (ADC). Illustrative targets for Treg depleting agents include without limitation CD25 (IL2RA; NCBI Gene ID: 3559), CTLA4 (CD152; NCBI Gene ID: 1493); GITR (TNFRSF18; NCBI Gene ID: 8784); 4-1BB (CD137; NCBI Gene ID: 3604), OX-40 (CD134; NCBI Gene ID: 7293), LAG3 (CD223; NCBI Gene ID: 3902), TIGIT (NCBI Gene ID: 201633), CCR4 (NCBI Gene ID: 1233), and CCR8 (NCBI Gene ID: 1237).

In some embodiments, the Treg inhibitor or Treg depleting agent that can be co-administered comprises an antibody or antigen-binding fragment thereof that selectively binds to a cell surface receptor selected from the group consisting of C-C motif chemokine receptor 4 (CCR4), C-C motif chemokine receptor 7 (CCR7), C-C motif chemokine receptor 8 (CCR8), C-X-C motif chemokine receptor 4 (CXCR4; CD184), TNFRSF4 (OX40), TNFRSF18 (GITR, CD357), TNFRSF9 (4-1BB, CD137), cytotoxic T-lymphocyte associated protein 4 (CTLA4, CD152), programmed cell death 1 (PDCD1, PD-1), Sialyl Lewis x (CD15s), CD27, ectonucleoside triphosphate diphosphohydrolase 1 (ENTPD1; CD39), protein tyrosine phosphatase receptor type C (PTPRC; CD45), neural cell adhesion molecule 1 (NCAM1; CD56), selectin L (SELL; CD62L), integrin subunit alpha E (ITGAE; CD103), interleukin 7 receptor (IL7R; CD127), CD40 ligand (CD40LG; CD154), folate receptor alpha (FOLR1), folate receptor beta (FOLR2), leucine rich repeat containing 32 (LRRC32; GARP), IKAROS family zinc finger 2 (IKZF2; HELIOS), inducible T cell costimulatory (ICOS; CD278), lymphocyte activating 3 (LAG3; CD223), transforming growth factor beta 1 (TGFB1), hepatitis A virus cellular receptor 2 (HAVCR2; CD366; TIM3), T cell immunoreceptor with Ig and ITIM domains (TIGIT), TNF receptor superfamily member 1B (CD120b; TNFR2), IL2RA (CD25) or a combination thereof.

Examples of Treg depleting anti-CCR8 antibodies that can be administered include without limitation JTX-1811 (GS-1811) (Jounce Therapeutics, Gilead Sciences), BMS-986340 (Bristol Meyers Squibb), S-531011 (Shionogi), FPA157 (Five Prime Therapeutics), SRF-114 (Surface Oncology), HBM1022 (Harbor BioMed), IO-1 (Oncurious), and antibodies disclosed in WO2021163064, WO2020138489, and WO2021152186.

Examples of Treg depleting anti-CCR4 antibodies that can be administered include mogamulizumab.

Inhibiting, depleting, or reprogramming of non-stimulatory myeloid cells in the tumor microenvironment can enhance anti-cancer immune responses (see, e.g., Binnewies et al., *Nat. Med.* (2018) 24(5): 541-550; WO2016049641). Illustrative targets for depleting or reprogramming non-stimulatory myeloid cells include triggering receptors expressed on myeloid cells, TREM-1 (CD354, NCBI Gene ID: 54210) and TREM-2 (NCBI Gene ID: 54209). In some embodiments, a compound provided herein is administered with one or more myeloid cell depleting or reprogramming agents, such as an anti-TREM-1 antibody (e.g. PY159; antibodies disclosed in WO2019032624) or an anti-TREM-2 antibody (e.g., PY314; antibodies disclosed in WO2019118513).

Cluster of Differentiation Agonists or Activators

In some embodiments, the compound provided herein is administered with agents targeting a cluster of differentiation (CD) marker. Exemplary CD marker targeting agents that can be co-administered include without limitation A6, AD-IL24, neratinib, tucatinib (ONT 380), mobocertinib (TAK-788), tesevatinib, trastuzumab (HERCEPTIN®), trastuzumab biosimimar (HLX-02), margetuximab, BAT-8001, pertuzumab (Perjeta), pegfilgrastim, RG6264, zanidatamab (ZW25), cavatak, AIC-100, tagraxofusp (SL-401), HLA-A2402/HLA-A0201 restricted epitope peptide vaccine, dasatinib, imatinib, nilotinib, sorafenib, lenvatinib mesylate, ofranergene obadenovec, cabozantinib malate, AL-8326, ZLJ-33, KBP-7018, sunitinib malate, pazopanib derivatives, AGX-73, rebastinib, NMS-088, lucitanib hydrochloride, midostaurin, cediranib, dovitinib, sitravatinib, tivozanib, masitinib, regorafenib, olverembatinib dimesylate (HQP-1351), cabozantinib, ponatinib, and famitinib L-malate, CX-2029 (ABBV-2029), SCB-313, CA-170, COM-701, CDX-301, GS-3583, asunercept (APG-101), APO-010, and compounds disclosed in WO2016196388, WO2016033570, WO2015157386, WO199203459, WO199221766, WO2004080462, WO2005020921, WO2006009755, WO2007078034, WO2007092403, WO2007127317, WO2008005877, WO2012154480, WO2014100620, WO2014039714, WO2015134536, WO2017167182, WO2018112136, WO2018112140, WO2019155067, WO2020076105, PCT/US2019/063091, WO19173692, WO2016179517, WO2017096179, WO2017096182, WO2017096281, WO2018089628, WO2017096179, WO2018089628, WO2018195321, WO2020014643, WO2019160882, WO2018195321, WO200140307, WO2002092784, WO2007133811, WO2009046541, WO2010083253, WO2011076781, WO2013056352, WO2015138600, WO2016179399, WO2016205042, WO2017178653, WO2018026600, WO2018057669, WO2018107058, WO2018190719, WO2018210793, WO2019023347, WO2019042470, WO2019175218, WO2019183266, WO2020013170, WO2020068752, Cancer Discov. 2019 Jan. 9(1):8; and Gariepy J., et al. 106th Annu Meet Am Assoc Immunologists (AAI) (May 9-13, San Diego, 2019, Abst 71.5).

In some embodiments, the CD marker targeting agent that can be co-administered include small molecule inhibitors, such as PBF-1662, BLZ-945, pemigatinib (INCB-054828), rogaratinib (BAY-1163877), AZD4547, roblitinib (FGF-401), quizartinib dihydrochloride, SX-682, AZD-5069, PLX-9486, avapritinib (BLU-285), ripretinib (DCC-2618), imatinib mesylate, JSP-191, BLU-263, CD117-ADC, AZD3229, telatinib, vorolanib, GO-203-2C, AB-680, PSB-12379, PSB-12441, PSB-12425, CB-708, HM-30181A, motixafortide (BL-8040), LY2510924, burixafor (TG-0054), X4P-002, mavorixafor (X4P-001-IO), plerixafor, CTX-5861, or REGN-5678 (PSMA/CD28).

In some embodiments, the CD marker targeting agent that can be co-administered include small molecule agonists, such as interleukin 2 receptor subunit gamma, eltrombopag, rintatolimod, poly-ICLC (NSC-301463), Riboxxon, Apoxxim, RIBOXXIM®, MCT-465, MCT-475, G100, PEPA-10, eftozanermin alfa (ABBV-621), E-6887, motolimod, resiquimod, selgantolimod (GS-9688), VTX-1463, NKTR-262, AST-008, CMP-001, cobitolimod, tilsotolimod, litenimod, MGN-1601, BB-006, IMO-8400, IMO-9200, agatolimod, DIMS-9054, DV-1079, lefitolimod (MGN-1703), CYT-003, and PUL-042.

In some embodiments, the CD marker targeting agent that can be co-administered include antibodies, such as tafasitamab (MOR208; MorphoSys AG), Inebilizumab (MEDI-551), obinutuzumab, IGN-002, rituximab biosimilar (PF-05280586), varlilumab (CDX-1127), AFM-13 (CD16/CD30), AMG330, otlertuzumab (TRU-016), isatuximab, felzartamab (MOR-202), TAK-079, TAK573, daratumumab (DARZALEX®), TTX-030, selicrelumab (RG7876), APX-005M, ABBV-428, ABBV-927, mitazalimab (JNJ-64457107), lenziluma, alemtuzuma, emactuzumab, AMG-820, FPA-008 (cabiralizumab), PRS-343 (CD-137/Her2), AFM-13 (CD16/CD30), belantamab mafodotin (GSK-2857916), AFM26 (BCMA/CD16A), simlukafusp alfa (RG7461), urelumab, utomilumab (PF-05082566), AGEN2373, ADG-106, BT-7480, PRS-343 (CD-137/HER2), FAP-4-IBBL (4-1BB/FAP), ramucirumab, CDX-0158, CDX-0159 and FSI-174, relatlimab (ONO-4482), LAG-525, MK-4280, fianlimab (REGN-3767), INCAGN2385, encelimab (TSR-033), atipotuzumab, BrevaRex (Mab-AR-20.5), MEDI-9447 (oleclumab), CPX-006, IPH-53, BMS-986179, NZV-930, CPI-006, PAT-SCi, lirilumab (IPH-2102), lacutamab (IPH-4102), monalizumab, BAY-1834942, NEO-201 (CEACAM 5/6), Iodine (131I) apamistamab (131I-BC8 (lomab-B)), MEDI0562 (tavolixizumab), GSK-3174998, INCAGN1949, BMS-986178, GBR-8383, ABBV-368, denosumab, BION-1301, MK-4166, INCAGN-1876, TRX-518, BMS-986156, MK-1248, GWN-323, CTB-006, INBRX-109, GEN-1029, pepinemab (VX-15), vopratelimab (JTX-2011), GSK3359609, cobolimab (TSR-022), MBG-453, INCAGN-2390, and compounds disclosed in WO 2017096179, WO2017096276, WO2017096189, and WO2018089628.

In some embodiments, the CD marker targeting agent that can be co-administered include cell therapies, such as CD19-ARTEMIS, TBI-1501, CTL-119 huCART-19 T cells, 1 iso-cel, lisocabtagene maraleucel (JCAR-017), axicabtagene ciloleucel (KTE-C19, Yescarta®), axicabtagene ciloleucel (KTE-X19), U.S. Pat. Nos. 7,741,465, 6,319,494, UCART-19, tabelecleucel (EBV-CTL), T tisagenlecleucel-T (CTLO19), CD19CAR-CD28-CD3zeta-EGFRt-expressing T cells, CD19/4-1BBL armored CAR T cell therapy, C-CAR-011, CIK-CAR.CD19, CDI9CAR-28-zeta T cells, PCAR-019, MatchCART, DSCAR-01, IM19 CAR-T, TC-110, anti-CD19 CAR T-cell therapy (B-cell acute lymphoblastic leukemia, Universiti Kebangsaan Malaysia), anti-CD19 CAR T-cell therapy (acute lymphoblastic leukemia/Non-Hodgkin's lymphoma, University Hospital Heidelberg), anti-CD19 CAR T-cell therapy (silenced IL-6 expression, cancer, Shanghai Unicar-Therapy Bio-medicine Technology), MB-CART2019.1 (CD19/CD20), GC-197 (CD19/CD7), CLIC-1901, ET-019003, anti-CD19-STAR-T cells, AVA-001, BCMA-CD19 cCAR (CD19/APRIL), ICG-134, ICG-132 (CD19/CD20), CTA-101, WZTL-002, dual anti-CD19/anti-CD20 CAR T-cells (chronic lymphocytic leukemia/B-cell lymphomas), HY-001, ET-019002, YTB-323, GC-012 (CD19/APRIL), GC-022 (CD19/CD22), CD19CAR-CD28-CD3zeta-EGFRt-expressing Tn/mem, UCAR-011, ICTCAR-014, GC-007F, PTG-01, CC-97540, GC-007G, TC-310, GC-197, tisagenlecleucel-T, CART-19, tisagenlecleucel (CTL-019)), anti-CD20 CAR T-cell therapy (non-Hodgkin's lymphoma), MB-CART2019.1 (CD19/CD20), WZTL-002 dual anti-CD19/anti-CD20 CAR-T cells, ICG-132 (CD19/CD20), ACTR707 ATTCK-20, PBCAR-20A, LB-1905, CIK-CAR.CD33, CD33CART, dual anti-BCMA/anti-CD38 CAR T-cell therapy, CART-ddBCMA, MB-102, IM-23, JEZ-567, UCART-123, PD-1 knockout T cell therapy (esophageal cancer/NSCLC), ICT-CAR-052, Tn MUC-1 CAR-T, ICTCAR-053, PD-1 knockout T cell therapy (esophageal cancer/NSCLC), AUTO-2, anti-BCMA CAR T-cell therapy, Descartes-011, anti-BCMA/anti-CD38 CAR T-cell therapy, CART-ddBCMA, BCMA-CSi cCAR, CYAD-01 (NKG2D LIGAND MODULATOR), KD-045, PD-L1 t-haNK, BCMA-CSi cCAR, MEDI5083, anti-CD276 CART, and therapies disclosed in WO2012079000 or WO2017049166.

Cluster of Differentiation 47 (CD47) Inhibitors

In some embodiments, the compound provided herein is administered with an inhibitor of CD47 (IAP, MER6, OA3; NCBI Gene ID: 961). Examples of CD47 inhibitors include anti-CD47 mAbs (Vx-1004), anti-human CD47 mAbs (CNTO-7108), CC-90002, CC-90002-ST-001, humanized anti-CD47 antibody or a CD47-blocking agent, NI-1701, NI-1801, RCT-1938, ALX148, SG-404, SRF-231, and TTI-621. Additional exemplary anti-CD47 antibodies include CC-90002, magrolimab (Hu5F9-G4), AO-176 (Vx-1004), letaplimab (IBI-188) (letaplimab), lemzoparlimab (TJC-4), SHR-1603, HLX-24, LQ-001, IMC-002, ZL-1201, IMM-01, B6H12, GenSci-059, TAY-018, PT-240, 1F8-GMCSF, SY-102, KD-015, ALX-148, AK-117, TTI-621, TTI-622, or compounds disclosed in WO199727873, WO199940940, WO2002092784, WO2005044857, WO2009046541, WO2010070047, WO2011143624, WO2012170250, WO2013109752, WO2013119714, WO2014087248, WO2015191861, WO2016022971, WO2016023040, WO2016024021, WO2016081423, WO2016109415, WO2016141328, WO2016188449, WO2017027422, WO2017049251, WO2017053423, WO2017121771, WO2017194634, WO2017196793, WO2017215585, WO2018075857, WO2018075960, WO2018089508, WO2018095428, WO2018137705, WO2018233575, WO2019027903, WO2019034895, WO2019042119, WO2019042285, WO2019042470, WO2019086573, WO2019108733, WO2019138367, WO2019144895, WO2019157843, WO2019179366, WO2019184912, WO2019185717, WO2019201236, WO2019238012, WO2019241732, WO2020019135, WO2020036977, WO2020043188, and WO2020009725. In some embodiments, the CD47 inhibitor is RRx-001, DSP-107, VT-1021, IMM-02, SGN-CD47M, or SIRPa-Fc-CD40L (SL-172154). In some embodiments, the CD47 inhibitor is magrolimab.

In some embodiments, the CD47 inhibitor is a bispecific antibodies targeting CD47, such as IBI-322 (CD47/PD-L1), IMM-0306 (CD47/CD20), TJ-L1C4 (CD47/PD-L1), HX-009 (CD47/PD-1), PMC-122 (CD47/PD-L1), PT-217, (CD47/DLL3), IMM-26011 (CD47/FLT3), IMM-0207 (CD47/VEGF), IMM-2902 (CD47/HER2), BH29xx (CD47/PD-L1), IMM-03 (CD47/CD20), IMM-2502 (CD47/PD-L1), HMBD-004B (CD47/BCMA), HMBD-004A (CD47/CD33), TG-1801 (NI-1701), or NI-1801.

SIRPa Targeting Agents

In some embodiments, the compound provided herein is administered with a SIRPa targeting agent (NCBI Gene ID: 140885; UniProt P78324). Examples of SIRPa targeting agents include SIRPa inhibitors, such as AL-008, RRx-001, and CTX-5861, and anti-SIRPa antibodies, such as FSI-189 (GS-0189), ES-004, BI-765063, ADU1805, CC-95251, Q-1801 (SIRPa/PD-L1). Additional SIRPu-targeting agents of use are described, for example, in WO200140307, WO2002092784, WO2007133811, WO2009046541, WO2010083253, WO2011076781, WO2013056352, WO2015138600, WO2016179399, WO2016205042, WO2017178653, WO2018026600, WO2018057669, WO2018107058, WO2018190719, WO2018210793, WO2019023347, WO2019042470, WO2019175218, WO2019183266, WO2020013170 and WO2020068752.

FLT3R Agonists

In some embodiments, the compound provided herein is administered with a FLT3R agonist. In some embodiments, the compound provided herein is administered with a FLT3 ligand. In some embodiments, the compound provided herein is administered with a FLT3L-Fc fusion protein, e.g., as described in WO2020263830. In some embodiments, the compound provided herein is administered with GS-3583 or CDX-301. In some embodiments, the compound provided herein is administered with GS-3583.

TNF Receptor Superfamily (TNFRSF) Member Agonists or Activators

In some embodiments, the compound provided herein is administered with an agonist of one or more TNF receptor superfamily (TNFRSF) members, e.g., an agonist of one or more of TNFRSF1A (NCBI Gene ID: 7132), TNFRSF1B (NCBI Gene ID: 7133), TNFRSF4 (OX40, CD134; NCBI Gene ID: 7293), TNFRSF5 (CD40; NCBI Gene ID: 958), TNFRSF6 (FAS, NCBI Gene ID: 355), TNFRSF7 (CD27, NCBI Gene ID: 939), TNFRSF8 (CD30, NCBI Gene ID: 943), TNFRSF9 (4-1BB, CD137, NCBI Gene ID: 3604), TNFRSF10A (CD261, DR4, TRAILR1, NCBI Gene ID: 8797), TNFRSF10B (CD262, DR5, TRAILR2, NCBI Gene ID: 8795), TNFRSF10C (CD263, TRAILR3, NCBI Gene ID: 8794), TNFRSF10D (CD264, TRAILR4, NCBI Gene ID: 8793), TNFRSF11A (CD265, RANK, NCBI Gene ID: 8792), TNFRSF11B (NCBI Gene ID: 4982), TNFRSF12A (CD266, NCBI Gene ID: 51330), TNFRSF13B (CD267, NCBI Gene ID: 23495), TNFRSF13C (CD268, NCBI Gene ID: 115650), TNFRSF16 (NGFR, CD271, NCBI Gene ID: 4804), TNFRSF17 (BCMA, CD269, NCBI Gene ID: 608), TNFRSF18 (GITR, CD357, NCBI Gene ID: 8784), TNFRSF19 (NCBI Gene ID: 55504), TNFRSF21 (CD358, DR6, NCBI Gene ID: 27242), and TNFRSF25 (DR3, NCBI Gene ID: 8718).

Example anti-TNFRSF4 (OX40) antibodies that can be co-administered include MEDI6469, MEDI6383, tavolixizumab (MEDI0562), MOXR0916, PF-04518600, RG-7888, GSK-3174998, INCAGN1949, BMS-986178, GBR-8383, ABBV-368, and those described in WO2016179517, WO2017096179, WO2017096182, WO2017096281, and WO2018089628.

Example anti-TNFRSF5 (CD40) antibodies that can be co-administered include RG7876, SEA-CD40, APX-005M, and ABBV-428.

In some embodiments, the anti-TNFRSF7 (CD27) antibody varlilumab (CDX-1127) is co-administered.

Example anti-TNFRSF9 (4-1BB, CD137) antibodies that can be co-administered include urelumab, utomilumab (PF-05082566), AGEN-2373, and ADG-106.

In some embodiments, the anti-TNFRSF17 (BCMA) antibody GSK-2857916 is co-administered.

Example anti-TNFRSF18 (GITR) antibodies that can be co-administered include MEDI1873, FPA-154, INCAGN-1876, TRX-518, BMS-986156, MK-1248, GWN-323, and those described in WO2017096179, WO2017096276, WO2017096189, and WO2018089628. In some embodiments, an antibody, or fragment thereof, co-targeting TNFRSF4 (OX40) and TNFRSF18 (GITR) is co-administered. Such antibodies are described, e.g., in WO2017096179 and WO2018089628.

Bi-specific antibodies targeting TNFRSF family members that can be co-administered include PRS-343 (CD-137/HER2), AFM26 (BCMA/CD16A), AFM-13 (CD16/CD30), odronextamab (REGN-1979; CD20/CD3), AMG-420 (BCMA/CD3), INHIBRX-105 (4-1BB/PDL1), FAP-4-IBBL (4-1BB/FAP), plamotamab (XmAb-13676; CD3/CD20), RG-7828 (CD20/CD3), CC-93269 (CD3/BCMA), REGN-5458 (CD3/BCMA), and IMM-0306 (CD47/CD20).

Bi-Specific T-Cell Engagers

In some embodiments, the compound provided herein is administered with a bi-specific T-cell engager (e.g., not having an Fc) or an anti-CD3 bi-specific antibody (e.g., having an Fc). Illustrative anti-CD3 bi-specific antibodies or BiTEs that can be co-administered include duvortuxizumab (JNJ-64052781; CD19/CD3), AMG-211 (CEA/CD3), AMG-160 (PSMA/CD3), RG7802 (CEA/CD3), ERY-974 (CD3/GPC3), PF-06671008 (Cadherins/CD3), APV0436 (CD123/CD3), flotetuzumab (CD123/CD3), odronextamab (REGN-1979; CD20/CD3), MCLA-117 (CD3/CLEC12A), JNJ-0819 (heme/CD3), JNJ-7564 (CD3/heme), AMG-757 (DLL3-CD3), AMG-330 (CD33/CD3), AMG-420 (BCMA/CD3), AMG-427 (FLT3/CD3), AMG-562 (CD19/CD3), AMG-596 (EGFRvIII/CD3), AMG-673 (CD33/CD3), AMG-701 (BCMA/CD3), AMG-757 (DLL3/CD3), AMG-211 (CEA/CD3), blinatumomab (CD19/CD3), huGD2-BsAb (CD3/GD2), ERY974 (GPC3/CD3), GEMoab (CD3/PSCA), RG6026 (CD20/CD3), RG6194 (HER2/CD3), PF-06863135 (BCMA/CD3), SAR440234 (CD3/CDwl23), JNJ-9383 (MGD-015), AMG-424 (CD38/CD3), tidutamab (XmAb-18087 (SSTR2/CD3)), JNJ-63709178 (CD123/CD3), MGD-007 (CD3/gpA33), MGD-009 (CD3/B7H3), IMCgp100 (CD3/gp100), XmAb-14045 (CD123/CD3), XmAb-13676 (CD3/CD20), tidutamab (XmAb-18087; SSTR2/CD3), catumaxomab (CD3/EpCAM), REGN-4018 (MUC16/CD3), mosunetuzumab (RG-7828; CD20/CD3), CC-93269 (CD3/BCMA), REGN-5458 (CD3/BCMA), GRB-1302 (CD3/Erbb2), GRB-1342 (CD38/CD3), GEM-333 (CD3/CD33). As appropriate, the anti-CD3 binding bi-specific molecules may or may not have an Fc. Illustrative bi-specific T-cell engagers that can be co-administered target CD3 and a tumor-associated antigen as described herein, including, e.g., CD19 (e.g., blinatumomab); CD33 (e.g., AMG330); CEA (e.g., MEDI-565); receptor tyrosine kinase-like orphan receptor 1 (ROR1) (Gohil, et al., Oncoimmunology. (2017) May 17; 6(7):e1326437); PD-L1 (Horn, et al., Oncotarget. 2017 Aug. 3; 8(35):57964-57980); and EGFRvIII (Yang, et al., Cancer Lett. 2017 Sep. 10; 403: 224-230).

Bi- and Tri-Specific Natural Killer (NK)-Cell Engagers

In some embodiments, the compound provided herein is administered with a bi-specific NK-cell engager (BiKE) or a tri-specific NK-cell engager (TriKE) (e.g., not having an Fc) or bi-specific antibody (e.g., having an Fc) against an NK cell activating receptor, e.g., CD16A, C-type lectin receptors (CD94/NKG2C, NKG2D, NKG2E/H and NKG2F), natural cytotoxicity receptors (NKp30, NKp44 and NKp46), killer cell C-type lectin-like receptor (NKp65, NKp80), Fc receptor FcγR (which mediates antibody-dependent cell cytotoxicity), SLAM family receptors (e.g., 2B4, SLAM6 and SLAM7), killer cell immunoglobulin-like receptors (KIR) (KIR-2DS and KIR-3DS), DNAM-1 and CD137 (41BB). Illustrative anti-CD16 bi-specific antibodies, BiKEs or TriKEs that can be co-administered include AFM26 (BCMA/CD16A) and AFM-13 (CD16/CD30). As appropriate, the anti-CD16 binding bi-specific molecules may or may not have an Fc. Illustrative bi-specific NK-cell engagers that can be co-administered target CD16 and one or more tumor-associated antigens as described herein, including, e.g., CD19, CD20, CD22, CD30, CD33, CD123, EGFR, EpCAM, ganglioside GD2, HER2/neu, HLA Class II and FOLR1. BiKEs and TriKEs are described, e.g., in Felices, et al., *Methods Mol Biol.* (2016) 1441:333-346; Fang, et al., Semin Immunol. (2017) 31:37-54.

MCL1 Apoptosis Regulator, BCL2 Family Member (MCL1) Inhibitors

In some embodiments, the compound provided herein is administered with an inhibitor of MCL1 apoptosis regulator, BCL2 family member (MCL1, TM; EAT; MCL1L; MCL1S; Mel-1; BCL2L3; MCL1-ES; bcl2-L-3; mcl1/EAT; NCBI Gene ID: 4170). Examples of MCL1 inhibitors include tapotoclax (AMG-176), AMG-397, S-64315, AZD-5991, 483-LM, A-1210477, UMI-77, JKY-5-037, PRT-1419, GS-9716, and those described in WO2018183418, WO2016033486, and WO2017147410.

SHP2 Inhibitors

In some embodiments, compound provided herein is administered with an inhibitor of protein tyrosine phosphatase non-receptor type 11 (PTPN11; BPTP3, CFC, JMML, METCDS, NS1, PTP-1D, PTP2C, SH-PTP2, SH-PTP3, SHP2; NCBI Gene ID: 5781). Examples of SHP2 inhibitors include TNO155 (SHP-099), RMC-4550, JAB-3068, RMC-4630, and those described in WO2018172984 and WO2017211303.

Hematopoietic Progenitor Kinase 1 (HPK1) Inhibitors and Degraders

In some embodiments, the compound provided herein is administered with an inhibitor of mitogen-activated protein kinase kinase kinase kinase 1 (MAP4K1, HPK1; NCBI Gene ID: 11184). Examples of Hematopoietic Progenitor Kinase 1 (HPK1) inhibitors include without limitation, those described in WO2020092621, WO2018183956, WO2018183964, WO2018167147, WO2018049152, WO2020092528, WO2016205942, WO2016090300, WO2018049214, WO2018049200, WO2018049191, WO2018102366, WO2018049152, and WO2016090300.

Apoptosis Signal-Regulating Kinase (ASK) Inhibitors

In some embodiments, the compound provided herein is administered with an ASK inhibitor, e.g., mitogen-activated protein kinase kinase kinase 5 (MAP3K5; ASK1, MAPKKK5, MEKK5; NCBI Gene ID: 4217). Examples of ASK1 inhibitors include those described in WO2011008709 (Gilead Sciences) and WO 2013112741 (Gilead Sciences).

Bruton Tyrosine Kinase (BTK) Inhibitors

In some embodiments, the compound provided herein is administered with an inhibitor of Bruton tyrosine kinase (BTK, AGMX1, AT, ATK, BPK, IGHD3, IMD1, PSCTK1, XLA; NCBI Gene ID: 695). Examples of BTK inhibitors include (S)-6-amino-9-(1-(but-2-ynoyl)pyrrolidin-3-yl)-7-(4-phenoxyphenyl)-7H-purin-8(9H)-one, acalabrutinib (ACP-196), zanubrutinib (BGB-3111), CB988, HM71224, ibrutinib, M-2951 (evobrutinib), M7583, tirabrutinib (ONO-4059), PRN-1008, spebrutinib (CC-292), TAK-020, vecabrutinib, ARQ-531, SHR-1459, DTRMWXHS-12, PCI-32765, and TAS-5315.

Cyclin-Dependent Kinase (CDK) Inhibitors

In some embodiments, the compound provided herein is administered with an inhibitor of cyclin dependent kinase 1 (CDK1, CDC2; CDC28A; P34CDC2; NCBI Gene ID: 983); cyclin dependent kinase 2 (CDK2, CDKN2; p33(CDK2); NCBI Gene ID: 1017); cyclin dependent kinase 3 (CDK3; NCBI Gene ID: 1018); cyclin dependent kinase 4 (CDK4, CMM3; PSK-J3; NCBI Gene ID: 1019); cyclin dependent kinase 6 (CDK6, MCPH12; PLSTIRE; NCBI Gene ID: 1021); cyclin dependent kinase 7 (CDK7, CAK; CAK1; HCAK; MO15; STK1; CDKN7; p39MO15; NCBI Gene ID: 1022), or cyclin dependent kinase 9 (CDK9, TAK; C-2k; CTK1; CDC2L4; PITALRE; NCBI Gene ID: 1025). Inhibitors of CDK 1, 2, 3, 4, 6, 7 and/or 9, include abemaciclib, alvocidib (HMR-1275, flavopiridol), AT-7519, dinaciclib, ibrance, FLX-925, LEE001, palbociclib, samuraciclib, ribociclib, rigosertib, selinexor, UCN-01, SY1365, CT-7001, SY-1365, G1T38, milciclib, trilaciclib, simurosertib hydrate (TAK931), and TG-02.

Discoidin Domain Receptor (DDR) Inhibitors

In some embodiments, the compound provided herein is combined with an inhibitor of discoidin domain receptor tyrosine kinase 1 (DDR1, CAK, CD167, DDR, EDDR1, HGK2, MCK10, NEP, NTRK4, PTK3, PTK3A, RTK6, TRKE; NCBI Gene ID: 780); and/or discoidin domain receptor tyrosine kinase 2 (DDR2, MIG20a, NTRKR3, TKT, TYRO10, WRCN; NCBI Gene ID: 4921). Examples of DDR inhibitors include dasatinib and those disclosed in WO2014/047624 (Gilead Sciences), US 2009-0142345 (Takeda Pharmaceutical), US 2011-0287011 (Oncomed Pharmaceuticals), WO 2013/027802 (Chugai Pharmaceutical), and WO2013/034933 (Imperial Innovations).

Targeted E3 Ligase Ligand Conjugates

In some embodiments, the compound provided herein is administered with a targeted E3 ligase ligand conjugate. Such conjugates have a target protein binding moiety and an E3 ligase binding moiety (e.g., an inhibitor of apoptosis protein (IAP) (e.g., XIAP, c-IAP1, c-IAP2, NIL-IAP, Bruce, and surviving) E3 ubiquitin ligase binding moiety, Von Hippel-Lindau E3 ubiquitin ligase (VHL) binding moiety, a cereblon E3 ubiquitin ligase binding moiety, mouse double minute 2 homolog (MDM2) E3 ubiquitin ligase binding moiety), and can be used to promote or increase the degradation of targeted proteins, e.g., via the ubiquitin pathway. In some embodiments, the targeted E3 ligase ligand conjugates comprise a targeting or binding moiety that targets or binds a protein described herein, and an E3 ligase ligand or binding moiety. In some embodiments, the targeted E3 ligase ligand conjugates comprise a targeting or binding moiety that targets or binds a protein selected from Cbl proto-oncogene B (CBLB; Cbl-b, Nbla00127, RNF56; NCBI Gene ID: 868) and hypoxia inducible factor 1 subunit alpha (HIF1A; NCBI Gene ID: 3091). In some embodiments, the targeted E3 ligase ligand conjugates comprise a kinase inhibitor (e.g., a small molecule kinase inhibitor, e.g., of BTK and an E3 ligase ligand or binding moiety. See, e.g., WO2018098280. In some embodiments, the targeted E3 ligase ligand conjugates comprise a binding moiety targeting or binding to Interleukin-1 (IL-1) Receptor-Associated Kinase-4 (IRAK-4); Rapidly Accelerated Fibrosarcoma (RAF, such as c-RAF, A-RAF and/or B-RAF), c-Met/p38, or a BRD protein; and an E3 ligase ligand or binding moiety. See, e.g., WO2019099926, WO2018226542, WO2018119448, WO2018223909, WO2019079701. Additional targeted E3 ligase ligand conjugates that can be co-administered are described, e.g., in WO2018237026, WO2019084026, WO2019084030, WO2019067733, WO2019043217, WO2019043208, and WO2018144649.

Histone Deacetylase (HDAC) Inhibitors

In some embodiments, the compound provided herein is administered with an inhibitor of a histone deacetylase, e.g., histone deacetylase 9 (HDAC9, HD7, HD7b, HD9, HDAC, HDAC7, HDAC7B, HDAC9B, HDAC9FL, HDRP, MITR; Gene ID: 9734). Examples of HDAC inhibitors include abexinostat, ACY-241, AR-42, BEBT-908, belinostat, CKD-581, CS-055 (HBI-8000), CUDC-907 (fimepinostat), entinostat, givinostat, mocetinostat, panobinostat, pracinostat, quisinostat (JNJ-26481585), resminostat, ricolinostat, SHP-141, valproic acid (VAL-001), vorinostat, tinostamustine, remetinostat, and entinostat.

Indoleamine-Pyrrole-2,3-Dioxygenase (IDO1) Inhibitors

In some embodiments, the compound provided herein is administered with an inhibitor of indoleamine 2,3-dioxygenase 1 (IDO1; NCBI Gene ID: 3620). Examples of IDO1 inhibitors include BLV-0801, epacadostat, linrodostat (F-001287, BMS-986205), GBV-1012, GBV-1028, GDC-0919, indoximod, NKTR-218, NLG-919-based vaccine, PF-06840003, pyranonaphthoquinone derivatives (SN-35837), resminostat, SBLK-200802, and shIDO-ST, EOS-200271, KHK-2455, and LY-3381916.

Janus Kinase (JAK) Inhibitors

In some embodiments, the compound provided herein is administered with an inhibitor of Janus kinase 1 (JAK1, JAK1A, JAK1B, JTK3; NCBI Gene ID: 3716); Janus kinase 2 (JAK2, JTK10, THCYT3; NCBI Gene ID: 3717); and/or Janus kinase 3 (JAK3, JAK-3, JAK3_HUMAN, JAKL, L-JAK, LJAK; NCBI Gene ID: 3718). Examples of JAK inhibitors include AT9283, AZD1480, baricitinib, BMS-911543, fedratinib, filgotinib (GLPG0634), gandotinib (LY2784544), INCB039110 (itacitinib), lestaurtinib, momelotinib (CYT0387), ilginatinib maleate (NS-018), pacritinib (SB1518), peficitinib (ASP015K), ruxolitinib, tofacitinib (formerly tasocitinib), INCB052793, and XL019.

Lysyl Oxidase-Like Protein (LOXL) Inhibitors

In some embodiments, the compound provided herein is administered with an inhibitor of a LOXL protein, e.g., LOXL1 (NCBI Gene ID: 4016), LOXL2 (NCBI Gene ID: 4017), LOXL3 (NCBI Gene ID: 84695), LOXL4 (NCBI Gene ID: 84171), and/or LOX (NCBI Gene ID: 4015). Examples of LOXL2 inhibitors include the antibodies described in WO 2009017833 (Arresto Biosciences), WO 2009035791 (Arresto Biosciences), and WO 2011097513 (Gilead Biologics).

Matrix Metalloprotease (MMP) Inhibitors

In some embodiments, the compound provided herein is administered with an inhibitor of a matrix metallopeptidase (MMP), e.g., an inhibitor of MMP1 (NCBI Gene ID: 4312), MMP2 (NCBI Gene ID: 4313), MMP3 (NCBI Gene ID: 4314), MMP7 (NCBI Gene ID: 4316), MMP8 (NCBI Gene ID: 4317), MMP9 (NCBI Gene ID: 4318); MMP10 (NCBI Gene ID: 4319); MMP11 (NCBI Gene ID: 4320); MMP12 (NCBI Gene ID: 4321), MMP13 (NCBI Gene ID: 4322), MMP14 (NCBI Gene ID: 4323), MMP15 (NCBI Gene ID: 4324), MMP16 (NCBI Gene ID: 4325), MMP17 (NCBI Gene ID: 4326), MMP19 (NCBI Gene ID: 4327), MMP20 (NCBI Gene ID: 9313), MMP21 (NCBI Gene ID: 118856), MMP24 (NCBI Gene ID: 10893), MMP25 (NCBI Gene ID: 64386), MMP26 (NCBI Gene ID: 56547), MMP27 (NCBI Gene ID: 64066) and/or MMP28 (NCBI Gene ID: 79148). Examples of MMP9 inhibitors include marimastat (BB-2516), cipemastat (Ro 32-3555), GS-5745 (andecaliximab), and those described in WO 2012027721 (Gilead Biologics).

RAS and RAS Pathway Inhibitors

In some embodiments, the compound provided herein is administered with an inhibitor of KRAS proto-oncogene, GTPase (KRAS; a.k.a., NS; NS3; CFC2; RALD; K-Ras; KRAS1; KRAS2; RASK2; KI-RAS; C-K-RAS; K-RAS2A; K-RAS2B; K-RAS4A; K-RAS4B; c-Ki-ras2; NCBI Gene ID: 3845); NRAS proto-oncogene, GTPase (NRAS; a.k.a., NS6; CMNS; NCMS; ALPS4; N-ras; NRAS1; NCBI Gene ID: 4893) or HRAS proto-oncogene, GTPase (HRAS; a.k.a., CTLO; KRAS; HAMSV; HRAS1; KRAS2; RASH1; RASK2; Ki-Ras; p2lras; C-H-RAS; c-K-ras; H-RASIDX; c-Ki-ras; C-BAS/HAS; C-HA-RAS1; NCBI Gene ID: 3265). The Ras inhibitors can inhibit Ras at either the polynucleotide (e.g., transcriptional inhibitor) or polypeptide (e.g., GTPase enzyme inhibitor) level. In some embodiments, the inhibitors target one or more proteins in the Ras pathway, e.g., inhibit one or more of EGFR, Ras, Raf (A-Raf, B-Raf, C-Raf), MEK (MEK1, MEK2), ERK, PI3K, AKT and mTOR. Illustrative K-Ras inhibitors that can be co-administered include sotorasib (AMG-510), COTI-219, ARS-3248, WDB-178, BI-3406, BI-1701963, SML-8-73-1 (G12C), adagrasib (MRTX-849), ARS-1620 (G12C), SML-8-73-1 (G12C), Compound 3144 (G12D), Kobe0065/2602 (Ras GTP), RT11, MRTX-849 (G12C) and K-Ras(G12D)-selective inhibitory peptides, including KRpep-2and KRpep-2d. Illustrative KRAS mRNA inhibitors include anti-KRAS U1 adaptor, AZD-4785, siG12D-LODER™, and siG12D exosomes. Illustrative MEK inhibitors that can be co-administered include binimetinib, cobimetinib, PD-0325901, pimasertib, RG-7304, selumetinib, trametinib, and those described below and herein. Illustrative Raf dimer inhibitors that can be co-administered include BGB-283, HM-95573, LXH-254, LY-3009120, RG7304 and TAK-580. Illustrative ERK inhibitors that can be co-administered include LTT-462, LY-3214996, MK-8353, ravoxertinib and ulixertinib. Illustrative Ras GTPase inhibitors that can be co-administered include rigosertib. Illustrative PI3K inhibitors that can be co-administered include idelalisib (Zydelig®), alpelisib, buparlisib, pictilisib, inavolisib (RG6114), ASN-003. Illustrative AKT inhibitors that can be co-administered include capivasertib and GSK2141795. Illustrative PI3K/mTOR inhibitors that can be co-administered include dactolisib, omipalisib, voxtalisib. gedatolisib, GSK2141795, GSK-2126458, inavolisib (RG6114), sapanisertib, ME-344, sirolimus (oral nano-amorphous formulation, cancer), racemetyrosine (TYME-88 (mTOR/cytochrome P450 3A4)), temsirolimus (TORISEL®, CCI-779), CC-115, onatasertib (CC-223), SF-1126, and PQR-309 (bimiralisib). In some embodiments, Ras-driven cancers (e.g., NSCLC) having CDKN2A mutations can be inhibited by co-administration of the MEK inhibitor selumetinib and the CDK4/6 inhibitor palbociclib. See, e.g., Zhou, et al., *Cancer Lett.* 2017 Nov. 1; 408:130-137. Also, K-RAS and mutant N-RAS can be reduced by the irreversible ERBB1/2/4 inhibitor neratinib. See, e.g., Booth, et al., *Cancer Biol Ther.* 2018 Feb. 1; 19(2):132-137.

Mitogen-Activated Protein Kinase (MEK) Inhibitors

In some embodiments, the compound provided herein is administered with an inhibitor of mitogen-activated protein kinase kinase 7 (MAP2K7, JNKK2, MAPKK7, MEK, MEK 7, MKK7, PRKMK7, SAPKK-4, SAPKK4; NCBI Gene ID: 5609). Examples of MEK inhibitors include antroquinonol, binimetinib, cobimetinib (GDC-0973, XL-518), MT-144, selumetinib (AZD6244), sorafenib, trametinib (GSK1120212), uprosertib+trametinib, PD-0325901, pimasertib, LTT462, AS703988, CC-90003, and refametinib.

Phosphatidylinositol 3-Kinase (PI3K) Inhibitors

In some embodiments, compounds provided herein is administered with an inhibitor of a phosphatidylinositol-4, 5-bisphosphate 3-kinase catalytic subunit, e.g., phosphatidylinositol-4,5-bisphosphate 3-kinase catalytic subunit alpha (PIK3CA, CLAPO, CLOVE, CWS5, MCAP, MCM, MCMTC, PI3K, PI3K-alpha, p110-alpha; NCBI Gene ID: 5290); phosphatidylinositol-4,5-bisphosphate 3-kinase catalytic subunit beta (PIK3CB, P110BETA, PI3K, PI3KBETA, PIK3C1; NCBI Gene ID: 5291); phosphatidylinositol-4,5-bisphosphate 3-kinase catalytic subunit gamma (PIK3CG, PI3CG, PI3K, PI3Kgamma, PIK3, p110gamma, p120-PI3K; Gene ID: 5494); and/or phosphatidylinositol-4,5-bisphosphate 3-kinase catalytic subunit delta (PIK3CD, APDS, IMD14, P110DELTA, PI3K, p110D, NCBI Gene ID: 5293). In some embodiments, the PI3K inhibitor is a pan-PI3K inhibitor. Examples of PI3K inhibitors include ACP-319, AEZA-129, AMG-319, AS252424, AZD8186, BAY 10824391, BEZ235, buparlisib (BKM120), BYL719 (alpelisib), CH5132799, copanlisib (BAY 80-6946), duvelisib, GDC-0032, GDC-0077, GDC-0941, GDC-0980, GSK2636771, GSK2269557, idelalisib (Zydelig®), INCB50465, IPI-145, IPI-443, IPI-549, KAR4141, LY294002, LY3023414, MLN1117, OXY111A, PA799, PX-866, RG7604, rigosertib, RP5090, RP6530, SRX3177, taselisib, TG100115, TGR-1202 (umbralisib), TGX221, WX-037, X-339, X-414, XL147 (SAR245408), XL499, XL756, wortmannin, ZSTK474, and the compounds described in WO2005113556 (ICOS), WO 2013/052699 (Gilead Calistoga), WO2013116562 (Gilead Calistoga), WO2014100765 (Gilead Calistoga), WO2014100767 (Gilead Calistoga), and WO2014201409 (Gilead Sciences).

Spleen Tyrosine Kinase (SYK) Inhibitors

In some embodiments, the compound provided herein is administered with an inhibitor of spleen associated tyrosine kinase (SYK, p72-Syk, NCBI Gene ID: 6850). Examples of SYK inhibitors include 6-(1H-indazol-6-yl)-N-(4-morpholinophenyl)imidazo[1,2-a]pyrazin-8-amine, BAY-61-3606, cerdulatinib (PRT-062607), entospletinib, fostamatinib (R788), HMPL-523, NVP-QAB 205 AA, R112, R343, tamatinib (R406), gusacitinib (ASN-002), and those described in U.S. Pat. No. 8,450,321 (Gilead Connecticut) and US20150175616.

Toll-Like Receptor (TLR) Agonists

In some embodiments, compound provided herein is administered with an agonist of a toll-like receptor (TLR), e.g., an agonist of TLR1 (NCBI Gene ID: 7096), TLR2 (NCBI Gene ID: 7097), TLR3 (NCBI Gene ID: 7098), TLR4 (NCBI Gene ID: 7099), TLR5 (NCBI Gene ID: 7100), TLR6 (NCBI Gene ID: 10333), TLR7 (NCBI Gene ID: 51284), TLR8 (NCBI Gene ID: 51311), TLR9 (NCBI Gene ID: 54106), and/or TLR10 (NCBI Gene ID: 81793). Example TLR7 agonists that can be co-administered include DS-0509, GS-9620 (vesatolimod), vesatolimod analogs, LHC-165, TMX-101 (imiquimod), GSK-2245035, resiquimod, DSR-6434, DSP-3025, IMO-4200, MCT-465, MEDI-9197, 3M-051, SB-9922, 3M-052, Limtop, TMX-30X, TMX-202, RG-7863, RG-7795, BDB-001, DSP-0509, and the compounds disclosed in US20100143301 (Gilead Sciences), US20110098248 (Gilead Sciences), and US20090047249 (Gilead Sciences), US20140045849 (Janssen), US20140073642 (Janssen), WO2014056953 (Janssen), WO2014076221 (Janssen), WO2014128189 (Janssen), US20140350031 (Janssen), WO2014023813 (Janssen), US20080234251 (Array Biopharma), US20080306050 (Array Biopharma), US20100029585 (Ventirx Pharma), US20110092485 (Ventirx Pharma), US20110118235 (Ventirx Pharma), US20120082658 (Ventirx Pharma), US20120219615 (Ventirx Pharma), US20140066432 (Ventirx Pharma), US20140088085 (Ventirx Pharma), US20140275167 (Novira Therapeutics), and US20130251673 (Novira Therapeutics). An TLR7/TLR8 agonist that can be co-administered is NKTR-262. Example TLR8 agonists that can be co-administered include E-6887, IMO-4200, IMO-8400, IMO-9200, MCT-465, MEDI-9197, motolimod, resiquimod, GS-9688, VTX-1463, VTX-763, 3M-051, 3M-052, and the compounds disclosed in US20140045849 (Janssen), US20140073642 (Janssen), WO2014/056953 (Janssen), WO2014/076221 (Janssen), WO2014/128189 (Janssen), US20140350031 (Janssen), WO2014/023813 (Janssen), US20080234251 (Array Biopharma), US20080306050 (Array Biopharma), US20100029585 (Ventirx Pharma), US20110092485 (Ventirx Pharma), US20110118235 (Ventirx Pharma), US20120082658 (Ventirx Pharma), US20120219615 (Ventirx Pharma), US20140066432 (Ventirx Pharma), US20140088085 (Ventirx Pharma), US20140275167 (Novira Therapeutics), and US20130251673 (Novira Therapeutics). Example TLR9 agonists that can be co-administered include AST-008, CMP-001, IMO-2055, IMO-2125, litenimod, MGN-1601, BB-001, BB-006, IMO-3100, IMO-8400, IR-103, IMO-9200, agatolimod, DIMS-9054, DV-1079, DV-1179, AZD-1419, leftolimod (MGN-1703), CYT-003, CYT-003-QbG10 and PUL-042. Examples of TLR3 agonist include rintatolimod, poly-ICLC, RIBOXXON®, Apoxxim, RIBOXXIM®, IPH-33, MCT-465, MCT-475, and ND-1.1.

Tyrosine-Kinase Inhibitors (TKIs)

In some embodiments, the compound provided herein is administered with a tyrosine kinase inhibitor (TKI). TKIs may target epidermal growth factor receptors (EGFRs) and receptors for fibroblast growth factor (FGF), platelet-derived growth factor (PDGF), and vascular endothelial growth factor (VEGF). Examples of TKIs include without limitation afatinib, ARQ-087 (derazantinib), asp5878, AZD3759, AZD4547, bosutinib, brigatinib, cabozantinib, cediranib, crenolanib, dacomitinib, dasatinib, dovitinib, E-6201, erdafitinib, erlotinib, gefitinib, gilteritinib (ASP-2215), FP-1039, HM61713, icotinib, imatinib, KX2-391 (Src), lapatinib, lestaurtinib, lenvatinib, midostaurin, nintedanib, ODM-203, osimertinib (AZD-9291), ponatinib, poziotinib, quizartinib, radotinib, rociletinib, sulfatinib (HMPL-012), sunitinib, famitinib L-malate, (MAC-4), tivoanib, TH-4000, and MEDI-575 (anti-PDGFR antibody). Exemplary EGFR targeting agents include neratinib, tucatinib (ONT-380), tesevatinib, mobocertinib (TAK-788), DZD-9008, varlitinib, abivertinib (ACEA-0010), EGF816 (nazartinib), olmutinib (BI-1482694), osimertinib (AZD-9291), AMG-596 (EGFRvIII/CD3), lifirafenib (BGB-283), vectibix, lazertinib (LECLAZA®), and compounds disclosed in Booth, et al., Cancer Biol Ther. 2018 Feb. 1; 19(2):132-137. Antibodies targeting EGFR include without limitation modotuximab, cetuximab sarotalocan (RM-1929), seribantumab, necitumumab, depatuxizumab mafodotin (ABT-414), tomuzotuximab, depatuxizumab (ABT-806), and cetuximab.

Chemotherapeutic Agents

In some embodiments, the compound provided herein is administered with a chemotherapeutic agent or anti-neoplastic agent.

As used herein, the term "chemotherapeutic agent" or "chemotherapeutic" (or "chemotherapy" in the case of treatment with a chemotherapeutic agent) is meant to encompass any non-proteinaceous (e.g., non-peptidic) chemical compound useful in the treatment of cancer. Examples of chemotherapeutic agents include but not limited to: alkylating agents such as thiotepa and cyclophosphamide (CYTOXAN®); alkyl sulfonates such as busulfan, improsulfan, and piposulfan; aziridines such as benzodepa, carboquone, meturedepa, and uredepa; ethylenimines and methylamelamines including altretamine, triethylenemelamine, triethylenephosphoramide, triethylenethiophosphoramide, and trimemylolomelamine; acetogenins, e.g., bullatacin and bullatacinone; a camptothecin, including synthetic analog topotecan; bryostatin, callystatin; CC-1065, including its adozelesin, carzelesin, and bizelesin synthetic analogs; cryptophycins, particularly cryptophycin 1 and cryptophycin 8; dolastatin; duocarmycin, including the synthetic analogs KW-2189 and CBI-TMI; eleutherobin; 5-azacytidine; pancratistatin; a sarcodictyin; spongistatin; nitrogen mustards such as chlorambucil, chlornaphazine, cyclophosphamide, glufosfamide, evofosfamide, bendamustine, estramustine, ifosfamide, mechlorethamine, mechlorethamine oxide hydrochloride, melphalan, novembichin, phenesterine, prednimustine, trofosfamide, and uracil mustard; nitrosoureas such as carmustine, chlorozotocin, foremustine, lomustine, nimustine, and ranimustine; antibiotics such as the enediyne antibiotics (e.g., calicheamicin, especially calicheamicin gammaII and calicheamicin phiI1), dynemicin including dynemicin A, bisphosphonates such as clodronate, an esperamicin, neocarzinostatin chromophore and related chromoprotein enediyne antibiotic chromomophores, aclacinomycins, actinomycin, authramycin, azaserine, bleomycins, cactinomycin, carabicin, carrninomycin, carzinophilin, chromomycins, dactinomycin, daunorubicin, detorubicin, 6-diazo-5-oxo-L-norleucine, doxorubicin (including morpholino-doxorubicin, cyanomorpholino-doxorubicin, 2-pyrrolino-doxorubicin, and deoxydoxorubicin), epirubicin, esorubicin, idarubicin, marcellomycin, mitomycins such as mitomycin C, mycophenolic acid, nogalamycin, olivomycins, peplomycin, porfiromycin, puromycin, quelamycin, rodorubicin, streptonigrin, streptozocin, tubercidin, ubenimex, zinostatin, and zorubicin; anti-metabolites such as methotrexate and 5-fluorouracil (5-FU); folic acid analogs such as demopterin, methotrexate, pteropterin, and trimetrexate; purine analogs such as cladribine, pentostatin, fludarabine, 6-mercaptopurine, thiamiprine, and thioguanine; pyrimidine analogs such as ancitabine, azacitidine, 6-azauridine, carmofur, cytarabine, dideoxyuridine, doxifluridine, enocitabine, and floxuridine; androgens such as calusterone, dromostanolone propionate, epitiostanol, mepitiostane, and testolactone; anti-adrenals such as aminoglutethimide, mitotane, and trilostane; folic acid replinishers such as frolinic acid; radiotherapeutic agents such as Radium-223; trichothecenes, especially T-2 toxin, verracurin A, roridin A, and anguidine; taxoids such as paclitaxel (TAXOL®), abraxane, docetaxel (TAXOTERE®), cabazitaxel, BIND-014, tesetaxel; sabizabulin (Veru-111); platinum analogs such as cisplatin and carboplatin, NC-6004 nanoplatin; aceglatone; aldophosphamide glycoside; aminolevulinic acid; eniluracil; amsacrine; hestrabucil; bisantrene; edatraxate; defofamine; demecolcine; diaziquone; elformthine; elliptinium acetate; an epothilone; etoglucid; gallium nitrate; hydroxyurea; lentinan; leucovorin; lonidamine; maytansinoids such as maytansine and ansamitocins; mitoguazone; mitoxantrone; mopidamol; nitracrine; pentostatin; phenamet; pirarubicin; losoxantrone; fluoropyrimidine; folinic acid; podophyllinic acid; 2-ethylhydrazide; procarbazine; polysaccharide-K (PSK); razoxane; rhizoxin; sizofiran; spirogermanium; tenuazonic acid; trabectedin, triaziquone; 2,2',2"-trichlorotriemylamine; urethane; vindesine; dacarbazine; mannomustine; mitobronitol; mitolactol; pipobroman; gacytosine; arabinoside ("Ara-C"); cyclophosphamide; thiopeta; chlorambucil; gemcitabine (GEMZAR®); 6-thioguanine; mercaptopurine; methotrexate; vinblastine; platinum; etoposide (VP-16); ifosfamide; mitroxantrone; vancristine; vinorelbine (NAVELBINE®); novantrone; teniposide; edatrexate; daunomycin; aminopterin; xeoloda; ibandronate; CPT-11; topoisomerase inhibitor RFS 2000; difluoromethylornithine (DFMO); retinoids such as retinoic acid; capecitabine; NUC-1031; FOLFOX (folinic acid, 5-fluorouracil, oxaliplatin); FOLFIRI (folinic acid, 5-fluorouracil, irinotecan); FOLFOXIRI (folinic acid, 5-fluorouracil, oxaliplatin, irinotecan), FOLFIRINOX (folinic acid, 5-fluorouracil, irinotecan, oxaliplatin), and pharmaceutically acceptable salts, acids, or derivatives of any of the above. Such agents can be conjugated onto an antibody or any targeting agent described herein to create an antibody-drug conjugate (ADC) or targeted drug conjugate.

Anti-Hormonal Agents

Also included in the definition of "chemotherapeutic agent" are anti-hormonal agents such as anti-estrogens and selective estrogen receptor modulators (SERMs), inhibitors of the enzyme aromatase, anti-androgens, and pharmaceutically acceptable salts, acids or derivatives of any of the above that act to regulate or inhibit hormone action on tumors.

Examples of anti-estrogens and SERMs include tamoxifen (including NOLVADEX™), raloxifene, droloxifene, 4-hydroxytamoxifen, trioxifene, keoxifene, LY117018, onapristone, and toremifene (FARESTON®).

Inhibitors of the enzyme aromatase regulate estrogen production in the adrenal glands. Examples include 4(5)-imidazoles, aminoglutethimide, megestrol acetate (MEGACE®), exemestane, formestane, fadrozole, vorozole (RIVISOR®), letrozole (FEMARA®), and anastrozole (ARIMIDEX®).

Examples of anti-androgens include apalutamide, abiraterone, enzalutamide, flutamide, galeterone, nilutamide, bicalutamide, leuprolide, goserelin, ODM-201, APC-100, ODM-204, enobosarm (GTX-024), darolutamide, and IONIS-AR-2.5Rx (antisense).

An example progesterone receptor antagonist includes onapristone. Additional progesterone targeting agents include TRI-CYCLEN LO (norethindrone+ethinyl estradiol), norgestimate+ethinylestradiol (Tri-Cyclen) and levonorgestrel.

Anti-Angiogenic Agents

In some embodiments, the compound provided herein is administered with an anti-angiogenic agent. Anti-angiogenic agents that can be co-administered include retinoid acid and derivatives thereof, 2-methoxyestradiol, ANGIOSTATIN®, ENDOSTATIN®, regorafenib, necuparanib, suramin, squalamine, tissue inhibitor of metalloproteinase-1, tissue inhibitor of metalloproteinase-2, plasminogen activator inhibitor-1, plasminogen activator inbibitor-2, cartilage-derived inhibitor, paclitaxel (nab-paclitaxel), platelet factor 4, protamine sulphate (clupeine), sulphated chitin derivatives (prepared from queen crab shells), sulphated polysaccharide peptidoglycan complex (sp-pg), staurosporine, modulators of matrix metabolism including proline analogs such as 1-azetidine-2-carboxylic acid (LACA), cishydroxyproline, d,I-3,4-dehydroproline, thiaproline, α,α'-dipyridyl, beta-aminopropionitrile fumarate, 4-propyl-5-(4-pyridinyl)-2 (3h)-oxazolone, methotrexate, mitoxantrone, heparin, interferons, 2 macroglobulin-serum, chicken inhibitor of metalloproteinase-3 (ChIMP-3), chymostatin, beta-cyclodextrin tetradecasulfate, eponemycin, fumagillin, gold sodium thiomalate, d-penicillamine, beta-1-anticollagenase-serum, alpha-2-antiplasmin, bisantrene, lobenzarit disodium, n-2-carboxyphenyl-4-chloroanthronilic acid disodium or "CCA", thalidomide, angiostatic steroid, carboxy aminoimidazole, metalloproteinase inhibitors such as BB-94, inhibitors of S100A9 such as tasquinimod. Other anti-angiogenesis agents include antibodies, preferably monoclonal antibodies against these angiogenic growth factors: beta-FGF, alpha-FGF, FGF-5, VEGF isoforms, VEGF-C, HGF/SF, and Ang-1/Ang-2. Examples for anti-VEGFA antibodies that can be co-administered include bevacizumab, vanucizumab, faricimab, dilpacimab (ABT-165; DLL4/VEGF), or navicixizumab (OMP-305B83; DLL4/VEGF).

Anti-Fibrotic Agents

In some embodiments, the compound provided herein is administered with an anti-fibrotic agent. Anti-fibrotic agents that can be co-administered include the compounds such as beta-aminoproprionitrile (BAPN), as well as the compounds disclosed in U.S. Pat. No. 4,965,288 relating to inhibitors of lysyl oxidase and their use in the treatment of diseases and conditions associated with the abnormal deposition of collagen and U.S. Pat. No. 4,997,854 relating to compounds which inhibit LOX for the treatment of various pathological fibrotic states, which are herein incorporated by reference. Further exemplary inhibitors are described in U.S. Pat. No. 4,943,593 relating to compounds such as 2-isobutyl-3-fluoro-, chloro-, or bromo-allylamine, U.S. Pat. Nos. 5,021,456, 5,059,714, 5,120,764, 5,182,297, 5,252,608 relating to 2-(1-naphthyloxymemyl)-3-fluoroallylamine, and US 20040248871, which are herein incorporated by reference.

Exemplary anti-fibrotic agents also include the primary amines reacting with the carbonyl group of the active site of the lysyl oxidases, and more particularly those which produce, after binding with the carbonyl, a product stabilized by resonance, such as the following primary amines: emylenemamine, hydrazine, phenylhydrazine, and their derivatives; semicarbazide and urea derivatives; aminonitriles such as BAPN or 2-nitroethylamine; unsaturated or saturated haloamines such as 2-bromo-ethylamine, 2-chloroethylamine, 2-trifluoroethylamine, 3-bromopropylamine, and p-halobenzylamines; and selenohomocysteine lactone.

Other anti-fibrotic agents are copper chelating agents penetrating or not penetrating the cells. Exemplary compounds include indirect inhibitors which block the aldehyde derivatives originating from the oxidative deamination of the lysyl and hydroxylysyl residues by the lysyl oxidases. Examples include the thiolamines, particularly D-penicillamine, and its analogs such as 2-amino-5-mercapto-5-methylhexanoic acid, D-2-amino-3-methyl-3-((2-acetamidoethyl)dithio)butanoic acid, p-2-amino-3-methyl-3-((2-aminoethyl)dithio)butanoic acid, sodium-4-((p-1-dimethyl-2-amino-2-carboxyethyl)dithio)butane sulphurate, 2-acetamidoethyl-2-acetamidoethanethiol sulphanate, and sodium-4-mercaptobutanesulphinate trihydrate.

Anti-Inflammatory Agents

In some embodiments, the compound provided herein is administered with an anti-inflammatory agent. Example anti-inflammatory agents include without limitation inhibitors of one or more of arginase (ARG1 (NCBI Gene ID: 383), ARG2 (NCBI Gene ID: 384)), carbonic anhydrase (CA1 (NCBI Gene ID: 759), CA2 (NCBI Gene ID: 760), CA3 (NCBI Gene ID: 761), CA4 (NCBI Gene ID: 762), CA5A (NCBI Gene ID: 763), CA5B (NCBI Gene ID: 11238), CA6 (NCBI Gene ID: 765), CA7 (NCBI Gene ID: 766), CA8 (NCBI Gene ID: 767), CA9 (NCBI Gene ID: 768), CA10 (NCBI Gene ID: 56934), CA11 (NCBI Gene ID: 770), CA12 (NCBI Gene ID: 771), CA13 (NCBI Gene ID: 377677), CA14 (NCBI Gene ID: 23632)), prostaglandin-endoperoxide synthase 1 (PTGS1, COX-1; NCBI Gene ID: 5742), prostaglandin-endoperoxide synthase 2 (PTGS2, COX-2; NCBI Gene ID: 5743), secreted phospholipase A2, prostaglandin E synthase (PTGES, PGES; Gene ID: 9536), arachidonate 5-lipoxygenase (ALOX5, 5-LOX; NCBI Gene ID: 240), soluble epoxide hydrolase 2 (EPHX2, SEH; NCBI Gene ID: 2053) and/or mitogen-activated protein kinase kinase kinase 8 (MAP3K8, TPL2; NCBI Gene ID: 1326). In some embodiments, the inhibitor is a dual inhibitor, e.g., a dual inhibitor of COX-2/COX-1, COX-2/SEH, COX-2/CA, COX-2/5-LOX.

Examples of inhibitors of prostaglandin-endoperoxide synthase 1 (PTGS1, COX-1; NCBI Gene ID: 5742) that can be co-administered include mofezolac, GLY-230, and TRK-700.

Examples of inhibitors of prostaglandin-endoperoxide synthase 2 (PTGS2, COX-2; NCBI Gene ID: 5743) that can be co-administered include diclofenac, meloxicam, parecoxib, etoricoxib, AP-101, celecoxib, AXS-06, diclofenac potassium, DRGT-46, AAT-076, meisuoshuli, lumiracoxib, meloxicam, valdecoxib, zaltoprofen, nimesulide, anitrazafen, apricoxib, cimicoxib, deracoxib, flumizole, firocoxib, mavacoxib, NS-398, pamicogrel, parecoxib, robenacoxib, rofecoxib, rutecarpine, tilmacoxib, and zaltoprofen. Examples of dual COX1/COX2 inhibitors that can be co-administered include HP-5000, lornoxicam, ketorolac tromethamine, bromfenac sodium, ATB-346, HP-5000. Examples of dual COX-2/carbonic anhydrase (CA) inhibitors that can be co-administered include polmacoxib and imrecoxib.

Examples of inhibitors of secreted phospholipase A2, prostaglandin E synthase (PTGES, PGES; Gene ID: 9536) that can be co-administered include LY3023703, GRC 27864, and compounds described in WO2015158204, WO2013024898, WO2006063466, WO2007059610, WO2007124589, WO2010100249, WO2010034796, WO2010034797, WO2012022793, WO2012076673, WO2012076672, WO2010034798, WO2010034799, WO2012022792, WO2009103778, WO2011048004, WO2012087771, WO2012161965, WO2013118071, WO2013072825, WO2014167444, WO2009138376, WO2011023812, WO2012110860, WO2013153535, WO2009130242, WO2009146696, WO2013186692, WO2015059618, WO2016069376, WO2016069374, WO2009117985, WO2009064250, WO2009064251, WO2009082347, WO2009117987, and WO2008071173. Metformin has further been found to repress the COX2/PGE2/STAT3 axis, and can be co-administered. See, e.g., Tong, et al., *Cancer Lett.* (2017) 389:23-32; and Liu, et al., Oncotarget. (2016) 7(19):28235-46.

Examples of inhibitors of carbonic anhydrase (e.g., one or more of CA1 (NCBI Gene ID: 759), CA2 (NCBI Gene ID: 760), CA3 (NCBI Gene ID: 761), CA4 (NCBI Gene ID: 762), CA5A (NCBI Gene ID: 763), CA5B (NCBI Gene ID: 11238), CA6 (NCBI Gene ID: 765), CA7 (NCBI Gene ID: 766), CA8 (NCBI Gene ID: 767), CA9 (NCBI Gene ID: 768), CA10 (NCBI Gene ID: 56934), CA11 (NCBI Gene ID: 770), CA12 (NCBI Gene ID: 771), CA13 (NCBI Gene ID: 377677), CA14 (NCBI Gene ID: 23632)) that can be co-administered include acetazolamide, methazolamide, dorzolamide, zonisamide, brinzolamide and dichlorphenamide. A dual COX-2/CA1/CA2 inhibitor that can be co-administered includes CG100649.

Examples of inhibitors of arachidonate 5-lipoxygenase (ALOX5, 5-LOX; NCBI Gene ID: 240) that can be co-administered include meclofenamate sodium, zileuton.

Examples of inhibitors of soluble epoxide hydrolase 2 (EPHX2, SEH; NCBI Gene ID: 2053) that can be co-administered include compounds described in WO2015148954. Dual inhibitors of COX-2/SEH that can be co-administered include compounds described in WO2012082647. Dual inhibitors of SEH and fatty acid amide hydrolase (FAAH; NCBI Gene ID: 2166) that can be co-administered include compounds described in WO2017160861.

Examples of inhibitors of mitogen-activated protein kinase kinase kinase 8 (MAP3K8, tumor progression loci-2, TPL2; NCBI Gene ID: 1326) that can be co-administered include GS-4875, GS-5290, BHM-078 and those described in WO2006124944, WO2006124692, WO2014064215, WO2018005435, Teli, et al., *J Enzyme Inhib Med Chem.* (2012) 27(4):558-70; Gangwall, et al., *Curr Top Med Chem.* (2013) 13(9):1015-35; Wu, et al., *Bioorg Med Chem Lett.* (2009) 19(13):3485-8; Kaila, et al., *Bioorg Med Chem.* (2007) 15(19):6425-42; and Hu, et al., *Bioorg Med Chem Lett.* (2011) 21(16):4758-61.

Tumor Oxygenation Agents

In some embodiments, the compound provided herein is administered with an agent that promotes or increases tumor oxygenation or reoxygenation, or prevents or reduces tumor hypoxia. Illustrative agents that can be co-administered include, e.g., Hypoxia inducible factor-1 alpha (HIF-1$\alpha$) inhibitors, such as PT-2977, PT-2385; VEGF inhibitors, such as bevasizumab, IMC-3C5, GNR-011, tanibirumab, LYN-00101, ABT-165; and/or an oxygen carrier protein (e.g., a heme nitric oxide and/or oxygen binding protein (HNOX)), such as OMX-302 and HNOX proteins described in WO2007137767, WO2007139791, WO2014107171, and WO2016149562.

Immunotherapeutic Agents

In some embodiments, the compound provided herein is administered with an immunotherapeutic agent. In some embodiments, the immunotherapeutic agent is an antibody. Example immunotherapeutic agents that can be co-administered include abagovomab, AB308, ABP-980, adecatumumab, afutuzumab, alemtuzumab, altumomab, amatuximab, anatumomab, arcitumomab, atezolizumab, bavituximab, bectumomab, bevacizumab, bivatuzumab, blinatumomab, brentuximab, camidanlumab, cantuzumab, catumaxomab, CC49, cetuximab, citatuzumab, cixutumumab, clivatuzumab, conatumumab, dacetuzumab, dalotuzumab, daratumumab, detumomab, dinutuximab, domvanalimab, drozitumab, duligotumab, dusigitumab, ecromeximab, elotuzumab, emibetuzumab, ensituximab, ertumaxomab, etaracizumab, farletuzumab, ficlatuzumab, figitumumab, flanvotumab, futuximab, ganitumab, gemtuzumab, girentuximab, glembatumumab, ibritumomab, igovomab, imgatuzumab, indatuximab, inotuzumab, intetumumab, ipilimumab (YERVOY®, MDX-010, BMS-734016, and MDX-101), iratumumab, labetuzumab, lexatumumab, lintuzumab, lorvotuzumab, lucatumumab, mapatumumab, matuzumab, milatuzumab, minretumomab, mitumomab, mogamulizumab, moxetumomab, naptumomab, narnatumab, necitumumab, nimotuzumab, nofetumomab, OBI-833, obinutuzumab, ocaratuzumab, ofatumumab, olaratumab, onartuzumab, oportuzumab, oregovomab, panitumumab, parsatuzumab, pasudotox, patritumab, pemtumomab, pertuzumab, pintumomab, pritumumab, racotumomab, radretumab, ramucirumab (Cyramza®), rilotumumab, rituximab, robatumumab, samalizumab, satumomab, sibrotuzumab, siltuximab, solitomab, simtuzumab, tacatuzumab, taplitumomab, tenatumomab, teprotumumab, tigatuzumab, tositumomab, trastuzumab, tucotuzumab, ubilituximab, veltuzumab, vorsetuzumab, votumumab, zalutumumab, zimberelimab, and 3F8. Rituximab can be used for treating indolent B-cell cancers, including marginal-zone lymphoma, WM, CLL, and small lymphocytic lymphoma. A combination of rituximab and chemotherapy agents is especially effective.

The exemplified therapeutic antibodies can be further labeled or combined with a radioisotope particle such as indium-111, yttrium-90 (90Y-clivatuzumab), or iodine-131.

In some embodiments, the immunotherapeutic agent is an antibody-drug conjugate (ADC). Illustrative ADCs that can be co-administered include without limitation drug-conjugated antibodies, fragments thereof, or antibody mimetics targeting the proteins or antigens listed above and herein. Example ADCs that can be co-administered include gemtuzumab, brentuximab, belantamab (e.g., belantamab mafodotin), camidanlumab (e.g., camidanlumab tesirine), trastuzumab (e.g., trastuzumab deruxtecan; trasuzumab emtansine), inotuzumab, glembatumumab, anetumab, mirvetuximab (e.g., mirvetuximab soravtansine), depatuxizumab, vadastuximab, labetuzumab, ladiratuzumab (e.g., ladiratuzumab vedotin), loncastuximab (e.g., loncastuximab tesirine), sacituzumab (e.g., sacituzumab govitecan), datopotamab (e.g., datopotamab deruxtecan; DS-1062; Dato-DXd), patritumab (e.g., patritumab deruxtecan), lifastuzumab, indusatumab, polatuzumab (e.g., polatuzumab vedotin), pinatuzumab, coltuximab, upifitamab (e.g., upifitamab rilsodotin), indatuximab, milatuzumab, rovalpituzumab (e.g., rovalpituzumab tesirine), enfortumab (e.g., enfortumab vedotin), tisotumab (e.g., tisotumab vedotin), tusamitamab (e.g., tusamitamab ravtansine), disitamab (e.g., disitamab vedotin), telisotuzumab vedotin (ABBV-399), AGS-16C3F, ASG-22ME, AGS67E, AMG172, AMG575, BAY1129980, BAY1187982, BAY94-9343, GSK2857916, Humax-TF-ADC, IMGN289, IMGN151, IMGN529, IMGN632, IMGN853, IMGC936, LOP628, PCA062, MDX-1203 (BMS936561), MEDI-547, PF-06263507, PF-06647020, PF-06647263, PF-06664178, RG7450, RG7458, RG7598, SAR566658, SGN-CD19A, SGN-CD33A, SGN-CD70A, SGN-LIV1A, SYD985, DS-7300, XMT-1660, IMMU-130, and IMMU-140. ADCs that can be co-administered are described, e.g., in Lambert, et al., Adv Ther (2017) 34:1015-1035 and in de Goeij, *Current Opinion in Immunology* (2016) 40:14-23.

Illustrative therapeutic agents (e.g., anticancer or antineoplastic agents) that can be conjugated to the drug-conjugated antibodies, fragments thereof, or antibody mimetics include without limitation monomethyl auristatin E (MMAE), monomethyl auristatin F (MMAF), a calicheamicin, ansamitocin, maytansine or an analog thereof (e.g., mertansine/emtansine (DM1), ravtansine/soravtansine (DM4)), an anthracyline (e.g., doxorubicin, daunorubicin, epirubicin, idarubicin), pyrrolobenzodiazepine (PBD) DNA cross-linking agent SC-DR002 (D6.5), duocarmycin, a microtubule inhibitors (MTI) (e.g., a taxane, a *vinca* alkaloid, an epothilone), a pyrrolobenzodiazepine (PBD) or dimer thereof, a duocarmycin (A, B1, B2, C1, C2, D, SA, CC-1065), and other anticancer or anti-neoplastic agents described herein. In some embodiments, the therapeutic agent conjugated to the drug-conjugated antibody is a topoisomerase I inhibitor (e.g., a camptothecin analog, such as irinotecan or its active metabolite SN38). In some embodiments, the therapeutic agents (e.g., anticancer or antineoplastic agents) that can be conjugated to the drug-conjugated antibodies, fragments thereof, or antibody mimetics include an immune checkpoint inhibitor. In some embodiments, the conjugated immune checkpoint inhibitor is a conjugated small molecule inhibitor of CD274 (PDL1, PD-L1), programmed cell death 1 (PDCD1, PD1, PD-1) or CTLA4. In some embodiments, the conjugated small molecule inhibitor of CD274 or PDCD1 is selected from the group consisting of GS-4224, GS-4416, INCB086550 and MAX10181. In some embodiments, the conjugated small molecule inhibitor of CTLA4 comprises BPI-002.

In some embodiments, the ADCs that can be co-administered include an antibody targeting tumor-associated calcium signal transducer 2 (TROP-2; TACSTD2; EGP-1; NCBI Gene ID: 4070). Illustrative anti-TROP-2 antibodies include without limitation TROP2-XPAT (Amunix), BAT-8003 (Bio-Thera Solutions), TROP-2-IR700 (Chiome Bioscience), datopotamab deruxtecan (Daiichi Sankyo, AstraZeneca), GQ-1003 (Genequantum Healthcare, Samsung BioLogics), DAC-002 (Hangzhou DAC Biotech, Shanghai Junshi Biosciences), sacituzumab govitecan (Gilead Sciences), E1-3s (Immunomedics/Gilead, IBC Pharmaceuticals), TROP2-TRACTr (Janux Therapeutics), LIV-2008 (LivTech/Chiome, Yakult Honsha, Shanghai Henlius BioTech), LIV-2008b (LivTech/Chiome), anti-TROP-2a (Oncoxx), anti-TROP-2b (Oncoxx), OXG-64 (Oncoxx), OXS-55 (Oncoxx), humanized anti-Trop2-SN38 antibody conjugate (Shanghai Escugen Biotechnology, TOT Biopharma), anti-Trop2 antibody-CLB-SN-38 conjugate (Shanghai Fudan-Zhangjiang Bio-Pharmaceutical), SKB-264 (Sichuan Kelun Pharmaceutical/Klus Pharma), TROP2-Ab8 (Abmart), Trop2-IgG (Nanjing Medical University (NMU)), 90Y-DTPA-AF650 (Peking University First Hospital), hRS7-CM (SynAffix), 89Zr-DFO-AF650 (University of Wisconsin-Madison), anti-Trop2 antibody (Mediterranea Theranostic, LegoChem Biosciences), KD-065 (Nanjing KAEDI Biotech), and those described in WO2020016662 (Abmart), WO2020249063 (Bio-Thera Solutions), US20190048095 (Bio-Thera Solutions), WO2013077458 (LivTech/Chiome), EP20110783675 (Chiome), WO2015098099 (Daiichi Sankyo), WO2017002776 (Daiichi Sankyo), WO2020130125 (Daiichi Sankyo), WO2020240467 (Daiichi Sankyo), US2021093730 (Daiichi Sankyo), U.S. Pat. No. 9,850,312 (Daiichi Sankyo), CN112321715 (Biosion), US2006193865 (Immunomedics/Gilead), WO2011068845 (Immunomedics/Gilead), US2016296633 (Immunomedics/Gilead), US2017021017 (Immunomedics/Gilead), US2017209594 (Immunomedics/Gilead), US2017274093 (Immunomedics/Gilead), US2018110772 (Immunomedics/Gilead), US2018185351 (Immunomedics/Gilead), US2018271992 (Immunomedics/Gilead), WO2018217227 (Immunomedics/Gilead), US2019248917 (Immunomedics/Gilead), CN111534585 (Immunomedics/Gilead), US2021093730 (Immunomedics/Gilead), US2021069343 (Immunomedics/Gilead), U.S. Pat. No. 8,435,539 (Immunomedics/Gilead), U.S. Pat. No. 8,435,529 (Immunomedics/Gilead), U.S. Pat. No. 9,492,566 (Immunomedics/Gilead), WO2003074566 (Gilead), WO2020257648 (Gilead), US2013039861 (Gilead), WO2014163684 (Gilead), U.S. Pat. No. 9,427,464 (LivTech/Chiome), U.S. Ser. No. 10/501,555 (Abruzzo Theranostic/Oncoxx), WO2018036428 (Sichuan Kelun Pharma), WO2013068946 (Pfizer), WO2007095749 (Roche), and WO2020094670 (SynAffix). In some embodiments, the anti-Trop-2 antibody is selected from hRS7, Trop-2-XPAT, and BAT-8003. In some embodiments, the anti-Trop-2 antibody is hRS7. In some embodiments, hRS7 is as disclosed in U.S. Pat. Nos. 7,238,785; 7,517,964 and 8,084,583, which are incorporated herein by reference. In some embodiments, the antibody-drug conjugate comprises an anti-Trop-2 antibody and an anticancer agent linked by a linker. In some embodiments, the linker includes the linkers disclosed in U.S. Pat. No. 7,999,083. In some embodiments, the linker is CL2A. In some embodiments, the drug moiety of antibody-drug conjugate is a chemotherapeutic agent. In some embodiments, the chemotherapeutic agent is selected from doxorubcin (DOX), epirubicin, morpholinodoxorubicin (morpholino-DOX), cyanomorpholino-doxorubicin (cyanomorpholino-DOX), 2-pyrrolino-doxorubicin (2-PDOX), CPT, 10-hydroxy camptothecin, SN-38, topotecan, lurtotecan, 9-aminocamptothecin, 9-nitrocamptothecin, taxanes, geldanamycin, ansamycins, and epothilones. In some embodiments, the chemotherapeutic moiety is SN-38. In some embodiments, the compound provided herein is administered with sacituzumab govitecan.

In some embodiments, the ADCs that can be co-administered include an antibody targeting carcinoembryonic antigen-related cell adhesion molecule 1 (CEACAM1; CD66a; NCBI Gene ID: 634). In some embodiments, the CEACAM1 antibody is hMN-14 (e.g., as described in WO1996011013). In some embodiments, the CEACAM1-ADC is as described in WO2010093395 (anti-CEACAM-1-CL2A-SN38). In some embodiments, the compound provided herein is administered with the CEACAM1-ADC IMMU-130.

In some embodiments, the ADCs that can be co-administered include an antibody targeting MHC class II cell surface receptor encoded by the human leukocyte antigen complex (HLA-DR). In some embodiments, the HLA-DR antibody is hL243 (e.g., as described in WO2006094192). In some embodiments, the HLA-DR-ADC is as described in WO2010093395 (anti-HLA-DR-CL2A-SN38). In some embodiments, the compound provided herein is administered with the HLA-DR-ADC IMMU-140.

Cancer Gene Therapy and Cell Therapy

In some embodiments, the compound provided herein is administered with a cancer gene therapy and cell therapy. Cancer gene therapies and cell therapies include the insertion of a normal gene into cancer cells to replace a mutated or altered gene; genetic modification to silence a mutated gene; genetic approaches to directly kill the cancer cells; including the infusion of immune cells designed to replace most of the patient's own immune system to enhance the immune response to cancer cells, or activate the patient's own immune system (T cells or Natural Killer cells) to kill cancer cells, or find and kill the cancer cells; genetic approaches to modify cellular activity to further alter endogenous immune responsiveness against cancer.

Cellular Therapies

In some embodiments, the compound provided herein is administered with one or more cellular therapies. Illustrative cellular therapies include without limitation co-administration of one or more of a population of natural killer (NK) cells, NK-T cells, T cells, cytokine-induced killer (CIK) cells, macrophage (MAC) cells, tumor infiltrating lymphocytes (TILs) and/or dendritic cells (DCs). In some embodiments, the cellular therapy entails a T cell therapy, e.g., co-administering a population of alpha/beta TCR T cells, gamma/delta TCR T cells, regulatory T (Treg) cells and/or TRuC™ T cells. In some embodiments, the cellular therapy entails a NK cell therapy, e.g., co-administering NK-92 cells. As appropriate, a cellular therapy can entail the co-administration of cells that are autologous, syngeneic or allogeneic to the subject.

In some embodiments, the cellular therapy entails co-administering cells comprising chimeric antigen receptors (CARs). In such therapies, a population of immune effector cells engineered to express a CAR, wherein the CAR comprises a tumor antigen-binding domain. In T cell therapies, the T cell receptors (TCRs) are engineered to target tumor derived peptides presented on the surface of tumor cells.

With respect to the structure of a CAR, in some embodiments, the CAR comprises an antigen binding domain, a transmembrane domain, and an intracellular signaling domain. In some embodiments, the intracellular domain comprises a primary signaling domain, a costimulatory domain, or both of a primary signaling domain and a costimulatory domain. In some embodiments, the primary signaling domain comprises a functional signaling domain of one or more proteins selected from the group consisting of CD3 zeta, CD3 gamma, CD3 delta, CD3 epsilon, common FcR gamma (FCERIG), FcR beta (Fc Epsilon Rlb), CD79a, CD79b, Fcgamma RIIa, DAP10, and DAP12.

In some embodiments, the costimulatory domain comprises a functional domain of one or more proteins selected from the group consisting of CD27, CD28, 4-1BB(CD137), OX40, CD30, CD40, PD-1, ICOS, CD2, CD7, LIGHT, NKG2C, B7-H3, a ligand that specifically binds with CD83, CDS, ICAM-1, GITR, BAFFR, HVEM (LIGHTR), SLAMF7, NKp80 (KLRFI), CD160, CD19, CD4, CD8alpha, CD8beta, IL2R beta, IL2R gamma, IL7R alpha, ITGA4, VLA1, CD49a, ITGA4, IA4, CD49D, ITGA6, VLA-6, CD49f, ITGAD, ITGAE, CD103, ITGAL, CD1A (NCBI Gene ID: 909), CD1B (NCBI Gene ID: 910), CD1C (NCBI Gene ID: 911), CD1D (NCBI Gene ID: 912), CDIE (NCBI Gene ID: 913), ITGAM, ITGAX, ITGB1, CD29, ITGB2 (CD18, LFA-1), ITGB7, TNFR2, TRANCE/RANKL, DNAM1 (CD226), SLAMF4 (CD244, 2B4), CD84, CD96 (Tactile), CEACAM1, CRTAM, Ly9 (CD229), CD160 (BY55), PSGL1, CD100 (SEMA4D), CD69, SLAMF6 (NTB-A, Ly108), SLAM (SLAMF1, CD150, IPO-3), BLAME (SLAMF8), SELPLG (CD162), LTBR, LAT, GADS, SLP-76, PAG/Cbp, NKp44, NKp30, NKp46, and NKG2D.

In some embodiments, the transmembrane domain comprises a transmembrane domain of a protein selected from the group consisting of the alpha, beta or zeta chain of the T-cell receptor, CD28, CD3 epsilon, CD45, CD4, CD5, CD8, CD9, CD16, CD22, CD33, CD37, CD64, CD80, CD86, CD134, CD137, CD154, KIRDS2, OX40, CD2, CD27, ICOS (CD278), 4-1BB(CD137), GITR, CD40, BAFFR, HVEM (LIGHTR), SLAMF7, NKp80 (KLRF1), CD160, CD19, IL2R beta, IL2R gamma, IL7R, ITGA1, VLA1, CD49a, ITGA4, IA4, CD49D, ITGA6, VLA-6, CD49f, ITGAD, CD1A, CD1B, CD1C, CD1D, CD1E, ITGAE, CD103, ITGAL, ITGAM, ITGAX, ITGB1, CD29, ITGB2 (LFA-1, CD18), ITGB7, TNFR2, DNAM1 (CD226), SLAMF4 (CD244, 2B4), CD84, CD96 (TACTILE), CEACAM1, CRTAM, Ly9 (CD229), CD160 (BY55), PSGL1, CD100 (SEMA4D), SLAMF6 (NTB-A, Ly108), SLAM (SLAMF1, CD150, IPO-3), BLAME (SLAMF8), SELPLG (CD162), LTBR, PAG/Cbp, NKp44, NKp30, NKp46, NKG2D, and NKG2C.

In some embodiments, the TCR or CAR antigen binding domain or the immunotherapeutic agent described herein (e.g., monospecific or multi-specific antibody or antigen-binding fragment thereof or antibody mimetic) binds a tumor-associated antigen (TAA). In some embodiments, the tumor-associated antigen is selected from the group consisting of: CD19; CD123; CD22; CD30; CD171; CS-1 (also referred to as CD2 subset 1, CRACC, SLAMF7, CD319, and 19A24); C-type lectin-like molecule-1 (CLL-1 or CLECL1); CD33; epidermal growth factor receptor variant III (EGFRylll); ganglioside G2 (GD2); ganglioside GD3 (αNeuSAc(2-8)αNeuSAc(2-3)βDGaip(1-4)bDGIcp(1-I) Cer); ganglioside GM3 (αNeuSAc(2-3)βDGalp(1-4) βDGlcp(1-1)Cer); TNF receptor superfamily member 17 (TNFRSF17, BCMA); Tn antigen ((Tn Ag) or (GaINAcu-Ser/Thr)); prostate-specific membrane antigen (PSMA); receptor tyrosine kinase-like orphan receptor 1 (RORI); tumor-associated glycoprotein 72 (TAG72); CD38; CD44v6; Carcinoembryonic antigen (CEA); epithelial cell adhesion molecule (EPCAM); B7H3 (CD276); KIT (CD117); interleukin-13 receptor subunit alpha-2 (IL-13Ra2 or CD213A2); mesothelin; interleukin 11 receptor alpha (IL-IIRa); prostate stem cell antigen (PSCA); protease serine 21 (Testisin or PRSS21); vascular endothelial growth factor receptor 2 (VEGFR2); Lewis(Y)antigen; CD24; platelet-derived growth factor receptor beta (PDGFR-beta); stage-specific embryonic antigen-4 (SSEA-4); CD20; delta like 3 (DLL3); folate receptor alpha; receptor tyrosine-protein kinase, ERBB2 (Her2/neu); mucin 1, cell surface associated (MUC1); epidermal growth factor receptor (EGFR); neural cell adhesion molecule (NCAM); prostase; prostatic acid phosphatase (PAP); elongation factor 2 mutated (ELF2M); ephrin B2; fibroblast activation protein alpha (FAP); insulin-like growth factor 1 receptor (IGF-I receptor), carbonic anhydrase IX (CAIX); proteasome (Prosome, Macropain) subunit, beta type, 9 (LMP2); glycoprotein 100 (gp100); oncogene fusion protein consisting of breakpoint cluster region (BCR) and Abelson murine leukemia viral oncogene homolog 1 (Abl) (bcr-abl); tyrosinase; ephrin type-A receptor 2 (EphA2); fucosyl GM1; sialyl Lewis adhesion molecule (sLe); transglutaminase 5 (TGS5); high molecular weight-melanoma associated antigen (HMWMAA); o-acetyl-GD2 ganglioside (OAcGD2); folate receptor beta; tumor endothelial marker 1 (TEM1/CD248); tumor endothelial marker 7-related (TEM7R); six transmembrane epithelial antigen of the prostate I (STEAP1); claudin 6 (CLDN6); thyroid stimulating hormone receptor (TSHR); G protein-coupled receptor class C group 5, member D (GPRCSD); chromosome X open reading frame 61 (CXORF61); CD97; CD179a; anaplastic lymphoma kinase (ALK); polysialic acid; placenta-specific 1 (PLAC1); hexasaccharide portion of globoH glycoceramide (GloboH); mammary gland differentiation antigen (NY-BR-1); uroplakin 2 (UPK2); hepatitis A virus cellular receptor 1 (HAVCR1); adrenoceptor beta 3 (ADRB3); pannexin 3 (PANX3); G protein-coupled receptor 20 (GPR20); lymphocyte antigen 6 complex, locus K 9 (LY6K); olfactory receptor 51E2 (ORS IE2); TCR Gamma Alternate Reading Frame Protein (TARP); Wilms tumor protein (WTi); cancer/testis antigen 1 (NY-ESO-1); cancer/testis antigen 2 (LAGE-la); melanoma associated antigen 1 (MAGE-A1); ETS translocation-variant gene 6, located on chromosome 12p (ETV6-AML); sperm protein 17 (SPA17); X Antigen Family, Member 1A (XAGE1); angiopoietin-binding cell surface receptor 2 (Tie 2); melanoma cancer testis antigen-1 (MADCT-1); melanoma cancer testis antigen-2 (MAD-CT-2); fos-related antigen 1; tumor protein p53, (p53); p53 mutant; prostein; survivin; telomerase; prostate carcinoma tumor antigen-1 (PCTA-1 or Galectin 8), melanoma antigen recognized by T cells 1 (MelanA or MARTI); rat sarcoma (Ras) mutant; human telomerase reverse transcriptase (hTERT); sarcoma translocation breakpoints; melanoma inhibitor of apoptosis (ML-IAP); ERG (transmembrane protease, serine 2 (TMPRSS2) ETS fusion gene); N-Acetyl glucosaminyl-transferase V (NA17); paired box protein Pax-3 (PAX3); androgen receptor; cyclin B1;v-myc avian myelocytomatosis viral oncogene neuroblastoma derived homolog (MYCN); ras homolog family member C (RhoC); tyrosinase-related protein 2 (TRP-2); cytochrome P450 1B1(CYP IBI); CCCTC-Binding Factor (Zinc Finger Protein)-Like (BORIS or Brother of the Regulator of Imprinted Sites), squamous cell carcinoma antigen recognized by T-cells 3 (SART3); paired box protein Pax-5 (PAX5); proacrosin binding protein sp32 (OY-TES I); lymphocyte-specific protein tyrosine kinase (LCK); A kinase anchor protein 4 (AKAP-4); synovial sarcoma, X breakpoint 2 (SSX2); receptor for advanced glycation end products (RAGE-I); renal ubiquitous 1 (RUI); renal ubiquitous 2 (RU2); legumain; human papilloma virus E6 (HPV E6); human papilloma virus E7 (HPV E7); intestinal carboxyl esterase; heat shock protein 70-2 mutated (mut hsp70-2); CD79a; CD79b; CD72; leukocyte-associated immunoglobulin-like receptor 1 (LAIRI); Fc fragment of IgA receptor (FCAR or CD89); leukocyte immunoglobulin-like receptor subfamily A member 2 (LILRA2); CD300 molecule-like family member f (CD300LF); C-type lectin domain family 12 member A (CLEC12A); bone marrow stromal cell antigen 2 (BST2); EGF-like module containing mucin-like hormone receptor-like 2 (EMR2); lymphocyte antigen 75 (LY75); Glypican-3 (GPC3); Fc receptor-like 5 (FCRL5); and immunoglobulin lambda-like polypeptide 1 (IGLL1). In some embodiments, the target is an epitope of the tumor associated antigen presented in an MHC.

In some embodiments, the tumor antigen is selected from CD150, 5T4, ActRIIA, B7, TNF receptor superfamily member 17 (TNFRSF17, BCMA), CA-125, CCNA1, CD123, CD126, CD138, CD14, CD148, CD15, CD19, CD20, CD200, CD21, CD22, CD23, CD24, CD25, CD26, CD261, CD262, CD30, CD33, CD362, CD37, CD38, CD4, CD40, CD40L, CD44, CD46, CD5, CD52, CD53, CD54, CD56, CD66a-d, CD74, CD8, CD80, CD92, CE7, CS-1, CSPG4, ED-B fibronectin, EGFR, EGFRvIII, EGP-2, EGP-4, EPHa2, ErbB2, ErbB3, ErbB4, FBP, HER1-HER2 in combination, HER2-HER3 in combination, HERV-K, HIV-1 envelope glycoprotein gp120, HIV-1 envelope glycoprotein gp41, HLA-DR, HM1.24, HMW-MAA, Her2, Her2/neu, IGF-1R, IL-11Ralpha, IL-13R-alpha2, IL-2, IL-22R-alpha, IL-6, IL-6R, Ia, Ii, L1-CAM, L1-cell adhesion molecule, Lewis Y, L1-CAM, MAGE A3, MAGE-A1, MART-1, MUC1, NKG2C ligands, NKG2D Ligands, NYESO-1, OEPHa2, PIGF, PSCA, PSMA, ROR1, T101, TAC, TAG72, TIM-3, TRAIL-R1, TRAIL-R1 (DR4), TRAIL-R2 (DR5), VEGF, VEGFR2, WT-I, a G-protein coupled receptor, alphafetoprotein (AFP), an angiogenesis factor, an exogenous cognate binding molecule (ExoCBM), oncogene product, anti-folate receptor, c-Met, carcinoembryonic antigen (CEA), cyclin (D 1), ephrinB2, epithelial tumor antigen, estrogen receptor, fetal acetylcholine e receptor, folate binding protein, gp100, hepatitis B surface antigen, kappa chain, kappa light chain, kdr, lambda chain, livin, melanoma-associated antigen, mesothelin, mouse double minute 2 homolog (MDM2), mucin 16 (MUC16), mutated p53, mutated ras, necrosis antigens, oncofetal antigen, ROR2, progesterone receptor, prostate specific antigen, tEGFR, tenascin, P2-Microgiobuiin, Fc Receptor-like 5 (FcRL5).

In some embodiments, the antigen binding domain binds to an epitope of a target or tumor associated antigen (TAA) presented in a major histocompatibility complex (MHC) molecule. In some embodiments, the TAA is a cancer testis antigen. In some embodiments, the cancer testis antigen is selected from the group consisting of acrosin binding protein (ACRBP; CT23, OY-TES-1, SP32; NCBI Gene ID: 84519), alpha fetoprotein (AFP; AFPD, FETA, HPAFP; NCBI Gene ID: 174); A-kinase anchoring protein 4 (AKAP4; AKAP 82, AKAP-4, AKAP82, CT99, FSC1, HI, PRKA4, hAKAP82, p82; NCBI Gene ID: 8852), ATPase family AAA domain containing 2 (ATAD2; ANCCA, CT137, PRO2000; NCBI Gene ID: 29028), kinetochore scaffold 1 (KNL1; AF15Q14, CASC5, CT29, D40, MCPH4, PPP1R55, Spc7, hKNL-1, hSpc105; NCBI Gene ID: 57082), centrosomal protein 55 (CEP55; C10orf3, CT111, MARCH, URCC6; NCBI Gene ID: 55165), cancer/testis antigen 1A (CTAG1A; ESO1; CT6.1; LAGE-2; LAGE2A; NY-ESO-1; NCBI Gene ID: 246100), cancer/testis antigen 1B (CTAG1B; CT6.1, CTAG, CTAG1, ESO1, LAGE-2, LAGE2B, NY-ESO-1; NCBI Gene ID: 1485), cancer/testis antigen 2 (CTAG2; CAMEL, CT2, CT6.2, CT6.2a, CT6.2b, ESO2, LAGE-1, LAGE2B; NCBI Gene ID: 30848), CCCTC-binding factor like (CTCFL; BORIS, CT27, CTCF-T, HMGB1L1, dJ579F20.2; NCBI Gene ID: 140690), catenin alpha 2 (CTNNA2; CAP-R, CAPR, CDCBM9, CT114, CTNR; NCBI Gene ID: 1496), cancer/testis antigen 83 (CT83; CXorf61, KK-LC-1, KKLC1; NCBI Gene ID: 203413), cyclin A1 (CCNA1; CT146; NCBI Gene ID: 8900), DEAD-box helicase 43 (DDX43; CT13, HAGE; NCBI Gene ID: 55510), developmental pluripotency associated 2 (DPPA2; CT100, ECAT15-2, PESCRG1; NCBI Gene ID: 151871), fetal and adult testis expressed 1 (FATE1; CT43, FATE; NCBI Gene ID: 89885), FMR1 neighbor (FMR1NB; CT37, NY-SAR-35, NYSAR35; NCBI Gene ID: 158521), HORMA domain containing 1 (HORMADI; CT46, NOHMA; NCBI Gene ID: 84072), insulin like growth factor 2 mRNA binding protein 3 (IGF2BP3; CT98, IMP-3, IMP3, KOC, KOC1, VICKZ3; NCBI Gene ID: 10643), leucine zipper protein 4 (LUZP4; CT-28, CT-8, CT28, HOM-TES-85; NCBI Gene ID: 51213), lymphocyte antigen 6 family member K (LY6K; CT97, HSJ001348, URLC10, ly-6K; NCBI Gene ID: 54742), maelstrom spermatogenic transposon silencer (MAEL; CT128, SPATA35; NCBI Gene ID: 84944), MAGE family member A1 (MAGEA1; CT1.1, MAGE1; NCBI Gene ID: 4100); MAGE family member A3 (MAGEA3; CT1.3, HIP8, HYPD, MAGE3, MAGEA6; NCBI Gene ID: 4102); MAGE family member A4 (MAGEA4; CT1.4, MAGE-41, MAGE-X2, MAGE4, MAGE4A, MAGE4B; NCBI Gene ID: 4103); MAGE family member A11 (MAGEAI1; CT1.11, MAGE-11, MAGE11, MAGEA-11; NCBI Gene ID: 4110); MAGE family member C1 (MAGEC1; CT7, CT7.1; NCBI Gene ID: 9947); MAGE family member C2 (MAGEC2; CT10, HCA587, MAGEE1; NCBI Gene ID: 51438); MAGE family member D1 (MAGED1; DLXIN-1, NRAGE; NCBI Gene ID: 9500); MAGE family member D2 (MAGED2; 11B6, BARTS5, BCG-1, BCG1, HCA10, MAGE-D2; NCBI Gene ID: 10916), kinesin family member 20B (KIF20B; CT90, KRMP1, MPHOSPH1, MPP-1, MPP1; NCBI Gene ID: 9585), NUF2 component of NDC80 kinetochore complex (NUF2; CDCA1, CT106, NUF2R; NCBI Gene ID: 83540), nuclear RNA export factor 2 (NXF2; CT39, TAPL-2, TCP11X2; NCBI Gene ID: 56001), PAS domain containing repressor 1 (PASD1; CT63, CT64, OXTES1; NCBI Gene ID: 139135), PDZ binding kinase (PBK; CT84, HEL164, Nori-3, SPK, TOPK; NCBI Gene ID: 55872), piwi like RNA-mediated gene silencing 2 (PIWIL2; CT80, HILI, PIWILIL, mili; NCBI Gene ID: 55124), preferentially expressed antigen in melanoma (PRAME; CT130, MAPE, OIP-4, OIP4; NCBI Gene ID: 23532), sperm associated antigen 9 (SPAG9; CT89, HLC-6, HLC4, HLC6, JIP-4, JIP4, JLP, PHET, PIG6; NCBI Gene ID: 9043), sperm protein associated with the nucleus, X-linked, family member A1 (SPANXA1; CT11.1, CT11.3, NAP-X, SPAN-X, SPAN-Xa, SPAN-Xb, SPANX, SPANX-A; NCBI Gene ID: 30014), SPANX family member A2 (SPANXA2; CT11.1, CT11.3, SPANX, SPANX-A, SPANX-C, SPANXA, SPANXC; NCBI Gene ID: 728712), SPANX family member C (SPANXC; CT11.3, CTp11, SPANX-C, SPANX-E, SPANXE; NCBI Gene ID: 64663), SPANX family member D (SPANXD; CT11.3, CT11.4, SPANX-C, SPANX-D, SPANX-E, SPANXC, SPANXE, dJ171K16.1; NCBI Gene ID: 64648), SSX family member 1 (SSX1; CT5.1, SSRC; NCBI Gene ID: 6756), SSX family member 2 (SSX2; CT5.2, CT5.2A, HD21, HOM-MEL-40, SSX; NCBI Gene ID: 6757), synaptonemal complex protein 3 (SYCP3; COR1, RPRGL4, SCP3, SPGF4; NCBI Gene ID: 50511), testis expressed 14, intercellular bridge forming factor (TEX14; CT113, SPGF23; NCBI Gene ID: 56155), transcription factor Dp family member 3 (TFDP3; CT30, DP4, HCA661; NCBI Gene ID: 51270), serine protease 50 (PRSS50; CT20, TSP50; NCBI Gene ID: 29122), TTK protein kinase (TTK; CT96, ESK, MPH1, MPS1, MPS1L1, PYT; NCBI Gene ID: 7272) and zinc finger protein 165 (ZNF165; CT53, LD65, ZSCAN7; NCBI Gene ID: 7718). T cell receptors (TCRs) and TCR-like antibodies that bind to an epitope of a cancer testis antigen presented in a major histocompatibility complex (MHC) molecule are known in the art and can be used in the herein described heterodimers. Cancer testis antigens associated with neoplasia are summarized, e.g., in Gibbs, et al., *Trends Cancer* 2018 October; 4(10):701-712 and the CT database website at cta.lncc.br/index.php. Illustrative TCRs and TCR-like antibodies that bind to an epitope of NY-ESO-1 presented in an MHC are described, e.g., in Stewart-Jones, et al., *Proc Natl Acad Sci USA*. 2009 Apr. 7; 106(14):5784-8; WO2005113595, WO2006031221, WO2010106431, WO2016177339, WO2016210365, WO2017044661, WO2017076308, WO2017109496, WO2018132739, WO2019084538, WO2019162043, WO2020086158 and WO2020086647. Illustrative TCRs and TCR-like antibodies that bind to an epitope of PRAME presented in an MHC are described, e.g., in WO2011062634, WO2016142783, WO2016191246, WO2018172533, WO2018234319 and WO2019109821. Illustrative TCRs and TCR-like antibodies that bind to an epitope of a MAGE variant presented in an MHC are described, e.g., in WO2007032255, WO2012054825, WO2013039889, WO2013041865, WO2014118236, WO2016055785, WO2017174822, WO2017174823, WO2017174824, WO2017175006, WO2018097951, WO2018170338, WO2018225732 and WO2019204683. Illustrative TCRs and TCR-like antibodies that bind to an epitope of alpha fetoprotein (AFP) presented in an MHC are described, e.g., in WO2015011450. Illustrative TCRs and TCR-like antibodies that bind to an epitope of SSX2 presented in an MHC are described, e.g., in WO2020063488. Illustrative TCRs and TCR-like antibodies that bind to an epitope of KK-LC-1 (CT83) presented in an MHC are described, e.g., in WO2017189254.

Examples of cell therapies include: Algenpantucel-L, Sipuleucel-T, (BPX-501) rivogenlecleucel U.S. Pat. No. 9,089,520, WO2016100236, AU-105, ACTR-087, activated allogeneic natural killer cells CNDO-109-AANK, MG-4101, AU-101, BPX-601, FATE-NK100, LFU-835 hematopoietic stem cells, Imilecleucel-T, baltaleucel-T, PNK-007, UCARTCS1, ET-1504, ET-1501, ET-1502, ET-190, CD19-ARTEMIS, ProHema, FT-1050-treated bone marrow stem cell therapy, CD4CARNK-92 cells, CryoStim, AlloStim, lentiviral transduced huCART-meso cells, CART-22 cells, EGFRt/19-28z/4-1BBL CAR T cells, autologous 4H11-28z/fIL-12/EFGRt T cell, CCR5-SBC-728-HSPC, CAR4-1BBZ, CH-296, dnTGFbRII-NY-ESOc259T, Ad-RTS-IL-12, IMA-101, IMA-201, CARMA-0508, TT-18, CMD-501, CMD-503, CMD-504, CMD-502, CMD-601, CMD-602, and CSG-005.

In some embodiments, the one or more additional co-administered therapeutic agents can be categorized by their mechanism of action, e.g., into the following groups:

- agents targeting adenosine deaminase, such as pentostatin or cladribine;
- agents targeting ATM, such as AZD1390;
- agents targeting MET, such as savolitinib, capmatinib, tepotinib, ABT-700, AG213, JNJ-38877618 (OMO-1), merestinib, HQP-8361, BMS-817378, or TAS-115;
- agents targeting mitogen-activated protein kinase, such as antroquinonol, binimetinib, cobimetinib, selumetinib, trametinib, uprosertib, mirdametinib (PD-0325901), pimasertib, refametinib, or compounds disclosed in WO2011008709, WO2013112741, WO2006124944, WO2006124692, WO2014064215, WO2018005435, Zhou, et al., Cancer Lett. 2017 Nov. 1, 408:130-137, Teli, et al., J Enzyme Inhib Med Chem. (2012) 27(4): 558-70; Gangwall, et al., Curr Top Med Chem. (2013) 13(9):1015-35; Wu, et al., Bioorg Med Chem Lett. (2009) 19(13):3485-8; Kaila, et al., Bioorg Med Chem. (2007) 15(19):6425-42, or Hu, et al., Bioorg Med Chem Lett. (2011) 21(16):4758-61;
- agents targeting thymidine kinase, such as aglatimagene besadenovec (ProstAtak, PancAtak, GliAtak, GMCI, or AdV-tk);
- agents targeting targeting an interleukin pathway, such as pegilodecakin (AM-0010) (pegylated IL10), CA-4948 (IRAK4 inhibitor);
- agents targeting cytochrome P450 family members, such as letrozole, anastrozole, aminoglutethimide, megestrol acetate (MEGACE®), exemestane, formestane, fadrozole, vorozole (RIVISOR®), letrozole (FEMARA®), or anastrozole (ARIMIDEX®);
- agents targeting CD73, such as a CD73 inhibitor (e.g., quemliclustat (AB680)) or an anti-CD73 antibody (e.g., oleclumab);
- agents targeting DKK3, such as MTG-201;
- agents targeting EEF1A2, such as plitidepsin;
- agents targeting EIF4A1, such as rohinitib;
- agents targeting endoglin, such as TRC105 (carotuximab);

agents targeting exportin-1, such as eltanexor;

agents targeting fatty acid amide hydrolase, such as compounds disclosed in WO2017160861;

agents targeting heat shock protein 90 beta family member 1, such as anlotinib;

agents targeting lactotransferrin, such as ruxotemitide (LTX-315);

agents targeting lysyl oxidase, such as compounds disclosed in U.S. Pat. Nos. 4,965,288, 4,997,854, 4,943, 593, 5,021,456, 5,059,714, 5,120,764, 5,182,297, 5,252,608, or US20040248871;

agents targeting MAGE family members, such as KITE-718, MAGE-A10C796T, or MAGE-A10 TCR;

agents targeting MDM2, such as ALRN-6924, CMG-097, milademetan monotosylate monohydrate (DS-3032b), or AMG-232;

agents targeting MDM4, such as ALRN-6924;

agents targeting melan-A, such as MART-1 F5 TCR engineered PBMCs;

agents targeting mesothelin, such as CSG-MESO or TC-210;

agents targeting METAP2, such as M8891 or APL-1202;

agents targeting NLRP3, such as BMS-986299;

agents targeting oxoglutarate dehydrogenase, such as devimistat (CPI-613);

agents targeting placenta growth factor, such as aflibercept;

agents targeting SLC10A3, such as compounds disclosed in WO2015148954, WO2012082647, or WO2017160861;

agents targeting transforming growth factor alpha (TGFa), such as compounds disclosed in WO2019103203;

agents targeting tumor protein p53, such as kevetrin (stimulator);

agents targeting vascular endothelial growth factor A, such as aflibercept;

agents targeting vascular endothelial growth factor receptor, such as fruquintinib or MP0250;

agents targeting VISTA, such as CA-170, or HMBD-002;

agents targeting WEE1, such as adavosertib (AZD-1775);

small molecule inhibitors targeting ABL1, such as imatinib, rebastinib, asciminib, or ponatinib (ICLUSIG®);

small molecule antagonists targeting adenosine receptor, such as CPI-444, AZD-4635, preladenant, etrumadenant (AB928), or PBF-509;

small molecule inhibitors targeting arachidonate 5-lipoxygenase, such as meclofenamate sodium or zileuton;

small molecule inhibitors targeting ATR serine/threonine kinase, such as BAY-937, ceralasertib (AZD6738), AZD6783, VX-803, or VX-970 (berzosertib);

small molecule inhibitors targeting AXL receptor tyrosine kinase, such as bemcentinib (BGB-324), SLC-0211, or gilteritinib (Axl/Flt3);

small molecule inhibitors targeting Bruton's tyrosine kinase (BTK), such as (S)-6-amino-9-(1-(but-2-ynoyl) pyrrolidin-3-yl)-7-(4-phenoxyphenyl)-7H-purin-8 (9H)-one, acalabrutinib (ACP-196), zanubrutinib (BGB-3111), CB988, poseltinib (HM71224), ibrutinib (Imbruvica), M-2951 (evobrutinib), tirabrutinib (ONO-4059), rilzabrutinib (PRN-1008), spebrutinib (CC-292), vecabrutinib, ARQ-531 (MK-1026), SHR-1459, DTRMWXHS-12, or TAS-5315;

small molecule inhibitors targeting neurotrophic receptor tyrosine kinase such as larotrectinib, entrectinib, or selitrectinib (LOXO-195);

small molecule inhibitors targeting ROS proto-oncogene 1, receptor tyrosine kinase, such as entrectinib, repotrectinib (TPX-0005), or lorlatinib;

small molecule inhibitors targeting SRC proto-oncogene, non-receptor tyrosine kinase, such as VAL-201, tirbanibulin (KX2-391), or ilginatinib maleate (NS-018);

small molecule inhibitors targeting B-cell lymphoma 2, such as navitoclax (ABT-263), venetoclax (ABT-199, RG-7601), or AT-101 (gossypol);

small molecule inhibitors targeting bromodomain and external domain (BET) bromodomain containing protein, such as ABBV-744, INCB-054329, INCB057643, AZD-5153, ABT-767, BMS-986158, CC-90010, NHWD-870, ODM-207, ZBC246, ZEN3694, CC-95775 (FT-1101), mivebresib, BI-894999, PLX-2853, PLX-51107, CPI-0610, or GS-5829;

small molecule inhibitors targeting carbohydrate sulfotransferase 15, such as STNM-01;

small molecule inhibitors targeting carbonic anhydrase, such as polmacoxib, acetazolamide, or methazolamide;

small molecule inhibitors targeting catenin beta 1, such as CWP-291, or PRI-724;

small molecule antagonists targeting a C-C motif chemokine receptor, such as CCX-872, BMS-813160 (CCR2/CCR5) or MK-7690 (vicriviroc);

small molecule antagonists targeting a C-X-C motif chemokine receptor (e.g., CXCR4), blixafortide;

small molecule inhibitors targeting cereblon, such as avadomide (CC-122), CC-92480, CC-90009, or iberdomide;

small molecule inhibitors targeting checkpoint kinase 1, such as SRA737;

small molecule inhibitors targeting a complement component, such as Imprime PGG (Biothera Pharmaceuticals);

small molecule inhibitor targeting a C-X-C motif chemokine ligand (e.g., CXCL12), such as olaptesed pegol (NOX-A12);

small molecule inhibitors targeting cytochrome P450 family, such as ODM-209, LAE-201, seviteronel (VT-464), CFG920, abiraterone, or abiraterone acetate;

small molecule inhibitors targeting DEAD-box helicase 5, such as supinoxin (RX-5902);

small molecule inhibitors targeting DGKa, e.g., such as described in WO2021130638;

small molecule inhibitors targeting diablo IAP-binding mitochondrial protein, such as BI-891065;

small molecule inhibitors targeting dihydrofolate reductase, such as pralatrexate or pemetrexed disodium;

small molecule inhibitors targeting DNA dependent protein kinase, such as MSC2490484A (nedisertib), VX-984, AsiDNA (DT-01), LXS-196, or sotrastaurin;

small molecule inhibitors targeting MARCKS, such as BIO-11006;

small molecule inhibitors targeting RIPK1, such as GSK-3145094;

small molecule inhibitors targeting Rho associated coiled-coil containing protein kinase, such as AT13148 or KD025;

small molecule inhibitors targeting DNA topoisomerase, such as irinotecan, firtecan pegol, or amrubicin;

small molecule inhibitors targeting dopamine receptor D2, such as ONC-201;

small molecule inhibitors targeting DOT1 like histone lysine methyltransferase, such as pinometostat (EPZ-5676);

small molecule inhibitors targeting EZH2, such as tazemetostat, CPI-1205, or PF-06821497;

small molecule inhibitors targeting fatty acid synthase, such as TVB-2640 (Sagimet Biosciences);

small molecule inhibitors targeting fibroblast growth factor receptor 2 (FGFR2), such as bemarituzumab (FPA144);

small molecule inhibitors targeting focal adhesion kinase (FAK, PTK2), such as VS-4718, defactinib, or GSK2256098;

small molecule inhibitors targeting folate receptor 1, such as pralatrexate;

small molecule inhibitors targeting FOXM1, such as thiostrepton;

small molecule inhibitors targeting galectin 3, such as belapectin (GR-MD-02);

small molecule antagonists targeting glucocorticoid receptor, such as relacorilant (CORT-125134);

small molecule inhibitors targeting glutaminase include without limitation CB-839 (telaglenastat), or bis-2-(5-phenylacetamido-1,3,4-thiadiazol-2-yl)ethyl sulfide (BPTES);

small molecule inhibitors targeting GNRHR, such as elagolix, relugolix, or degarelix;

small molecule inhibitors targeting EPAS1, such as belzutifan (PT-2977 (Merck & Co.));

small molecule inhibitors targeting isocitrate dehydrogenase (NADP(+)), such as limitation ivosidenib (AG-120), vorasidenib (AG-881) (IDH1 and IDH2), IDH-305, or enasidenib (AG-221);

small molecule inhibitors targeting lysine demethylase 1A, such as CC-90011;

small molecule inhibitors targeting MAPK interacting serine/threonine kinase, such as tomivosertib (eFT-508);

small molecule inhibitors targeting notch receptor, such as AL-101 (BMS-906024);

small molecule inhibitors targeting polo like kinase 1 (PLK1), such as volasertib or onvansertib;

small molecule inhibitors targeting poly(ADP-ribose) polymerase (PARP), such as olaparib (MK7339), rucaparib, veliparib, talazoparib, ABT-767, pamiparib (BGB-290), fluazolepali (SHR-3162), niraparib (JNJ-64091742), stenoparib (2X-121 (e-7499)), simmiparib, IMP-4297, SC-10914, IDX-1197, HWH-340, CEP 9722, CEP-8983, E7016, 3-aminobenzamide, or CK-102;

small molecule inhibitors targeting polycomb protein EED, such as MAK683;

small molecule inhibitors targeting porcupine O-acyltransferase, such as WNT-974;

small molecule inhibitors targeting prostaglandin-endoperoxide synthase, such as HP-5000, lornoxicam, ketorolac tromethamine, bromfenac sodium, otenaproxesul (ATB-346), mofezolac, GLY-230, TRK-700, diclofenac, meloxicam, parecoxib, etoricoxib, celecoxib, AXS-06, diclofenac potassium, reformulated celecoxib (DRGT-46), AAT-076, meisuoshuli, lumiracoxib, meloxicam, valdecoxib, zaltoprofen, nimesulide, anitrazafen, apricoxib, cimicoxib, deracoxib, flumizole, firocoxib, mavacoxib, pamicogrel, parecoxib, robenacoxib, rofecoxib, rutecarpine, tilmacoxib, zaltoprofen, or imrecoxib;

small molecule inhibitors targeting protein arginine N methyltransferase, such as MS203, PF-06939999, GSK3368715, or GSK3326595;

small molecule inhibitors targeting PTPN11, such as TNO155 (SHP-099), RMC-4550, JAB-3068, RMC-4630 (SAR442720), or compounds disclosed in WO2018172984 or WO2017211303;

small molecule antagonist targeting retinoic acid receptor, such as tamibarotene (SY-1425);

small molecule inhibitors targeting ribosomal protein S6 kinase B1, such as MSC2363318A;

small molecule inhibitors targeting S100 calcium binding protein A9, such as tasquinimod;

small molecule inhibitors targeting selectin E, such as uproleselan sodium (GMI-1271);

small molecule inhibitors targeting SF3B1, such as H3B-8800;

small molecule inhibitors targeting Sirtuin-3, such as YC8-02;

small molecule inhibitors targeting SMO, such as sonidegib (Odomzo®, formerly LDE-225), vismodegib (GDC-0449), glasdegib (PF-04449913), itraconazole, or patidegib, taladegib;

small molecule antagonists targeting somatostatin receptor, such as OPS-201;

small molecule inhibitors targeting sphingosine kinase 2, such as opaganib (Yeliva®, ABC294640);

small molecule inhibitors targeting STAT3, such as napabucasin (BBI-608);

small molecule inhibitors targeting tankyrase, such as G007-LK or stenoparib (2X-121 (e-7499));

small molecule inhibitors targeting TFGBR1, such as galunisertib, PF-06952229;

small molecule inhibitors targeting thymidylate synthase, such as idetrexed (ONX-0801);

small molecule inhibitors targeting tumor protein p53, such as CMG-097;

small molecule inhibitors targeting valosin-containing protein, such as CB-5083;

small molecule inhibitors targeting WT1, such as ombipepimut-S (DSP-7888);

small molecule agonists targeting adenosine receptor, such as namodenoson (CF102);

small molecule agonist(s) targeting asparaginase, such as crisantaspase (Erwinase®), GRASPA (ERY-001, ERY-ASP), calaspargase pegol, or pegaspargase;

small molecule agonists targeting CCAAT enhancer binding protein alpha, such as MTL-501;

small molecule agonists targeting cytochrome P450 family, such as mitotane;

small molecule agonists targeting DExD/H-box helicase 58, such as RGT-100;

small molecule agonists targeting GNRHR, such as leuprorelin acetate, leuprorelin acetate sustained release depot (ATRIGEL), triptorelin pamoate, or goserelin acetate;

small molecule agonists targeting GRB2, such as prexigebersen (BP1001);

small molecule agonists targeting NFE2L2, such as omaveloxolone (RTA-408);

small molecule agonists targeting NOD2, such as mifamurtide (liposomal);

small molecule agonists targeting RAR-related orphan receptor gamma, such as cintirorgon (LYC-55716);

small molecule agonists targeting retinoic acid receptor (RAR), such as tretinoin;

small molecule agonists targeting STINGI, such as ADU-S100 (MIW-815), SB-11285, MK-1454, SR-8291, AdVCA0848, GSK-532, SYN-STING, MSA-1, SR-8291, cyclic-GAMP (cGAMP), or cyclic-di-AMP;

small molecule agonists targeting thyroid hormone receptor beta, such as levothyroxine sodium;
small molecule agonists targeting tumor necrosis factor, such as tasonermin;
antisense agents targeting baculoviral IAP repeat containing 5, such as EZN-3042;
antisense agents targeting GRB2, such as prexigebersen;
antisense agents targeting heat shock protein 27, such as apatorsen;
antisense agents targeting STAT3, such as danvatirsen (IONIS-STAT3-2.5Rx);
gene therapies targeting a C-C motif chemokine receptor, such as SB-728-T;
gene therapies targeting an interleukin, such as EGENE-001, tavokinogene telseplasmid, nogapendekin alfa (ALT-803), NKTR-255, NIZ-985 (hetIL-15), SAR441000, or MDNA-55;
antibodies targeting claudin 18, such as claudiximab;
antibodies targeting clusterin, such as AB-16B5;
antibodies targeting a complement component, such as ravulizumab (ALXN-1210);
antibodies targeting a C-X-C motif chemokine ligand, such as BMS-986253 (HuMax-Inflam);
antibodies targeting delta like canonical Notch ligand 4 (DLL4), such as demcizumab, navicixizumab (DLL4/VEGF);
antibodies targeting EPH receptor A3, such as fibatuzumab (KB-004);
antibodies targeting epithelial cell adhesion molecule, such as oportuzumab monatox (VB4-845);
antibodies targeting fibroblast growth factor, such as GAL-F2, B-701 (vofatamab);
antibodies targeting hepatocyte growth factor, such as MP-0250;
antibodies targeting an interleukin, such as canakinumab (ACZ885), gevokizumab (VPM087), CJM-112, guselkumab, talacotuzumab (JNJ-56022473), siltuximab, or tocilizumab;
antibodies targeting LRRC15, such as ABBV-085 or cusatuzumab (ARGX-110);
antibodies targeting mesothelin, such as BMS-986148, SEL-403, or anti-MSLN-MMAE;
antibodies targeting myostatin, such as landogrozumab;
antibodies targeting notch receptor, such as tarextumab;
antibodies targeting TGFB1 (TGFbl), such as SAR439459, ABBV-151, NIS793, SRK-181, XOMA089, or compounds disclosed in WO2019103203;
vaccines targeting fms related receptor tyrosine kinase, such as HLA-A2402/HLA-A0201 restricted epitope peptide vaccine;
vaccines targeting heat shock protein 27, such as PSV-AML (PhosphoSynVax);
vaccines targeting PD-L1, such as IO-120+IO-103 (PD-L1/PD-L2 vaccines) or IO-103;
vaccines targeting tumor protein p53, such as MVA-p53;
vaccines targeting WT1, such as WT-1 analog peptide vaccine (WT1-CTL);
cell therapies targeting baculoviral IAP repeat containing 5, such as tumor lysate/MUC1/survivin PepTivator-loaded dendritic cell vaccine;
cell therapies targeting carbonic anhydrase, such as DC-Ad-GMCAIX;
cell therapies targeting C-C motif chemokine receptor, such as CCR5-SBC-728-HSPC;
cell therapies targeting folate hydrolase 1, such as CIK-CAR.PSMA or CART-PSMA-TGFORDN;
cell therapies targeting GSTP1, such as CPG3-CAR (GLYCAR);
cell therapies targeting HLA-A, such as FH-MCVA2TCR or NeoTCR-P1;
cell therapies targeting an interleukin, such as CST-101;
cell therapies targeting KRAS, such as anti-KRAS G12D mTCR PBL;
cell therapies targeting MET, such as anti-cMet RNA CAR T;
cell therapies targeting MUC16, such as JCAR-020;
cell therapies targeting PD-1, such as PD-1 knockout T cell therapy (esophageal cancer/NSCLC);
cell therapies targeting PRAME, such as BPX-701;
cell therapies targeting transforming protein E7, such as KITE-439;
cell therapies targeting WTi, such as WT1-CTL, ASP-7517, or JTCR-016.

Exemplified Combination Therapies

Lymphoma or Leukemia Combination Therapy

Some chemotherapy agents are suitable for treating lymphoma or leukemia. These agents include aldesleukin, alvocidib, amifostine trihydrate, aminocamptothecin, antineoplaston A10, antineoplaston AS2-1, anti-thymocyte globulin, arsenic trioxide, Bcl-2 family protein inhibitor ABT-263, beta alethine, BMS-345541, bortezomib (VELCADE®), bortezomib (VELCADE®, PS-341), bryostatin 1, bulsulfan, campath-1H, carboplatin, carfilzomib (Kyprolis®), carmustine, caspofungin acetate, CC-5103, chlorambucil, CHOP (cyclophosphamide, doxorubicin, vincristine, and prednisone), cisplatin, cladribine, clofarabine, curcumin, CVP (cyclophosphamide, vincristine, and prednisone), cyclophosphamide, cyclosporine, cytarabine, denileukin diftitox, dexamethasone, docetaxel, dolastatin 10, doxorubicin, doxorubicin hydrochloride, DT-PACE (dexamethasone, thalidomide, cisplatin, doxorubicin, cyclophosphamide, and etoposide), enzastaurin, epoetin alfa, etoposide, everolimus (RAD001), FCM (fludarabine, cyclophosphamide, and mitoxantrone), FCR (fludarabine, cyclophosphamide, and rituximab), fenretinide, filgrastim, flavopiridol, fludarabine, FR (fludarabine and rituximab), geldanamycin (17 AAG), hyperCVAD (hyperfractionated cyclophosphamide, vincristine, doxorubicin, dexamethasone, methotrexate, and cytarabine), ICE (iphosphamide, carboplatin, and etoposide), ifosfamide, irinotecan hydrochloride, interferon alpha-2b, ixabepilone, lenalidomide (REVLIMID®, CC-5013), lymphokine-activated killer cells, MCP (mitoxantrone, chlorambucil, and prednisolone), melphalan, mesna, methotrexate, mitoxantrone hydrochloride, motexafin gadolinium, mycophenolate mofetil, nelarabine, obatoclax (GX15-070), oblimersen, octreotide acetate, omega-3 fatty acids, Omr-IgG-am (WNIG, Omrix), oxaliplatin, paclitaxel, palbociclib (PD0332991), pegfilgrastim, PEGylated liposomal doxorubicin hydrochloride, perifosin, prednisolone, prednisone, recombinant flt3 ligand, recombinant human thrombopoietin, recombinant interferon alfa, recombinant interleukin-11, recombinant interleukin-12, rituximab, R-CHOP (rituximab and CHOP), R-CVP (rituximab and CVP), R-FCM (rituximab and FCM), R-ICE (rituximab and ICE), and R MCP (rituximab and MCP), R-roscovitine (seliciclib, CYC202), sargramostim, sildenafil citrate, simvastatin, sirolimus, styryl sulphones, tacrolimus, tanespimycin, temsirolimus (CCl-779), thalidomide, therapeutic allogeneic lymphocytes, thiotepa, tipifarnib, vincristine, vincristine sulfate, vinorelbine ditartrate, SAHA (suberanilohydroxamic acid, or suberoyl, anilide, and hydroxamic acid), vemurafenib (Zelboraf®), venetoclax (ABT-199).

One modified approach is radioimmunotherapy, wherein a monoclonal antibody is combined with aradioisotope particle, such as indium-111, yttrium-90, and iodine-131. Examples of combination therapies include, but are not limited to, iodine-131 tositumomab (BEXXAR®), yttrium-90 ibritumomab tiuxetan (ZEVALIN®), and BEXXAR® with CHOP.

The abovementioned therapies can be supplemented or combined with stem cell transplantation or treatment. Therapeutic procedures include peripheral blood stem cell transplantation, autologous hematopoietic stem cell transplantation, autologous bone marrow transplantation, antibody therapy, biological therapy, enzyme inhibitor therapy, total body irradiation, infusion of stem cells, bone marrow ablation with stem cell support, in vitro-treated peripheral blood stem cell transplantation, umbilical cord blood transplantation, immunoenzyme technique, low-LET cobalt-60 gamma ray therapy, bleomycin, conventional surgery, radiation therapy, and nonmyeloablative allogeneic hematopoietic stem cell transplantation.

Non-Hodgkin's Lymphomas Combination Therapy

Treatment of non-Hodgkin's lymphomas (NHL), especially those of B cell origin, includes using monoclonal antibodies, standard chemotherapy approaches (e.g., CHOP (cyclophosphamide, doxorubicin, vincristine, and prednisone), CVP (cyclophosphamide, vincristine, and prednisone), FCM (fludarabine, cyclophosphamide, and mitoxantrone), MCP (Mitoxantrone, Chlorambucil, Prednisolone), all optionally including rituximab (R) and the like), radioimmunotherapy, and combinations thereof, especially integration of an antibody therapy with chemotherapy.

Examples of unconjugated monoclonal antibodies for the treatment of NHL/B-cell cancers include rituximab, alemtuzumab, human or humanized anti-CD20 antibodies, lumiliximab, anti-TNF-related apoptosis-inducing ligand (anti-TRAIL), bevacizumab, galiximab, epratuzumab, SGN-40, and anti-CD74.

Examples of experimental antibody agents used in treatment of NHL/B-cell cancers include ofatumumab, ha20, PRO131921, alemtuzumab, galiximab, SGN-40, CHIR-12.12, epratuzumab, lumiliximab, apolizumab, milatuzumab, and bevacizumab.

Examples of standard regimens of chemotherapy for NHL/B-cell cancers include CHOP, FCM, CVP, MCP, R-CHOP (rituximab, cyclophosphamide, doxorubicin, vincristine, and prednisone), R-FCM, R-CVP, and R MCP.

Examples of radioimmunotherapy for NHL/B-cell cancers include yttrium-90 ibritumomab tiuxetan (ZEVALIN®) and iodine-131 tositumomab (BEXXAR®).

Mantle Cell Lymphoma Combination Therapy

Therapeutic treatments for mantle cell lymphoma (MCL) include combination chemotherapies such as CHOP, hyperCVAD, and FCM. These regimens can also be supplemented with the monoclonal antibody rituximab to form combination therapies R-CHOP, hyperCVAD-R, and R-FCM. Any of the abovementioned therapies may be combined with stem cell transplantation or ICE in order to treat MCL.

An alternative approach to treating MCL is immunotherapy. One immunotherapy uses monoclonal antibodies like rituximab. Another uses cancer vaccines, such as GTOP-99, which are based on the genetic makeup of an individual patient's tumor.

A modified approach to treat MCL is radioimmunotherapy, wherein a monoclonal antibody is combined with a radioisotope particle, such as iodine-131 tositumomab (BEXXAR®) and yttrium-90 ibritumomab tiuxetan (ZEVALIN®). In another example, BEXXAR® is used in sequential treatment with CHOP.

Other approaches to treating MCL include autologous stem cell transplantation coupled with high-dose chemotherapy, administering proteasome inhibitors such as bortezomib (VELCADE® or PS-341), or administering antiangiogenesis agents such as thalidomide, especially in combination with rituximab.

Another treatment approach is administering drugs that lead to the degradation of Bcl-2 protein and increase cancer cell sensitivity to chemotherapy, such as oblimersen, in combination with other chemotherapeutic agents.

A further treatment approach includes administering mTOR inhibitors, which can lead to inhibition of cell growth and even cell death. Non-limiting examples are sirolimus, temsirolimus (TORISEL®, CCI-779), CC-115, CC-223, SF-1126, PQR-309 (bimiralisib), voxtalisib, GSK-2126458, and temsirolimus in combination with RITUXAN®, VELCADE®, or other chemotherapeutic agents.

Other recent therapies for MCL have been disclosed. Such examples include flavopiridol, palbociclib (PD0332991), R-roscovitine (selicicilib, CYC202), styryl sulphones, obatoclax (GX15-070), TRAIL, Anti-TRAIL death receptors DR4 and DR5 antibodies, temsirolimus (TORISEL®, CCI-779), everolimus (RAD001), BMS-345541, curcumin, SAHA, thalidomide, lenalidomide (REVLIMID®, CC-5013), and geldanamycin (17 AAG).

Waldenstrom's Macroglobulinemia Combination Therapy

Therapeutic agents used to treat Waldenstrom's Macroglobulinemia (WM) include aldesleukin, alemtuzumab, alvocidib, amifostine trihydrate, aminocamptothecin, antineoplaston A10, antineoplaston AS2-1, anti-thymocyte globulin, arsenic trioxide, autologous human tumor-derived HSPPC-96, Bcl-2 family protein inhibitor ABT-263, beta alethine, bortezomib (VELCADE®), bryostatin 1, busulfan, campath-1H, carboplatin, carmustine, caspofungin acetate, CC-5103, cisplatin, clofarabine, cyclophosphamide, cyclosporine, cytarabine, denileukin diftitox, dexamethasone, docetaxel, dolastatin 10, doxorubicin hydrochloride, DT-PACE, enzastaurin, epoetin alfa, epratuzumab (hLL2-anti-CD22 humanized antibody), etoposide, everolimus, fenretinide, filgrastim, fludarabine, ibrutinib, ifosfamide, indium-111 monoclonal antibody MN-14, iodine-131 tositumomab, irinotecan hydrochloride, ixabepilone, lymphokine-activated killer cells, melphalan, mesna, methotrexate, mitoxantrone hydrochloride, monoclonal antibody CD19 (such as tisagenlecleucel-T, CART-19, CTL-019), monoclonal antibody CD20, motexafin gadolinium, mycophenolate mofetil, nelarabine, oblimersen, octreotide acetate, omega-3 fatty acids, oxaliplatin, paclitaxel, pegfilgrastim, PEGylated liposomal doxorubicin hydrochloride, pentostatin, perifosine, prednisone, recombinant flt3 ligand, recombinant human thrombopoietin, recombinant interferon alfa, recombinant interleukin-11, recombinant interleukin-12, rituximab, sargramostim, sildenafil citrate (VIAGRA®), simvastatin, sirolimus, tacrolimus, tanespimycin, thalidomide, therapeutic allogeneic lymphocytes, thiotepa, tipifarnib, tositumomab, ulocuplumab, veltuzumab, vincristine sulfate, vinorelbine ditartrate, vorinostat, WTi 126-134 peptide vaccine, WT-1 analog peptide vaccine, yttrium-90 ibritumomab tiuxetan, yttrium-90 humanized epratuzumab, and any combination thereof.

Examples of therapeutic procedures used to treat WM include peripheral blood stem cell transplantation, autologous hematopoietic stem cell transplantation, autologous bone marrow transplantation, antibody therapy, biological therapy, enzyme inhibitor therapy, total body irradiation, infusion of stem cells, bone marrow ablation with stem cell support, in vitro-treated peripheral blood stem cell transplantation, umbilical cord blood transplantation, immunoenzyme techniques, low-LET cobalt-60 gamma ray therapy, bleomycin, conventional surgery, radiation therapy, and nonmyeloablative allogeneic hematopoietic stem cell transplantation.

Diffuse Large B-Cell Lymphoma (DLBCL) Combination Therapy

Therapeutic agents used to treat diffuse large B-cell lymphoma (DLBCL) include cyclophosphamide, doxorubicin, vincristine, prednisone, anti-CD20 monoclonal antibodies, etoposide, bleomycin, many of the agents listed for WM, and any combination thereof, such as ICE and RICE. In some embodiments, therapeutic agents used to treat DLBCL include rituximab (Rituxan®), cyclophosphamide, doxorubicin hydrochloride (hydroxydaunorubicin), vincristine sulfate (Oncovin®), prednisone, bendamustine, ifosfamide, carboplatin, etoposide, ibrutinib, polatuzumab vedotin piiq, bendamustine, copanlisib, lenalidomide (Reylimid®), dexamethasone, cytarabine, cisplatin, Yescarta®, Kymriah®, Polivy® (polatuzumab vedotin), BR (bendamustine (Treanda®), gemcitabine, oxiplatin, oxaliplatin, tafasitamab, polatuzumab, cyclophosphamide, or combinations thereof. In some embodiments, therapeutic agents used to treat DLBCL include R-CHOP (rituximab+cyclophosphamide+doxorubicin hydrochloride (hydroxydaunorubicin)+vincristine sulfate (Oncovin®), +prednisone), rituximab+bendamustine, R-ICE (Rituximab+Ifosfamide+Carboplatin+Etoposide), rituximab+lenalomide, R-DHAP (rituximab+dexamethasone+high-dose cytarabine (Ara C)+cisplatin), Polivy® (polatuzumab vedotin)+BR (bendamustine (Treanda®) and rituximab (Rituxan®), R-GemOx (Gemcitabine+oxaliplatin+rituximab), Tafa-Len (tafasitamab+lenalidomide), Tafasitamab+Reylimid®, polatuzumab+bendamustine, Gemcitabine+oxaliplatin, R-EPOCH (rituximab+etoposide phosphate+prednisone+vincristine sulfate (Oncovin®)+cyclophosphamide+doxorubicin hydrochloride (hydroxydaunorubicin)), or CHOP (cyclophosphamide+doxorubicin hydrochloride (hydroxydaunorubicin)+vincristine sulfate (Oncovin®)+prednisone). In some embodiments, therapeutic agents used to treat DLBCL include tafasitamab, glofitamab, epcoritamab, Lonca-T (loncastuximab tesirine), Debio-1562, polatuzumab, Yescarta, JCAR017, ADCT-402, brentuximab vedotin, MT-3724, odronextamab, Auto-03, Allo-501A, or TAK-007.

Chronic Lymphocytic Leukemia Combination Therapy

Therapeutic agents used to treat chronic lymphocytic leukemia (CLL) include chlorambucil, cyclophosphamide, fludarabine, pentostatin, cladribine, doxorubicin, vincristine, prednisone, prednisolone, alemtuzumab, many of the agents listed for WM, and combination chemotherapy and chemoimmunotherapy, including the following common combination regimens: CVP, R-CVP, ICE, R-ICE, FCR, and FR.

High Risk Myelodysplastic Syndrome (HR MDS) Combination Therapy

Therapeutic agents used to treat HR MDS include azacitidine (Vidaza®), decitabine (Dacogen®), lenalidomide (Reylimid®), cytarabine, idarubicin, daunorubicin, and combinations thereof. In some embodiments, combinations include cytarabine+daunorubicin and cytarabine+idarubicin. In some embodiments, therapeutic agents used to treat HR MDS include pevonedistat, venetoclax, sabatolimab, guadecitabine, rigosertib, ivosidenib, enasidenib, selinexor, BGB324, DSP-7888, or SNS-301.

Low Risk Myelodysplastic Syndrome (LR MDS) Combination Therapy

Therapeutic agents used to treat LR MDS include lenalidomide, azacytidine, and combinations thereof. In some embodiments, therapeutic agents used to treat LR MDS include roxadustat, luspatercept, imetelstat, LB-100, or rigosertib.

High Risk Myelodysplastic Syndrome (HR MDS) Combination Therapy

Therapeutic agents used to treat HR MDS include azacitidine (Vidaza®), decitabine (Dacogen®), lenalidomide (Reylimid®), cytarabine, idarubicin, daunorubicin, and combinations thereof. In some embodiments, combinations include cytarabine+daunorubicin and cytarabine+idarubicin. In some embodiments, therapeutic agents used to treat HR MDS include pevonedistat, venetoclax, sabatolimab, guadecitabine, rigosertib, ivosidenib, enasidenib, selinexor, BGB324, DSP-7888, or SNS-301.

Low Risk Myelodysplastic Syndrome (LR MDS) Combination Therapy

Therapeutic agents used to treat LR MDS include lenalidomide, azacytidine, and combinations thereof. In some embodiments, therapeutic agents used to treat LR MDS include roxadustat, luspatercept, imetelstat, LB-100, or rigosertib.

Acute Myeloid Leukemia (AML) Combination Therapy

Therapautic agents used to treat AML include cytarabine, idarubicin, daunorubicin, midostaurin (Rydapt®), venetoclax, azacitidine, ivasidenib, gilteritinib, enasidenib, low-dose cytarabine (LoDAC), mitoxantrone, fludarabine, granulocyte-colony stimulating factor, idarubicin, gilteritinib (Xospata®), enasidenib (Idhifa®), ivosidenib (Tibsovo®), decitabine (Dacogen®), mitoxantrone, etoposide, Gemtuzumab ozogamicin (Mylotarg®), glasdegib (Daurismo®), and combinations thereof. In some embodiments, therapeutic agents used to treat AML include FLAG-Ida (fludarabine, cytarabine (Ara-C), granulocyte-colony stimulating factor (G-CSF) and idarubicin), cytarabine+idarubicin, cytarabine+daunorubicin+midostaurin, venetoclax+azacitidine, cytarabine+daunorubicin, or MEC (mitoxantrone, etoposide, and cytarabine). In some embodiments, therapeutic agents used to treat AML include pevonedistat, venetoclax, sabatolimab, eprenetapopt, or lemzoparlimab.

Multiple Myeloma (MM) Combination Therapy

Therapeutic agents used to treat MM include lenalidomide, bortezomib, dexamethasone, daratumumab (Darzalex®), pomalidomide, Cyclophosphamide, Carfilzomib (Kyprolis®), Elotuzumab (Empliciti), and combinations thereof. In some embodiments, therapeutic agents used to treat MM include RVS (lenalidomide+bortezomib+dexamethasone), RevDex (lenalidomide plus dexamethasone), CYBORD (Cyclophosphamide+Bortezomib+Dexamethasone), Vel/Dex (bortezomib plus dexamethasone), or PomDex (Pomalidomide+low-dose dexamethasone). In some embodiments, therapeutic agents used to treat MM include JCARH125, TAK-573, belantamab-m, ide-cel (CAR-T).

Breast Cancer Combination Therapy

Therapeutic agents used to treat breast cancer include albumin-bound paclitaxel, anastrozole, atezolizumab, capecitabine, carboplatin, cisplatin, cyclophosphamide, docetaxel, doxorubicin, epirubicin, everolimus, exemestane, fluorouracil, fulvestrant, gemcitabine, Ixabepilone, lapatinib, letrozole, methotrexate, mitoxantrone, paclitaxel, pegylated liposomal doxorubicin, pertuzumab, tamoxifen, toremifene, trastuzumab, vinorelbine, and any combinations thereof. In some embodiments, therapeutic agents used to treat breast cancer (e.g., HR+/−/HER2+/−) include trastuzumab (Herceptin®), pertuzumab (Perjeta®), docetaxel, carboplatin, palbociclib (Ibrance®), letrozole, trastuzumab emtansine (Kadcyla®), fulvestrant (Faslodex®), olaparib (Lynparza®), eribulin, tucatinib, capecitabine, lapatinib, everolimus (Afinitor®), exemestane, eribulin mesylate (Halaven®), and combinations thereof. In some embodiments, therapeutic agents used to treat breast cancer include trastuzumab+pertuzumab+docetaxel, trastuzumab+pertuzumab+docetaxel+carboplatin, palbociclib+letrozole, tucatinib+capecitabine, lapatinib+capecitabine, palbociclib+fulvestrant, or everolimus+exemestane. In some embodiments, therapeutic agents used to treat breast cancer include trastuzumab deruxtecan (Enhertu®), datopotamab deruxtecan (DS-1062), enfortumab vedotin (Padcev®), balixafortide, elacestrant, or a combination thereof. In some embodiments, therapeutic agents used to treat breast cancer include balixafortide+eribulin.

Triple Negative Breast Cancer (TNBC) Combination Therapy

Therapeutic agents used to treat TNBC include atezolizumab, cyclophosphamide, docetaxel, doxorubicin, epirubicin, fluorouracil, paclitaxel, and combinations thereof. In some embodiments, therapeutic agents used to treat TNBC include olaparib (Lynparza®), atezolizumab (Tecentriq®), paclitaxel (Abraxane®), eribulin, bevacizumab (Avastin®), carboplatin, gemcitabine, eribulin mesylate (Halaven®), sacituzumab govitecan (Trodelvy®), pembrolizumab (Keytruda®), cisplatin, doxorubicin, epirubicin, or a combination thereof. In some embodiments, therapeutic agents to treat TNBC include atezolizumab+paclitaxel, bevacizumab+paclitaxel, carboplatin+paclitaxel, carboplatin+gemcitabine, or paclitaxel+gemcitabine. In some embodiments, therapeutic agents used to treat TNBC include eryaspase, capivasertib, alpelisib, rucaparib+nivolumab, atezolumab+paclitaxel+gemcitabine+capecitabine+carboplatin, ipatasertib+paclitaxel, ladiratuzumab vedotin+pembrolimab, durvalumab+DS-8201a, trilaciclib+gemcitabine+carboplatin. In some embodiments, therapeutic agents used to treat TNBC include trastuzumab deruxtecan (Enhertu®), datopotamab deruxtecan (DS-1062), enfortumab vedotin (Padcev®), balixafortide, adagloxad simolenin, nelipepimut-s (NeuVax®), nivolumab (Opdivo®), rucaparib, toripalimab (Tuoyi®), camrelizumab, capivasertib, durvalumab (Imfinzi®), and combinations thereof. In some embodiments, therapeutic agents use to treat TNBC include nivolumab+rucaparib, bevacizumab (Avastin®)+chemotherapy, toripalimab+paclitaxel, toripalimab+albumin-bound paclitaxel, camrelizumab+chemotherapy, pembrolizumab+chemotherapy, balixafortide+eribulin, durvalumab+trastuzumab deruxtecan, durvalumab+paclitaxel, or capivasertib+paclitaxel.

Bladder Cancer Combination Therapy

Therapeutic agents used to treat bladder cancer include datopotamab deruxtecan (DS-1062), trastuzumab deruxtecan (Enhertu®), erdafitinib, eganelisib, lenvatinib, bempegaldesleukin (NKTR-214), or a combination thereof. In some embodiments, therapeutic agents used to treat bladder cancer include eganelisib+nivolumab, pembrolizumab (Keytruda®)+enfortumab vedotin (Padcev®), nivolumab+ipilimumab, duravalumab+tremelimumab, lenvatinib+pembrolizumab, enfortumab vedotin (Padcev®)+pembrolizumab, and bempegaldesleukin+nivolumab.

Colorectal Cancer (CRC) Combination Therapy

Therapeutic agents used to treat CRC include bevacizumab, capecitabine, cetuximab, fluorouracil, irinotecan, leucovorin, oxaliplatin, panitumumab, ziv-aflibercept, and any combinations thereof. In some embodiments, therapeutic agents used to treat CRC include bevacizumab (Avastin®), leucovorin, 5-FU, oxaliplatin (FOLFOX), pembrolizumab (Keytruda®), FOLFIRI, regorafenib (Stivarga®), aflibercept (Zaltrap®), cetuximab (Erbitux®), Lonsurf (Orcantas®), XELOX, FOLFOXIRI, or a combination thereof. In some embodiments, therapeutic agents used to treat CRC include bevacizumab+leucovorin+5-FU, bevacizumab+leucovorin+5-FU+oxaliplatin (FOLFOX), bevacizumab+FOLFIRI, bevacizumab+FOLFOX, aflibercept+FOLFIRI, cetuximab+FOLFIRI, cetuximab+FOLFOX, bevacizumab+XELOX, and bevacizumab+FOLFOXIRI. In some embodiments, therapeutic agents used to treat CRC include binimetinib+encorafenib+cetuximab, trametinib+dabrafenib+panitumumab, trastuzumab+pertuzumab, napabucasin+FOLFIRI+bevacizumab, nivolumab+ipilimumab.

Esophageal and Esophagogastric Junction Cancer Combination Therapy

Therapeutic agents used to treat esophageal and esophagogastric junction cancer include capecitabine, carboplatin, cisplatin, docetaxel, epirubicin, fluoropyrimidine, fluorouracil, irinotecan, leucovorin, oxaliplatin, paclitaxel, ramucirumab, trastuzumab, and any combinations thereof. In some embodiments, therapeutic agents used to treat gastroesophageal junction cancer (GEJ) include herceptin, cisplatin, 5-FU, ramicurimab, or paclitaxel. In some embodiments, therapeutic agents used to treat GEJ cancer include ALX-148, AO-176, or IBI-188.

Gastric Cancer Combination Therapy

Therapeutic agents used to treat gastric cancer include capecitabine, carboplatin, cisplatin, docetaxel, epirubicin, fluoropyrimidine, fluorouracil, Irinotecan, leucovorin, mitomycin, oxaliplatin, paclitaxel, ramucirumab, trastuzumab, and any combinations thereof.

Head and Neck Cancer Combination Therapy

Therapeutic agents used to treat head & neck cancer include afatinib, bleomycin, capecitabine, carboplatin, cetuximab, cisplatin, docetaxel, fluorouracil, gemcitabine, hydroxyurea, methotrexate, nivolumab, paclitaxel, pembrolizumab, vinorelbine, and any combinations thereof.

Therapeutic agents used to treat head and neck squamous cell carcinoma (HNSCC) include pembrolizumab, carboplatin, 5-FU, docetaxel, cetuximab (Erbitux®), cisplatin, nivolumab (Opdivo®), and combinations thereof. In some embodiments, therapeutic agents used to treat HNSCC include pembrolizumab+carboplatin+5-FU, cetuximab+cisplatin+5-FU, cetuximab+carboplatin+5-FU, cisplatin+5-FU, and carboplatin+5-FU. In some embodiments, therapeutic agents used to treat HNSCC include durvalumab, durvalumab+tremelimumab, nivolumab+ipilimumab, rovaluecel, pembrolizumab, pembrolizumab+epacadostat, GSK3359609+pembrolizumab, lenvatinib+pembrolizumab, retifanlimab, retifanlimab+enobituzumab, ADU-S100+pembrolizumab, epacadostat+nivolumab+ipilimumab/lirilumab.

Non-Small Cell Lung Cancer Combination Therapy

Therapeutic agents used to treat non-small cell lung cancer (NSCLC) include afatinib, albumin-bound paclitaxel, alectinib, atezolizumab, bevacizumab, bevacizumab, cabozantinib, carboplatin, cisplatin, crizotinib, dabrafenib, docetaxel, erlotinib, etoposide, gemcitabine, nivolumab, paclitaxel, pembrolizumab, pemetrexed, ramucirumab, trametinib, trastuzumab, vandetanib, vemurafenib, vinblastine, vinorelbine, and any combinations thereof. In some embodiments, therapeutic agents used to treat NSCLC include alectinib (Alecensa®), dabrafenib (Tafinlar®), trametinib (Mekinist®), osimertinib (Tagrisso®), entrectinib (Tarceva®), crizotinib (Xalkori®), pembrolizumab (Keytruda®), carboplatin, pemetrexed (Alimta®), nab-paclitaxel (Abraxane®), ramucirumab (Cyramza®), docetaxel, bevacizumab (Avastin®), brigatinib, gemcitabine, cisplatin, afatinib (Gilotrif®), nivolumab (Opdivo®), gefitinib (Iressa®), and combinations thereof. In some embodiments, therapeutic agents used to treat NSCLC include dabrafenib+trametinib, pembrolizumab+carboplatin+pemetrexed, pembrolizumab+carboplatin+paclitaxel, pembrolizumab+carboplatin+nab-paclitaxel, ramucirumab+docetaxel, bevacizumab+carboplatin+pemetrexed, pembrolizumab+pemetrexed+cisplatin, cisplatin+pemetrexed, bevacizumab+carboplatin+nab-paclitaxel, cisplatin+gemcitabine, nivolumab+docetaxel, nivolumab+ipilimumab, carboplatin+pemetrexed, carboplatin+nab-paclitaxel, or pemetrexed+cisplatin+carboplatin. In some embodiments, therapeutic agents used to NSCLC include datopotamab deruxtecan (DS-1062), ipilimumab, trastuzumab deruxtecan (Enhertu®), enfortumab vedotin (Padcev®), durvalumab, canakinumab, cemiplimab, nogapendekin alfa, avelumab, tiragolumab, domvanalimab, vibostolimab, ociperlimab, or a combination thereof. In some embodiments, therapeutic agents used to treat NSCLC include datopotamab deruxtecan+pembrolizumab, datopotamab deruxtecan+durvalumab, durvalumab+tremelimumab, pembrolizumab+lenvatinib+pemetrexed, pembrolizumab+olaparib, nogapendekin alfa (N-803)+pembrolizumab, tiragolumab+atezolizumab, vibostolimab+pembrolizumab, or ociperlimab+tislelizumab.

Small Cell Lung Cancer Combination Therapy

Therapeutic agents used to treat small cell lung cancer (SCLC) include atezolizumab, bendamustime, carboplatin, cisplatin, cyclophosphamide, docetaxel, doxorubicin, etoposide, gemcitabine, ipillimumab, irinotecan, nivolumab, paclitaxel, temozolomide, topotecan, vincristine, vinorelbine, and any combinations thereof. In some embodiments, therapeutic agents used to treat SCLC include atezolizumab, carboplatin, cisplatin, etoposide, paclitaxel, topotecan, nivolumab, durvalumab, trilaciclib, or combinations thereof. In some embodiments, therapeutic agents used to treat SCLC include atezolizumab+carboplatin+etoposide, atezolizumab+carboplatin, atezolizumab+etoposide, or carboplatin+paclitaxel.

Ovarian Cancer Combination Therapy

Therapeutic agents used to treat ovarian cancer include 5-flourouracil, albumin bound paclitaxel, altretamine, anastrozole, bevacizumab, capecitabine, carboplatin, cisplatin, cyclophosphamide, docetaxel, doxorubicin, etoposide, exemestane, gemcitabine, ifosfamide, irinotecan, letrozole, leuprolide acetate, liposomal doxorubicin, megestrol acetate, melphalan, olaparib, oxaliplatin, paclitaxel, pazopanib, pemetrexed, tamoxifen, topotecan, vinorelbine, and any combinations thereof.

Pancreatic Cancer Combination Therapies

Therapeutic agents used to treat pancreatic cancer include 5-FU, leucovorin, oxaliplatin, irinotecan, gemcitabine, nab-paclitaxel (Abraxane®), FOLFIRINOX, FOLFOX, XELOX, and combinations thereof. In some embodiments, therapeutic agents used to treat pancreatic cancer include 5-FU+leucovorin+oxaliplatin+irinotecan, 5-FU+nanoliposomal irinotecan, cisplatin+gemcitabine, leucovorin+nanoliposomal irinotecan, 5-FU+gemcitabine, and gemcitabine+nab-paclitaxel.

Endometrial Cancer Combination Therapies

Therapeutic treatments used to treat endometrial cancer include surgery, chemotherapy, radiation therapy, hormone therapy, targeted therapy, and immunotherapy. In some embodiments, the therapeutic treatments include Anti-angiogenesis therapy, Mammalian target of rapamycin (mTOR) inhibitors, Targeted therapy to treat a rare type of uterine cancer.

Therapeutic agents used to treat endometrial cancer include carboplatin, paclitaxel, cisplatin, doxorubicin, ifosfamide, progesterone, anastrozole (Arimidex®), letrozole (Femara®), and exemestane (Aromasin®), pembrolizumab (Keytruda®), lenvatinib (Lenvima®), dostarlimab (Jemperli®), and combinations thereof.

Prostate Cancer Combination Therapies

Therapeutic agents used to treat prostate cancer include enzalutamide (Xtandi®), leuprolide, trifluridine, tipiracil (Lonsurf), cabazitaxel, prednisone, abiraterone (Zytiga®), docetaxel, mitoxantrone, bicalutamide, LHRH, flutamide, ADT, sabizabulin (Veru-111), and combinations thereof. In some embodiments, therapeutic agents used to treat prostate cancer include enzalutamide+leuprolide, trifluridine+tipiracil (Lonsurf), cabazitaxel+prednisone, abiraterone+prednisone, docetaxel+prednisone, mitoxantrone+prednisone, bicalutamide+LHRH, flutamide+LHRH, leuprolide+flutamide, and abiraterone+prednisone+ADT.

Additional Exemplified Combination Therapies

In some embodiments, the compound provided herein is administered with one or more therapeutic agents selected from a PI3K inhibitor, a Trop-2 binding agent, CD47 antagonist, a SIRPα antagonist, a FLT3R agonist, a PD-1 antagonist, a PD-L1 antagonist, an MCL1 inhibitor, a CCR8 binding agent, an HPK1 antagonist, a DGKa inhibitor, a CISH inhibitor, a PARP-7 inhibitor, a Cbl-b inhibitor, a KRAS inhibitor (e.g., a KRAS G12C or G12D inhibitor), a KRAS degrader, a beta-catenin degrader, a helios degrader, a CD73 inhibitor, an adenosine receptor antagonist, a TIGIT antagonist, a TREM1 binding agent, a TREM2 binding agent, a CD137 agonist, a GITR binding agent, an OX40 binding agent, and a CAR-T cell therapy.

In some embodiments, the compound provided herein is administered with one or more therapeutic agents selected from a PI3Kd inhibitor (e.g., idealisib), an anti-Trop-2 antibody drug conjugate (e.g., sacituzumab govitecan, datopotamab deruxtecan (DS-1062)), an anti-CD47 antibody or a CD47-blocking agent (e.g., magrolimab, DSP-107, AO-176, ALX-148, letaplimab (IBI-188), lemzoparlimab, TTI-621, TTI-622), an anti-SIRPα antibody (e.g., GS-0189), a FLT3L-Fc fusion protein (e.g., GS-3583), an anti-PD-1 antibody (pembrolizumab, nivolumab, zimberelimab), a small molecule PD-L1 inhibitor (e.g., GS-4224), an anti-PD-L1 antibody (e.g., atezolizumab, avelumab), a small molecule MCL1 inhibitor (e.g., GS-9716), a small molecule HPK1 inhibitor (e.g., GS-6451), a HPK1 degrader (PROTAC; e.g., ARV-766), a small molecule DGKa inhibitor, a small molecule CD73 inhibitor (e.g., quemliclustat (AB680)), an anti-CD73 antibody (e.g., oleclumab), a dual $A_{2a}/A_{2b}$ adenosine receptor antagonist (e.g., etrumadenant (AB928)), an anti-TIGIT antibody (e.g., tiragolumab, vibostolimab, domvanalimab, AB308), an anti-TREM1 antibody (e.g., PY159), an anti-TREM2 antibody (e.g., PY314), a CD137 agonist (e.g., AGEN-2373), a GITR/OX40 binding agent (e.g., AGEN-1223) and a CAR-T cell therapy (e.g., axicabtagene ciloleucel, brexucabtagene autoleucel, tisagenlecleucel).

In some embodiments, the compound provided herein is administered with one or more therapeutic agents selected from idealisib, sacituzumab govitecan, magrolimab, GS-0189, GS-3583, zimberelimab, GS-4224, GS-9716, GS-6451, quemliclustat (AB680), etrumadenant (AB928), domvanalimab, AB308, PY159, PY314, AGEN-1223, AGEN-2373, axicabtagene ciloleucel and brexucabtagene autoleucel.

IX. Compound Preparation

In some embodiments, the present disclosure provides processes and intermediates useful for preparing the compounds disclosed herein or pharmaceutically acceptable salts thereof.

Compounds disclosed herein can be purified by any of the means known in the art, including chromatographic means, including but not limited to high-performance liquid chromatography (HPLC), preparative thin layer chromatography, flash column chromatography, and ion exchange chromatography. Any suitable stationary phase can be used, including but not limited to, normal and reversed phases as well as ionic resins. In some embodiments, the disclosed compounds are purified via silica gel and/or alumina chromatography.

During any of the processes for preparation of the compounds provided herein, it can be necessary and/or desirable to protect sensitive or reactive groups on any of the molecules concerned. This can be achieved by means of conventional protecting groups as described in standard works, such as T. W. Greene and P. G. M. Wuts, Protective Groups in Organic Synthesis, $4^{th}$ ed., Wiley, New York 2006. The protecting groups can be removed at a convenient subsequent stage using methods known from the art.

Exemplary chemical entities useful in methods of the embodiments will now be described by reference to illustrative synthetic schemes for their general preparation herein and the specific examples that follow. Skilled artisans will recognize that, to obtain the various compounds herein, starting materials can be suitably selected so that the ultimately desired substituents will be carried through the reaction scheme with or without protection as appropriate to yield the desired product. Alternatively, it can be necessary or desirable to employ, in the place of the ultimately desired substituent, a suitable group that can be carried through the reaction scheme and replaced as appropriate with the desired substituent. Furthermore, one of skill in the art will recognize that the transformations shown in the schemes below can be performed in any order that is compatible with the functionality of the particular pendant groups.

The methods of the present disclosure generally provide a specific enantiomer or diastereomer as the desired product, although the stereochemistry of the enantiomer or diastereomer was not determined in all cases. When the stereochemistry of the specific stereocenter in the enantiomer or diastereomer is not determined, the compound is drawn without showing any stereochemistry at that specific stereocenter even though the compound can be substantially enantiomerically or diastereomerically pure.

Compounds disclosed herein can be prepared from commercially available reagents using the synthetic methods and reaction schemes described herein, or using other reagents and conventional methods known to persons of ordinary skill in the art. For instance, representative syntheses of compounds of the present disclosure are described in the schemes below, and the particular examples that follow.

EXAMPLES

I. Abbreviations

Certain abbreviations and acronyms are used in describing the experimental details. Although most of these would be understood by one skilled in the art, Table 1 contains a list of many of these abbreviations and acronyms.

TABLE 1

List of Abbreviations and Acronyms

| Abbreviation | Meaning |
|---|---|
| ° C. | degree(s) Celsius |
| μg or ug | microgram(s) |
| μL or uL | microliter(s) |
| μm or um | micron(s) |
| μmol or umol | micromole(s) |
| ACN | acetonitrile |
| aq | aqueous |
| 9-BBN | 9-borabicyclo[3.3.1]nonane |
| Boc | tert-butoxycarbonyl |
| br s | broad singlet |
| cataCXium A Pd G3 | mesylate[(di(1-adamantyl)-n-butylphosphine)-2-(2'-amino-1,1'-biphenyl)]palladium(II) (CAS # 1651823-59-4) |
| Cbz | benzyloxycarbonyl |
| CPhos Pd G3 | [(2-dicyclohexylphosphino-2',6'-bis(N,N-dimethylamino)-1,1'-biphenyl)-2-(2'-amino-1,1'-biphenyl)] palladium(II) methanesulfonate (CAS # 1447963-73-6) |
| d | doublet |
| DCM | dichloromethane |
| dd | doublet of doublets |
| ddd | doublet of doublet of doublets |
| ddt | doublet of doublet of triplets |
| DIPEA | N,N-diisopropylethylamine |
| DMAP | 4-dimethylamiopyridine |
| DMF | dimethylformamide |
| DMP | Dess-Martin periodinane |
| DMSO | dimethyl sulfoxide |
| dt | doublet of triplets |
| Et | ethyl |
| EtOAc or EA | ethyl acetate |
| g | gram(s) |
| h | hour(s) |
| HATU | hexafluorophosphate azabenzotriazole tetramethyl uronium |

TABLE 1-continued

| List of Abbreviations and Acronyms | |
|---|---|
| Abbreviation | Meaning |
| HPLC | high-performance liquid chromatography |
| Hz | hertz |
| $^i$Pr | isopropyl |
| J | coupling constant |
| KHMDS | potassium bis(trimethylsilyl)amide |
| KOAc | potassium acetate |
| LAH | lithium aluminum hydride |
| LCMS | liquid chromatography mass spectrometry |
| LDA | lithium diisopropylamide |
| LiHMDS | lithium bis(trimethylsilyl)amide |
| m | multiplet |
| M | molarity |
| Me | methyl |
| MeCN | acetonitrile |
| MeOH | methanol |
| mg | milligram(s) |
| MHz | megahertz |
| min | minute(s) |
| mL | milliliter(s) |
| mm | millimeter(s) |
| mmol | millimole(s) |
| MOMO or OMOM | methoxymethoxy |
| NaOMe | sodium methoxide |
| n-BuLi | n-butyllithium |
| NMR | nuclear magnetic resonance |
| OSEM | 2-(trimethylsilyl)ethoxymethoxy |
| OTf | trifluoromethanesulfonate |
| Pd(dppf)$Cl_2$ | [1,1'-bis(diphenylphosphino)ferrocene]dichloropalladium(II) (CAS # 72287-26-4) |
| PE | petroleum ether |
| Piv | pivaloyl |
| qd | quartet of doublets |
| rt | room temperature |
| S | singlet |
| SFC | supercritical fluid chromatography |
| t | triplet |
| TBAF | tetrabutylammonium fluoride |
| TBS | tert-butyldimethylsilyl |
| TBSCl | tert-Butyldimethylsilyl chloride |
| $^t$Bu | tert-butyl |
| td | triplet of doublets |
| TES | triethylsilane |
| $TF_2O$ or $Tf_2O$ | trifluoromethanesulfonic anhydride |
| TFA | trifluoroacetic acid |
| THF | tetrahydrofuran |
| TIPS | triisopropylsilyl |
| TMS | trimethylsilyl |
| tt | triplet of triplets |
| v/v | volume/volume |
| wt | weight |
| δ | parts per million referenced to residual non-deuterated solvent peak |

II. Intermediates

Intermediate 2-1: tert-butyl (5S,5aS,6S,9R)-2-(8-ethynyl-7-fluoro-3-hydroxynaphthalen-1-yl)-1-fluoro-12-(((2R,7aS)-2-fluorotetrahydro-1H-pyrrolizin-7a(5H)-yl)methoxy)-5-methyl-4,5,5a,6,7,8,9,10-octahydro-3,10a,11,13,14-pentaaza-6,9-methanonaphtho[1,8-ab]heptalene-14-carboxylate

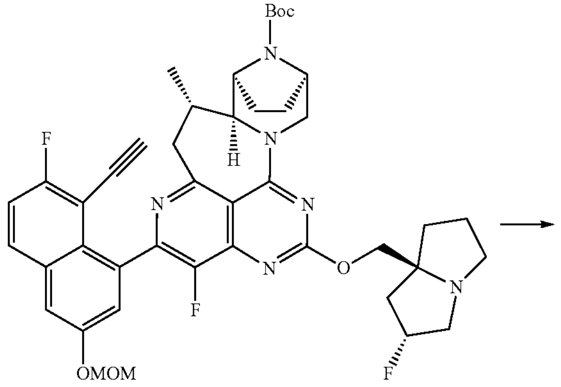

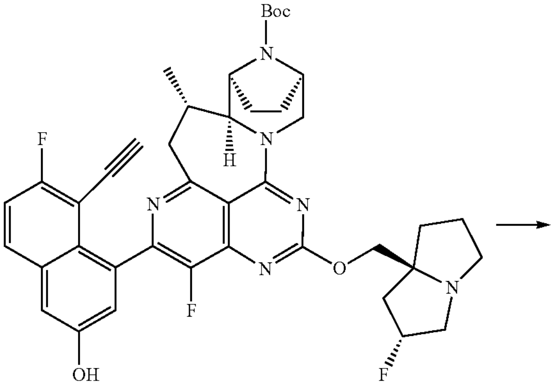

2-1

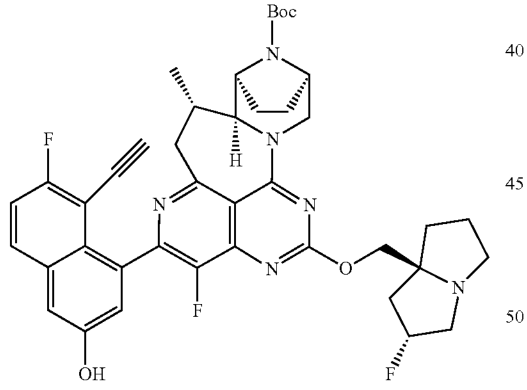

2-1

The solution of HCl in 1,4-dioxane (4 M, 0.287 mL, 1.15 mmol) was added dropwise to the solution of tert-butyl (5S,5aS,6S,9R)-2-(8-ethynyl-7-fluoro-3-(methoxymethoxy)naphthalen-1-yl)-1-fluoro-12-(((2R,7aS)-2-fluorotetrahydro-1H-pyrrolizin-7a(5H)-yl)methoxy)-5-methyl-4,5,5a,6,7,8,9,10-octahydro-3,10a,11,13,14-pentaaza-6,9-methanonaphtho[1,8-ab]heptalene-14-carboxylate (150 mg, 0.191 mmol, prepared according the procedure described for Comparative Example 64 of U.S. application Ser. No. 18/303,813, published as US 2023/0374036) in DCM (4 mL) at 0° C. The resulting reaction mixture was warmed to rt and stirred for 2 h. It was quenched by 10 mL of saturated aqueous solution of $NaHCO_3$. The mixture was extracted with EtOAc (3×15 mL). The combined organic phase was dried over $Na_2SO_4$, filtered, and concentrated in vacuo. The residue was purified by silica gel column chromatography (MeOH in DCM, 0-10%) to give Intermediate 2-1. LCMS: 741.2.

Intermediate 2-2: tert-butyl (5S,5aS,6S,9R)-2-(8-ethynyl-7-fluoro-3-((5-methyl-2-oxo-1,3-dioxol-4-yl)methoxy)naphthalen-1-yl)-1-fluoro-12-(((2R,7aS)-2-fluorotetrahydro-1H-pyrrolizin-7a(5H)-yl)methoxy)-5-methyl-4,5,5a,6,7,8,9,10-octahydro-3,10a,11,13,14-pentaaza-6,9-methanonaphtho[1,8-ab]heptalene-14-carboxylate

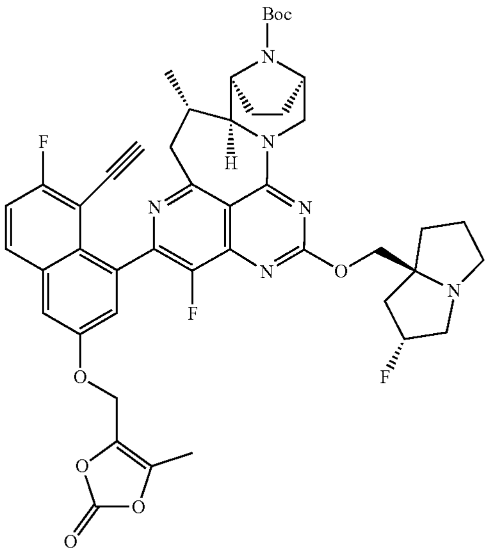

2-2

$PPh_3$ (46 mg, 0.176 mmol) and DIAD (0.0532 mL, 0.27 mmol) were added sequentially to the solution of Intermediate 2-1 (100 mg, 0.135 mmol) in THE at 0° C. The resulting solution was stirred for 10 min. 4-(Hydroxymethyl)-5-methyl-1,3-dioxol-2-one (26.3 mg, 0.202 mmol) was added. The reaction mixture was stirred at rt for 1 h and concentrated in vacuo. The residue was purified by silica gel column chromatography (MeOH in DCM, 0-10%) to give Intermediate 2-2. LCMS: 853.2.

Intermediate 2-3: 4-(((5-ethynyl-6-fluoro-4-((5S,5aS,6S,9R)-1-fluoro-12-(((2R,7aS)-2-fluorotetrahydro-1H-pyrrolizin-7a(5H)-yl)methoxy)-5-methyl-4,5,5a,6,7,8,9,10-octahydro-3,10a,11,13,14-pentaaza-6,9-methanonaphtho[1,8-ab]heptalen-2-yl)naphthalen-2-yl)oxy)methyl)-5-methyl-1,3-dioxol-2-one

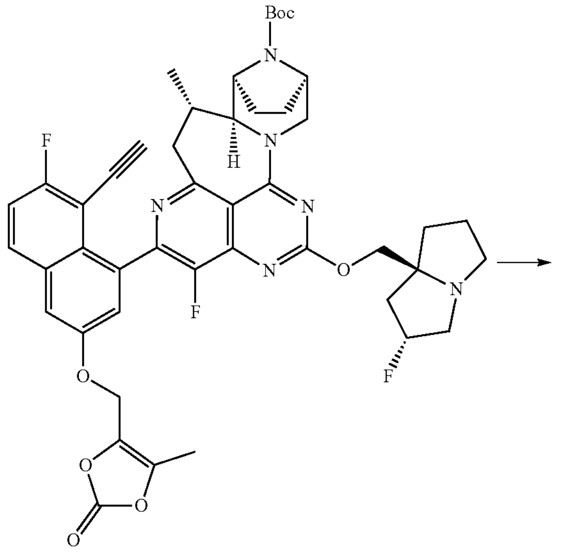

2-2

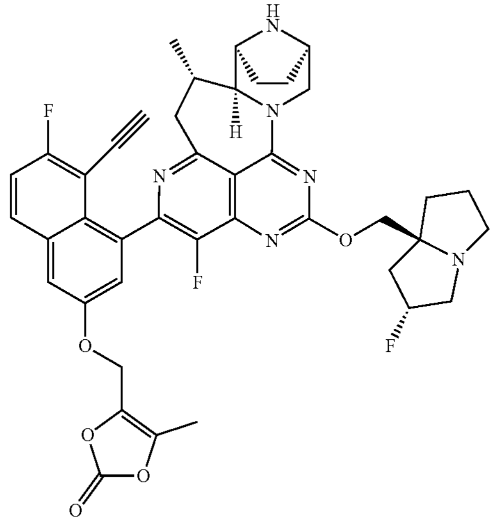

2-3

To a vigorously stirred solution of Intermediate 2-2 (80 mg, 0.094 mmol) in anhydrous DCM (2 mL), 2,6-lutidine (60.3 mg, 0.563 mmol) and TMSOTf (125 mg, 0.563 mmol) were added sequentially at 0° C. under $N_2$ atmosphere. The resulting solution was stirred at 0° C. for 0.5 hour. The reaction was quenched by water (5 mL) and extracted with EtOAc (2×10 mL). The combined organic phase was dried over $Na_2SO_4$, filtered, and concentrated in vacuo to give the crude product of Intermediate 2-3, which was used for the next step without purification. LCMS: 753.1.

Intermediate B5-1: tert-butyl (1S,2R,5R)-3-(5,7-dibromo-6-chloro-8-fluoro-2-(methylthio)quinazolin-4-yl)-2-vinyl-3,8-diazabicyclo[3.2.1]octane-8-carboxylate

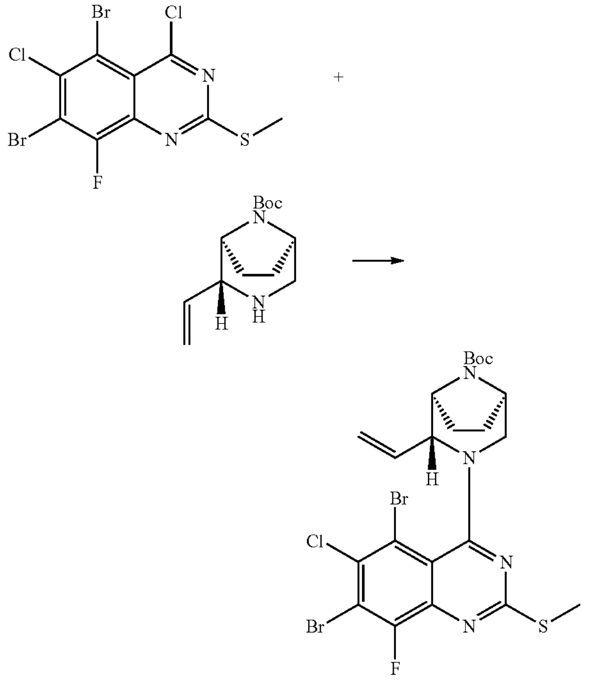

B5-1

Intermediate B5-1 was synthesized in a manner similar to Intermediate C2-10 using intermediate tert-butyl (1S,2R,5R)-2-vinyl-3,8-diazabicyclo[3.2.1]octane-8-carboxylate (prepared according to Comparative Intermediate 27-5 of U.S. application Ser. No. 18/303,813, published as US 2023/0374036 and reproduced below) instead of intermediate tert-butyl (1S,2R,5R)-2-allyl-3,8-diazabicyclo[3.2.1]octane-8-carboxylate. LCMS: 623.1.

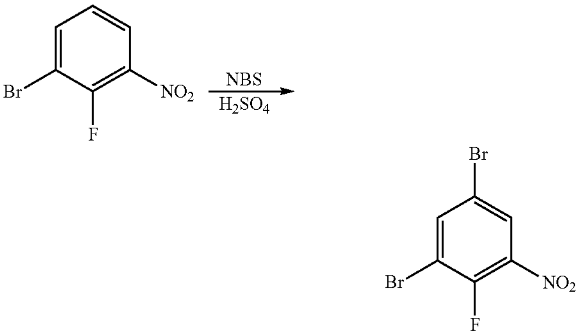

C2-1

To a solution of 1-bromo-2-fluoro-3-nitro-benzene (250.0 g, 1136.3 mmol, 1.0 equiv.) in $H_2SO_4$ (70 mL) was added NBS (202.2 g, 318.2 mmol, 1.0 equiv.) at 25° C. The mixture was heated to 50° C. and stirred at 50° C. for 3 hours. The resulting mixture was cooled to 25° C. and quenched with ice water (2000 mL), extracted with EA (3×1000 mL). The combined organic phase was dried over $Na_2SO_4$, filtered and concentrated under reduced pressure to give a residue. The residue was purified by flash silica gel chromatography (PE/EA=10/1) to give Intermediate C2-1. $^1H$ NMR (400 MHz, $CDCl_3$) 8.06 (dd, J=5.9 Hz, 1H), 7.93 (dd, J=5.5 Hz, 1H).

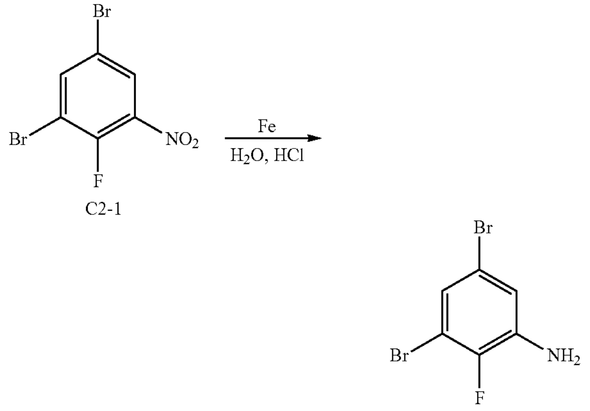

C2-1

C2-2

To a solution of Intermediate C2-1 (230.0 g, 768.9 mmol, 1.0 equiv.) and Fe (129.2 g, 2306.9 mmol, 3.0 equiv.) in $H_2O$ (100 mL) was added con. HCl (400 mL) at 25° C. The mixture was heated to 100° C. and stirred at 100° C. for 1 hour. The resulting mixture was cooled to 25° C. and diluted with ice water (1000 mL). After filtration, the filter cake was washed with EA (600 mL), then the filtrate was washed with brine. The organic phase was dried over $Na_2SO_4$, filtered and concentrated under reduce pressure to give Intermediate C2-2. LCMS: 269.9.

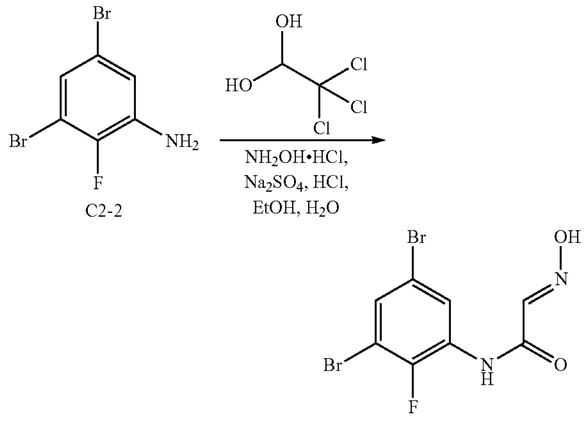

C2-2

C2-3

To a solution of 2,2,2-trichloroethane-1,1-diol (193.6 g, 1171.0 mmol, 1.5 equiv.), $Na_2SO_4$ (889.4 g, 6.2 mol, 8.0 equiv.) and $NH_2OH·HCl$ (189.8 g, 2732.3 mmol, 3.5 equiv.) in $H_2O$ (900 mL) was added a mixture of Intermediate C2-2 (210.0 g, 780.6 mmol, 1.0 equiv.) in EtOH (135 mL) and con. HCl (18 mL) and $H_2O$ (450 mL) at 50° C. The mixture was heated to 70° C. and stirred at 70° C. for 12 hours. The resulting mixture was cooled to 25° C. The mixture was filtered and the filtrate was concentrated under reduced pressure to afford Intermediate C2-3. LCMS: 340.8.

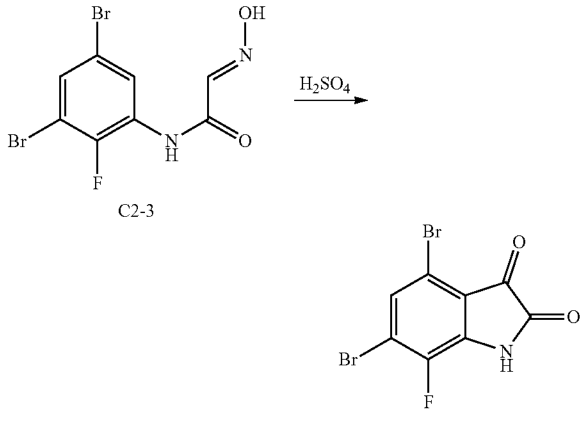

C2-3

C2-4

To a stirred solution of $H_2SO_4$ (150 mL) was added Intermediate C2-3 (195.0 g, 573.5 mmol, 1.0 equiv.) at 50° C., then the mixture was heated to 70° C. stirred at 70° C. for 1 hour. The reaction mixture was cooled to at 25° C. and quenched with ice water (600 mL). After filtration, and the filter cake was washed with water (3×200 mL). The solid was concentrated under reduced pressure to afford Intermediate C2-4. LCMS: 323.9.

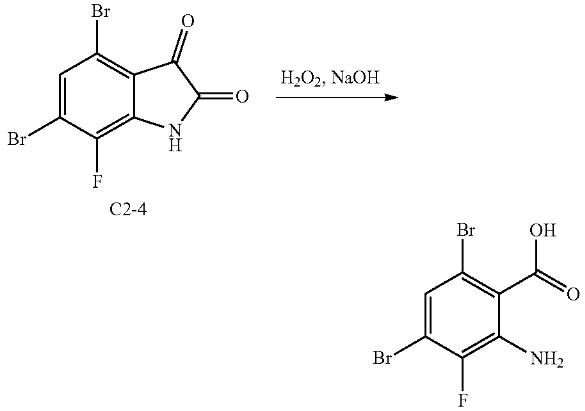

C2-4

C2-5

To a solution of Intermediate C2-4 (20.0 g, 61.9 mmol, 1.0 equiv.) in NaOH (2.0 M, 309.6 mL, 10.0 equiv.) was added $H_2O_2$ (35.1 g, 309.6 mmol, 30% purity, 5.0 equiv.) at 0° C. The mixture was stirred at 25° C. for 16 hours. The reaction mixture was adjusted to pH 2 with 1.0 M HCl (200 mL). After filtration, the filter cake was washed with water (3×200 mL). The solid was concentrated under reduced pressure to give Intermediate C2-5. LCMS: 313.8.

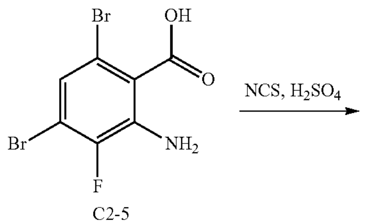

C2-5

-continued

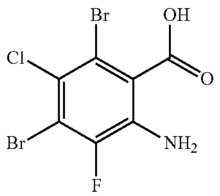

C2-6

To a solution of Intermediate C2-5 (22.0 g, 70.3 mmol, 1.0 equiv.) in $H_2SO_4$ (100 mL) was added NCS (18.7 g, 140.6 mmol, 2.0 equiv.) at 25° C. The mixture was heated to 80° C. and stirred at 80° C. for 12 hours. The reaction mixture was quenched with ice $H_2O$ (300 mL). After filtration, the filter cake was washed with water (3×100 mL). The solid was concentrated under reduced pressure to give Intermediate C2-6. LCMS: 347.8.

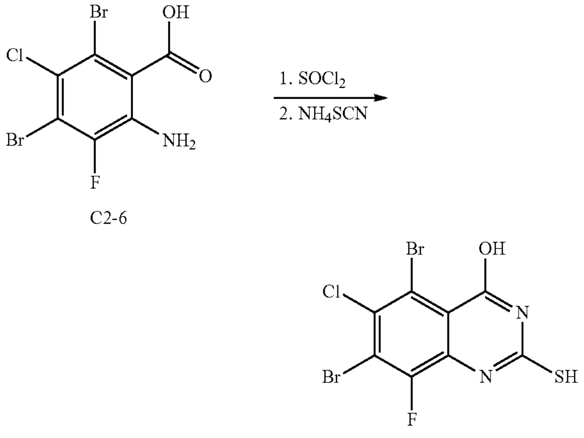

C2-6

C2-7

To a solution of Intermediate C2-6 (8.0 g, 23.0 mmol, 1.0 equiv.) in DCM (40 mL) was added $SOCl_2$ (16.4 g, 138.2 mmol, 6.0 equiv.) and DMF (168 mg, 2.3 mmol, 0.1 equiv.), the reaction mixture was heated to 60° C. and stirred at 60° C. for 5 hours. The resulting mixture was cooled to 25° C. The resulting mixture was concentrated under reduced pressure to give a residue. The residue was dissolved in acetone (40 mL) and added $NH_4SCN$ (2.6 g, 34.5 mmol, 1.5 equiv.) at 25° C. The reaction mixture was stirred at 25° C. for 2 hours. The resulting mixture was filtered, the filter cake was washed with $H_2O$ (100 mL) and 10% NaOH (30 mL), then the solid was triturated with MeOH (50 mL) and ACN (50 mL) to give Intermediate C2-7.

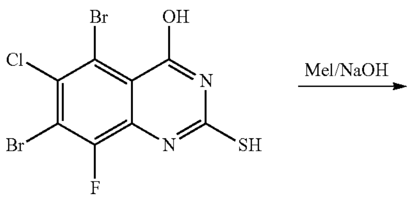

C2-7

-continued

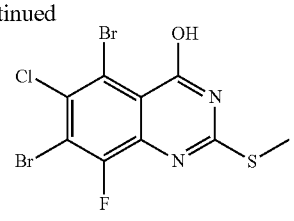

C2-8

To a mixture of Intermediate C2-7 (1.0 g, 2.5 mmol, 1.0 equiv.) in MeOH (20 mL) and $H_2O$ (10 mL) was added NaOH (206 mg, 5.1 mmol, 2.0 equiv.) and MeI (731 mg, 5.1 mmol, 2.0 equiv.) at 25° C., the reaction mixture was stirred at 25° C. for 0.5 hour. The resulting mixture was adjusted to pH 6 with 1 N HCl. After filtration, the filter cake was washed with water (3×50 mL). The solid was collected and purified by trituration with MeOH (50 mL) and ACN (50 mL) at 25° C. to afford this product. This reaction was repeated for thirteen times to afford Intermediate $C_{2-8}$. LCMS: 400.90.

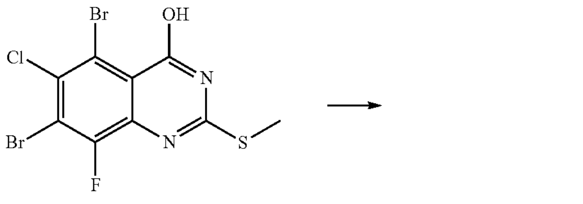

C2-8

C2-9

DIPEA (0.210 mL, 1.17 mmol) was added dropwise to the suspension of Intermediate C2-8 (157 mg, 0.390 mmol) in $POCl_3$ (0.365 mL, 3.90 mmol) at rt. The resulting reaction mixture was stirred at rt for 30 min. The volatile components were evaporated in vacuo to give the crude product of Intermediate C2-9, which was used for the next step without purification. LCMS: 420.9.

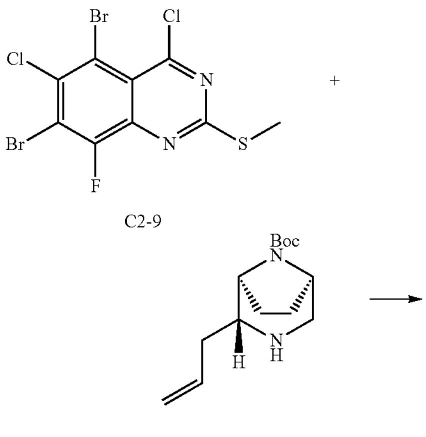

C2-9

-continued

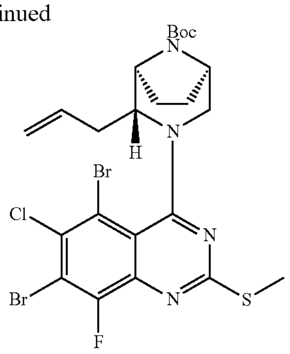

C2-10 tert-Butyl (1S,2R,5R)-2-allyl-3,8-diazabicyclo[3.2.1]octane-8-carboxylate (200 mg, 0.793 mmol, synthesized according to Comparative Intermediate 75-5 of U.S. application Ser. No. 18/303,813, published as US 2023/0374036, described below) and DIPEA (0.690 mL, 3.96 mmol) were added sequentially to the solution of Intermediate C2-9 (334 mg, 0.793 mmol) in DCM (4 mL) at 0° C. The reaction mixture was warmed at rt and stirred for 12 h. The volatile components were evaporated in vacuo and the residue was purified by flash column chromatography (silica gel, EtOAc-hexanes 0-70%) to give Intermediate C2-10. LCMS: 637.1.

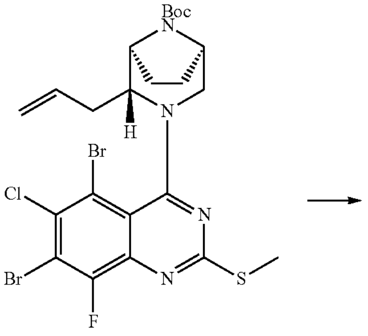

C2-10

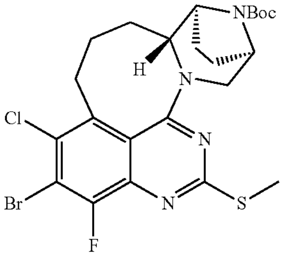

C2-11

To a vigorously stirred solution of Intermediate C2-10 (150 mg, 2.36 mmol) in anhydrous 2-methyl THE (2 mL), the solution of 9-borabicyclo[3.3.1]nonane (0.50 M in tetrahydrofuran, 0.587 mL, 0.293 mmol) was added at room temperature. The resulting solution was stirred at 50° C. for 0.5 hour before it was cooled to room temperature. The solution was transferred to a reaction vial containing Pd(dppf)$Cl_2$ (19.5 mg, 0.0236 mmol), potassium phosphate (150 mg, 0.708 mmol) and degassed water (0.5 mL) at rt under nitrogen atmosphere. The reaction mixture was stirred at 90° C. for 10 minutes before it was cooled to room temperature. The mixture was washed with water (2 mL) and extracted with ethyl acetate (3×5 mL). The organic layer was collected and combined, dried over magnesium sulfate, concentrated under reduced pressure. The crude was purified by silica gel column chromatography (0 to 50% ethyl acetate in hexanes) to give Intermediate C2-11. LCMS: 557.1.

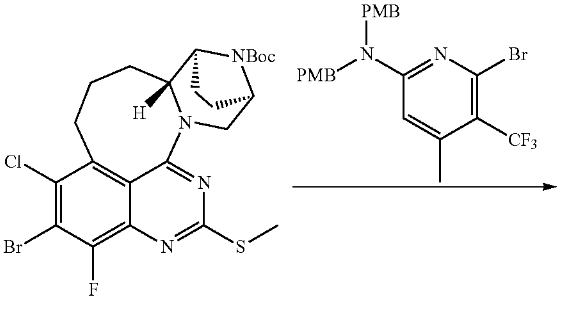

C2-11

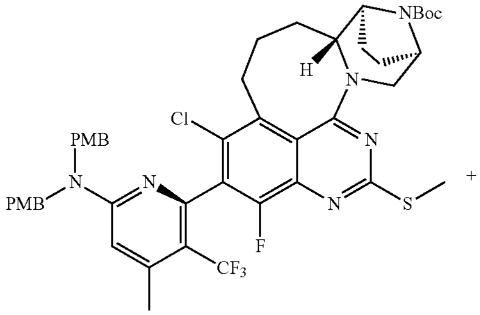

C2-12

+

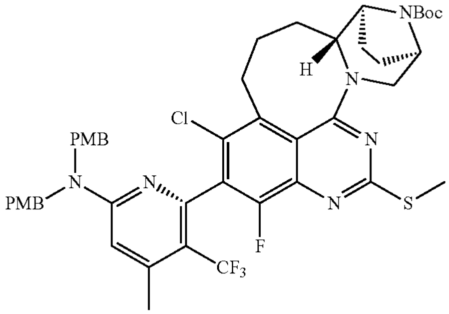

3-1

Isopropylmagnesium chloride lithium chloride complex solution (0.05 mL, 0.065 mmol, 1.30 mol/L) was added dropwise to the solution of Intermediate C2-11 (30 mg, 0.0538 mmol) in dry THE at −78° C. under $N_2$ atmosphere. The mixture was stirred at −78° C. for 15 min before the solution of ZnCl2 in 2-methyl THE (1.9 mol/L, 0.0368 mL, 0.0699 mmol) was added dropwise at −78° C. The reaction mixture was stirred at −78° C. for 10 min and wared to rt and stirred for another min. The solution was transferred to a vial containing 6-bromo-N,N-bis[(4-methoxyphenyl)methyl]-4-methyl-5-(trifluoromethyl)pyridin-2-amine (29.3 mg, 0.0591 mmol) and Pd$(PPh_3)_2Cl_2$ (3.79 mg, 0.0054 mmol) under $N_2$ atmosphere. The reaction mixture was stirred at 50° C. overnight. After cooling to rt, water (3 mL) was added. The mixture was extracted with EtOAc (3×5 mL). The combined organic phase was washed with brine (10 mL), dried over $Na_2SO_4$, and concentrated. The residue was purified with silica gel column chromatography (0 to 80% ethyl acetate in hexanes) to give the inseparable mixture of Intermediate C2-12 and Intermediate 3-1. LCMS: 893.4.

C2-13

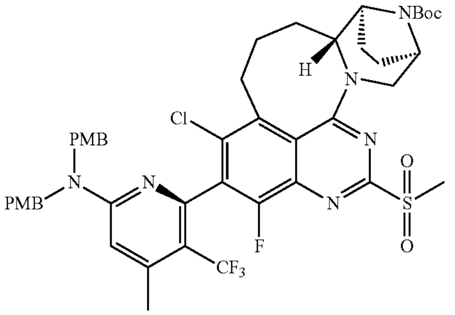

3-2

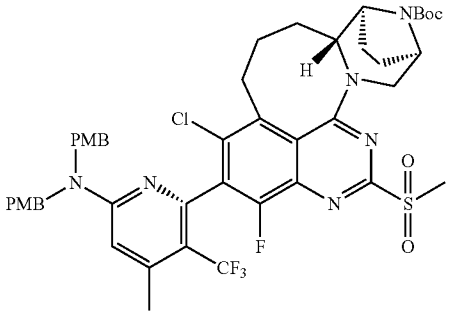

m-CPBA (77%, 14.4 mg, 0.644 mmol) was added to the solution of Intermediate C2-12 and Intermediate 3-1 (23 mg, 0.0257 mmol) in DCM (0.5 mL) at 0° C. The reaction mixture was stirred at 0° C. for 1 h. It was purified with silica gel column chromatography (0 to 80% ethyl acetate in hexanes) to give Intermediate C2-13 (faster eluted, LCMS: 925.3) and Intermediate 3-2 (slower eluted, LCMS: 925.3).

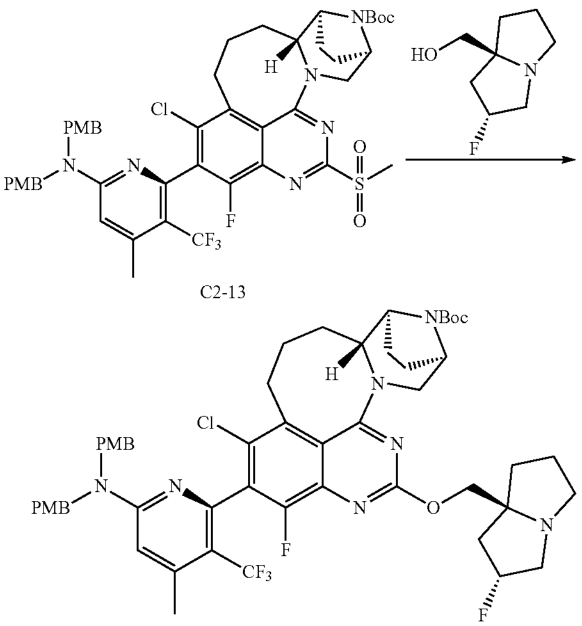

C2-13

C2-14

Lithium bis(trimethylsilyl)amide solution (1.0 M in tetrahydrofuran, 10.8 μL, 10.8 μmol) was added via syringe to a stirred mixture of Intermediate C2-13 (5 mg, 5.4 μmol), (2R,7aS)-2-fluorotetrahydro-1H-pyrrolizine-7a(5H)-methanol (2.58 mg, 16.2 μmol), and tetrahydrofuran (0.5 mL) at 0° C. After 30 min, ethyl acetate (3 mL), and saturated aqueous sodium chloride solution (5 mL) were added sequentially. The organic layer was separated, dried over anhydrous magnesium sulfate, filtered, and concentrated under reduced pressure to give the crude product of Intermediate C2-14. LCMS: 1004.3.

Intermediate B5-2: tert-butyl (1S,4R,14aR)-11-bromo-12-chloro-10-fluoro-8-(methylthio)-1,2,3,4,5,13,14,14a-octahydro-1,4-epiminoazepino[1',2':1,7]azepino[2,3,4-de]quinazoline-15-carboxylate

B5-2

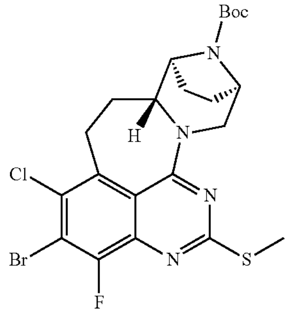

Intermediate B5-2 was synthesized in a manner similar to Intermediate C2-11 using Intermediate B5-1 instead of Intermediate C2-10. LCMS: 543.3, 545.2.

Intermediate B5-3: tert-butyl (1S,4R,14aR)-11-((S)-6-(bis(4-methoxybenzyl)amino)-4-methyl-3-(trifluoromethyl)pyridin-2-yl)-12-chloro-10-fluoro-8-(methylthio)-1,2,3,4,5,13,14,14a-octahydro-1,4-epiminoazepino[1',2':1,7]azepino[2,3,4-de]quinazoline-15-carboxylate Intermediate B6-1: tert-butyl (1S,4R,14aR)-11-((R)-6-(bis(4-methoxybenzyl)amino)-4-methyl-3-(trifluoromethyl)pyridin-2-yl)-12-chloro-10-fluoro-8-(methylthio)-1,2,3,4,5,13,14,14a-octahydro-1,4-epiminoazepino[1',2':1,7]azepino[2,3,4-de]quinazoline-15-carboxylate

B5-3

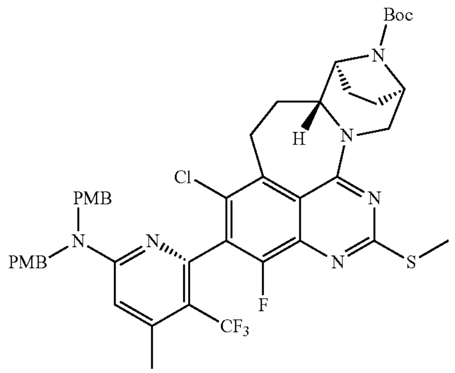

-continued

B6-1

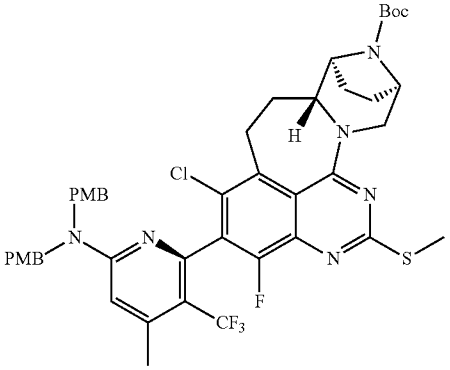

The mixture of Intermediate B5-3 and Intermediate B6-1 was synthesized in a manner similar to Intermediate C2-12 and Intermediate 3-1 using Intermediate B5-2 instead of Intermediate C2-11. LCMS: 879.5.

Intermediate B5-4: tert-butyl (1S,4R,14aR)-11-((S)-6-(bis(4-methoxybenzyl)amino)-4-methyl-3-(trifluoromethyl)pyridin-2-yl)-12-chloro-10-fluoro-8-(methylsulfonyl)-1,2,3,4,5,13,14,14a-octahydro-1,4-epiminoazepino[1',2':1,7]azepino[2,3,4-de]uinazoline-15-carboxylate Intermediate B6-2: tert-butyl (1S,4R,14aR)-11-((R)-6-(bis(4-methoxybenzyl)amino)-4-methyl-3-(trifluoromethyl)pyridin-2-yl)-12-chloro-10-fluoro-8-(methylsulfonyl)-1,2,3,4,5,13,14,14a-octahydro-1,4-epiminoazepino[1',2':1,7]azepino[2,3,4-de]uinazoline-15-carboxylate

B5-4

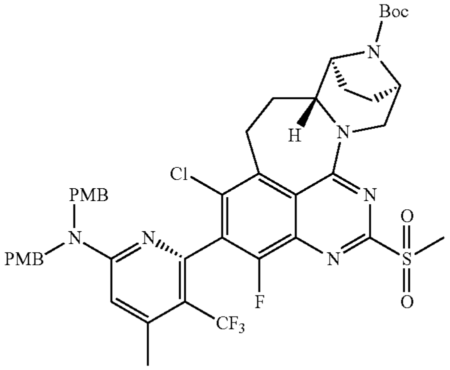

-continued

B6-2

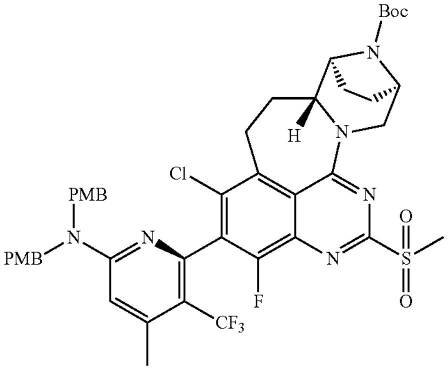

The mixture of Intermediate B5-4 and Intermediate B6-2 was synthesized in a manner similar to Intermediate C2-13 and Intermediate 3-2 using Intermediate B5-3 and Intermediate B6-1 instead of Intermediate C2-12 and Intermediate 3-1. LCMS: 911.4.

Intermediate B5-5: tert-butyl (1S,4R,14aR)-11-((S)-6-(bis(4-methoxybenzyl)amino)-4-methyl-3-(trifluoromethyl)pyridin-2-yl)-12-chloro-10-fluoro-8-(((2R,7aS)-2-fluorotetrahydro-1H-pyrrolizin-7a(5H)-yl)methoxy)-1,2,3,4,5,13,14,14a-octahydro-1,4-epiminoazepino[1',2':1,7]azepino[2,3,4-de]quinazoline-15-carboxylate Intermediate B6-3: tert-butyl (1S,4R,14aR)-11-((R)-6-(bis(4-methoxybenzyl)amino)-4-methyl-3-(trifluoromethyl)pyridin-2-yl)-12-chloro-10-fluoro-8-(((2R,7aS)-2-fluorotetrahydro-1H-pyrrolizin-7a(5H)-yl)methoxy)-1,2,3,4,5,13,14,14a-octahydro-1,4-epiminoazepino[1',2':1,7]azepino[2,3,4-de]quinazoline-15-carboxylate

B5-5

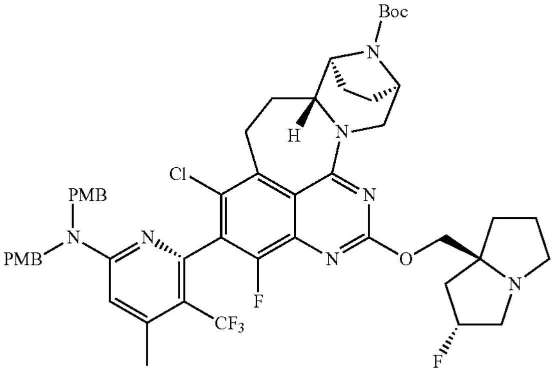

-continued

B6-3

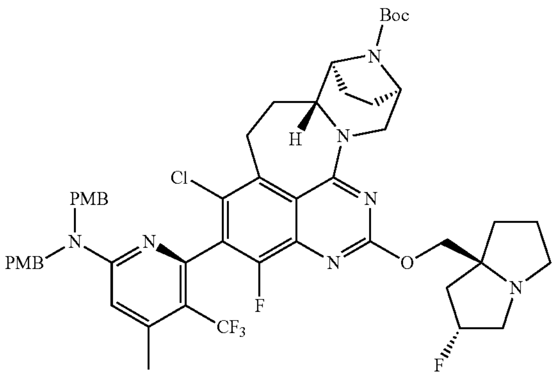

The mixture of Intermediate B5-5 and Intermediate B6-3 was synthesized in a manner similar to Intermediate C2-14 using the mixture of Intermediate B5-4 and Intermediate B6-2 instead of Intermediate C2-13. LCMS: 990.3.

Comparative Intermediate 27-5 of U.S. application Ser. No. 18/303,813, Published as US 2023/0374036: tert-butyl (1S,2R,5R)-2-vinyl-3,8-diazabicyclo[3.2.1]octane-8-carboxylate

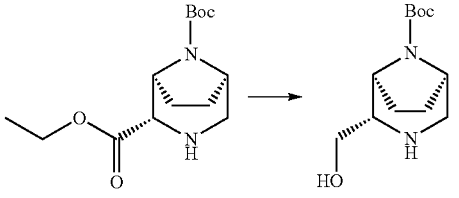

27-1

LAH (1.0 M in tetrahydrofuran, 20.0 mL, 20.0 mmol) was added dropwise to a vigorously stirred solution of 8-(tert-butyl) 2-ethyl (1R,2S,5S)-3,8-diazabicyclo[3.2.1]octane-2,8-dicarboxylate (4.00 g, 14.1 mmol) in tetrahydrofuran (40.0 mL) at 0° C. The reaction mixture was stirred at 0° C. for 2 hours before it was quenched with solid sodium sulfate decahydrate. The mixture was filtered and concentrated under reduced pressure to give the crude Intermediate 27-1, which was used for the next step without purification. LCMS: 243.0.

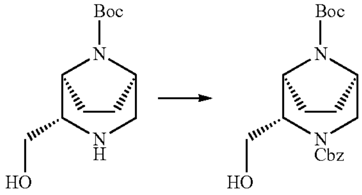

27-1 27-2

To a vigorously stirred solution of Intermediate 27-1 (1.50 g, 6.19 mmol) in ethyl acetate (15 mL) and water (15 mL) was added sodium bicarbonate (1.56 g, 18.6 mmol) in one portion, then benzyl chloroformate (1.32 mL, 9.28 mmol) was added to the solution slowly with stirring at 0° C. The resulted solution was stirred at room temperature for 12 hours. The organic layer was separated from the reaction mixture. The aqueous phase was extracted with ethyl acetate (3x30 mL). The organic layer was collected and combined, dried over magnesium sulfate, concentrated under reduced pressure. The residue was purified by silica gel column chromatography (0 to 50% ethyl acetate in hexanes) to give Intermediate 27-2. LCMS: 376.8 $[M+H]^+$, 399.1 $[M+Na]^+$.

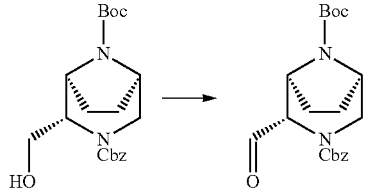

27-2 27-3

To a vigorously stirred solution of Intermediate 27-2 (2.01 g, 5.30 mmol) in dichloromethane (25 mL) under nitrogen was added Dess Martin periodinane (2.49 g, 5.80 mmol) at room temperature. The mixture was stirred at room temperature for 12 hours before saturated aqueous sodium bicarbonate (50 mL) was added. The mixture was extracted with ethyl acetate (3x50 mL) and the combined organic phase was dried over magnesium sulfate and concentrated under reduced pressure. The residue was purified by silica gel column chromatography (0% to 50% ethyl acetate in hexanes) to give Intermediate 27-3. LCMS: 375.0.

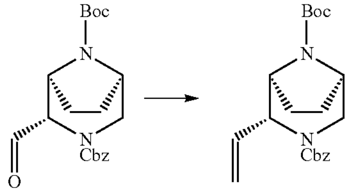

27-3 27-4

To a vigorously stirred solution of methyltriphenylphosphonium bromide (4.99 g, 14.0 mmol) in tetrahydrofuran (22 mL) at room temperature was added KHMDS solution (1.0 M in tetrahydrofuran, 14.0 mL, 14.0 mmol) dropwise to afford a solution. The mixture was stirred for 1 hour at room temperature and was cooled to −78° C. whereupon a solution of Intermediate 27-3 (1.74 g, 4.65 mmol) in tetrahydrofuran (22 mL) was added dropwise over 20 minutes. The resulting solution was allowed to gradually warm to room temperature and stir for 3 hours. The mixture was quenched with methanol (40 mL) and stirred for 15 min. Saturated aqueous ammonium chloride solution (50 mL) was added and the mixture was extracted with ethyl acetate (3x50 mL). The combined organic phase was dried over magnesium sulfate and concentrated under reduced pressure. The residue was purified by silica gel column chromatography (0% to 40% ethyl acetate in hexanes) to give Intermediate 27-4. LCMS: 395.1 $[M+Na]^+$.

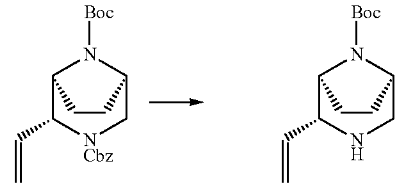

27-4 Comparative Intermediates 27-5

To a vigorously stirred solution of palladium(II) acetate (9.5 mg, 0.0426 mmol) in dichloromethane (5.3 mL), triethyl silane (0.27 mL, 1.70 mmol) was added dropwise, followed by the addition of triethylamine (0.12 μL, 0.851 μmol). The resulting mixture was stirred for 15 minutes at room temperature before the solution of Intermediate 27-4 (317 mg, 0.851 mmol) in dichloromethane (2 mL) was added dropwise. The reaction mixture was stirred for 90 hours at room temperature. The mixture was diluted with saturated aqueous sodium bicarbonate (20 mL). The organic layer was separated, and the aqueous layer was extracted with dichloromethane (3×20 mL). The combined organic layer was dried over magnesium sulfate and concentrated under reduced pressure. The residue was purified by silica gel column chromatography (0% to 100% ethyl acetate in hexanes then 0% to 20% methanol in dichloromethane) to give Comparative Intermediate 27-5. LCMS: 238.9.

Intermediate 7-1: tert-butyl (5S,5aS,6S,9R)-1-fluoro-2-(7-fluoro-3-(methoxymethoxy)-8-((triisopropylsilyl)ethynyl)naphthalen-1-yl)-12-(((2R,7aS)-2-fluorotetrahydro-1H-pyrrolizin-7a(5H)-yl)methoxy)-5-methyl-4,5,5a,6,7,8,9,10-octahydro-3,10a,11,13,14-pentaaza-6,9-methanonaphtho[1,8-ab]heptalene-14-carboxylate 7-1

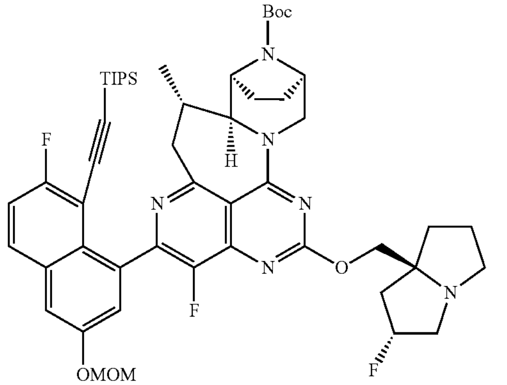

Intermediate 7-1 was synthesized in a manner similar to Comparative Intermediate 13-10 of U.S. application Ser. No. 18/303,813, published as US 2023/0374036, using Comparative Intermediate 64-4 of U.S. application Ser. No. 18/303,813 instead of Comparative Intermediate 13-9 of U.S. application Ser. No. 18/303,813 and using ((2R,7aS)-2-fluorotetrahydro-1H-pyrrolizin-7a(5H)-yl)methanol instead of ((2R,7aR)-2-fluoro-6-methylenetetrahydro-1H-pyrrolizin-7a(5H)-yl)methanol. LCMS: 941.9.

Intermediate 7-2: tert-butyl (5S,5aS,6S,9R)-2-(8-ethynyl-7-fluoro-3-(methoxymethoxy)naphthalen-1-yl)-1-fluoro-12-(((2R,7aS)-2-fluorotetrahydro-1H-pyrrolizin-7a(5H)-yl)methoxy)-5-methyl-4,5,5a,6,7,8,9,10-octahydro-3,10a,11,13,14-pentaaza-6,9-methanonaphtho[1,8-ab]heptalene-14-carboxylate 7-2

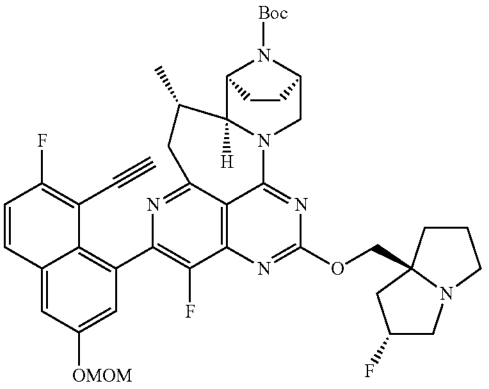

Intermediate 7-2 was synthesized in a manner similar to Comparative Intermediate 13-11 of U.S. application Ser. No. 18/303,813, published as US 2023/0374036, using Intermediate 7-1 instead of Comparative Intermediate 13-10 of U.S. application Ser. No. 18/303,813. LCMS: 785.2.

Intermediate 7-3: (5S,5aS,6S,9R)-2-(8-ethynyl-7-fluoro-3-(methoxymethoxy)naphthalen-1-yl)-1-fluoro-12-(((2R,7aS)-2-fluorotetrahydro-1H-pyrrolizin-7a(5H)-yl)methoxy)-5-methyl-4,5,5a,6,7,8,9,10-octahydro-3,10a,11,13,14-pentaaza-6,9-methanonaphtho[1,8-ab]heptalene 7-3

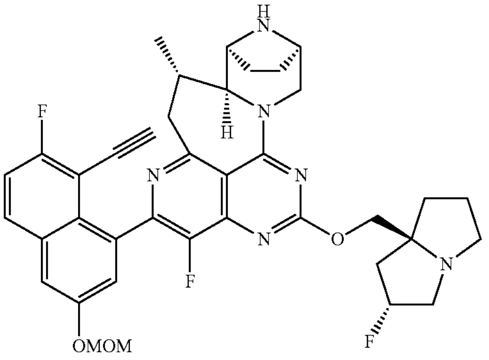

Intermediate 7-3 was synthesized in a manner similar to Intermediate 2-3 using Intermediate 7-2 instead of Intermediate 2-2. LCMS: 685.2.

Intermediate 7-4: 4-(((5S,5aS,6S,9R)-2-(8-ethynyl-7-fluoro-3-(methoxymethoxy)naphthalen-1-yl)-1-fluoro-12-(((2R,7aS)-2-fluorotetrahydro-1H-pyrrolizin-7a(5H)-yl)methoxy)-5-methyl-4,5,5a,6,7,8,9,10-octahydro-3,10a,11,13,14-pentaaza-6,9-methanonaphtho[1,8-ab]heptalen-14-yl)methyl)-5-methyl-1,3-dioxol-2-one 7-4

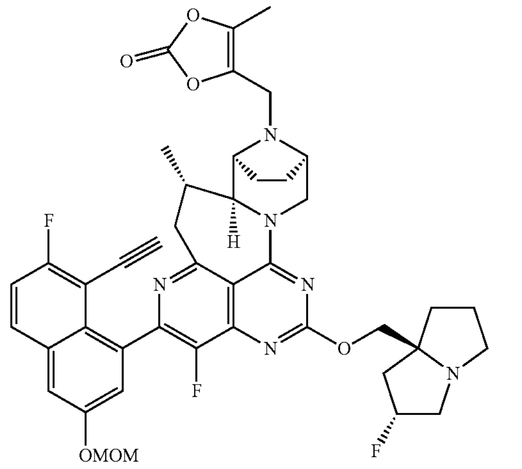

Intermediate 7-4 was synthesized in a manner similar to Example 2 using Intermediate 7-3 instead of Intermediate 2-3. LCMS: 797.1.

Intermediate 8-1: (6aR,7S,10R)-2-(8-ethynyl-7-fluoro-3-(methoxymethoxy)naphthalen-1-yl)-1-fluoro-13-(((2R,7aS)-2-fluorotetrahydro-1H-pyrrolizin-7a(5H)-yl)methoxy)-5,6,6a,7,8,9,10,11-octahydro-4H-3,11a,12,14,15-pentaaza-7,10-methanocyclohepta[4,5]cycloocta[1,2,3-de]naphthalene

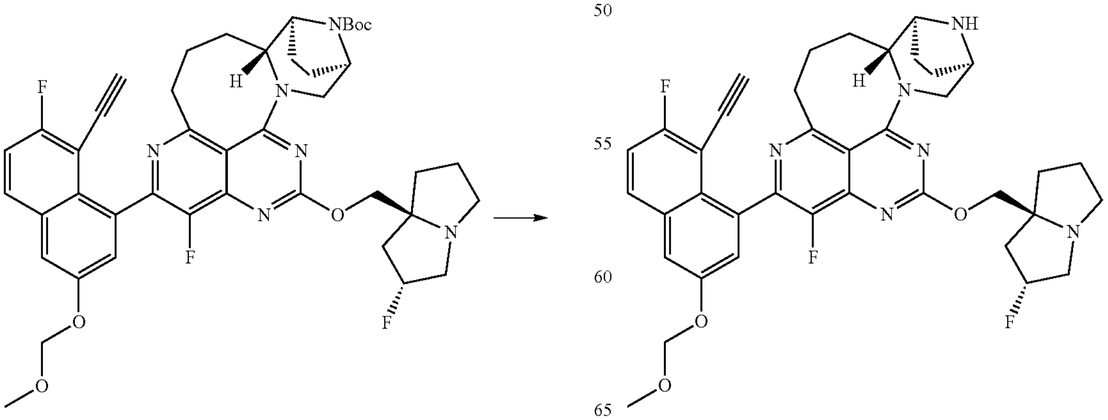

Comparative intermediate 75-11

8-1

-continued

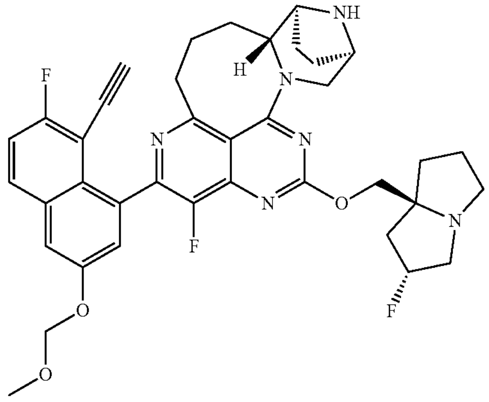

8-1

Intermediate 8-1 was synthesized in a manner similar to Intermediate 11-5 using Comparative Intermediate 75-11 from U.S. application Ser. No. 18/303,813, published as US 2023/0374036, instead of Intermediate 11-4. LCMS: 685.2.

Intermediate 8-2: 4-(((6aR,7S,10R)-2-(8-ethynyl-7-fluoro-3-(methoxymethoxy)naphthalen-1-yl)-1-fluoro-13-(((2R,7aS)-2-fluorotetrahydro-1H-pyrrolizin-7a(5H)-yl)methoxy)-5,6,6a,7,8,9,10,11-octahydro-4H-3,11a,12,14,15-pentaaza-7,10-methanocyclohepta[4,5]cycloocta[1,2,3-de]naphthalen-15-yl)methyl)-5-methyl-1,3-dioxol-2-one -continued

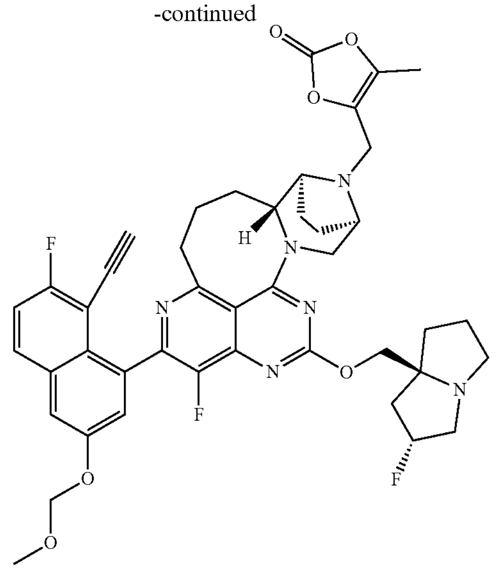

8-2

Intermediate 8-2 was synthesized in a manner similar to Intermediate 11-6 using Intermediate 8-1 instead of Intermediate 11-5. LCMS: 797.3.

Intermediate 11-1: tert-butyl (4R,6aR,7S,10R)-2-chloro-13-(ethylthio)-1-fluoro-4-methyl-5,6,6a,7,8,9,10,11-octahydro-4H-3,11a,12,14,15-pentaaza-7,10-methanocyclohepta[4,5]cycloocta[1,2,3-de]naphthalene-15-carboxylate

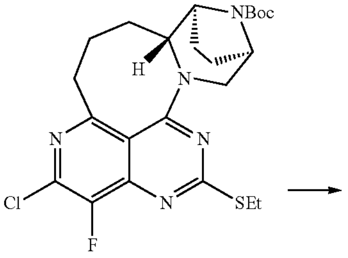

Comparative Intermediate 75-7

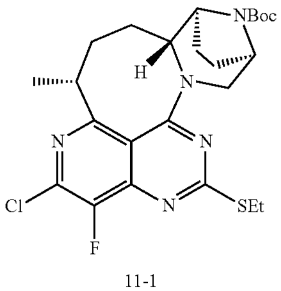

11-1

2,2,6,6-Tetramethylpiperidinylmagnesium chloride lithium chloride complex solution (1.0 M in tetrahydrofuran/toluene, 113 mL, 110 mmol) was added over 10 min via syringe to vigorously stirred Comparative Intermediate 75-7 of U.S. application Ser. No. 18/303,813, published as US 2023/0374036 (11.1 g, 22.5 mmol) at −20° C., and the resulting mixture was warmed to room temperature. After 5 h, the resulting mixture was cooled to −30° C., and iodomethane (9.84 mL, 158 mmol) was added over 3 min via syringe. Copper(I) cyanide di(lithium chloride) complex solution (1.0 M in tetrahydrofuran, 2.25 mL, 2.3 mmol) was added via syringe. After 2 min, the resulting mixture was warmed to room temperature. After 165 min, the resulting mixture was cooled to 0° C. Water (40 ml), brine (100 mL), aqueous ammonia solution (30% wt, 15 mL), diethyl ether (150 mL), ethyl acetate (1.5 L), and water (1.0 L) were added sequentially. The resulting mixture was filtered, and the biphasic filtrate was agitated. The aqueous layer was removed, and the organic layer was dried over anhydrous magnesium sulfate, was filtered, and was concentrated under reduced pressure. The residue was purified by flash column chromatography on silica gel (0 to 15% ethyl acetate in hexanes) to give Intermediate 11-1. LCMS: 508.2.

Intermediate 11-2: tert-butyl (4R,6aR,7S,10R)-2-chloro-13-(ethylsulfonyl)-1-fluoro-4-methyl-5,6,6a,7,8,9,10,11-octahydro-4H-3,11a,12,14,15-pentaaza-7,10-methanocyclohepta[4,5]cycloocta[1,2,3-de]naphthalene-15-carboxylate

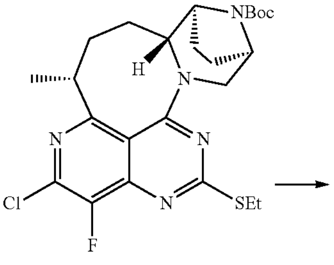

11-1

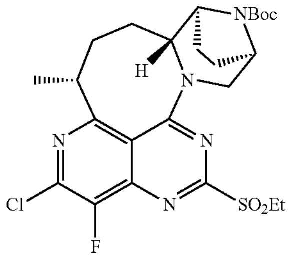

11-2

3-Chlorobenzoic peracid (77% wt, 6.63 g, 30 mmol) was added in three equal portions over 4 min to a vigorously stirred solution of Intermediate 11-1 (7.15 g, 14.1 mmol) in dichloromethane (20 mL) at 0° C. After 1 min, the resulting mixture was warmed to room temperature. After about 45 min, the resulting mixture was purified by flash column chromatography on silica gel (0 to 55% ethyl acetate in hexanes) to give Intermediate 11-2. LCMS: 540.1.

Intermediate 11-3: tert-butyl (4R,6aR,7S,10R)-2-chloro-1-fluoro-13-(((2R,7aS)-2-fluorotetrahydro-1H-pyrrolizin-7a(5H)-yl)methoxy)-4-methyl-5,6,6a,7,8,9,10,11-octahydro-4H-3,11a,12,14,15-pentaaza-7,10-methanocyclohepta[4,5]cycloocta[1,2,3-de]naphthalene-15-carboxylate

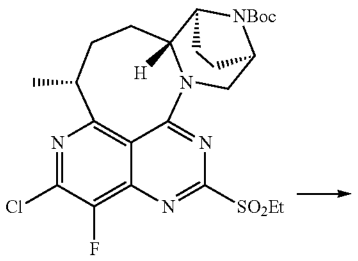

11-2

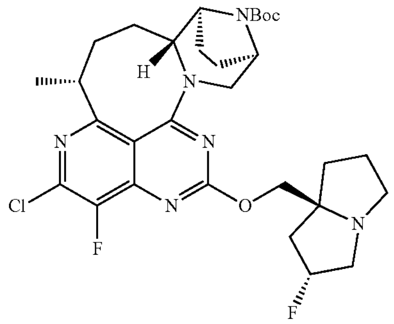

11-3

Lithium bis(trimethylsilylamide) solution (1.0 M in tetrahydrofuran, 14.6 mL, 15 mmol) was added over 3 min via syringe to a vigorously stirred mixture of Intermediate 11-2 (6.32 g, 11.7 mmol), ((2R,7aS)-2-fluorotetrahydro-1H-pyrrolizin-7a(5H)-yl)methanol (2.33 g, 14.6 mmol), and 2-methyltetrahydrofuran (25 mL) at 0° C. After 80 min, saturated aqueous sodium bicarbonate solution (15 mL), saturated aqueous sodium carbonate solution (15 mL), diethyl ether (200 mL), and ethyl acetate (50 mL) were added sequentially. The organic layer was washed with a mixture of water and brine (1:1 v:v, 75 mL), was dried over anhydrous magnesium sulfate, was filtered, and was concentrated under reduced pressure. The residue was purified by flash column chromatography on silica gel (0 to 6% methanol in dichloromethane) to give Intermediate 11-3. LCMS: 605.3.

Intermediate 11-4: tert-butyl (4R,6aR,7S,10R)-2-(8-ethynyl-7-fluoro-3-(methoxymethoxy)naphthalen-1-yl)-1-fluoro-13-(((2R,7aS)-2-fluorotetrahydro-1H-pyrrolizin-7a(5H)-yl)methoxy)-4-methyl-5,6,6a,7,8,9,10,11-octahydro-4H-3,11a,12,14,15-pentaaza-7,10-methanocyclohepta[4,5]cycloocta[1,2,3-de]naphthalene-15-carboxylate

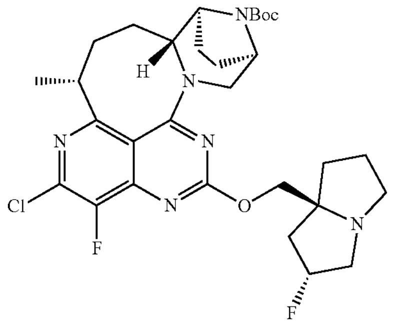

11-3

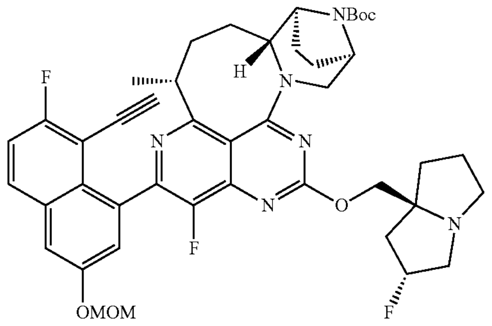

11-4

Aqueous potassium phosphate solution (2.0 M, 13.9 mL, 28 mmol) was added via syringe to a vigorously stirred mixture of Intermediate 11-3 (5.59 g, 9.24 mmol), 2-[2-fluoro-6-(methoxymethoxy)-8-(4,4,5,5-tetramethyl-1,3,2-dioxaborolan-2-yl)-1-naphthyl]ethynyl-triisopropyl-silane (5.68 g, 11.1 mmol), [(di(1-adamantyl)-butylphosphine)-2-(2'-amino-1,1'-biphenyl)]palladium(II) methanesulfonate (336 mg, 462 μmol), and tetrahydrofuran (20 mL) at room temperature, and the resulting mixture was heated to 70° C. After 80 min, the resulting mixture was cooled to room temperature, and diethyl ether (200 mL) and ethyl acetate (25 mL) were added sequentially. The organic layer was washed with water (30 mL), was dried over anhydrous magnesium sulfate, was filtered, and was concentrated under reduced pressure. The residue was dissolved in N,N-dimethylformamide (20 mL), 1,1,1,3,3,3-hexafluoropropan-2-ol (973 μL, 9.24 mmol) was added via syringe, and the resulting mixture was stirred vigorously at room temperature. Cesium fluoride (14.0 g, 92.4 mmol) was added, and the resulting mixture was heated to 50° C. After 40 min, the resulting mixture was cooled to room temperature, and diethyl ether (500 mL), ethyl acetate (50 mL), saturated sodium bicarbonate solution (20 mL), and saturated sodium carbonate solution (20 mL) were added sequentially. The organic layer was washed with water (2×400 mL), was dried over anhydrous magnesium sulfate, was filtered, and was concentrated under reduced pressure. The residue was purified by flash column chromatography on silica gel (0 to 6% methanol in dichloromethane) to give Intermediate 11-4. LCMS: 799.2.

Intermediate 11-5: (4R,6aR,7S,10R)-2-(8-ethynyl-7-fluoro-3-(methoxymethoxy)naphthalen-1-yl)-1-fluoro-13-(((2R,7aS)-2-fluorotetrahydro-1H-pyrrolizin-7a(5H)-yl)methoxy)-4-methyl-5,6,6a,7,8,9,10,11-octahydro-4H-3,11a,12,14,15-pentaaza-7,10-methanocyclohepta[4,5]cycloocta[1,2,3-de]naphthalene

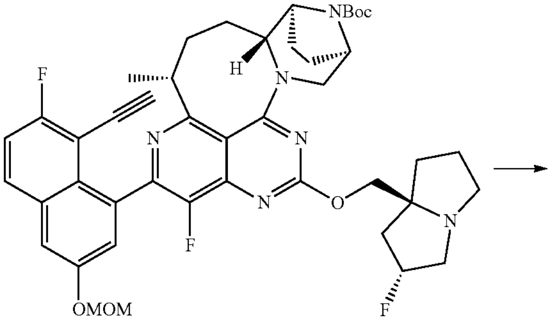

11-4

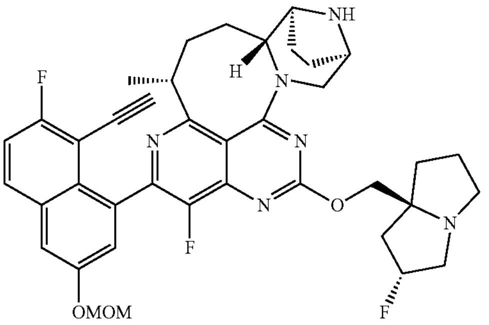

11-5

Trimethylsilyl trifluoromethanesulfonate (2.51 mL, 13.8 mmol) was added over 3 min via syringe to a stirred mixture of Intermediate 11-4 (7.37 g, 9.23 mmol), 2,6-lutidine (1.72 mL, 14.8 mmol), and dichloromethane (14 mL) at 0° C. After 40 min, methanol (10 mL) was added via syringe, and the resulting mixture was warmed to room temperature. After 10 min, the resulting mixture was concentrated under reduced pressure, and the residue was purified by flash column chromatography on silica gel (0 to 34% [8:1 ethanol: 30% aqueous ammonia solution] in dichloromethane) to give Intermediate 11-5. LCMS: 699.2.

Intermediate 11-6: 4-(((4R,6aR,7S,10R)-2-(8-ethynyl-7-fluoro-3-(methoxymethoxy)naphthalen-1-yl)-1-fluoro-13-(((2R,7aS)-2-fluorotetrahydro-1H-pyrrolizin-7a(5H)-yl)methoxy)-4-methyl-5,6,6a,7,8,9,10,11-octahydro-4H-3,11a,12,14,15-pentaaza-7,10-methanocyclohepta[4,5]cycloocta[1,2,3-de]naphthalen-15-yl)methyl)-5-methyl-1,3-dioxol-2-one

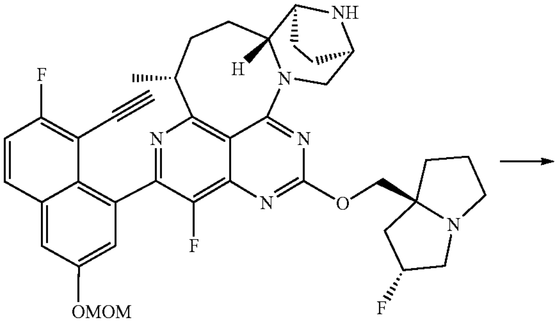

11-5

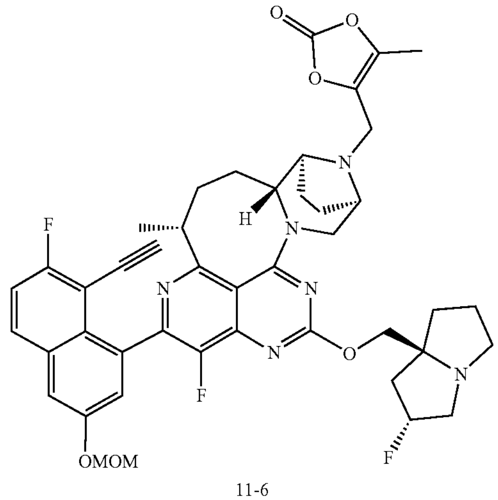

11-6

4-(Bromomethyl)-5-methyl-1,3-dioxol-2-one (9.5 μL, 86 μmol) was added over 1 min via syringe to a vigorously stirred mixture of Intermediate 11-5 (50.0 mg, 71.6 μmol), potassium carbonate (237 mg, 1.72 mmol), and N,N-dimethylformamide (0.40 mL) at 0° C. After 100 min, acetic acid (246 μL, 4.29 mmol) was added slowly via syringe, and the resulting mixture was filtered. The filtrate was purified by reverse phase preparative HPLC (0.1% acetic acid in acetonitrile/water) to give Intermediate 11-6. LCMS: 811.1.

Intermediate 16-1: 4-(bromomethyl)-5-hexyl-1,3-dioxol-2-one 16-1

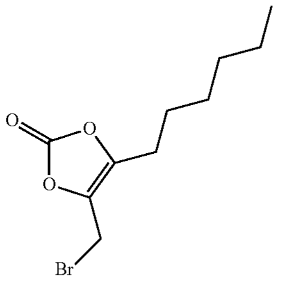

Intermediate 16-1 was synthesized in a manner similar to 4-(bromomethyl)-5-butyl-1,3-dioxol-2-one (Tetrahedron Lett. 2002, 43, 1161) using heptanoyl chloride instead of pentanoyl chloride. $^1$H NMR (400 MHz, Chloroform-d) δ 4.18 (s, 2H), 2.44 (t, J=7.4 Hz, 2H), 1.68-1.58 (m, 2H), 1.40-1.26 (m, 6H), 0.90 (t, J=6.8 Hz, 3H).

Intermediate 18-1: tert-butyl (6aR,7S,10R)-1-fluoro-2-(7-fluoro-3-(methoxymethoxy)-8-(trifluoromethoxy)naphthalen-1-yl)-13-(((2R,7aS)-2-fluorotetrahydro-1H-pyrrolizin-7a(5H)-yl)methoxy)-5,6,6a,7,8,9,10,11-octahydro-4H-3,11a,12,14,15-pentaaza-7,10-methanocyclohepta[4,5]cycloocta[1,2,3-de]naphthalene-15-carboxylate

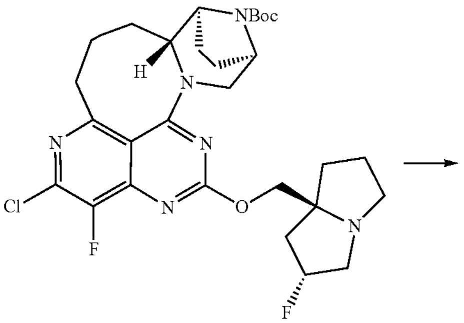

Comparative Intermediate 75-9

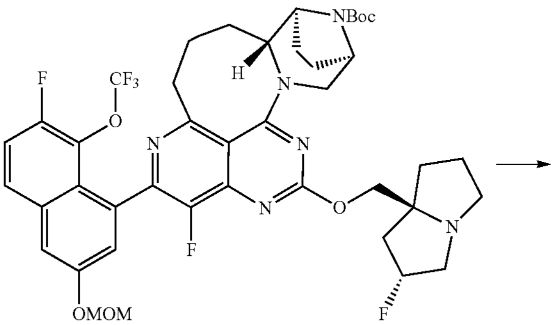

18-1

Aqueous potassium phosphate solution (2.0 M, 8.25 mL, 17 mmol) was added via syringe to a vigorously stirred mixture of Comparative Intermediate 75-9 (3.25 g, 5.50 mmol), 2-(7-fluoro-3-(methoxymethoxy)-8-(trifluoromethoxy)naphthalen-1-yl)-4,4,5,5-tetramethyl-1,3,2-dioxaborolane (Comparative Intermediate 7-5 from U.S. application Ser. No. 18/303,813, published as US 2023/0374036, 2.29 g, 5.50 mmol), [(di(1-adamantyl)-butylphosphine)-2-(2'-amino-1,1'-biphenyl)]palladium(II) methanesulfonate (200 mg, 275 μmol), and 2-methyltetrahydrofuran (15.0 mL) at room temperature, and the resulting mixture was heated to 80° C. After 150 min, the resulting mixture was cooled to room temperature, and diethyl ether (200 mL) and ethyl acetate (50 mL) were added sequentially. The organic layer was washed with water (75 mL), was dried over anhydrous magnesium sulfate, was filtered, and was concentrated under reduced pressure. The residue was purified by flash column chromatography on silica gel (0 to 5% methanol in dichloromethane) to give Intermediate 18-1. LCMS: 845.3.

Intermediate 18-2: (6aR,7S,10R)-1-fluoro-2-(7-fluoro-3-(methoxymethoxy)-8-(trifluoromethoxy)naphthalen-1-yl)-13-(((2R,7aS)-2-fluorotetrahydro-1H-pyrrolizin-7a(5H)-yl)methoxy)-5,6,6a,7,8,9,10,11-octahydro-4H-3,11a,12,14,15-pentaaza-7,10-methanocyclohepta[4,5]cycloocta[1,2,3-de]naphthalene

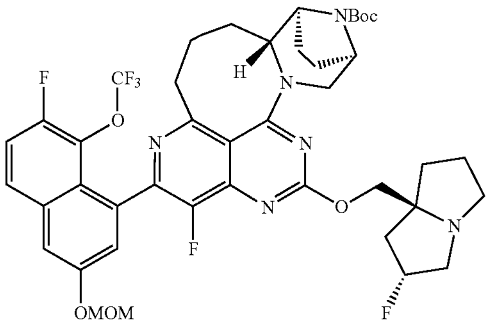

18-1

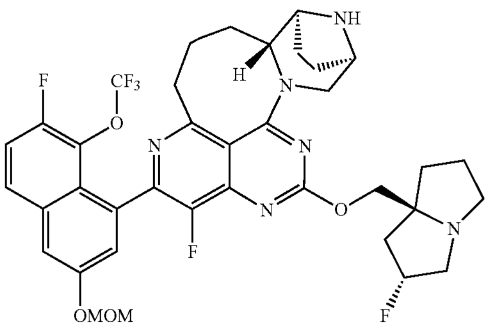

18-2

Intermediate 18-2 was synthesized in a manner similar to Intermediate 11-5 using Intermediate 18-1 instead of Intermediate 11-4. LCMS: 745.3.

Intermediate 18-3: 4-(((6aR,7S,10R)-1-fluoro-2-(7-fluoro-3-(methoxymethoxy)-8-(trifluoromethoxy)naphthalen-1-yl)-13-(((2R,7aS)-2-fluorotetrahydro-1H-pyrrolizin-7a(5H)-yl)methoxy)-5,6,6a,7,8,9,10,11-octahydro-4H-3,11a,12,14,15-pentaaza-7,10-methanocyclohepta[4,5]cycloocta[1,2,3-de]naphthalen-15-yl)methyl)-5-methyl-1,3-dioxol-2-one

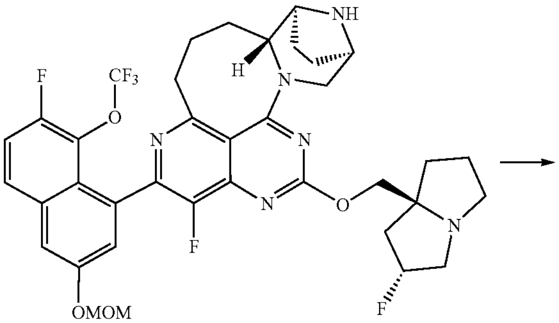

18-2

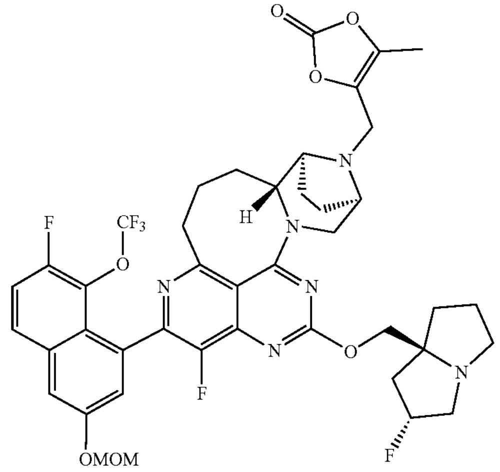

18-3

4-(Bromomethyl)-5-methyl-1,3-dioxol-2-one (286 μL, 2.58 mmol) was added over 1 min via syringe to a vigorously stirred mixture of Intermediate 18-2 (1.60 g, 2.15 mmol), potassium carbonate (7.12 g, 51.5 mmol), and N,N-dimethylformamide (5.0 mL) at 0° C. After 200 min, the resulting mixture was filtered, the filter cake was extracted with acetonitrile, acetic acid (1.0 mL) was added to the filtrate, and the resulting homogeneous mixture was purified by flash column chromatography on C18 reverse phase silica gel (0.1% trifluoroacetic acid in acetonitrile/water) to give Intermediate 18-3. LCMS: 857.3.

Intermediate 20-1: 4-(bromomethyl)-5-pentyl-1,3-dioxol-2-one 20-1

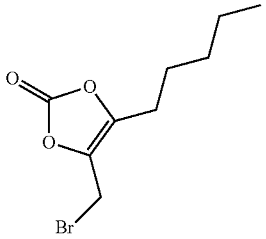

Intermediate 20-1 was synthesized in a manner similar to 4-(bromomethyl)-5-butyl-1,3-dioxol-2-one (Tetrahedron Lett. 2002, 43, 1161) using hexanoyl chloride instead of pentanoyl chloride. $^{1}H$ NMR (400 MHz, Chloroform-d) δ 4.22 (s, 2H), 2.45 (t, J=7.4 Hz, 2H), 1.70-1.58 (m, 2H), 1.42-1.28 (m, 4H), 0.92 (t, J=6.8 Hz, 3H).

Intermediate 28-1: tert-butyl (1S,2R,5R)-2-allyl-3-(5-bromo-6,8-difluoro-2-(methylthio)quinazolin-4-yl)-3,8-diazabicyclo[3.2.1]octane-8-carboxylate

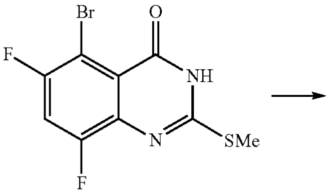

2-15

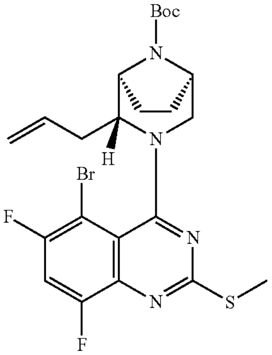

28-1

To a reaction mixture of Intermediate 2-15 (1.3 g, 4.2 mmol) and 2-(7-Aza-1H-benzotriazole-1-yl)-1,1,3,3-tetramethyluroniumhexafluorophosphate (HATU) (2.48 g, 6.5 mmol) in 25 ml of acetonitrile was added N,N-diisopropylethylamine (2.2 ml, 13 mmol). After stirring at room temperature for 1 hour, to it was added a solution of tert-butyl (1S,2R,5R)-2-allyl-3,8-diazabicyclo[3.2.1]octane-8-carboxylate (1.07 g, 4.2 mmol) in 5 ml of acetonitrile. The reaction was stirred at room temperature for 1 day. Upon completion, the reaction mixture was partitioned between EtOAc and water, and the aqueous layer was extracted with EtOAc twice. The combined organic layer was washed with brine, filtered, and concentrated to dryness. The residue was purified by silica gel chromatography eluting with EtOAc/hexane to afford Intermediate 28-1. LCMS: 543.1.

Intermediate 28-2: tert-butyl (1S,4R,15aR)-10,12-difluoro-8-(methylthio)-2,3,4,5,13,14,15,15a-octahydro-1H-1,4-epiminoazepino[1',2':1,8]azocino[2,3,4-de]quinazoline-16-carboxylate

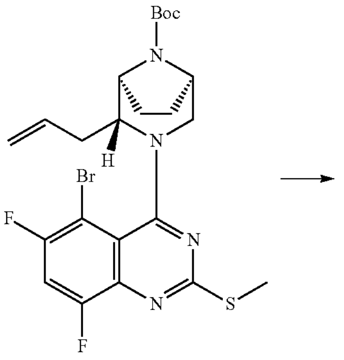

28-1

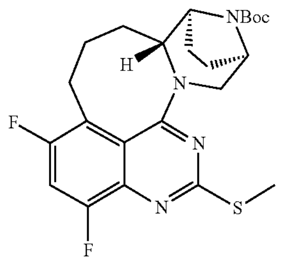

28-2

A solution of Intermediate 28-1 (1.0 g, 1.85 mmol; azeotroped with toluene 3 x) dissolved in 0.5 M 9-BBN in THE (11.1 mL, 5.55 mmol). The resulting solution was stirred at room temperature for 1 hour until Intermediate 28-1 was consumed. The reaction solution was cooled to 0° C. as 1.5 M $K_3PO_4$ (6.2 mL, 9.3 mmol) was added and, after 5 minutes stirring, was added cataCXium A Pd G3 (134.91 mg, 185 umol) and THE (22.7 mL) at 0° C. The resulting mixture was purged with Argon gas for 15 minutes at room temperature, then stirred at 60° C. in preheated oil bath. After 30 minutes, the reaction mixture was cooled to room temperature and diluted with ethyl acetate (~120 mL) before washing with brine (120 mL). After the aqueous fraction was extracted with EtOAc (100 mL×1), combined organic layer was dried ($MgSO_4$), and concentrated. The residue was purified by silica gel chromatography eluting with EtOAc/hexane to afford Intermediate 28-2. LCMS: 463.3.

Intermediate 28-3: tert-butyl (1S,4R,15aR)-11-bromo-10,12-difluoro-8-(methylthio)-2,3,4,5,13,14,15,15a-octahydro-1H-1,4-epiminoazepino[1',2':1,8]azocino[2,3,4-de]quinazoline-16-carboxylate

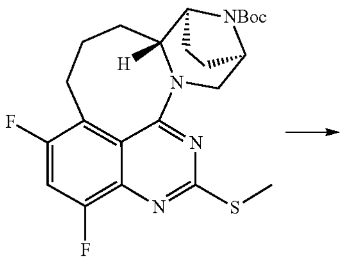

28-2

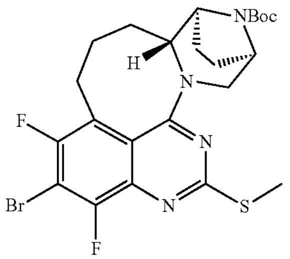

28-3

Intermediate 28-2 (1.0 g. 2.16 mmol) in a dry flask was evacuated under vacuum and filled with nitrogen three times. The bis(2,2,6,6-tetramethylpiperidinyl)zinc, lithium chloride, and magnesium chloride complex ($(TMP)_2Zn\cdot 2 MgCl_2\cdot 2 LiCl$) (16.6 mL of a 0.26 M solution in THF, 4.32 mmol) was added and the reaction mixture was allowed to stir for 2 hours at room temperature. The mixture was cooled to 0~5° C. under nitrogen. Bromine (2.22 mL of 10% solution in THF, 4.32 mmol) was added dropwise into the reaction mixture and stirred at 0~5° C. for 0.5 hour. Upon completion, quenched the reaction with half saturated $NH_4Cl$ aqueous solution, and extracted with ethyl acetate three times; filtered thru a pad of celite if see insoluble. The organic layer was combined and washed with brine, dried over $Na_2SO_4$, filtered and concentrated. The residue was purified by silica gel chromatography eluting with EtOAc/hexane to afford Intermediate 28-3. LCMS: 543.2.

Intermediate 28-4: tert-butyl (1S,4R,15aR)-10,12-difluoro-11-(7-fluoro-3-(methoxymethoxy)-8-((triisopropylsilyl)ethynyl)naphthalen-1-yl)-8-(methylthio)-2,3,4,5,13,14,15,15a-octahydro-1H-1,4-epiminoazepino[1',2':1,8]azocino[2,3,4-de]quinazoline-16-carboxylate

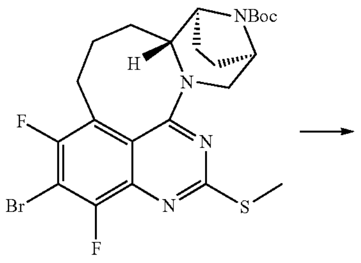

28-3

-continued

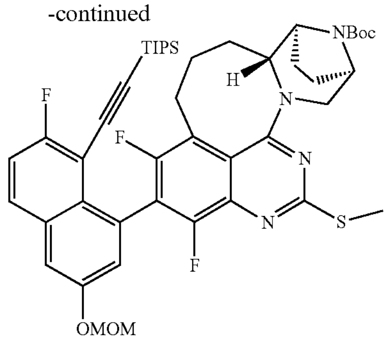

28-4

-continued

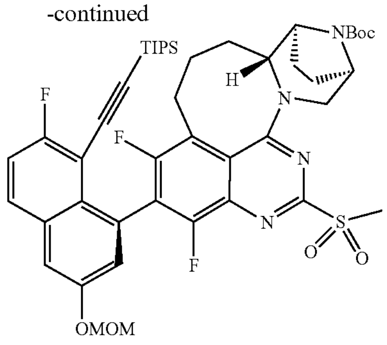

28-5B

Intermediate 28-4 was synthesized in a manner similar to Intermediate 13-8 using Intermediate 28-3 instead of Intermediate 13-7. LCMS:847.5.

Intermediate 28-5B: tert-butyl (1S,4R,15aR)-10,12-difluoro-11-((R)-7-fluoro-3-(methoxymethoxy)-8-((triisopropylsilyl)ethynyl)naphthalen-1-yl)-8-(methylsulfonyl)-2,3,4,5,13,14,15,15a-octahydro-1H-1,4-epiminoazepino[1',2':1,8]azocino[2,3,4-de]quinazoline-16-carboxylate

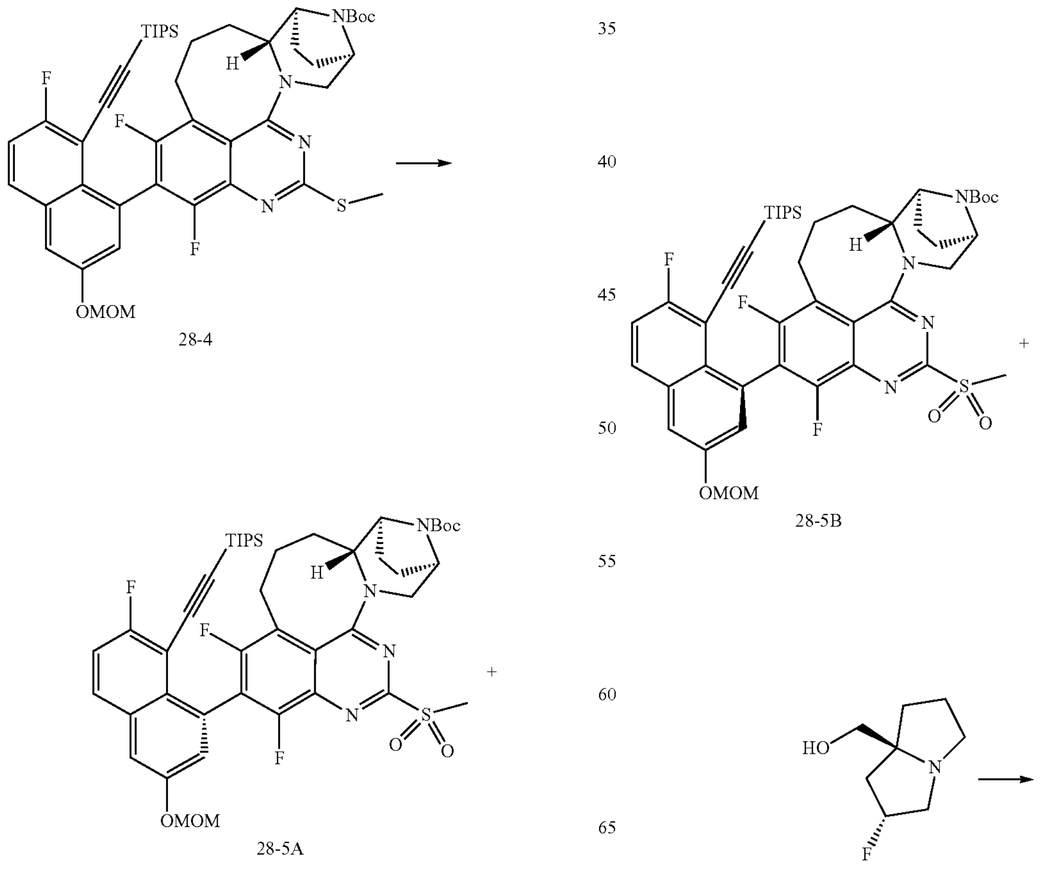

28-4

28-5B 28-5A

3-Chloroperbenzoic acid (77% wt, 821 mg, 3.66 mmol) was added portion wise to Intermediate 28-4 (1.41 g, 1.66 mmol) in dichloromethane (5 mL) at 0° C. The resulting mixture was stirred for 1 hour. Upon completion, the resulting mixture was purified by flash column chromatography on silica gel (0 to 50% ethyl acetate in hexanes) to give Intermediate 28-5A (early eluent peak from silica gel column) and Intermediate 28-5B (late eluent peak from silica gel column). LCMS: 879.4.

Intermediate 28-6: tert-butyl (1S,4R,15aR)-10,12-difluoro-11-((R)-7-fluoro-3-(methoxymethoxy)-8-((triisopropylsilyl)ethynyl)naphthalen-1-yl)-8-(((2R,7aS)-2-fluorotetrahydro-1H-pyrrolizin-7a(5H)-yl)methoxy)-2,3,4,5,13,14,15,15a-octahydro-1H-1,4-epiminoazepino[1',2':1,8]azocino[2,3,4-de]quinazoline-16-carboxylate -continued

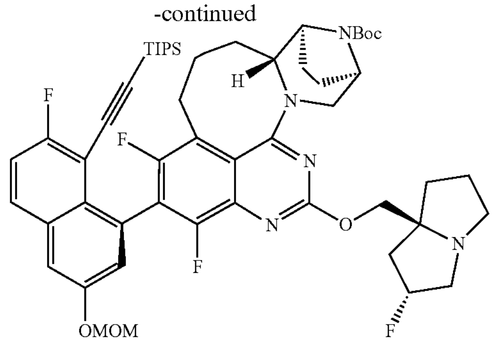

28-6

Intermediate 28-6 was synthesized in a manner similar to Comparative Intermediate 75-9 of U.S. application Ser. No. 18/303,813, published as US 2023/0374036 using Intermediate 28-5B instead of Comparative Intermediate 75-8 of U.S. application Ser. No. 18/303,813, published as US 2023/0374036. LCMS: 958.6.

Intermediate 28-7: tert-butyl (1S,4R,15aR)-11-((R)-8-ethynyl-7-fluoro-3-(methoxymethoxy)naphthalen-1-yl)-10,12-difluoro-8-(((2R,7aS)-2-fluorotetrahydro-1H-pyrrolizin-7a(5H)-yl)methoxy)-2,3,4,5,13,14,15,15a-octahydro-1H-1,4-epiminoazepino[1',2':1,8]azocino[2,3,4-de]quinazoline-16-carboxylate

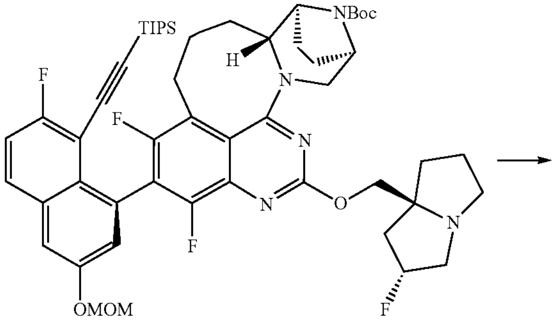

28-6

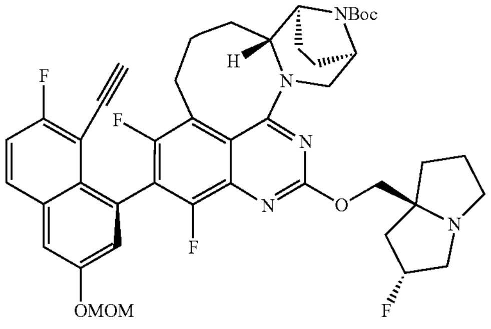

28-7

Intermediate 28-7 was synthesized in a manner similar to Intermediate 76-2 using Intermediate 28-6 instead of Intermediate 76-1. LCMS: 802.4.

Intermediate 28-8: (1S,4R,15aR)-11-((R)-8-ethynyl-7-fluoro-3-(methoxymethoxy)naphthalen-1-yl)-10,12-difluoro-8-(((2R,7aS)-2-fluorotetrahydro-1H-pyrrolizin-7a(5H)-yl)methoxy)-2,3,4,5,13,14,15,15a-octahydro-1H-1,4-epiminoazepino[1',2':1,8]azocino[2,3,4-de]quinazoline

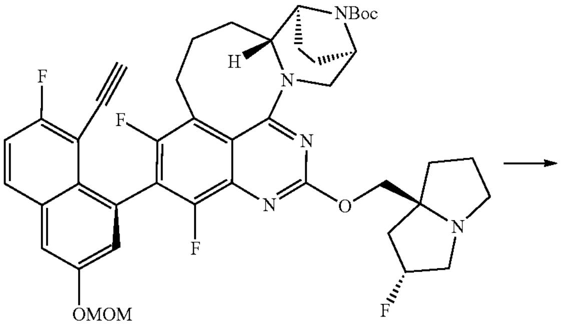

28-7

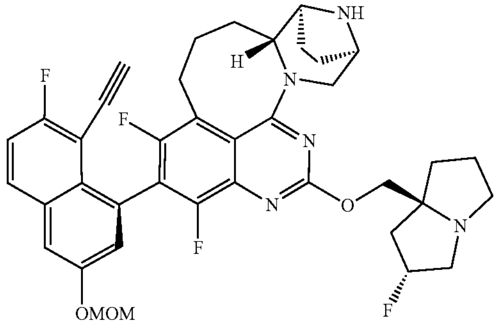

28-8

Intermediate 28-8 was synthesized in a manner similar to Intermediate 11-5 using Intermediate 28-7 instead of Intermediate 11-4. LCMS: 702.3.

Intermediate 28-9: 4-(((1S,4R,11R,15aR)-11-(8-ethynyl-7-fluoro-3-(methoxymethoxy)naphthalen-1-yl)-10,12-difluoro-8-(((2R,7aS)-2-fluorotetrahydro-1H-pyrrolizin-7a(5H)-yl)methoxy)-2,3,4,5,13,14,15,15a-octahydro-1H-1,4-epiminoazepino[1',2':1,8]azocino[2,3,4-de]quinazolin-16-yl)methyl)-5-methyl-1,3-dioxol-2-one

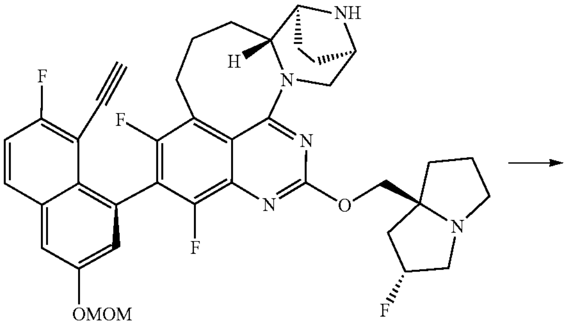

28-8

-continued

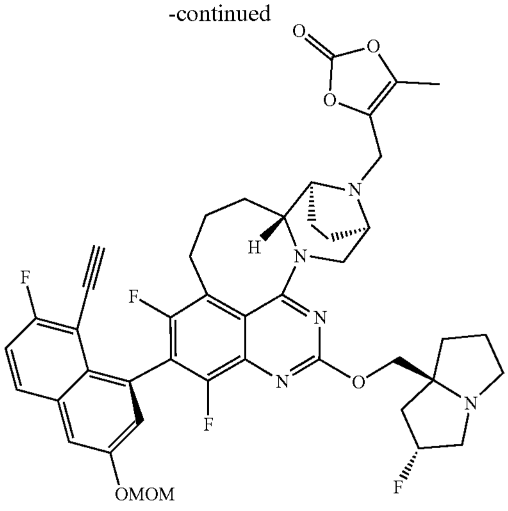

28-9

Intermediate 28-9 was synthesized in a manner similar to Intermediate 11-6 using Intermediate 28-8 instead of Intermediate 11-5. LCMS: 814.4.

Intermediate 29-1: tert-butyl (1S,2S,5R)-2-((S)-but-3-en-2-yl)-3,8-diazabicyclo[3.2.1]octane-8-carboxylate

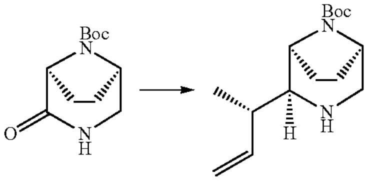

29-1

Intermediate 29-1 was synthesized in a manner similar to Intermediate 42-1 using (E)-2-(but-2-en-1-yl)-4,4,5,5-tetramethyl-1,3,2-dioxaborolane instead of (E)-2-(hepta-2,6-dien-1-yl)-4,4,5,5-tetramethyl-1,3,2-dioxaborolane. LCMS: 267.1.

Intermediate 29-2: tert-butyl (1S,2S,5R)-3-(5-bromo-7-chloro-2-(ethylthio)-8-fluoropyrido[4,3-d]pyrimidin-4-yl)-2-((S)-but-3-en-2-yl)-3,8-diazabicyclo[3.2.1]octane-8-carboxylate

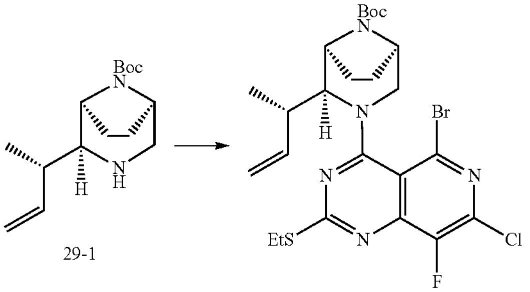

29-1

29-2

Intermediate 29-2 was synthesized in a manner similar to Intermediate 42-2 using Intermediate 29-1 instead of Intermediate 42-1. LCMS: 586.2.

Intermediate 29-3: tert-butyl (8S,8aS,9S,12R)-5-chloro-2-(ethylthio)-4-fluoro-8-methyl-7-methylene-7,8,8a,9,10,11,12,13-octahydro-1,3,6,13a,14-pentaaza-9,12-methanonaphtho[1,8-ab]heptalene-14-carboxylate

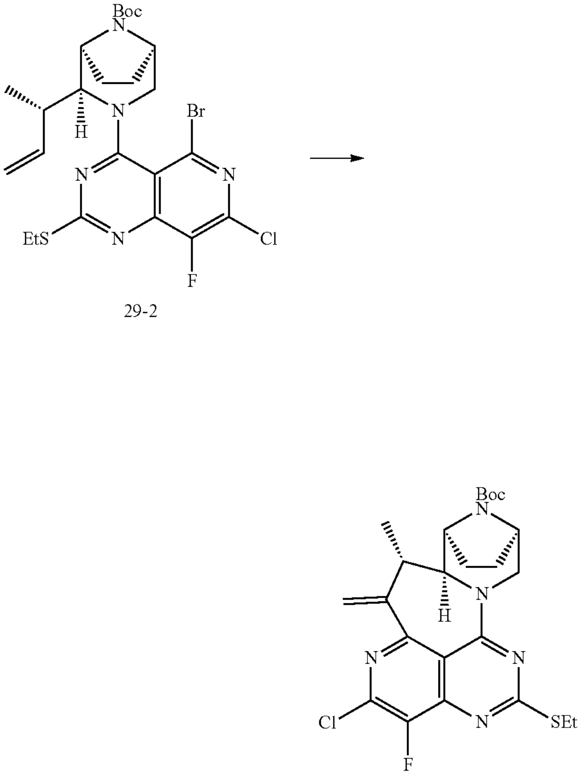

29-2

29-3

Triethylamine (2.67 mL, 19.2 mmol) was added via syringe to a vigorously stirred mixture of Intermediate 29-2 (6.62 g, 11.3 mmol), bis(tri-tert-butylphosphine)palladium (0) (284 mg, 338 μmol), and heptane (115 mL) at room temperature, and the resulting mixture was heated to 70° C. After 45 min, the resulting mixture was cooled to room temperature, and ethyl ether (150 mL) and hexanes (80 mL) were added sequentially. The organic layer was washed with a mixture of water and brine (2:1 v:v, 75 mL), was dried over anhydrous magnesium sulfate, was filtered, and was concentrated under reduced pressure. The residue was purified by flash column chromatography on silica gel (0 to 3.5% ethyl acetate in toluene) to give Intermediate 29-3. LCMS: 506.2.

Intermediate 29-4: tert-butyl (7R,8S,8aS,9S,12R)-5-chloro-2-(ethylthio)-4-fluoro-7,8-dimethyl-7,8,8a,9,10,11,12,13-octahydro-1,3,6,13a,14-pentaaza-9,12-methanonaphtho[1,8-ab]heptalene-14-carboxylate

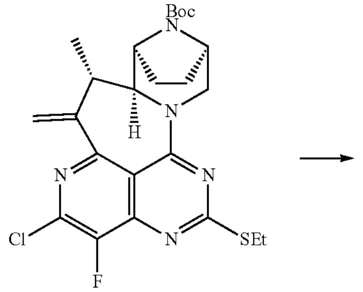

29-3

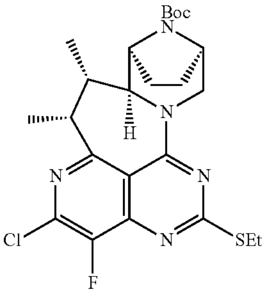

29-4

A vigorously stirred mixture of Intermediate 29-3 (3.21 g, 6.34 mmol), p-toluenesulfonyl hydrazide (5.91 g, 31.7 mmol), sodium acetate (5.20 g, 63.4 mmol), 1,4-dioxane (90 mL), and water (45 mL) was heated to 80° C. After 103 min, p-toluenesulfonyl hydrazide (5.91 g, 31.7 mmol) and sodium acetate (3.90 g, 47.6 mmol) were added sequentially. After 255 min, the resulting mixture was cooled to room temperature and was concentrated under reduced pressure to remove most of the 1,4-dioxane. Ethyl ether (200 mL), ethyl acetate (50 mL), and aqueous phosphoric acid solution (85% wt, 12 mL) were added sequentially. The organic layer was washed sequentially with water (300 mL) and a mixture of water and saturated aqueous sodium carbonate solution (300 mL), was dried over anhydrous magnesium sulfate, was filtered, and was concentrated under reduced pressure. The residue was purified by flash column chromatography on silica gel (0 to 8% ethyl acetate in hexanes) to give Intermediate 29-4. LCMS: 508.2.

Intermediate 37-1: tert-butyl (1S,2R,5R)-3-(5-bromo-6,8-difluoro-2-(methylthio)quinazolin-4-yl)-2-vinyl-3,8-diazabicyclo[3.2.1]octane-8-carboxylate

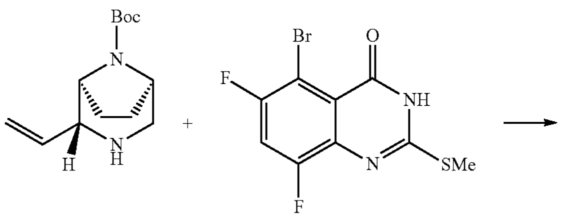

-continued

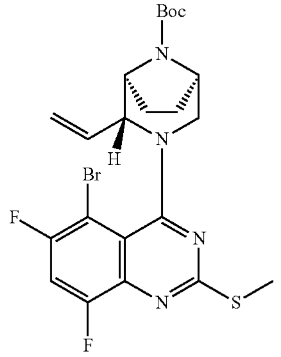

37-1

Intermediate 37-1 was synthesized in a manner similar to Intermediate 28-1 using tert-butyl (1S,2R,5R)-2-vinyl-3,8-diazabicyclo[3.2.1]octane-8-carboxylate instead of tert-butyl (1S,2R,5R)-2-allyl-3,8-diazabicyclo[3.2.1]octane-8-carboxylate. LCMS: 529.1.

Intermediate 37-2: tert-butyl (1S,4R,14aR)-10,12-difluoro-8-(methylthio)-1,2,3,4,5,13,14,14a-octahydro-1,4-epiminoazepino[1',2':1,7]azepino[2,3,4-de]quinazoline-15-carboxylate

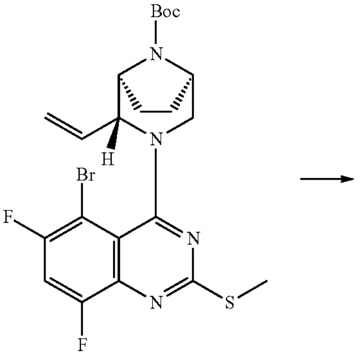

37-1

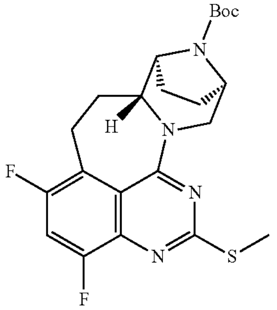

37-2

Intermediate 37-2 was synthesized in a manner similar to Intermediate 28-2 using Intermediate 37-1 instead of Intermediate 28-1. LCMS: 449.2.

Intermediate 37-3: tert-butyl (1S,4R,14aR)-10,12-difluoro-8-(methylsulfonyl)-1,2,3,4,5,13,14,14a-octahydro-1,4-epiminoazepino[1',2':1,7]azepino[2,3,4-de]quinazoline-15-carboxylate

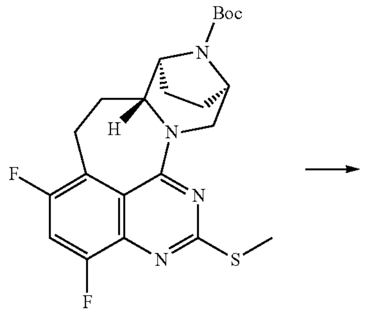

37-2

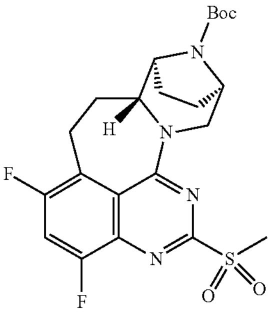

37-3

Intermediate 37-3 was synthesized in a manner similar to Intermediate 11-2 using Intermediate 37-2 instead of Intermediate 11-1. LCMS: 481.2.

Intermediate 37-4: tert-butyl (1S,4R,14aR)-10,12-difluoro-8-(((2R,7aS)-2-fluorotetrahydro-1H-pyrrolizin-7a(5H)-yl)methoxy)-1,2,3,4,5,13,14,14a-octahydro-1,4-epiminoazepino[1',2':1,7]azepino[2,3,4-de]quinazoline-15-carboxylate

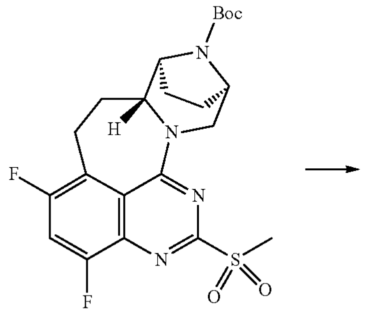

37-3

-continued

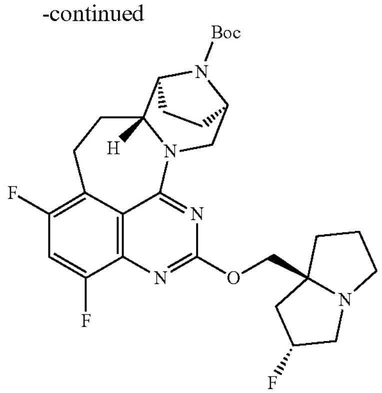

37-4

A mixture of Intermediate 37-3 (395 mg, 0.822 mmol), [(2R,8S)-2-fluoro-1,2,3,5,6,7-hexahydropyrrolizin-8-yl]methanol (196 mg, 1.23 mmol), cesium carbonate (402 mg, 1.23 mmol) and 1,4-diazabicyclo[2.2.2]octane (18.4 mg, 0.164 mmol) in DMF (3 ml) and THE (3 ml) was heated at 60° C. for 3 hour. Upon completion, the mixture was partitioned between EtOAc and brine, and the aqueous layer was extracted with EtOAc twice. The combined organic layer was dried over magnesium sulfate, filtered, and concentrated to dryness. The residue was purified by alumina basic column eluting with EtOAc/hexane to afford the title product. LCMS: 560.3.

Intermediate 37-5: tert-butyl (1S,4R,14aR)-11-bromo-10,12-difluoro-8-(((2R,7aS)-2-fluorotetrahydro-1H-pyrrolizin-7a(5H)-yl)methoxy)-1,2,3,4,5,13,14,14a-octahydro-1,4-epiminoazepino[1',2':1,7]azepino[2,3,4-de]quinazoline-15-carboxylate

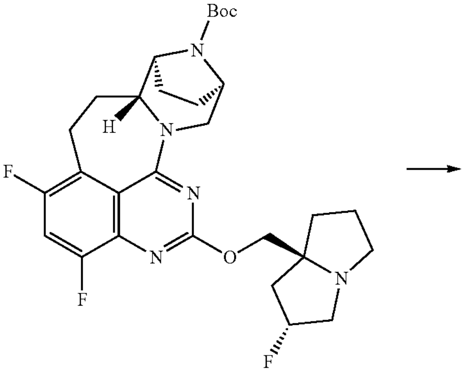

37-4

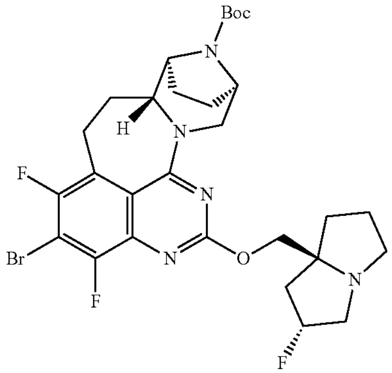

37-5

Intermediate 37-5 was synthesized in a manner similar to Intermediate 28-3 using Intermediate 37-4 instead of Intermediate 28-2. LCMS: 638.3.

Intermediate 37-6: tert-butyl (1S,4R,14aR)-10,12-difluoro-11-(7-fluoro-3-(methoxymethoxy)-8-((triisopropylsilyl)ethynyl)naphthalen-1-yl)-8-(((2R,7aS)-2-fluorotetrahydro-1H-pyrrolizin-7a(5H)-yl)methoxy)-1,2,3,4,5,13,14,14a-octahydro-1,4-epiminoazepino[1',2':1,7]azepino[2,3,4-de]quinazoline-15-carboxylate

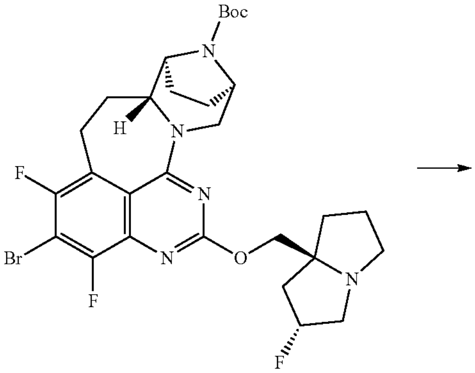

37-5

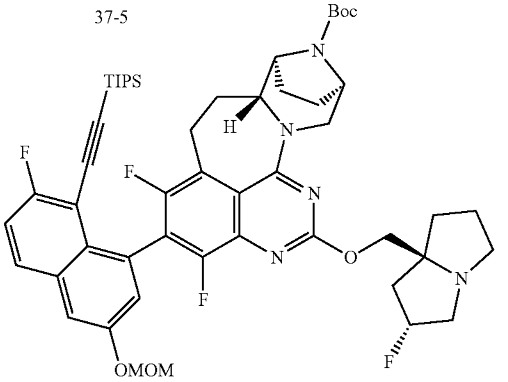

37-6

Intermediate 37-6 was synthesized in a manner similar to Intermediate 13-8 using Intermediate 37-5 instead of Intermediate 13-7. LCMS: 944.5.

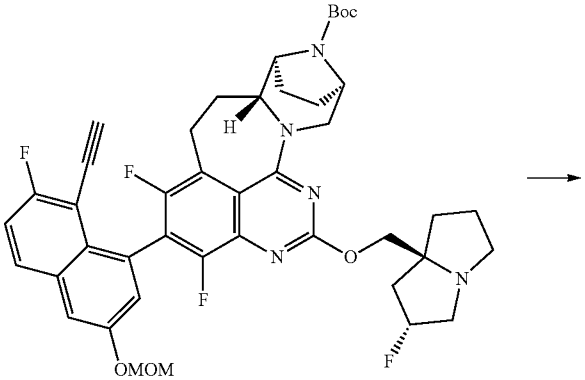

37-7

Intermediate 37-7: tert-butyl (1S,4R,14aR)-11-(8-ethynyl-7-fluoro-3-(methoxymethoxy)naphthalen-1-yl)-10,12-difluoro-8-(((2R,7aS)-2-fluorotetrahydro-1H-pyrrolizin-7a(5H)-yl)methoxy)-1,2,3,4,5,13,14,14a-octahydro-1,4-epiminoazepino[1',2':1,7]azepino[2,3,4-de]quinazoline-15-carboxylate

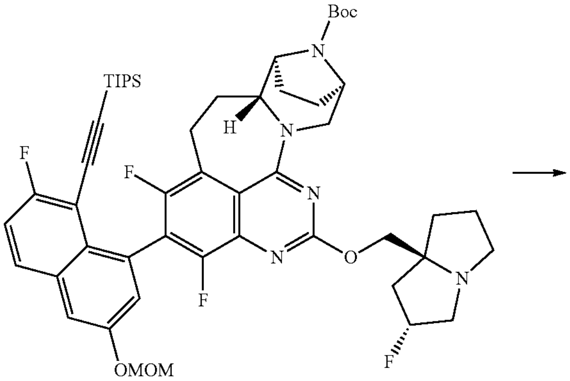

37-6

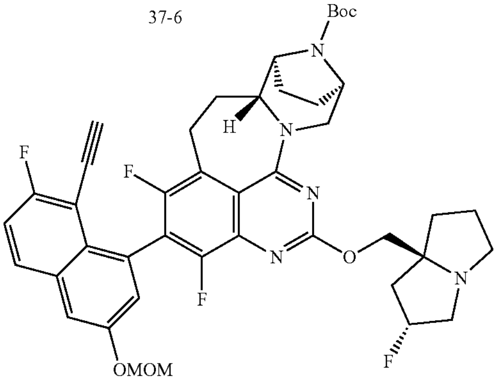

37-7

Intermediate 37-7 was synthesized in a manner similar to Intermediate 76-2 using Intermediate 37-5 instead of Intermediate 76-1. LCMS: 788.4.

Intermediate 37-8A: tert-butyl (1S,4R,11R,14aR)-11-(8-ethynyl-7-fluoro-3-(methoxymethoxy)naphthalen-1-yl)-10,12-difluoro-8-(((2R,7aS)-2-fluorotetrahydro-1H-pyrrolizin-7a(5H)-yl)methoxy)-1,2,3,4,5,13,14,14a-octahydro-1,4-epiminoazepino[1',2':1,7]azepino[2,3,4-de]quinazoline-15-carboxylate -continued

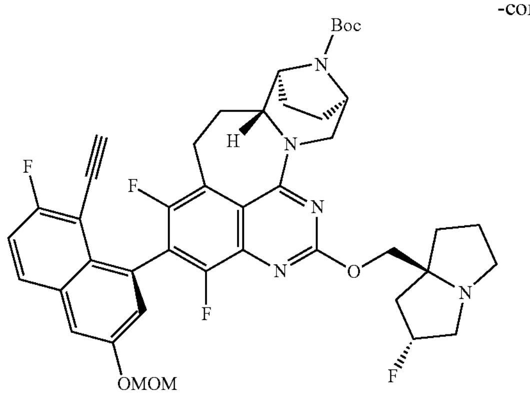

37-8A

+

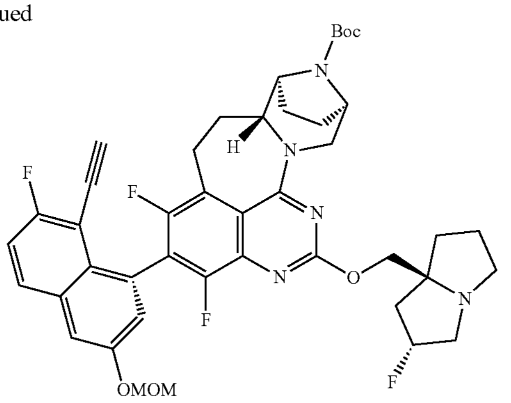

37-8B

Intermediate 37-7 was purified by chiral SFC separation (Chiralpak® AD-H column; ADH column) to yield two atropisomers. Intermediate 37-8A was the first eluting peak. LCMS: 788.4.

Intermediate 37-9: (1S,4R,11R,14aR)-11-(8-ethynyl-7-fluoro-3-(methoxymethoxy)naphthalen-1-yl)-10,12-difluoro-8-(((2R,7aS)-2-fluorotetrahydro-1H-pyrrolizin-7a(5H)-yl)methoxy)-1,2,3,4,5,13,14,14a-octahydro-1,4-epiminoazepino[1',2':1,7]azepino[2,3,4-de]quinazoline Intermediate 37-10: 4-(((1S,4R,11R,14aR)-11-(8-ethynyl-7-fluoro-3-(methoxymethoxy)naphthalen-1-yl)-10,12-difluoro-8-(((2R,7aS)-2-fluorotetrahydro-1H-pyrrolizin-7a(5H)-yl)methoxy)-1,2,3,4,5,13,14,14a-octahydro-1,4-epiminoazepino[1',2':1,7]azepino[2,3,4-de]quinazolin-15-yl)methyl)-5-methyl-1,3-dioxol-2-one

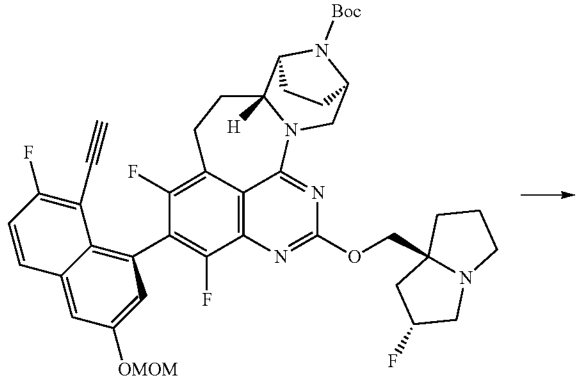

37-8A

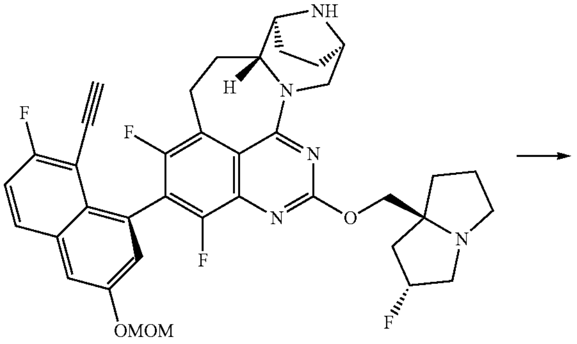

37-9

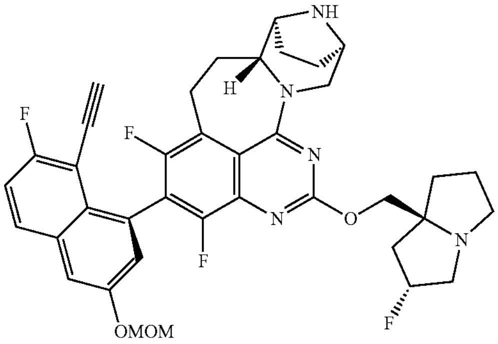

37-9

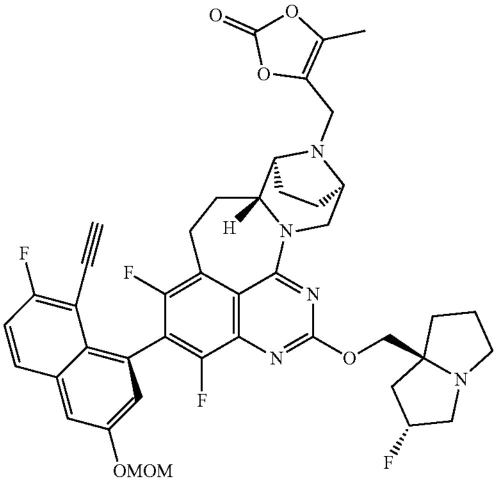

37-10

Intermediate 37-9 was synthesized in a manner similar to Intermediate 11-5 using Intermediate 37-8A instead of Intermediate 11-4. LCMS: 688.3.

Intermediate 37-10 was synthesized in a manner similar to Intermediate 11-6 using Intermediate 37-9 instead of Intermediate 11-5. LCMS: 800.4.

Intermediate 39-1: (S)-3-methylbutan-2-yl 1H-imidazole-1-carboxylate

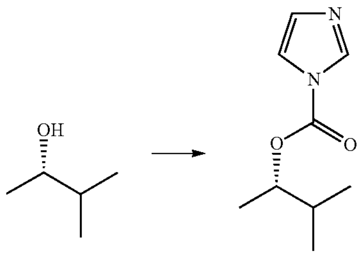

39-1

(S)-3-methylbutan-2-ol (123 µL, 1.13 mmol) was added via syringe to a stirred mixture of 1,1'-carbonyldiimidazole (184 mg, 1.13 mmol) and dichloromethane (3.0 mL) at 10° C., and the resulting mixture was warmed to room temperature. After 252 min, dichloromethane was added, and the organic layer was washed sequentially with water and brine, was dried over anhydrous magnesium sulfate, was filtered, and was concentrated under reduced pressure. The residue was purified by flash column chromatography on silica gel (0 to 10% ethyl acetate in hexanes) to give Intermediate 39-1. LCMS: 182.9.

Intermediate 39-2: (S)-3-methyl-1-(((3-methylbutan-2-yl)oxy)carbonyl)-1H-imidazol-3-ium iodide

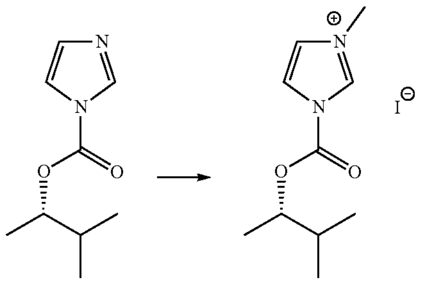

39-1 39-2

Iodomethane (212 µL, 3.40 mmol) was added via syringe to a stirred mixture of Intermediate 39-1 (155 mg, 851 µmol) and acetonitrile (1.5 mL) at room temperature. After 21 h, the resulting mixture was concentrated under reduced pressure to give Intermediate 39-2. LCMS: 196.7 [M−I]$^+$.

Intermediate 41-1: 4-(((6aR,7S,10R)-2-(8-ethynyl-7-fluoro-3-(methoxymethoxy)naphthalen-1-yl)-1-fluoro-13-(((2R,7aS)-2-fluorotetrahydro-1H-pyrrolizin-7a(5H)-yl)methoxy)-5,6,6a,7,8,9,10,11-octahydro-4H-3,11a,12,14,15-pentaaza-7,10-methanocyclohepta[4,5]cycloocta[1,2,3-de]naphthalen-15-yl)methyl)-5-propyl-1,3-dioxol-2-one

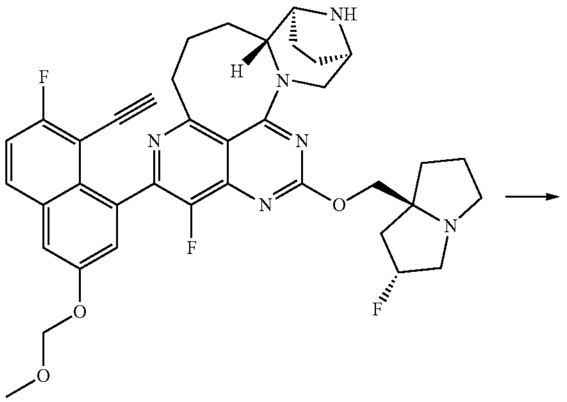

8-1

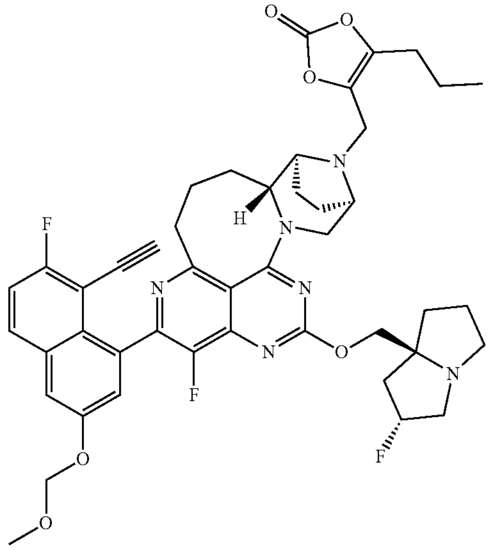

41-1

Intermediate 41-1 was synthesized in a manner similar to Intermediate 8-2 using 4-(bromomethyl)-5-propyl-1,3-dioxol-2-one instead of 4-(bromomethyl)-5-phenyl-1,3-dioxol-2-one. LCMS: 825.0.

Intermediate 42-1: tert-butyl (1S,2S,5R)-2-((S)-hepta-1,6-dien-3-yl)-3,8-diazabicyclo[3.2.1]octane-8-carboxylate

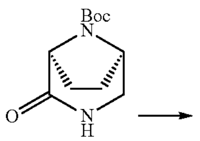

-continued

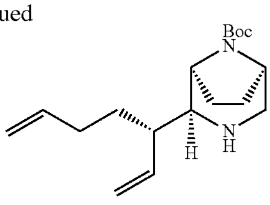

42-1

Bis(cyclopentadienyl)zirconium(IV) chloride hydride (5.49 g, 21.2 mmol) was added to a vigorously stirred mixture of tert-butyl (1S,5R)-2-oxo-3,8-diazabicyclo[3.2.1]octane-8-carboxylate (3.00 g, 13.3 mmol) in tetrahydrofuran (22 mL) at 0° C. After 34 min, water (478 μL, 26.5 mmol) and 42-methylmorpholine (2.33 mL, 21.2 mmol) were added sequentially. After 10 min, the resulting mixture was cooled to −40° C. over 17 min. A solution of (E)-2-(hepta-2,6-dien-42-yl)-4,4,5,5-tetramethyl-1,3,2-dioxaborolane (3.98 g, 17.9 mmol) in tetrahydrofuran (5.0 mL) was added over 2 min via cannula, and the resulting mixture was allowed to warm to room temperature over 20 h. Saturated aqueous sodium carbonate solution (70 mL), ethyl ether (200 mL), 2-methyltetrahydrofuran (50 mL), and water (20 mL) were added sequentially to the mixture. The biphasic mixture was agitated, and the layers were separated. The aqueous layer was extracted with 2-methyltetrahydrofuran (50 mL). The combined organic layers were dried over anhydrous magnesium sulfate, were filtered, and were concentrated under reduced pressure. The residue was redissolved in tetrahydrofuran (34 mL) and methanol (27 mL), and the resulting mixture was stirred vigorously at room temperature. Aqueous sodium hydroxide solution (6.0 M, 13.3 mL, 80 mmol) was added via syringe. After 230 min, saturated aqueous ammonium chloride solution (20 mL) was added, and the resulting mixture was concentrated under reduced pressure to remove most of the tetrahydrofuran and methanol. Saturated aqueous sodium carbonate solution (15 mL) was added, and the aqueous layer was extracted with a mixture of ethyl ether and ethyl acetate (3:1 v:v, 2×150 mL). The combined organic layers were dried over anhydrous magnesium sulfate, were filtered, and were concentrated under reduced pressure. The residue was purified by flash column chromatography on silica gel (0 to 10% methanol in dichloromethane) to give Intermediate 42-1. LCMS: 307.2.

Intermediate 42-2: tert-butyl (1S,2S,5R)-3-(5-bromo-7-chloro-2-(ethylthio)-8-fluoropyrido[4,3-d]pyrimidin-4-yl)-2-((S)-hepta-1,6-dien-3-yl)-3,8-diazabicyclo[3.2.1]octane-8-carboxylate

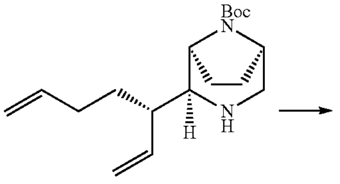

42-1

-continued

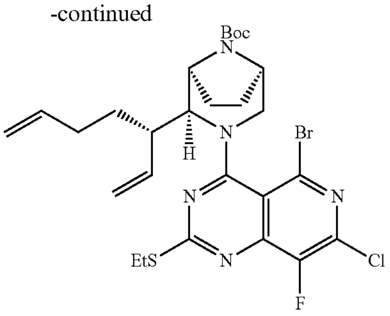

42-2

5-Bromo-4,7-dichloro-2-(ethylthio)-8-fluoropyrido[4,3-d]pyrimidine (2.28 g, 6.39 mmol) was added to a vigorously stirred mixture of Intermediate 42-1 (1.78 g, 5.81 mmol), N,N-diisopropylethylamine (1.37 mL, 7.84 mmol), and dichloromethane (8.0 mL) at room temperature. After 5 min, the resulting mixture was heated to 50° C. After 150 min, the resulting mixture was cooled to room temperature and was concentrated under reduced pressure. The residue was purified by flash column chromatography on silica gel (0 to 11% ethyl acetate in hexanes) to give Intermediate 42-2. LCMS: 626.1.

Intermediate 42-3: tert-butyl (1S,2S,5R)-3-(5-bromo-7-chloro-2-(ethylthio)-8-fluoropyrido[4,3-d]pyrimidin-4-yl)-2-((S)-cyclopent-2-en-42-yl)-3,8-diazabicyclo[3.2.1]octane-8-carboxylate

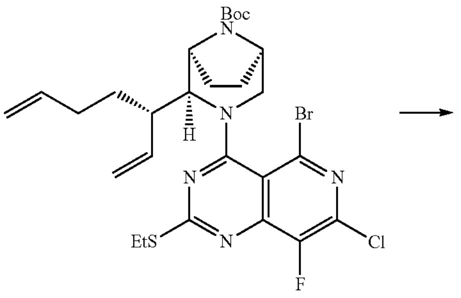

42-2

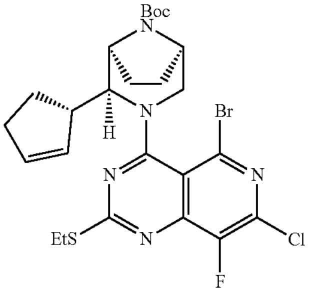

42-3

(1,3-Bis-(2,4,6-trimethylphenyl)-2-imidazolidinylidene)dichloro(o-isopropoxyphenylmethylene)ruthenium (246 mg, 392 μmol) was added to a stirred solution of Intermediate 42-2 (12.3 g, 19.6 mmol) in 1,2-dichloroethane (300 mL) at room temperature, and the resulting mixture was heated to 60° C. After 220 min, the resulting mixture was cooled to room temperature and was concentrated under reduced pressure. The residue was purified by flash column chromatography on silica gel (0 to 10% ethyl acetate in hexanes) to give Intermediate 42-3. LCMS: 598.1.

Intermediate 42-4: tert-butyl (3aS,3bS,4S,7R,14bR)-13-chloro-10-(ethylthio)-12-fluoro-3a,3b,4,5,6,7,8,14b-octahydro-3H-8a,9,11,14,15-pentaaza-4,7-methanocyclopenta[d]naphtho[1,8-ab]heptalene-15-carboxylate

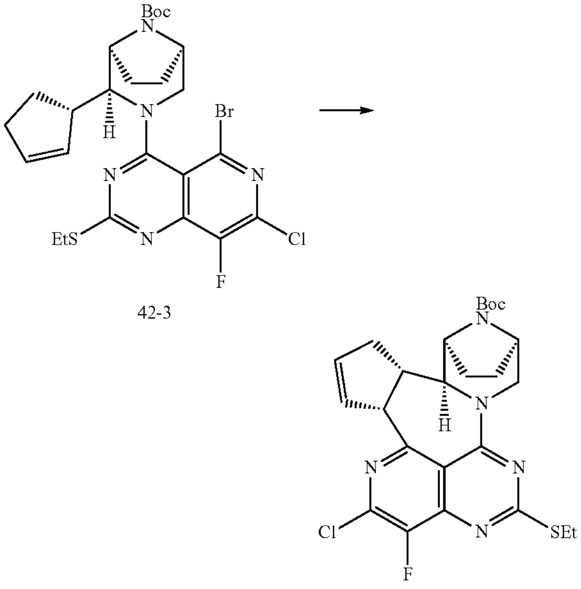

42-3

42-4

Triethylamine (308 mL, 2.21 mol) was added via syringe to a vigorously stirred mixture of Intermediate 42-3 (9.43 g, 15.7 mmol), bis(tri-tert-butylphosphine)palladium(0) (402 mg, 787 μmol), and toluene (300 mL) at room temperature, and the resulting mixture was heated to 75° C. After 30 min, the resulting mixture was heated to 83° C. After 135 min, the resulting mixture was cooled to room temperature and was concentrated under reduced pressure. The residue was purified by flash column chromatography on silica gel (0 to 25% ethyl acetate in hexanes) to give Intermediate 42-4. LCMS: 518.1.

Intermediate 42-5: tert-butyl (3aS,3bS,4S,7R,14bR)-13-chloro-10-(ethylthio)-12-fluoro-2,3,3a,3b,4,5,6,7,8,14b-decahydro-1H-8a,9,11,14,15-pentaaza-4,7-methanocyclopenta[d]naphtho[1,8-ab]heptalene-15-carboxylate

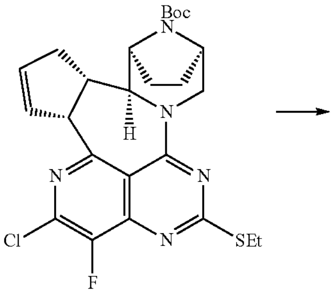

42-4

-continued

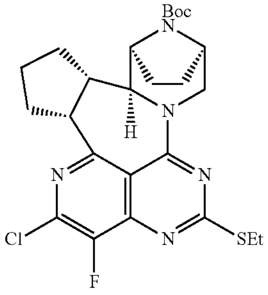

42-5

Triethylamine (6.38 mL, 45.8 mmol) was added via syringe to a stirred mixture of Intermediate 42-4 (5.93 g, 11.4 mmol), 2-nitrobenzenesulfonyl hydrazide (4.97 g, 22.9 mmol), tetrahydrofuran (80 mL), and 2-propanol (80 mL) at room temperature. After 375 min, 2-nitrobenzenesulfonyl hydrazide (7.46 g, 34.3 mmol) and triethylamine (9.57 mL, 68.7 mmol) were added sequentially. After 19 h 15 min, the resulting mixture was concentrated under reduced pressure. Ethyl ether (500 mL), ethyl acetate (50 mL), and saturated aqueous sodium carbonate solution (40 mL) were added sequentially. The organic layer was washed with water (300 mL), was dried over anhydrous magnesium sulfate, was filtered, and was concentrated under reduced pressure. The residue was purified by flash column chromatography on silica gel (0 to 15% ethyl acetate in hexanes) to give Intermediate 42-5. LCMS: 520.2.

Intermediate 42-6: tert-butyl (3aS,3bS,4S,7R,14bR)-10-(ethylthio)-12-fluoro-13-(7-fluoro-3-(methoxymethoxy)-8-((triisopropylsilyl)ethynyl)naphthalen-42-yl)-2,3,3a,3b,4,5,6,7,8,14b-decahydro-1H-8a,9,11,14,15-pentaaza-4,7-methanocyclopenta[d]naphtho[1,8-ab]heptalene-15-carboxylate

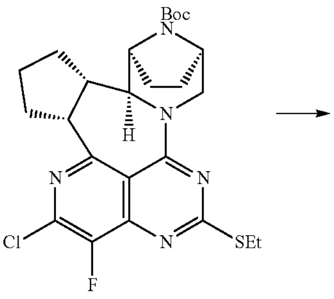

42-5

-continued

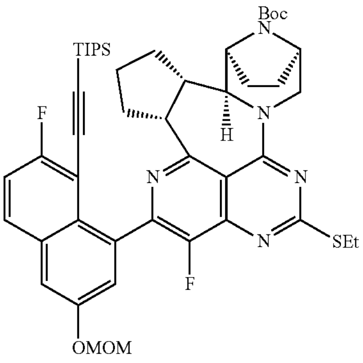

42-6

-continued

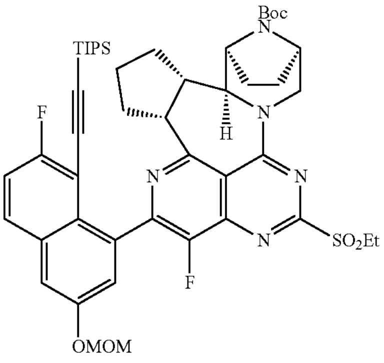

42-7

Aqueous potassium phosphate solution (2.0 M, 8.67 mL, 17 mmol) was added via syringe to a vigorously stirred mixture of Intermediate 42-5 (3.00 g, 5.78 mmol), ((2-fluoro-6-(methoxymethoxy)-8-(4,4,5,5-tetramethyl-1,3,2-dioxaborolan-2-yl)naphthalen-42-yl)ethynyl)triisopropylsilane (3.11 g, 6.07 mmol), [(di(42-adamantyl)-butylphosphine)-2-(2'-amino-1,1'-biphenyl)]palladium(II) methanesulfonate (421 mg, 578 μmol), and tetrahydrofuran (10 mL) at room temperature, and the resulting mixture was heated to 70° C. After 120 min, the resulting mixture was cooled to room temperature, and ethyl ether (100 mL) and ethyl acetate (25 mL) were added sequentially. The organic layer was washed with a mixture of water and brine (2:1 v:v, 60 mL), was dried over anhydrous magnesium sulfate, was filtered, and was concentrated under reduced pressure. The residue was purified by flash column chromatography on silica gel (0 to 25% ethyl acetate in hexanes) to give Intermediate 42-6. LCMS: 870.4.

Intermediate 42-7: tert-butyl (3aS,3bS,4S,7R,14bR)-10-(ethylsulfonyl)-12-fluoro-13-(7-fluoro-3-(methoxymethoxy)-8-((triisopropylsilyl)ethynyl) naphthalen-42-yl)-2,3,3a,3b,4,5,6,7,8,14b-decahydro-1H-8a,9,11,14,15-pentaaza-4,7-methanocyclopenta[d]naphtho[1,8-ab]heptalene-15-carboxylate

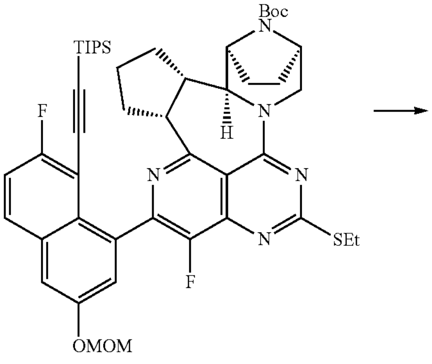

42-6

3-Chloroperbenzoic acid (77% wt, 2.53 g, 11 mmol) was added in three equal portions over 5 min to Intermediate 42-5 (4.80 g, 5.52 mmol) in dichloromethane (10 mL) at 0° C. After 2 min, the resulting mixture was warmed to room temperature. After 35 min, the resulting mixture was purified by flash column chromatography on silica gel (0 to 65% ethyl acetate in hexanes) to give Intermediate 42-7. LCMS: 902.3.

Intermediate 42-8: tert-butyl (3aS,3bS,4S,7R,14bR)-13-(8-ethynyl-7-fluoro-3-(methoxymethoxy)naphthalen-1-yl)-12-fluoro-10-(((2R,7aS)-2-fluorotetrahydro-1H-pyrrolizin-7a(5H)-yl)methoxy)-2,3,3a,3b,4,5,6,7,8,14b-decahydro-1H-8a,9,11,14,15-pentaaza-4,7-methanocyclopenta[d]naphtho[1,8-ab]heptalene-15-carboxylate 42-8

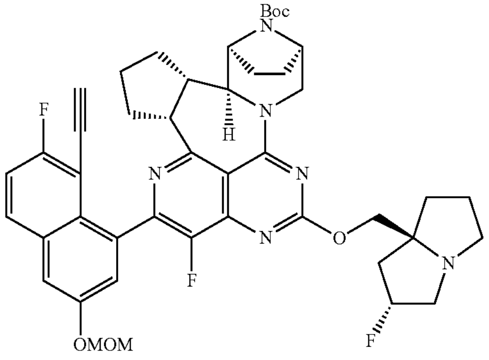

Intermediate 42-8 was synthesized in a manner similar to Intermediate 13-11 using Intermediate 42-7 instead of Intermediate 13-9 and using ((2R,7aS)-2-fluorotetrahydro-1H-pyrrolizin-7a(5H)-yl)methanol instead of Intermediate 13-14. LCMS: 811.2.

Intermediate 42-9: (3aS,3bS,4S,7R,14bR)-13-(8-ethynyl-7-fluoro-3-(methoxymethoxy)naphthalen-1-yl)-12-fluoro-10-(((2R,7aS)-2-fluorotetrahydro-1H-pyrrolizin-7a(5H)-yl)methoxy)-2,3,3a,3b,4,5,6,7,8,14b-decahydro-1H-8a,9,11,14,15-pentaaza-4,7-methanocyclopenta[d]naphtho[1,8-ab]heptalene 42-9

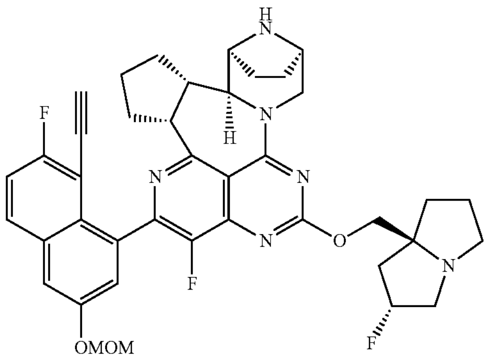

Intermediate 42-9 was synthesized in a manner similar to Intermediate 11-5 using Intermediate 42-8 instead of Intermediate 11-4. LCMS: 711.1.

Intermediate 51-1: tert-butyl (5S,5aS,6S,9R)-2-(3-((dimethylcarbamoyl)oxy)-8-ethynyl-7-fluoronaphthalen-1-yl)-1-fluoro-12-(((2R,7aS)-2-fluorotetrahydro-1H-pyrrolizin-7a(5H)-yl)methoxy)-5-methyl-4,5,5a,6,7,8,9,10-octahydro-3,10a,11,13,14-pentaaza-6,9-methanonaphtho[1,8-ab]heptalene-14-carboxylate

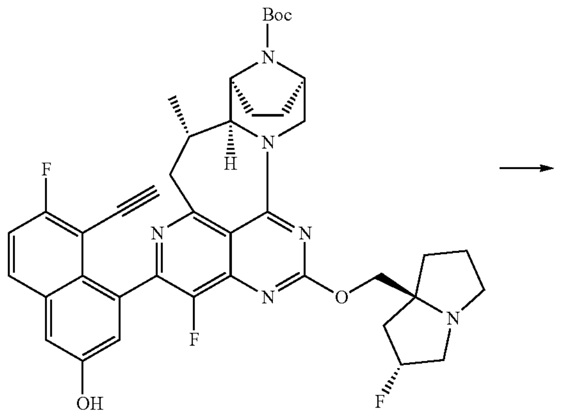

2-1

-continued

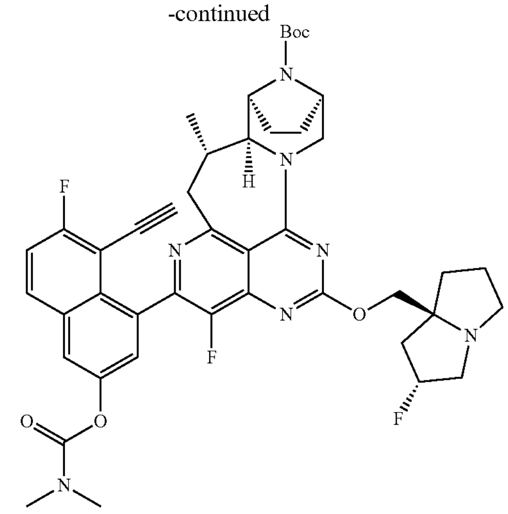

51-1

Dimethylcarbamoyl chloride (12.2 mg, 0.113 mmol) was added to the suspension of Intermediate 2-1 (70 mg, 0.0945 mmol) and potassium carbonate (19.6 mg, 0.142 mmol) in MeCN (1 mL) at rt. The mixture was stirred at 90° C. for 1 h before it was cooled to rt. It was filtered and concentrated. The residue was separated by column chromatography (alumina, EtOAc-hexanes 0-100%) to give Intermediate 51-1. LCMS 812.0.

Intermediate 51-2: 5-ethynyl-6-fluoro-4-((5S,5aS,6S,9R)-1-fluoro-12-(((2R,7aS)-2-fluorotetrahydro-1H-pyrrolizin-7a(5H)-yl)methoxy)-5-methyl-4,5,5a,6,7,8,9,10-octahydro-3,10a,11,13,14-pentaaza-6,9-methanonaphtho[1,8-ab]heptalen-2-yl)naphthalen-2-yl dimethylcarbamate 51-2

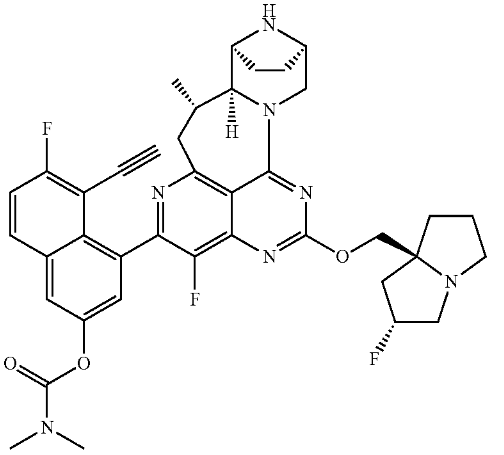

Intermediate 51-2 was synthesized in a manner similar to Intermediate 2-3 using Intermediate 51-1 instead of Intermediate 2-2. LCMS 712.2.

Intermediate 67-1: tert-butyl (5S,5aS,6S,9R)-2-(3-((5-(tert-butyl)-2-oxo-1,3-dioxol-4-yl)methoxy)-8-ethynyl-7-fluoronaphthalen-1-yl)-1-fluoro-12-(((2R,7aS)-2-fluorotetrahydro-1H-pyrrolizin-7a(5H)-yl)methoxy)-5-methyl-4,5,5a,6,7,8,9,10-octahydro-3,10a,11,13,14-pentaaza-6,9-methanonaphtho[1,8-ab]heptalene-14-carboxylate

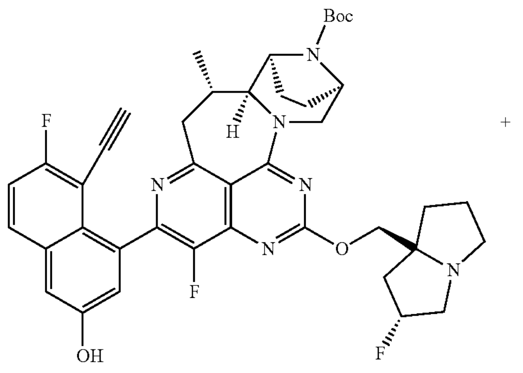

2-1

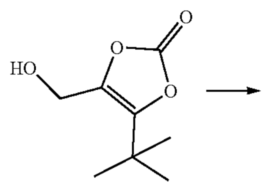

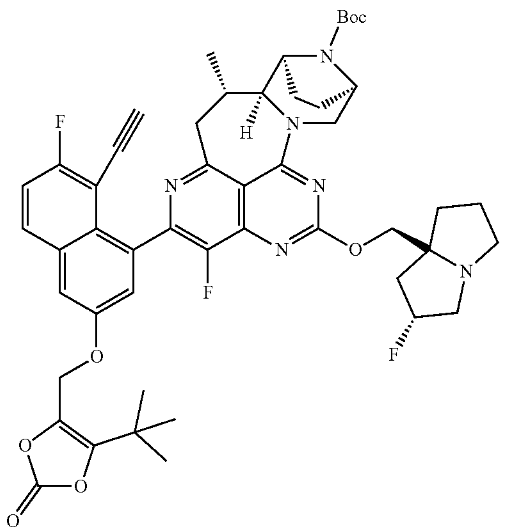

67-1

To a stirred solution of Intermediate 2-1 (65 mg, 0.088 mmol) and triphenylphosphine (57.5 mg, 0.219 mmol) in tetrahydrofuran (0.6 mL) was added diisopropyl azadicarboxylate (0.043 ml, 0.219 mmol)) at 0° C. under nitrogen atmosphere and the resulting reaction mixture was allowed to stir at room temperature for 10 minute followed by addition of 4-tert-butyl-5-(hydroxymethyl)-1,3-dioxol-2-one (22.7 mg, 0.13 mmol). Upon completion (about 1 hour), the reaction mixture was concentrated in vacuo. The residue was purified by silica gel chromatography eluting with EtOAc/hexane and then repurified by RP-HPLC eluting with ACN/water (w/0.1% TFA) to afford the title product. LCMS: 895.5.

Intermediate 71-1: tert-butyl (1S,2S,5R)-3-(5-bromo-6-chloro-8-fluoro-2-(methylthio)quinazolin-4-yl)-2-(prop-1-en-2-yl)-3,8-diazabicyclo[3.2.1]octane-8-carboxylate 71-1

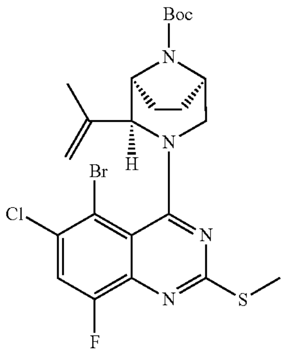

Intermediate 71-1 was synthesized in a manner similar to Intermediate C2-10 using Intermediate A-14 and tert-butyl (1S,2S,5R)-2-(prop-1-en-2-yl)-3,8-diazabicyclo[3.2.1]octane-8-carboxylate (U.S. application Ser. No. 18/303,813, published as US 2023/0374036) instead of Intermediate C2-9 and tert-butyl (1S,2R,5R)-2-allyl-3,8-diazabicyclo[3.2.1]octane-8-carboxylate. LCMS 558.1, 559.5.

Intermediate 71-2: tert-butyl (1S,4R,14S,14aS)-12-chloro-10-fluoro-14-methyl-8-(methylthio)-1,2,3,4,5,13,14,14a-octahydro-1,4-epiminoazepino[1',2':1,7]azepino[2,3,4-de]quinazoline-15-carboxylate 71-2

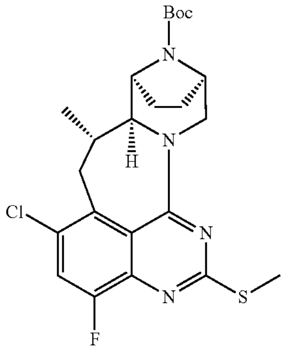

Intermediate 71-2 was synthesized in a manner similar to Intermediate 37-2 using Intermediate 71-1 instead of Intermediate 37-1. LCMS 479.4.

Intermediate 71-3: tert-butyl (1S,4R,14S,14aS)-12-chloro-10-fluoro-14-methyl-8-(methylsulfonyl)-1,2,3,4,5,13,14,14a-octahydro-1,4-epiminoazepino[1',2':1,7]azepino[2,3,4-de]quinazoline-15-carboxylate 71-3

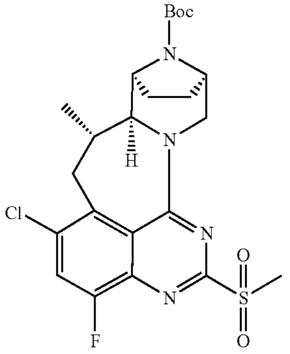

Intermediate 71-3 was synthesized in a manner similar to Intermediate 37-3 using Intermediate 71-2 instead of Intermediate 37-2. LCMS 511.7.

Intermediate 71-4: tert-butyl (1S,4R,14S,14aS)-12-chloro-10-fluoro-8-(((2R,7aS)-2-fluorotetrahydro-1H-pyrrolizin-7a(5H)-yl)methoxy)-14-methyl-1,2,3,4,5,13,14,14a-octahydro-1,4-epiminoazepino[1',2':1,7]azepino[2,3,4-de]quinazoline-15-carboxylate 71-4

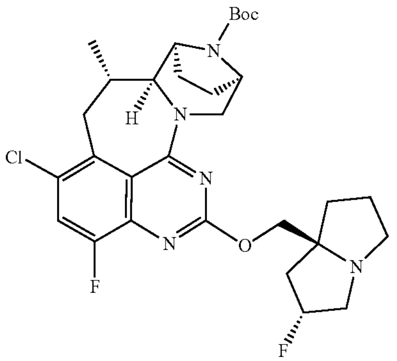

Intermediate 71-4 was synthesized in a manner similar to Intermediate 37-4 using Intermediate 71-3 instead of Intermediate 37-3.

Intermediate 71-5: tert-butyl (1S,4R,11R,14S,14aS)-11-(2-((tert-butoxycarbonyl)amino)-3-cyano-7-fluorobenzo[b]thiophen-4-yl)-12-chloro-10-fluoro-8-(((2R,7aS)-2-fluorotetrahydro-1H-pyrrolizin-7a(5H)-yl)methoxy)-14-methyl-1,2,3,4,5,13,14,14a-octahydro-1,4-epiminoazepino[1',2':1,7]azepino[2,3,4-de]quinazoline-15-carboxylate 71-5

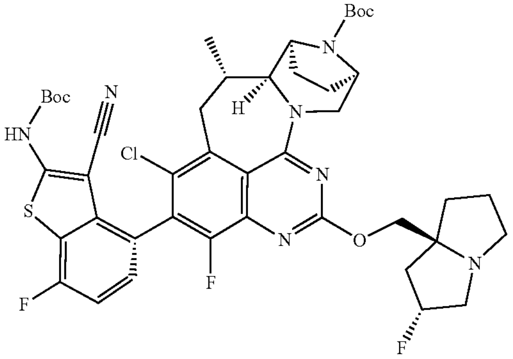

$(TMP)_2Zn{\cdot}2MgCl_2{\cdot}2LiCl$ (23.5 mL, 0.25 M) was added to the vial containing Intermediate 71-4 (800 mg, 1.36 mmol) under $N_2$ atmosphere. The resulting solution was stirred at 50° C. for 1.5 h before it was cooled to rt. A solution of tert-butyl (4-bromo-3-cyano-7-fluorobenzo[b]thiophen-2-yl)carbamate (755 mg, 2.0 mmol) and CPhos Pd G3 (164 mg, 0.2 mmol) in 10 mL of dioxane was added. The mixture was stirred at 55° C. for 0.5 h before it was cooled to rt. Saturated aqueous solution of $NH_4Cl$ was added to quench the reaction. The mixture was extracted with EtOAc (2×50 mL). The organic phase was separated, combined, dried over $Na_2SO_4$, filtered and concentrated. The residue was purified with flash column chromatography (alumina, MeOH-DCM 0-10%) to give the product. LCMS 880.7.

Intermediate A-1: 1,5-dibromo-2-fluoro-3-nitrobenzene

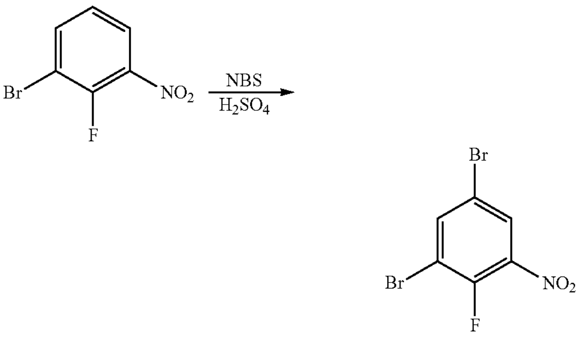

A-1

To a solution of 1-bromo-2-fluoro-3-nitro-benzene (250.0 g, 1136.3 mmol, 1.0 equiv.) in $H_2SO_4$ (70 mL) was added NBS (202.2 g, 318.2 mmol, 1.0 equiv.) at 25° C. The mixture was heated to 50° C. and stirred at 50° C. for 3 hours. The resulting mixture was cooled to 25° C. and quenched with ice water (2000 mL), extracted with EA (3×1000 mL). The combined organic phase was dried over $Na_2SO_4$, filtered and concentrated under reduced pressure to give a residue. The residue was purified by flash silica gel chromatography (PE/EA=10/1) to give Intermediate A-1. $^1H$ NMR (400 MHz, $CDCl_3$) 8.06 (dd, J=5.9 Hz, 1H), 7.93 (dd, J=5.5 Hz, 1H).

Intermediate A-2: 3,5-dibromo-2-fluoroaniline

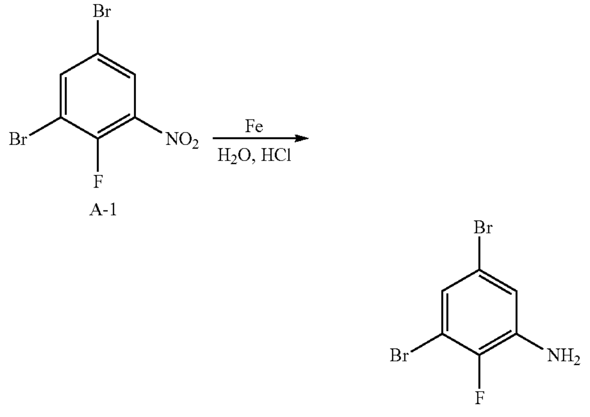

A-1
A-2

To a solution of Intermediate A-1 (230.0 g, 768.9 mmol, 1.0 equiv.) and Fe (129.2 g, 2306.9 mmol, 3.0 equiv.) in $H_2O$ (100 mL) was added con. HCl (400 mL) at 25° C. The mixture was heated to 100° C. and stirred at 100° C. for 1 hour. The resulting mixture was cooled to 25° C. and diluted with ice water (1000 mL). After filtration, the filter cake was washed with EA (600 mL), then the filtrate was washed with brine. The organic phase was dried over $Na_2SO_4$, filtered and concentrated under reduce pressure to give Intermediate A-2. LCMS: 269.9.

Intermediate A-3: (E)-N-(3,5-dibromo-2-fluorophenyl)-2-(hydroxyimino)acetamide

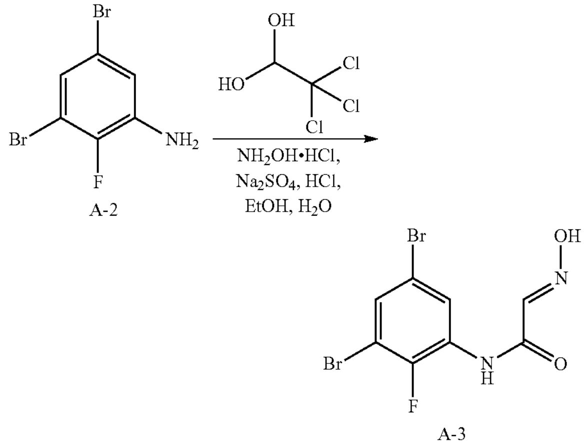

A-2
A-3

To a solution of 2,2,2-trichloroethane-1,1-diol (193.6 g, 1171.0 mmol, 1.5 equiv.), $Na_2SO_4$ (889.4 g, 6.2 mol, 8.0 equiv.) and $NH_2OH·HCl$ (189.8 g, 2732.3 mmol, 3.5 equiv.) in $H_2O$ (900 mL) was added a mixture of Intermediate A-2 (210.0 g, 780.6 mmol, 1.0 equiv.) in EtOH (135 mL) and con. HCl (18 mL) and $H_2O$ (450 mL) at 50° C. The mixture was heated to 70° C. and stirred at 70° C. for 12 hours. The resulting mixture was cooled to 25° C. The mixture was filtered and the filtrate was concentrated under reduced pressure to afford Intermediate A-3. LCMS: 340.8.

Intermediate A-4: 4,6-dibromo-7-fluoroindoline-2,3-dione

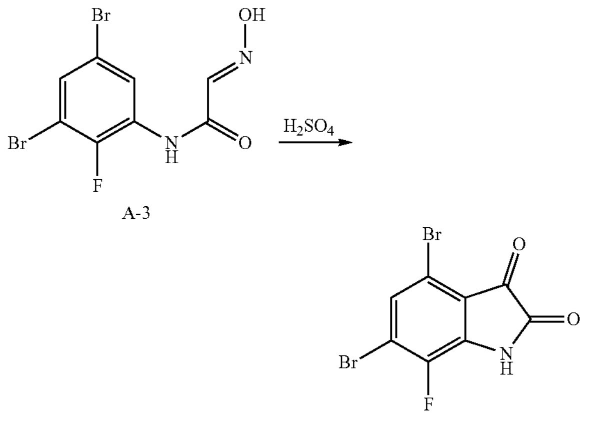

A-3
A-4

To a stirred solution of $H_2SO_4$ (150 mL) was added Intermediate A-3 (195.0 g, 573.5 mmol, 1.0 equiv.) at 50° C., then the mixture was heated to 70° C. stirred at 70° C. for 1 hour. The reaction mixture was cooled to at 25° C. and quenched with ice water (600 mL). After filtration, and the filter cake was washed with water (3×200 mL). The solid was concentrated under reduced pressure to afford Intermediate A-4. LCMS: 323.9.

Intermediate A-5: 2-amino-4,6-dibromo-3-fluorobenzoic acid

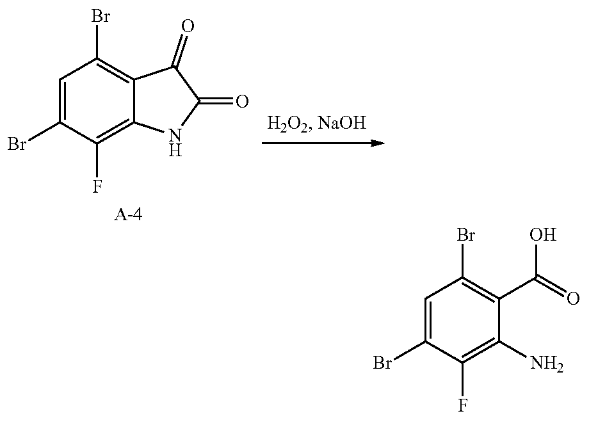

A-4
A-5

To a solution of Intermediate A-4 (20.0 g, 61.9 mmol, 1.0 equiv.) in NaOH (2.0 M, 309.6 mL, 10.0 equiv.) was added $H_2O_2$ (35.1 g, 309.6 mmol, 30% purity, 5.0 equiv.) at 0° C. The mixture was stirred at 25° C. for 16 hours. The reaction mixture was adjusted to pH 2 with 1.0 M HCl (200 mL). After filtration, the filter cake was washed with water (3×200 mL). The solid was concentrated under reduced pressure to give Intermediate A-5. LCMS: 313.8.

Intermediate A-6: 2-amino-4,6-dibromo-5-chloro-3-fluorobenzoic acid

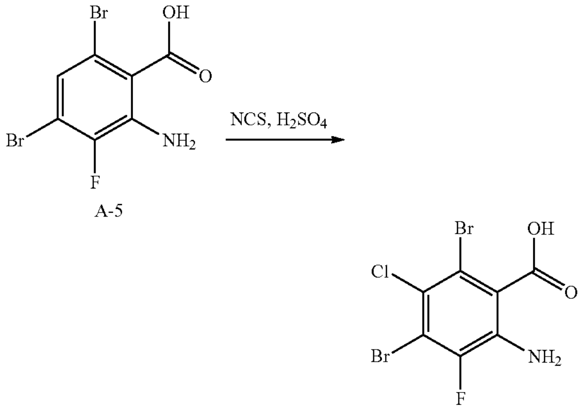

A-5
A-6

To a solution of Intermediate A-5 (22.0 g, 70.3 mmol, 1.0 equiv.) in $H_2SO_4$ (100 mL) was added NCS (18.7 g, 140.6 mmol, 2.0 equiv.) at 25° C. The mixture was heated to 80° C. and stirred at 80° C. for 12 hours. The reaction mixture was quenched with ice $H_2O$ (300 mL). After filtration, the filter cake was washed with water (3×100 mL). The solid was concentrated under reduced pressure to give Intermediate A-6. LCMS: 347.8.

Intermediate A-7: 5,7-dibromo-6-chloro-8-fluoro-2-mercaptoquinazolin-4-ol

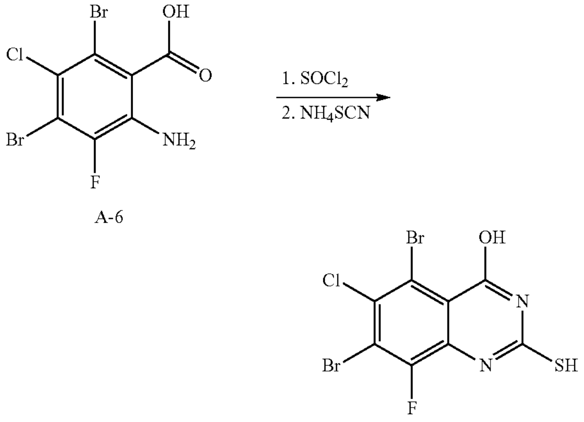

A-6
A-7

To a solution of Intermediate A-6 (8.0 g, 23.0 mmol, 1.0 equiv.) in DCM (40 mL) was added $SOCl_2$ (16.4 g, 138.2 mmol, 6.0 equiv.) and DMF (168 mg, 2.3 mmol, 0.1 equiv.), the reaction mixture was heated to 60° C. and stirred at 60° C. for 5 hours. The resulting mixture was cooled to 25° C. The resulting mixture was concentrated under reduced pressure to give a residue. The residue was dissolved in acetone (40 mL) and added $NH_4SCN$ (2.6 g, 34.5 mmol, 1.5 equiv.) at 25° C. The reaction mixture was stirred at 25° C. for 2 hours. The resulting mixture was filtered, the filter cake was washed with $H_2O$ (100 mL) and 10% NaOH (30 mL), then the solid was triturated with MeOH (50 mL) and ACN (50 mL) to give Intermediate A-7.

Intermediate A-8: 5,7-dibromo-6-chloro-8-fluoro-2-(methylthio)quinazolin-4-ol

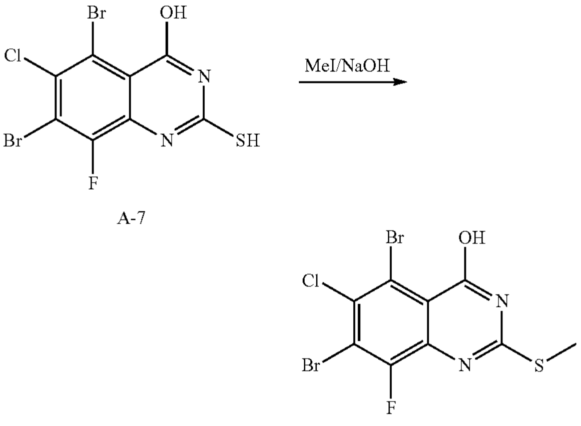

A-7
A-8

To a mixture of Intermediate A-7 (1.0 g, 2.5 mmol, 1.0 equiv.) in MeOH (20 mL) and $H_2O$ (10 mL) was added NaOH (206 mg, 5.1 mmol, 2.0 equiv.) and MeI (731 mg, 5.1 mmol, 2.0 equiv.) at 25° C., the reaction mixture was stirred at 25° C. for 0.5 hour. The resulting mixture was adjusted to pH 6 with 1 N HCl. After filtration, the filter cake was washed with water (3×50 mL). The solid was collected and purified by trituration with MeOH (50 mL) and ACN (50 mL) at 25° C. to afford this product. This reaction was repeated for thirteen times to afford Intermediate A-8. LCMS: 400.90.

Intermediate A-9: 5,7-dibromo-4,6-dichloro-8-fluoro-2-(methylthio)quinazoline

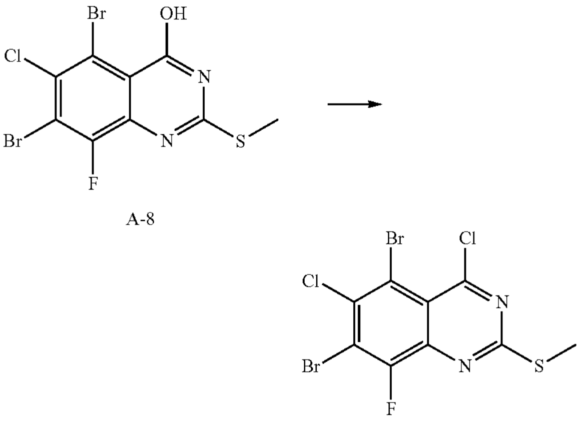
A-8
A-9

DIPEA (0.210 mL, 1.17 mmol) was added dropwise to the suspension of Intermediate A-8 (157 mg, 0.390 mmol) in $POCl_3$ (0.365 mL, 3.90 mmol) at rt. The resulting reaction mixture was stirred at rt for 30 min. The volatile components were evaporated in vacuo to give the crude product of Intermediate A-9, which was used for the next step without purification. LCMS: 420.9.

Intermediate A-10: tert-butyl (1S,2R,5R)-2-allyl-3-(5,7-dibromo-6-chloro-8-fluoro-2-(methylthio)quinazolin-4-yl)-3,8-diazabicyclo[3.2.1]octane-8-carboxylate

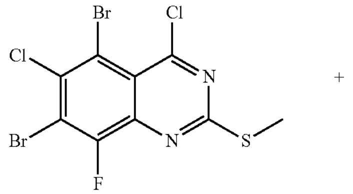

A-9

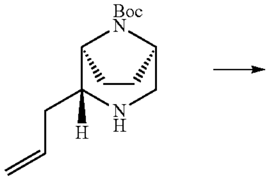

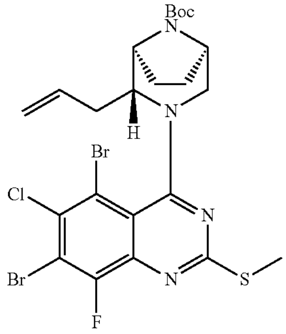

A-10 tert-Butyl (1S,2R,5R)-2-allyl-3,8-diazabicyclo[3.2.1]octane-8-carboxylate (200 mg, 0.793 mmol, synthesized according to Comparative Intermediate 75-5 of U.S. application Ser. No. 18/303,813, published as US 2023/0374036) and DIPEA (0.690 mL, 3.96 mmol) were added sequentially to the solution of Intermediate A-9 (334 mg, 0.793 mmol) in DCM (4 mL) at 0° C. The reaction mixture was warmed at rt and stirred for 12 h. The volatile components were evaporated in vacuo and the residue was purified by flash column chromatography (silica gel, EtOAc-hexanes 0-70%) to give Intermediate A-10. LCMS: 637.1.

Intermediate A-11: 2-amino-6-bromo-5-chloro-3-fluorobenzoic acid

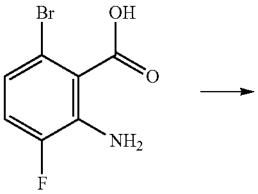

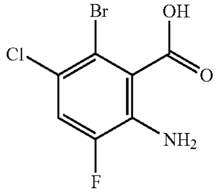

A-11

To a stirred solution of 2-amino-6-bromo-3-fluorobenzoic acid (95 g, 406 mmol) in acetonitrile (1 L) was added NCS (64.6 g, 406 mmol) at 0° C. Then the mixture was stirred for 16 hrs at 60° C. The reaction mixture was concentrated under reduced pressure to give crude product which was further purified by column chromatography using petroleum ether/ethyl acetate (I/O to 4/1) to afford Intermediate A-11. LCMS: 266 $[M-H]^+$.

Intermediate A-12: 5-bromo-6-chloro-8-fluoro-2-thioxo-2,3-dihydroquinazolin-4(1H)-one

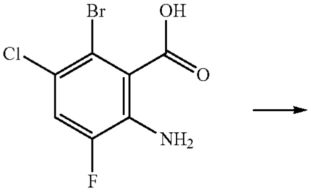

A-11

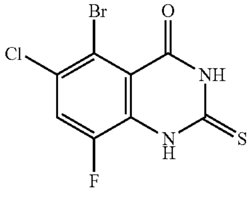

A-12

To a stirred solution of Intermediate A-11 (85.0 g, 285 mmol) in anhydrous DCM (850 mL) was added $SOCl_2$ (100 mL) at 0° C., and then stirred for 6 hrs at 80° C. The mixture was allowed to cool down to 25° C. The resulting mixture was concentrated under reduced pressure. The residue was dissolved in acetone (1.7 L), and then $NH_4SCN$ (43.4 g, 570 mmol) was added to the mixture, and then stirred for 1 hr at 25° C. The product was precipitated by the addition of ice water (1.7 L). The precipitated solids were collected by filtration and washed with water (2×500 mL) to give Intermediate A-12. LCMS: 307 $[M-H]^-$.

Intermediate A-13: 5-bromo-6-chloro-8-fluoro-2-(methylthio)quinazolin-4(3H)-one

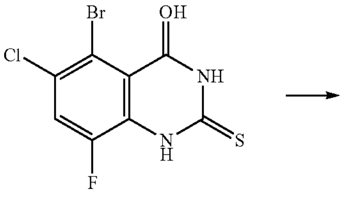

A-12

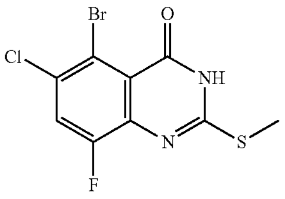

A-13

To a stirred solution of Intermediate A-12 (90 g, 291 mmol) in MeOH (900 mL) and $H_2O$ (450 mL) was added NaOH (23.3 g, 582 mmol) and MeI (82.5 g, 582 mmol) in portions at 25° C. and stirred for 1 hrs. After completion of reaction, the reaction mixture was diluted with $H_2O$ (450 mL). The mixture was acidified to pH 6 with HCl (1 M). The precipitated solids were collected by filtration and washed with $CS_2$ (500 mL) and ACN/MeOH (1/1, 1 L) to afford Intermediate A-13. LCMS: 323. $^1$H NMR (400 MHz, DMSO-$d_6$) δ: 12.93 (s, 1H), 8.00-7.97 (m, 1H), 2.55 (s, 3H).

Intermediate A-14: 5-bromo-4,6-dichloro-8-fluoro-2-(methylthio)quinazoline

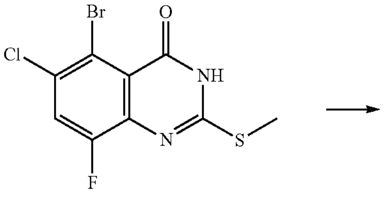

A-13

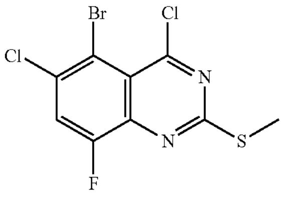

A-14

Intermediate A-14 was synthesized in a manner similar to Intermediate A-9 using Intermediate A-13 instead of Intermediate A-8. LCMS: 340.9.

Intermediate A-15: 5-bromo-6,8-difluoro-2-(methylthio)quinazolin-4(3H)-one

A-15

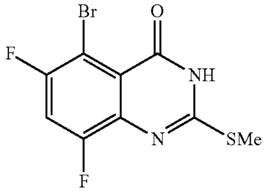

Intermediate A-15 was synthesized in a manner similar to Intermediate A-13 using 2-amino-6-bromo-3,5-difluorobenzoic acid instead of Intermediate A-11. LCMS: 307.0.

Intermediate A-16: 5-bromo-4-chloro-6,8-difluoro-2-(methylthio)quinazoline

A-16

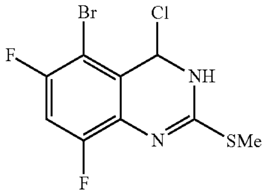

Intermediate A-16 was synthesized in a manner similar to Intermediate A-9 using Intermediate A-15 instead of Intermediate A-8. LCMS: 324.9.

Intermediate 72-1: 4-(((6aR,7S,10R)-2-(8-ethynyl-7-fluoro-3-(methoxymethoxy)naphthalen-1-yl)-1-fluoro-13-(((2R,7aS)-2-fluorotetrahydro-1H-pyrrolizin-7a(5H)-yl)methoxy)-5,6,6a,7,8,9,10,11-octahydro-4H-3,11a,12,14,15-pentaaza-7,10-methanocyclohepta[4,5]cycloocta[1,2,3-de]naphthalen-15-yl)methyl)-5-phenyl-1,3-dioxol-2-one

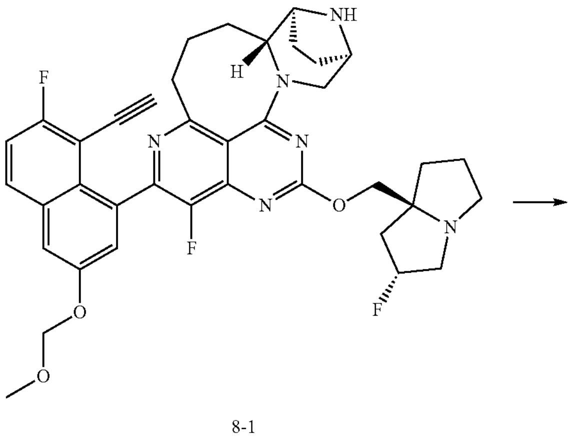

8-1

-continued

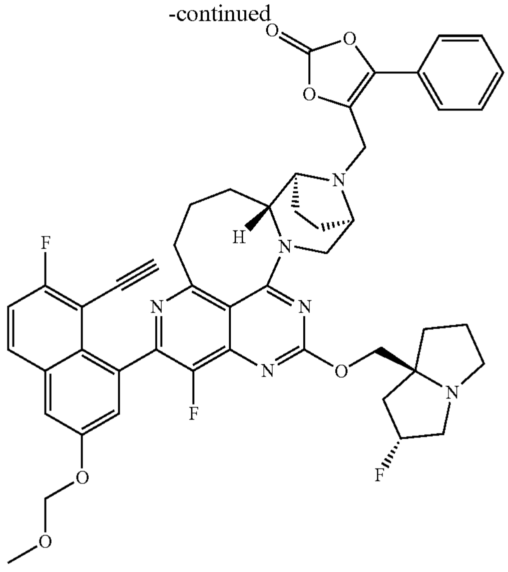

72-1

Intermediate 72-1 was synthesized in a manner similar to Intermediate 8-2 using 4-(bromomethyl)-5-phenyl-1,3-dioxol-2-one instead of 4-(bromomethyl)-5-phenyl-1,3-dioxol-2-one. LCMS: 859.2.

Intermediate 73-P-1: 3-(bis(4-methoxybenzyl)amino)-7-fluoro-8-((triisopropylsilyl)ethynyl)isoquinolin-1-yl trifluoromethanesulfonate

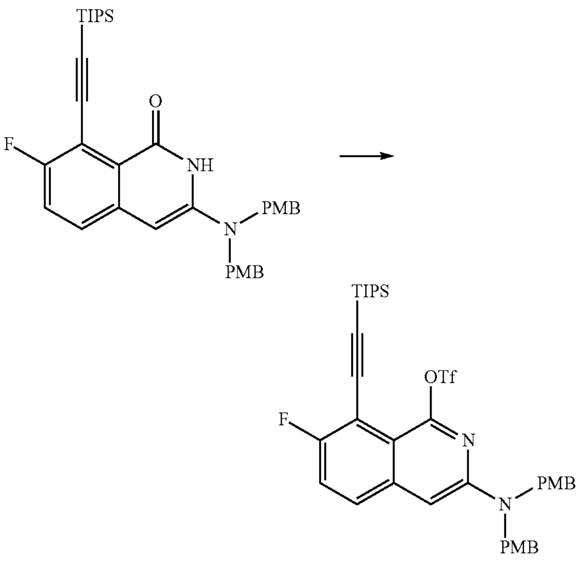

73-P-1

To a solution of 3-(bis(4-methoxybenzyl)amino)-7-fluoro-8-((triisopropylsilyl)ethynyl)isoquinolin-1(2H)-one (prepared according to US 2024/0239788) (1.02 g, 1.7 mmol) in dichloromethane (20 mL) were added triethylamine (1.42 mL, 10.2 mmol) and trifluoromethanesulfonic anhydride (0.86 mL, 5.11 mmol) at −78° C. under nitrogen. The reaction mixture was stirred at −78° C. for 20 minutes until all the starting material was consumed. The reaction mixture was concentrated under reduced pressure to give the residue which purified by silica gel chromatography eluting with EtOAc/hexane to afford Intermediate 73-P-1. LCMS: 731.3

Intermediate 73-P-2: tert-butyl (1S,4R,15aR)-10,12-difluoro-8-(methylsulfonyl)-2,3,4,5,13,14,15,15a-octahydro-1H-1,4-epiminoazepino[1',2':1,8]azocino[2,3,4-de]quinazoline-16-carboxylate

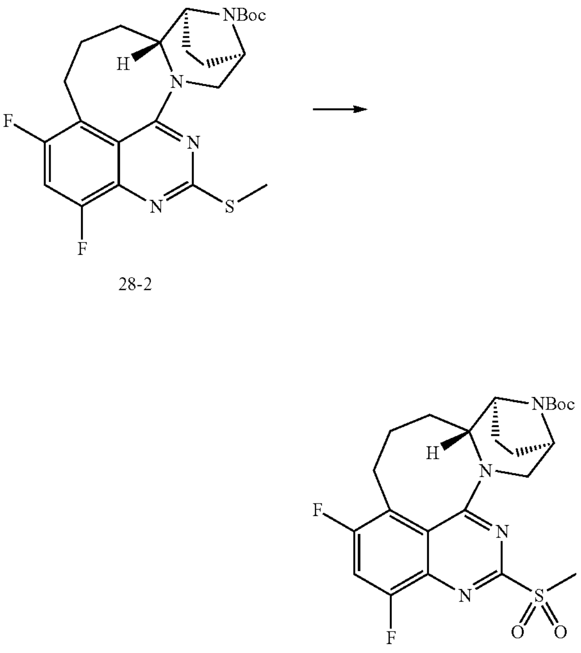

28-2

73-P-2

Intermediate 73-P-2 was synthesized in a manner similar to Intermediate 37-3 using Intermediate 28-2 instead of Intermediate 37-2. LCMS: 495.2

Intermediate 73-P-3: tert-butyl (1S,4R,15aR)-11-bromo-10,12-difluoro-8-(methylthio)-2,3,4,5,13,14,15,15a-octahydro-1H-1,4-epiminoazepino[1',2':1,8]azocino[2,3,4-de]quinazoline-16-carboxylate

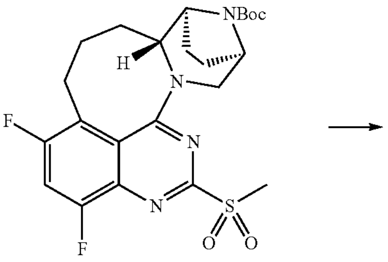

73-P-2

-continued

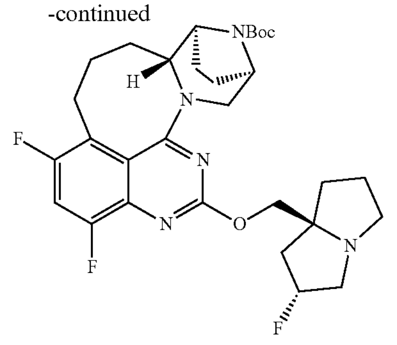

73-P-3

Intermediate 73-P-3 was synthesized in a manner similar to Intermediate 37-4 using Intermediate 73-P-2 instead of Intermediate 37-3. LCMS:574.4

Intermediate 73-P-4: tert-butyl (1S,4R,15aR)-11-(3-(bis(4-methoxybenzyl)amino)-7-fluoro-8-((triisopropylsilyl)ethynyl)isoquinolin-1-yl)-10,12-difluoro-8-(((2R,7aS)-2-fluorotetrahydro-1H-pyrrolizin-7a(5H)-yl)methoxy)-2,3,4,5,13,14,15,15a-octahydro-1H-1,4-epiminoazepino[1',2':1,8]azocino[2,3,4-de]quinazoline-16-carboxylate Intermediate 73-P-3 (30 mg. 0.052 mmol) in a dry flask was evacuated under vacuum and filled with nitrogen three times. The bis(2,2,6,6-tetramethylpiperidinyl)zinc, lithium chloride, and magnesium chloride complex ($(TMP)_2Zn\cdot 2MgCl_2\cdot 2LiCl$) (0.75 mL of a 0.25 M solution in THF, 0.188 mmol) was added and the reaction was allowed to stir for 2 hours at room temperature, check reaction by take a small aliquot quenched with Iodine. Then a solution of Intermediate 73-P-1 (76.4 mg, 0.105 mmol) in 0.75 ml of 1,4-dioxane was added and degassed by bubbling nitrogen through the solution for 3 minutes. CPhos Pd G3 (4.2 mg, 0.0052 mmol) was added, and the mixture was heated to 50° C. for overnight. The reaction was cooled in an ice bath and slowly quenched with a 1:1 solution of brine and water and ethyl acetate was added. Filtered thru a pad of celite if see insoluble. The layers were separated, and the aqueous layer was extracted with ethyl acetate. The combined organic layers were dried over magnesium sulfate, filtered, and concentrated. The residue was purified by silica gel chromatography eluting with ethyl acetate/hexane to yield the title product. LCMS:1155.6.

Intermediate 73-P-5: tert-butyl (1S,4R,15aR)-11-(3-(bis(4-methoxybenzyl)amino)-8-ethynyl-7-fluoroisoquinolin-1-yl)-10,12-difluoro-8-(((2R,7aS)-2-fluorotetrahydro-1H-pyrrolizin-7a(5H)-yl)methoxy)-2,3,4,5,13,14,15,15a-octahydro-1H-1,4-epiminoazepino[1',2':1,8]azocino[2,3,4-de]quinazoline-16-carboxylate

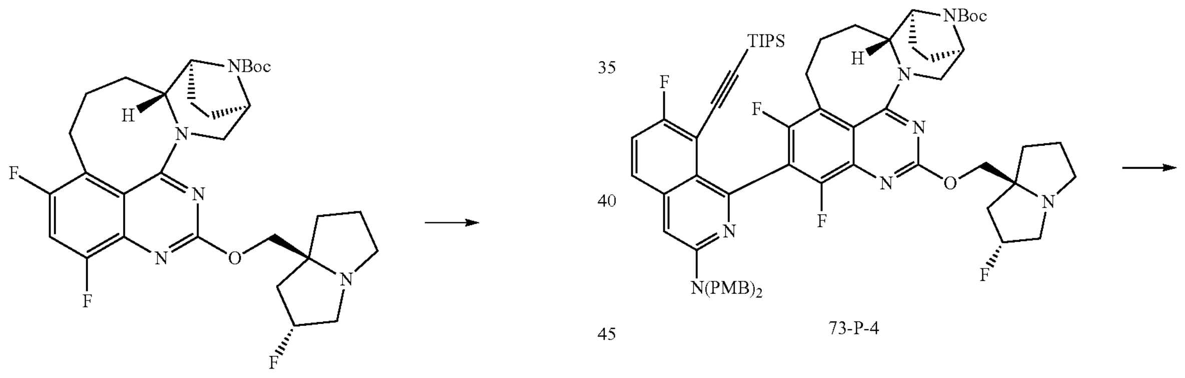

73-P-3

73-P-4

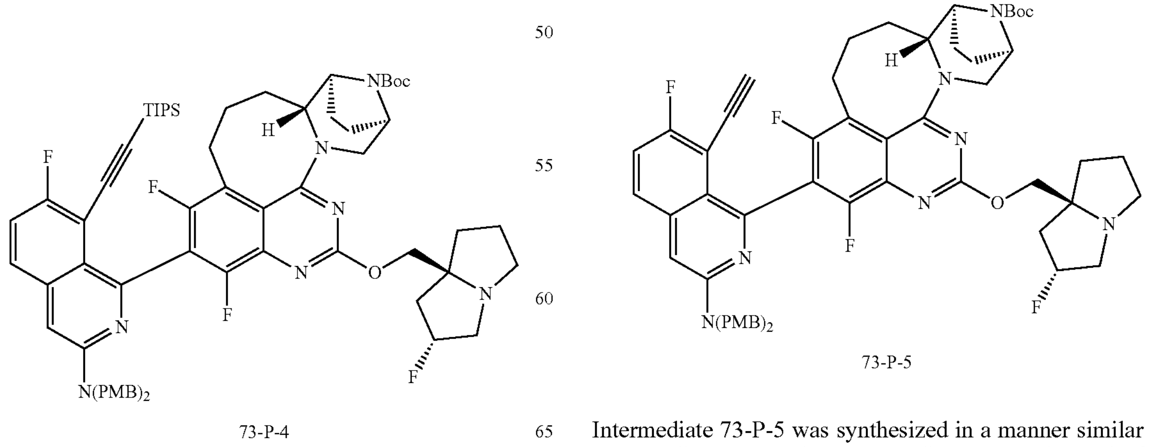

73-P-4

73-P-5

Intermediate 73-P-5 was synthesized in a manner similar to Intermediate 76-2 using Intermediate 73-P-4 instead of Intermediate 76-1. LCMS:998.5.

Intermediate 73-P-6A: tert-butyl (1S,4R,15aR)-11-((S)-3-(bis(4-methoxybenzyl)amino)-8-ethynyl-7-fluoroisoquinolin-1-yl)-10,12-difluoro-8-(((2R,7aS)-2-fluorotetrahydro-1H-pyrrolizin-7a(5H)-yl)methoxy)-2,3,4,5,13,14,15,15a-octahydro-1H-1,4-epiminoazepino[1',2':1,8]azocino[2,3,4-de]quinazoline-16-carboxylate

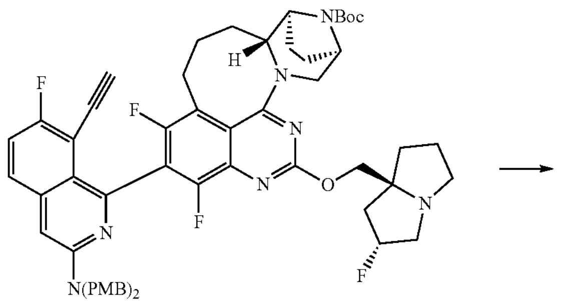

73-P-5

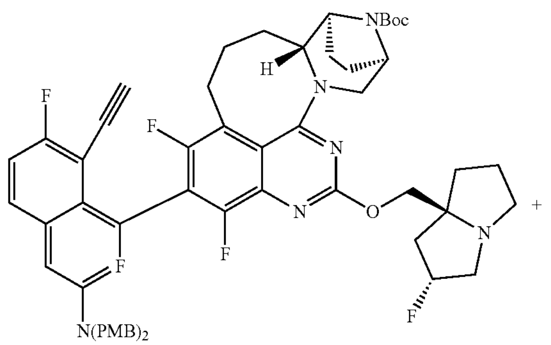

73-P-6A

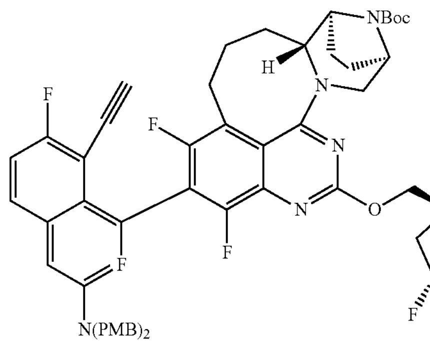

73-P-6B

Intermediate 73-P-6A was purified by chiral SFC separation (ODH column) to yield two atropisomers. Intermediate 73-P-6A is the fast eluted peak. LCMS: 998.5.

Intermediate 74-1: (R)-1-tert-butyl 3-methyl 3-methyl-4-oxopiperidine-1,3-dicarboxylate

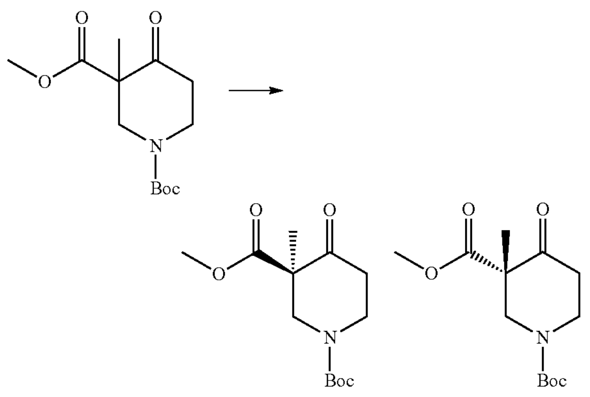

74-1

1-tert-Butyl 3-methyl 3-methyl-4-oxopiperidine-1,3-dicarboxylate (25.0 g, 0.0921 mol) was separated by SFC (SFC:column: Daicel Chiralpak® IG (250 mm*50 mm, 10 um); mobile phase: [A: $CO_2$; B: MeOH (0.1% $NH_3$—$H_2O$)]; B %: 11.00%-11.00%, 5.00 min). The peak with retention time=0.635 was assigned as Intermediate 74-1. The peak with retention time=0.837 was assigned as (S)-1-tert-butyl 3-methyl 3-methyl-4-oxopiperidine-1,3-dicarboxylate.

Intermediate 74-2: 1-(tert-butyl) 3-methyl (S)-4-(difluoromethylene)-3-methylpiperidine-1,3-dicarboxylate

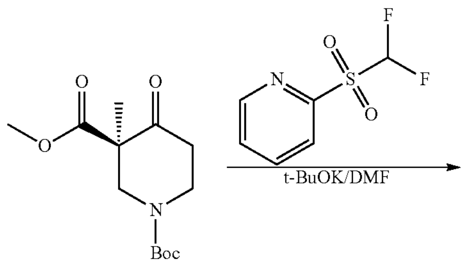

74-1

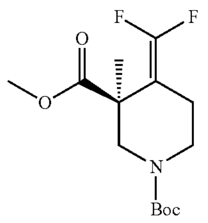

74-2

To the mixture of Intermediate 74-1 (1.50 g, 0.00553 mol) and 2-(difluoromethylsulfonyl)pyridine (2.14 g, 0.0111 mol) in N,N-dimethylformamide (12.0 mL) and tetrahydrofuran (4.00 mL) was added potassium tert-butoxide (1.00 mol/L, 16.6 mL, 0.0166 mol) at −78° C., the mixture was stirred at 25° C. for 12 hrs. The reaction mixture was filtered. To the filtrate was added EtOAc (20 mL) and then extracted with saturated aqueous LiCl (15 mL×3). The combined organic layers were dried over $Na_2SO_4$, filtered and concentrated under reduced pressure to give a residue. The residue was purified by purified by flash silica gel chromatography (12 g Silica Flash Column, Eluent of 0-20% PE/EtOAc gradient at 60 mL/min) to give Intermediate 74-2. LCMS: 250.1 $[M+H-56]^+$.

Intermediate 74-3: 1-(tert-butyl) 3-methyl (3S,4S)-4-(difluoromethyl)-3-methylpiperidine-1,3-dicarboxylate

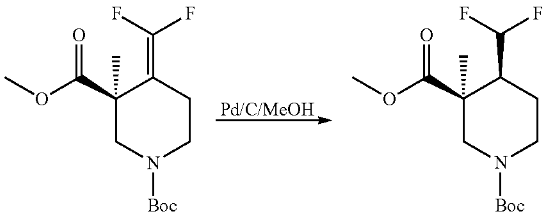

74-2 74-3

To the mixture of Pd/C (0.2 g, 10% purity) in MeOH (10 mL) was added Intermediate 74-2 (500 mg, 1.64 mmol) under $N_2$, the mixture was stirred at 30° C. for 2 hrs under $H_2$ (15 PSI). The mixture was filtered and concentrated under reduced pressure to give a residue. The residue was purified by purified by flash silica gel chromatography (8 g Silica Flash Column, Eluent of 0-30% PE/EtOAc gradient at 40 mL/min) to give Intermediate 74-3. LCMS: 252.0 $[M+H-56]^+$.

Intermediate 74-4: methyl (3S,4S)-4-(difluoromethyl)-3-methylpiperidine-3-carboxylate

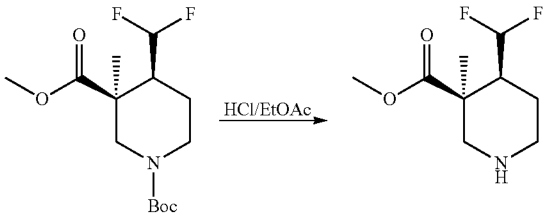

74-3 74-4

A mixture of Intermediate 74-3 (400 mg, 0.00130 mol) and chlorohydricacid (4M) in ethyl acetate (3.00 mL) was stirred at 25° C. for 1 hr. The reaction mixture was concentrated under reduced pressure to give Intermediate 74-4. LCMS: 208.1.

Intermediate 74-5: methyl (3S,4S)-4-(difluoromethyl)-1,3-dimethylpiperidine-3-carboxylate

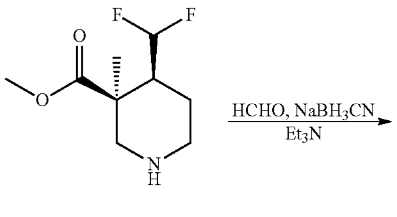

74-4

-continued

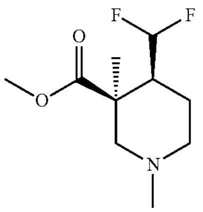

74-5

To the mixture of Intermediate 74-4 (450 mg, 0.00217 mol) in methanol (5.00 mL) was added triethylamine (0.220 g, 0.00217 mol) and aqueous formaldehyde solution (37.0% wt, 0.529 g, 0.00651 mol) and sodium cyanoborohydride (0.273 g, 0.00434 mol), and the resulting mixture was warmed to 20° C. for 1.5 hrs. The reaction mixture was filtered, and the filtrate was concentrated under reduced pressure to give a residue. The residue was purified by purified by flash silica gel chromatography (4 g Silica Flash Column, Eluent of 0-20% DCM/EtOAc gradient at 30 mL/min) to give Intermediate 74-5. LCMS: 222.0.

Intermediate 74-6: ((3S,4S)-4-(difluoromethyl)-1,3-dimethylpiperidin-3-yl)methanol

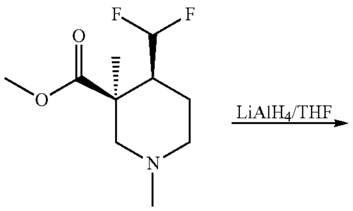

74-5

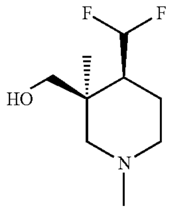

74-6

To the mixture of Intermediate 74-5 (200 mg, 0.000904 mol) in tetrahydrofuran (2.00 mL) was added lithium aluminum hydride (2.50 mol/L in tetrahydrofuran, 0.542 mL, 0.00136 mol) at 0° C. The mixture was stirred at 25° C. for 2 hrs. The product was triturated with $Na_2SO_4 \cdot 10H_2O$ (0.5 g) at 0° C. and stirred 12 hrs and under $N_2$. Then the mixture was filtered and collected to give Intermediate 74-6. LCMS: 194.1.

Intermediate 74-7: tert-butyl (6aR,7S,10R)-13-(((3S,4S)-4-(difluoromethyl)-1,3-dimethylpiperidin-3-yl)methoxy)-2-(8-ethynyl-7-fluoro-3-(methoxymethoxy)naphthalen-1-yl)-1-fluoro-5,6,6a,7,8,9,10,11-octahydro-4H-3,11a,12,14,15-pentaaza-7,10-methanocyclohepta[4,5]cycloocta[1,2,3-de]naphthalene-15-carboxylate

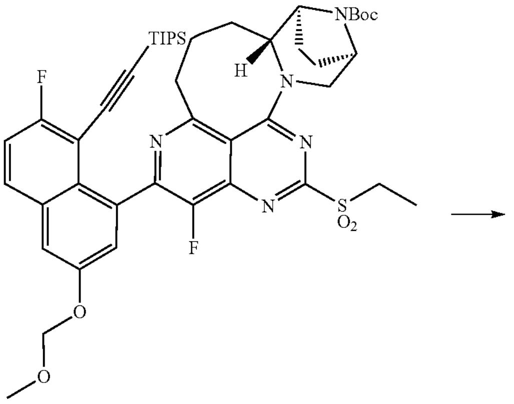

Comparative Intermediate 161-2

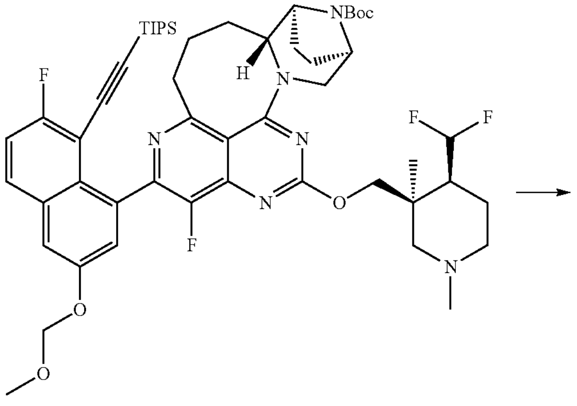

74-7

Intermediate 74-7 was synthesized in a manner similar to Intermediate 11-3 using Intermediate 74-6 instead of ((2R,7aS)-2-fluorotetrahydro-1H-pyrrolizin-7a(5H)-yl)methanol and using Comparative Intermediate 161-2 of U.S. application Ser. No. 18/303,813, published as US 2023/0374036 instead of Intermediate 11-2. LCMS: 975.9.

Intermediate 74-8: tert-butyl (6aR,7S,10R)-13-(((3S,4S)-4-(difluoromethyl)-1,3-dimethylpiperidin-3-yl)methoxy)-2-(8-ethynyl-7-fluoro-3-(methoxymethoxy)naphthalen-1-yl)-1-fluoro-5,6,6a,7,8,9,10,11-octahydro-4H-3,11a,12,14,15-pentaaza-7,10-methanocyclohepta[4,5]cycloocta[1,2,3-de]naphthalene-15-carboxylate

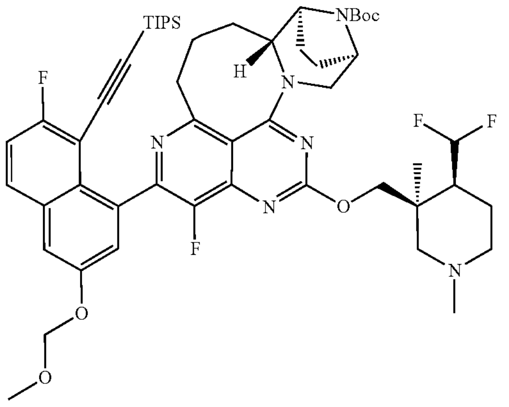

74-7

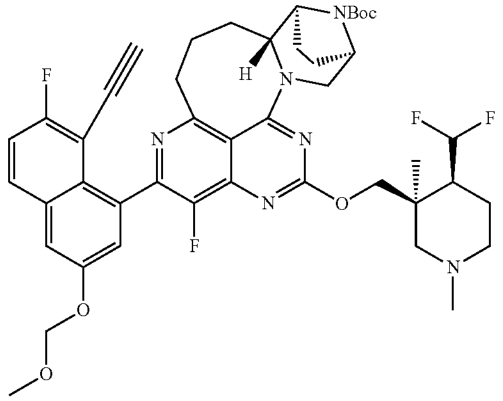

74-8

Intermediate 74-8 was synthesized in a manner similar to Comparative Intermediate 13-11 of U.S. application Ser. No. 18/303,813, published as US 2023/0374036, using Intermediate 74-7 instead of Comparative Intermediate 13-10 of U.S. application Ser. No. 18/303,813. LCMS: 819.0.

Intermediate 74-9: (6aR,7S,10R)-13-(((3S,4S)-4-(difluoromethyl)-1,3-dimethylpiperidin-3-yl)methoxy)-2-(8-ethynyl-7-fluoro-3-(methoxymethoxy)naphthalen-1-yl)-1-fluoro-5,6,6a,7,8,9,10,11-octahydro-4H-3,11a,12,14,15-pentaaza-7,10-methanocyclohepta[4,5]cycloocta[1,2,3-de]naphthalene

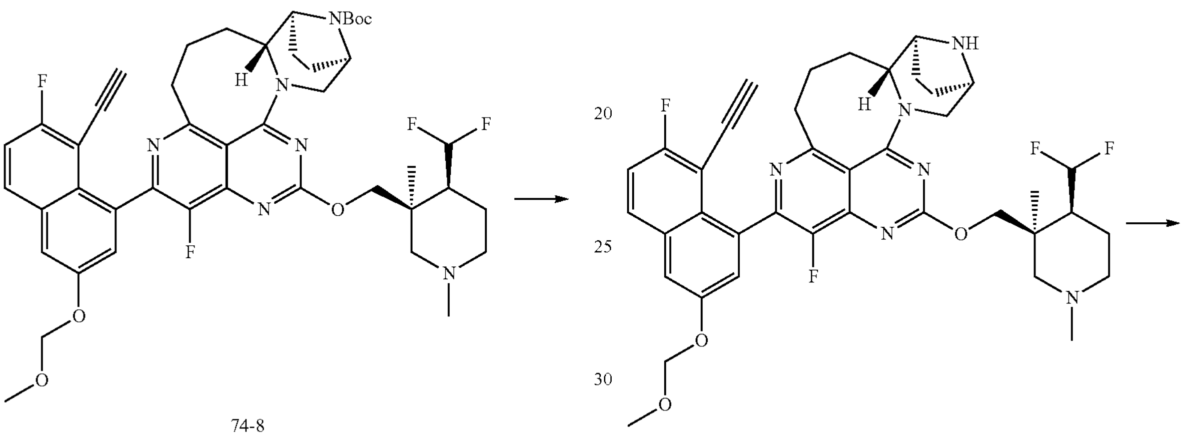

74-8

74-9

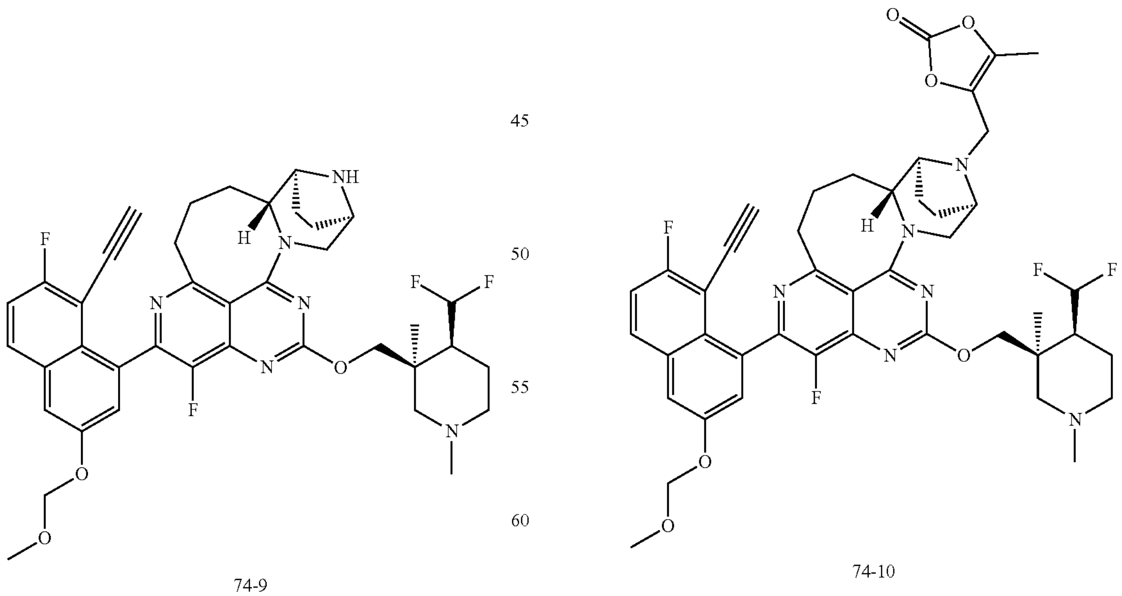

74-9

Intermediate 74-9 was synthesized in a manner similar to Intermediate 11-5 using Intermediate 74-8 instead of Intermediate 11-4. LCMS: 719.0.

Intermediate 74-10: 4-(((6aR,7S,10R)-13-(((3S,4S)-4-(difluoromethyl)-1,3-dimethylpiperidin-3-yl)methoxy)-2-(8-ethynyl-7-fluoro-3-(methoxymethoxy)naphthalen-1-yl)-1-fluoro-5,6,6a,7,8,9,10,11-octahydro-4H-3,11a,12,14,15-pentaaza-7,10-methanocyclohepta[4,5]cycloocta[1,2,3-de]naphthalen-15-yl)methyl)-5-methyl-1,3-dioxol-2-one 74-10

Intermediate 74-10 was synthesized in a manner similar to Intermediate 11-6 using Intermediate 74-9 instead of Intermediate 11-5. LCMS: 831.2.

Intermediate 75-1: ((3S,4S)-4-(difluoromethyl)-3-methyl-1-(methyl-$d_3$)piperidin-3-yl)methan-$d_2$-ol

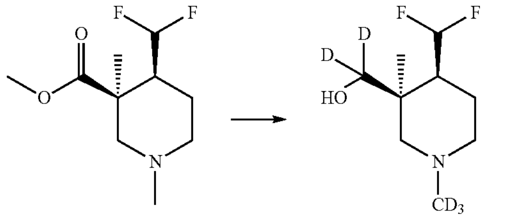

74-5 75-1

Lithium aluminum deuteride (116 mg, 2.76 mmol) was added to a vigorously stirred solution of Intermediate 74-5 (178 mg, 620 μmol) in tetrahydrofuran (7.0 mL) at room temperature, and the resulting mixture was heated to 60° C. After 19.5 h, the resulting mixture was cooled to 0° C., and sodium sulfate decahydrate (1.78 g, 5.52 mmol) was added slowly. The resulting mixture was warmed to room temperature. After 1 h, the resulting mixture was filtered through celite, the filter cake was extracted with ethyl acetate (30 mL), and the combined filtrates were concentrated under reduced pressure. Aqueous hydrogen chloride solution (1.0 M, 15 mL) was added, and the aqueous layer was washed with ethyl acetate (3×15 mL). Saturated sodium carbonate solution (10 mL) was added, and the aqueous layer was extracted with ethyl acetate (3×30 mL). The combined organic extracts were dried over anhydrous magnesium sulfate, were filtered, and were concentrated under reduced pressure to give Intermediate 75-1. LCMS: 199.2.

Intermediate 75-2: (6aR,7S,10R)-13-(((3S,4S)-4-(difluoromethyl)-3-methyl-1-(methyl-$d_3$)piperidin-3-yl)methoxy-$d_2$)-2-(8-ethynyl-7-fluoro-3-(methoxymethoxy)naphthalen-1-yl)-1-fluoro-5,6,6a,7,8,9,10,11-octahydro-4H-3,11a,12,14,15-pentaaza-7,10-methanocyclohepta[4,5]cycloocta[1,2,3-de]naphthalene 75-2

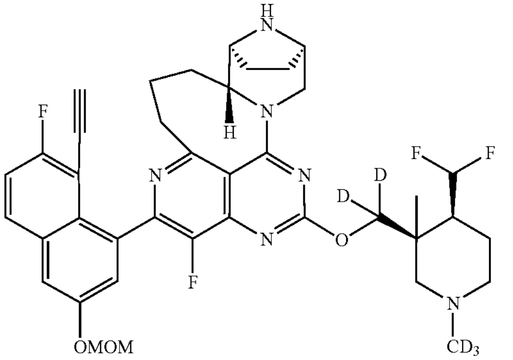

Intermediate 75-2 was synthesized in a manner similar to Intermediate 11-5 using Intermediate 75-1 instead of ((2R,7aS)-2-fluorotetrahydro-1H-pyrrolizin-7a(5H)-yl)methanol and using Comparative Intermediate 161-2 of U.S. application Ser. No. 18/303,813, published as US 2023/0374036 instead of Intermediate 11-4. LCMS: 724.3.

Intermediate 75-3: 4-(((6aR,7S,10R)-13-(((3S,4S)-4-(difluoromethyl)-3-methyl-1-(methyl-$d_3$)piperidin-3-yl)methoxy-$d_2$)-2-(8-ethynyl-7-fluoro-3-(methoxymethoxy)naphthalen-1-yl)-1-fluoro-5,6,6a,7,8,9,10,11-octahydro-4H-3,11a,12,14,15-pentaaza-7,10-methanocyclohepta[4,5]cycloocta[1,2,3-de]naphthalen-15-yl)methyl)-5-methyl-1,3-dioxol-2-one 75-3

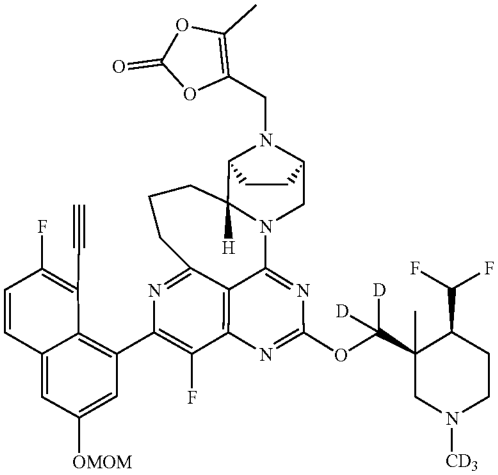

4-(Bromomethyl)-5-methyl-1,3-dioxol-2-one (21.1 μL, 191 μmol) was added via syringe to a vigorously stirred mixture of Intermediate 75-2 (132 mg, 182 μmol) in N,N-dimethylformamide (0.5 mL) at 0° C. After 135 min, acetic acid (100 μL), ethyl ether (40 mL), and ethyl acetate (20 mL) were added sequentially, and the resulting biphasic mixture was agitated. Saturated aqueous sodium bicarbonate solution (5.0 mL) was added, and the organic layer was washed with water (2×30 mL), was dried over anhydrous magnesium sulfate, was filtered, and was concentrated under reduced pressure. The residue was purified by flash column chromatography on silica gel (0 to 100% ethyl acetate in hexanes, each containing 3% triethylamine) to give Intermediate 75-3. LCMS: 836.3.

Intermediate 76-1: tert-butyl (6aR,7S,10R)-2-chloro-13-(ethylsulfonyl)-1-fluoro-5,6,6a,7,8,9,10,11-octahydro-4H-3,11a,12,14,15-pentaaza-7,10-methanocyclohepta[4,5]cycloocta[1,2,3-de]naphthalene-15-carboxylate

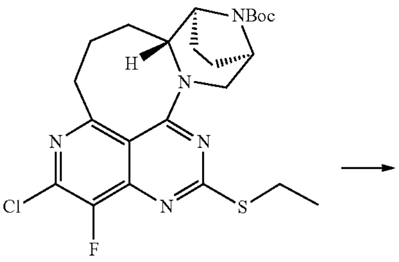

Comparative Intermediate 75-7

-continued

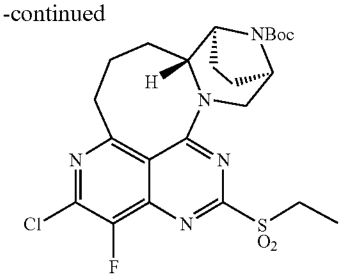

76-1

3-Chloroperoxybenzoic acid (77% wt, 710 mg, 3.2 mmol) was added to a vigorously stirred solution of Comparative Intermediate 75-7 of U.S. application Ser. No. 18/303,813, published as US 2023/0374036 (626 mg, 1.27 mmol) in dichloromethane (2.0 mL) at room temperature. After 25 min, the resulting mixture was purified by flash column chromatography on silica gel (0 to 40% ethyl acetate in hexanes) to give Intermediate 76-1. LCMS: 526.2.

Intermediate 76-2: tert-butyl (6aR,7S,10R)-2-chloro-13-(((3S,4S)-4-(difluoromethyl)-1,3-dimethylpiperidin-3-yl)methoxy)-1-fluoro-5,6,6a,7,8,9,10,11-octahydro-4H-3,11a,12,14,15-pentaaza-7,10-methanocyclohepta[4,5]cycloocta[1,2,3-de]naphthalene-15-carboxylate

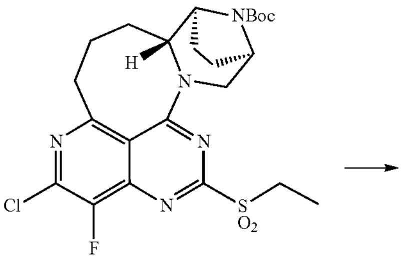

76-1

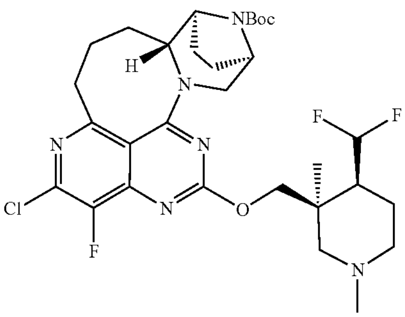

76-2

Intermediate 76-2 was synthesized in a manner similar to Intermediate 11-3 using Intermediate 74-6 instead of ((2R, 7aS)-2-fluorotetrahydro-1H-pyrrolizin-7a(5H)-yl)methanol and using Intermediate 76-1 instead of Intermediate 11-2. LCMS: 625.0.

Intermediate 76-3: tert-butyl (6aR,7S,10R)-13-(((3S,4S)-4-(difluoromethyl)-1,3-dimethylpiperidin-3-yl)methoxy)-2-(3-((diphenylmethylene)amino)-7-fluoro-8-((triisopropylsilyl)ethynyl)naphthalen-1-yl)-1-fluoro-5,6,6a,7,8,9,10,11-octahydro-4H-3,11a,12,14,15-pentaaza-7,10-methanocyclohepta[4,5]cycloocta[1,2,3-de]naphthalene-15-carboxylate

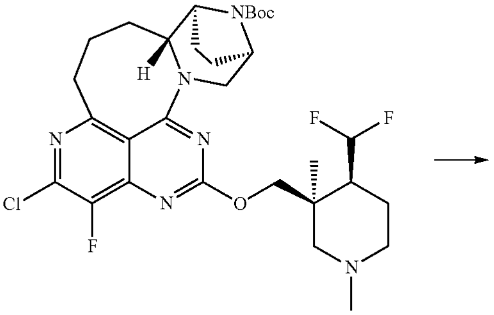

76-2

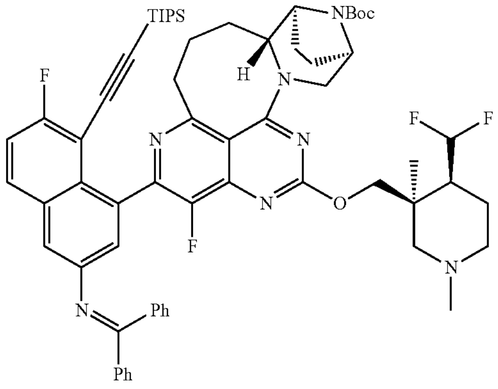

76-3

Intermediate 76-3 was synthesized in a manner similar to Intermediate 80-1 using Intermediate 76-2 instead of Comparative Intermediate 75-9 of U.S. application Ser. No. 18/303,813, published as US 2023/0374036. LCMS: 1094.5.

Intermediate 76-4: tert-butyl (6aR,7S,10R)-13-(((3S,4S)-4-(difluoromethyl)-1,3-dimethylpiperidin-3-yl)methoxy)-2-(3-((diphenylmethylene)amino)-8-ethynyl-7-fluoronaphthalen-1-yl)-1-fluoro-5,6,6a,7,8,9,10,11-octahydro-4H-3,11a,12,14,15-pentaaza-7,10-methanocyclohepta[4,5]cycloocta[1,2,3-de]naphthalene-15-carboxylate

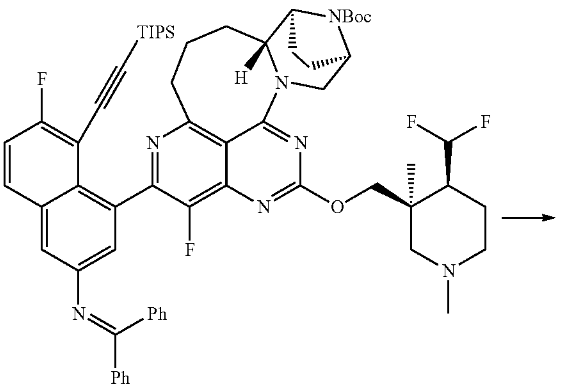

Comparative Intermediate 76-3

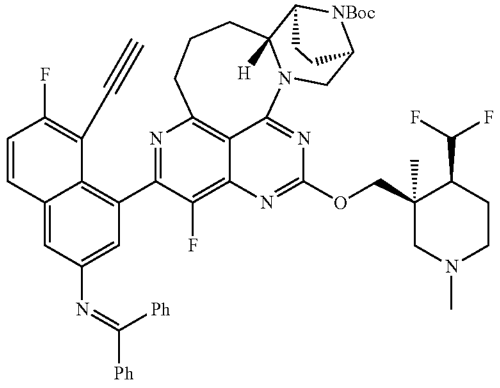

76-4

Intermediate 76-4 was synthesized in a manner similar to Comparative Intermediate 13-11 of U.S. application Ser. No. 18/303,813, published as US 2023/0374036, using Intermediate 76-3 instead of Comparative Intermediate 13-10 of U.S. application Ser. No. 18/303,813. LCMS: 938.2.

Intermediate 76-5: N-(4-((6aR,7S,10R)-13-(((3S,4S)-4-(difluoromethyl)-1,3-dimethylpiperidin-3-yl)methoxy)-1-fluoro-5,6,6a,7,8,9,10,11-octahydro-4H-3,11a,12,14,15-pentaaza-7,10-methanocyclohepta[4,5]cycloocta[1,2,3-de]naphthalen-2-yl)-5-ethynyl-6-fluoronaphthalen-2-yl)-1,1-diphenylmethanimine

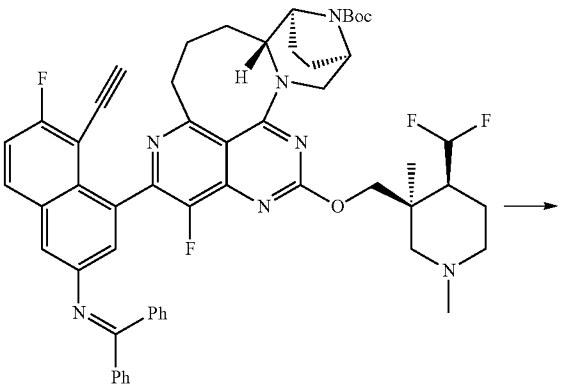

76-4

-continued

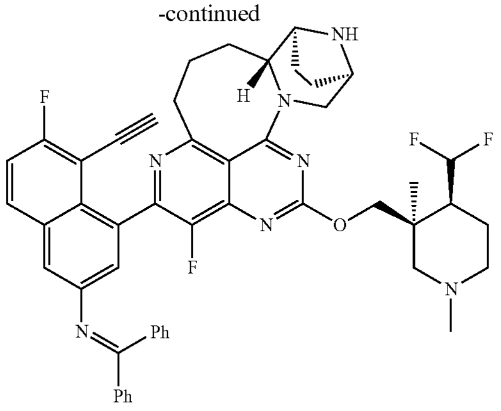

76-5

Intermediate 76-5 was synthesized in a manner similar to Intermediate 11-5 using Intermediate 76-4 instead of Intermediate 11-4. LCMS: 838.3.

Intermediate 76-6: 4-(((6aR,7S,10R)-13-(((3S,4S)-4-(difluoromethyl)-1,3-dimethylpiperidin-3-yl)methoxy)-2-(3-((diphenylmethylene)amino)-8-ethynyl-7-fluoronaphthalen-1-yl)-1-fluoro-5,6,6a,7,8,9,10,11-octahydro-4H-3,11a,12,14,15-pentaaza-7,10-methanocyclohepta[4,5]cycloocta[1,2,3-de]naphthalen-15-yl)methyl)-5-methyl-1,3-dioxol-2-one

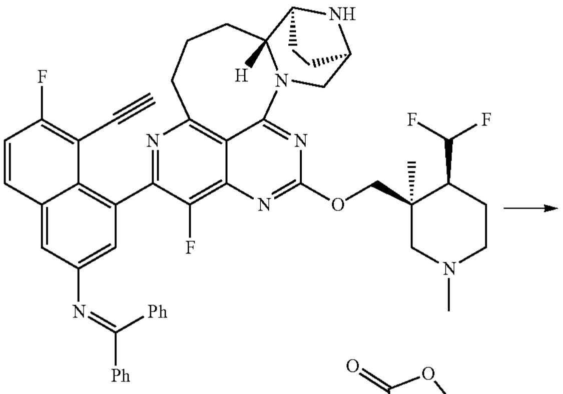

76-5

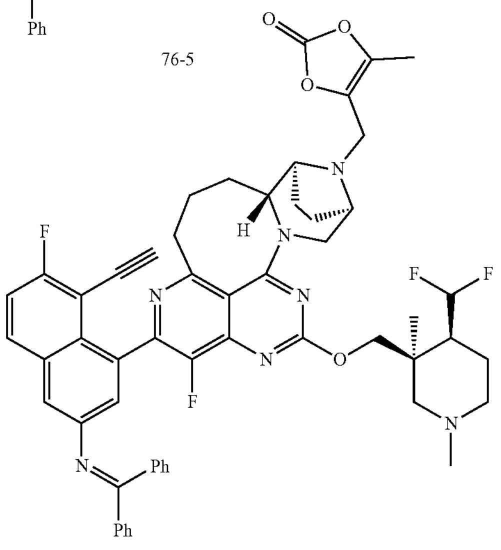

76-6

Intermediate 76-6 was synthesized in a manner similar to Intermediate 11-6 using Intermediate 76-5 instead of Intermediate 11-5. LCMS: 950.2.

Intermediate 77-1: tert-butyl (1S,4R,11R,15aR)-11-(8-ethyl-7-fluoro-3-(methoxymethoxy)naphthalen-1-yl)-10,12-difluoro-8-(((2R,7aS)-2-fluorotetrahydro-1H-pyrrolizin-7a(5H)-yl)methoxy)-2,3,4,5,13,14,15,15a-octahydro-1H-1,4-epiminoazepino[1',2':1,8]azocino[2,3,4-de]quinazoline-16-carboxylate

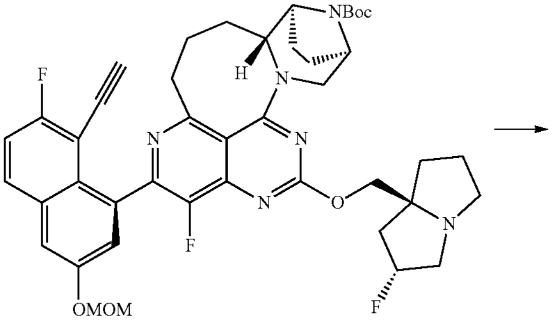

28-7

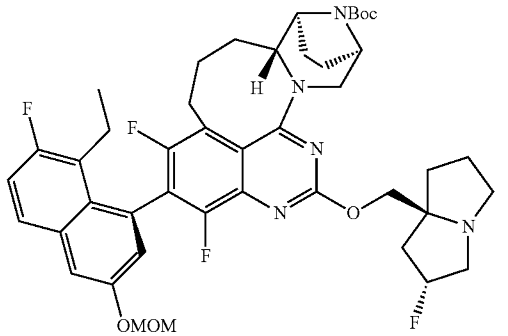

77-1

Intermediate 28-7 (10 mg, 0.013 mmol) was dissolved in 3 ml of ethanol and 3 ml of ethyl acetate. The reaction solution was sparged under an argon atmosphere. Palladium hydroxide on carbon (20 wt. % loading, 1.8 mg, 0.0025 mmol) was added. The reaction mixture was sparged under a hydrogen atmosphere (1 atm, balloon) and allowed to stir vigorously for 1 hour. Upon completion, the mixture was sparged with argon and filtered through a pad of Celite®. The filter pad was washed with ethyl acetate. The filtrate was concentrated to dryness and directly used for next step. LCMS: 806.4.

Intermediate 77-2: (1S,4R,11R,15aR)-11-(8-ethyl-7-fluoro-3-(methoxymethoxy)naphthalen-1-yl)-10,12-difluoro-8-(((2R,7aS)-2-fluorotetrahydro-1H-pyrrolizin-7a(5H)-yl)methoxy)-2,3,4,5,13,14,15,15a-octahydro-1H-1,4-epiminoazepino[1',2':1,8]azocino[2,3,4-de]quinazoline

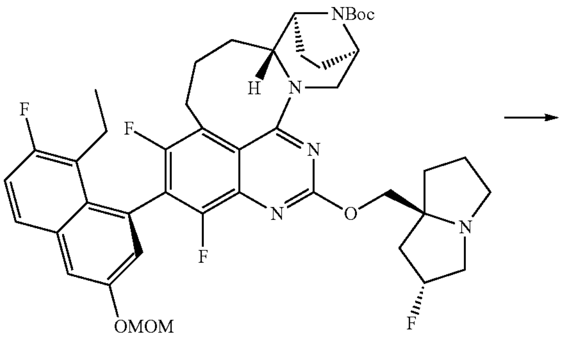

77-1

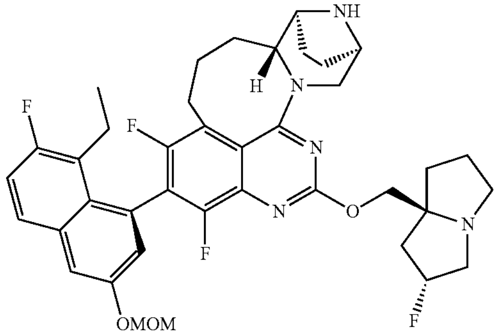

77-2

Intermediate 77-2 was synthesized in a manner similar to Intermediate 11-5 using Intermediate 77-1 instead of Intermediate 11-4. LCMS: 706.4.

Intermediate 77-3: 4-(((1S,4R,11R,15aR)-11-(8-ethyl-7-fluoro-3-(methoxymethoxy)naphthalen-1-yl)-10,12-difluoro-8-(((2R,7aS)-2-fluorotetrahydro-1H-pyrrolizin-7a(5H)-yl)methoxy)-2,3,4,5,13,14,15,15a-octahydro-1H-1,4-epiminoazepino[1',2':1,8]azocino[2,3,4-de]quinazolin-16-yl)methyl)-5-methyl-1,3-dioxol-2-one

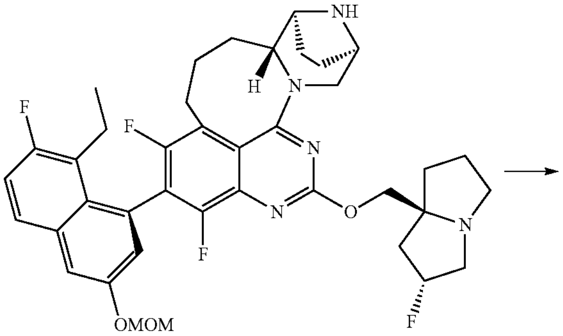

77-2

-continued

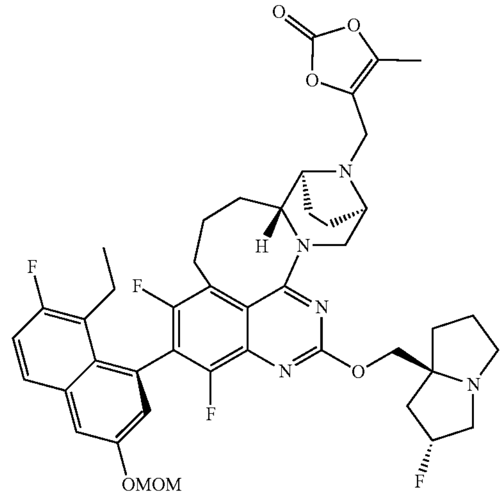

77-3

Intermediate 77-3 was synthesized in a manner similar to Intermediate 11-6 using Intermediate 77-2 instead of Intermediate 11-5. LCMS: 818.4.

Intermediate 78-1: tert-butyl (1S,4R,15aR)-8-(((3S,4S)-4-(difluoromethyl)-1,3-dimethylpiperidin-3-yl)methoxy)-10,12-difluoro-11-((R)-7-fluoro-3-(methoxymethoxy)-8-((triisopropylsilyl)ethynyl)naphthalen-1-yl)-2,3,4,5,13,14,15,15a-octahydro-1H-1,4-epiminoazepino[1',2':1,8]azocino[2,3,4-de]quinazoline-16-carboxylate 78-1

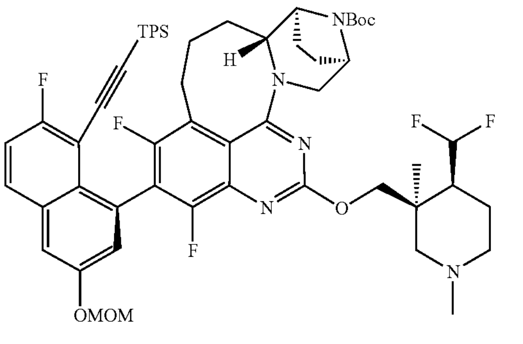

Intermediate 78-1 was synthesized in a manner similar to Intermediate 28-5B using Intermediate 74-6 instead of Intermediate 1-12. LCMS: 992.6.

Intermediate 78-2: tert-butyl (1S,4R,15aR)-8-(((3S,4S)-4-(difluoromethyl)-1,3-dimethylpiperidin-3-yl)methoxy)-11-((R)-8-ethynyl-7-fluoro-3-(methoxymethoxy)naphthalen-1-yl)-10,12-difluoro-2,3,4,5,13,14,15,15a-octahydro-1H-1,4-epiminoazepino[1',2':1,8]azocino[2,3,4-de]quinazoline-16-carboxylate 78-2

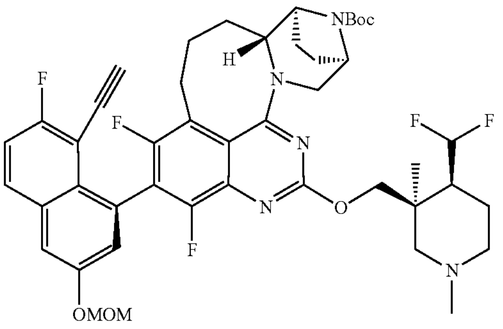

Intermediate 78-2 was synthesized in a manner similar to Intermediate 76-2 using Intermediate 78-1 instead of Intermediate 76-1. LCMS: 836.4.

Intermediate 78-3: (1S,4R,15aR)-8-(((3S,4S)-4-(difluoromethyl)-1,3-dimethylpiperidin-3-yl)methoxy)-11-((R)-8-ethynyl-7-fluoro-3-(methoxymethoxy)naphthalen-1-yl)-10,12-difluoro-2,3,4,5,13,14,15,15a-octahydro-1H-1,4-epiminoazepino[1',2':1,8]azocino[2,3,4-de]guinazoline

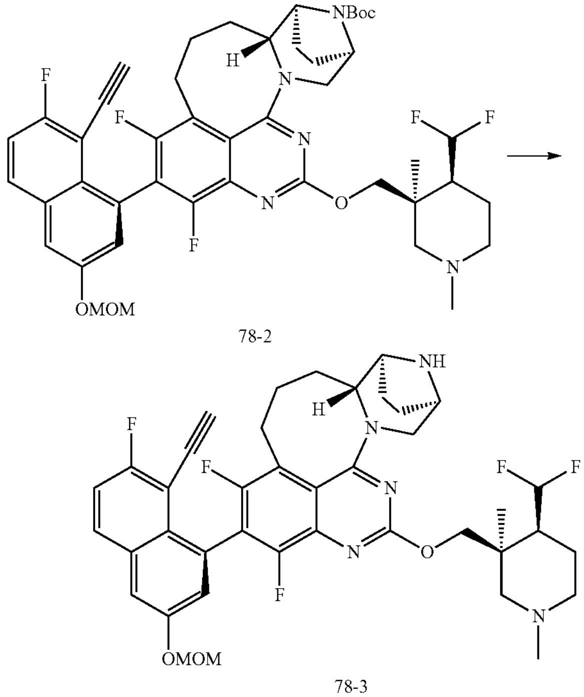

78-2

78-3

Intermediate 78-3 was synthesized in a manner similar to Intermediate 11-5 using Intermediate 78-2 instead of Intermediate 11-4. LCMS: 736.4.

Intermediate 78-4: 4-(((1S,4R,15aR)-8-(((3S,4S)-4-(difluoromethyl)-1,3-dimethylpiperidin-3-yl)methoxy)-11-((R)-8-ethynyl-7-fluoro-3-(methoxymethoxy)naphthalen-1-yl)-10,12-difluoro-2,3,4,5,13,14,15,15a-octahydro-1H-1,4-epiminoazepino[1',2':1,8]azocino[2,3,4-de]quinazolin-16-yl)methyl)-5-methyl-1,3-dioxol-2-one

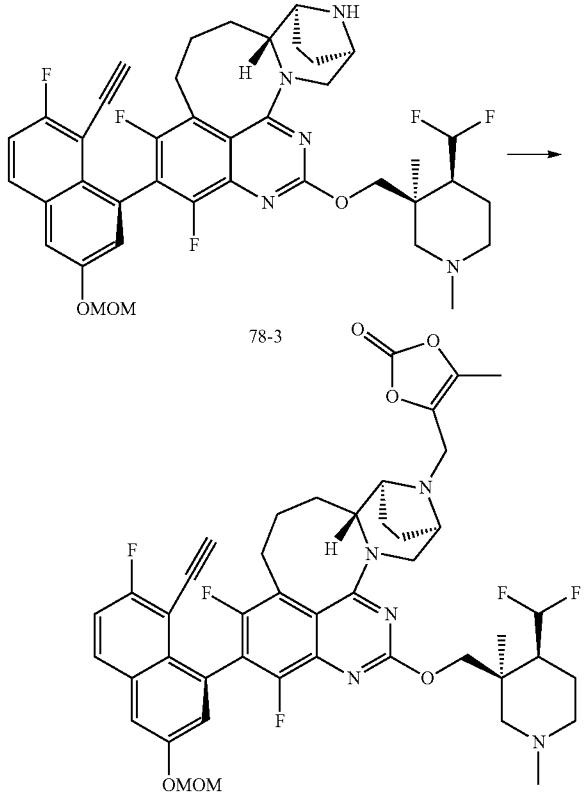

78-3

78-4

Intermediate 78-4 was synthesized in a manner similar to Intermediate 11-6 using Intermediate 78-3 instead of Intermediate 11-5. LCMS: 848.4.

Intermediate 80-0: tert-butyl (6aR,7S,10R)-2-chloro-1-fluoro-13-(((2R,7aS)-2-fluorotetrahydro-1H-pyrrolizin-7a(5H)-yl)methoxy)-5,6,6a,7,8,9,10,11-octahydro-4H-3,11a,12,14,15-pentaaza-7,10-methanocyclohepta[4,51cycloocta[1,2,3-de]naphthalene-15-carboxylate

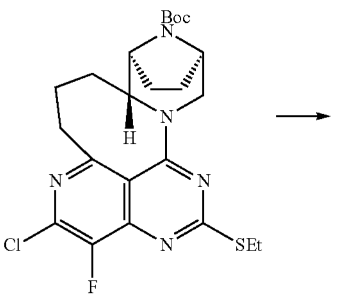

76-1

-continued

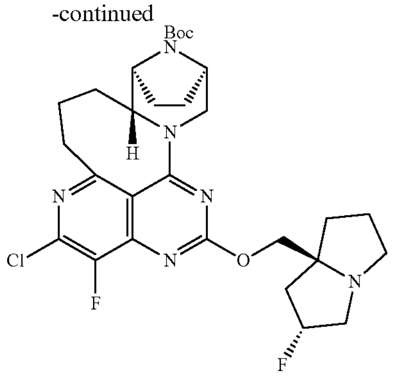

80-0

Lithium bis(trimethylsilyl)amide solution (1.0 M in tetrahydrofuran, 1.58 mL, 1.6 mmol) was added over 1 min via syringe to a vigorously stirred solution of Intermediate 76-1 (666 mg, 1.27 mmol) in 2-methyltetrahydrofuran (2.0 mL) at 0° C. After 30 min, saturated aqueous sodium bicarbonate solution (5.0 mL), ethyl ether (100 mL), and ethyl acetate (25 mL) were added sequentially. The organic layer was washed with a mixture of water and brine (3:1 v:v, 40 mL), was dried over anhydrous magnesium sulfate, was filtered, and was concentrated under reduced pressure. The residue was purified by flash column chromatography on basic alumina (0 to 30% ethyl acetate in hexanes) to give Intermediate 80-0. LCMS: 591.2.

Intermediate 80-1: tert-butyl (6aR,7S,10R)-2-(3-((diphenylmethylene)amino)-8-ethynyl-7-fluoronaphthalen-1-yl)-1-fluoro-13-(((2R,7aS)-2-fluorotetrahydro-1H-pyrrolizin-7a(5H)-yl)methoxy)-5,6,6a,7,8,9,10,11-octahydro-4H-3,11a,12,14,15-pentaaza7,10-methanocyclohepta[4,5]cycloocta[1,2,3-de]naphthalene-15-carboxylate

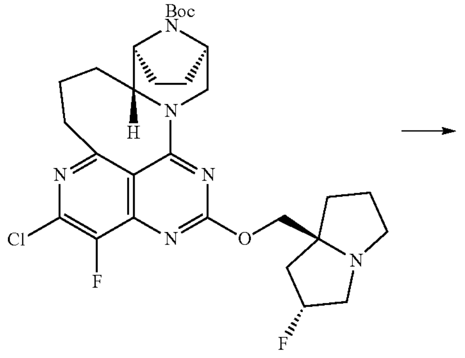

80-0

-continued

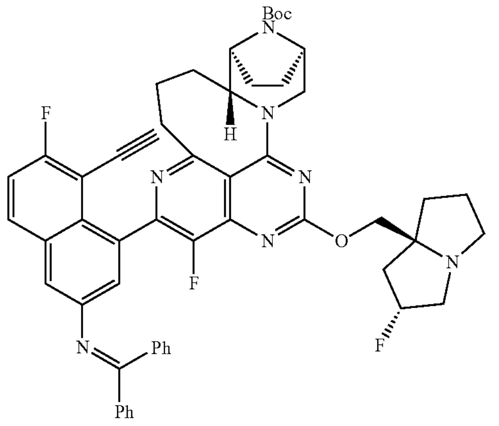

80-1

Aqueous potassium phosphate solution (2.0 M, 51.8 mL, 100 mmol) was added via syringe to a vigorously stirred mixture of Intermediate 80-0 (20.4 g, 34.5 mmol), N-(6-fluoro-4-(4,4,5,5-tetramethyl-1,3,2-dioxaborolan-2-yl)-5-((triisopropylsilyl)ethynyl)naphthalen-2-yl)-1,1-diphenyl-methanimine (24.0 g, 38.0 mmol), [(di(1-adamantyl)-butylphosphine)-2-(2'-amino-1,1'-biphenyl)]palladium(II) methanesulfonate (1.26 g, 1.73 mmol), and 1,4-dioxane (80 mL) at room temperature, and the resulting mixture was heated to 80° C. After 75 min, the resulting mixture was cooled to room temperature. Ethyl ether (500 mL) and ethyl acetate (50 mL) were added sequentially to the mixture. The organic layer was washed with a mixture of water and brine (1:1 v:v, 150 mL), was dried over anhydrous magnesium sulfate, was filtered, and was concentrated under reduced pressure. The residue was dissolved in N,N-dimethylformamide (40 mL) and 2-methyltetrahydrofuran (20 mL), and the resulting mixture was vigorously stirred at room temperature. 1,1,1,3,3,3-Hexafluoropropan-2-ol (3.64 mL, 34.5 mmol) and cesium fluoride (26.2 g, 173 mmol) were added sequentially, and the resulting mixture was heated to 60° C. After 55 min, the resulting mixture was cooled to room temperature. Ethyl ether (1.0 L), ethyl acetate (100 mL), saturated aqueous sodium bicarbonate solution (50 mL), and saturated aqueous sodium carbonate solution (50 mL) were added sequentially. The organic layer was washed sequentially with water (900 mL) and a mixture of water and brine (8:1 v:v, 900 mL), was dried over anhydrous magnesium sulfate, was filtered, and was concentrated under reduced pressure. The residue was purified by flash column chromatography on silica gel (0 to 100% ethyl acetate in hexanes) to give Intermediate 80-1. LCMS: 904.4.

Intermediate 80-2: N-(5-ethynyl-6-fluoro-4-((6aR,7S,10R)-1-fluoro-13-(((2R,7aS)-2-fluorotetrahydro-1H-pyrrolizin-7a(5H)-yl)methoxy)-5,6,6a,7,8,9,10,11-octahydro-4H-3,11a,12,14,15-pentaaza-7,10-methanocyclohepta[4,5]cycloocta[1,2,3-de]naphthalen-2-yl)naphthalen-2-yl)-1,1-diphenylmethanimine

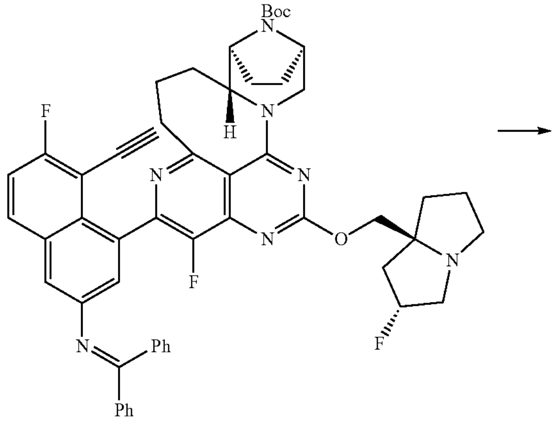

80-1

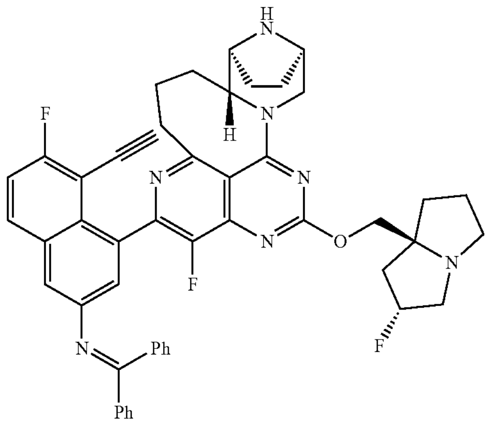

80-2

Trimethylsilyl trifluoromethanesulfonate (1.87 mL, 10.3 mmol) was added over 2 min to a stirred mixture of Intermediate 80-1 (6.23 g, 6.89 mmol), triethylamine (288 μL, 2.07 mmol), and dichloromethane (16.0 mL) at 0° C. After 28 min, methanol (16 mL) and triethylamine (1.3 mL) were added sequentially, and the resulting mixture was warmed to room temperature. After 15 min, the resulting mixture was concentrated under reduced pressure. The residue was dissolved in ethyl acetate (250 mL), and saturated aqueous sodium carbonate solution (30 mL) and brine (10 mL) were added sequentially. The organic layer was washed with water (100 mL), was dried over anhydrous magnesium sulfate, was filtered, and was concentrated under reduced pressure to give Intermediate 80-2. LCMS: 804.3.

Intermediate 80-3: 4-(((6aR,7S,10R)-2-(3-((diphenylmethylene)amino)-8-ethynyl-7-fluoronaphthalen-1-yl)-1-fluoro-13-(((2R,7aS)-2-fluorotetrahydro-1H-pyrrolizin-7a(5H)-yl)methoxy)-5,6,6a,7,8,9,10,11-octahydro-4H-3,11a,12,14,15-pentaaza-7,10-methanocyclohepta[4,5]cycloocta[1,2,3-de]naphthalen-15-yl)methyl)-5-isopropyl-1,3-dioxol-2-one

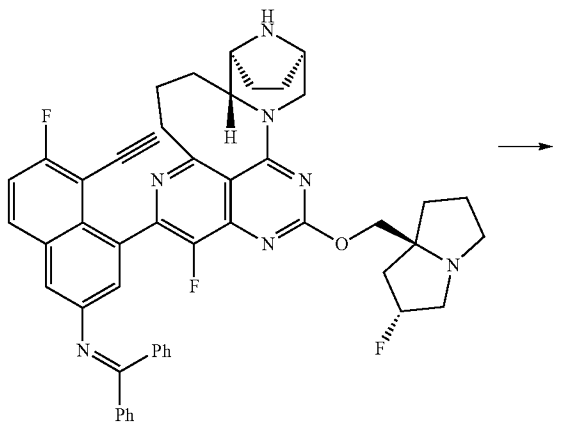

80-2

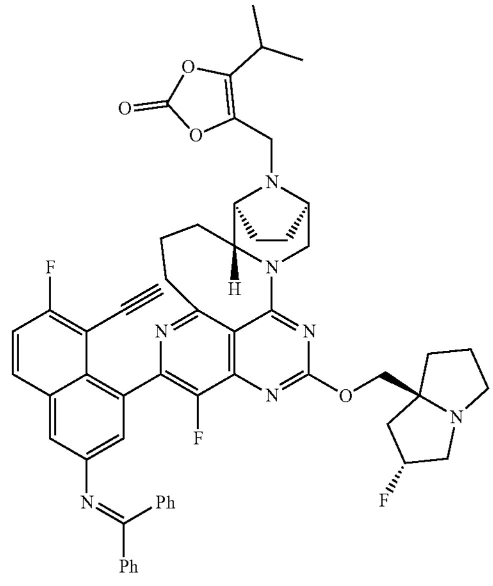

80-3

4-(Bromomethyl)-5-isopropyl-1,3-dioxol-2-one (Tetrahedron Lett. 2002, 43, 1161) (24.3 mg, 110 μmol) was added to a vigorously stirred mixture of Intermediate 80-2 (84.0 mg, 104 μmol), potassium carbonate (86.6 mg, 627 μmol), and N,N-dimethylformamide (0.3 mL) at 0° C. After 100 min, acetic acid (70 μL), ethyl ether (40 mL), and ethyl acetate (20 mL) were added sequentially, the resulting biphasic mixture was agitated. Saturated aqueous sodium bicarbonate solution (10 mL) was added, and the organic layer was washed with water (2×30 mL), was dried over anhydrous magnesium sulfate, was filtered, and was concentrated under reduced pressure. The residue was purified by flash column chromatography on silica gel (0 to 100% ethyl acetate in hexanes, each containing 3% triethylamine) to give Intermediate 80-3. LCMS: 944.2.

III. Compounds

Example 1, Compound 1: 4-(((6aR,7S,10R)-2-(8-ethynyl-7-fluoronaphthalen-1-yl)-1-fluoro-13-(((2R,7aS)-2-fluorotetrahydro-1H-pyrrolizin-7a(5H)-yl)methoxy)-5,6,6a,7,8,9,10,11-octahydro-4H-3,11a,12,14,15-pentaaza-7,10-methanocyclohepta[4,5]cycloocta[1,2,3-de]naphthalen-15-yl)methyl)-5-methyl-1,3-dioxol-2-one

1

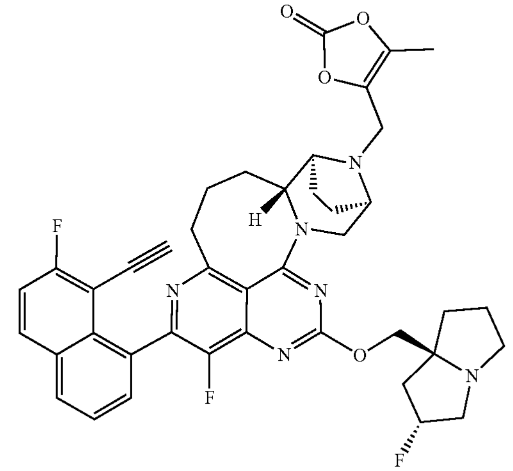

4-(Bromomethyl)-5-methyl-1,3-dioxol-2-one (187 μL, 1.69 mmol) was added over 6 min to a vigorously stirred mixture of (6aR,7S,10R)-2-(8-ethynyl-7-fluoronaphthalen-1-yl)-1-fluoro-13-(((2R,7aS)-2-fluorotetrahydro-1H-pyrrolizin-7a(5H)-yl)methoxy)-5,6,6a,7,8,9,10,11-octahydro-4H-3,11a,12,14,15-pentaaza-7,10-methanocyclohepta[4,5]cycloocta[1,2,3-de]naphthalene prepared according to Comparative Example 76 of U.S. application Ser. No. 18/303,813, published as US 2023/0374036 (1.00 g, 1.61 mmol), N,N-diisopropylethylamine (294 μL, 1.69 mmol), acetonitrile (14 mL), and dichloromethane (2.0 mL) at room temperature. After 14 min, the resulting mixture was heated to 65° C. After 50 min, the resulting mixture was concentrated under reduced pressure. The residue was purified by reverse phase preparative HPLC (0.1% acetic acid in acetonitrile/water) to give Example 1. $^1$H NMR (400 MHz, Acetonitrile-d3) δ 8.09 (tt, J=7.3, 4.2 Hz, 2H), 7.74-7.53 (m, 2H), 7.50-7.36 (m, 1H), 5.70-4.09 (m, 5H), 4.08-2.85 (m, 12H), 2.83-1.08 (m, 17H). LCMS: 737.3.

Example 2, Compound 2: 4-(((5-ethynyl-6-fluoro-4-((5S,5aS,6S,9R)-1-fluoro-12-(((2R,7aS)-2-fluorotetrahydro-1H-pyrrolizin-7a(5H)-yl)methoxy)-5-methyl-14-((5-methyl-2-oxo-1,3-dioxol-4-yl)methyl)-4,5,5a,6,7,8,9,10-octahydro-3,10a,11,13,14-pentaaza-6,9-methanonaphtho[1,8-ab]heptalen-2-yl)naphthalen-2-yl)oxy)methyl)-5-methyl-1,3-dioxol-2-one

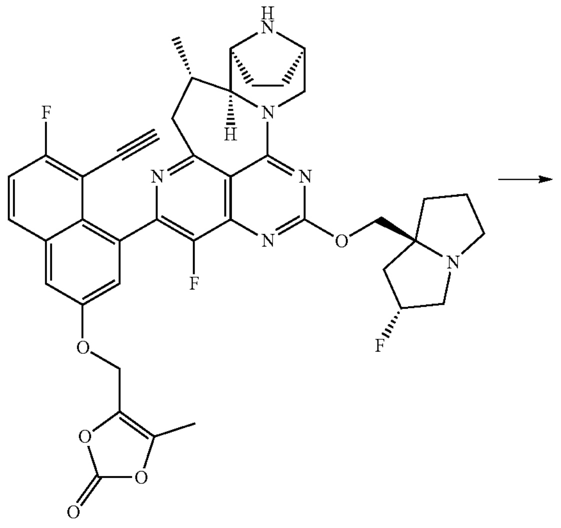

2-3

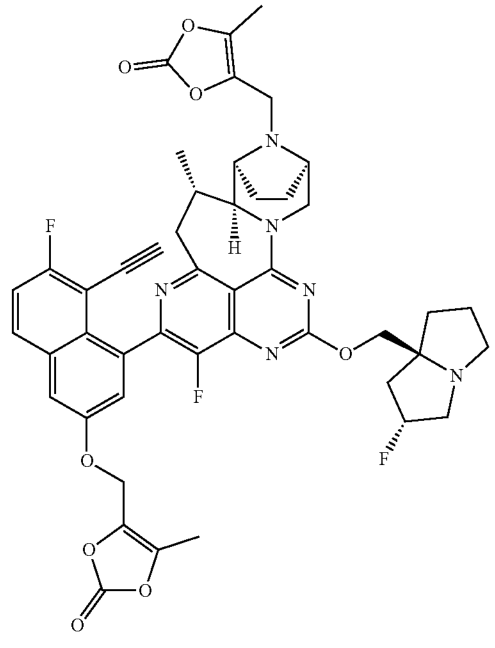

2

4-(Bromomethyl)-5-methyl-1,3-dioxol-2-one (7.9 mg, 0.041 mmol) was added to the solution of Intermediate 2-3 (28 mg, 0.037 mmol) and DIPEA (14.4 mg, 0.112 mmol) in DCM (1 mL) at 0° C. The reaction mixture was warmed to rt and stirred for 2 h. The reaction mixture was filtered and the filtrate was purified by reverse phase preparative HPLC (0.1% TFA in acetonitrile/water) to give Example 2. $^{1}H$ NMR (400 MHz, Methanol-$d_4$) δ 8.07 (dd, J=9.1, 5.7 Hz, 1H), 7.71 (dd, J=4.1, 2.7 Hz, 1H), 7.50-7.35 (m, 2H), 5.60 (d, J=51.6 Hz, 1H), 5.13 (d, J=2.4 Hz, 2H), 5.03-4.96 (m, 1H), 4.78 (dd, J=12.4, 6.9 Hz, 1H), 4.63 (d, J=12.4 Hz, 1H), 4.11-3.41 (m, 10H), 3.26-2.30 (m, 8H), 2.27-2.10 (m, 9H), 1.22-1.11 (m, 3H). LCMS: 865.2.

Example 3, Compound 3: 4-(((1R,4S,14aR)-11-((R)-6-amino-4-methyl-3-(trifluoromethyl)pyridin-2-yl)-12-chloro-10-fluoro-8-(((2R,7aS)-2-fluorotetrahydro-1H-pyrrolizin-7a(5H)-yl)methoxy)-1,2,3,4,5,13,14,14a-octahydro-1,4-epiminoazepino[1',2':1,7]azepino[2,3,4-de]quinazolin-15-yl)methyl)-5-methyl-1,3-dioxol-2-one

3

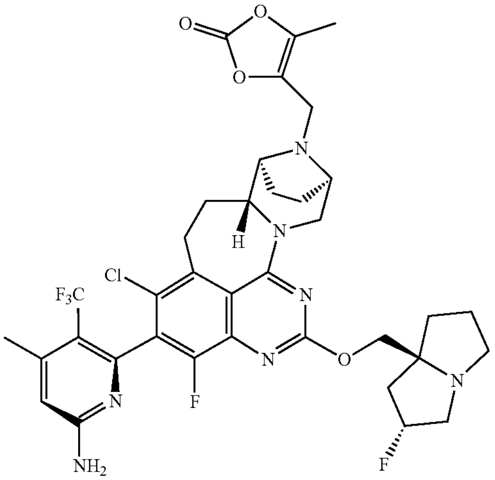

Example 3 was synthesized in a manner similar to Example 1 using (R)-6-((1R,4S,14aR)-12-chloro-10-fluoro-8-(((2R,7aS)-2-fluorotetrahydro-1H-pyrrolizin-7a(5H)-yl)methoxy)-1,2,3,4,5,13,14,14a-octahydro-1,4-epiminoazepino[1',2':1,7]azepino[2,3,4-de]quinazolin-11-yl)-4-methyl-5-(trifluoromethyl)pyridin-2-amine (Comparative Example 6) instead of (6aR,7S,10R)-2-(8-ethynyl-7-fluoronaphthalen-1-yl)-1-fluoro-13-(((2R,7aS)-2-fluorotetrahydro-1H-pyrrolizin-7a(5H)-yl)methoxy)-5,6,6a,7,8,9,10,11-octahydro-4H-3,11a,12,14,15-pentaaza-7,10-methanocyclohepta[4,5]cycloocta[1,2,3-de]naphthalene. $^{1}H$ NMR (400 MHz, Methanol-$d_4$) δ 6.68 (d, J=1.4 Hz, 1H), 5.73-5.41 (m, 2H), 4.76-4.59 (m, 2H), 4.46-4.23 (m, 4H), 4.16-3.82 (m, 5H), 3.69-3.43 (m, 2H), 3.19-3.02 (m, 1H), 2.81-1.88 (m, 15H). LCMS: 762.2.

Example 4, Compound 4: 4-(((6aR,7S,10R)-2-(8-ethynyl-7-fluoronaphthalen-1-yl)-1-fluoro-13-(((2R,7aS)-2-fluorotetrahydro-1H-pyrrolizin-7a(5H)-yl)methoxy)-5,6,6a,7,8,9,10,11-octahydro-4H-3,11a,12,14,15-pentaaza-7,10-methanocyclohepta[4,5]cycloocta[1,2,3-de]naphthalen-15-yl)methyl)-5-phenyl-1,3-dioxol-2-one

4

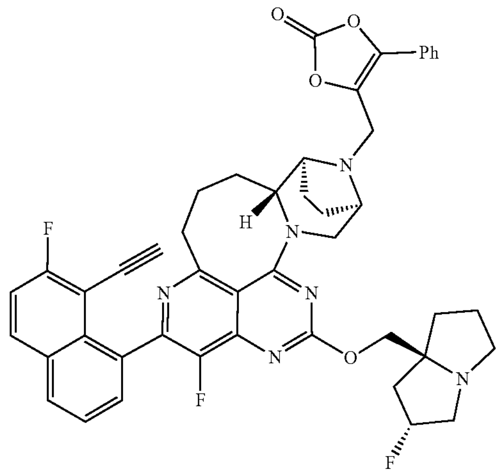

Example 4 was synthesized in a manner similar to Example 1 using 4-(bromomethyl)-5-phenyl-1,3-dioxol-2-one instead of 4-(bromomethyl)-5-methyl-1,3-dioxol-2-one. $^1H$ NMR (400 MHz, Acetonitrile-$d_3$) δ 8.18-8.08 (m, 2H), 7.74 (d, J=7.7 Hz, 2H), 7.71-7.63 (m, 2H), 7.59-7.42 (m, 4H), 5.56-5.03 (m, 2H), 4.32-2.42 (m, 15H), 2.36-1.18 (m, 14H). LCMS: 799.2.

Example 5, Compound 5: 4-(((6aR,7S,10R)-2-(8-ethynyl-7-fluoronaphthalen-1-yl)-1-fluoro-13-(((2R,7aS)-2-fluorotetrahydro-1H-pyrrolizin-7a(5H)-yl)methoxy)-5,6,6a,7,8,9,10,11-octahydro-4H-3,11a,12,14,15-pentaaza-7,10-methanocyclohepta[4,5]cycloocta[1,2,3-de]naphthalen-15-yl)methyl)-3,5-dimethyloxazol-2(3H)-one

5

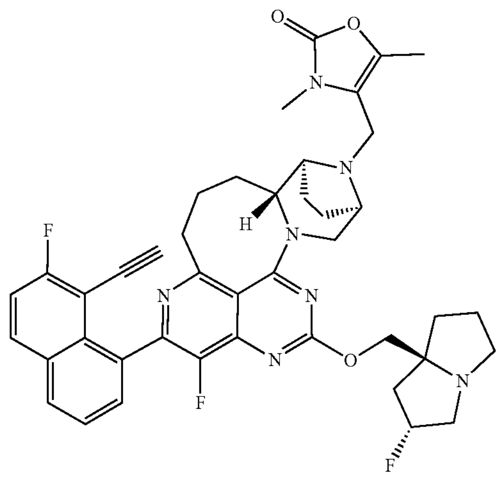

Triphenylphosphine (29.0 mg, 111 μmol) was added to a vigorously stirred mixture of (6aR,7S,10R)-2-(8-ethynyl-7-fluoronaphthalen-1-yl)-1-fluoro-13-(((2R,7aS)-2-fluorotetrahydro-1H-pyrrolizin-7a(5H)-yl)methoxy)-5,6,6a,7,8,9,10,11-octahydro-4H-3,11a,12,14,15-pentaaza-7,10-methanocyclohepta[4,5]cycloocta[1,2,3-de]naphthalene prepared according to Example 76 of U.S. application Ser. No. 18/303,813, published as US 2023/0374036 (60.1 mg, 96.2 μmol), 4-(hydroxymethyl)-3,5-dimethyloxazol-2(3H)-one (WO2021154842) (14.5 mg, 101 μmol), carbon tetrabromide (63.8 mg, 192 μmol), N,N-diisopropylethylamine (17.6 μL, 101 μmol), and dichloromethane at 0° C. After 2 min, the resulting mixture was warmed to room temperature. After 44 min, the resulting mixture was heated to 50° C. After 120 min, the resulting mixture was cooled to room temperature and was purified by reverse phase preparative HPLC (0.1% acetic acid in acetonitrile/water) to give Example 5. $^1H$ NMR (400 MHz, Acetonitrile-$d_3$) δ 8.31-8.01 (m, 2H), 7.81-7.58 (m, 2H), 7.54-7.38 (m, 1H), 5.48-5.09 (m, 1.5H), 4.32-3.69 (m, 2.5H), 3.54-2.42 (m, 16H), 2.40-1.15 (m, 17H). LCMS: 750.2.

Example 6, Compound 6: 4-(tert-butyl)-5-(((6aR,7S,10R)-2-(8-ethynyl-7-fluoronaphthalen-1-yl)-1-fluoro-13-(((2R,7aS)-2-fluorotetrahydro-1H-pyrrolizin-7a(5H)-yl)methoxy)-5,6,6a,7,8,9,10,11-octahydro-4H-3,11a,12,14,15-pentaaza-7,10-methanocyclohepta[4,5]cycloocta[1,2,3-de]naphthalen-15-yl)methyl)-1,3-dioxol-2-one

6

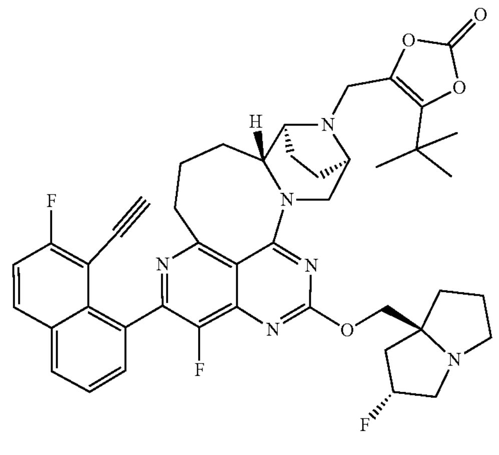

Example 6 was synthesized in a manner similar to Example 1 using 4-(bromomethyl)-5-(tert-butyl)-1,3-dioxol-2-one instead of 4-(bromomethyl)-5-methyl-1,3-dioxol-2-one. $^1H$ NMR (400 MHz, Acetonitrile-$d_3$) δ 8.18-8.05 (m, 2H), 7.73-7.57 (m, 2H), 7.49-7.40 (m, 1H), 5.42-5.12 (m, 2H), 4.26-4.07 (m, 2H), 3.82 (d, J=10.0 Hz, 1H), 3.50-3.01 (m, 9H), 2.98-2.84 (m, 1H), 2.84-2.70 (m, 1H), 2.57-2.42 (m, 1H), 2.25-1.36 (m, 14H), 1.32 (s, 9H). LCMS: 779.1.

Comparative Example 5, Comparative Compound 5: (S)-6-((1S,4R,14aR)-12-chloro-10-fluoro-8-(((2R,7aS)-2-fluorotetrahydro-1H-pyrrolizin-7a(5H)-yl)methoxy)-1,2,3,4,5,13,14,14a-octahydro-1,4-epiminoazepino[1',2':1,7]azepino[2,3,4-de]quinazolin-11-yl)-4-methyl-5-(trifluoromethyl)pyridin-2-amine Comparative Example 6, Comparative Compound 6: (R)-6-((1S,4R,14aR)-12-chloro-10-fluoro-8-(((2R,7aS)-2-fluorotetrahydro-1H-pyrrolizin-7a(5H)-yl)methoxy)-1,2,3,4,5,13,14,14a-octahydro-1,4-epiminoazepino[1',2':1,7]azepino[2,3,4-de]quinazolin-11-yl)-4-methyl-5-(trifluoromethyl)pyridin-2-amine

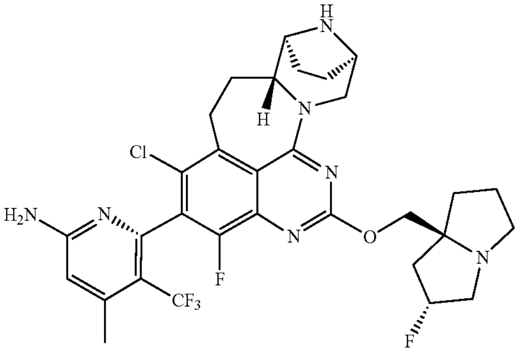

Comparative Example 5

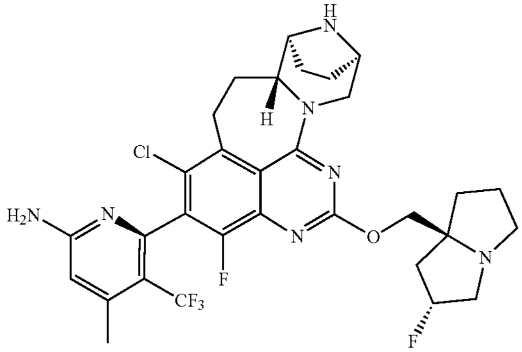

Comparative Example 6

The solution of the mixture of Intermediate B5-5 and Intermediate B6-3 (120 mg, 0.121 mmol) in TFA (2 mL) was stirred at 50° C. for 3.5 h before it was cooled to rt. After concentrated in vacuo, the resulting mixture was purified by reverse phase preparative HPLC (0.1% TFA in acetonitrile/water). The mixture was separated by chiral SFC [column: $C_{9-5}$ (3×25 cm), 50% methanol (0.1% DEA)/$CO_2$, 100 bar, 85 mL/min] to give Comparative Example 5 (faster eluted fraction) and Comparative Example 6 (slower eluted fraction). Comparative Example 5: $^1$H NMR (400 MHz, Methanol-$d_4$) δ 6.61 (s, 1H), 5.41-5.22 (m, 2H), 4.32-4.15 (m, 2H), 4.07-3.96 (m, 1H), 3.83-3.60 (m, 2H), 3.44-3.35 (m, 2H), 3.30-3.14 (m, 4H), 3.07-2.84 (m, 3H), 2.45 (d, J=2.1 Hz, 3H), 2.40-1.56 (m, 11H), 1.25 (dd, J=7.2 Hz, 1H); LCMS: 650.1 $[M+H]^+$. Comparative Example 6: $^1$H NMR (400 MHz, Methanol-$d_4$) δ 6.63-6.58 (m, 1H), 5.41-5.12 (m, 2H), 4.32-4.14 (m, 2H), 3.99 (dd, J=11.7, 5.0 Hz, 1H), 3.76 (dd, J=16.0, 8.7 Hz, 1H), 3.65 (d, J=4.6 Hz, 1H), 3.41 (d, J=4.5 Hz, 1H), 3.30-3.14 (m, 4H), 3.07-2.72 (m, 3H), 2.50-2.42 (m, 3H), 2.39-1.64 (m, 11H), 1.21 (dd, J=7.2 Hz, 1H). LCMS: 650.1.

Comparative Example 64, Comparative Compound 64 of U.S. application Ser. No. 18/303,813, published as US 2023/0374036: 5-ethynyl-6-fluoro-4-((5S,5aS,6S,9R)-1-fluoro-12-(((2R,7aS)-2-fluorotetrahydro-1H-pyrrolizin-7a(5H)-yl)methoxy)-5-methyl-4,5,5a,6,7,8,9,10-octahydro-3,10a,11,13,14-pentaaza-6,9-methanonaphtho[1,8-ab]heptalen-2-yl)naphthalen-2-ol

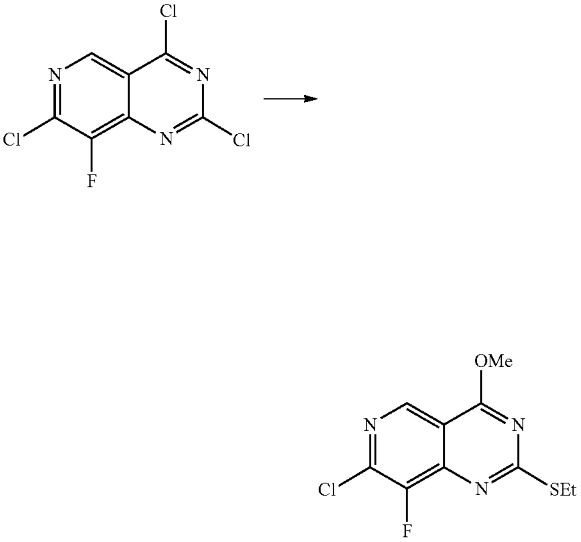

13-1

Sodium methoxide solution (25% wt in methanol, 4.54 mL, 20 mmol) was added over 15 min via syringe pump to a vigorously stirred solution of 2,4,7-trichloro-8-fluoro-pyrido[4,3-d]pyrimidine (5.01 g, 19.8 mmol) in 2-methyltetrahydrofuran (70 mL) at −20° C. After 11 min, ethanethiol (4.41 mL, 59.5 mmol) was added over 1 min via syringe. After 1 min, N,N-diisopropylethylamine (11.1 mL, 63.5 mmol) was added over 2 min via syringe. After 11 min, the resulting mixture was warmed to room temperature. After 20 min, the resulting mixture was heated to 70° C. After 22 h, the resulting mixture was cooled to room temperature, and citric acid (3.0 g), diethyl ether (200 mL), and ethyl acetate (25 mL) were added sequentially. The organic layer was washed with water (200 mL), was dried over anhydrous magnesium sulfate, was filtered, and was concentrated under reduced pressure. The residue was purified by flash column chromatography on silica gel (0% to 11% ethyl acetate in hexanes) to give Intermediate 13-1. LCMS: 274.0.

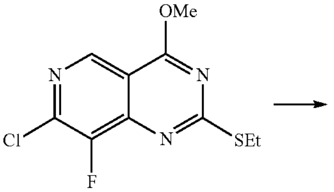

13-1

-continued

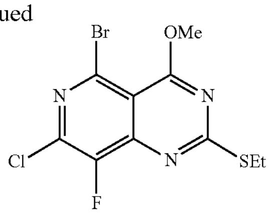

13-2

2,2,6,6-Tetramethylpiperidinylmagnesium chloride lithium chloride complex solution (1.0 M in tetrahydrofuran, 14.4 mL, 14 mmol) was added over 20 min via syringe pump to a vigorously stirred solution of Intermediate 13-1 (1.00 g, 3.65 mmol) in tetrahydrofuran (3.0 mL) at 0° C. After 60 min, a solution of 1,2-dibromo-1,1,2,2-tetrachloroethane (4.76 g, 14.6 mmol) in tetrahydrofuran (8.0 mL) was added via syringe. After 120 min, citric acid (5.0 g), diethyl ether (200 mL), and ethyl acetate (25 mL) were added sequentially. The organic layer was washed with water (2×150 mL), was dried over anhydrous magnesium sulfate, was filtered, and was concentrated under reduced pressure. The residue was purified by flash column chromatography on silica gel (0% to 5% ethyl acetate in hexanes) to give Intermediate 13-2. LCMS: 351.9.

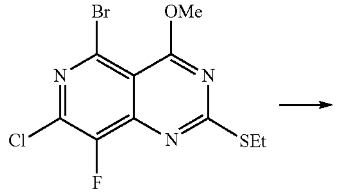

13-2

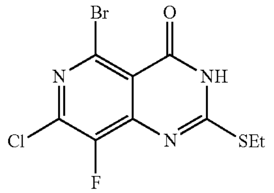

13-3

Sodium iodide (1.90 g, 12.7 mmol) was added to a vigorously stirred solution of Intermediate 13-2 (895 mg, 2.54 mmol) in acetic acid (12.0 mL) at room temperature, and the resulting mixture was heated to 80° C. After 2.5 h, the resulting mixture was cooled to room temperature, and ethyl acetate (100 mL) and aqueous sodium thiosulfate solution (1.0 M, 2.0 mL) were added sequentially. The organic layer was washed with water (100 mL), was dried over anhydrous magnesium sulfate, was filtered, and was concentrated under reduced pressure to give Intermediate 13-3. LCMS: 337.9.

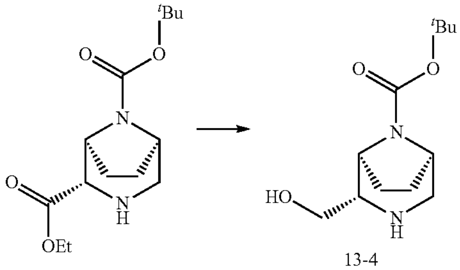 [SMILES: CCOC(=O)[C@H]1NC[C@H]2CC[C@@H]1N2C(=O)OC(C)(C)C ; CC(C)(C)OC(=O)N1[C@@H]2CC[C@H]1[C@@H](CO)NC2]

13-4

Lithium aluminum hydride (818 mg, 21.6 mmol) was added to a vigorously stirred solution of 8-(tert-butyl) 2-ethyl (1S,2S,5R)-3,8-diazabicyclo[3.2.1]octane-2,8-dicarboxylate (3.07 g, 10.8 mmol) in tetrahydrofuran (60 mL) at 0° C. After 60 min, water (820 μL), aqueous sodium hydroxide solution (2.0 M, 1.53 mL), water (1.74 mL), and dichloromethane (100 mL) were added sequentially. The resulting suspension was dried over anhydrous sodium sulfate, was filtered, and was concentrated under reduced pressure to give Intermediate 13-4. LCMS: 243.2.

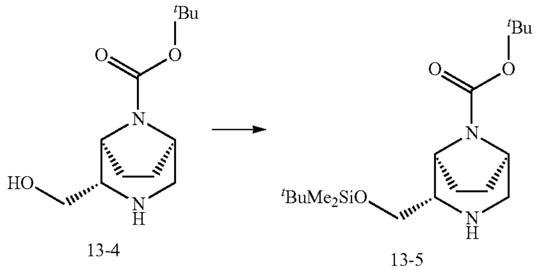

13-4

13-5 tert-Butyldimethylsilyl chloride (2.44 g, 16.2 mmol) was added to a stirred mixture of Intermediate 13-4 (2.61 g, 10.8 mmol), 4-(dimethylamino)pyridine (132 mg, 1.08 mmol), triethylamine (3.00 mL, 21.6 mmol), and dichloromethane (70 mL) at room temperature. After 15 h, diethyl ether (200 mL) and ethyl acetate (20 mL) were added sequentially. The organic layer was washed with water (150 mL), was dried over anhydrous magnesium sulfate, was filtered, and was concentrated under reduced pressure. The residue was purified by flash column chromatography on silica gel (0% to 70% ethyl acetate in hexanes) to give Intermediate 13-5. LCMS: 357.2.

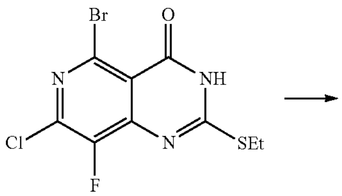

13-3

-continued

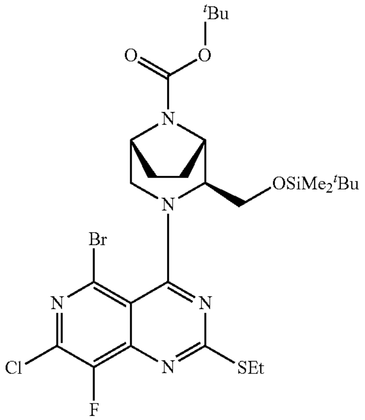

13-6

-continued

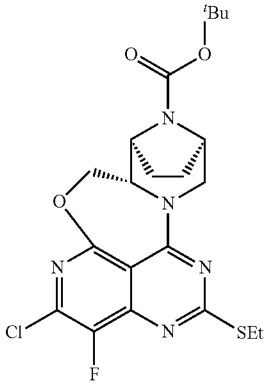

13-7

N,N-Diisopropylethylamine (884 μL, 5.08 mmol) was added via syringe to a mixture of Intermediate 13-3 (839 mg, 2.48 mmol) and phosphorous(V) oxychloride (10 mL) at room temperature, and the resulting mixture was heated to 80° C. After 10 min, the resulting mixture was cooled to room temperature and was concentrated under reduced pressure. Dichloromethane (20 mL) was added, the resulting mixture was cooled to 0° C., and N,N-diisopropylethylamine (1.33 mL, 7.61 mmol) and a solution of Intermediate 13-5 (905 mg, 2.54 mmol) in dichloromethane (4.0 mL) were added sequentially. After 50 min, citric acid (2.0 g), diethyl ether (100 mL), and ethyl acetate (20 mL) were added sequentially. The organic layer was washed with water (2×75 mL), was dried over anhydrous magnesium sulfate, was filtered, and was concentrated under reduced pressure. The residue was purified by flash column chromatography on silica gel (0% to 13% ethyl acetate in hexanes) to give Intermediate 13-6. LCMS: 676.1.

Tetrabutylammonium fluoride solution (1.0 M in tetrahydrofuran, 8.18 mL, 8.2 mmol) was added over 2 min via syringe to a stirred solution of Intermediate 13-6 (1.39 g, 2.05 mmol) in tetrahydrofuran (110 mL) at 0° C., and the resulting mixture was warmed to room temperature. After 23 h, saturated aqueous ammonium chloride solution (20 mL) and diethyl ether (400 mL) were added sequentially. The organic layer was washed with water (2×400 mL), was dried over anhydrous magnesium sulfate, was filtered, and was concentrated under reduced pressure. The residue was purified by flash column chromatography on silica gel (0% to 35% ethyl acetate in hexanes) to give Intermediate 13-7. LCMS: 482.1.

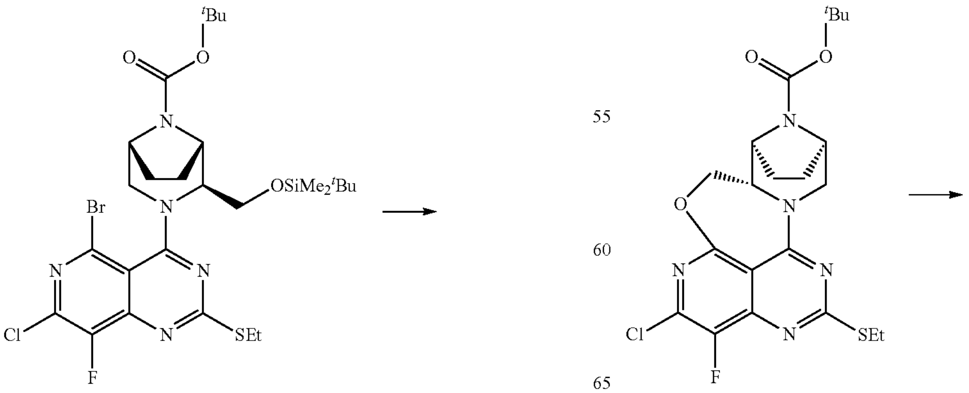

13-6

13-7

-continued

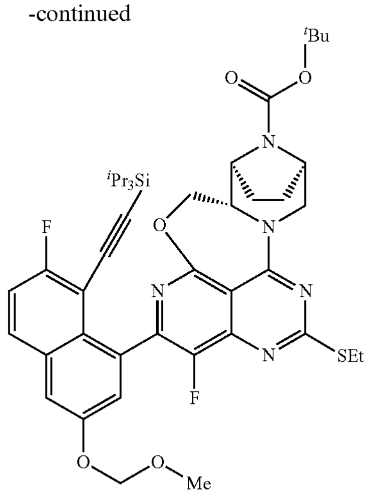

13-8

-continued

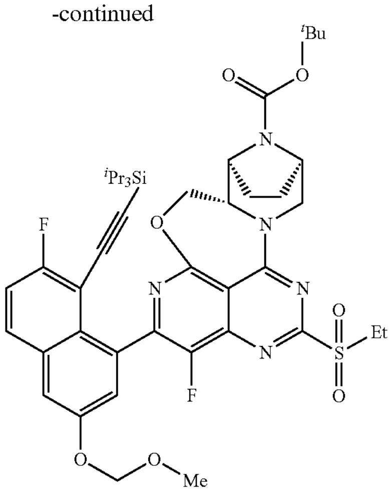

13-9

A vigorously stirred mixture of Intermediate 13-7 (722 mg, 1.50 mmol), ((2-fluoro-6-(methoxymethoxy)-8-(4,4,5,5-tetramethyl-1,3,2-dioxaborolan-2-yl)naphthalen-1-yl)ethynyl)triisopropylsilane (prepared according to, for instance, WO 2021/041671) (768 mg, 1.50 mmol), aqueous potassium phosphate solution (1.5 M, 4.99 mL, 7.5 mmol), [(di(1-adamantyl)-butylphosphine)-2-(2'-amino-1,1'-biphenyl)]palladium(II) methanesulfonate (218 mg, 300 μmol), and tetrahydrofuran (8.0 mL) was heated to 70° C. After 105 min, the resulting mixture was cooled to room temperature and diethyl ether (100 mL) and ethyl acetate (20 mL) were added sequentially. The organic layer was washed with water (60 mL), was dried over anhydrous magnesium sulfate, was filtered, and was concentrated under reduced pressure. The residue was purified by flash column chromatography on silica gel (0% to 45% ethyl acetate in hexanes) to give Intermediate 13-8. LCMS: 832.4.

3-Chloroperoxybenzoic acid (77% wt, 524 mg, 2.3 mmol) was added in two equal portions over 5 min to a vigorously stirred solution of Intermediate 13-8 (884 mg, 1.06 mmol) in dichloromethane (8.0 mL) at 0° C. After 25 min, the resulting mixture was warmed to room temperature. After 60 min, diethyl ether (100 mL), ethyl acetate (20 mL), and aqueous sodium thiosulfate solution (1.0 M, 8.0 mL) were added sequentially. The organic layer was washed sequentially with water (60 mL), a mixture of water and saturated aqueous sodium bicarbonate solution (7:1 v:v, 80 mL), and water (80 mL); was dried over anhydrous magnesium sulfate; was filtered; and was concentrated under reduced pressure. The residue was purified by flash column chromatography on silica gel (0% to 75% ethyl acetate in hexanes) to give Intermediate 13-9. LCMS: 864.4.

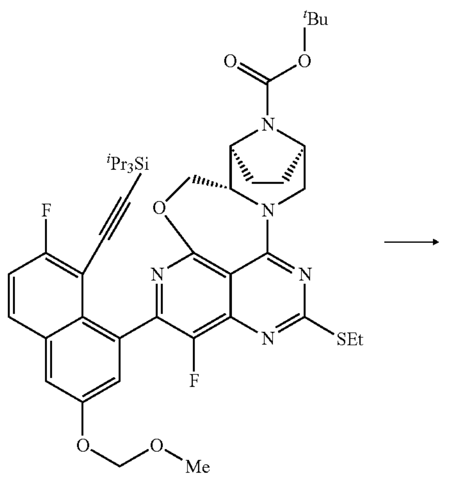

13-8

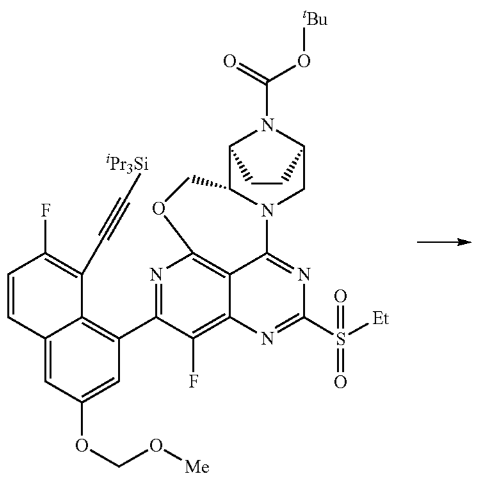

13-9

-continued

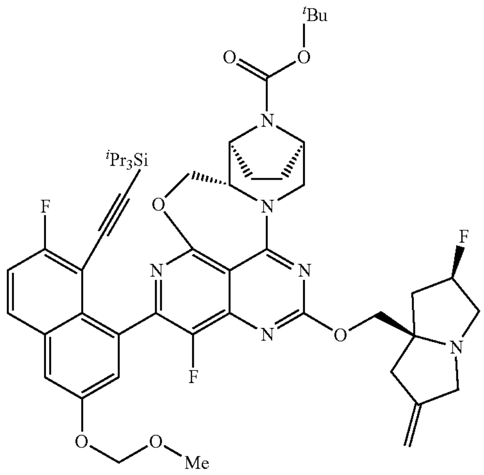

13-10

-continued

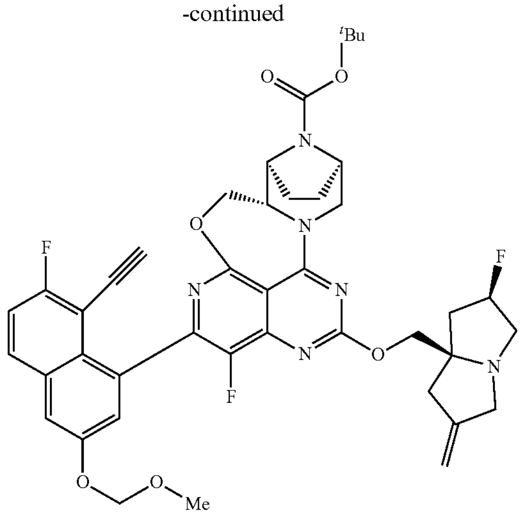

13-11

Lithium bis(trimethylsilyl)amide solution (1.0 M in tetrahydrofuran, 46.3 μL, 46 μmol) was added over 1 min via syringe to a stirred mixture of Intermediate 13-9 (20.0 mg, 23.1 μmol), Intermediate 13-14 (7.9 mg, 46 μmol), and tetrahydrofuran (0.5 mL) at room temperature. After 10 min, diethyl ether (40 mL), ethyl acetate (20 mL), and saturated aqueous sodium bicarbonate solution (5 mL) were added sequentially. The organic layer was washed with water (30 mL), was dried over anhydrous magnesium sulfate, was filtered, and was concentrated under reduced pressure to give Intermediate 13-10. LCMS: 941.4.

Cesium fluoride (84.4 mg, 556 μmol) was added to a vigorously stirred solution of Intermediate 13-10 (21.8 mg, 23.1 μmol) in N,N-dimethylformamide (0.5 mL) at room temperature. After 30 min, diethyl ether (40 mL), ethyl acetate (20 mL), and saturated aqueous sodium bicarbonate solution (10 mL) were added sequentially. The organic layer was washed with water (2×40 mL), was dried over anhydrous magnesium sulfate, was filtered, and was concentrated under reduced pressure to give Intermediate 13-11. LCMS: 785.3.

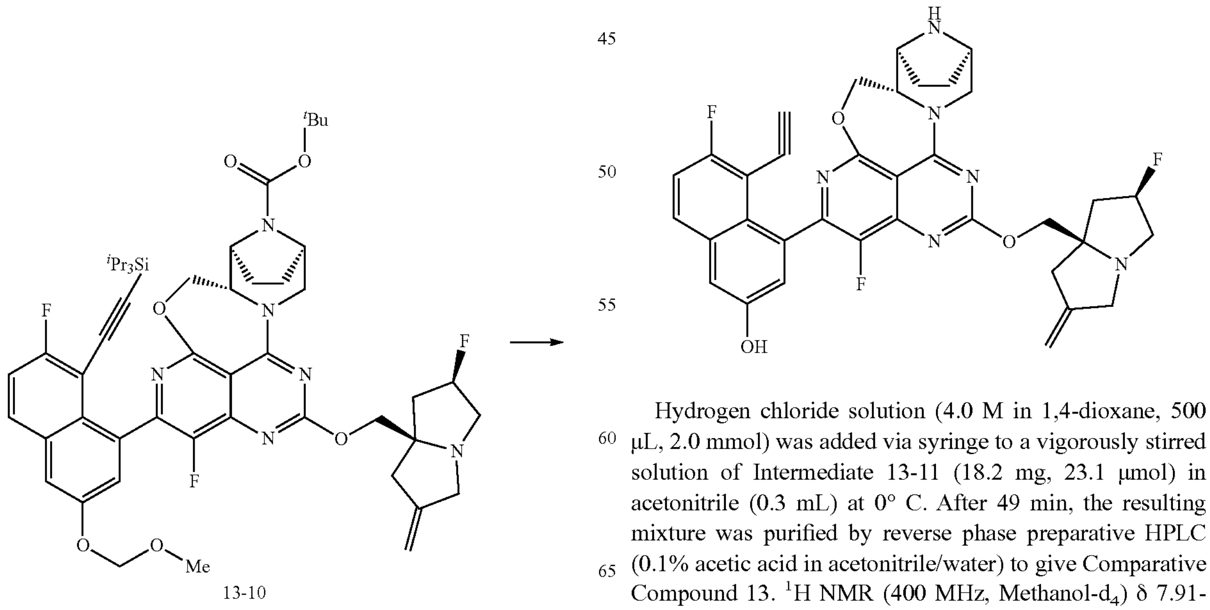

13-10

Comparative Compound 13

Hydrogen chloride solution (4.0 M in 1,4-dioxane, 500 μL, 2.0 mmol) was added via syringe to a vigorously stirred solution of Intermediate 13-11 (18.2 mg, 23.1 μmol) in acetonitrile (0.3 mL) at 0° C. After 49 min, the resulting mixture was purified by reverse phase preparative HPLC (0.1% acetic acid in acetonitrile/water) to give Comparative Compound 13. $^1$H NMR (400 MHz, Methanol-$d_4$) δ 7.91-7.78 (m, 1H), 7.38-7.27 (m, 2H), 7.26-7.14 (m, 1H), 5.35 (d, J=53.2 Hz, 1H), 5.14-5.07 (m, 1H), 5.03 (d, J=3.4 Hz, 2H), 4.62 (dd, J=13.2, 8.0 Hz, 1H), 4.59-4.44 (m, 1H), 4.44-4.36 (m, 1H), 4.30 (d, J=10.4 Hz, 1H), 4.17 (d, J=7.2 Hz, 1H), 3.78 (d, J=13.9 Hz, 2H), 3.74-3.66 (m, 1H), 3.55-3.11 (m, 4H), 3.04-2.81 (m, 2H), 2.51 (q, J=12.0, 10.6 Hz, 2H), 2.15 (dd, J=40.8, 14.3 Hz, 1H), 2.07-1.74 (m, 4H), 1.96 (s, 6H). LCMS: 641.2.

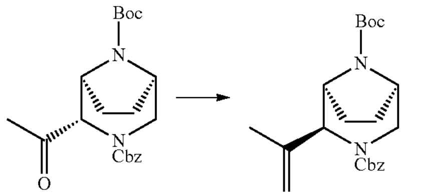

61-1 64-1

Intermediate 64-1 was synthesized in a manner similar to Intermediate 27-4 using Intermediate 61-1 instead of Intermediate 27-3. LCMS: 387.0.

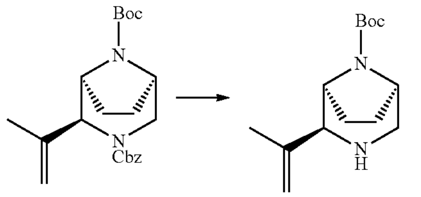

64-1 64-2

Intermediate 64-2 was synthesized in a manner similar to Comparative Intermediate 27-5 using Intermediate 64-1 instead of Intermediate 27-4. LCMS: 252.9.

64-3

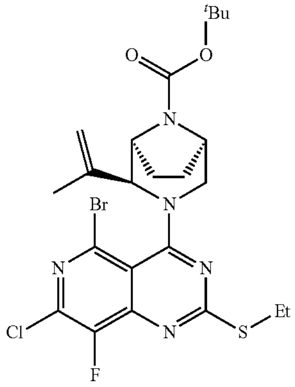

Intermediate 64-3 was synthesized in a manner similar to 63-5 using Intermediate 64-2 instead of Intermediate 13-6. LCMS: 572.4, 574.0.

64-4

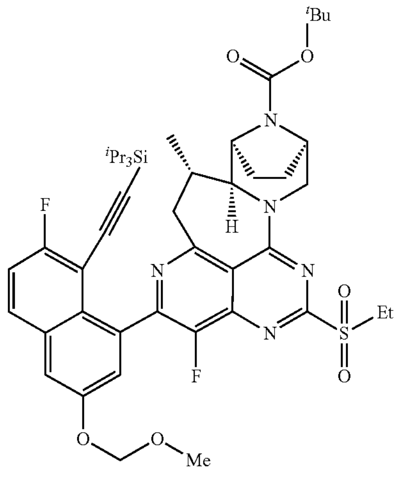

Intermediate 64-4 was synthesized in a manner similar to Intermediate 13-9 using Intermediate 64-3 instead of Intermediate 13-8. LCMS: 876.4.

Comparative Example 64

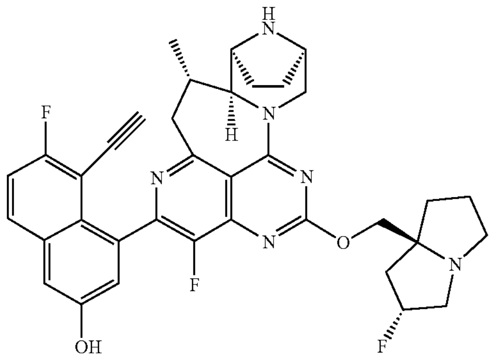

Comparative Example 64 was synthesized in a manner similar to Comparative Compound 13 using Intermediate 64-4 instead of Intermediate 13-9 and using ((2R,7aS)-2-fluorotetrahydro-1H-pyrrolizin-7a(5H)-yl)methanol instead of Intermediate 13-14. $^{1}H$ NMR (400 MHz, Methanol-$d_4$) δ 7.96-7.85 (m, 1H), 7.46-7.13 (m, 3H), 5.61 (d, J=51.5 Hz, 1H), 5.19 (d, J=14.7 Hz, 1H), 4.81-4.64 (m, 2H), 4.46-3.40 (m, 8H), 3.28-2.10 (m, 11H), 1.38-1.19 (m, 3H). LCMS: 640.9.

Comparative Example 76, Comparative Compound 76 of U.S. application Ser. No. 18/303,813, published as US 2023/0374036: (6aR,7S,10R)-2-(8-ethynyl-7-fluoronaphthalen-1-yl)-1-fluoro-13-(((2R,7aS)-2-fluorotetrahydro-1H-pyrrolizin-7a(5H)-yl)methoxy)-5,6,6a,7,8,9,10,11-octahydro-4H-3,11a,12,14,15-pentaaza-7,10-methanocyclohepta[4,5]cycloocta[1,2,3-de]naphthalene

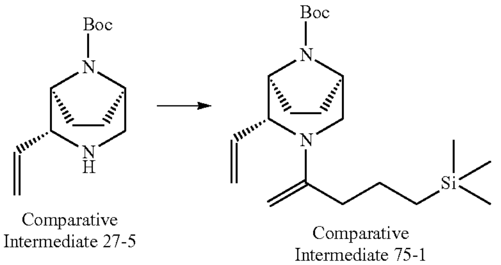 [SMILES: C=C[C@H]1NC[C@H]2CC[C@@H]1N2C(=O)OC(C)(C)C ; C=C[C@@H]1[C@@H]2CC[C@H](CN1C(=C)CCC[Si](C)(C)C)N2C(=O)OC(C)(C)C]

Comparative Intermediate 27-5

Comparative Intermediate 75-1

To a vigorously stirred solution of Comparative Intermediate 27-5 (1.00 g, 4.20 mmol) and (2,5-dioxopyrrolidin-1-yl) 2-trimethylsilylethyl carbonate (1.14 g, 4.41 mmol) in dichloromethane (13.9 mL) was added 4-methylmorpholine (0.46 mL, 4.20 mmol) slowly with stirring at room temperature. The resulted solution was stirred at room temperature for 72 hours. The mixture was washed with water (15 mL) and extracted with ethyl acetate (3×30 mL). The organic layer was collected and combined, dried over magnesium sulfate, concentrated under reduced pressure to give a liquid. The liquid was purified by silica gel column chromatography (0 to 50% ethyl acetate in hexanes) to give Comparative Intermediate 75-1. LCMS: 405.1 [M+Na]$^+$.

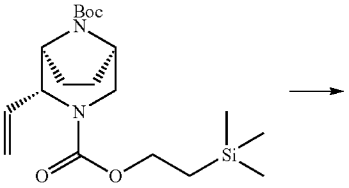

Comparative Intermediate 75-1

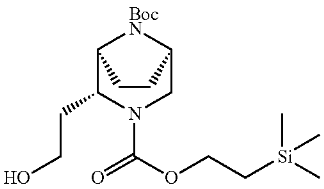

Comparative Intermediate 75-2

To a vigorously stirred solution of Comparative Intermediate 75-1 (50.0 mg, 0.13 mmol) in tetrahydrofuran (1.5 mL) was added the solution of 9-borabicyclo[3.3.1]nonane (0.50 M in tetrahydrofuran, 0.4 mL, 0.20 mmol) dropwise at 0° C. The resulted solution was stirred at 50° C. for 45 minutes. Then hydrogen peroxide (50% wt in water, 0.2 mL, 0.13 mmol) and sodium hydroxide (20 mg, 0.33 mmol) were added at room temperature and the resulting mixture was stirred at room temperature for 30 minutes then quenched with saturated sodium thiosulfate solution (1.5 mL) at 0° C.

The mixture was extracted with dichloromethane (3×10 mL). The organic layer was collected and combined, dried over magnesium sulfate, concentrated under reduced pressure to give a liquid. The liquid was purified by silica gel column chromatography (0 to 100% ethyl acetate in hexanes) to give Comparative Intermediate 75-2. LCMS: 400.7 [M+H]$^+$, 423.1 [M+Na]$^+$.

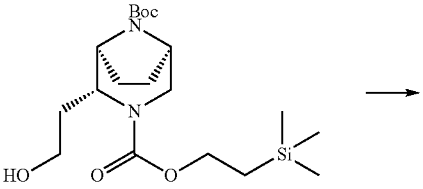

Comparative Intermediate 75-2

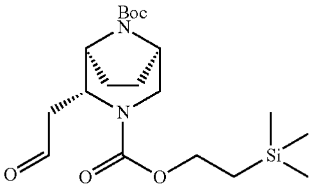

Comparative Intermediate 75-3

To a vigorously stirred solution of Comparative Intermediate 75-2 (0.55 g, 1.37 mmol) in dichloromethane (5 mL) under nitrogen was added Dess Martin periodinane (0.64 g, 1.51 mmol) at room temperature. The mixture was stirred at room temperature for 12 hours before saturated aqueous sodium bicarbonate (10 mL) was added. The mixture was extracted with ethyl acetate (3×10 mL) and the combined organic phase was dried over magnesium sulfate and concentrated under reduced pressure. The residue was purified by silica gel column chromatography (0% to 50% ethyl acetate in hexanes) to give Comparative Intermediate 75-3. LCMS: 421.1 [M+Na]$^+$.

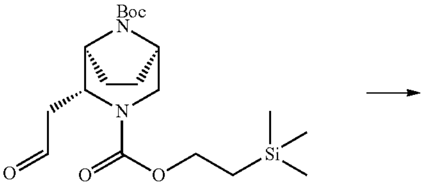

Comparative Intermediate 75-3

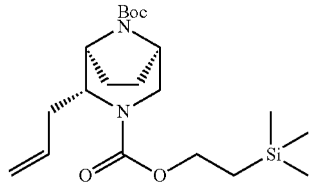

Comparative Intermediate 75-4

To a vigorously stirred solution of methyltriphenylphosphonium bromide (1.29 g, 3.62 mmol) in tetrahydrofuran (5.8 mL) at room temperature was added KHMDS solution (1.0 M in tetrahydrofuran, 3.30 mL, 3.30 mmol) dropwise to afford a solution. The mixture was stirred for 1 hour at room temperature and was cooled to −78° C. whereupon a solution of Comparative Intermediate 75-3 (0.44 g, 1.10 mmol) in tetrahydrofuran (5.8 mL) was added dropwise over 20 minutes. The resulting solution was allowed to gradually warm to room temperature and stir for 3 hours. The mixture was quenched with methanol (10 mL) and stirred for 15 min. Saturated aqueous ammonium chloride solution (12 mL) was added and the mixture was extracted with ethyl acetate (3×12 mL). The combined organic phase was dried over magnesium sulfate and concentrated under reduced pressure. The residue was purified by silica gel column chromatography (0% to 40% ethyl acetate in hexanes) to give Comparative Intermediate 75-4. LCMS: 419.2 $[M+Na]^+$.

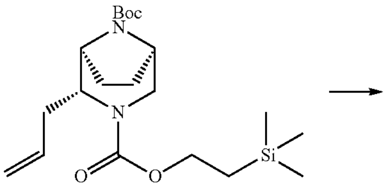

Comparative Intermediate 75-4

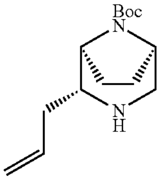

Comparative Intermediate 75-5

Cesium fluoride (95.8 mg, 0.63 mmol) was added to a vigorously stirred solution of Comparative Intermediate 75-4 (50.0 mg, 0.13 mmol) in N,N-dimethylformamide (0.8 mL) at room temperature. The resulting mixture was stirred at 90° C. for 30 minutes. After cooled to room temperature, the mixture was filtered, washed by dichloromethane (5 mL), and the filtrate was concentrated under reduced pressure to give crude product of Comparative Intermediate 75-5, which was used for the next step without purification. LCMS: 253.0.

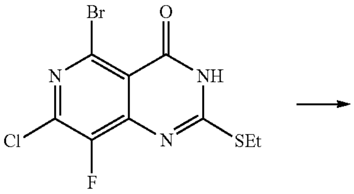

13-3

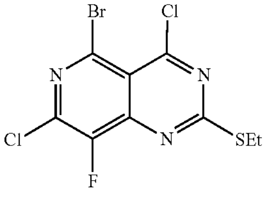

Comparative Intermediate 53-1

N,N-Diisopropylethylamine (884 μL, 5.08 mmol) was added via syringe to a mixture of Intermediate 13-3 (839 mg, 2.48 mmol) and phosphorous(V) oxychloride (10 mL) at room temperature, and the resulting mixture was stirred at rt for 15 min before it was concentrated under reduced pressure. The residue was purified by flash column chromatography on silica gel (0 to 13% ethyl acetate in hexanes) to give Comparative Intermediate 53-1. LCMS: 357.9.

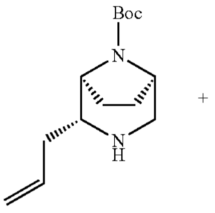

Comparative Intermediate 75-5

+

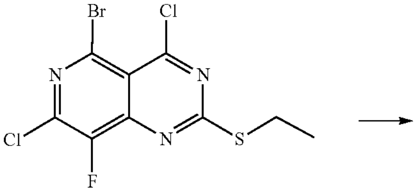

Comparative Intermediate 53-1

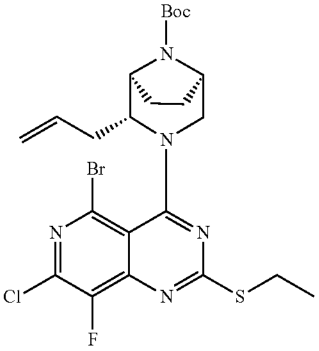

Comparative Intermediate 75-6

A mixture of Comparative Intermediate 75-5 (230 mg, 0.911 mmol), Comparative Intermediate 53-1 (342 mg, 0.957 mmol) and DIPEA (384 mg, 2.97 mmol) in DCM (1.3 mL) was stirred at room temperature for 24 minutes. The mixture was purified by flash column chromatography on silica gel (0 to 80% EtOAc in hexanes) to give Comparative Intermediate 75-6. LCMS: 574.0.

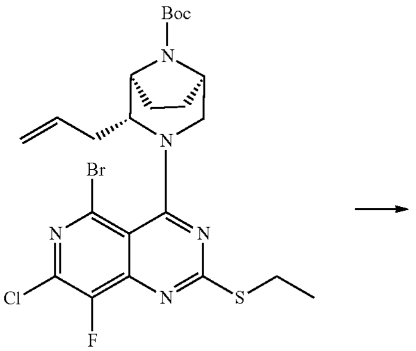

Comparative Intermediate 75-6

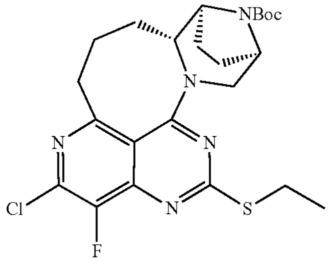

Comparative Intermediate 75-7

To a vigorously stirred solution of Comparative Intermediate 75-6 (30.0 mg, 0.052 mmol) in anhydrous 1,4-dioxane (0.5 mL), the solution of 9-borabicyclo[3.3.1]nonane (0.50 M in tetrahydrofuran, 0.12 mL, 0.06 mmol) was added at room temperature. The resulting solution was stirred at 50° C. for 1 hour before it was cooled to room temperature. The solution was transferred to a reaction vial containing Pd(dppf)$Cl_2$ (3.70 mg, 0.0052 mmol), potassium phosphate (36.6 mg, 0.16 mmol) and degassed water (0.1 mL) at rt under nitrogen atmosphere. The reaction mixture was stirred at 90° C. for 10 minutes before it was cooled to room temperature. The mixture was washed with water (2 mL) and extracted with ethyl acetate (3×5 mL). The organic layer was collected and combined, dried over magnesium sulfate, concentrated under reduced pressure. The crude was purified by silica gel column chromatography (0 to 50% ethyl acetate in hexanes) to give Comparative Intermediate 75-7. LCMS: 494.1.

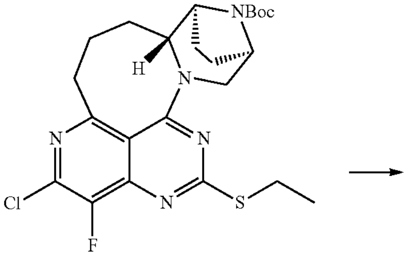

Comparative Intermediate 75-7

-continued

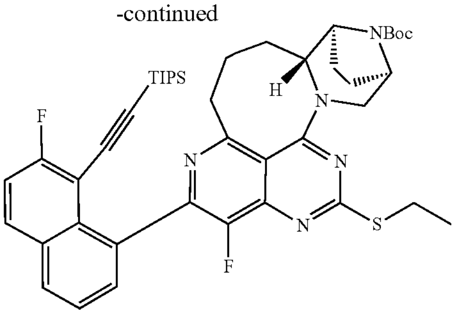

Comparative Intermediate 115-1

A vigorously stirred mixture of Comparative Intermediate 75-7 (181 mg, 0.367 mmol), ((2-fluoro-8-(4,4,5,5-tetramethyl-1,3,2-dioxaborolan-2-yl)naphthalen-1-yl)ethynyl)triisopropylsilane (prepared according to WO 2021/041671) (249 mg, 0.550 mmol), [(di(1-adamantyl)-butylphosphine)-2-(2'-amino-1,1'-biphenyl)]palladium(II) methanesulfonate (13.2 mg, 36.7 μmol), potassium phosphate (253 mg, 1.10 mmol), tetrahydrofuran (5.4 mL), and degassed water (1.1 mL) was heated to 70° C. After 80 min, the resulting mixture was cooled to room temperature, and diethyl ether (40 mL) and ethyl acetate (20 mL) were added sequentially. The organic layer was washed with water (30 mL), was dried over anhydrous magnesium sulfate, was filtered, and was concentrated under reduced pressure. The residue was purified by silica gel column chromatography (0 to 50% ethyl acetate in hexanes) to give Comparative Intermediate 115-1. LCMS: 784.4.

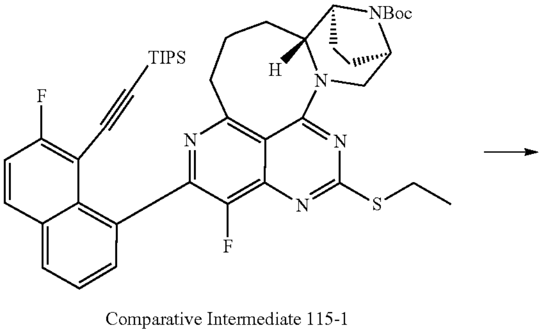

Comparative Intermediate 115-1

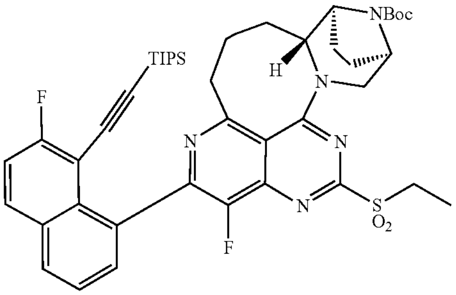

Comparative Intermediate 76-0

3-Chloroperoxybenzoic acid (77% wt, 4590 mg, 20.5 mmol) was added in two equal portions over 5 min to a vigorously stirred solution of Comparative Intermediate 115-1 (7.30 g, 9.31 mmol) in dichloromethane (131 mL) at 0° C. After 125 min, the resulting mixture was warmed to room temperature. The residue was purified by flash column chromatography on silica gel (0% to 75% ethyl acetate in hexanes) to give Comparative Intermediate 76-0. LCMS: 816.4.

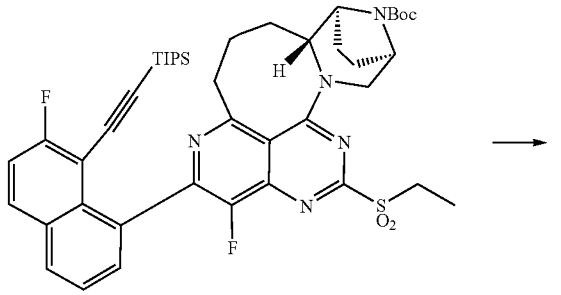

Comparative Intermediate 76-0

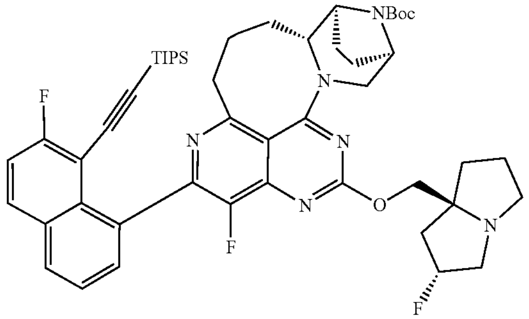

Comparative Intermediate 76-1

Lithium bis(trimethylsilyl)amide solution (1.0 M in tetrahydrofuran, 1.84 mL, 1.84 mmol) was added over 1 min via syringe to a stirred mixture of Comparative Intermediate 76-0 (1000 mg, 1.23 mmol), [(2R,8S)-2-fluoro-1,2,3,5,6,7-hexahydropyrrolizin-8-yl]methanol (725.4 mg, 4.56 mmol), and 2-methyltetrahydrofuran (25.8 mL) 0° C. After 2 hours, ethyl acetate (20 mL), and water (5 mL) were added sequentially at 0° C. The aqueous layer was washed with ethyl acetate (3x20 mL). The organic layers were combined and dried over anhydrous magnesium sulfate, was filtered, and was concentrated under reduced pressure to give Comparative Intermediate 76-1. LCMS: 881.1.

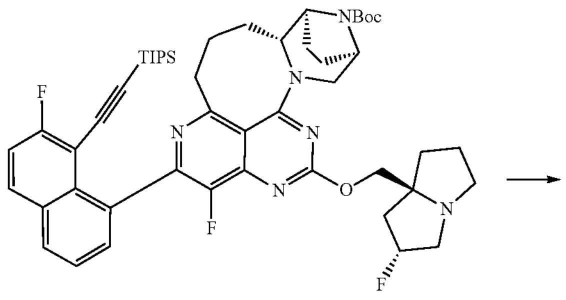

Comparative Intermediate 76-1

-continued

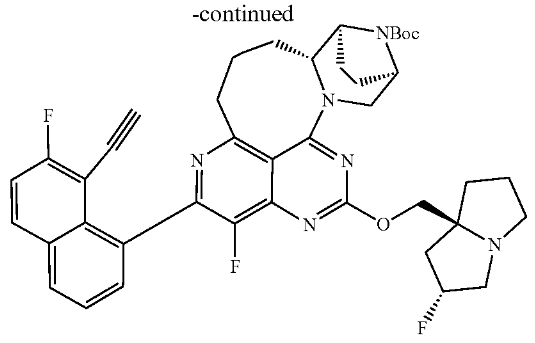

Comparative Intermediate 76-2

Cesium fluoride (37.8 mg, 0.249 mmol) was added to a vigorously stirred solution of Comparative Intermediate 76-1 (21.9 mg, 24.9 μmol) in N,N-dimethylformamide (0.6 mL) at room temperature. After 1 hour, diethyl ether (4 mL), ethyl acetate (2 mL), and saturated aqueous sodium bicarbonate solution (1 mL) were added sequentially. The organic layer was washed with water (2x4 mL), was dried over anhydrous magnesium sulfate, was filtered, and was concentrated under reduced pressure. The residue was purified by silica gel column chromatography (0 to 60% ethyl acetate in hexanes) to give Comparative Intermediate 76-2. LCMS: 724.9.

Comparative Example 76

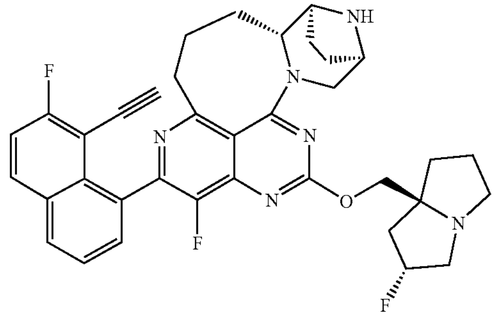

Hydrogen chloride solution (4.0 M in 1,4-dioxane, 91.7 μL, 0.367 mmol) was added via syringe to a vigorously stirred solution of Comparative Intermediate 76-2 (18.0 mg, 24.9 μmol) in acetonitrile (0.3 mL) at room temperature. After 75 min, the resulting mixture was purified by reverse phase preparative HPLC (0.1% trifluoroacetic acid in acetonitrile/water) to give Comparative Example 76. $^1$H NMR (400 MHz, Methanol-$d_4$) δ 8.23-8.01 (m, 2H), 7.67 (q, J=10.0, 8.5 Hz, 2H), 7.47 (td, J=9.0, 3.3 Hz, 1H), 5.59 (d, J=51.9 Hz, 1H), 5.40 (d, J=13.6 Hz, 1H), 4.95-4.88 (m, 2H), 4.83-4.68 (m, 3H), 4.40-4.26 (m, 1H), 4.17 (d, J=9.4 Hz, 1H), 4.11-3.99 (m, 1H), 3.98-3.82 (m, 2H), 3.67 (d, J=14.6 Hz, 1H), 3.63-3.35 (m, 1H), 3.16-1.62 (m, 15H). LCMS: 625.0.

Example 7, Compound 7: 4-(((5S,5aS,6S,9R)-2-(8-ethynyl-7-fluoro-3-hydroxynaphthalen-1-yl)-1-fluoro-12-(((2R,7aS)-2-fluorotetrahydro-1H-pyrrolizin-7a(5H)-yl)methoxy)-5-methyl-4,5,5a,6,7,8,9,10-octahydro-3,10a,11,13,14-pentaaza-6,9-methanonaphtho[1,8-ab]heptalen-14-yl)methyl)-5-methyl-1,3-dioxol-2-one

7

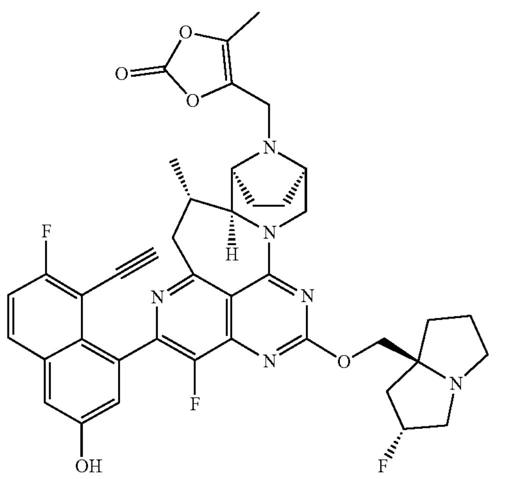

Hydrogen chloride solution (4.0 M in 1,4-dioxane, 1000 μL, 4.0 mmol) was added via syringe to a vigorously stirred solution of Intermediate 7-4 (600 mg, 753 μmol) in acetonitrile (10 mL) and MeOH (0.5 mL) at 0° C. After 1.5 h, the resulting mixture was neutralized to pH 7 by slow addition of saturated aqueous solution of $NaHCO_3$. The mixture was extracted by EtOAc (3×50 mL). The combined organic phase was dried over $Na_2SO_4$ and filtered. The filtrate was concentrated in vacuum to give Example 7. $^1H$ NMR (400 MHz, Methanol-$d_4$) δ 7.96-7.78 (m, 1H), 7.42-7.11 (m, 3H), 5.49-5.21 (m, 1H), 4.94-4.88 (m, 1H), 4.48-4.12 (m, 2H), 3.71-3.36 (m, 6H), 3.29-2.61 (m, 5H), 2.43-1.52 (m, 14H), 1.19-1.05 (m, 3H). LCMS: 753.1.

Example 8, Compound 8: 4-(((6aR,7S,10R)-2-(8-ethynyl-7-fluoro-3-hydroxynaphthalen-1-yl)-1-fluoro-13-(((2R,7aS)-2-fluorotetrahydro-1H-pyrrolizin-7a(5H)-yl)methoxy)-5,6,6a,7,8,9,10,11-octahydro-4H-3,11a,12,14,15-pentaaza-7,10-methanocyclohepta[4,5]cycloocta[1,2,3-de]naphthalen-15-yl)methyl)-5-methyl-1,3-dioxol-2-one

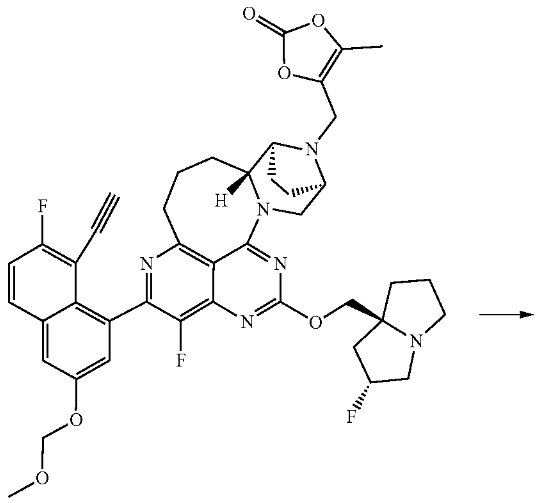

8-2

-continued

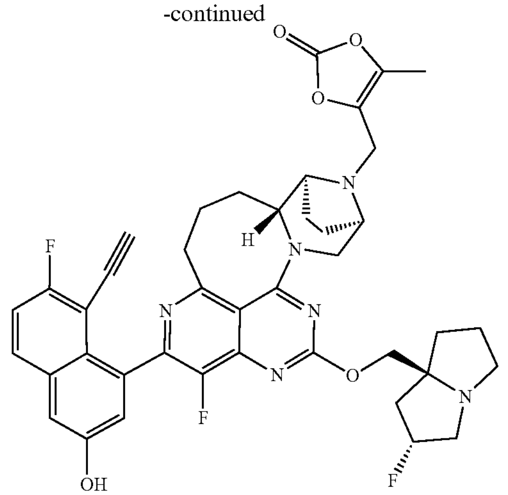

8

Compound 8 was synthesized in a manner similar to Compound 11 using Intermediate 8-2 instead of Intermediate 11-6. $^1H$ NMR (400 MHz, Methanol-$d_4$) δ 7.87 (dt, J=9.1, 6.0 Hz, 1H), 7.44-7.28 (m, 2H), 7.20 (dd, J=14.7, 2.5 Hz, 1H), 5.44-5.22 (m, 2H), 4.44-4.17 (m, 2H), 4.12 (q, J=7.1 Hz, 1H), 3.97 (d, J=10.1 Hz, 1H), 3.74-3.65 (m, 1H), 3.56-3.12 (m, 6H), 3.04 (td, J=9.6, 5.4 Hz, 1H), 2.90 (t, J=13.8 Hz, 1H), 2.61-1.19 (m, 16H), 2.03 (s, 3H). LCMS: 753.1.

Example 9, Compound 9: 4-(tert-butyl)-5-(((6aR,7S,10R)-2-(8-ethynyl-7-fluoro-3-hydroxynaphthalen-1-yl)-1-fluoro-13-(((2R,7aS)-2-fluorotetrahydro-1H-pyrrolizin-7a(5H)-yl)methoxy)-5,6,6a,7,8,9,10,11-octahydro-4H-3,11a,12,14,15-pentaaza-7,10-methanocyclohepta[4,5]cycloocta[1,2,3-de]naphthalen-15-yl)methyl)-1,3-dioxol-2-one

9

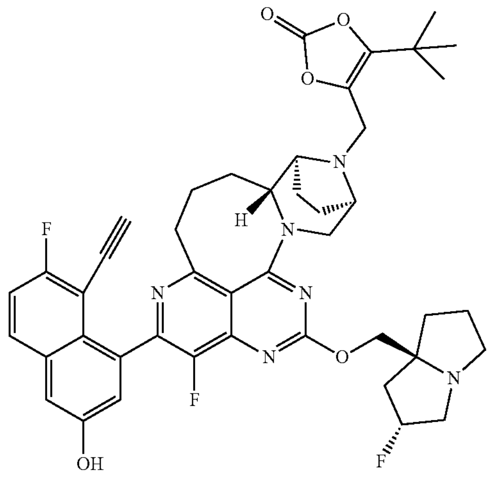

Compound 9 was synthesized in a manner similar to Compound 8 using 4-(bromomethyl)-5-(tert-butyl)-1,3-dioxol-2-one instead of 4-(bromomethyl)-5-methyl-1,3-dioxol-2-one. $^1H$ NMR (400 MHz, Methanol-$d_4$) δ 7.87 (dt, J=9.2, 6.0 Hz, 1H), 7.41-7.29 (m, 2H), 7.20 (dd, J=15.8, 2.5

Hz, 1H), 5.47-5.22 (m, 2H), 4.40-4.20 (m, 2H), 3.97 (d, J=10.1 Hz, 1H), 3.62-3.42 (m, 3H), 3.41-3.19 (m, 6H), 3.04 (td, J=9.5, 5.2 Hz, 1H), 2.89 (t, J=14.1 Hz, 1H), 2.61-1.08 (m, 15H), 1.37 (s, 9H). LCMS: 795.5.

Example 10, Compound 10: 4-(((6aR,7S,10R)-2-(8-ethynyl-7-fluoro-3-hydroxynaphthalen-1-yl)-1-fluoro-13-(((2R,7aS)-2-fluorotetrahydro-1H-pyrrolizin-7a(5H)-yl)methoxy)-5,6,6a,7,8,9,10,11-octahydro-4H-3,11a,12,14,15-pentaaza-7,10-methanocyclohepta[4,5]cycloocta[1,2,3-de]naphthalen-15-yl)methyl)-5-octyl-1,3-dioxol-2-one

10

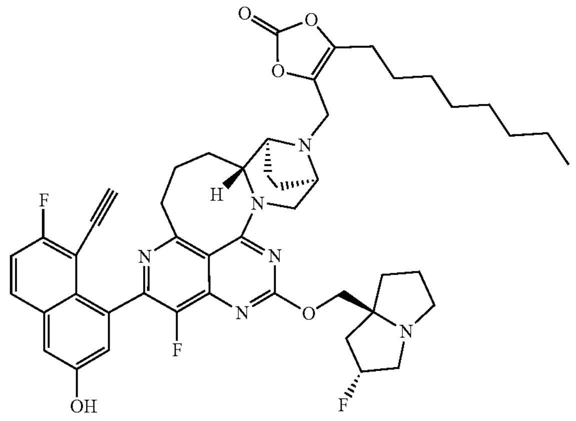

Compound 10 was synthesized in a manner similar to Compound 8 using 4-(bromomethyl)-5-octyl-1,3-dioxol-2-one instead of 4-(bromomethyl)-5-methyl-1,3-dioxol-2-one. $^{1}$H NMR (400 MHz, Acetonitrile-$d_3$) δ 7.89 (dt, J=10.3, 5.2 Hz, 1H), 7.42-7.30 (m, 2H), 7.30-7.12 (m, 1H), 5.40-5.08 (m, 2H), 4.31-4.10 (m, 2H), 3.83 (d, J=10.0 Hz, 1H), 3.57-2.73 (m, 13H), 2.50 (t, J=7.3 Hz, 3H), 2.12-2.05 (m, 2H), 1.94-1.47 (m, 10H), 1.45-1.15 (m, 12H), 0.98-0.80 (m, 3H). LCMS: 851.6.

Example 11, Compound 11: 4-(((4R,6aR,7S,10R)-2-(8-ethynyl-7-fluoro-3-hydroxynaphthalen-1-yl)-1-fluoro-13-(((2R,7aS)-2-fluorotetrahydro-1H-pyrrolizin-7a(5H)-yl)methoxy)-4-methyl-5,6,6a,7,8,9,10,11-octahydro-4H-3,11a,12,14,15-pentaaza-7,10-methanocyclohepta[4,5]cycloocta[1,2,3-de]naphthalen-15-yl)methyl)-5-methyl-1,3-dioxol-2-one

11

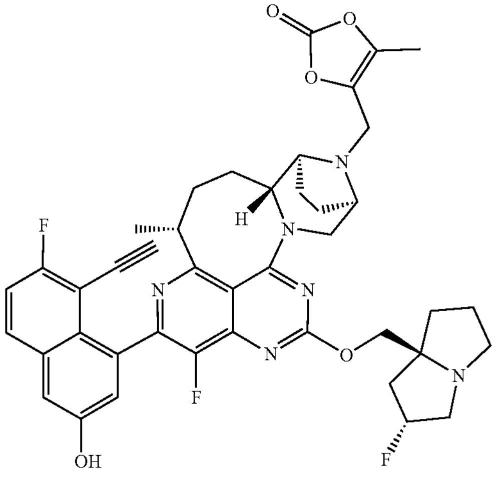

Hydrogen chloride solution (4.0 M in 1,4-dioxane, 500 μL, 2.0 mmol) was added via syringe to a vigorously stirred solution of Intermediate 11-6 (46.4 mg, 60.5 μmol) in acetonitrile (0.30 mL) at 0° C. After 80 min, the resulting mixture was purified by reverse phase preparative HPLC (0.1% acetic acid in acetonitrile/water) to give Example 11. $^{1}$H NMR (400 MHz, Acetonitrile-$d_3$) δ 7.86 (ddd, J=9.2, 7.2, 5.8 Hz, 1H), 7.39-7.26 (m, 2.67H), 7.15 (d, J=2.6 Hz, 0H.33), 5.41-5.11 (m, 2H), 4.32-4.15 (m, 2H), 3.83 (dd, J=10.2, 4.9 Hz, 1H), 3.59-3.43 (m, 1H), 3.39 (t, J=3.8 Hz, 1H), 3.36-3.08 (m, 7.67H), 3.05 (s, 0.33H), 3.01-2.88 (m, 1H), 2.45-1.06 (m, 17H), 2.09 (s, 3H). LCMS: 767.1.

Example 11-P, Compound 11-P: 5-ethynyl-6-fluoro-4-((4R,6aR,7S,10R)-1-fluoro-13-(((2R,7aS)-2-fluorotetrahydro-1H-pyrrolizin-7a(5H)-yl)methoxy)-4-methyl-5,6,6a,7,8,9,10,11-octahydro-4H-3,11a,12,14,15-pentaaza-7,10-methanocyclohepta[4,5]cycloocta[1,2,3-de]naphthalen-2-yl)naphthalen-2-ol

11-P

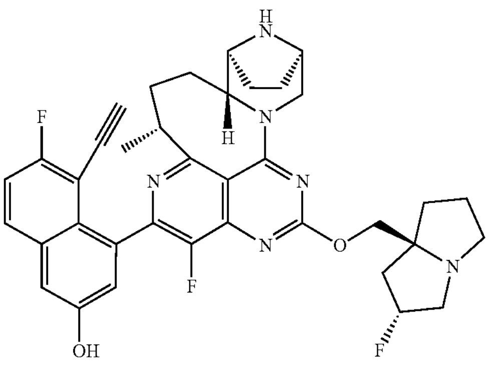

Hydrogen chloride solution (4.0 M in 1,4-dioxane, 500 μL, 2.0 mmol) was added via syringe to a vigorously stirred solution of Intermediate 11-4 (39.7 mg, 49.7 μmol) in acetonitrile (0.20 mL) at 0° C., and the resulting mixture was warmed to room temperature. After 60 min, the resulting mixture was purified by reverse phase preparative HPLC (0.1% acetic acid in acetonitrile/water) to give Example 11-P. $^{1}$H NMR (400 MHz, Methanol-$d_4$) δ 7.92-7.82 (m, 1H), 7.38-7.29 (m, 2H), 7.27 (d, J=2.6 Hz, 0.62H), 7.13 (d, J=2.6 Hz, 0.38H), 5.50-5.24 (m, 2H), 4.46-4.34 (m, 1H), 4.31 (dd, J=10.6, 2.1 Hz, 1H), 4.09-3.90 (m, 1H), 3.88-3.78 (m, 1H), 3.66-3.53 (m, 2H), 3.45-3.04 (m, 5H), 2.69-2.52 (m, 1H), 2.52-1.23 (m, 17H). LCMS: 655.1.

Example 12, Compound 12: 4-(tert-butyl)-5-(((4R,6aR,7S,10R)-2-(8-ethynyl-7-fluoro-3-hydroxynaphthalen-1-yl)-1-fluoro-13-(((2R,7aS)-2-fluorotetrahydro-1H-pyrrolizin-7a(5H)-yl)methoxy)-4-methyl-5,6,6a,7,8,9,10,11-octahydro-4H-3,11a,12,14,15-pentaaza-7,10-methanocyclohepta[4,5]cycloocta[1,2,3-de]naphthalen-15-yl)methyl)-1,3-dioxol-2-one

12

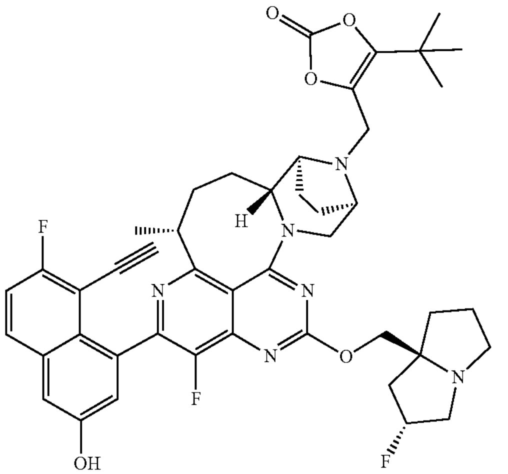

Example 12 was synthesized in a manner similar to Example 11 using 4-(bromomethyl)-5-(tert-butyl)-1,3-dioxol-2-one instead of 4-(bromomethyl)-5-methyl-1,3-dioxol-2-one. $^1$H NMR (400 MHz, Acetonitrile-$d_3$) δ 7.87 (dt, J=9.2, 5.8 Hz, 1H), 7.40-7.28 (m, 2H), 7.25 (d, J=2.6 Hz, 0.67H), 7.13 (d, J=2.6 Hz, 0.33H), 5.40-5.13 (m, 2H), 4.28-4.16 (m, 1H), 4.15-4.08 (m, 1H), 3.83 (d, J=10.1 Hz, 1H), 3.59-3.48 (m, 1H), 3.46-3.33 (m, 3H), 3.28-3.02 (m, 5.67H), 3.03-2.96 (m, 0.33H), 2.95-2.84 (m, 1H), 2.46-2.34 (m, 1H), 2.30-1.08 (m, 13H), 1.31 (s, 6H), 1.30 (s, 3H), 1.22 (d, J=6.4 Hz, 3H). LCMS: 809.2.

Example 13, Compound 13: 4-(((4R,6aR,7S,10R)-2-(8-ethynyl-7-fluoro-3-hydroxynaphthalen-1-yl)-1-fluoro-13-(((2R,7aS)-2-fluorotetrahydro-1H-pyrrolizin-7a(5H)-yl)methoxy)-4-methyl-5,6,6a,7,8,9,10,11-octahydro-4H-3,11a,12,14,15-pentaaza-7,10-methanocyclohepta[4,5]cycloocta[1,2,3-de]naphthalen-15-yl)methyl)-5-octyl-1,3-dioxol-2-one

13

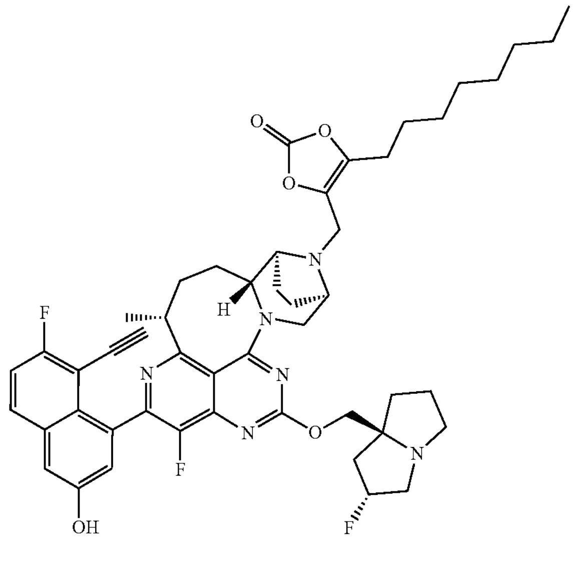

Example 13 was synthesized in a manner similar to Example 11 using 4-(bromomethyl)-5-octyl-1,3-dioxol-2-one instead of 4-(bromomethyl)-5-methyl-1,3-dioxol-2-one. $^1$H NMR (400 MHz, Acetonitrile-$d_3$) δ 7.88 (dt, J=9.2, 6.0 Hz, 1H), 7.43-7.28 (m, 2H), 7.26 (d, J=2.6 Hz, 0.67H), 7.12 (d, J=2.6 Hz, 0.33H), 5.40-5.13 (m, 2H), 4.20 (dd, J=10.4, 7.4 Hz, 1H), 4.14 (d, J=10.4 Hz, 1H), 3.83 (d, J=10.2 Hz, 1H), 3.64-3.47 (m, 1H), 3.40 (s, 1H), 3.35-3.04 (m, 7.67H), 3.00 (d, J=1.1 Hz, 0.33H), 2.99-2.82 (m, 1H), 2.58-1.06 (m, 28H), 1.22 (d, J=6.4 Hz, 3H), 0.92-0.78 (m, 3H). LCMS: 865.2.

Example 14, Compound 14: 4-(((6aR,7S,10R)-2-(8-ethynyl-7-fluoro-3-hydroxynaphthalen-1-yl)-1-fluoro-13-(((2R,7aS)-2-fluorotetrahydro-1H-pyrrolizin-7a(5H)-yl)methoxy)-5,6,6a,7,8,9,10,11-octahydro-4H-3,11a,12,14,15-pentaaza-7,10-methanocyclohepta[4,5]cycloocta[1,2,3-de]naphthalen-15-yl)methyl)-5-hexyl-1,3-dioxol-2-one

14

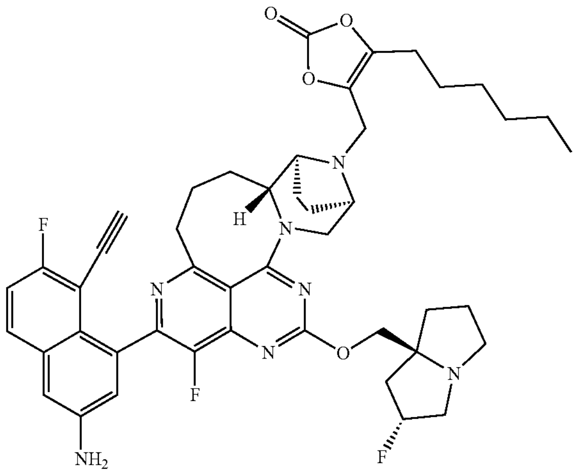

Compound 14 was synthesized in a manner similar to Compound 8 using Intermediate 16-1 instead of 4-(bromomethyl)-5-methyl-1,3-dioxol-2-one. $^1$H NMR (400 MHz, Acetonitrile-$d_3$) δ 7.86 (dt, J=9.2, 6.6 Hz, 1H), 7.44-7.28 (m, 2H), 7.28-7.14 (m, 1H), 5.43-5.06 (m, 2H), 4.33-4.13 (m, 2H), 3.82 (d, J=10.1 Hz, 1H), 3.54-2.71 (m, 12H), 2.49 (t, J=7.4 Hz, 3H), 2.12-2.03 (m, 2H), 1.94-1.46 (m, 11H), 1.46-1.19 (m, 8H), 0.91 (q, J=5.2, 3.8 Hz, 3H). LCMS: 823.6.

Example 15, Compound 15: 4-cyclohexyl-5-(((6aR,7S,10R)-2-(8-ethynyl-7-fluoro-3-hydroxynaphthalen-1-yl)-1-fluoro-13-(((2R,7aS)-2-fluorotetrahydro-1H-pyrrolizin-7a(5H)-yl)methoxy)-5,6,6a,7,8,9,10,11-octahydro-4H-3,11a,12,14,15-pentaaza-7,10-methanocyclohepta[4,5]cycloocta[1,2,3-de]naphthalen-15-yl)methyl)-1,3-dioxol-2-one

15

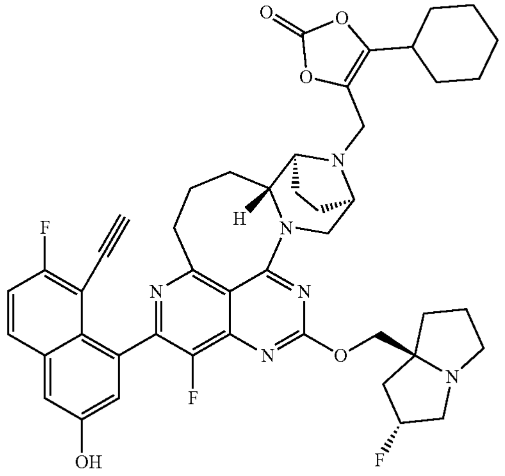

Compound 15 was synthesized in a manner similar to Compound 8 using 4-(bromomethyl)-5-cyclohexyl-1,3-dioxol-2-one instead of 4-(bromomethyl)-5-methyl-1,3-dioxol-2-one. $^1$H NMR (400 MHz, Acetonitrile-$d_3$) δ 7.91 (ddd, J=9.3, 6.0, 3.4 Hz, 1H), 7.46-7.29 (m, 2H), 7.29-7.16 (m, 1H), 5.45-5.12 (m, 2H), 4.35-4.07 (m, 2H), 3.84 (d, J=10.1 Hz, 1H), 3.52-3.00 (m, 11H), 3.00-2.90 (m, 1H), 2.80 (d, J=11.9 Hz, 1H), 2.71-2.58 (m, 1H), 2.50 (t, J=10.8 Hz, 1H), 1.92-1.15 (m, 22H). LCMS: 821.2.

Example 16, Compound 16: 4-(((4R,6aR,7S,10R)-2-(8-ethynyl-7-fluoro-3-hydroxynaphthalen-1-yl)-1-fluoro-13-(((2R,7aS)-2-fluorotetrahydro-1H-pyrrolizin-7a(5H)-yl)methoxy)-4-methyl-5,6,6a,7,8,9,10,11-octahydro-4H-3,11a,12,14,15-pentaaza-7,10-methanocyclohepta[4,5]cycloocta[1,2,3-de]naphthalen-15-yl)methyl)-5-hexyl-1,3-dioxol-2-one

16

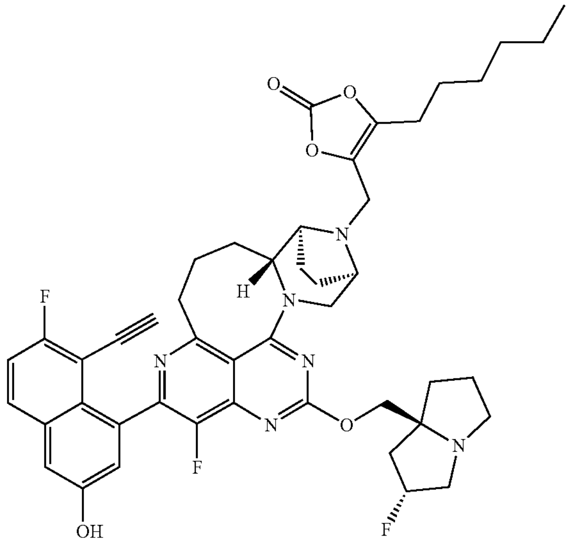

Example 16 was synthesized in a manner similar to Example 11 using Intermediate 16-1 instead of 4-(bromomethyl)-5-methyl-1,3-dioxol-2-one. $^1$H NMR (400 MHz, Acetonitrile-$d_3$) δ 7.90 (dt, J=9.2, 6.2 Hz, 1H), 7.40-7.31 (m, 2H), 7.26 (d, J=2.6 Hz, 0.67H), 7.13 (d, J=2.6 Hz, 0.33H), 5.39-5.14 (m, 2H), 4.20 (dd, J=10.4, 6.1 Hz, 1H), 4.12 (d, J=10.4 Hz, 1H), 3.84 (d, J=10.3 Hz, 1H), 3.67-3.46 (m, 1H), 3.41 (s, 1H), 3.36-3.03 (m, 7.67H), 3.00 (s, 0.33H), 2.97-2.81 (m, 1H), 2.59-1.08 (m, 27H), 0.97-0.82 (m, 3H). LCMS: 837.2.

Example 17, Compound 17: 4-cyclohexyl-5-(((4R,6aR,7S,10R)-2-(8-ethynyl-7-fluoro-3-hydroxynaphthalen-1-yl)-1-fluoro-13-(((2R,7aS)-2-fluorotetrahydro-1H-pyrrolizin-7a(5H)-yl)methoxy)-4-methyl-5,6,6a,7,8,9,10,11-octahydro-4H-3,11a,12,14,15-pentaaza-7,10-methanocyclohepta[4,5]cycloocta[1,2,3-de]naphthalen-15-yl)methyl)-1,3-dioxol-2-one

17

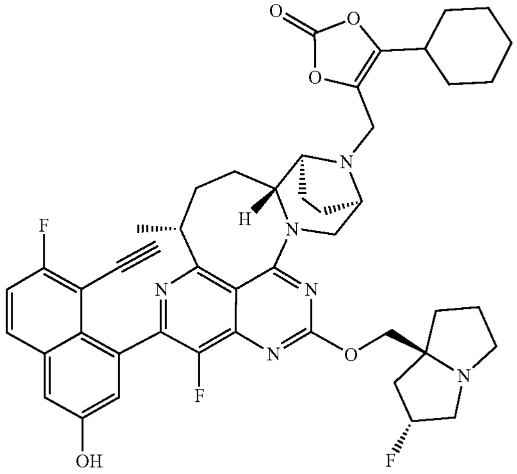

Example 17 was synthesized in a manner similar to Example 11 using 4-(bromomethyl)-5-cyclohexyl-1,3-dioxol-2-one instead of 4-(bromomethyl)-5-methyl-1,3-dioxol-2-one. $^1$H NMR (400 MHz, Acetonitrile-$d_3$) δ 7.90 (dt, J=9.2, 6.2 Hz, 1H), 7.47-7.29 (m, 2H), 7.27 (d, J=2.6 Hz, 0.67H), 7.13 (d, J=2.6 Hz, 0.33H), 5.44-5.12 (m, 2H), 4.21 (dd, J=10.4, 6.5 Hz, 1H), 4.11 (d, J=10.6 Hz, 1H), 3.84 (d, J=10.4 Hz, 1H), 3.67-3.46 (m, 1H), 3.41 (s, 1H), 3.40-3.02 (m, 7.67H), 3.02-2.98 (m, 0.33H), 2.98-2.81 (m, 1H), 2.71-2.57 (m, 1H), 2.45-2.35 (m, 1H), 2.32-0.99 (m, 26H). LCMS: 835.2.

Example 18, Compound 18: 4-(((6aR,7S,10R)-1-fluoro-2-(7-fluoro-3-hydroxy-8-(trifluoromethoxy)naphthalen-1-yl)-13-(((2R,7aS)-2-fluorotetrahydro-1H-pyrrolizin-7a(5H)-yl)methoxy)-5,6,6a,7,8,9,10,11-octahydro-4H-3,11a,12,14,15-pentaaza-7,10-methanocyclohepta[4,5]cycloocta[1,2,3-de]naphthalen-15-yl)methyl)-5-methyl-1,3-dioxol-2-one

18

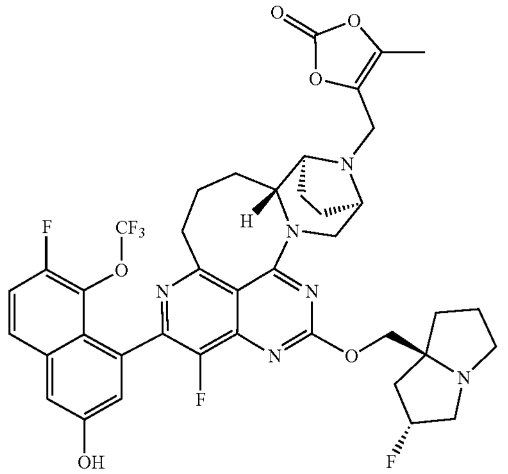

Hydrogen chloride solution (4.0 M in 1,4-dioxane, 2.68 mL, 11 mmol) was added via syringe to Intermediate 18-3 (969.5 mg, 1.13 mmol) in acetonitrile (2.5 mL) at 0° C. After 80 min, sodium acetate (564 mg, 6.87 mmol), sodium trifluoroacetate (1.17 g, 8.59 mmol), and water (1.0 mL) were added sequentially, and the resulting mixture was purified by flash column chromatography on C18 reverse phase silica gel (0.1% trifluoroacetic acid in acetonitrile/water) to give Example 18. $^1$H NMR (400 MHz, Acetonitrile-$d_3$) δ 7.91 (dd, J=9.2, 5.2 Hz, 1H), 7.49 (dd, J=10.0, 9.2 Hz, 1H), 7.46-7.40 (m, 1.75H), 7.30 (s, 0.25H), 5.53 (d, J=51.8 Hz, 1H), 5.31 (dd, J=14.7, 3.1 Hz, 1H), 4.69 (d, J=12.3 Hz, 1H), 4.57 (d, J=12.5 Hz, 1H), 4.50 (d, J=9.3 Hz, 1H), 4.25 (s, 1H), 4.15-3.57 (m, 7H), 3.45-3.23 (m, 2H), 3.01-2.81 (m, 2H), 2.76-1.39 (m, 13H), 2.19 (s, 3H). LCMS: 813.3.

Example 18-P, Compound 18-P: 6-fluoro-4-((6aR,7S,10R)-1-fluoro-13-(((2R,7aS)-2-fluorotetrahydro-1H-pyrrolizin-7a(5H)-yl)methoxy)-5,6,6a,7,8,9,10,11-octahydro-4H-3,11a,12,14,15-pentaaza-7,10-methanocyclohepta[4,5]cycloocta[1,2,3-de]naphthalen-2-yl)-5-(trifluoromethoxy)naphthalen-2-ol

18-P

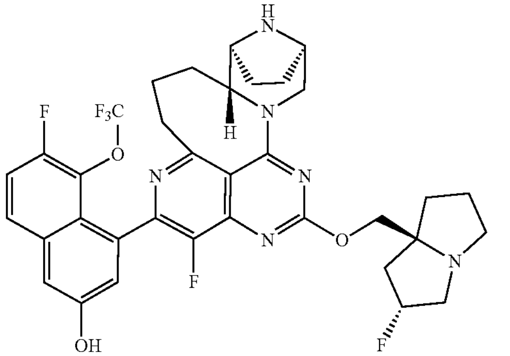

Trifluoroacetic acid (1.0 mL) was added to a stirred solution of Intermediate 18-1 (7.2 mg, 8.5 μmol) in dichloromethane (3.0 mL) at room temperature, and the resulting mixture was heated to 50° C. After 15 min, the resulting mixture was cooled to room temperature and was concentrated under reduced pressure. The residue was purified by reverse phase preparative HPLC (0.1% trifluoracetic acid in acetonitrile/water) to give Example 18-P. $^1$H NMR (400 MHz, Methanol-$d_4$) δ 7.91-7.84 (m, 1H), 7.46 (t, J=9.6 Hz, 1H), 7.42-7.34 (m, 1.75H), 7.26 (s, 0.25H), 5.43-5.22 (m, 2H), 4.44-4.26 (m, 2H), 4.03-3.91 (m, 1H), 3.85-3.73 (m, 1H), 3.61-3.54 (m, 1H), 3.44-3.14 (m, 5H), 3.11-3.02 (m, 1H), 3.01-2.85 (m, 1H), 2.69-2.54 (m, 1H), 2.49-1.04 (m, 13H). LCMS: 701.3.

Example 19, Compound 19: 4-butyl-5-(((6aR,7S,10R)-2-(8-ethynyl-7-fluoronaphthalen-1-yl)-1-fluoro-13-(((2R,7aS)-2-fluorotetrahydro-1H-pyrrolizin-7a(5H)-yl)methoxy)-5,6,6a,7,8,9,10,11-octahydro-4H-3,11a,12,14,15-pentaaza-7,10-methanocyclohepta[4,5]cycloocta[1,2,3-de]naphthalen-15-yl)methyl)-1,3-dioxol-2-one

19

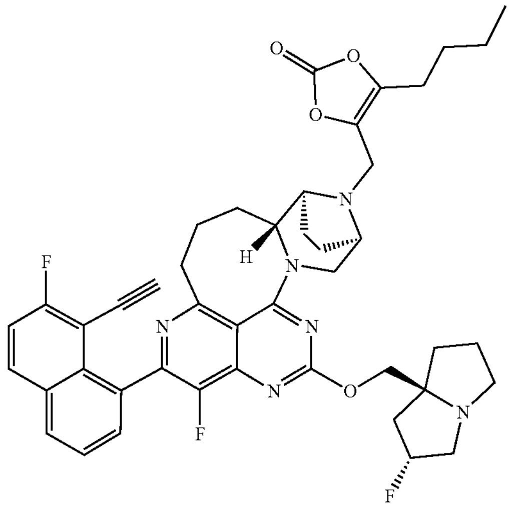

Example 19 was synthesized in a manner similar to Intermediate 18-3 using Comparative Example 76 of U.S. application Ser. No. 18/303,813, published as US 2023/0374036, instead of Intermediate 18-2 and using 4-(bromomethyl)-5-cyclohexyl-1,3-dioxol-2-one instead of 4-(bromomethyl)-5-methyl-1,3-dioxol-2-one. $^1$H NMR (400 MHz, Acetonitrile-$d_3$) δ 8.18-8.10 (m, 2H), 7.74-7.59 (m, 2H), 7.46 (td, J=9.1, 2.8 Hz, 1H), 5.52 (dd, J=51.8, 4.2 Hz, 1H), 5.29 (dd, J=14.7, 3.2 Hz, 1H), 4.77-4.66 (m, 1H), 4.59 (d, J=12.7 Hz, 1H), 4.47 (d, J=8.9 Hz, 1H), 4.24 (s, 1H), 4.15-3.57 (m, 7H), 3.43-3.24 (m, 2.75H), 3.17 (s, 0.25H), 3.02-2.81 (m, 2H), 2.78-1.65 (m, 15H), 1.59 (p, J=7.5 Hz, 2H), 1.40 (h, J=7.4 Hz, 2H), 0.94 (t, 3H). LCMS: 779.1.

Example 20, Compound 20: 4-(((6aR,7S,10R)-2-(8-ethynyl-7-fluoronaphthalen-1-yl)-1-fluoro-13-(((2R,7aS)-2-fluorotetrahydro-1H-pyrrolizin-7a(5H)-yl)methoxy)-5,6,6a,7,8,9,10,11-octahydro-4H-3,11a,12,14,15-pentaaza-7,10-methanocyclohepta[4,5]cycloocta[1,2,3-de]naphthalen-15-yl)methyl)-5-pentyl-1,3-dioxol-2-one

20

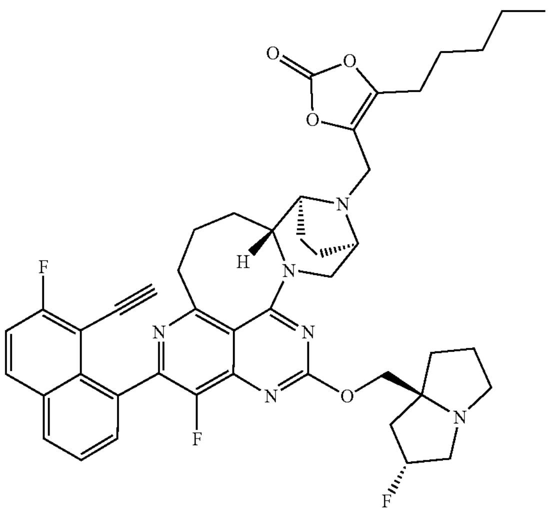

Example 20 was synthesized in a manner similar to Intermediate 18-3 using Comparative Example 76 of U.S. application Ser. No. 18/303,813, published as US 2023/0374036, instead of Intermediate 18-2 and using Intermediate 20-1 instead of 4-(bromomethyl)-5-methyl-1,3-dioxol-2-one. $^1$H NMR (400 MHz, Acetonitrile-$d_3$) δ 8.17-8.08 (m, 2H), 7.73-7.57 (m, 2H), 7.46 (td, J=9.0, 2.9 Hz, 1H), 5.52 (d, J=51.9 Hz, 1H), 5.27 (d, J=14.5 Hz, 1H), 4.75-4.63 (m, 1H), 4.58 (d, J=12.8 Hz, 1H), 4.30 (s, 1H), 4.06-3.57 (m, 8H), 3.44-3.23 (m, 2.75H), 3.17 (s, 0.35H), 2.94-1.49 (m, 19H), 1.44-1.23 (m, 4H), 0.98-0.80 (m, 3H). LCMS: 793.1.

Example 21, Compound 21: 4-(((6aR,7S,10R)-2-(8-ethynyl-7-fluoronaphthalen-1-yl)-1-fluoro-13-(((2R,7aS)-2-fluorotetrahydro-1H-pyrrolizin-7a(5H)-yl)methoxy)-5,6,6a,7,8,9,10,11-octahydro-4H-3,11a,12,14,15-pentaaza-7,10-methanocyclohepta[4,5]cycloocta[1,2,3-de]naphthalen-15-yl)methyl)-5-hexyl-1,3-dioxol-2-one

21

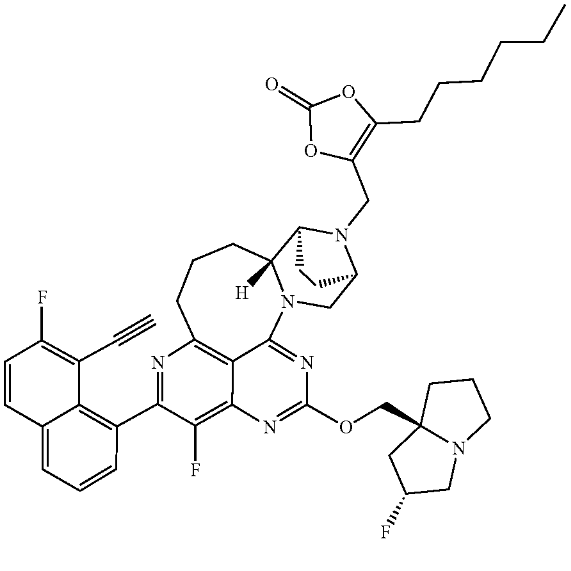

Example 21 was synthesized in a manner similar to Intermediate 18-3 using Comparative Example 76 of U.S. application Ser. No. 18/303,813, published as US 2023/0374036, instead of Intermediate 18-2 and using Intermediate 16-1 instead of 4-(bromomethyl)-5-methyl-1,3-dioxol-2-one. $^1$H NMR (400 MHz, Acetonitrile-$d_3$) δ 8.18-8.08 (m, 2H), 7.73-7.58 (m, 2H), 7.46 (td, J=9.0, 2.9 Hz, 1H), 5.53 (dd, J=51.9, 4.2 Hz, 1H), 5.28 (dd, J=14.6, 3.1 Hz, 1H), 4.83-4.63 (m, 1H), 4.57 (d, J=12.4 Hz, 1H), 4.43 (d, J=9.3 Hz, 1H), 4.17 (s, 1H), 4.06-3.57 (m, 7H), 3.48-3.24 (m, 2.75H), 3.18 (s, 0.25H), 2.98-2.75 (m, 2H), 2.73-1.46 (m, 17H), 1.46-1.23 (m, 6H), 0.98-0.75 (m, 3H). LCMS: 807.2.

Example 22, Compound 22: 4-butyl-5-(((6aR,7S,10R)-1-fluoro-2-(7-fluoro-3-hydroxy-8-(trifluoromethoxy)naphthalen-1-yl)-13-(((2R,7aS)-2-fluorotetrahydro-1H-pyrrolizin-7a(5H)-yl)methoxy)-5,6,6a,7,8,9,10,11-octahydro-4H-3,11a,12,14,15-pentaaza-7,10-methanocyclohepta[4,5]cycloocta[1,2,3-de]naphthalen-15-yl)methyl)-1,3-dioxol-2-one

22

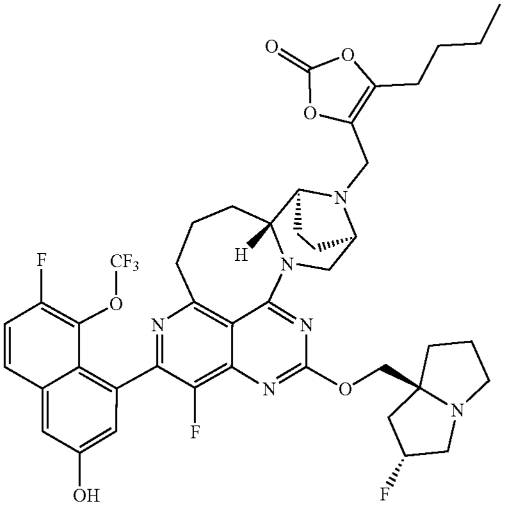

Example 22 was synthesized in a manner similar to Example 18 using 4-(bromomethyl)-5-butyl-1,3-dioxol-2-one instead of 4-(bromomethyl)-5-methyl-1,3-dioxol-2-one. $^1$H NMR (400 MHz, Acetonitrile-$d_3$) δ 7.91 (dd, J=9.2, 5.2 Hz, 1H), 7.49 (t, J=9.6 Hz, 1H), 7.46-7.41 (m, 1.75H), 7.30 (s, 0.25H), 5.53 (d, J=51.7 Hz, 1H), 5.29 (dd, J=14.4, 3.2 Hz, 1H), 4.68 (d, J=11.9 Hz, 1H), 4.57 (d, J=12.6 Hz, 1H), 4.47-4.30 (m, 1H), 4.12 (s, 1H), 4.01-3.74 (m, 6H), 3.67 (t, J=16.2 Hz, 1H), 3.49-3.19 (m, 2H), 2.98-1.51 (m, 19H), 1.40 (h, J=7.4 Hz, 2H), 0.94 (t, J=7.3 Hz, 3H). LCMS: 855.3.

Example 23, Compound 23: 4-(((6aR,7S,10R)-1-fluoro-2-(7-fluoro-3-hydroxy-8-(trifluoromethoxy)naphthalen-1-yl)-13-(((2R,7aS)-2-fluorotetrahydro-1H-pyrrolizin-7a(5H)-yl)methoxy)-5,6,6a,7,8,9,10,11-octahydro-4H-3,11a,12,14,15-pentaaza-7,10-methanocyclohepta[4,5]cycloocta[1,2,3-de]naphthalen-15-yl)methyl)-5-pentyl-1,3-dioxol-2-one

23

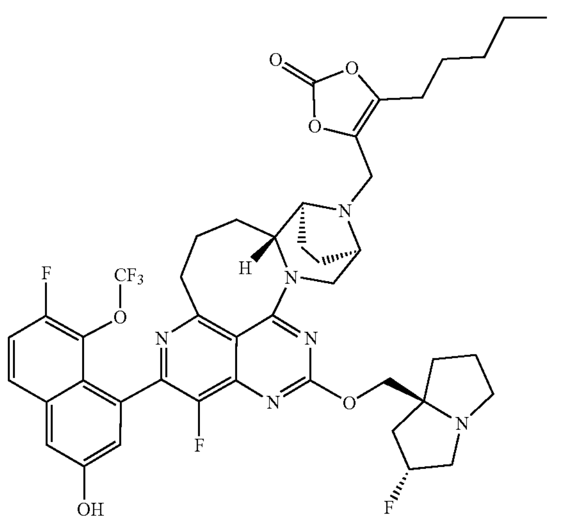

Example 23 was synthesized in a manner similar to Example 18 using Intermediate 20-1 instead of 4-(bromomethyl)-5-methyl-1,3-dioxol-2-one. $^1$H NMR (400 MHz, Acetonitrile-$d_3$) δ 7.94 (dd, J=9.3, 5.2 Hz, 1H), 7.52 (t, J=9.6 Hz, 1H), 7.48-7.43 (m, 1.75H), 7.32 (s, 0.25H), 5.72-5.39 (m, 1H), 5.33 (dd, J=14.5, 3.1 Hz, 1H), 4.79-4.66 (m, 1H), 4.59 (d, J=12.5 Hz, 1H), 4.51-4.38 (m, 1H), 4.19 (s, 1H), 4.08-3.76 (m, 6H), 3.70 (t, J=16.1 Hz, 1H), 3.44-3.26 (m, 2H), 3.05-2.82 (m, 2H), 2.77-1.53 (m, 17H), 1.47-1.33 (m, 4H), 1.03-0.87 (m, 3H). LCMS: 869.3.

Example 24, Compound 24: 4-(((6aR,7S,10R)-1-fluoro-2-(7-fluoro-3-hydroxy-8-(trifluoromethoxy)naphthalen-1-yl)-13-(((2R,7aS)-2-fluorotetrahydro-1H-pyrrolizin-7a(5H)-yl)methoxy)-5,6,6a,7,8,9,10,11-octahydro-4H-3,11a,12,14,15-pentaaza-7,10-methanocyclohepta[4,5]cycloocta[1,2,3-de]naphthalen-15-yl)methyl)-5-hexyl-1,3-dioxol-2-one

24

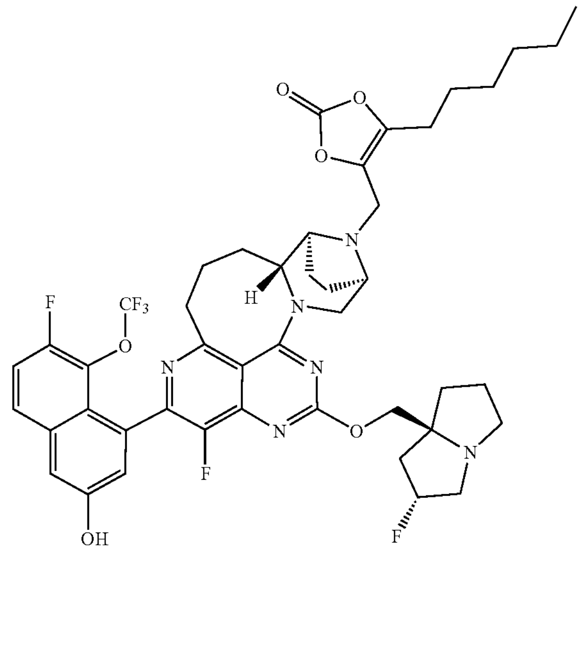

Example 24 was synthesized in a manner similar to Example 18 using Intermediate 16-1 instead of 4-(bromomethyl)-5-methyl-1,3-dioxol-2-one. $^1$H NMR (400 MHz, Acetonitrile-$d_3$) δ 7.92 (dd, J=9.3, 5.2 Hz, 1H), 7.49 (t, J=9.6 Hz, 1H), 7.46-7.40 (m, 1.75H), 7.30 (s, 0.25H), 5.52 (d, J=51.2 Hz, 1H), 5.29 (dd, J=14.3, 3.1 Hz, 1H), 4.67 (d, J=11.9 Hz, 1H), 4.58 (d, J=12.7 Hz, 1H), 4.46-4.28 (m, 1H), 4.09 (s, 1H), 3.98-3.59 (m, 7H), 3.43-3.21 (m, 2H), 2.99-1.46 (m, 19H), 1.46-1.23 (m, 6H), 0.96-0.75 (m, 3H). LCMS: 883.3.

Example 25, Compound 25: 1-(butyryloxy)ethyl (6aR,7S,10R)-2-(8-ethynyl-7-fluoronaphthalen-1-yl)-1-fluoro-13-(((2R,7aS)-2-fluorotetrahydro-1H-pyrrolizin-7a(5H)-yl)methoxy)-5,6,6a,7,8,9,10,11-octahydro-4H-3,11a,12,14,15-pentaaza-7,10-methanocyclohepta[4,5]cycloocta[1,2,3-de]naphthalene-15-carboxylate

25

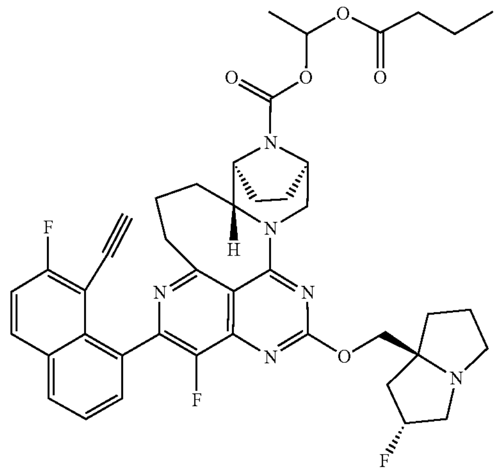

1-(4-Nitrophenoxy)carbonyloxyethyl butanoate (42.8 mg, 144 μmol), triethylamine (27.9 μL, 200 μmol), and 4-(dimethylamino)pyridine (2.0 mg, 16 μmol) were added sequentially to a stirred mixture of Comparative Example 76 of U.S. application Ser. No. 18/303,813, published as US 2023/0374036 (50.0 mg, 80.0 μmol) and dichloromethane (2.0 mL) at room temperature, and the resulting mixture was heated to 40° C. After 60 min, the resulting mixture was concentrated under reduced pressure, and the residue was purified sequentially by flash column chromatography on basic alumna (ethyl acetate/hexanes) and by reverse phase preparative HPLC (acetonitrile/water) to give Example 25. $^1$H NMR (400 MHz, $CD_3CN$) δ 8.19-8.10 (m, 3H), 7.78-7.63 (m, 2H), 7.53-7.45 (m, 1H), 5.54 (d, J=52.0 Hz, 1H), 5.22 (d, J=12.6 Hz, 1H), 4.80-4.55 (m, 2H), 4.43 (s, 1H), 4.17 (s, 1H), 3.90-3.62 (m, 5H), 3.40-3.28 (m, 3H), 2.72-2.51 (m, 5H), 2.30-2.23 (m, 5H), 1.87-1.80 (m, 4H), 1.72-1.49 (m, 7H), 0.99-0.93 (m, 4H). LCMS: 783.1.

Example 28, Compound 28: 4-(((1S,4R,11R,15aR)-11-(8-ethynyl-7-fluoro-3-hydroxynaphthalen-1-yl)-10,12-difluoro-8-(((2R,7aS)-2-fluorotetrahydro-1H-pyrrolizin-7a(5H)-yl)methoxy)-2,3,4,5,13,14,15,15a-octahydro-1H-1,4-epiminoazepino[1',2':1,8]azocino[2,3,4-de]quinazolin-16-yl)methyl)-5-methyl-1,3-dioxol-2-one

28

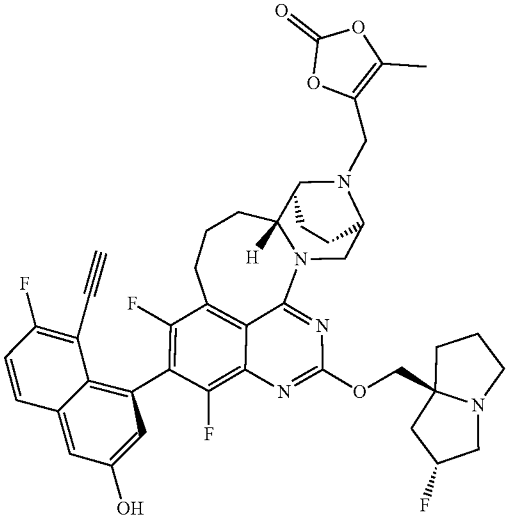

Example 28 was synthesized in a manner similar to Example 18 using Intermediate 28-9 instead of Intermediate 18-3. $^1$H NMR (400 MHz, $CD_3CN$) δ 12.43 (s, 1H), 7.95 (dd, J=9.2, 5.8 Hz, 1H), 7.46 (s, 1H), 7.41 (d, J=9.0 Hz, 1H), 7.24 (d, J=2.6 Hz, 1H), 5.53 (d, J=51.4 Hz, 1H), 5.19 (dd, J=14.7, 2.9 Hz, 1H), 4.72-4.57 (m, 2H), 4.44 (d, J=7.9 Hz, 1H), 4.36-4.21 (m, 1H), 4.23-4.03 (m, 3H), 4.02-3.86 (m, 4H), 3.82-3.58 (m, 2H), 3.45-3.31 (m, 1H), 3.25 (s, 1H), 3.24-2.95 (m, 3H), 2.71-2.49 (m, 2H), 2.46-2.28 (m, 2H), 2.28-2.00 (m, 5H), 1.88-1.80 (m, 1H), 1.75-1.56 (m, 4H). LCMS: 770.3.

Example 28-P, Compound 28-P: (R)-4-((1S,4R,15aR)-10,12-difluoro-8-(((2R,7aS)-2-fluorotetrahydro-1H-pyrrolizin-7a(5H)-yl)methoxy)-2,3,4,5,13,14,15,15a-octahydro-1H-1,4-epiminoazepino[1',2':1,8]azocino[2,3,4-de]quinazolin-11-yl)-5-ethynyl-6-fluoronaphthalen-2-ol

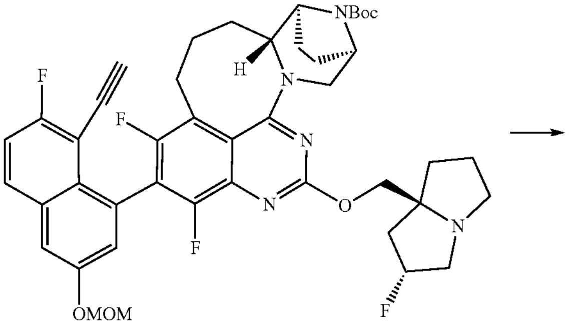

28-7

-continued

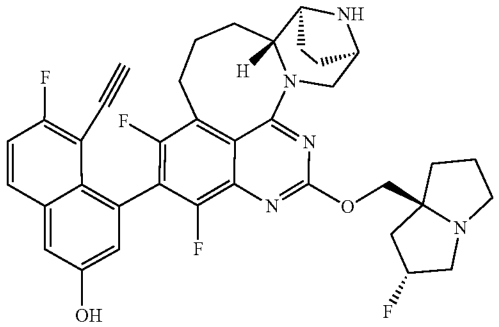

28-P

Example 28-P was synthesized in a manner similar to Example 37-P using Intermediate 28-7 instead of Intermediate 37-8A. $^1$H NMR (400 MHz, MeOD) δ 7.90 (dd, J=9.1, 5.7 Hz, 1H), 7.52-7.31 (m, 2H), 7.14 (d, J=15.8 Hz, 1H), 5.59 (d, J=51.8 Hz, 1H), 5.26 (d, J=14.6 Hz, 1H), 4.82-4.61 (m, 2H), 4.42-3.99 (m, 4H), 4.00-3.85 (m, 3H), 3.66 (d, J=14.4 Hz, 1H), 3.61-3.38 (m, 2H), 3.17 (dt, J=48.7, 12.6 Hz, 3H), 2.89-2.72 (m, 1H), 2.73-2.43 (m, 2H), 2.41-2.26 (m, 1H), 2.26-1.56 (m, 8H). LCMS: 658.3.

Example 29, Compound 29: 4-(((7R,8S,8aS,9S,12R)-5-(8-ethynyl-7-fluoro-3-hydroxynaphthalen-1-yl)-4-fluoro-2-(((2R,7aS)-2-fluorotetrahydro-1H-pyrrolizin-7a(5H)-yl)methoxy)-7,8-dimethyl-7,8,8a,9,10,11,12,13-octahydro-1,3,6,13a,14-pentaaza-9,12-methanonaphtho[1,8-ab]heptalen-14-yl)methyl)-5-methyl-1,3-dioxol-2-one

29

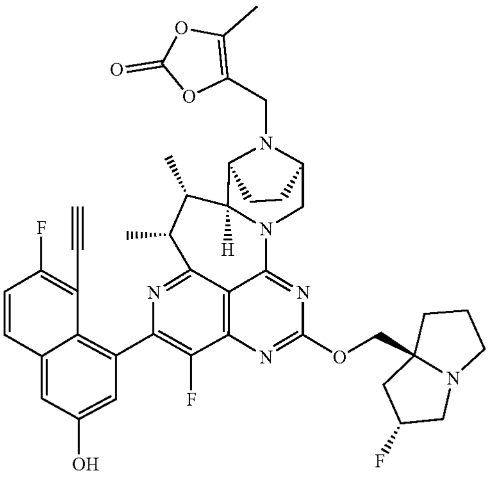

Example 29 was synthesized in a manner similar to Example 42 using Intermediate 29-4 instead of Intermediate 42-5. $^{1}H$ NMR (400 MHz, Acetonitrile-$d_3$) δ 7.95 (ddd, J=8.9, 5.9, 3.0 Hz, 1H), 7.49-7.31 (m, 2.7H), 7.18 (d, J=2.6 Hz, 0.3H), 5.52 (d, J=50.3 Hz, 1H), 5.00 (dt, J=13.7, 1.8 Hz, 1H), 4.77-4.60 (m, 2H), 4.10-3.96 (m, 1H), 3.96-3.63 (m, 7H), 3.55-3.42 (m, 1H), 3.40-3.10 (m, 3H), 3.08-2.89 (m, 1H), 2.65-1.60 (m, 13H), 1.21 (dd, J=6.8, 2.1 Hz, 3H), 1.04-0.82 (m, 3H). LCMS: 767.1.

Example 30, Compound 30: 5-ethynyl-6-fluoro-4-((6aR,7S,10R)-1-fluoro-13-(((2R,7aS)-2-fluorotetrahydro-1H-pyrrolizin-7a(5H)-yl)methoxy)-15-((5-methyl-2-oxo-1,3-dioxol-4-yl)methyl)-5,6,6a,7,8,9,10,11-octahydro-4H-3,11a,12,14,15-pentaaza-7,10-methanocyclohepta[4,5]cycloocta[1,2,3-de]naphthalen-2-yl)naphthalen-2-yl isobutyrate

30

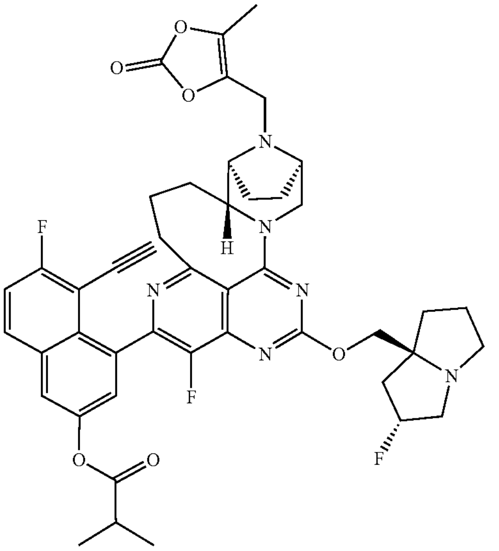

Isopropyl chloroformate solution (1.0 M in toluene, 81.2 μL, 81 μmol) was added via syringe to a stirred solution of Example 8 (80.8 mg, 73.8 μmol) in dichloromethane (1.0 mL) at 0° C. After 3 min, the resulting mixture was warmed to room temperature. After 28 min, acetic acid (42.2 μL, 738 μmol) was added via syringe, and the resulting mixture was concentrated under reduced pressure. The residue was purified by reverse phase preparative HPLC (0.1% trifluoroacetic acid in acetonitrile/water) to give Example 30. $^{1}H$ NMR (400 MHz, Acetonitrile-$d_3$) δ 8.19-8.08 (m, 1H), 8.02-7.94 (m, 1H), 7.67-7.44 (m, 2H), 5.54 (d, J=52.0 Hz, 1H), 5.30 (d, J=14.4 Hz, 1H), 5.06-4.88 (m, 1H), 4.76-4.57 (m, 2H), 4.45-4.33 (m, 1H), 4.17-3.03 (m, 11H), 3.03-1.44 (m, 18H), 1.46-1.33 (m, 6H). LCMS: 839.1.

Example 31, Compound 31: 5-ethynyl-6-fluoro-4-((7R,8S,8aS,9S,12R)-4-fluoro-2-(((2R,7aS)-2-fluorotetrahydro-1H-pyrrolizin-7a(5H)-yl)methoxy)-7,8-dimethyl-14-((5-methyl-2-oxo-1,3-dioxol-4-yl)methyl)-7,8,8a,9,10,11,12,13-octahydro-1,3,6,13a,14-pentaaza-9,12-methanonaphtho[1,8-ab]heptalen-5-yl)naphthalen-2-yl isobutyrate

31

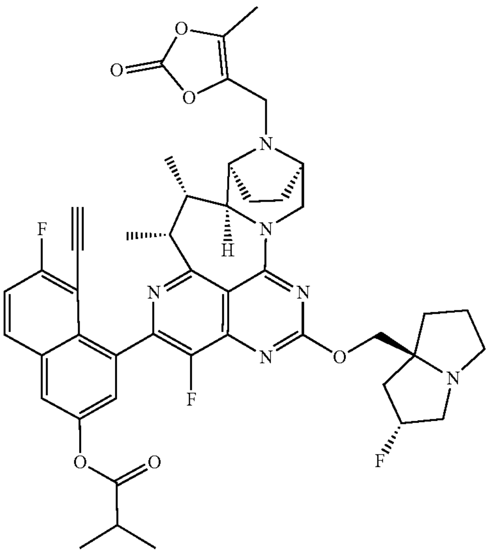

Example 31 was synthesized in a manner similar to Example 30 using Example 29 instead of Example 8. $^{1}H$ NMR (400 MHz, Acetonitrile-$d_3$) δ 8.18-8.09 (m, 1H), 8.02-7.90 (m, 1H), 7.64 (d, J=2.7 Hz, 0.64H), 7.53 (td, J=9.0, 1.7 Hz, 1H), 7.48 (d, J=2.5 Hz, 0.36H), 5.51 (d, J=53.7 Hz, 1H), 5.05-4.93 (m, 1H), 4.93-4.80 (m, 1H), 4.74-4.56 (m, 2H), 3.98-3.18 (m, 11H), 3.14-2.97 (m, 1H), 2.83 (t, J=12.2 Hz, 1H), 2.66-1.46 (m, 13H), 1.39 (d, J=6.3 Hz, 6H), 1.28-1.13 (m, 3H), 0.99-0.83 (m, 3H). LCMS: 853.2.

Example 32, Compound 32: 5-ethynyl-6-fluoro-4-((8S,8aS,9S,12R)-4-fluoro-2-(((S,E)-4-(fluoromethylene)-1,3-dimethylpiperidin-3-yl)methoxy)-8-methyl-7,8,8a,9,10,11,12,13-octahydro-1,3,6,13a,14-pentaaza-9,12-methanonaphtho[1,8-ab]heptalen-5-yl)naphthalen-2-ol

32

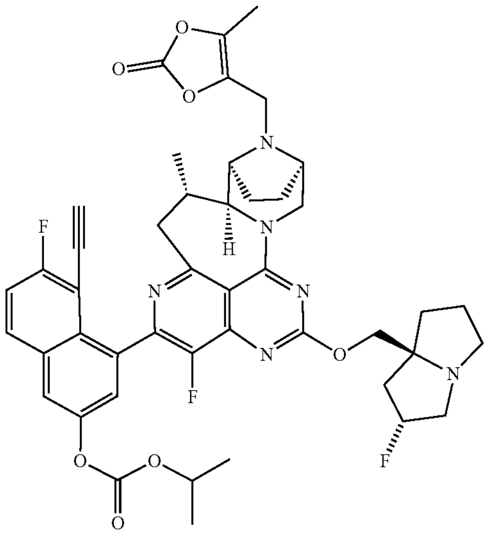

Example 32 was synthesized in a manner similar to Example 31 using Example 7 instead of Example 8. $^{1}$H NMR (400 MHz, Acetonitrile-$d_3$) δ 8.10 (ddd, J=8.1, 5.8, 2.1 Hz, 1H), 7.94 (dd, J=2.6, 1.1 Hz, 1H), 7.59 (d, J=2.5 Hz, 1H), 7.54-7.47 (m, 1H), 5.49 (d, J=51.6 Hz, 1H), 5.02-4.96 (m, 1H), 4.94 (d, J=6.3 Hz, 1H), 4.90 (d, J=13.3 Hz, 1H), 4.69-4.59 (m, 2H), 3.86-3.69 (m, 4H), 3.63 (dd, J=14.9, 7.5 Hz, 3H), 3.38-3.25 (m, 3H), 3.24-3.12 (m, 2H), 3.10-2.97 (m, 1H), 2.97-2.70 (m, 1H), 2.67 (d, J=13.2 Hz, 1H), 2.56 (s, 1H), 2.52-2.41 (m, 1H), 2.41-2.31 (m, 1H), 2.25 (qd, J=12.8, 12.4, 5.0 Hz, 3H), 2.14 (d, J=1.3 Hz, 4H), 1.87-1.73 (m, 2H), 1.36 (dd, J=6.3, 1.4 Hz, 6H), 1.10 (t, J=6.9 Hz, 3H). LCMS: 839.1.

Example 33, Compound 33: 4-(((6aR,7S,10R)-2-(3-amino-8-ethynyl-7-fluoronaphthalen-1-yl)-1-fluoro-13-(((2R,7aS)-2-fluorotetrahydro-1H-pyrrolizin-7a(5H)-yl)methoxy)-5,6,6a,7,8,9,10,11-octahydro-4H-3,11a,12,14,15-pentaaza-7,10-methanocyclohepta[4,5]cycloocta[1,2,3-de]naphthalen-15-yl)methyl)-5-methyl-1,3-dioxol-2-one Example 70, Compound 70: 4-(((5-ethynyl-6-fluoro-4-((6aR,7S,10R)-1-fluoro-13-(((2R,7aS)-2-fluorotetrahydro-1H-pyrrolizin-7a(5H)-yl)methoxy)-15-((5-methyl-2-oxo-1,3-dioxol-4-yl)methyl)-5,6,6a,7,8,9,10,11-octahydro-4H-3,11a,12,14,15-pentaaza-7,10-methanocyclohepta[4,5]cycloocta[1,2,3-de]naphthalen-2-yl)naphthalen-2-yl)amino)methyl)-5-methyl-1,3-dioxol-2-one

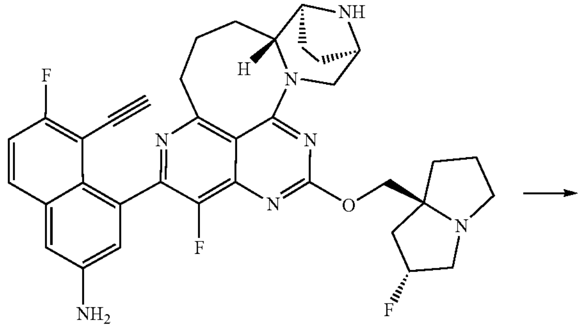

69-P

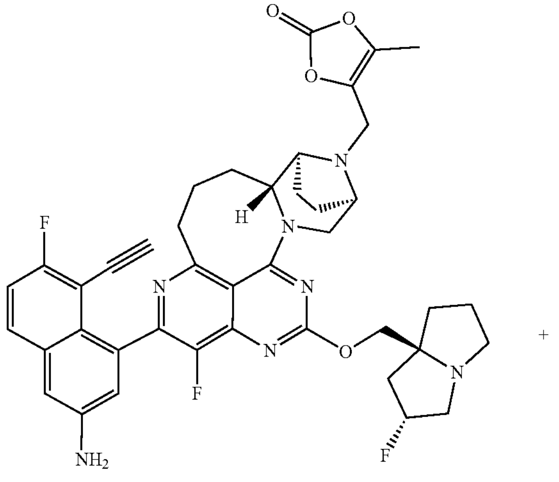

33

-continued

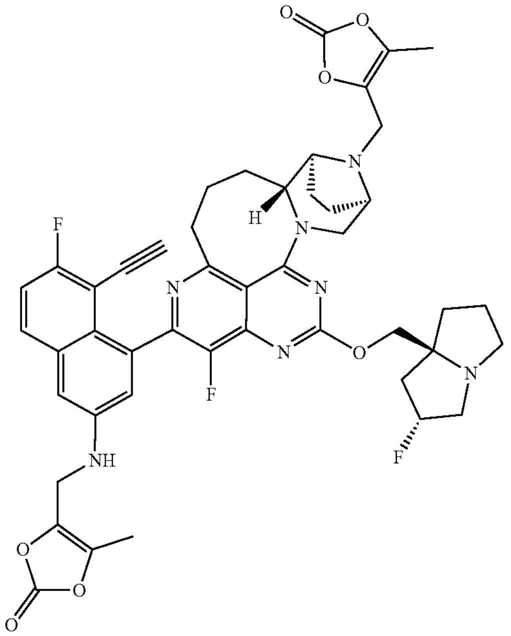

70

Example 33 and Example 70 were synthesized in a manner similar to Example 69 using 4-(bromomethyl)-5-methyl-1,3-dioxol-2-one instead of 4-(bromomethyl)-5-phenyl-1,3-dioxol-2-one and using 0.1% trifluoroacetic acid in acetonitrile/water for reverse phase preparative HPLC instead of 0.1% acetic acid in acetonitrile/water.

Example 33 $^{1}$H NMR (400 MHz, Acetonitrile-$d_3$) δ 7.85-7.70 (m, 1H), 7.28 (td, J=9.1, 2.8 Hz, 1H), 7.21-7.01 (m, 2H), 5.52 (dd, J=51.8, 3.9 Hz, 1H), 5.29 (dd, J=14.7, 3.3 Hz, 1H), 4.71 (dd, J=12.7, 7.5 Hz, 1H), 4.60 (d, J=12.8 Hz, 1H), 4.50 (d, J=7.7 Hz, 1H), 4.41-3.02 (m, 14H), 2.93 (dt, J=12.8, 9.4 Hz, 2H), 2.76-2.47 (m, 2H), 2.37 (d, J=8.0 Hz, 1H), 2.26 (q, J=7.6, 6.7 Hz, 2H), 2.17-1.99 (m, 4H), 1.89-1.52 (m, 4H). LCMS: 752.1.

Example 70 $^{1}$H NMR (400 MHz, DMSO-$d_6$) δ 11.01 (d, J=38.9 Hz, 1H), 7.87 (ddd, J=9.0, 5.9, 3.1 Hz, 1H), 7.42 (td, J=9.1, 2.1 Hz, 1H), 7.16-7.02 (m, 2H), 5.60 (d, J=52.4 Hz, 1H), 5.20 (dd, J=14.8, 3.3 Hz, 1H), 5.07-3.43 (m, 13H), 3.31 (s, 2H), 2.93-2.55 (m, 3H), 2.41-2.29 (m, 3H), 2.26-2.15 (m, 7H), 1.87 (m, 9H). LCMS: 864.6.

Example 34, Compound 34: 4-(((6aR,7S,10R)-2-(3-amino-8-ethynyl-7-fluoronaphthalen-1-yl)-1-fluoro-13-(((2R,7aS)-2-fluorotetrahydro-1H-pyrrolizin-7a(5H)-yl)methoxy)-5,6,6a,7,8,9,10,11-octahydro-4H-3,11a,12,14,15-pentaaza-7,10-methanocyclohepta[4,5]cycloocta[1,2,3-de]naphthalen-15-yl)methyl)-5-ethyl-1,3-dioxol-2-one

34

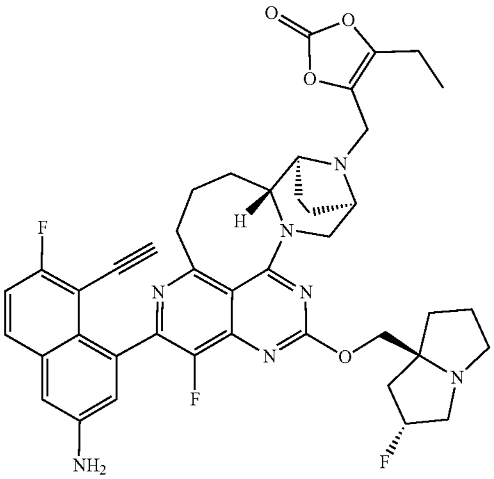

Example 34 was synthesized in a manner similar to Example 69 using 4-(bromomethyl)-5-ethyl-1,3-dioxol-2-one instead of 4-(bromomethyl)-5-phenyl-1,3-dioxol-2-one and using 0.1% trifluoroacetic acid in acetonitrile/water for reverse phase preparative HPLC instead of 0.1% acetic acid in acetonitrile/water. $^{1}H$ NMR (400 MHz, Acetonitrile-$d_3$) δ 7.78 (ddd, J=9.2, 5.9, 3.2 Hz, 1H), 7.27 (td, J=9.1, 2.9 Hz, 1H), 7.18-7.04 (m, 2H), 5.53 (dt, J=51.6, 4.0 Hz, 1H), 5.29 (dt, J=14.7, 3.8 Hz, 1H), 4.72 (dd, J=12.7, 8.0 Hz, 1H), 4.58 (d, J=12.7 Hz, 1H), 4.48 (d, J=8.3 Hz, 1H), 4.33-2.71 (m, 14H), 2.57 (dq, J=15.7, 9.4, 8.5 Hz, 4H), 2.36 (p, J=8.3, 6.9 Hz, 1H), 2.25 (q, J=7.6, 6.8 Hz, 2H), 2.18-2.00 (m, 3H), 1.88-1.73 (m, 2H), 1.72-1.52 (m, 2H), 1.20 (t, J=7.5 Hz, 3H). LCMS: 766.2.

Example 35, Compound 35: 4-(((6aR,7S,10R)-2-(3-amino-8-ethynyl-7-fluoronaphthalen-1-yl)-1-fluoro-13-(((2R,7aS)-2-fluorotetrahydro-1H-pyrrolizin-7a(5H)-yl)methoxy)-5,6,6a,7,8,9,10,11-octahydro-4H-3,11a,12,14,15-pentaaza-7,10-methanocyclohepta[4,5]cycloocta[1,2,3-de]naphthalen-15-yl)methyl)-5-propyl-1,3-dioxol-2-one

35

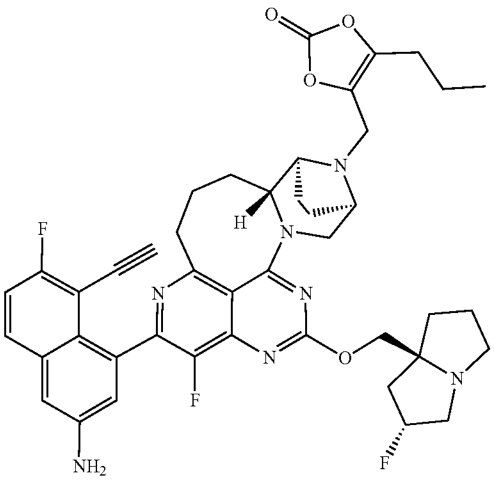

Example 35 was synthesized in a manner similar to Example 69 using 4-(bromomethyl)-5-propyl-1,3-dioxol-2-one instead of 4-(bromomethyl)-5-phenyl-1,3-dioxol-2-one and using 0.1% trifluoroacetic acid in acetonitrile/water for reverse phase preparative HPLC instead of 0.1% acetic acid in acetonitrile/water. $^{1}H$ NMR (400 MHz, Acetonitrile-$d_3$) δ 7.80 (ddd, J=9.2, 5.9, 3.3 Hz, 1H), 7.30 (td, J=9.1, 2.9 Hz, 1H), 7.22-7.03 (m, 2H), 5.55 (dd, J=52.1, 4.2 Hz, 1H), 5.31 (dd, J=14.6, 3.3 Hz, 1H), 4.75 (dd, J=12.7, 7.7 Hz, 1H), 4.61 (d, J=12.7 Hz, 1H), 4.50 (d, J=8.7 Hz, 1H), 4.37-2.65 (m, 14H), 2.63-2.48 (m, 4H), 2.45-2.34 (m, 1H), 2.28 (q, J=7.6, 6.8 Hz, 2H), 2.20-2.05 (m, 3H), 1.90-1.76 (m, 2H), 1.67 (h, J=6.7 Hz, 4H), 1.01 (t, J=7.4 Hz, 3H). LCMS: 780.2.

Example 36, Compound 36: 4-(((6aR,7S,10R)-2-(3-amino-8-ethynyl-7-fluoronaphthalen-1-yl)-1-fluoro-13-(((2R,7aS)-2-fluorotetrahydro-1H-pyrrolizin-7a(5H)-yl)methoxy)-5,6,6a,7,8,9,10,11-octahydro-4H-3,11a,12,14,15-pentaaza-7,10-methanocyclohepta[4,5]cycloocta[1,2,3-de]naphthalen-15-yl)methyl)-5-hexyl-1,3-dioxol-2-one

36

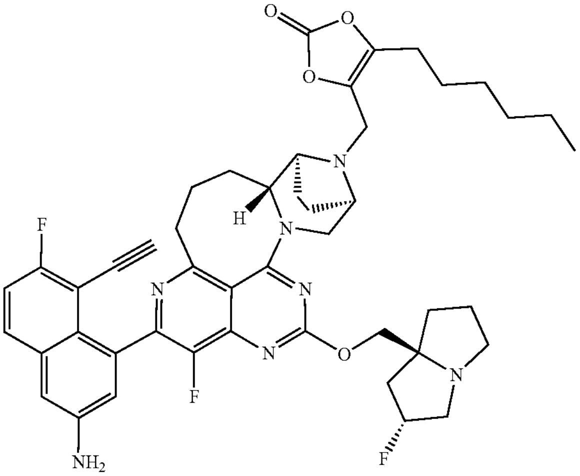

Example 36 was synthesized in a manner similar to Example 69 using 4-(bromomethyl)-5-hexyl-1,3-dioxol-2-one instead of 4-(bromomethyl)-5-phenyl-1,3-dioxol-2-one. $^{1}H$ NMR (400 MHz, Acetonitrile-$d_3$) δ 7.80 (ddd, J=9.2, 5.9, 3.3 Hz, 1H), 7.30 (td, J=9.1, 2.8 Hz, 1H), 7.21-7.06 (m, 2H), 5.56 (dt, J=51.9, 3.8 Hz, 1H), 5.32 (dt, J=14.7, 4.0 Hz, 1H), 4.75 (dd, J=12.7, 8.4 Hz, 1H), 4.61 (d, J=12.6 Hz, 1H), 4.50 (d, J=8.4 Hz, 1H), 4.35-2.64 (m, 14H), 2.61-2.51 (m, 4H), 2.39 (p, J=8.0, 6.7 Hz, 1H), 2.34-2.21 (m, 2H), 2.20-2.02 (m, 3H), 1.91-1.75 (m, 2H), 1.65 (dq, J=22.5, 7.6 Hz, 4H), 1.47-1.26 (m, 6H), 1.05-0.84 (m, 3H). LCMS: 822.5.

Example 37, Compound 37: 4-(((1S,4R,11R,14aR)-11-(8-ethynyl-7-fluoro-3-hydroxynaphthalen-1-yl)-10,12-difluoro-8-(((2R,7aS)-2-fluorotetrahydro-1H-pyrrolizin-7a(5H)-yl)methoxy)-1,2,3,4,5,13,14,14a-octahydro-1,4-epiminoazepino[1',2':1,71azepino[2,3,4-de]quinazolin-15-yl)methyl)-5-methyl-1,3-dioxol-2-one

37

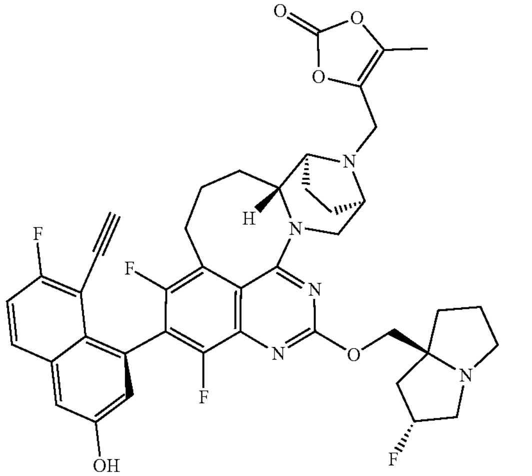

Example 37 was synthesized in a manner similar to Example 18 using Intermediate 37-10 instead of Intermediate 18-3. $^1$H NMR (400 MHz, $CD_3CN$) δ 12.71 (s, 1H), 7.94 (dd, J=9.2, 5.9 Hz, 1H), 7.46 (d, J=2.6 Hz, 1H), 7.39 (t, J=9.1 Hz, 1H), 7.25 (d, J=2.6 Hz, 1H), 5.63-5.39 (m, 2H), 4.68-4.54 (m, 3H), 4.40-4.23 (m, 1H), 4.20-3.92 (m, 3H), 3.96-3.62 (m, 4H), 3.54 (dd, J=16.2, 8.0 Hz, 1H), 3.38-3.30 (m, 1H), 3.29 (s, 1H), 2.83 (dd, J=16.4, 11.2 Hz, 1H), 2.67-2.47 (m, 4H), 2.39 (q, J=8.3 Hz, 2H), 2.31-2.22 (m, 2H), 2.20 (s, 5H), 2.10-1.99 (m, 1H), 1.92-1.75 (m, 1H). LCMS: 756.3.

Example 37-P, Compound 37-P: 4-((1S,4R,11R,14aR)-10,12-difluoro-8-(((2R,7aS)-2-fluorotetrahydro-1H-pyrrolizin-7a(5H)-yl)methoxy)-1,2,3,4,5,13,14,14a-octahydro-1,4-epiminoazepino[1',2':1,7]azepino[2,3,4-de]quinazolin-11-yl)-5-ethynyl-6-fluoronaphthalen-2-ol

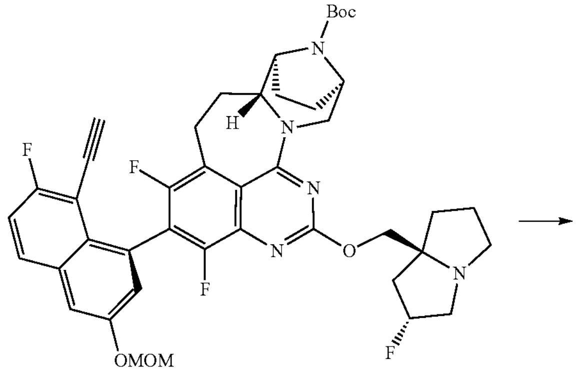

37-8A

-continued

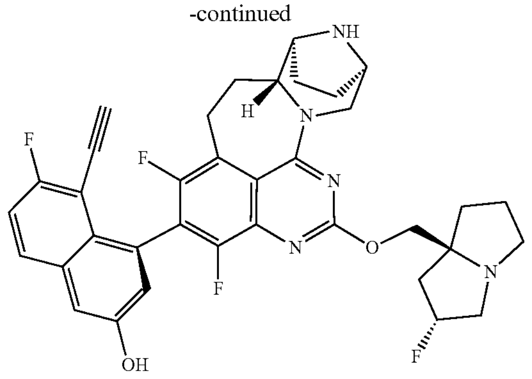

37-P

Intermediate 37-8A (30 mg, 0.038 mmol) was dissolved in 1 ml of acetonitrile and cooled to 0° C. To it was added 1 mL of HCl solution (4 N in dioxane.). The reaction mixture was stirred at 0° C. for one hour. Upon completion, concentrated to dryness and the residue was purified by RP-HPLC (5% to 60% 0.1% TFA in MeCN/0.1% TFA in $H_2O$). Fractions containing the product were pooled and lyophilized to yield Example 37-P. $^1$H NMR (400 MHz, MeOD) δ 7.89 (dd, J=9.2, 5.7 Hz, 1H), 7.40-7.31 (m, 2H), 7.12 (d, J=2.5 Hz, 1H), 5.69-5.47 (m, 2H), 4.68 (q, J=12.7 Hz, 2H), 4.34 (dd, J=12.2, 4.4 Hz, 2H), 4.11-4.00 (m, 2H), 4.00-3.73 (m, 3H), 3.65 (dd, J=16.3, 7.8 Hz, 1H), 3.56-3.42 (m, 3H), 3.02-2.90 (m, 1H), 2.52-2.39 (m, 2H), 2.40-2.28 (m, 2H), 2.06 (d, J=9.4 Hz, 3H), 2.02-1.91 (m, 1H), 2.82-2.52 (m, 3H). LCMS: 644.3.

Example 38, Compound 38: 4-(((6aR,7S,10R)-2-(8-ethynyl-7-fluoro-3-hydroxynaphthalen-1-yl)-1-fluoro-13-(((3S,7aS)-3-(((1,1,1,3,3,3-hexafluoro-2-(trifluoromethyl)propan-2-yl)oxy)methyl)tetrahydro-1H-pyrrolizin-7a(5H)-yl)methoxy)-5,6,6a,7,8,9,10,11-octahydro-4H-3,11a,12,14,15-pentaaza-7,10-methanocyclohepta[4,5]cycloocta[1,2,3-de]naphthalen-15-yl)methyl)-5-methyl-1,3-dioxol-2-one

38

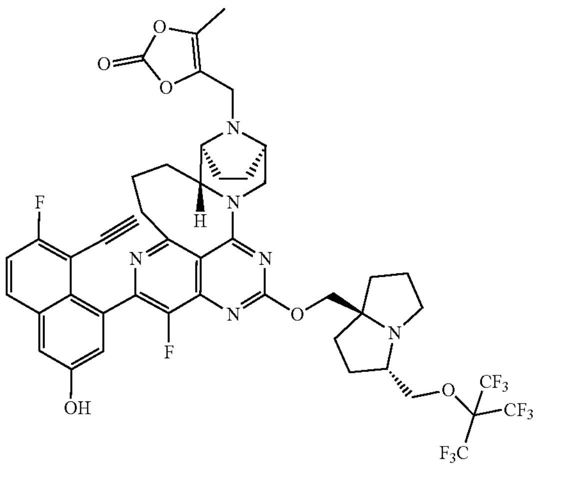

Example 38 was synthesized in a manner similar to Example 42 using Comparative Intermediate 161-2 of U.S.

application Ser. No. 18/303,813, published as US 2023/0374036 instead of Intermediate 42-7 and using Comparative Intermediate 63-4 of U.S. application Ser. No. 18/303,813, published as US 2023/0374036 instead of ((2R,7aS)-2-fluorotetrahydro-1H-pyrrolizin-7a(5H)-yl)methanol. $^1$H NMR (400 MHz, Acetonitrile-$d_3$) δ 8.04-7.82 (m, 1H), 7.46-7.35 (m, 2H), 7.28 (d, J=2.6 Hz, 0.62H), 7.22 (s, 0.38H), 5.41-5.21 (m, 1H), 4.78-4.56 (m, 2H), 4.56-4.32 (m, 3H), 4.25-4.09 (m, 1H), 4.13-2.84 (m, 10H), 2.77-1.14 (m, 19H). LCMS: 983.3.

Example 39, Compound 39: 5-ethynyl-6-fluoro-4-((6aR,7S,10R)-1-fluoro-13-(((2R,7aS)-2-fluorotetrahydro-1H-pyrrolizin-7a(5H)-yl)methoxy)-15-((5-methyl-2-oxo-1,3-dioxol-4-yl)methyl)-5,6,6a,7,8,9,10,11-octahydro-4H-3,11a,12,14,15-pentaaza-7,10-methanocyclohepta[4,5]cycloocta[1,2,3-de]naphthalen-2-yl)naphthalen-2-yl ((S)-3-methylbutan-2-yl) carbonate

39

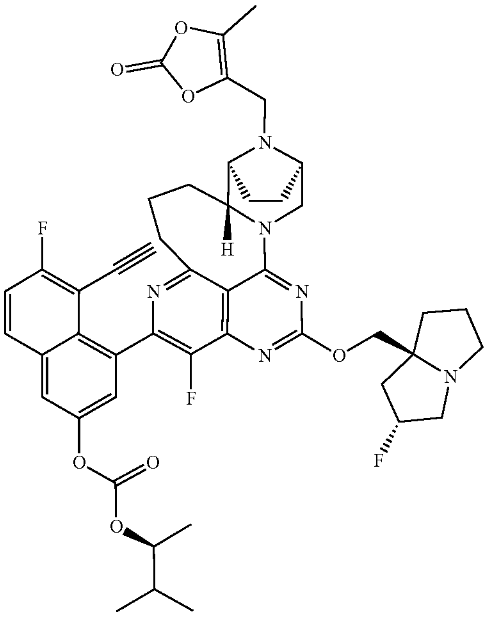

Triethylamine (111 μL, 797 μmol) was added via syringe to a stirred mixture of Example 8 (100 mg, 133 μmol), Intermediate 39-2 (47.4 mg, 146 μmol), and dichloromethane (1.0 mL) at 0° C. After 3 min, the resulting mixture was warmed to room temperature. After 85 min, acetic acid (76.0 μL, 1.33 mmol) was added via syringe, and the resulting mixture was concentrated under reduced pressure. The residue was purified by reverse phase preparative HPLC (0.1% trifluoroacetic acid in acetonitrile/water) to give Example 39. $^1$H NMR (400 MHz, Acetone-$d_6$) δ 8.26-8.16 (m, 1H), 8.04 (d, J=2.6 Hz, 1H), 7.66-7.50 (m, 2H), 5.70 (d, J=52.2 Hz, 1H), 5.46-5.23 (m, 1H), 5.08-4.85 (m, 1H), 4.83-4.55 (m, 3H), 4.46-3.77 (m, 9H), 3.72 (s, 1H), 3.67-1.55 (m, 17H), 2.24 (s, 3H), 1.31 (d, J=6.4 Hz, 3H), 1.05-0.85 (m, 6H). LCMS: 867.2.

Example 40, Compound 40: 4-ethyl-5-(((6aR,7S,10R)-2-(8-ethynyl-7-fluoro-3-hydroxynaphthalen-1-yl)-1-fluoro-13-(((2R,7aS)-2-fluorotetrahydro-1H-pyrrolizin-7a(5H)-yl)methoxy)-5,6,6a,7,8,9,10,11-octahydro-4H-3,11a,12,14,15-pentaaza-7,10-methanocyclohepta[4,5]cycloocta[1,2,3-de]naphthalen-15-yl)methyl)-1,3-dioxol-2-one

40

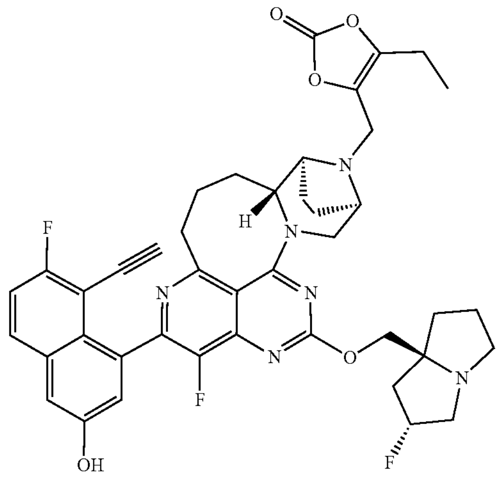

Example 40 was synthesized in a manner similar to Example 11 using Intermediate 40-1 instead of Intermediate 11-6 and using 0.1% trifluoroacetic acid in acetonitrile/water for reverse phase preparative HPLC instead of 0.1% acetic acid in acetonitrile/water. $^1$H NMR (400 MHz, Acetonitrile-$d_3$) δ 7.90 (ddd, J=9.4, 5.9, 3.5 Hz, 1H), 7.44-7.16 (m, 3H), 5.53 (d, J=52.1 Hz, 1H), 5.33-5.22 (m, 1H), 4.74 (dd, J=15.9, 12.4 Hz, 1H), 4.61-4.50 (m, 1H), 4.43 (d, J=9.1 Hz, 1H), 4.18 (s, 1H), 3.99 (s, 2H), 3.93-3.73 (m, 4H), 3.73-3.58 (m, 2H), 3.44-2.43 (m, 7H), 2.36 (d, J=5.2 Hz, 2H), 2.31-2.19 (m, 3H), 2.17-2.03 (m, 3H), 1.88-1.71 (m, 2H), 1.66 (d, J=10.9 Hz, 2H), 1.19 (t, J=7.4 Hz, 3H). LCMS: 767.4.

Example 41, Compound 41: 4-(((6aR,7S,10R)-2-(8-ethynyl-7-fluoro-3-hydroxynaphthalen-1-yl)-1-fluoro-13-(((2R,7aS)-2-fluorotetrahydro-1H-pyrrolizin-7a(5H)-yl)methoxy)-5,6,6a,7,8,9,10,11-octahydro-4H-3,11a,12,14,15-pentaaza-7,10-methanocyclohepta[4,5]cycloocta[1,2,3-de]naphthalen-15-yl)methyl)-5-propyl-1,3-dioxol-2-one

41

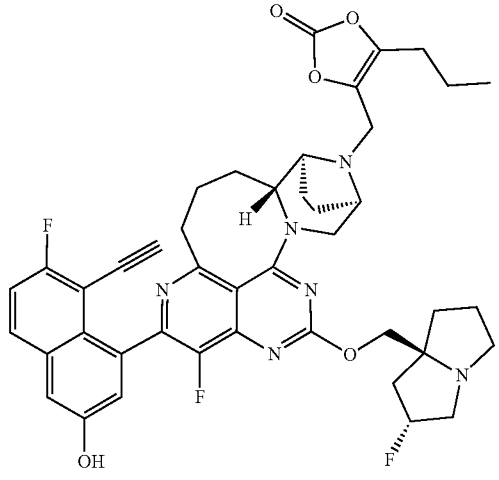

Example 41 was synthesized in a manner similar to Example 11 using Intermediate 41-1 instead of Intermediate 11-6 and using 0.1% trifluoroacetic acid in acetonitrile/water for reverse phase preparative HPLC instead of 0.1% acetic acid in acetonitrile/water. $^1$H NMR (400 MHz, Methanol-$d_4$) δ 7.89 (ddd, J=9.3, 5.6, 3.6 Hz, 1H), 7.44-7.29 (m, 2H), 7.21 (dd, J=8.7, 2.5 Hz, 1H), 5.59 (d, J=51.6 Hz, 1H), 5.49-5.38 (m, 1H), 4.79-4.68 (m, 2H), 4.25 (dd, J=15.1, 9.2 Hz, 4H), 4.10-3.98 (m, 1H), 3.98-3.85 (m, 3H), 3.75 (d, J=14.4 Hz, 1H), 3.52-3.35 (m, 2H), 2.97 (p, J=13.6, 12.6 Hz, 2H), 2.84-2.53 (m, 4H), 2.53-2.41 (m, 1H), 2.36 (td, J=12.1, 10.1, 4.3 Hz, 2H), 2.14 (d, J=43.4 Hz, 4H), 1.99-1.62 (m, 6H), 1.04 (td, J=7.4, 1.4 Hz, 3H). LCMS: 781.5.

Example 42, Compound 42: 4-(((3aS,3bS,4S,7R,14bR)-13-(8-ethynyl-7-fluoro-3-hydroxynaphthalen-1-yl)-12-fluoro-10-(((2R,7aS)-2-fluorotetrahydro-1H-pyrrolizin-7a(5H)-yl)methoxy)-2,3,3a,3b,4,5,6,7,8,14b-decahydro-1H-8a,9,11,14,15-pentaaza-4,7-methanocyclopenta[d]naphtho[1,8-ab]heptalen-15-yl)methyl)-5-methyl-1,3-dioxol-2-one

42

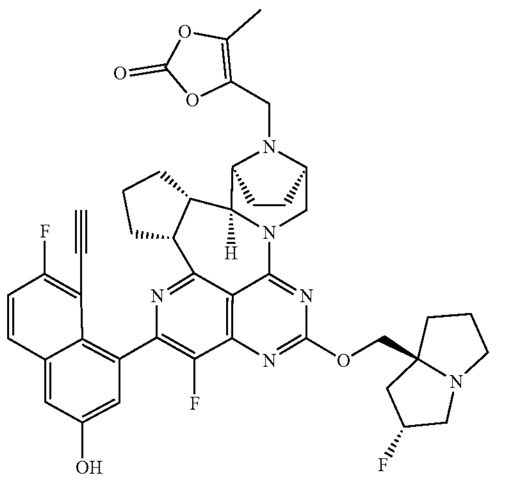

Example 42 was synthesized in a manner similar to Example 11 using Intermediate 42-9 instead of Intermediate 11-6. $^1$H NMR (400 MHz, Acetonitrile-$d_3$) δ 8.00-7.88 (m, 1H), 7.48-7.29 (m, 2.64H), 7.20-7.11 (m, 0.36H), 5.50 (d, J=51.9 Hz, 1H), 4.86 (d, J=12.5 Hz, 1H), 4.74-4.56 (m, 2H), 3.95-3.15 (m, 13H), 2.79-1.14 (m, 19H). LCMS: 779.1.

Example 42-P, Compound 42-P: 5-ethynyl-6-fluoro-4-((3aS,3bS,4S,7R,14bR)-12-fluoro-10-(((2R,7aS)-2-fluorotetrahydro-1H-pyrrolizin-7a(5H)-yl)methoxy)-2,3,3a,3b,4,5,6,7,8,14b-decahydro-1H-8a,9,11,14,15-pentaaza-4,7-methanocyclopenta[d]naphtho[1,8-ab]heptalen-13-yl)naphthalen-2-ol

42-P

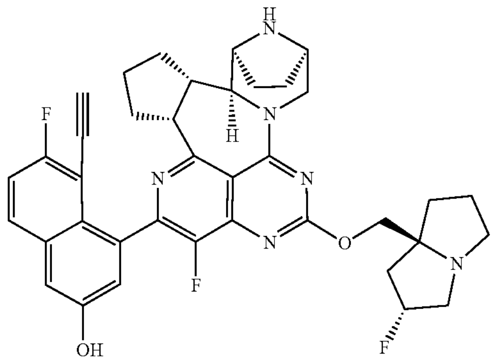

Example 42-P was synthesized in a manner similar to Example 11-P using Intermediate 42-8 instead of Intermediate 11-4. $^1$H NMR (400 MHz, Methanol-$d_4$) δ 7.88-7.80 (m, 1H), 7.31 (dd, J=5.8, 2.8 Hz, 2H), 7.28 (d, J=2.4 Hz, 0.67H), 7.09 (d, J=2.5 Hz, 0.33H), 5.39 (d, J=53.2 Hz, 1H), 5.01-4.71 (m, 1H), 4.52-4.38 (m, 1H), 4.33-4.21 (m, 1H), 3.77-3.68 (m, 1H), 3.64-3.02 (m, 7H), 2.89-2.72 (m, 1H), 2.58-0.99 (m, 18H), 1.95 (s, 3H). LCMS: 667.1.

Example 51, Compound 51: 5-ethynyl-6-fluoro-4-((5S,5aS,6S,9R)-1-fluoro-12-(((2R,7aS)-2-fluorotetrahydro-1H-pyrrolizin-7a(5H)-yl)methoxy)-5-methyl-14-((5-methyl-2-oxo-1,3-dioxol-4-yl)methyl)-4,5,5a,6,7,8,9,10-octahydro-3,10a,11,13,14-pentaaza-6,9-methanonaphtho[1,8-ab]heptalen-2-yl)naphthalen-2-yl dimethylcarbamate

51

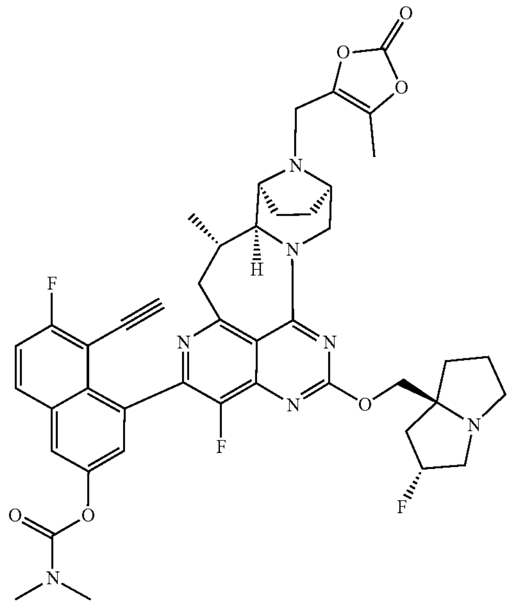

Example 51 was synthesized in a manner similar to Example 2 using Intermediate 51-2 instead of Intermediate 2-3. $^1$H NMR (400 MHz, Methanol-$d_4$) δ 8.12 (dd, J=9.2, 5.7 Hz, 1H), 7.93 (t, J=2.3 Hz, 1H), 7.59-7.45 (m, 2H), 5.60 (d, J=51.7 Hz, 1H), 5.04-4.94 (m, 1H), 4.82-4.55 (m, 2H), 4.14-3.43 (m, 9H), 3.20 (d, J=1.8 Hz, 3H), 3.04 (d, J=1.2 Hz, 3H), 2.88-1.57 (m, 10H), 1.21-1.10 (m, 3H). LCMS 824.2.

Example 67, Compound 67: 4-(tert-butyl)-5-(((5-ethynyl-6-fluoro-4-((5S,5aS,6S,9R)-1-fluoro-12-(((2R,7aS)-2-fluorotetrahydro-1H-pyrrolizin-7a(5H)-yl)methoxy)-5-methyl-4,5,5a,6,7,8,9,10-octahydro-3,10a,11,13,14-pentaaza-6,9-methanonaphtho[1,8-ab]heptalen-2-yl)naphthalen-2-yl)oxy)methyl)-1,3-dioxol-2-one

67

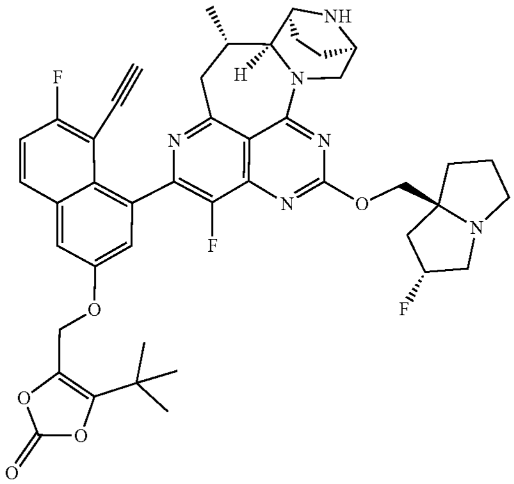

To a vigorously stirred solution of Intermediate 67-1 (27 mg, 0.03 mmol) in anhydrous DCM (0.6 mL), 2,6-lutidine (5.17 mg, 0.048 mmol) and TMSOTf (10.1 mg, 0.045 mmol) were added sequentially at 0° C. under $N_2$ atmosphere. The resulting solution was stirred at 0° C. for 0.5 hour. The reaction was quenched by water (0.1 mL) and concentrated. The residue was purified by RP-HPLC (5% to 70% 0.1% TFA in MeCN/0.1% TFA in $H_2O$). Fractions containing the product were pooled and lyophilized to yield the title compound. $^1$H NMR (400 MHz, $CD_3CN$): δ 8.10-7.99 (m, 1H), 7.65 (d, J=2.7 Hz, 1H), 7.54-7.38 (m, 2H), 5.53 (d, J=51.8 Hz, 1H), 5.16-4.99 (m, 3H), 4.75-4.61 (m, 2H), 4.43-4.15 (m, 2H), 4.03-3.59 (m, 5H), 3.48-3.09 (m, 5H), 2.77 (dd, J=19.7, 13.3 Hz, 1H), 2.71-2.45 (m, 2H), 2.45-2.34 (m, 1H), 2.35-2.15 (m, 4H), 2.06 (d, J=21.5 Hz, 1H), 1.94-1.76 (m, 1H), 1.32 (s, 9H), 1.18 (dd, J=8.4, 6.0 Hz, 3H). LCMS (m/z): 795.4.

Example 68, Compound 68: 4-(((8aR,9S,12R)-5-(8-ethynyl-7-fluoro-3-hydroxynaphthalen-1-yl)-4-fluoro-2-(((3S,7aS)-3-(((1,1,1,3,3,3-hexafluoro-2-(trifluoromethyl)propan-2-yl)oxy)methyl)tetrahydro-1H-pyrrolizin-7a(5H)-yl)methoxy)-7,8,8a,9,10,11,12,13-octahydro-1,3,6,13a,14-pentaaza-9,12-methanonaphtho[1,8-ab]heptalen-14-yl)methyl)-5-methyl-1,3-dioxol-2-one

68

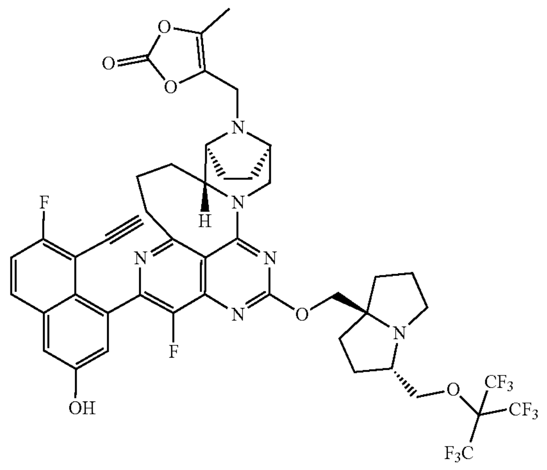

Example 68 was synthesized in a manner similar to Example 38 using Comparative Intermediate 63-7 of U.S. application Ser. No. 18/303,813, published as US 2023/0374036 instead of Comparative Intermediate 161-2 of U.S. application Ser. No. 18/303,813, published as US 2023/0374036. $^1$H NMR (400 MHz, Acetonitrile-$d_3$) δ 7.91 (ddd, J=9.0, 6.0, 3.0 Hz, 1H), 7.40 (t, J=3.0 Hz, 1H), 7.35 (td, J=9.0, 4.9 Hz, 1H), 7.22 (t, J=2.6 Hz, 1H), 5.60 (ddd, J=26.7, 14.4, 3.2 Hz, 1H), 4.65-4.51 (m, 2H), 4.51-4.29 (m, 1H), 4.28-3.88 (m, 3H), 3.78-3.42 (m, 2H), 3.41-3.03 (m, 4H), 2.94-2.33 (m, 9H), 2.31-2.07 (m, 7H), 1.61-1.18 (m, 5H). LCMS: 968.9.

Example 69, Compound 69: 4-(((6aR,7S,10R)-2-(3-amino-8-ethynyl-7-fluoronaphthalen-1-yl)-1-fluoro-13-(((2R,7aS)-2-fluorotetrahydro-1H-pyrrolizin-7a(5H)-yl)methoxy)-5,6,6a,7,8,9,10,11-octahydro-4H-3,11a,12,14,15-pentaaza-7,10-methanocyclohepta[4,5]cycloocta[1,2,3-de]naphthalen-15-yl)methyl)-5-phenyl-1,3-dioxol-2-one

69

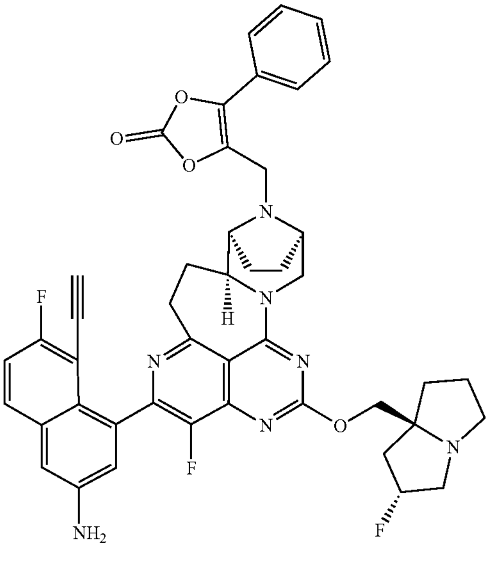

4-(Bromomethyl)-5-phenyl-1,3-dioxol-2-one (28.2 mg, 110 μmol) was added to a vigorously stirred mixture of Example 69-P (67.3 mg, 105 μmol), 2,6-lutidine (18.4 μL, 158 μmol), and acetonitrile (0.40 mL) at room temperature. After 110 min, the resulting mixture was purified by reverse phase preparative HPLC (0.1% trifluoroacetic acid in acetonitrile/water) to give Example 69. $^1H$ NMR (400 MHz, Acetonitrile-$d_3$) δ 7.82-7.67 (m, 3H), 7.59-7.49 (m, 3H), 7.32-7.24 (m, 1H), 7.16 (d, J=2.3 Hz, 1H), 7.09 (d, J=2.4 Hz, 0.67H), 7.05 (s, 0.33H), 5.50 (d, J=51.5 Hz, 1H), 5.26 (d, J=14.2 Hz, 1H), 4.75-4.50 (m, 2H), 4.28 (d, J=9.3 Hz, 1H), 4.15-3.95 (m, 3H), 3.94-3.59 (m, 4H), 3.39-3.24 (m, 2H), 3.21 (s, 0.67H), 3.07 (s, 0.33H), 3.02-1.31 (m, 16H). LCMS: 814.2.

Example 69-P, Compound 69-P: 5-ethynyl-6-fluoro-4-((6aR,7S,10R)-1-fluoro-13-(((2R,7aS)-2-fluorotetrahydro-1H-pyrrolizin-7a(5H)-yl)methoxy)-5,6,6a,7,8,9,10,11-octahydro-4H-3,11a,12,14,15-pentaaza-7,10-methanocyclohepta[4,5]cycloocta[1,2,3-de]naphthalen-2-yl)naphthalen-2-amine

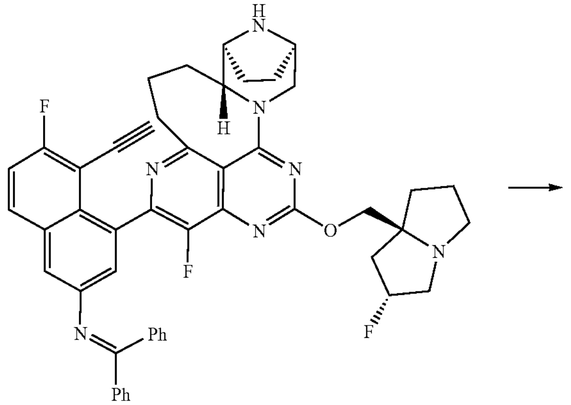

80-2

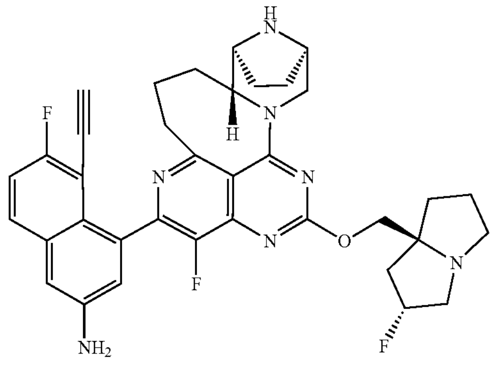

69-P

Hydroxylamine hydrochloride (89.6 mg, 1.29 mmol) was added to a vigorously stirred mixture of Intermediate 80-2 (69.1 mg, 86.0 μmol), sodium acetate (105.8 mg, 1.29 mmol), and methanol (1.2 mL) at room temperature. After 30 min, the resulting mixture was purified by reverse phase preparative HPLC (0.1% trifluoroacetic acid in acetonitrile/water) to give Example 69-P. $^1H$ NMR (400 MHz, Methanol-$d_4$) δ 7.91-7.82 (m, 1H), 7.46-7.27 (m, 2H), 7.24 (d, J=2.4 Hz, 0.67H), 7.21 (s, 0.33H), 5.61 (d, J=51.6 Hz, 1H), 5.50-5.32 (m, 1H), 4.82-4.68 (m, 2H), 4.42-4.21 (m, 1H), 4.17 (d, J=9.1 Hz, 1H), 4.14-3.84 (m, 5H), 3.68 (d, J=14.9 Hz, 1H), 3.57-3.17 (m, 3H), 3.10-1.64 (m, 14H). LCMS: 640.1.

Example 71-P, Compound 71-P: 2-amino-4-((1S,4R,11R,14S,14aS)-12-chloro-10-fluoro-8-(((2R,7aS)-2-fluorotetrahydro-1H-pyrrolizin-7a(5H)-yl)methoxy)-14-methyl-1,2,3,4,5,13,14,14a-octahydro-1,4-epiminoazepino[1',2':1,7]azepino[2,3,4-de]quinazolin-11-yl)-7-fluorobenzo[b]thiophene-3-carbonitrile

71-P

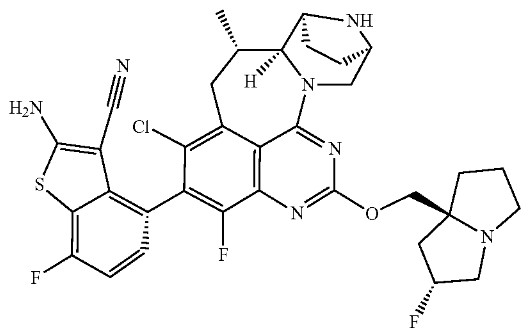

Example 71-P was synthesized in manner similar to Intermediate 37-8 using Intermediate 71-5 instead of Intermediate 37-7. $^1H$ NMR (400 MHz, Methanol-$d_4$) δ 7.19 (dd, J=8.4, 5.0 Hz, 1H), 7.12-7.00 (m, 1H), 5.58 (d, J=51.7 Hz, 1H), 5.15 (d, J=14.3 Hz, 1H), 4.68 (dd, J=76.5, 12.6 Hz, 2H), 4.32 (dd, J=26.1, 5.5 Hz, 2H), 4.13-3.73 (m, 4H), 3.47 (dd, J=12.3, 5.8 Hz, 2H), 3.23-1.80 (m, 13H), 1.28 (d, J=6.5 Hz, 3H). LCMS 680.0.

Example 71, Compound 71: 2-amino-4-((1S,4R,11R,14S,14aS)-12-chloro-10-fluoro-8-(((2R,7aS)-2-fluorotetrahydro-1H-pyrrolizin-7a(5H)-yl)methoxy)-14-methyl-15-((5-methyl-2-oxo-1,3-dioxol-4-yl)methyl)-1,2,3,4,5,13,14,14a-octahydro-1,4-epiminoazepino[1',2':1,7]azepino[2,3,4-de]quinazolin-11-yl)-7-fluorobenzo[b]thiophene-3-carbonitrile Example 71

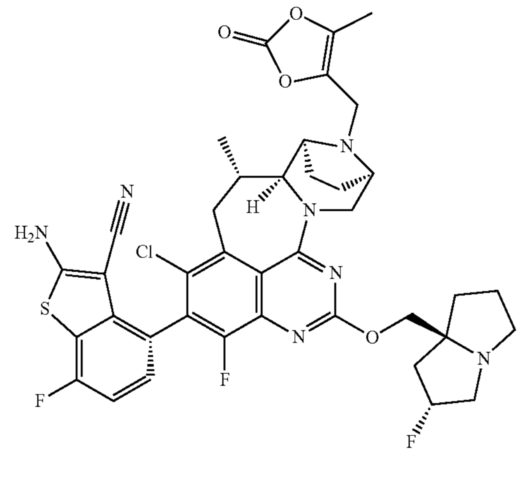

Example 71 was synthesized in a manner similar to Example 2 using Intermediate 71-P instead of Intermediate 2-3. $^1$H NMR (400 MHz, Methanol-$d_4$) δ 7.20 (dd, J=8.4, 5.0 Hz, 1H), 7.06 (dd, J=9.4, 8.4 Hz, 1H), 5.58 (d, J=51.8 Hz, 1H), 4.64 (dd, J=80.4, 12.6 Hz, 2H), 4.13-3.41 (m, 11H), 3.21-1.68 (m, 17H), 1.58-1.46 (m, 1H), 1.15 (d, J=6.4 Hz, 3H). LCMS 792.0.

Example 72, Compound 72: 4-(((6aR,7S,10R)-2-(8-ethynyl-7-fluoro-3-hydroxynaphthalen-1-yl)-1-fluoro-13-(((2R,7aS)-2-fluorotetrahydro-1H-pyrrolizin-7a(5H)-yl)methoxy)-5,6,6a,7,8,9,10,11-octahydro-4H-3,11a,12,14,15-pentaaza-7,10-methanocyclohepta[4,5]cycloocta[1,2,3-de]naphthalen-15-yl)methyl)-5-phenyl-1,3-dioxol-2-one

72

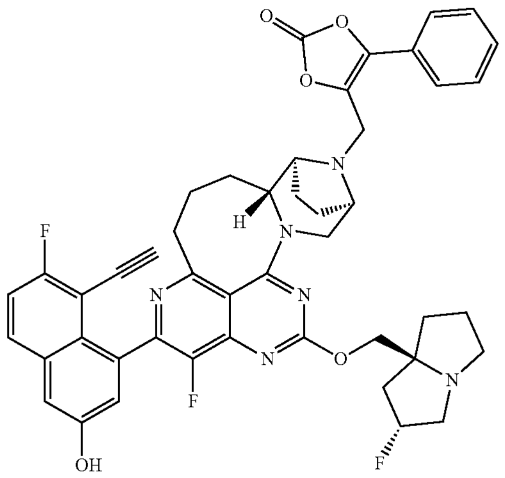

Example 72 was synthesized in a manner similar to Example 11 using Intermediate 72-1 instead of Intermediate 11-6 and using 0.1% trifluoroacetic acid in acetonitrile/water for reverse phase preparative HPLC instead of 0.1% acetic acid in acetonitrile/water. $^1$H NMR (400 MHz, Acetonitrile-$d_3$) δ 7.91 (ddd, J=8.9, 5.9, 3.0 Hz, 1H), 7.70 (dt, J=7.6, 3.4 Hz, 2H), 7.58-7.49 (m, 3H), 7.43-7.30 (m, 2H), 7.24 (dd, J=14.9, 2.6 Hz, 1H), 5.60-5.40 (m, 1H), 5.29 (dd, J=14.7, 3.1 Hz, 1H), 4.74-3.47 (m, 13H), 3.39-3.08 (m, 3H), 2.98-2.75 (m, 2H), 2.71-2.45 (m, 2H), 2.35 (q, J=9.2, 8.7 Hz, 1H), 2.26 (ddd, J=15.6, 9.2, 6.5 Hz, 2H), 2.15-2.00 (m, 1H), 1.78 (qt, J=5.5, 2.2 Hz, 2H), 1.60 (q, J=16.1, 13.7 Hz, 3H). LCMS: 815.3.

Example 73-P, Compound 73-P: (S)-1-((1S,4R,15aR)-10,12-difluoro-8-(((2R,7aS)-2-fluorotetrahydro-1H-pyrrolizin-7a(5H)-yl)methoxy)-2,3,4,5,13,14,15,15a-octahydro-1H-1,4-epiminoazepino[1',2':1,8]azocino[2,3,4-de]quinazolin-11-yl)-8-ethynyl-7-fluoroisoquinolin-3-amine

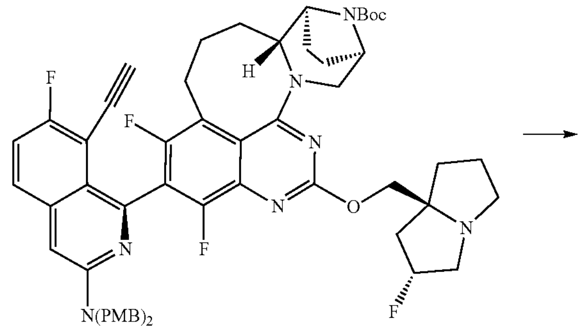

73-P-6A

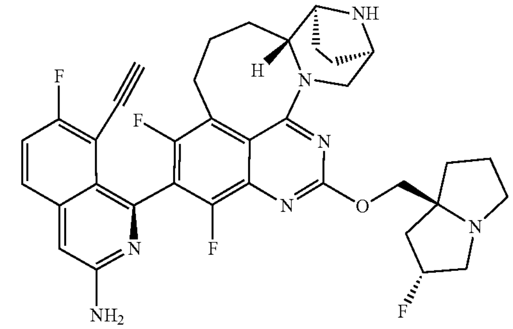

73-P

Intermediate 73-P-6A (133 mg, 0.133 mmol) was dissolved in TFA (1 mL) and stirred at 50° C. for 0.5 hour. Upon completion, cooled to room temperature, diluted it with toluene and concentrated to dryness. The residue was purified by RP-HPLC (5% to 60% 0.1% TFA in MeCN/0.1% TFA in $H_2O$). Fractions containing the product were pooled and lyophilized to yield Example 73-P. $^1$H NMR (400 MHz, MeOD) δ 7.81 (dd, J=9.3, 5.5 Hz, 1H), 7.47 (t, J=9.0 Hz, 1H), 7.07 (s, 1H), 5.69-5.50 (m, 1H), 5.27 (d, J=14.7 Hz, 1H), 4.81-4.61 (m, 2H), 4.46-4.16 (m, 1H), 4.17-3.79 (m, 5H), 3.68 (d, J=14.6 Hz, 1H), 3.61 (s, 1H), 3.57-3.44 (m, 1H), 3.31-3.21 (m, 1H), 3.11 (q, J=11.3 Hz, 2H), 2.77 (dd, J=15.4, 4.6 Hz, 1H), 2.74-2.55 (m, 2H), 2.48 (d, J=12.7 Hz, 1H), 2.41-2.14 (m, 3H), 2.15-1.94 (m, 2H), 1.91-1.62 (m, 4H). LCMS: 658.3.

Example 73, Compound 73: 4-(((1S,4R,11S,15aR)-11-(3-amino-8-ethynyl-7-fluoroisoquinolin-1-yl)-10,12-difluoro-8-(((2R,7aS)-2-fluorotetrahydro-1H-pyrrolizin-7a(5H)-yl)methoxy)-2,3,4,5,13,14,15,15a-octahydro-1H-1,4-epiminoazepino[1',2':1,8]azocino[2,3,4-de]quinazolin-16-yl)methyl)-5-methyl-1,3-dioxol-2-one

73

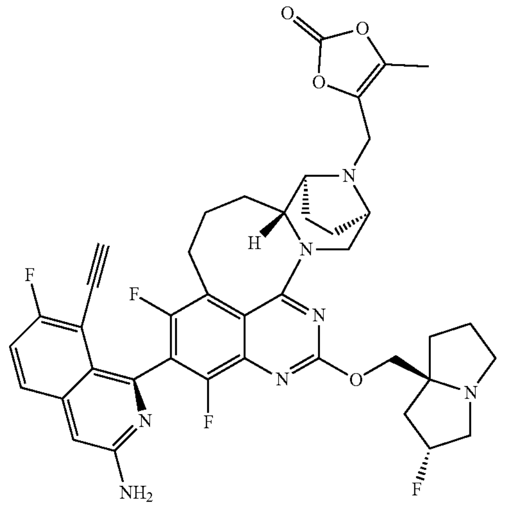

Example 73 was synthesized in a manner similar to Intermediate 11-6 using Example 73-P instead of Intermediate 11-5. $^{1}$H NMR (400 MHz, CD3CN) δ 7.83 (dd, J=9.3, 5.6 Hz, 1H), 7.48 (t, J=9.1 Hz, 1H), 7.04 (s, 1H), 5.53 (d, J=51.7 Hz, 1H), 5.21 (d, J=16.0 Hz, 1H), 4.72 (d, J=13.2 Hz, 1H), 4.65-4.46 (m, 2H), 4.46-4.24 (m, 2H), 4.22-3.95 (m, 4H), 3.95-3.55 (m, 4H), 3.49-3.15 (m, 2H), 3.16-2.99 (m, 2H), 2.76-2.49 (m, 2H), 2.49-2.27 (m, 3H), 2.25 (s, 3H), 2.23-1.99 (m, 3H), 1.92-1.76 (m, 1H), 1.73-1.60 (m, 4H). LCMS: 770.2.

Example 74, Compound 74: 4-(((6aR,7S,10R)-13-(((3S,4S)-4-(difluoromethyl)-1,3-dimethylpiperidin-3-yl)methoxy)-2-(8-ethynyl-7-fluoro-3-hydroxynaphthalen-1-yl)-1-fluoro-5,6,6a,7,8,9,10,11-octahydro-4H-3,11a,12,14,15-pentaaza-7,10-methanocyclohepta[4,5]cycloocta[1,2,3-de]naphthalen-15-yl)methyl)-5-methyl-1,3-dioxol-2-one

74

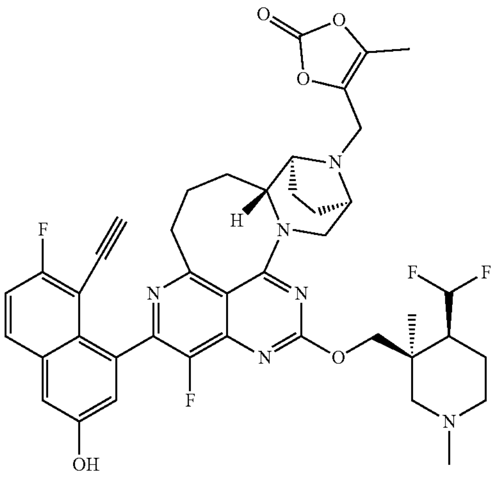

Example 74 was synthesized in a manner similar to Example 11 using Intermediate 74-10 instead of Intermediate 11-6 and using 0.1% trifluoroacetic acid in acetonitrile/water for reverse phase preparative HPLC instead of 0.1% acetic acid in acetonitrile/water. $^{1}$H NMR (400 MHz, Acetonitrile-$d_3$) δ 7.92 (td, J=9.6, 5.8 Hz, 1H), 7.43-7.30 (m, 2H), 7.25 (dd, J=16.9, 2.6 Hz, 1H), 6.21 (t, J=54.9 Hz, 1H), 5.33 (dd, J=14.7, 3.0 Hz, 1H), 4.87 (dd, J=12.1, 7.7 Hz, 1H), 4.46 (dd, J=14.0, 8.3 Hz, 1H), 4.26 (d, J=11.9 Hz, 2H), 4.05 (dd, J=19.3, 13.3 Hz, 1H), 3.96 (d, J=7.3 Hz, 1H), 3.91-3.79 (m, 3H), 3.69-3.44 (m, 2H), 3.41-3.27 (m, 1H), 3.25 (d, J=1.1 Hz, 1H), 3.16-2.31 (m, 12H), 2.12-1.98 (m, 3H), 1.80-1.52 (m, 4H), 1.34 (d, J=5.0 Hz, 3H). LCMS: 787.1.

Example 74-P, Compound 74-P: 4-((6aR,7S,10R)-13-(((3S,4S)-4-(difluoromethyl)-1,3-dimethylpiperidin-3-yl)methoxy)-1-fluoro-5,6,6a,7,8,9,10,11-octahydro-4H-3,11a,12,14,15-pentaaza-7,10-methanocyclohepta[4,5]cycloocta[1,2,3-de]naphthalen-2-yl)-5-ethynyl-6-fluoronaphthalen-2-ol

74-P

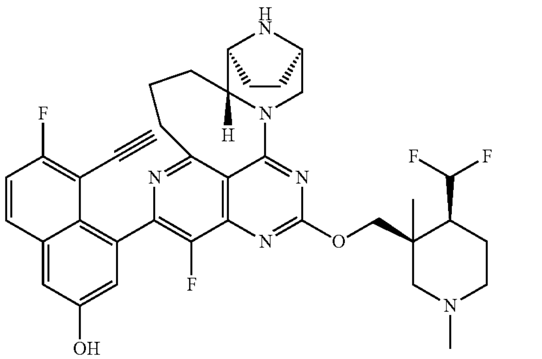

Example 74-P was synthesized in a manner similar to Example 11-P using Intermediate 74-8 instead of Intermediate 11-4. $^{1}$H NMR (400 MHz, Methanol-$d_4$) δ 7.93-7.84 (m, 1H), 7.43-7.29 (m, 2H), 7.23 (s, 0.67H), 7.19 (s, 0.33H), 6.26 (t, J=55.6 Hz, 1H), 5.51-5.30 (m, 1H), 4.73-4.47 (m, 2H), 4.00 (d, J=10.2 Hz, 1H), 3.89-3.80 (m, 1H), 3.78-2.86 (m, 7H), 2.79-0.93 (m, 16H), 2.33 (s, 3H). LCMS: 675.2.

Example 75, Compound 75: 4-(((6aR,7S,10R)-13-(((3S,4S)-4-(difluoromethyl)-3-methyl-1-(methyl-$d_3$)piperidin-3-yl)methoxy-$d_2$)-2-(8-ethynyl-7-fluoro-3-hydroxynaphthalen-1-yl)-1-fluoro-5,6,6a,7,8,9,10,11-octahydro-4H-3,11a,12,14,15-pentaaza-7,10-methanocyclohepta[4,5]cycloocta[1,2,3-de]naphthalen-15-yl)methyl)-5-methyl-1,3-dioxol-2-one

75

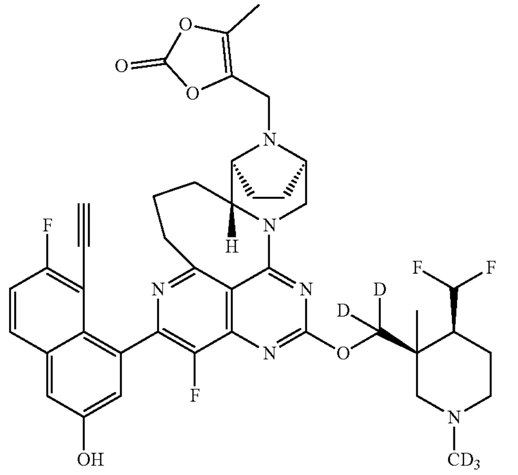

Example 75 was synthesized in a manner similar to Example 11 using Intermediate 75-3 instead of Intermediate 11-6. $^1$H NMR (400 MHz, Acetonitrile-$d_3$) δ 7.98-7.84 (m, 1H), 7.47-7.31 (m, 2H), 7.27 (d, J=2.6 Hz, 0.67H), 7.21 (d, J=2.6 Hz, 0.33H), 6.22 (t, J=55.3 Hz, 1H), 5.31 (dd, J=14.4, 3.0 Hz, 1H), 4.49-4.35 (m, 1H), 4.26-4.09 (m, 1H), 4.05-3.73 (m, 4H), 3.69-3.44 (m, 2H), 3.43-3.28 (m, 1H), 3.25 (d, J=3.8 Hz, 1H), 3.09-1.37 (m, 14H), 2.19 (s, 3H), 1.38-1.30 (m, 3H). LCMS: 792.3.

Example 75-P, Compound 75-P: 4-((6aR,7S,10R)-13-(((3S,4S)-4-(difluoromethyl)-3-methyl-1-(methyl-$d_3$)piperidin-3-yl)methoxy-$d_2$)-1-fluoro-5,6,6a,7,8,9,10,11-octahydro-4H-3,11a,12,14,15-pentaaza-7,10-methanocyclohepta[4,5]cycloocta[1,2,3-de]naphthalen-2-yl)-5-ethynyl-6-fluoronaphthalen-2-ol

75-P

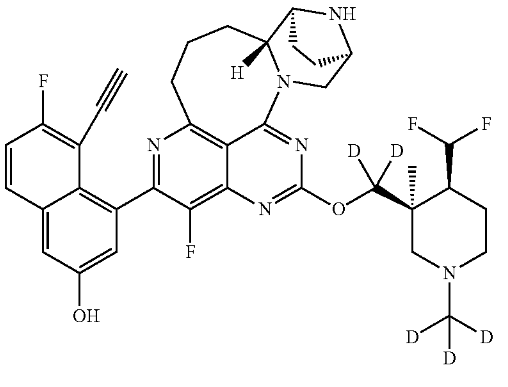

Example 75-P was synthesized in a manner similar to Example 11 using Intermediate 75-2 instead of Intermediate 11-6 and using 0.1% trifluoroacetic acid in acetonitrile/water for reverse phase preparative HPLC instead of 0.1% acetic acid in acetonitrile/water. $^1$H NMR (400 MHz, Methanol-$d_4$) δ 7.90 (dd, J=9.2, 5.6 Hz, 1H), 7.41-7.31 (m, 2H), 7.29-7.14 (m, 1H), 6.29 (t, J=54.4 Hz, 1H), 5.42 (dt, J=14.9, 3.9 Hz, 1H), 4.42-3.99 (m, 3H), 3.73 (dd, J=27.7, 13.5 Hz, 3H), 3.40 (s, 1H), 3.16-2.93 (m, 3H), 2.88 (d, J=9.9 Hz, 1H), 2.39-1.65 (m, 10H), 1.35 (d, J=5.2 Hz, 3H). LCMS: 680.3.

Example 76, Compound 76: 4-(((6aR,7S,10R)-2-(3-amino-8-ethynyl-7-fluoronaphthalen-1-yl)-13-(((3S,4S)-4-(difluoromethyl)-1,3-dimethylpiperidin-3-yl)methoxy)-1-fluoro-5,6,6a,7,8,9,10,11-octahydro-4H-3,11a,12,14,15-pentaaza-7,10-methanocyclohepta[4,5]cycloocta[1,2,3-de]naphthalen-15-yl)methyl)-5-methyl-1,3-dioxol-2-one

76

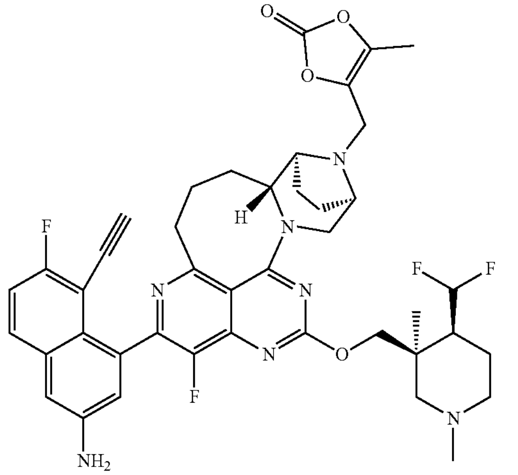

The mixture of Intermediate 76-6 (58.2 mg, 0.0695 mmol) in Ethyl Acetate (5 mL) was treated with 1 M hydrogen chloride solution (5 mL) and agitated for 1 minute before separating layers. The organic layer was washed with 1 M hydrogen chloride solution (2 mL), and the aqueous layers were combined and added to ethyl acetate (5 mL) at 0° C. Solid Sodium bicarbonate was added to the mixture at 0° C. until gas evolution ceased and aqueous phase pH was close to 8. The mixture was extracted with ethyl acetate (5 mL) three times and the combined organic layers were dried over sodium sulfate, filtered, and concentrated to give Example 76. $^1$H NMR (400 MHz, Acetonitrile-$d_3$) δ 7.76 (dd, J=9.1, 5.9 Hz, 1H), 7.25 (td, J=9.1, 2.7 Hz, 1H), 7.10 (dd, J=18.2, 2.4 Hz, 2H), 6.36-5.99 (m, 1H), 5.27-5.13 (m, 1H), 4.53 (dq, J=19.2, 10.5 Hz, 4H), 3.82 (d, J=10.1 Hz, 1H), 3.60 (s, 2H), 3.44-3.08 (m, 6H), 2.89 (dt, J=20.9, 11.3 Hz, 2H), 2.77 (d, J=11.3 Hz, 1H), 2.52 (t, J=10.6 Hz, 1H), 2.12-2.08 (m, 7H), 1.88-1.59 (m, 10H), 1.17 (s, 3H). LCMS: 786.3.

Example 76-P, Compound 76-P: 4-((6aR,7S,10R)-13-(((3S,4S)-4-(difluoromethyl)-1,3-dimethylpiperidin-3-yl)methoxy)-1-fluoro-5,6,6a,7,8,9,10,11-octahydro-4H-3,11a,12,14,15-pentaaza-7,10-methanocyclohepta[4,5]cycloocta[1,2,3-de]naphthalen-2-yl)-5-ethynyl-6-fluoronaphthalen-2-amine

76-P

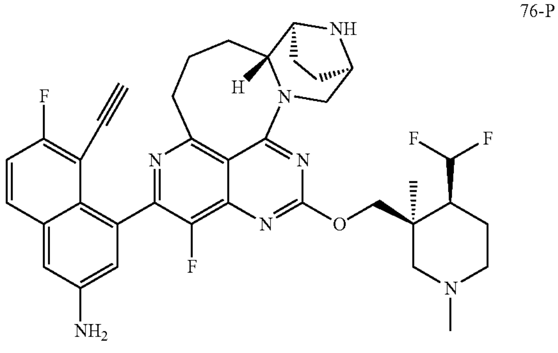

Example 76-P was synthesized in a manner similar to Example 11 using Intermediate 76-4 instead of Intermediate 11-6 and using 0.1% trifluoroacetic acid in acetonitrile/water for reverse phase preparative HPLC instead of 0.1% acetic acid in acetonitrile/water. $^1$H NMR (400 MHz, Methanol-$d_4$) δ 7.82 (dd, J=9.2, 5.5 Hz, 1H), 7.34-7.25 (m, 2H), 7.25-7.13 (m, 1H), 6.29 (t, J=54.8 Hz, 1H), 5.42 (d, J=15.2 Hz, 1H), 4.45-4.27 (m, 2H), 4.12 (dd, J=25.1, 8.2 Hz, 2H), 3.70 (t, J=13.6 Hz, 3H), 3.57-3.36 (m, 3H), 3.20-2.79 (m, 8H), 2.43-2.17 (m, 3H), 2.07 (d, J=14.6 Hz, 4H), 1.78 (dd, J=27.7, 13.3 Hz, 3H), 1.31 (d, J=19.5 Hz, 5H). LCMS: 674.2.

Example 77, Compound 77: 4-(((1S,4R,11R,15aR)-11-(8-ethyl-7-fluoro-3-hydroxynaphthalen-1-yl)-10,12-difluoro-8-(((2R,7aS)-2-fluorotetrahydro-1H-pyrrolizin-7a(5H)-yl)methoxy)-2,3,4,5,13,14,15,15a-octahydro-1H-1,4-epiminoazepino[1',2':1,8]azocino[2,3,4-de]quinazolin-16-yl)methyl)-5-methyl-1,3-dioxol-2-one

77

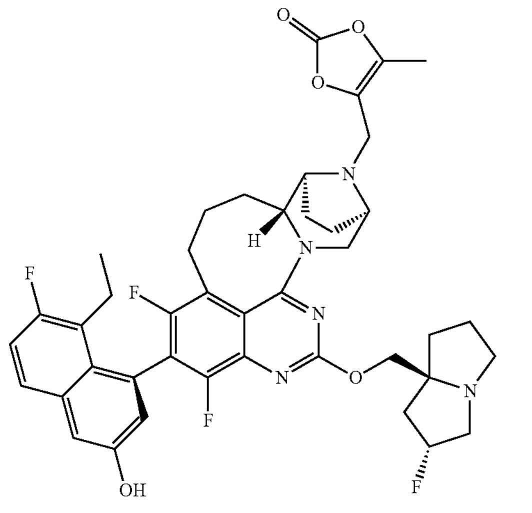

Example 77 was synthesized in a manner similar to Example 18 using Intermediate 77-3 instead of Intermediate 18-3. $^1$H NMR (400 MHz, CD3CN) δ 12.23 (s, 1H), 7.77 (dd, J=9.1, 5.9 Hz, 1H), 7.41 (d, J=2.7 Hz, 1H), 7.34 (t, J=9.4 Hz, 1H), 7.08 (d, J=2.7 Hz, 1H), 5.52 (dt, J=51.7, 3.7 Hz, 1H), 5.24 (dd, J=14.8, 3.0 Hz, 1H), 4.70 (d, J=13.1 Hz, 1H), 4.56 (d, J=13.0 Hz, 1H), 4.45 (d, J=8.7 Hz, 1H), 4.36-4.27 (m, 1H), 4.24-4.00 (m, 3H), 4.02-3.77 (m, 5H), 3.79-3.57 (m, 2H), 3.56-2.93 (m, 4H), 2.81-2.41 (m, 4H), 2.45-2.20 (m, 5H), 2.17-2.02 (m, 1H), 1.93-1.56 (m, 5H), 0.84 (t, J=7.4 Hz, 3H). LCMS: 774.3.

Example 77-P, Compound 77-P: 4-((1S,4R,11R,15aR)-10,12-difluoro-8-(((2R,7aS)-2-fluorotetrahydro-1H-pyrrolizin-7a(5H)-yl)methoxy)-2,3,4,5,13,14,15,15a-octahydro-1H-1,4-epiminoazepino[1',2':1,8]azocino[2,3,4-de]quinazolin-11-yl)-5-ethyl-6-fluoronaphthalen-2-ol

77-P

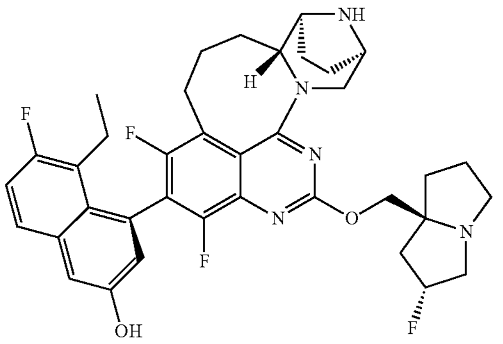

Example 77-P was synthesized in a manner similar to Example 37-P using Intermediate 77-1 instead of Intermediate 37-8A. $^1$H NMR (400 MHz, MeOD) δ 7.71 (dd, J=9.1, 5.8 Hz, 1H), 7.35-7.23 (m, 2H), 7.00 (d, J=10.7 Hz, 1H), 5.59 (d, J=51.8 Hz, 1H), 5.29 (d, J=14.6 Hz, 1H), 4.78-4.59 (m, 2H), 4.42-4.00 (m, 3H), 3.99-3.81 (m, 3H), 3.66 (d, J=14.5 Hz, 1H), 3.50 (dd, J=10.3, 6.3 Hz, 1H), 3.29-2.98 (m, 2H), 2.88-2.59 (m, 2H), 2.62-2.39 (m, 3H), 2.44-2.18 (m, 4H), 2.16-1.81 (m, 3H), 1.72 (s, 3H), 0.92-0.68 (m, 3H). LCMS: 662.4.

Example 78, Compound 78: 4-(((1S,4R,15aR)-8-(((3S,4S)-4-(difluoromethyl)-1,3-dimethylpiperidin-3-yl)methoxy)-11-((R)-8-ethynyl-7-fluoro-3-hydroxynaphthalen-1-yl)-10,12-difluoro-2,3,4,5,13,14,15,15a-octahydro-1H-1,4-epiminoazepino[1',2':1,8]azocino[2,3,4-de]quinazolin-16-yl)methyl)-5-methyl-1,3-dioxol-2-one

78

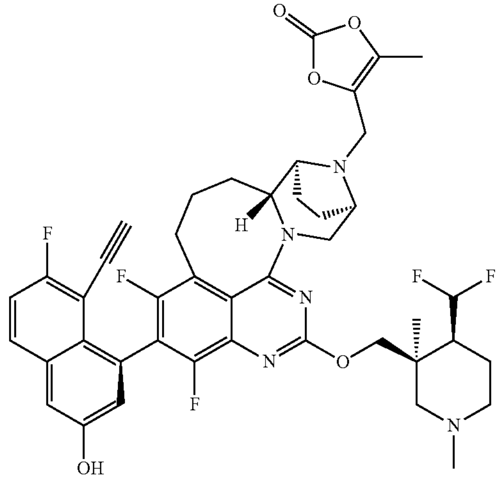

Example 78 was synthesized in a manner similar to Example 18 using Intermediate 78-4 instead of Intermediate 18-3. $^1$H NMR (400 MHz, CD3CN) δ 9.69 (s, 1H), 7.96 (dd, J=9.2, 5.8 Hz, 1H), 7.47 (d, J=2.6 Hz, 1H), 7.41 (t, J=9.0 Hz, 1H), 7.21 (d, J=2.6 Hz, 1H), 6.23 (td, J=54.8, 2.2 Hz, 1H), 5.29 (dd, J=14.9, 3.0 Hz, 1H), 4.87 (d, J=12.2 Hz, 1H), 4.47-4.35 (m, 1H), 4.35-4.30 (m, 1H), 4.27 (dd, J=12.2, 2.5 Hz, 1H), 4.18-3.96 (m, 3H), 3.96-3.87 (m, 1H), 3.67-3.57 (m, 1H), 3.54-3.45 (m, 1H), 3.26 (d, J=1.0 Hz, 1H), 3.23-3.14 (m, 1H), 3.13-2.94 (m, 4H), 2.91-2.71 (m, 5H), 2.32-2.15 (m, 6H), 2.14-2.01 (m, 1H), 1.96-1.84 (m, 1H), 1.80-1.59 (m, 3H), 1.35 (s, 3H). LCMS: 804.2.

Example 78-P, Compound 78-P: (R)-4-((1S,4R,15aR)-8-(((3S,4S)-4-(difluoromethyl)-1,3-dimethylpiperidin-3-yl)methoxy)-10,12-difluoro-2,3,4,5,13,14,15,15a-octahydro-1H-1,4-epiminoazepino[1',2':1,8]azocino[2,3,4-de]quinazolin-11-yl)-5-ethynyl-6-fluoronaphthalen-2-ol

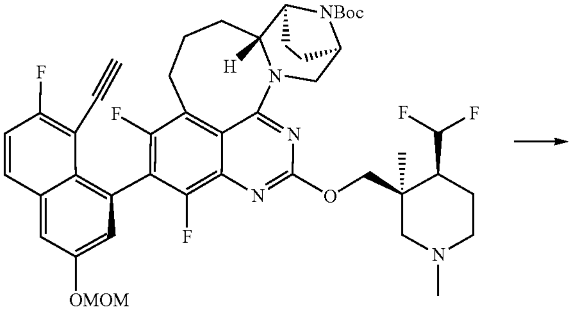

78-2

-continued

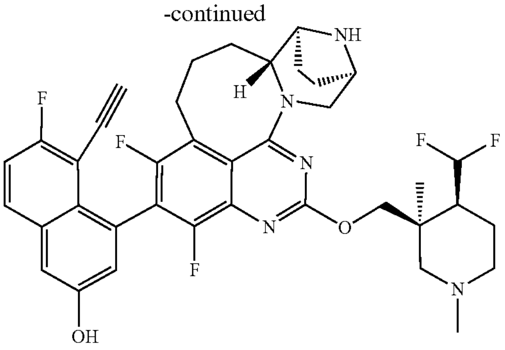

78-P

Example 78-P was synthesized in a manner similar to Example 37-P using Intermediate 78-2 instead of Intermediate 37-8A. $^1$H NMR (400 MHz, MeOD) δ 7.90 (dd, J=9.2, 5.7 Hz, 1H), 7.47-7.31 (m, 2H), 7.25-7.08 (m, 1H), 6.30 (t, J=54.8 Hz, 1H), 5.31 (d, J=14.7 Hz, 1H), 4.45-4.18 (m, 2H), 4.08 (dd, J=21.1, 7.7 Hz, 2H), 3.70 (t, J=11.2 Hz, 4H), 3.47 (s, 1H), 3.26-3.00 (m, 5H), 2.92 (s, 4H), 2.29 (s, 4H), 2.00-1.61 (m, 5H), 1.35 (s, 3H). LCMS: 692.3.

Example 79, Compound 79: 4-(((1S,4R,11S,15aR)-11-(3-amino-8-ethynyl-7-fluoroisoquinolin-1-yl)-10,12-difluoro-8-(((2R,7aS)-2-fluorotetrahydro-1H-pyrrolizin-7a(5H)-yl)methoxy)-2,3,4,5,13,14,15,15a-octahydro-1H-1,4-epiminoazepino[1',2':1,8]azocino[2,3,4-de]quinazolin-16-yl)methyl)-5-ethyl-1,3-dioxol-2-one

79

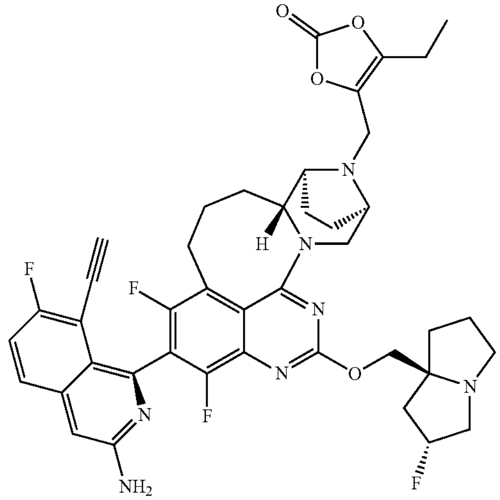

Example 79 was synthesized in a manner similar to Example 73 using 4-(bromomethyl)-5-ethyl-1,3-dioxol-2-one instead of 4-(bromomethyl)-5-methyl-1,3-dioxol-2-one. $^1$H NMR (400 MHz, CD3CN) δ 12.15 (s, 1H), 7.83 (dd, J=9.3, 5.6 Hz, 1H), 7.47 (t, J=9.1 Hz, 1H), 7.03 (s, 1H), 5.53 (d, J=52.1 Hz, 1H), 5.21 (dd, J=14.8, 3.0 Hz, 1H), 4.72 (d, J=13.2 Hz, 1H), 4.57 (d, J=13.1 Hz, 1H), 4.53-4.39 (m, 1H), 4.38-4.21 (m, 1H), 4.22-3.96 (m, 3H), 3.96-3.57 (m, 5H), 3.50-2.89 (m, 4H), 2.87-2.39 (m, 5H), 2.39-2.01 (m, 4H), 1.94-1.78 (m, 2H), 1.76-1.53 (m, 4H), 1.22 (t, J=7.4 Hz, 3H). LCMS: 784.2.

Example 80, Compound 80: 4-(((6aR,7S,10R)-2-(3-amino-8-ethynyl-7-fluoronaphthalen-1-yl)-1-fluoro-13-(((2R,7aS)-2-fluorotetrahydro-1H-pyrrolizin-7a(5H)-yl)methoxy)-5,6,6a,7,8,9,10,11-octahydro-4H-3,11a,12,14,15-pentaaza-7,10-methanocyclohepta[4,5]cycloocta[1,2,3-de]naphthalen-15-yl)methyl)-5-isopropyl-1,3-dioxol-2-one

80

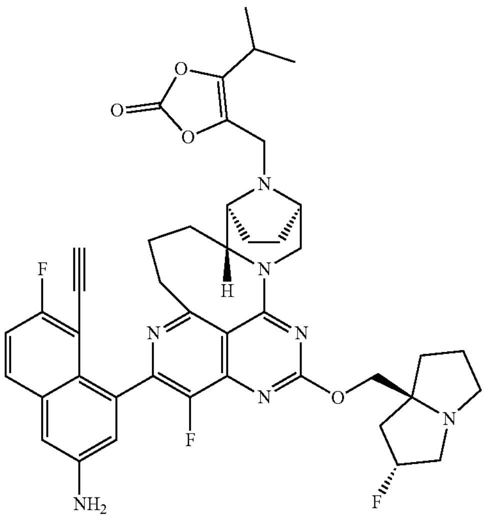

Aqueous hydrogen chloride solution (2.0 M, 500 μL, 1.0 mmol) was added via syringe to a stirred solution of Intermediate 80-3 (66.8 mg, 70.8 μmol) in acetonitrile (0.50 mL) at −30° C., and the resulting mixture was warmed to 0° C. After 4 min, sodium acetate (200 mg) was added, and the resulting mixture was purified by reverse phase preparative HPLC (0.1% trifluoroacetic acid in acetonitrile/water) to give Example 80. $^1$H NMR (400 MHz, Acetonitrile-$d_3$) δ 7.81-7.74 (m, 1H), 7.32-7.22 (m, 1H), 7.18-7.14 (m, 1H), 7.10 (d, J=2.4 Hz, 0.67H), 7.06 (s, 0.33H), 5.65-5.41 (m, 1H), 5.36-5.18 (m, 1H), 4.75-4.64 (m, 1H), 4.60 (d, J=12.8 Hz, 1H), 4.47 (d, J=8.5 Hz, 1H), 4.33-4.16 (m, 1H), 4.12-3.97 (m, 3H), 3.98-3.57 (m, 4H), 3.42-3.26 (m, 2H), 3.22 (s, 0.67H), 3.18-2.79 (m, 4.33H), 2.72-1.38 (m, 12H), 1.28-1.12 (m, 6H). LCMS: 780.1.

Example 81, Compound 81: 4-(((6aR,7S,10R)-2-(3-amino-8-ethynyl-7-fluoronaphthalen-1-yl)-1-fluoro-13-(((2R,7aS)-2-fluorotetrahydro-1H-pyrrolizin-7a(5H)-yl)methoxy)-5,6,6a,7,8,9,10,11-octahydro-4H-3,11a,12,14,15-pentaaza-7,10-methanocyclohepta[4,5]cycloocta[1,2,3-de]naphthalen-15-yl)methyl)-5-(tert-butyl)-1,3-dioxol-2-one

81

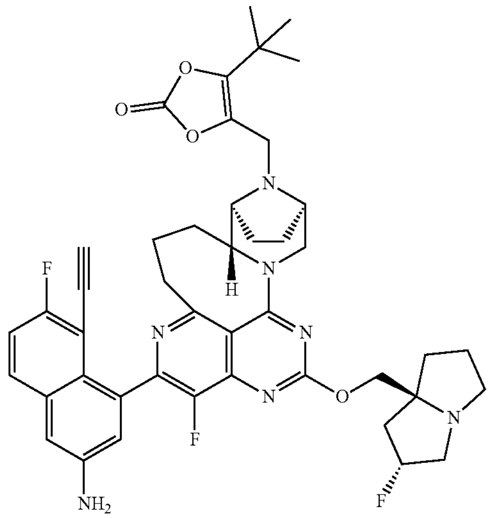

Example 81 was synthesized in a manner similar to Example 80 using 4-(bromomethyl)-5-tert-butyl-1,3-dioxol-2-one (see Tetrahedron Lett. 2002, 43, 1161) instead of 4-(bromomethyl)-5-isopropyl-1,3-dioxol-2-one. $^1$H NMR (400 MHz, Acetonitrile-$d_3$) δ 7.83-7.74 (m, 1H), 7.33-7.22 (m, 1H), 7.19-7.11 (m, 1H), 7.10 (d, J=2.4 Hz, 0.67H), 7.07 (s, 0.33H), 5.64-5.41 (m, 1H), 5.35-5.23 (m, 1H), 4.77-4.48 (m, 3H), 4.33-4.19 (m, 1H), 4.08-3.57 (m, 7H), 3.42-3.27 (m, 2H), 3.23 (s, 0.67H), 3.18-2.70 (m, 4H), 3.07 (s, 0.33H), 2.69-1.47 (m, 11H), 1.34 (s, 9H). LCMS: 794.3.

IV. Biological Examples

Example A. KRAS G12D (GDP) Biochemical Assay

Compounds were tested for binding to GDP-loaded KRAS G12D in a 384-well assay format using a TR-FRET probe displacement assay in buffer consisting of 50 mM Hepes (pH 7.4), 150 mM NaCl, 5 mM $MgCl_2$ and 0.005% Tween-20. 0.5 nM enzyme was used in this assay with 0.25 nM Eu-streptavidin and 200 nM (2×$K_D$) Cy-5 labelled probe. Compounds were serially diluted (1:3) in DMSO. The LabCyte ECHO Acoustic dispenser system was used to pre-spot the assay plates (384-well Non-Binding Surface plates, Corning, Catalog #3824) with 50 nL of compound. The compounds were pre-incubated with 5 μL of 2× final enzyme concentration for 30 minutes before adding 5 μL of 2× final concentration of Eu-streptavidin and TR-FRET probe (10 μL final reaction volume). The plates were incubated at room temperature for 2 hours before measuring TR-FRET ratio on the Envision plate reader. $IC_{50}$ values were defined as the compound concentration that causes a 50% decrease in TR-FRET ratio and were calculated using a sigmoidal dose-response model to generate curve fits.

Example B. 2D Cell Viability Assay

Compounds were tested in a 384-well format for their ability to inhibit the viability of GP2D (KRAS G12D) cells in 2D assays. Compounds were serially diluted (1:3) in DMSO. The LabCyte ECHO Acoustic dispenser system was used to pre-spot assay plates with 200 nL of test molecule per well. 1000 cells/well (40 μL volume per well) in RPMI medium with 10% FBS, and Penicillin-Streptomycin-Glutamine were plated in pre-spotted 384-well plates (Greiner, Catalog #781076) on the BioTEK EL406 liquid dispenser with a 5 μL dispensing cassette (BioTek 7170011). The plates were incubated at 37° C., 5% $CO_2$ for 4 days before addition of CellTiter-Glo (CTG) reagent and measurement of luminescence signal. $EC_{50}$ values were defined as the compound concentration that causes a 50% decrease in luminescence signal and were calculated using a sigmoidal dose-response model to generate curve fits.

Example C. 3D Cell Viability Assay

Compounds were tested in a 384-well format for their ability to inhibit the viability of AsPC-1 (KRAS G12D) cells in 3D assays. On day 0, 1000 cells/well (80 μL volume per well) in DMEM with 10% FBS, and Penicillin-Streptomycin-Glutamine were plated in 384-well Ultra-Low Attachment Spheroid Microplates (Corning, Catalog #3830) on the BioTEK EL406 liquid dispenser with a 5 μL dispensing cassette (BioTek 7170011). The plates were incubated at 37° C., 5% $CO_2$ for 3 days to allow spheroid formation. On day 3, compounds were serially diluted (1:3) in DMSO. The Biomek FX was used to add 400 nL of test molecule per well. The plates were incubated at 37° C., 5% $CO_2$ for 4 days before addition of CellTiter-Glo 3D (Promega, Catalog #9683) reagent and measurement of luminescence signal. $EC_{50}$ values were defined as the compound concentration that causes a 50% decrease in luminescence signal and were calculated using a sigmoidal dose-response model to generate curve fits.

Example D. Pharmacokinetic Profiling

Rat Oral Pharmacokinetics

Test compounds were formulated in solution formulations (10 w/v % Sulfobutylether-p-cyclodextrin; 90% w/v % 50 mM Citrate Buffer) and administered orally to a group of three Male Sprague Dawley rats. The animals were fasted overnight prior to dose administration and up to four hours after dosing. The test articles were administrated by oral gavage at a dose volume of 5 mL-eq/kg.

Blood samples were collected at predose and 0.25, 0.5, 1, 2, 4, 6, 8, 12, 24, 48 and 72 hours post dose into $K_2$EDTA tubes and stored on wet ice until processed. Whole blood was processed to plasma by centrifugation (3500 rpm for 10 minutes at 5° C.) within 30 minutes of collection. Plasma samples were placed in Micronic 96 well tubes and stored at −80° C. until transferred. Plasma concentration of the test compounds was determined by LC-MS/MS. Pharmacokinetic parameters were estimated using non-compartment model analysis. The maximum observed concentration ($C_{max}$) and area under the curve from time of dosing to last measured concentration ($AUC_{last}$) were calculated and reported.

Mouse Oral Cassette Pharmacokinetics

Test compounds (1-3 compounds per cassette) were formulated in solution formulations (10 w/v % Captisol in 50 mM Citrate buffer) and administered orally at 30 mg-eq./kg each compound to a group of four male CD-1 mice. The test articles were administrated by oral gavage at a dose volume of 10 mL-eq/kg.

Blood samples were collected at 0.5, 1, 3, 6, 8, and 24 hours post dose into $K_2$EDTA tubes and stored on wet ice until processed. Whole blood was processed to plasma by centrifugation (3500 rpm for 10 minutes at 5° C.) within 30 minutes of collection. Plasma samples were placed in Micronic 96 well tubes and stored at −80° C. until transferred. Plasma concentration of the test compounds was determined by LC-MS/MS. Pharmacokinetic parameters were estimated using non-compartment model analysis. The maximum observed concentration ($C_{max}$) and area under the curve from time of dosing to last measured concentration ($AUC_{last}$) were calculated and reported.

Dog Oral Pharmacokinetics

Test compounds were formulated in solution formulations (10% w/v % Sulfobutylether-p-cyclodextrin; 90% w/v % 50 mM Citrate Buffer) and administered orally at 5 or 10 mg-eq./kg to a group of three Male Beagle dogs. The animals were fasted overnight prior to dose administration and up to four hours after dosing. The test articles were administrated by oral gavage at a dose volume of 5 ml/kg.

Blood samples were collected into $K_2$EDTA tubes at predose and 0.25, 0.5, 1, 2, 4, 6, 8, 12, 24 hours post dose, and once daily collection post 24 hours up to 168 hours. Whole blood were stored on wet ice and processed to plasma by centrifugation (3500 rpm for 10 minutes at 5° C.) within 1 hour of collection. Plasma samples were placed in Micronic 96 well tubes and stored at −80° C. until transferred. Plasma concentration of the test compounds was determined by LC-MS/MS. Pharmacokinetic parameters were estimated using non-compartment model analysis. The maximum observed concentration ($C_{max}$) and area under the curve from time of dosing to last measured concentration ($AUC_{last}$) were calculated and reported.

Biological Data

Provided below in Table 2 is data related to compounds disclosed herein.

TABLE 2

Biological Data for Compounds Disclosed Herein

| Example No. | G12D $IC_{50}$ (nM) | G12D 2D $EC_{50}$ (nM) |
|---|---|---|
| 1 | 2.5 | 5.8 |
| 2 | 40 | 0.24 |
| 3 | 4.7 | 0.92 |
| 4 | 3.3 | 2.3 |
| 5 | 4.7 | 78 |
| 6 | 31 | 26 |
| 7 | 2.8 | 0.18 |
| 8 | 4.8 | 0.49 |
| 9 | 12 | 1.9 |
| 10 | 7.8 | 0.16 |
| 11-P | 0.09 | 0.09 |
| 11 | 4.4 | 0.12 |
| 12 | 73 | 0.28 |
| 13 | 24 | 0.19 |
| 14 | 7.3 | 0.14 |
| 15 | 7.9 | 0.20 |
| 16 | 40 | 0.16 |
| 17 | 48 | 0.20 |
| 18-P | 0.06 | 0.24 |
| 18 | N/A | N/A |
| 19 | N/A | N/A |
| 20 | N/A | 5.0 |
| 21 | N/A | 5.2 |
| 22 | N/A | 0.85 |
| 23 | N/A | 0.92 |

TABLE 2-continued

| Biological Data for Compounds Disclosed Herein | | |
|---|---|---|
| Example No. | G12D $IC_{50}$ (nM) | G12D 2D $EC_{50}$ (nM) |
| 24 | N/A | 1.1 |
| 28-P | 0.07 | 0.13 |
| 28 | N/A | 0.18 |
| 29 | N/A | 0.13 |
| 30 | N/A | 0.22 |
| 31 | N/A | 0.20 |
| 32 | N/A | 0.30 |
| 33 | N/A | 0.71 |
| 34 | N/A | 0.40 |
| 35 | N/A | 0.46 |
| 36 | N/A | 0.49 |
| 37-P | 0.07 | 0.26 |
| 37 | 1.0 | 0.23 |
| 38 | N/A | 0.25 |
| 39 | N/A | 0.26 |
| 40 | N/A | 0.22 |
| 41 | N/A | 0.18 |
| 42-P | 0.15 | 1.7 |
| 42 | N/A | 1.7 |
| 51 | >100 | 34 |
| 67 | N/A | 1.3 |
| 68 | N/A | 0.65 |
| 69 | N/A | 0.48 |
| 69-P | 0.07 | 0.50 |
| 70 | N/A | 0.31 |
| 71-P | 0.03 | 0.18 |
| 71 | N/A | 0.41 |
| 72 | N/A | 0.11 |
| 73 | N/A | 0.82 |
| 74-P | 0.03 | 0.15 |
| 74 | N/A | 0.06 |
| 75-P | 0.03 | 0.10 |
| 75 | N/A | 0.08 |
| 76-P | 0.07 | 0.27 |
| 76 | N/A | 0.89 |
| 77-P | N/A | 0.29 |
| 77 | N/A | 0.26 |
| 78-P | 0.04 | 0.14 |
| 78 | N/A | 0.08 |
| 79 | N/A | 1.2 |
| 80 | N/A | 0.37 |
| 81 | N/A | 0.63 |

Pharmacokinetic Data

The following compounds were evaluated according to procedures described in Example D (Table 3). Comparative Examples 64, 75, 76, and 87 were described as Examples 64, 75, 76, and 87, respectively, in U.S. application Ser. No. 18/303,813, published as US 2023/0374036. The structures of Comparative Examples 64, 75, 76, and 87 follow.

Comparative Ex. 64

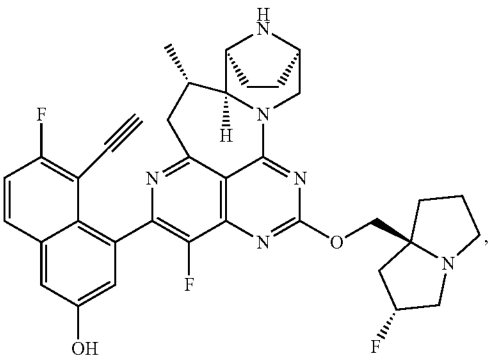

-continued

Comparative Ex. 75

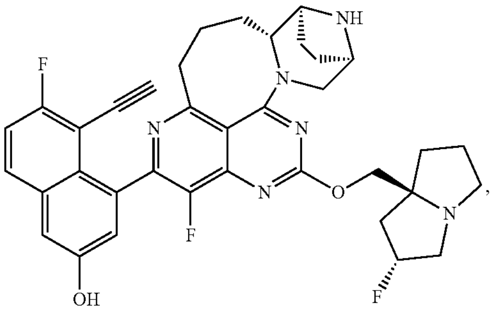

Comparative Ex. 76

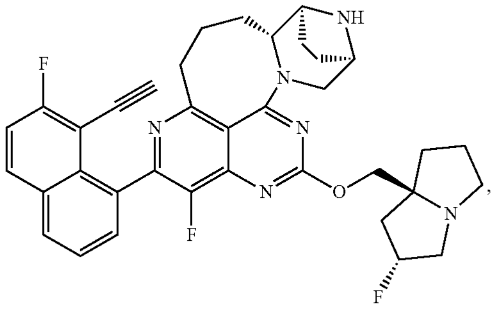

and

Comparative Ex. 87

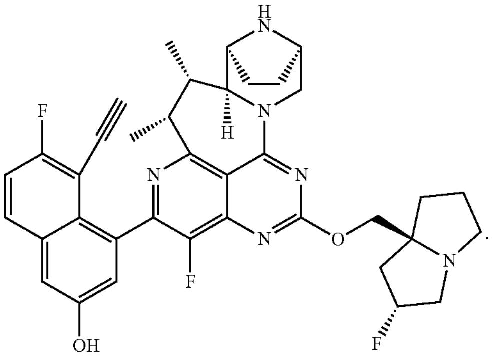

TABLE 3

Pharmacokinetic Data for Compounds Disclosed Herein

| Example No. | Mouse Parent AUC (nM * h) | Rat Parent AUC (nM * h) | Rat Dose (mg/kg equiv to parent) | Rat Parent % F | Dog Parent AUC (nM * h) | Dog Dose (mg/kg equiv to parent) | Dog Parent % F |
|---|---|---|---|---|---|---|---|
| Comp. Ex. 64 | 830 | N/A | N/A | N/A | N/A | N/A | N/A |
| Comp. Ex. 75 | 51 | N/A | N/A | N/A | 71 | 10 | 0.6 |
| Comp. Ex. 76 | 1,400 | 59 | 5 | 2 | N/A | N/A | N/A |
| Comp. Ex. 87 | 900 | N/A | N/A | N/A | N/A | N/A | N/A |
| 1 | 3600 | 580 | 5 | 18 | N/A | N/A | N/A |
| 3 | 5700 | 250 | 5 | 2 | N/A | N/A | N/A |
| 4 | N/A | 190 | 5 | 6 | N/A | N/A | N/A |
| 6 | N/A | 450 | 5 | 14 | N/A | N/A | N/A |
| 8 | 1100 | N/A | N/A | N/A | 1100 | 10 | 10 |
| 9 | 160 | N/A | N/A | N/A | N/A | N/A | N/A |
| 10 | 440 | N/A | N/A | N/A | N/A | N/A | N/A |
| 11 | 960 | N/A | N/A | N/A | N/A | N/A | N/A |
| 11-P | 140 | N/A | N/A | N/A | N/A | N/A | N/A |
| 12 | 200 | N/A | N/A | N/A | N/A | N/A | N/A |
| 13 | 420 | N/A | N/A | N/A | N/A | N/A | N/A |
| 14 | 940 | N/A | N/A | N/A | N/A | N/A | N/A |
| 15 | 250 | N/A | N/A | N/A | N/A | N/A | N/A |
| 16 | 950 | N/A | N/A | N/A | N/A | N/A | N/A |
| 17 | 161 | N/A | N/A | N/A | N/A | N/A | N/A |
| 18 | N/A | N/A | N/A | N/A | 600 | 10 | 12 |
| 18-P | N/A | N/A | N/A | N/A | 91 | 5 | 3.6 |
| 25 | N/A | 37 | 5 | 1 | N/A | N/A | N/A |
| 28 | 700 | N/A | N/A | N/A | N/A | N/A | N/A |
| 29 | 750 | N/A | N/A | N/A | N/A | N/A | N/A |
| 30 | 660 | N/A | N/A | N/A | N/A | N/A | N/A |
| 31 | 990 | N/A | N/A | N/A | N/A | N/A | N/A |
| 33 | 1,500 | 180 | 15 | 3.3 | 2,200 | 10 | 11 |
| 34 | 1,300 | 270 | 15 | 5 | 1,200 | 5 | 12 |
| 35 | N/A | 270 | 15 | 5 | N/A | N/A | N/A |
| 36 | N/A | 52 | 7.5 | 1.9 | N/A | N/A | N/A |
| 37 | 130 | N/A | N/A | N/A | N/A | N/A | N/A |
| 38 | 2,100 | 280 | 7.5 | 3 | 210 | 5 | 4.2 |
| 42 | N/A | 200 | 7.5 | 0.3 | N/A | N/A | N/A |
| 51 | N/A | 3 | 5 | 0.1 | N/A | N/A | N/A |
| 69-P | 500 | 11 | 15 | 0.2 | N/A | N/A | N/A |
| 73 | N/A | 300 | 7.5 | 2 | N/A | N/A | N/A |
| 77 | N/A | 430 | 7.5 | | N/A | N/A | N/A |
| 79 | N/A | 220 | 7.5 | N/A | N/A | N/A | N/A |
| 80 | N/A | 57 | 7.5 | 2.1 | N/A | N/A | N/A |
| 81 | N/A | 11 | 7.5 | 0.4 | N/A | N/A | N/A |

The present disclosure provides reference to various embodiments and techniques. However, it should be understood that many variations and modifications can be made while remaining within the spirit and scope of the present disclosure. The description is made with the understanding that it is to be considered an exemplification of the claimed subject matter, and is not intended to limit the appended claims to the specific embodiments illustrated.

The invention claimed is:

1. A compound having the structure of Formula (Ib-1):

(Ib-1)

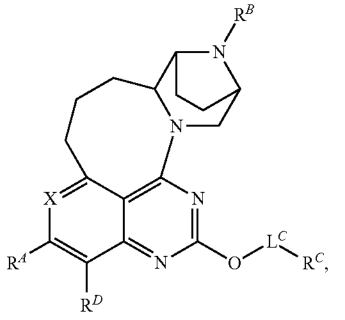

or a pharmaceutically acceptable salt thereof, wherein $R^A$ is

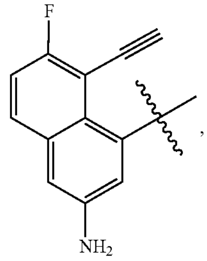

,

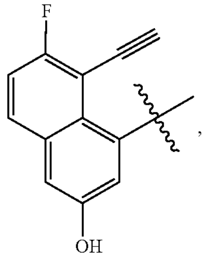

, or

-continued

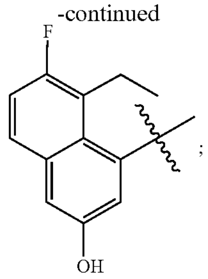

X is N;
$R^D$ is F;
$R^B$ is

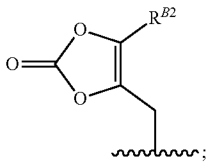

$R^{B2}$ is $C_1$-$C_4$ alkyl; and
—O-$L^C$-$R^C$ moiety is

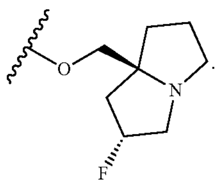 [SMILES: *OC[C@@]12CCCN1C[C@H](F)C2]

2. The compound of claim 1, or a pharmaceutically acceptable salt thereof, having the structure of Formula (Ib-2):

(Ib-2)

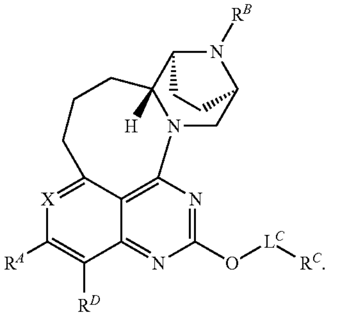

3. The compound of claim 1, or a pharmaceutically acceptable salt thereof, wherein the compound has the structure:

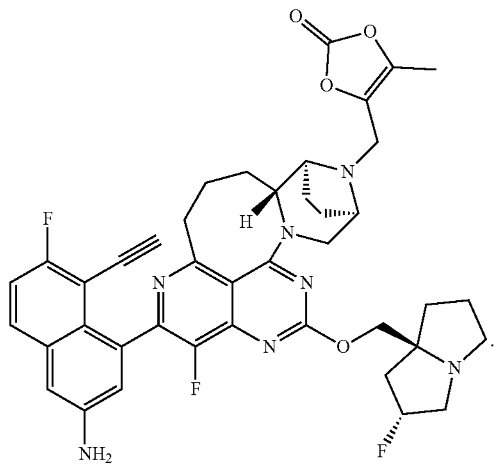

4. The compound of claim 1, or a pharmaceutically acceptable salt thereof, wherein the compound has the structure:

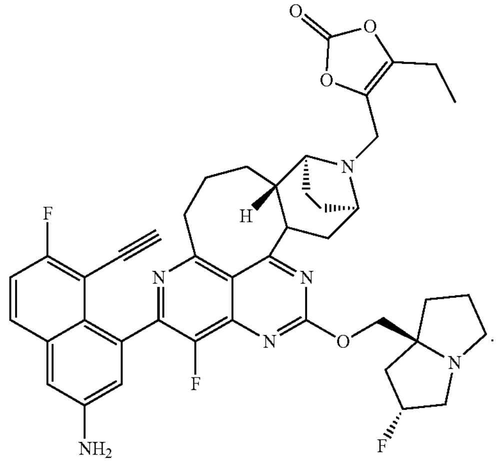

5. The compound of claim 1, or a pharmaceutically acceptable salt thereof, wherein the compound has the structure:

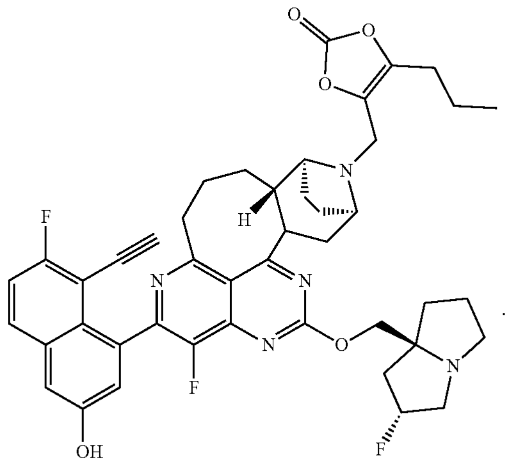

6. The compound of claim 1, or a pharmaceutically acceptable salt thereof, wherein the compound has the structure:

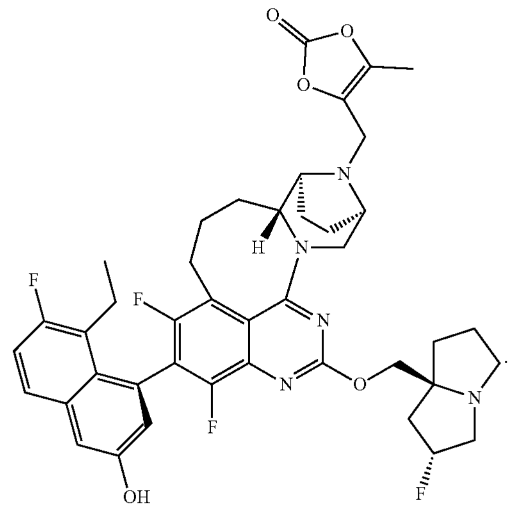

7. The compound of claim 1, or a pharmaceutically acceptable salt thereof, wherein the compound has the structure:

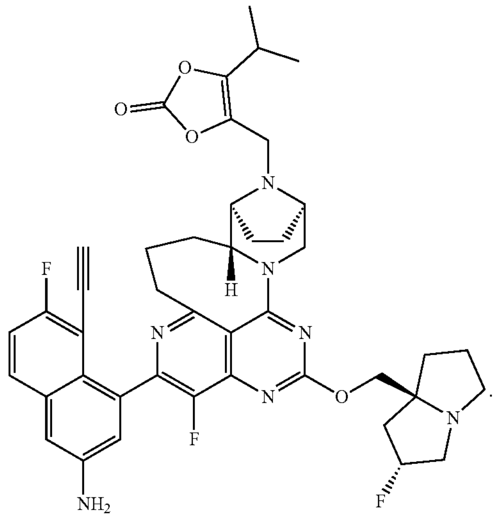

8. The compound of claim 1, or a pharmaceutically acceptable salt thereof, wherein the compound has the structure:

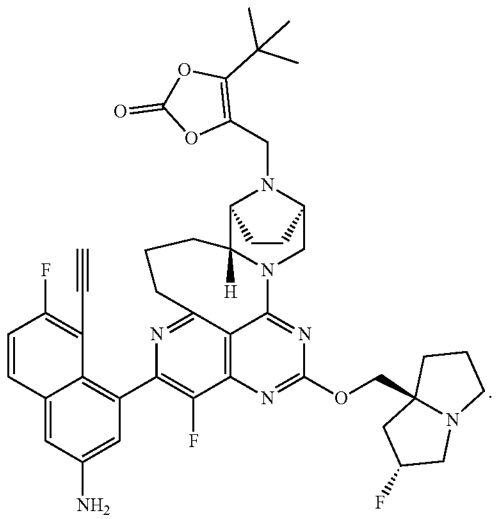

9. A pharmaceutical composition comprising a compound of claim 1, and a pharmaceutically acceptable excipient.

10. A pharmaceutical composition comprising the compound of claim 3 or pharmaceutically acceptable salt thereof, and a pharmaceutically acceptable excipient.

11. A pharmaceutical composition comprising the compound of claim 4 or pharmaceutically acceptable salt thereof, and a pharmaceutically acceptable excipient.

12. A pharmaceutical composition comprising the compound of claim 5 or pharmaceutically acceptable salt thereof, and a pharmaceutically acceptable excipient.

13. A pharmaceutical composition comprising the compound of claim 6 or pharmaceutically acceptable salt thereof, and a pharmaceutically acceptable excipient.

14. A pharmaceutical composition comprising the compound of claim 7 or pharmaceutically acceptable salt thereof, and a pharmaceutically acceptable excipient.

15. A pharmaceutical composition comprising the compound of claim 8 or pharmaceutically acceptable salt thereof, and a pharmaceutically acceptable excipient.

* * * * *